US011117863B2

(12) United States Patent
Umetani et al.

(10) Patent No.: US 11,117,863 B2
(45) **Date of Patent: *Sep. 14, 2021**

(54) PYRIDONE COMPOUNDS AND AGRICULTURAL AND HORTICULTURAL FUNGICIDES CONTAINING THE SAME AS ACTIVE INGREDIENTS

(71) Applicant: MITSUI CHEMICALS AGRO, INC., Tokyo (JP)

(72) Inventors: Hideki Umetani, Ritto (JP); Hideaki Ikishima, Chiba (JP); Kouji Takagi, Mobara (JP); Takeshi Fukumoto, Chiba (JP); Ryohei Naito, Kusatsu (JP); Tomomi Shirakawa, Ritto (JP); Hikaru Koishihara, Chiba (JP); Hisaki Yamanaka, Yasu (JP); Miyuki Kawashima, Chiba (JP); Akane Sakurada, Mobara (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/615,445

(22) PCT Filed: Jun. 7, 2018

(86) PCT No.: PCT/JP2018/021900

§ 371 (c)(1),
(2) Date: Nov. 21, 2019

(87) PCT Pub. No.: WO2018/225829

PCT Pub. Date: Dec. 13, 2018

(65) Prior Publication Data

US 2020/0172486 A1 Jun. 4, 2020

(30) Foreign Application Priority Data

Jun. 8, 2017 (JP) ............................ JP2017-113810

(51) Int. Cl.

| | |
|---|---|
| ***A01N 43/40*** | (2006.01) |
| ***C07D 213/80*** | (2006.01) |
| ***C07D 213/74*** | (2006.01) |
| ***C07D 213/75*** | (2006.01) |
| ***C07D 401/10*** | (2006.01) |
| ***C07D 409/10*** | (2006.01) |
| ***C07D 417/10*** | (2006.01) |

(52) U.S. Cl.

CPC .......... *C07D 213/80* (2013.01); *A01N 43/40* (2013.01); *C07D 213/74* (2013.01); *C07D 213/75* (2013.01); *C07D 401/10* (2013.01); *C07D 409/10* (2013.01); *C07D 417/10* (2013.01)

(58) Field of Classification Search

None

See application file for complete search history.

(56) References Cited

U.S. PATENT DOCUMENTS

| | | | |
|---|---|---|---|
| 6,200,982 | B1 | 3/2001 | Collins et al. |
| 2001/0018438 | A1 | 8/2001 | Collins et al. |
| 2017/0121335 | A1 | 5/2017 | Soldermann et al. |
| 2017/0217890 | A1 | 8/2017 | Johns et al. |
| 2018/0030061 | A1 | 2/2018 | Soldermann et al. |
| 2018/0279614 | A1 | 10/2018 | Umetani et al. |

FOREIGN PATENT DOCUMENTS

| | | | |
|---|---|---|---|
| EP | 0308020 | A2 | 3/1989 |
| JP | 1128969 | A | 5/1989 |
| JP | 2002503244 | A | 1/2002 |
| WO | 9855480 | A1 | 12/1998 |
| WO | 2015181747 | A1 | 12/2015 |

(Continued)

OTHER PUBLICATIONS

Keller, Product class 2: pyridinones and related systems, Science of Synthesis (2005), 15, 285-387 (Year: 2005).*

(Continued)

*Primary Examiner* — Alton N Pryor
(74) *Attorney, Agent, or Firm* — Buchanan, Ingersoll & Rooney PC

(57) ABSTRACT

Provided are a pyridone compound represented by Formula (1):

(1)

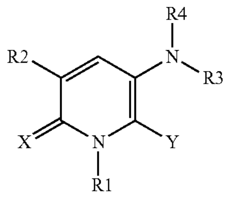

wherein

R1 represents a C1-C6 alkyl group which may be substituted, etc.,

R2 represents a halogen atom, a cyano group, etc.,

R3 and R4 are independent to each other, and each represents a hydrogen atom, a C1-C6 alkyl group which may be substituted, etc., or in combination with the nitrogen atom to which they are bonded form a pyrrolidinyl group, a piperidinyl group, etc., which may be substituted, Y represents a phenyl group which may be substituted, etc., X represents an oxygen atom or a sulfur atom, and an agricultural and horticultural fungicide containing the same as an active ingredient.

8 Claims, No Drawings

(56) References Cited

FOREIGN PATENT DOCUMENTS

| | | | |
|---|---|---|---|
| WO | 2016012913 | A1 | 1/2016 |
| WO | 2017061525 | A1 | 4/2017 |

OTHER PUBLICATIONS

Shamma et al., Unsaturated lactams. III. New synthesis of pyridines and unsaturated lactams, Tetrahedron (1965), 21(12), 3255-62 (Year: 1965).*

Ross, Preparation of some 4-substituted nicotinic acids and nicotinamides, Journal of the Chemical Society [Section] C: Organic (1966), (20), 1816-21 (Year: 1966).*

International Search Report (PCT/ISA/210) and translation and Written Opinion (PCT/ISA/237) dated Aug. 14, 2018, by the Japanese Patent Office as the International Searching Authority for International Application No. PCT/JP2018/021900.

* cited by examiner

PYRIDONE COMPOUNDS AND AGRICULTURAL AND HORTICULTURAL FUNGICIDES CONTAINING THE SAME AS ACTIVE INGREDIENTS

TECHNICAL FIELD

The present invention relates to a pyridone compound and a pesticide containing the compound as an active ingredient.

BACKGROUND ART

Protection of agricultural and horticultural crops from diseases is important to ensure stable agricultural production. For this purpose, various fungicides are used. However, use of fungicides over years causes emergence of fungi resistant to drugs. Thus, novel fungicides that are effective not only to drug-sensitive fungi but also to drug-resistant fungi are demanded.

By the way, prior examples related to 1,3,5,6-substituted-2-pyridone compounds have been known. For example, 1,3,5,6-substituted-2-pyridone compounds each having an aryl group or a heteroaryl group at the 3-position are disclosed as GABA alpha 2/3 ligands (for example, see Patent Literature 1). As therapeutic agents for bacterial infection, 1,3,5,6-substituted-2-pyridone compounds each having a carboxyl group at the 3-position are disclosed (for example, see Patent Literature 2). Further, as anti-HIV drugs, 1,3,5,6-substituted-2-pyridone compounds each in which 4,4-dimethylpentanoic acid is introduced at the 1-position are disclosed (for example, see Patent Literature 3).

CITATION LIST

Patent Literature

Patent Literature 1: WO 98/55480
Patent Literature 2: EP 0308020A
Patent Literature 3: WO 2016/12913

SUMMARY OF INVENTION

Problems to be Solved by Invention

However, the uses of the compounds disclosed in Patent Literature 1, Patent Literature 2 and Patent Literature 3 are each medicine and differ from the technical field to which the agricultural and horticultural fungicide according to the present invention belongs.

An object of the present invention is to provide a novel pyridone compound effective as an agricultural and horticultural fungicide.

Means to Solve the Problems

In order to solve the problems above, the present inventors have extensively studied a 1,3,5,6-substituted-2-pyridone compound group and a 1,5,6-substituted-2-pyridone compound group. As a result, it has been found that a group of novel compounds each in which a substituent containing a nitrogen atom is introduced at the 5-position in the 2-pyridone skeleton exhibit an excellent activity in the control of plant diseases, thus completing the present invention.

That is, the present invention resides in the following aspects.

[1] A compound represented by Formula (1):

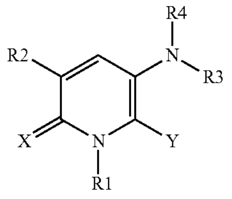

(1)

[wherein
R1 represents
- a hydroxyl group,
- a cyano group,
- a C1-C6 alkyl group optionally substituted with substituent A,
- a C1-C6 haloalkyl group,
- a C3-C8 cycloalkyl group optionally substituted with substituent A,
- a C2-C6 alkenyl group optionally substituted with substituent A,
- a C2-C6 haloalkenyl group,
- a C2-C6 alkynyl group optionally substituted with substituent A,
- a C2-C6 haloalkynyl group,
- a C1-C6 alkoxy group optionally substituted with substituent A,
- a C1-C6 haloalkoxy group,
- a C3-C8 cycloalkoxy group optionally substituted with substituent A,
- a C2-C6 alkenyloxy group optionally substituted with substituent A,
- a C2-C6 haloalkenyloxy group,
- a C3-C6 alkynyloxy group optionally substituted with substituent A,
- a C3-C6 haloalkynyloxy group, or
- an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group);

R2 represents
- a hydrogen atom,
- a cyano group,
- a nitro group,
- a halogen atom,
- a C1-C6 alkyl group optionally substituted with substituent A,
- a C1-C6 haloalkyl group,
- a C3-C8 cycloalkyl group optionally substituted with substituent A,
- a C2-C6 alkenyl group optionally substituted with substituent A,
- a C2-C6 haloalkenyl group,
- a C2-C6 alkynyl group optionally substituted with substituent A,
- a C2-C6 haloalkynyl group,
- a C1-C6 alkoxy group optionally substituted with substituent A,
- a C1-C6 haloalkoxy group,
- a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, an Rc-L- (wherein Rc represents a C1-C6 alkyl group or a C1-C6 haloalkyl group, and L represents S, SO or $SO_2$), an RaRbN— (wherein Ra and Rb are the same as defined above), or an RdC(=O)— (wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)), R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), a C1-C6 haloalkyl group having a phenyl group optionally substituted with 0 to 5 substituent D (with the proviso that when there are two or more substituents D, they are independent to each other), an Rc-L- (wherein Rc and L are the same as defined above), or an ReC(=O)— (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are the same as defined above)), or R3 and R4 in combination with the nitrogen atom to which they are bonded form an aziridinyl group optionally substituted with substituent E, an azetidinyl group optionally substituted with substituent E, a pyrrolidinyl group optionally substituted with substituent E, a piperidinyl group optionally substituted with substituent E, a homopiperidinyl group optionally substituted with substituent E, an azocanyl group optionally substituted with substituent E, a morpholinyl group optionally substituted with substituent E or a C1-C6 alkylidene group optionally substituted with substituent F;

X represents an oxygen atom or a sulfur atom;

Y represents a phenyl group optionally substituted with 0 to 5 R5 (with the proviso that when there are two or more R5, they are independent to each other), a pyridyl group optionally substituted with 0 to 4 R5 (with the proviso that when there are two or more R5, they are independent to each other), a pyridazinyl group optionally substituted with 0 to 3 R5 (with the proviso that when there are two or more R5, they are independent to each other), a pyrimidinyl group optionally substituted with 0 to 3 R5 (with the proviso that when there are two or more R5, they are independent to each other), a pyradinyl group optionally substituted with 0 to 3 R5 (with the proviso that when there are two or more R5, they are independent to each other), a triazinyl group optionally substituted with 0 to 2 R5 (with the proviso that when there are two R5, they are independent to each other), a tetrazinyl group optionally substituted with R5, a thienyl group optionally substituted with 0 to 3 R5 (with the proviso that when there are two or more R5, they are independent to each other), a thiazolyl group optionally substituted with 0 to 2 R5 (with the proviso that when there are two R5, they are independent to each other), an isothiazolyl group optionally substituted with 0 to 2 R5 (with the proviso that when there are two R5, they are independent to each other), or a thiadiazolyl group optionally substituted with R5, R5 represents a hydroxyl group, a cyano group, a nitro group, a halogen atom, a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G, a C2-C6 haloalkenyl group, a C2-C6 alkynyl group optionally substituted with substituent G, a C2-C6 haloalkynyl group, a C1-C6 alkoxy group optionally substituted with substituent G, a C1-C6 haloalkoxy group, a C3-C8 cycloalkoxy group optionally substituted with substituent G, a C2-C6 alkenyloxy group optionally substituted with substituent G, a C2-C6 haloalkenyloxy group, a C3-C6 alkynyloxy group optionally substituted with substituent G, a C3-C6 haloalkynyloxy group, an RdC(═O)— (wherein Rd is the same as defined above), an RdC(═O)O— (wherein Rd is the same as defined above), an Rc-L- (wherein Rc and L are the same as defined above), or an RaRbN— (wherein Ra and Rb are the same as defined above); and the substituent A is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— (wherein Ra and Rb are the same as defined above) and an Rc-L- (wherein Rc and L are the same as defined above);

the substituent B is at least one member selected from the group consisting of a cyano group, a C1-C6 alkoxy group, a C1-C6 haloalkoxy group and a C3-C8 cycloalkoxy group;

the substituent C is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group and an Rc-L- (wherein Rc and L are the same as defined above);

the substituent D is at least one member selected from the group consisting of a hydroxyl group, a cyano group, a nitro group, a halogen atom, a C1-C6 alkyl group optionally substituted with substituent B, a C1-C6 haloalkyl group, a C3-C8 cycloalkyl group, a C1-C6 alkoxy group, a C1-C6 haloalkoxy group and a C3-C8 cycloalkoxy group;

the substituent E is at least one member selected from the group consisting of an oxo group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group;

the substituent F is at least one member selected from the group consisting of a C1-C6 alkoxy group, an RaRbN— (wherein Ra and Rb are the same as defined above) and an RdC(═O)— (wherein Rd is the same as defined above); and the substituent G is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an RaRbN— (wherein Ra and Rb are the same as defined above), an Rc-L- (wherein Rc and L are the same as defined above), an RdC(═O)— (wherein Rd is the same as defined above), an RdC(═O)O— (wherein Rd is the same as defined above) and a group of a 3-6 membered ring containing 1-2 oxygen atoms] or a salt thereof.

[2] The compound of [1], wherein R1 represents a C1-C6 alkyl group optionally substituted with substituent A, a C1-C6 haloalkyl group, a C2-C6 alkenyl group optionally substituted with substituent A, a C2-C6 haloalkenyl group, a C2-C6 alkynyl group optionally substituted with substituent A, or a C2-C6 haloalkynyl group;

R2 represents a hydrogen atom, a cyano group, a halogen atom, a C1-C6 alkyl group optionally substituted with substituent A, a C1-C6 haloalkyl group, a C2-C6 alkynyl group optionally substituted with substituent A, a C2-C6 haloalkynyl group, a C1-C6 alkoxy group optionally substituted with substituent A, a C1-C6 haloalkoxy group, an Rc-L- (wherein Rc represents a C1-C6 alkyl group or a C1-C6 haloalkyl group, and L represents S, SO or $SO_2$), or an RdC(═O)— (wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group));

R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), an Rc-L- (wherein Rc and L are the same as defined above), or an ReC(═O)— (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are the same as defined above)), or R3 and R4 in combination with the nitrogen atom to which they are bonded form a pyrrolidinyl group optionally substituted with substituent E, a piperidinyl group optionally substituted with substituent E, a morpholinyl group optionally substituted with substituent E, or a C1-C6 alkylidene group optionally substituted with substituent F;

Y represents a phenyl group optionally substituted with 0 to 5 R5 (with the proviso that when there are two or more R5, they are independent to each other), or a pyridyl group optionally substituted with 0 to 4 R5 (with the proviso that when there are two or more R5, they are independent to each other), R5 represents a hydroxyl group, a cyano group, a halogen atom, a C1-C6 alkyl group optionally substituted with substituent G, a C1-C6 alkoxy group optionally substituted with substituent G, a C1-C6 haloalkoxy group, a C2-C6 alkenyloxy group optionally substituted with substituent G, a C2-C6 haloalkenyloxy group, a C3-C6 alkynyloxy group optionally substituted with substituent G, a C3-C6 haloalkynyloxy group, or an RdC(═O)O— (wherein Rd is the same as defined above), or a salt thereof.

[3] The compound of [2], wherein R1 represents a C1-C6 alkyl group optionally substituted with substituent A, or C1-C6 haloalkyl group;

R2 represents a hydrogen atom, a cyano group, a halogen atom, a C1-C6 alkyl group optionally substituted with substituent A, a C2-C6 alkynyl group optionally substituted with substituent A, or a C1-C6 alkoxy group optionally substituted with substituent A;

R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 alkynyl group optionally substituted with substituent C, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other)

an Rc-L- (wherein Rc represents a C1-C6 alkyl group or a C1-C6 haloalkyl group, and L represents S, SO or $SO_2$), or an ReC(═O)— (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)), or R3 and R4 in combination with the nitrogen atom to which they are bonded form a pyrrolidinyl group optionally substituted with substituent E, a piperidinyl group optionally substituted with substituent E, a morpholinyl group optionally substituted with substituent E, or a C1-C6 alkylidene group optionally substituted with substituent F;

Y represents a phenyl group optionally substituted with 0 to 5 R5 (with the proviso that when there are two or more R5, they are independent to each other), R5 represents a hydroxyl group, a cyano group, a halogen atom, a C1-C6 alkyl group optionally substituted with substituent G, a C1-C6 alkoxy group optionally substituted with substituent G, a C2-C6 alkenyloxy group optionally substituted with substituent G, or a C3-C6 alkynyloxy group optionally substituted with substituent G, or a salt thereof.

[4] A compound represented by Formula (2)

(2)

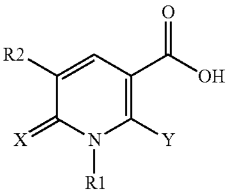

[wherein

R1 represents a hydroxyl group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group);

R2 represents a hydrogen atom, a cyano group, a nitro group, a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, an Rc-L- (wherein Rc represents a C1-C6 alkyl group or a C1-C6 haloalkyl group, and L represents S, SO or $SO_2$), an RaRbN— (wherein Ra and Rb are the same as defined above), or an RdC(═O)— (wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above));

X represents an oxygen atom or a sulfur atom;

Y represents a phenyl group optionally substituted with 0 to 5 R5 (with the proviso that when there are two or more R5, they are independent to each other), a pyridyl group optionally substituted with 0 to 4 R5 (with the proviso that when there are two or more R5, they are independent to each other), a pyridazinyl group optionally substituted with 0 to 3 R5 (with the proviso that when there are two or more R5, they are independent to each other), a pyrimidinyl group optionally substituted with 0 to 3 R5 (with the proviso that when there are two or more R5, they are independent to each other), a pyradinyl group optionally substituted with 0 to 3 R5 (with the proviso that when there are two or more R5, they are independent to each other), a triazinyl group optionally substituted with 0 to 2 R5 (with the proviso that when there are two R5, they are independent to each other), a tetrazinyl group optionally substituted with R5, a thienyl group optionally substituted with 0 to 3 R5 (with the proviso that when there are two or more R5, they are independent to each other), a thiazolyl group optionally substituted with 0 to 2 R5 (with the proviso that when there are two R5, they are independent to each other), an isothiazolyl group optionally substituted with 0 to 2 R5 (with the proviso that when there are two R5, they are independent to each other), or a thiadiazolyl group optionally substituted with R5, R5 represents a hydroxyl group, a cyano group, a nitro group, a halogen atom, a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G, a C2-C6 haloalkenyl group, a C2-C6 alkynyl group optionally substituted with substituent G, a C2-C6 haloalkynyl group, a C1-C6 alkoxy group optionally substituted with substituent G, a C1-C6 haloalkoxy group, a C3-C8 cycloalkoxy group optionally substituted with substituent G, a C2-C6 alkenyloxy group optionally substituted with substituent G, a C2-C6 haloalkenyloxy group, a C3-C6 alkynyloxy group optionally substituted with substituent G, a C3-C6 haloalkynyloxy group, an RdC(═O)— (wherein Rd is the same as defined above), an RdC(═O)O— (wherein Rd is the same as defined above), an Rc-L- (wherein Rc and L are the same as defined above), or an RaRbN— (wherein Ra and Rb are the same as defined above)]

or a salt thereof.

[5] The compound of any one of [1] to [3], wherein R1 represents a C1-C6 alkyl group or a C1-C6 haloalkyl group, or a salt thereof.

[6] The compound of any one of [1] to [3], wherein R1 represents a methyl group, an ethyl group, a propyl group, an isopropyl group, a butyl group, an isobutyl group, a hexyl group, a 2-fluoroethyl group, a 2,2-difluoroethyl group or a 2,2,2-trifluoroethyl group, or a salt thereof.

[7] The compound of any one of [1] to [3], wherein R1 represents a methyl group, an ethyl group, a propyl group, a butyl group, a hexyl group or a 2,2-difluoroethyl group, or a salt thereof.

[8] The compound of any one of [1] to [3] and [5] to [7], wherein R2 represents a cyano group, a halogen atom or a C2-C6 alkynyl group optionally substituted with substituent A, or a salt thereof.

[9] The compound of any one of [1] to [3] and [5] to [7], wherein R2 represents a hydrogen atom, a cyano group, a fluorine atom, a chlorine atom, a bromine atom, an iodine atom, a methyl group, an ethyl group, an ethynyl group, a 1-propynyl group, a propargyl group, a methoxy group, an ethoxy group, a propyloxy group or an isopropyloxy group, or a salt thereof.

[10] The compound of any one of [1] to [3] and [5] to [7], wherein R2 represents a cyano group, a chlorine atom, a bromine atom or an ethynyl group, or a salt thereof.

[11] The compound of any one of [1] to [3] and [5] to [10], wherein R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 alkynyl group optionally substituted with substituent C, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), or an ReC(═O)— (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)), or R3 and R4 in combination with the nitrogen atom to which they are bonded form a pyrrolidinyl group optionally substituted with substituent E, a piperidinyl group optionally substituted with substituent E, a morpholinyl group optionally substituted with substituent E, or a C1-C6 alkylidene group optionally substituted with substituent F, or a salt thereof.

[12] The compound of any one of [1] to [3] and [5] to [10], wherein R3 and R4 are independent to each other, and each represents a hydrogen atom, a methyl group, an ethyl group, a propyl group, an isopropyl group, a butyl group, an isobutyl group, a sec-butyl group, a pentyl group, a 1,2-dimethylpropyl group, a cyanomethyl group, a 2-cyanoethyl group, a cyclopropylmethyl group, a 2-cyclopropylethyl group, a methoxymethyl group, a 2-methoxyethyl group, an ethoxymethyl group, a 2-ethoxyethyl group, a difluoromethyl group, a trifluoromethyl group, a 2,2-difluoroethyl group, a 2,2,2-trifluoroethyl group, a cyclopropyl group, a cyclopentyl group, a cyclohexyl group, a vinyl group, a 1-propenyl group, an allyl group, an ethynyl group, a 1-propynyl group, a propargyl group, a 2-butynyl group, a phenyl group, a 2-fluorophenyl group, a 2-chlorophenyl group, a 2-bromophenyl group, a 2-methylphenyl group, a 2-methoxyphenyl group, a 3-fluorophenyl group, a 3-chlorophenyl group, a 3-bromophenyl group, a 3-methylphenyl group, a 3-methoxyphenyl group, a 4-chlorophenyl group, a 4-bromophenyl group, a 4-methylphenyl group, a 4-methoxyphenyl group, a 2,3-difluorophenyl group, a 2,4-difluorophenyl group, a 2,5-difluorophenyl group, a 2-chloro-3-fluorophenyl group, a 2-chloro-4-fluorophenyl group, a 2-chloro-5-fluorophenyl group, a 2-bromo-3-fluorophenyl group, a 2-bromo-4-fluorophenyl group, a 2-bromo-5-fluorophenyl group, a 2-fluoro-3-methoxyphenyl group, a 2-fluoro-4-methoxyphenyl group, a 2-fluoro-5-methoxyphenyl group, a 2-chloro-3-methoxyphenyl group, a 2-chloro-4-methoxyphenyl group, a 2-chloro-5-methoxyphenyl group, a 2-bromo-3-methoxyphenyl group, a 2-bromo-4-methoxyphenyl group, a 2-bromo-5-methoxyphenyl group, a 2,3,5-trifluorophenyl group, a 2,3,6-trifluorophenyl group, a 2-chloro-3,5-difluorophenyl group, a 2-bromo-3,5-difluorophenyl group, a 2-fluoro-3,5-dimethoxyphenyl group, a 2-chloro-3,5-dimethoxyphenyl group, a 2-bromo-3,5-dimethoxyphenyl group, a phenylmethyl group, a 2-phenylethyl group, a 1-phenylethyl group, a 1-phenylpropyl group, a methylthio group, a methanesulfinyl group, a methanesulfonyl group, an ethylthio group, an ethanesulfinyl group, an ethanesulfonyl group, an acetyl group, a methoxyacetyl group, a cyanoacetyl group, a difluoroacetyl group, a trifluoroacetyl group, a methoxycarbonyl group, an ethoxycarbonyl group, a propyloxycarbonyl group, an isopropyloxycarbonyl group, a butyloxycarbonyl group, an isobutyloxycarbonyl group or a t-butyloxycarbonyl group, or R3 and R4 in combination with the nitrogen atom to which they are bonded represent a pyrrolidinyl group, a 2-oxopyrrolidinyl group, a 2-methyl-pyrrolidinyl group, a 2-methoxy-pyrrolidinyl group, a piperidinyl group, a 2-oxopiperidinyl group, a 4-oxopiperidinyl group, a 4-methyl-piperidinyl group, a 4-methoxy-piperidinyl group, a morpholinyl group, a 3-methyl-morpholinyl group, a 3-methoxy-morpholinyl group, a 3-oxomorpholinyl group, a dimethylformimidamide group, an ethylmethylformimidamide group, a diethylformimidamide group, a 1-(pyrrolidin-1-yl)methaneimino group, a methyl iminoacetate group, or an ethyl iminoacetate group, or a salt thereof.

[13] The compound of any one of [1] to [3] and [5] to [10], wherein R3 and R4 are independent to each other, and each represents a hydrogen atom, a methyl group, an ethyl group, a propyl group, an isopropyl group, a butyl group, an isobutyl group, a sec-butyl group, a 1,2-dimethylpropyl group, a cyanomethyl group, a cyclopropylmethyl group, a 2,2-difluoroethyl group, a 2,2,2-trifluoroethyl group, a cyclopentyl group, a cyclohexyl group, an allyl group, a propargyl group, a 2-butynyl group, a phenyl group, a 2-methylphenyl group, a 3-chlorophenyl group, a 3-methoxyphenyl group, a 4-fluorophenyl group, a 4-chlorophenyl group, a 4-methylphenyl group, a 4-methoxyphenyl group, a 2-chloro-4-fluorophenyl group, a phenylmethyl group, an acetyl group, a methoxycarbonyl group or a t-butyloxycarbonyl group, or R3 and R4 in combination with the nitrogen atom to which they are bonded represent a pyrrolidinyl group, a 2-oxopyrrolidinyl group, a piperidinyl group, a 2-oxopiperidinyl group, a 4-methyl-piperidinyl group, a morpholinyl group, a dimethylformimidamide group, an ethylmethylformimidamide group, a 1-(pyrrolidin-1-yl)methaneimino group or an ethyl iminoacetate group, or a salt thereof.

[14] The compound of any one of [1] to [3] and [5] to [13], wherein Y represents a partial structure of Formula (a-1), Formula (a-2), Formula (a-3), Formula (a-4), Formula (a-5), Formula (a-6), Formula (a-7), Formula (a-8), Formula (a-9), Formula (a-10), Formula (a-11) or Formula (a-12)

(a-1)

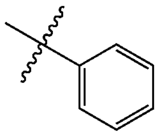

(a-2)

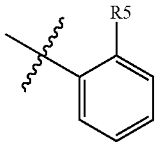

(a-3)

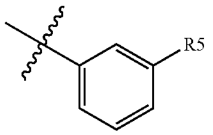

(a-4)

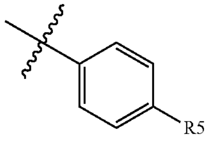

(a-5)

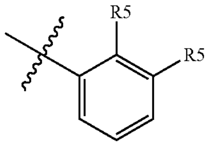

(a-6)

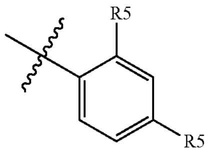

(a-7)

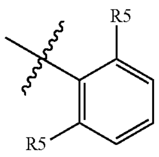

-continued (a-8)

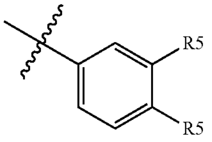

(a-9)

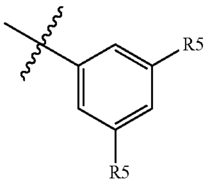

(a-10)

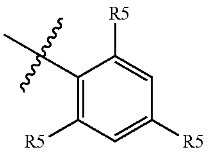

(a-11)

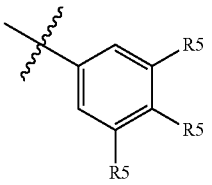

(a-12)

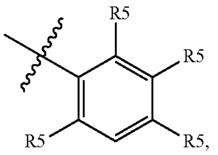

or a salt thereof.

[15] The compound of any one of [1] to [3] and [5] to [13], wherein Y represents a partial structure of Formula (a-1), Formula (a-2), Formula (a-4), Formula (a-6), Formula (a-7), Formula (a-8), Formula (a-9) or Formula (a-10)

(a-1)

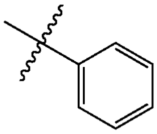

(a-2)

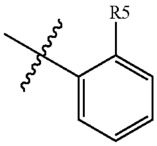

(a-4)

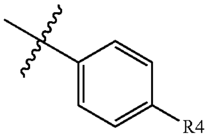

-continued (a-6)

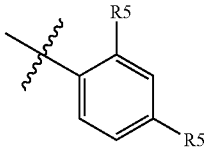

(a-7)

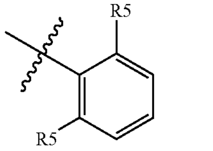

(a-8)

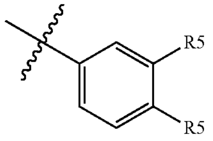

(a-9)

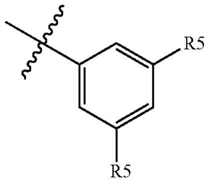

(a-10)

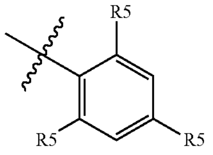

or a salt thereof.

[16] The compound of any one of [1] to [3] and [5] to [15], wherein R5 represents a cyano group, a halogen atom, a C1-C6 alkyl group optionally substituted with substituent G, a C1-C6 alkoxy group optionally substituted with substituent G or a C3-C6 alkynyloxy group optionally substituted with substituent G, or a salt thereof.

[17] The compound of any one of [1] to [3] and [5] to [15], wherein R5 represents a hydroxyl group, a cyano group, a fluorine atom, a chlorine atom, a bromine atom, an iodine atom, a methyl group, an ethyl group, a propyl group, an isopropyl group, a methoxy group, an ethoxy group, a propyloxy group, an isopropyloxy group, a butoxy group, a cyanomethoxy group, a methoxymethoxy group, an methoxyethoxy group, a vinyloxy group, a 1-propenyloxy group, an allyloxy group, a propargyloxy group, a 2-butynyloxy group or a 3-butynyloxy group, or a salt thereof.

[18] The compound of any one of [1] to [3] and [5] to [15], wherein R5 represents a cyano group, a fluorine atom, a chlorine atom, a bromine atom, a methyl group, a methoxy group, an methoxyethoxy group or a propargyloxy group, or a salt thereof.

[19] The compound of any one of [1] to [3] and [5] to [13], wherein Y represents a 2,6-difluorophenyl group, a 4-fluorophenyl group, a 2,4,6-trifluorophenyl group, a 2,6-difluoro-4-methoxyphenyl group, a 2-chloro-4-fluorophenyl group, a 2-chloro-4-methoxyphenyl group, a 4-cyanophenyl group, a 2,4-difluoro-6-methoxyphenyl group, a 4-bromophenyl group, a 4-methoxyphenyl group, a 3,4-difluorophenyl group, a 3,5-difluorophenyl group, a phenyl group, a 2-chlorophenyl group, a 2,6-difluoro-4-(prop-2-yn-1-yloxy)phenyl group, a 2,6-difluoro-4-(2-methoxyethoxy)phenyl group, a 2,4-difluorophenyl group, a 2-bromo-4-fluorophenyl group, a 2-chloro-6-fluorophenyl group, a 2-fluorophenyl group, a 4-fluoro-2-methylphenyl group or a 2-bromophenyl group, or a salt thereof.

[20] The compound of any one of [1] to [3] and [5] to [19], wherein X represents an oxygen atom, or a salt thereof.

[21] The compound of any one of [1] to [3] and [5] to [19], wherein X represents a sulfur atom, or a salt thereof.

[22] An agricultural and horticultural pest control agent comprising the compound of any one of [1] to [3] and [5] to [21] or a salt thereof as an active ingredient.

[23] An agricultural and horticultural fungicide comprising the compound of any one of [1] to [3] and [5] to [21] or a salt thereof as an active ingredient.

[24] A method for controlling plant diseases, which comprises applying the agricultural and horticultural pest control agent of [22] to a plant, a plant seed or a soil for growing a plant.

[25] A method for controlling plant diseases, which comprises applying the agricultural and horticultural fungicide of [23] to a plant, a seed of a plant or a soil for growing a plant.

[26] Use of the compound of any one of [1] to [3] and [5] to [21] as an agricultural and horticultural pest control agent

[27] Use of the compound of any one of [1] to [3] and [5] to [21] as an agricultural and horticultural fungicide.

Effects of Invention

According to the present invention, a novel compound effective as an agricultural and horticultural fungicide can be provided.

DESCRIPTION OF EMBODIMENTS

Hereinbelow, embodiments for carrying out the present invention will be explained in detail.

The terminologies used in the claims and the specification are understood in accordance with the definitions which are usually used in the art unless otherwise specified.

The abbreviations used in the present specification are explained below.

DMF: N,N-dimethylformamide, THF: tetrahydrofuran, Me: methyl group, Et: ethyl group, Pr: propyl group, Bu: butyl group, Pent: pentyl group, Hex: hexyl group, Ac: acetyl group, Ph: phenyl group, c: cyclo, is iso, sec: secondary, t: tertiary, =: double bond and ≡: triple bond. Each of Pr, Bu, Pent and Hex in columns of tables with no prefix means that the group is in a normal form.

The definitions of the terminologies used in the present specification will be explained below.

The description Cx-Cy indicates that it has carbon atoms from the number of x to y. Here, x and y each represents an integer and it is to be understood that all the integers between x and y are each independently disclosed. For example, C1-C6 means that 1, 2, 3, 4, 5 or 6 carbon atom(s) is/are present, C2-C6 means that 2, 3, 4, 5 or 6 carbon atoms are present, C3-C8 means that 3, 4, 5, 6, 7 or 8 carbon atoms are present, C3-C6 means that 3, 4, 5 or 6 carbon atoms are present and C1-C3 means that 1, 2 or 3 carbon atoms are present, respectively.

The term "optionally substituted" mean that it may be substituted or unsubstituted. Use of this term with no explicitly indicated number of substituent indicates that the number of the substituent is 1. On the other hand, for example, when the number of the substituent(s) is specified as "optionally substituted with 0 to 5", it is to be understood that all the integers between 0 and 5 are independently disclosed. That is, it is meant that the number of the substituent is none, 1, 2, 3, 4 or 5. Similarly, by "optionally substituted with 0 to 4", it is meant that the number of the substituent is none, 1, 2, 3 or 4, by "optionally substituted with 0 to 3", it is meant that the number of the substituent is none, 1, 2 or 3 and by"optionally substituted with 0 to 2", it is meant that the number of the substituent is none, 1 or 2, respectively.

The description "compound of the present invention" refers to a compound represented by Formula (1), unless otherwise specified.

A C1-C6 alkyl group may be linear or branched and examples thereof include a methyl group, an ethyl group, a propyl group, an isopropyl group, a butyl group, an isobutyl group, a sec-butyl group, a t-butyl group, a pentyl group, an isopentyl group, a 1-methylbutyl group, a 2-methylbutyl group, a neopentyl group, a 1-ethylpropyl group, a 1,2-dimethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a 1-isopropylpropyl group, a 1,1,2-trimethylpropyl group, a 1,2,2-trimethylpropyl group, and the like.

Examples of halogen atoms include a fluorine atom, a chlorine atom, a bromine atom, an iodine atom, and the like.

A C1-C6 haloalkyl group refers to the above-mentioned C1-C6 alkyl group with any hydrogen atom(s) therein substituted with 1 or 2 or more halogen atom(s). When this group is substituted with two or more halogen atoms, these halogen atoms may be the same or different, and the number of the substituents is not particularly limited as long as this group can exist as a substituent. Specific examples of the C1-C6 haloalkyl group include a monofluoromethyl group, a difluoromethyl group, a trifluoromethyl group, a monochloromethyl group, a monobromomethyl group, a monoiodomethyl group, a chlorodifluoromethyl group, a bromodifluoromethyl group, a 1-fluoroethyl group, a 2-fluoroethyl group, a 1,1-difluoroethyl group, a 2,2-difluoroethyl group, a 2,2,2-trifluoroethyl group, a 1,1,2,2-tetrafluoroethyl group, a pentafluoroethyl group, a 2,2,2-trichloroethyl group, a 3,3-difluoropropyl group, a 3,3,3-trifluoropropyl group, a heptafluoropropyl group, a heptafluoroisopropyl group, a 2,2,2-trifluoro-1-(trifluoromethyl)ethyl group, a nonafluorobutyl group, a nonafluoro-sec-butyl group, a 3,3,4,4,5,5,5-heptafluoropentyl group, an undecafluoropentyl group, a tridecafluorohexyl group, and the like.

Examples of C3-C8 cycloalkyl groups include a cyclopropyl group, a cyclobutyl group, a cyclopentyl group, a cyclohexyl group, a cycloheptyl group, a cyclooctyl group, and the like.

A C2-C6 alkenyl group refers to a linear or branched, unsaturated hydrocarbon group having 1 or 2 or more double bond(s). When a geometric isomer is present, this group may be either one of the E-isomer or the Z-isomer, or a mixture of the E-isomer and Z-isomer in any ratio, and there is no particular limitation as long as the number of carbon atoms falls within the specified range. Specific examples of the C2-C6 alkenyl group include a vinyl group, a 1-propenyl group, an allyl group, a 1-butenyl group, a 2-butenyl group, a 3-butenyl group, a 2-methyl-1-propenyl group, a 1-pentenyl group, a 2-pentenyl group, a 3-pentenyl group, a 4-pentenyl group, a 2-methyl-1-butenyl group, a 3-methyl-2-butenyl group, a 1-hexenyl group, a 2-hexenyl group, a 3-hexenyl group, a 4-hexenyl group, a 5-hexenyl group, a 4-methyl-3-pentenyl group, a 3-methyl-2-pentenyl group, and the like.

A C2-C6 haloalkenyl group refers to the above-mentioned C2-C6 alkenyl group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C2-C6 haloalkenyl group include a 2-fluorovinyl group, a 2,2-difluorovinyl group, a 2,2-dichlorovinyl group, a 3-fluoroallyl group, a 3,3-difluoroallyl group, a 3,3-dichloroallyl group, a 4,4-difluoro-3-butenyl group, a 5,5-difluoro-4-pentenyl group, a 6,6-difluoro-5-hexenyl group, and the like.

A C2-C6 alkynyl group refers to a linear or branched, unsaturated hydrocarbon group having 1 or 2 or more triple bond(s). Specific examples of the C2-C6 alkynyl group include an ethynyl group, a 1-propynyl group, a propargyl group, a 1-butynyl group, a 2-butynyl group, a 3-butynyl group, a 1-pentynyl group, a 2-pentynyl group, a 3-pentynyl group, a 4-pentynyl group, a 1,1-dimethyl-2-propynyl group, a 1-hexynyl group, a 2-hexynyl group, a 3-hexynyl group, a 4-hexynyl group, a 5-hexynyl group, and the like.

A C2-C6 haloalkynyl group refers to the above-mentioned C2-C6 alkynyl group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C2-C6 haloalkynyl group include a 2-fluoroethynyl group, a 2-chloroethynyl group, a 2-bromoethynyl group, a 2-iodoethynyl group, a 3,3-difluoro-1-propynyl group, a 3-chloro-3,3-difluoro-1-propynyl group, a 3-bromo-3,3-difluoro-1-propynyl group, a 3,3,3-trifluoro-1-propynyl group, a 4,4-difluoro-1-butynyl group, a 4,4-difluoro-2-butynyl group, a 4-chloro-4,4-difluoro-1-butynyl group, a 4-chloro-4,4-difluoro-2-butynyl group, a 4-bromo-4,4-difluoro-1-butynyl group, a 4-bromo-4,4-difluoro-2-butynyl group, a 4,4,4-trifluoro-1-butynyl group, a 4,4,4-trifluoro-2-butynyl group, a 5,5-difluoro-3-pentynyl group, a 5-chloro-5,5-difluoro-3-pentynyl group, a 5-bromo-5,5-difluoro-3-pentynyl group, a 5,5,5-trifluoro-3-pentynyl group, a 6,6-difluoro-4-hexynyl group, a 6-chloro-6,6-difluoro-4-hexynyl group, a 6-bromo-6,6-difluoro-4-hexynyl group, a 6,6,6-trifluoro-4-hexynyl group, and the like.

A C1-C6 alkoxy group refers to the above-mentioned C1-C6 alkyl group being bonded through an oxygen atom. Specific examples of the C1-C6 alkoxy group include a methoxy group, an ethoxy group, a propyloxy group, an isopropyloxy group, a butoxy group, an isobutoxy group, a sec-butoxy group, a t-butoxy group, a pentyloxy group, an isopentyloxy group, a 2-methylbutoxy group, a neopentyloxy group, a 1-ethylpropyloxy group, a hexyloxy group, a 1-methylpentyloxy group, a 2-methylpentyloxy group, a 3-methylpentyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 2-ethylbutoxy group, and the like.

A C1-C6 haloalkoxy group refers to the above-mentioned C1-C6 alkoxy group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C1-C6 haloalkoxy group include a difluoromethoxy group, a trifluoromethoxy group, a chlorodifluoromethoxy group, a bromodifluoromethoxy group, a 2-fluoroethoxy group, a 2,2-difluoroethoxy group, a 2,2,2-trifluoroethoxy group, a 1,1,2,2-tetrafluoroethoxy group, a pentafluoroethoxy group, a 2,2,2-trichloroethoxy group, a 3,3-difluoropropyloxy group, a 3,3,3-trifluoropropyloxy group, a heptafluoropropyloxy group, a heptafluoroan isopropyloxy group, 2,2,2-trifluoro-1-(trifluoromethyl)-ethoxy group, a nonafluorobutoxy group, a nonafluoro-sec-butoxy group, a 3,3,4,4,5,5,5-heptafluoropentyloxy group, a undecafluoropentyloxy group, a tridecafluorohexyloxy group, and the like.

A C3-C8 cycloalkoxy group refers to the above-mentioned C3-C8 cycloalkyl group being bonded through an oxygen atom. Specific examples of the C3-C8 cycloalkoxy group include a cyclopropyloxy group, a cyclobutoxy group, a cyclopentyloxy group, a cyclohexyloxy group, a cycloheptyloxy group, a cyclooctyloxy group, and the like.

A C2-C6 alkenyloxy group refers to the above-mentioned C2-C6 alkenyl group being bonded through an oxygen atom. When a geometric isomer is present, this group may be either one of the E-isomer or the Z-isomer, or a mixture of the E-isomer and Z-isomer in any ratio, and there is no particular limitation as long as the number of carbon atoms falls within the specified range. Specific examples of the C2-C6 alkenyloxy group include a vinyloxy group, a 1-propenyloxy group, an allyloxy group, a 1-butenyloxy group, a 2-butenyloxy group, a 3-butenyloxy group, a 2-methyl-1-propenyloxy group, a 1-pentenyloxy group, a 2-pentenyloxy group, a 3-pentenyloxy group, a 4-pentenyloxy group, a 2-methyl-1-butenyloxy group, a 3-methyl-2-butenyloxy group, a 1-hexenyloxy group, a 2-hexenyloxy group, a 3-hexenyloxy group, a 4-hexenyloxy group, a 5-hexenyloxy group, a 4-methyl-3-pentenyloxy group, a 3-methyl-2-pentenyloxy group, and the like.

A C2-C6 haloalkenyloxy group refers to the above-mentioned C2-C6 alkenyloxy group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C2-C6 haloalkenyloxy group include a 2-fluorovinyloxy group, a 2,2-difluorovinyloxy group, a 2,2-dichlorovinyloxy group, a 3-fluoroallyloxy group, a 3,3-difluoroallyloxy group, a 3,3-dichloroallyloxy group, a 4,4-difluoro-3-butenyloxy group, a 5,5-difluoro-4-pentenyloxy group, a 6,6-difluoro-5-hexenyloxy group, and the like.

A C3-C6 alkynyloxy group refers to a C3-C6 alkynyl group among the above-mentioned C2-C6 alkynyl group being bonded through an oxygen atom. Specific examples of the C3-C6 alkynyloxy group include a propargyloxy group, a 2-butynyloxy group, a 3-butynyloxy group, a 2-pentynyloxy group, a 3-pentynyloxy group, a 4-pentynyloxy group, a 1,1-dimethyl-2-propynyloxy group, a 2-hexynyloxy group, a 3-hexynyloxy group, a 4-hexynyloxy group, a 5-hexynyloxy group, and the like.

A C3-C6 haloalkynyloxy group refers to the above-mentioned C3-C6 alkynyloxy group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C3-C6 haloalkynyloxy group include a 1,1-difluoro-2-propynyloxy group, a 4,4-difluoro-2-butynyloxy group, a 4-chloro-4,4-difluoro-2-butynyloxy group, a 4-bromo-4,4-difluoro-2-butynyloxy group, a 4,4,4-trifluoro-2-butynyloxy group, a 5,5-difluoro-3-pentynyloxy group, a 5-chloro-5,5-difluoro-3-pentynyloxy group, a 5-bromo-5,5-difluoro-3-pentynyloxy group, a 5,5,5-trifluoro-3-pentynyloxy group, a 6,6-difluoro-4-hexynyloxy group, a 6-chloro-6,6-difluoro-4-hexynyloxy group, a 6-bromo-6,6-difluoro-4-hexynyloxy group, a 6,6,6-trifluoro-4-hexynyloxy group, and the like.

A C1-C6 alkylidene group may have a linear or branched structure, and examples of this group include a methylidene group, an ethylidene group, a 1-methylethylidene group, a propylidene group, a 1-methylpropylidene group, a butylidene group, 1-methylbutylidene group, a pentylidene group, 1-methylpentylidene group, a hexylidene group, and the like.

A C2-C6 alkoxyalkoxy group refers to a C1-C5 alkoxy group among the above-mentioned C1-C6 alkoxy group with any hydrogen atom(s) therein substituted with 1 or 2 or more C1-C5 alkoxy group(s). There is no particular limitation as long as the total number of carbon atoms falls within the specified range. Specific examples of the C2-C6 alkoxyalkoxy group include a methoxymethoxy group, an ethoxymethoxy group, a propyloxymethoxy group, an isopropyloxymethoxy group, a methoxyethoxy group, an ethoxyethoxy group, a propyloxyethoxy group, an isopropyloxyethoxy group, a methoxypropyloxy group, an ethoxypropyloxy group, a propyloxypropyloxy group, an isopropyloxypropyloxy group, and the like.

Specific examples of the group of a 3-6 membered ring containing 1-2 oxygen atoms include a 1,2-epoxyethanyl group, an oxetanyl group, an oxolanyl group, an oxanyl group, a 1,3-dioxolanyl group, a 1,3-dioxanyl group, a 1,4-dioxanyl group, and the like.

The pyridone compound of the present invention encompasses the compound represented by Formula (1) below and a salt thereof.

(1)

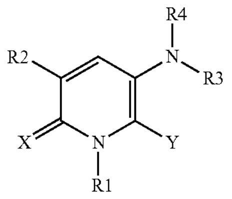

In addition, the compound represented by Formula (1) includes its N-oxide form represented by Formula (1a).

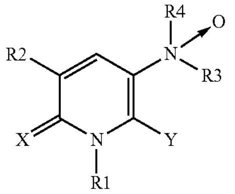

(1a)

In the following, Formula (1) will be explained.

R1 in Formula (1) represents a hydroxyl group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group).

Among them, R1 is preferably a C1-C6 alkyl group optionally substituted with substituent A, a C1-C6 haloalkyl group, a C2-C6 alkenyl group optionally substituted with substituent A, a C2-C6 haloalkenyl group, a C2-C6 alkynyl group optionally substituted with substituent A or a C2-C6 haloalkynyl group, particularly preferably a C1-C6 alkyl group optionally substituted with substituent A or a C1-C6 haloalkyl group, and further preferably a C1-C6 alkyl group or a C1-C6 haloalkyl group.

In R1 of Formula (1), a hydroxyl group and a cyano group are included.

The C1-C6 alkyl group for the "C1-C6 alkyl group optionally substituted with substituent A" as R1 of Formula (1) is the same as defined above, and preferably a methyl group, an ethyl group, a propyl group, an isopropyl group, a butyl group, an isobutyl group or a hexyl group, more preferably a methyl group, an ethyl group, a propyl group, a butyl group or a hexyl group. When substituent A is present, any hydrogen atom in the C1-C6 alkyl group is substituted with substituent A.

The "C1-C6 haloalkyl group" as R1 of Formula (1) is the same as defined above, and preferably a 2-fluoroethyl group, a 2,2-difluoroethyl group, a 2,2,2-trifluoroethyl group, a 3,3-difluoropropyl group or a 3,3,3-trifluoropropyl group, more preferably a 2-fluoroethyl group, a 2,2-difluoroethyl group or a 2,2,2-trifluoroethyl group, especially preferably a 2,2-difluoroethyl group.

The C3-C8 cycloalkyl group for the "C3-C8 cycloalkyl group optionally substituted with substituent A" as R1 of Formula (1) is the same as defined above, and preferably a cyclopropyl group, a cyclobutyl group, a cyclopentyl group or a cyclohexyl group, more preferably a cyclopropyl group or a cyclobutyl group. When substituent A is present, any hydrogen atom in the C3-C8 cycloalkyl group is substituted with substituent A.

The C2-C6 alkenyl group for the "C2-C6 alkenyl group optionally substituted with substituent A" as R1 of Formula (1) is the same as defined above, and preferably a vinyl group, a 1-propenyl group or an allyl group, more preferably a vinyl group or an allyl group. When substituent A is present, any hydrogen atom in the C2-C6 alkenyl group is substituted with substituent A.

The "C2-C6 haloalkenyl group" as R1 of Formula (1) is the same as defined above, and preferably a 2-fluorovinyl group, a 2,2-difluorovinyl group, a 3-fluoroallyl group or a 3,3-difluoroallyl group, more preferably a 2-fluorovinyl group or a 2,2-difluorovinyl group.

The C2-C6 alkynyl group for the "C2-C6 alkynyl group optionally substituted with substituent A" as R1 of Formula (1) is the same as defined above, and preferably a propargyl group, a 2-butynyl group or a 3-butynyl group, more preferably a propargyl group. When substituent A is present, any hydrogen atom in the C2-C6 alkynyl group is substituted with substituent A.

The "C2-C6 haloalkynyl group" as R1 of Formula (1) is the same as defined above, and preferably a 4,4-difluoro-2-butynyl group, a 4-chloro-4,4-difluoro-2-butynyl group, a 4-bromo-4,4-difluoro-2-butynyl group or a 4,4,4-trifluoro-2-butynyl group, more preferably a 4,4-difluoro-2-butynyl group or a 4,4,4-trifluoro-2-butynyl group.

The C1-C6 alkoxy group for the "C1-C6 alkoxy group optionally substituted with substituent A" as R1 of Formula (1) is the same as defined above, and preferably a methoxy group, an ethoxy group, a propyloxy group, an isopropyloxy group, a butoxy group or an isobutoxy group, more preferably a methoxy group or an ethoxy group. When substituent A is present, any hydrogen atom in the C1-C6 alkoxy group is substituted with substituent A.

The "C1-C6 haloalkoxy group" as R1 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent A" as R1 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent A is present, any hydrogen atom in the C3-C8 cycloalkoxy group is substituted with substituent A.

The C2-C6 alkenyloxy group for the "C2-C6 alkenyloxy group optionally substituted with substituent A" as R1 of Formula (1) is the same as defined above, and preferably a vinyloxy group, a 1-propenyloxy group or an allyloxy group, more preferably a vinyloxy group. When substituent A is present, any hydrogen atom in the C2-C6 alkenyloxy group is substituted with substituent A.

The "C2-C6 haloalkenyloxy group" as R1 of Formula (1) is the same as defined above, and preferably a 2-fluorovinyloxy group, a 2,2-difluorovinyloxy group, a 3-fluoroallyloxy group or a 3,3-difluoroallyloxy group, more preferably a 2-fluorovinyloxy group or a 2,2-difluorovinyloxy group.

The C3-C6 alkynyloxy group for the "C3-C6 alkynyloxy group optionally substituted with substituent A" as R1 of Formula (1) is the same as defined above, and preferably a propargyloxy group, a 2-butynyloxy group or a 3-butynyloxy group, more preferably a propargyloxy group. When substituent A is present, any hydrogen atom in the C3-C6 alkynyloxy group is substituted with substituent A.

The "C3-C6 haloalkynyloxy group" as R1 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

Each of the terms for the "RaRbN—" (wherein Ra and Rb are independent to each other, and each represent a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group) as R1 of Formula (1) is the same as defined above. With regard to the "C1-C6 alkyl group optionally substituted with substituent B", when substituent B is present, any hydrogen atom in the C1-C6 alkyl group is substituted with substituent B. The "RaRbN—" is preferably an amino group, a methylamino group, an ethylamino group, a (methoxymethyl)amino group, a (2-methoxyethyl)amino group, a (cyanomethyl) amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group and a piperidinyl group, more preferably an amino group, a dimethylamino group, an ethylmethylamino group and a diethylamino group.

R2 in Formula (1) represents a hydrogen atom, a cyano group, a nitro group, a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, an Rc-L- (wherein Rc represents a C1-C6 alkyl group or a C1-C6 haloalkyl group, and L represents S, SO or $SO_2$), an RaRbN— (wherein Ra and Rb are the same as defined above) or RdC(═O)— (wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)).

Among them, R2 is preferably a hydrogen atom, a cyano group, a halogen atom, a C1-C6 alkyl group optionally substituted with substituent A, a C1-C6 haloalkyl group, a C2-C6 alkynyl group optionally substituted with substituent A, a C2-C6 haloalkynyl group, a C1-C6 alkoxy group optionally substituted with substituent A, a C1-C6 haloalkoxy group, an Rc-L- (wherein Rc and L are the same as defined above) or an RdC(═O)— (wherein Rd is the same as defined above), particularly preferably a hydrogen atom, a cyano group, a halogen atom, a C1-C6 alkyl group optionally substituted with substituent A, a C2-C6 alkynyl group optionally substituted with substituent A or a C1-C6 alkoxy group optionally substituted with substituent A, and further preferably a cyano group, a halogen atom or a C2-C6 alkynyl group optionally substituted with substituent A.

In R2 of Formula (1), a hydrogen atom, a cyano group and a nitro group are included.

The halogen atom as R2 of Formula (1) is the same as defined above, and preferably a fluorine atom, a chlorine atom, a bromine atom or an iodine atom, more preferably a chlorine atom or a bromine atom.

The C1-C6 alkyl group for the "a C1-C6 alkyl group optionally substituted with substituent A" as R2 of Formula (1) is the same as defined above, and preferably a methyl group, an ethyl group, a propyl group, an isopropyl group, a butyl group or an isobutyl group, more preferably a methyl group or an ethyl group. When substituent A is present, any hydrogen atom in the C1-C6 alkyl group is substituted with substituent A.

The "C1-C6 haloalkyl group" as R2 of Formula (1) is the same as defined above, and preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group, a trifluoromethyl group, a 2,2-difluoroethyl group or a 2,2,2-trifluoroethyl group.

The C3-C8 cycloalkyl group for the "C3-C8 cycloalkyl group optionally substituted with substituent A" as R2 of Formula (1) is the same as defined above, and preferably a cyclopropyl group, a cyclobutyl group, a cyclopentyl group or a cyclohexyl group, more preferably a cyclopropyl group or a cyclobutyl group. When substituent A is present, any hydrogen atom in the C3-C8 cycloalkyl group is substituted with substituent A.

The C2-C6 alkenyl group for the "C2-C6 alkenyl group optionally substituted with substituent A" as R2 of Formula (1) is the same as defined above, and preferably a vinyl group, a 1-propenyl group, an allyl group, 1-butenyl group, 2-butenyl group or a 3-butenyl group, more preferably a vinyl group, a 1-propenyl group or an allyl group. When substituent A is present, any hydrogen atom in the C2-C6 alkenyl group is substituted with substituent A.

The "C2-C6 haloalkenyl group" as R2 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent A" as R2 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group, particularly preferably an ethynyl group. When substituent A is present, any hydrogen atom in the C2-C6 alkynyl group is substituted with substituent A.

The "C2-C6 haloalkynyl group" as R2 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxy group optionally substituted with substituent A" as R2 of Formula (1) is the same as defined above, and preferably a methoxy group, an ethoxy group, a propyloxy group, an isopropyloxy group, a butoxy group or an isobutoxy group, more preferably a methoxy group, an ethoxy group, a propyloxy group or an isopropyloxy group. When substituent A is present, any hydrogen atom in the C1-C6 alkoxy group is substituted with substituent A.

The "C1-C6 haloalkoxy group" as R2 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent A" as R2 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent A is present, any hydrogen atom in the C3-C8 cycloalkoxy group is substituted with substituent A.

The C2-C6 alkenyloxy group for the "C2-C6 alkenyloxy group optionally substituted with substituent A" as R2 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent A is present, any hydrogen atom in the C2-C6 alkenyloxy group is substituted with substituent A.

The "C2-C6 haloalkenyloxy group" as R2 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent A" as R2 of Formula (1) is the same as defined above, and preferably a propargyloxy group, a 2-butynyloxy group or a 3-butynyloxy group, more preferably a propargyloxy group. When substituent A is present, any hydrogen atom in the C3-C6 alkynyloxy group is substituted with substituent A.

The "C3-C6 haloalkynyloxy group" as R2 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

Each of the terms for the "Rc-L-" (wherein Rc represents a C1-C6 alkyl group or a C1-C6 haloalkyl group, and L represents S, SO or $SO_2$) as R2 of Formula (1) is the same as defined above. The "Rc-L-" is preferably a methylthio group, a methanesulfinyl group, a methanesulfonyl group, a trifluoromethylthio group, a trifluoromethanesulfinyl group or a trifluoromethanesulfonyl group, more preferably a methylthio group, a methanesulfinyl group or a methanesulfonyl group.

Ra and Rb for the "RaRbN—" as R2 of Formula (1) are the same as defined above. The "RaRbN—" is preferably an amino group, a methylamino group, an ethylamino group, a propylamino group, an isopropyl amino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl)amino group, a diethylamino group, an ethyl(propyl)amino group, an ethyl(isopropyl)amino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, more preferably a dimethylamino group, an ethyl(methyl)amino group or a diethylamino group.

Each of the terms for the "RdC(═O)—" (wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)) as R2 of Formula (1) is the same as defined above. With regard to the "C1-C6 alkyl group optionally substituted with substituent B", when substituent B is present, any hydrogen atom in the C1-C6 alkyl group is substituted with substituent B. The "RdC(═O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl(methyl)aminocarbonyl group, a pyrrolidinylcarbonyl group or a piperidinylcarbonyl group, more preferably an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethyl(methyl)aminocarbonyl group or a diethylaminocarbonyl group.

R3 and R4 in Formula (1) are independent to each other, and each represent a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), a C1-C6 haloalkyl group having a phenyl group optionally substituted with 0 to 5 substituent D (with the proviso that when there are two or more substituents D, they are independent to each other), an Rc-L- (wherein Rc and L are the same as defined above) or an ReC(═O)— (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are the same as defined above)), or R3 and R4 in combination with the nitrogen atom to which they are bonded form an aziridinyl group optionally substituted with substituent E, an azetidinyl group optionally substituted with substituent E, a pyrrolidinyl group optionally substituted with substituent E, a piperidinyl group optionally substituted with substituent E, a homopiperidinyl group optionally substituted with substituent E, an azocanyl group optionally substituted with substituent E, a morpholinyl group optionally substituted with substituent E or a C1-C6 alkylidene group optionally substituted with substituent F.

Among them, it is preferred that R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), an Rc-L- (wherein Rc and L are the same as defined above) or an ReC(═O)— (wherein Re is the same as defined above), or R3 and R4 in combination with the nitrogen atom to which they are bonded form a pyrrolidinyl group optionally substituted with substituent E, a piperidinyl group optionally substituted with substituent E, a morpholinyl group optionally substituted with substituent E or a C1-C6 alkylidene group optionally substituted with substituent F;

it is particularly preferred that R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 alkynyl group optionally substituted with substituent C, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), an Rc-L- (wherein Rc and L are the same as defined above) or an ReC(═O)— (wherein Re is the same as defined above), or R3 and R4 in combination with the nitrogen atom to which they are bonded form a pyrrolidinyl group optionally substituted with substituent E, a piperidinyl group optionally substituted with substituent E, a morpholinyl group optionally substituted with substituent E or a C1-C6 alkylidene group optionally substituted with substituent F; and it is further preferred that R3 and R4 are independent to each other, and each represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 alkynyl group optionally substituted with substituent C, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other) or an ReC(═O)— (wherein Re is the same as defined above), or R3 and R4 in combination with the nitrogen atom to which they are bonded form a pyrrolidinyl group optionally substituted with substituent E, a piperidinyl group optionally substituted with substituent E, a morpholinyl group optionally substituted with substituent E or a C1-C6 alkylidene group optionally substituted with substituent F.

In R3 of Formula (1), a hydrogen atom is included.

The C1-C6 alkyl group for the "C1-C6 alkyl group optionally substituted with substituent C" as R3 of Formula (1) is the same as defined above, and preferably a methyl group, an ethyl group, a propyl group, an isopropyl group, a butyl group, an isobutyl group, a sec-butyl group, a t-butyl group, a pentyl group, a 1,2-dimethylpropyl group or a hexyl group, more preferably a methyl group, an ethyl group, a propyl group, an isopropyl group, a butyl group, an isobutyl group, a sec-butyl group, a pentyl group or a 1,2-dimethylpropyl group, particularly preferably a methyl group, an ethyl group, a propyl group, an isopropyl group, a butyl group, an isobutyl group, a sec-butyl group or a 1,2-dimethylpropyl group. When substituent C is present, any hydrogen atom in the C1-C6 alkyl group is substituted with substituent C. The substituent C for the "C1-C6 alkyl group optionally substituted with substituent C" is preferably a cyano group, a C3-C8 cycloalkyl group, a C1-C6 alkoxy group, a C1-C6 haloalkoxy group or an Rc-L- (wherein Rc and L are the same as defined above), more preferably a cyano group, a C3-C8 cycloalkyl group, a C1-C6 alkoxy group or an Rc-L- (wherein Rc and L are the same as defined above), particularly preferably a cyano group or a C3-C8 cycloalkyl group. The "C1-C6 alkyl group substituted by the substituent C" is preferably a cyanomethyl group, a 2-cyanoethyl group, a cyclopropylmethyl group, a cyclobutylmethyl group, a 2-cyclopropylethyl group, a 2-cyclobutylethyl group, a methoxymethyl group, a 2-methoxyethyl group, an ethoxymethyl group or a 2-ethoxyethoxy group, more preferably a cyanomethyl group, a 2-cyanoethyl group, a cyclopropylmethyl group, a 2-cyclopropylethyl group, a methoxymethyl group, a 2-methoxyethyl group, an ethoxymethyl group or a 2-ethoxyethyl group, particularly preferably a cyanomethyl group or a cyclopropylmethyl group.

The "C1-C6 haloalkyl group" as R3 of Formula (1) is the same as defined above, and preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group, a trifluoromethyl group, a 2,2-difluoroethyl group or a 2,2,2-trifluoroethyl group, particularly preferably a 2,2-difluoroethyl group or a 2,2,2-trifluoroethyl group.

The C3-C8 cycloalkyl group for the "C3-C8 cycloalkyl group optionally substituted with substituent C" as R3 of Formula (1) is the same as defined above, and preferably a cyclopropyl group, a cyclobutyl group, a cyclopentyl group or a cyclohexyl group, more preferably a cyclopropyl group, a cyclopentyl group or a cyclohexyl group, particularly preferably a cyclopentyl group or a cyclohexyl group. When substituent C is present, any hydrogen atom in the C3-C8 cycloalkyl group is substituted with substituent C.

The C2-C6 alkenyl group for the "C2-C6 alkenyl group optionally substituted with substituent C" as R3 of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group, particularly preferably allyl group. When substituent C is present, any hydrogen atom in the C2-C6 alkenyl group is substituted with substituent C.

The "C2-C6 haloalkenyl group" as R3 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent C" as R3 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group, a propargyl group or a 2-butynyl group, particularly preferably a propargyl group or a 2-butynyl group. When substituent C is present, any hydrogen atom in the C2-C6 alkynyl group is substituted with substituent C.

The "C2-C6 haloalkynyl group" as R3 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxy group optionally substituted with substituent C" as R3 of Formula (1) is the same as defined above, and preferably a methoxy group, an ethoxy group, a propyloxy group, an isopropyloxy group, a butoxy group, an isobutoxy group or a pentyloxy group, more preferably a methoxy group, an ethoxy group, a propyloxy group, an isopropyloxy group or a butoxy group. When substituent C is present, any hydrogen atom in the C1-C6 alkoxy group is substituted with substituent C.

The "C1-C6 haloalkoxy group" as R3 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent C" as R3 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent C is present, any hydrogen atom in the C3-C8 cycloalkoxy group is substituted with substituent C.

The C2-C6 alkenyloxy group for the "C2-C6 alkenyloxy group optionally substituted with substituent C" as R3 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent C is present, any hydrogen atom in the C2-C6 alkenyloxy group is substituted with substituent C.

The "C2-C6 haloalkenyloxy group" as R3 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent C" as R3 of Formula (1) is the same as defined above, and preferably a propargyloxy group, a 2-butynyloxy group or a 3-butynyloxy group, more preferably a propargyloxy group. When substituent C is present, any hydrogen atom in the C3-C6 alkynyloxy group is substituted with substituent C.

The "C3-C6 haloalkynyloxy group" as R3 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

With regard to the "phenyl group optionally substituted with 0 to 5 substituent D" (with the proviso that when there are two or more substituents D, they are independent to each other) as R3 of Formula (1), when substituent D is present, any hydrogen atom in the phenyl group is substituted with substituent D. Each of the 2 to 6-positions of the phenyl group, when the position of the phenyl group substituted with the nitrogen atom which is bonded to the 5-position of the 2-pyridone compound is regarded as the 1-position, may be independently substituted with substituent D. Substituent D is preferably a cyano group, a halogen atom, a C1-C6 alkyl group optionally substituted with substituent B, a C1-C6 alkoxy group or C3-C8 cycloalkoxy group, more preferably a halogen atom, a C1-C6 alkyl group optionally substituted with substituent B or a C1-C6 alkoxy group. With regard to the "C1-C6 alkyl group optionally substituted with substituent B", when substituent B is present, any hydrogen atom in the C1-C6 alkyl group is substituted with substituent B. The "phenyl group optionally substituted with 0 to 5 substituent D" is preferably a phenyl group, a 2-fluorophenyl group, a 2-chlorophenyl group, a 2-bromophenyl group, a 2-iodophenyl group, a 2-methylphenyl group, a 2-methoxyphenyl group, a 3-fluorophenyl group, a 3-chlorophenyl group, a 3-bromophenyl group, a 3-iodophenyl group, a 3-methylphenyl group, a 3-methoxyphenyl group, a 4-chlorophenyl group, a 4-bromophenyl group, a 4-iodophenyl group, a 4-methylphenyl group, a 4-methoxyphenyl group, a 2,3-difluorophenyl group, a 2,4-difluorophenyl group, a 2,5-difluorophenyl group, a 2,6-difluorophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-fluoro-3-methoxyphenyl group, a 2-fluoro-4-methoxyphenyl group, a 2-fluoro-5-methoxyphenyl group, a 2-fluoro-6-methoxyphenyl group, a 2-chloro-3-methoxyphenyl group, a 2-chloro-4-methoxyphenyl group, a 2-chloro-5-methoxyphenyl group, a 2-chloro-6-methoxyphenyl group, a 2-bromo-3-methoxyphenyl group, a 2-bromo-4-methoxyphenyl group, a 2-bromo-5-methoxyphenyl group, a 2-bromo-6-methoxyphenyl group, a 2,3,4-trifluorophenyl group, a 2,3,5-trifluorophenyl group, a 2,3,6-trifluorophenyl group, a 2-chloro-3,4-difluorophenyl group, a 2-chloro-3,5-difluorophenyl group, a 2-chloro-3,6-difluorophenyl group, a 2-bromo-3,4-difluorophenyl group, a 2-bromo-3,5-difluorophenyl group, a 2-bromo-3,6-difluorophenyl group, a 2-fluoro-3,4-dimethoxyphenyl group, a 2-fluoro-3,5-dimethoxyphenyl group, a 2-fluoro-3,6-dimethoxyphenyl group, a 2-chloro-3,4-dimethoxyphenyl group, a 2-chloro-3,5-dimethoxyphenyl group, a 2-chloro-3,6-dimethoxyphenyl group, a 2-bromo-3,4-dimethoxyphenyl group, a 2-bromo-3,5-dimethoxyphenyl group or a 2-bromo-3,6-dimethoxyphenyl group, more preferably a phenyl group, a 2-fluorophenyl group, a 2-chlorophenyl group, a 2-bromophenyl group, a 2-methylphenyl group, a 2-methoxyphenyl group, a 3-fluorophenyl group, a 3-chlorophenyl group, a 3-bromophenyl group, a 3-methylphenyl group, a 3-methoxyphenyl group, a 4-chlorophenyl group, a 4-bromophenyl group, a 4-methylphenyl group, a 4-methoxyphenyl group, a 2,3-difluorophenyl group, a 2,4-difluorophenyl group, a 2,5-difluorophenyl group, a 2-chloro-3-fluorophenyl group, a 2-chloro-4-fluorophenyl group, a 2-chloro-5-fluorophenyl group, a 2-bromo-3-fluorophenyl group, a 2-bromo-4-fluorophenyl group, a 2-bromo-5-fluorophenyl group, a 2-fluoro-3-methoxyphenyl group, a 2-fluoro-4-methoxyphenyl group, a 2-fluoro-5-methoxyphenyl group, a 2-chloro-3-methoxyphenyl group, a 2-chloro-4-methoxyphenyl group, a 2-chloro-5-methoxyphenyl group, a 2-bromo-3-methoxyphenyl group, a 2-bromo-4-methoxyphenyl group, a 2-bromo-5-methoxyphenyl group, a 2,3,5-trifluorophenyl group, a 2,3,6-trifluorophenyl group, a 2-chloro-3,5-difluorophenyl group, a 2-bromo-3,5-difluorophenyl group, a 2-fluoro-3,5-dimethoxyphenyl group, a 2-chloro-3,5-dimethoxyphenyl group or a 2-bromo-3,5-dimethoxyphenyl group, particularly preferably a phenyl group, a 2-methylphenyl group, a 3-chlorophenyl group, a 3-methoxyphenyl group, a 4-fluorophenyl group, a 4-chlorophenyl group, a 4-methylphenyl group, a 4-methoxyphenyl group or a 2-chloro-a 4-fluorophenyl group.

Each of the "phenyl group optionally substituted with 0 to 5 substituent D" and "C1-C6 alkyl group" for the "C1-C6 alkyl group having a phenyl group optionally substituted with 0 to 5 substituent D" (with the proviso that when there are two or more substituents D, they are independent to each other) as R3 of Formula (1) is the same as defined above. The "C1-C6 alkyl group having a phenyl group" is preferably a phenylmethyl group, a 2-phenylethyl group, a 1-phenylethyl group, a 3-phenylpropyl group, a 2-phenylpropyl group, a 1-phenylpropyl group, a 4-phenylbutyl group or a 5-phenylpentyl group, more preferably a phenylmethyl group, a 2-phenylethyl group, a 1-phenylethyl group or a 1-phenylpropyl group, particularly preferably a phenylmethyl group. When substituent D is present, any hydrogen atom in the phenyl group is substituted with substituent D.

Each of the "phenyl group optionally substituted with 0 to 5 substituent D" and "C1-C6 haloalkyl group" for the "C1-C6 haloalkyl group having a phenyl group optionally substituted with 0 to 5 substituent D" (with the proviso that when there are two or more substituents D, they are independent to each other) as R3 of Formula (1) is the same as defined above. The "C1-C6 haloalkyl group having a phenyl group" is preferably a 2,2,2-trifluoro-1-phenylethyl group or a 2,2-difluoro-1-phenylethyl group, more preferably a 2,2,2-trifluoro-1-phenylethyl group. When substituent D is present, any hydrogen atom in the phenyl group is substituted with substituent D.

Each of terms for the "Rc-L-" (wherein Rc represents a C1-C6 alkyl group or a C1-C6 haloalkyl group, and L represents S, SO or $SO_2$) as R3 of Formula (1) is the same as defined above. The "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group or a trifluoromethanesulfonyl group, more preferably a methylthio group, a methanesulfinyl group, a methanesulfonyl group, an ethylthio group, an ethanesulfinyl group or an ethanesulfonyl group, particularly preferably an ethanesulfonyl group.

Each of the terms for the "ReC(═O)—" (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are the same as defined above)) as R3 of Formula (1) is the same as defined above. Re is preferably a C1-C6 alkyl group optionally substituted with substituent B, a C1-C6 haloalkyl group, a C1-C6 alkoxy group, a C1-C6 haloalkoxy group or C3-C8 cycloalkoxy group, more preferably a C1-C6 alkyl group optionally substituted with substituent B or a C1-C6 alkoxy group. The "ReC(═O)—" is preferably a formyl group, an acetyl group, a propionyl group, a 2-methylpropionyl group, a 2,2-dimethylpropionyl group, a butanoyl group, a methoxyacetyl group, a cyanoacetyl group, a difluoroacetyl group, a trifluoroacetyl group, a cyclopropanecarbonyl group, a propenoyl group, a 2-butenoyl group, a 3,3-dichloropropenoyl group, a 3,3-difluoropropenoyl group, a propynoyl group, a 2-butynoyl group, a 4,4,4-trifluoro-2-butynoyl group, a methoxycarbonyl group, an ethoxycarbonyl group, a propyloxycarbonyl group, an isopropyloxycarbonyl group, a butyloxycarbonyl group, an isobutyloxycarbonyl group, a t-butyloxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, a vinyloxycarbonyl group, an allyloxycarbonyl group, a 3,3-difluoroallyloxycarbonyl group, a propargyloxycarbonyl group, a 4,4,4-trifluoro-2-butynyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl (methyl)aminocarbonyl group, a pyrrolidinylcarbonyl group or a piperidinylcarbonyl group, more preferably an acetyl group, a methoxyacetyl group, a cyanoacetyl group, a difluoroacetyl group, a trifluoroacetyl group, a methoxycarbonyl group, an ethoxycarbonyl group, a propyloxycarbonyl group, an isopropyloxycarbonyl group, a butyloxycarbonyl group, an isobutyloxycarbonyl group or a t-butyloxycarbonyl group, and particularly preferably an acetyl group, a methoxycarbonyl group or a t-butyloxycarbonyl group.

R4 in Formula (1) is the same as defined in the aforementioned R3. That is, in R4 of Formula (1), a hydrogen atom is included.

The C1-C6 alkyl group for the "C1-C6 alkyl group optionally substituted with substituent C" as R4 of Formula (1) is the same as defined above, preferably a methyl group, an ethyl group, a propyl group, an isopropyl group, a butyl group, an isobutyl group, a sec-butyl group, a t-butyl group, a pentyl group, a 1,2-dimethylpropyl group or a hexyl group, more preferably a methyl group, an ethyl group, a propyl group, an isopropyl group, a butyl group, an isobutyl group, a sec-butyl group, a pentyl group or a 1,2-dimethylpropyl group, and particularly preferably a methyl group, an ethyl group, a propyl group, an isopropyl group, a butyl group, an isobutyl group, a sec-butyl group or a 1,2-dimethylpropyl group. When substituent C is present, any hydrogen atom in the C1-C6 alkyl group is optionally substituted with substituent C. Substituent C for the "C1-C6 alkyl group optionally substituted with substituent C" is preferably a cyano group, a C3-C8 cycloalkyl group, a C1-C6 alkoxy group, a C1-C6 haloalkoxy group or an Rc-L- (wherein Rc and L are the same as defined above), more preferably a cyano group, a C3-C8 cycloalkyl group, a C1-C6 alkoxy group or an Rc-L- (wherein Rc and L are the same as defined above), and particularly preferably a cyano group or a C3-C8 cycloalkyl group. The "C1-C6 alkyl group substituted with substituent C" is preferably a cyanomethyl group, a 2-cyanoethyl group, a cyclopropylmethyl group, a cyclobutylmethyl group, a 2-cyclopropylethyl group, a 2-cyclobutylethyl group, a methoxymethyl group, a 2-methoxyethyl group, an ethoxymethyl group or a 2-ethoxyethoxy group, more preferably a cyanomethyl group, a 2-cyanoethyl group, a cyclopropylmethyl group, a 2-cyclopropylethyl group, a methoxymethyl group, a 2-methoxyethyl group, an ethoxymethyl group or a 2-ethoxyethyl group, and particularly preferably a cyanomethyl group or a cyclopropylmethyl group.

The "C1-C6 haloalkyl group" as R4 of Formula (1) is the same as defined above, preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group, a trifluoromethyl group, a 2,2-difluoroethyl group or a 2,2,2-trifluoroethyl group, and particularly preferably a 2,2-difluoroethyl group or a 2,2,2-trifluoroethyl group.

The C3-C8 cycloalkyl group for the "C3-C8 cycloalkyl group optionally substituted with substituent C" as R4 of Formula (1) is the same as defined above, preferably a cyclopropyl group, a cyclobutyl group, a cyclopentyl group or a cyclohexyl group, more preferably a cyclopropyl group, a cyclopentyl group or a cyclohexyl group, and particularly preferably a cyclopentyl group or a cyclohexyl group. When substituent C is present, any hydrogen atom in the C3-C8 cycloalkyl group is substituted with substituent C.

The C2-C6 alkenyl group for the "C2-C6 alkenyl group optionally substituted with substituent C" as R4 of Formula (1) is the same as defined above, preferably a vinyl group, a 1-propenyl group, an allyl group, a 1-butenyl group, a 2-butenyl group or a 3-butenyl group, more preferably a vinyl group, a 1-propenyl group or an allyl group, and particularly preferably an allyl group. When substituent C is present, any hydrogen atom in the C2-C6 alkenyl group is substituted with substituent C.

The "C2-C6 haloalkenyl group" as R4 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent C" as R4 of Formula (1) is the same as defined above, preferably an ethynyl group, a 1-propynyl group, a propargyl group, a 1-butynyl group, a 2-butynyl group or a 3-butynyl group, more preferably an ethynyl group, a 1-propynyl group, a propargyl group or a 2-butynyl group, and particularly preferably a propargyl group or a 2-butynyl group. When substituent C is present, any hydrogen atom in the C2-C6 alkynyl group is substituted with substituent C.

The "C2-C6 haloalkynyl group" as R4 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxy group optionally substituted with substituent C" as R4 of Formula (1) is the same as defined above, and preferably a methoxy group, an ethoxy group, a propyloxy group, an isopropyloxy group, a butoxy group, an isobutoxy group or a pentyloxy group, more preferably a methoxy group, an ethoxy group, a propyloxy group, an isopropyloxy group or a butoxy group. When substituent C is present, any hydrogen atom in the C1-C6 alkoxy group is substituted with substituent C.

The "C1-C6 haloalkoxy group" as R4 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent C" as R4 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent C is present, any hydrogen atom in the C3-C8 cycloalkoxy group is substituted with substituent C.

The C2-C6 alkenyloxy group for the "C2-C6 alkenyloxy group optionally substituted with substituent C" as R4 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent C is present, any hydrogen atom in the C2-C6 alkenyloxy group is substituted with substituent C.

The "C2-C6 haloalkenyloxy group" as R4 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent C" as R4 of Formula (1) is the same as defined above, and preferably a propargyloxy group, a 2-butynyloxy group or a 3-butynyloxy group, more preferably a propargyloxy group. When substituent C is present, any hydrogen atom in the C3-C6 alkynyloxy group is substituted with substituent C.

The "C3-C6 haloalkynyloxy group" as R4 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

With regard to the "phenyl group optionally substituted with 0 to 5 substituent D" (with the proviso that when there are two or more substituents D, they are independent to each other) as R4 of Formula (1), when substituent D is present, any hydrogen atom in the phenyl group is substituted with substituent D. Each of the 2 to 6-positions of the phenyl group, when the position of the phenyl group substituted with the nitrogen atom which is bonded to the 5-position of the 2-pyridone compound is regarded as the 1-position, may be independently substituted with substituent D. Substituent D is preferably a cyano group, a halogen atom, a C1-C6 alkyl group optionally substituted with substituent B, a C1-C6 alkoxy group or C3-C8 cycloalkoxy group, more preferably a halogen atom, a C1-C6 alkyl group optionally substituted with substituent B or a C1-C6 alkoxy group. With regard to the "C1-C6 alkyl group optionally substituted with substituent B", when substituent B is present, any hydrogen atom in the C1-C6 alkyl group is substituted with substituent B. The "phenyl group optionally substituted with 0 to 5 substituent D" is preferably a phenyl group, a 2-fluorophenyl group, a 2-chlorophenyl group, a 2-bromophenyl group, a 2-iodophenyl group, a 2-methylphenyl group, a 2-methoxyphenyl group, a 3-fluorophenyl group, a 3-chlorophenyl group, a 3-bromophenyl group, a 3-iodophenyl group, a 3-methylphenyl group, a 3-methoxyphenyl group, a 4-chlorophenyl group, a 4-bromophenyl group, a 4-iodophenyl group, a 4-methylphenyl group, a 4-methoxyphenyl group, a 2,3-difluorophenyl group, a 2,4-difluorophenyl group, a 2,5-difluorophenyl group, a 2,6-difluorophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-fluoro-3-methoxyphenyl group, a 2-fluoro-4-methoxyphenyl group, a 2-fluoro-5-methoxyphenyl group, a 2-fluoro-6-methoxyphenyl group, a 2-chloro-3-methoxyphenyl group, a 2-chloro-4-methoxyphenyl group, a 2-chloro-5-methoxyphenyl group, a 2-chloro-6-methoxyphenyl group, a 2-bromo-3-methoxyphenyl group, a 2-bromo-4-methoxyphenyl group, a 2-bromo-5-methoxyphenyl group, 2-bromo-6-methoxyphenyl group, 2,3,4-trifluorophenyl group, a 2,3,5-trifluorophenyl group, a 2,3,6-trifluorophenyl group, a 2-chloro-3,4-difluorophenyl group, a 2-chloro-3,5-difluorophenyl group, a 2-chloro-3,6-difluorophenyl group, 2-bromo-a 3,4-difluorophenyl group, a 2-bromo-3,5-difluorophenyl group, a 2-bromo-3,6-difluorophenyl group, a 2-fluoro-3,4-dimethoxyphenyl group, a 2-fluoro-3,5-dimethoxyphenyl group, a 2-fluoro-3,6-dimethoxyphenyl group, a 2-chloro-3,4-dimethoxyphenyl group, a 2-chloro-3,5-dimethoxyphenyl group, a 2-chloro-3,6-dimethoxyphenyl group, a 2-bromo-3,4-dimethoxyphenyl group, a 2-bromo-3,5-dimethoxyphenyl group or a 2-bromo-3,6-dimethoxyphenyl group, more preferably a phenyl group, a 2-fluorophenyl group, a 2-chlorophenyl group, a 2-bromophenyl group, a 2-methylphenyl group, a 2-methoxyphenyl group, a 3-fluorophenyl group, a 3-chlorophenyl group, a 3-bromophenyl group, a 3-methylphenyl group, a 3-methoxyphenyl group, a 4-chlorophenyl group, a 4-bromophenyl group, a 4-methylphenyl group, a 4-methoxyphenyl group, a 2,3-difluorophenyl group, a 2,4-difluorophenyl group, a 2,5-difluorophenyl group, a 2-chloro-3-fluorophenyl group, a 2-chloro-4-fluorophenyl group, a 2-chloro-5-fluorophenyl group, a 2-bromo-3-fluorophenyl group, a 2-bromo-4-fluorophenyl group, a 2-bromo-5-fluorophenyl group, a 2-fluoro-3-methoxyphenyl group, a 2-fluoro-4-methoxyphenyl group, a 2-fluoro-5-methoxyphenyl group, a 2-chloro-3-methoxyphenyl group, a 2-chloro-4-methoxyphenyl group, a 2-chloro-5-methoxyphenyl group, a 2-bromo-3-methoxyphenyl group, a 2-bromo-4-methoxyphenyl group, a 2-bromo-5-methoxyphenyl group, a 2,3,5-trifluorophenyl group, a 2,3,6-trifluorophenyl group, a 2-chloro-3,5-difluorophenyl group, a 2-bromo-3,5-difluorophenyl group, a 2-fluoro-3,5-dimethoxyphenyl group, a 2-chloro-3,5-dimethoxyphenyl group or a 2-bromo-3,5-dimethoxyphenyl group, and particularly preferably a phenyl group, a 2-methylphenyl group, a 3-chlorophenyl group, a 3-methoxyphenyl group, a 4-fluorophenyl group, a 4-chlorophenyl group, a 4-methylphenyl group, a 4-methoxyphenyl group or a 2-chloro-a 4-fluorophenyl group.

Each of the "phenyl group optionally substituted with 0 to 5 substituent D" and "C1-C6 alkyl group" for the "C1-C6 alkyl group having a phenyl group optionally substituted with 0 to 5 substituent D" (with the proviso that when there is two or more substituents D, they are independent to each other) as R4 of Formula (1) is the same as defined above. The "C1-C6 alkyl group having a phenyl group" is preferably a phenylmethyl group, a 2-phenylethyl group, a 1-phenylethyl group, a 3-phenylpropyl group, a 2-phenylpropyl group, a 1-phenylpropyl group, a 4-phenylbutyl group or a 5-phenylpentyl group, more preferably a phenylmethyl group, a 2-phenylethyl group, a 1-phenylethyl group or a 1-phenylpropyl group, and particularly preferably a phenylmethyl group. When substituent D is present, any hydrogen atom in the phenyl group is substituted with substituent D.

Each of the "phenyl group optionally substituted with 0 to 5 substituent D" and "C1-C6 haloalkyl group" for the "C1-C6 haloalkyl group having a phenyl group optionally substituted with 0 to 5 substituent D" (with the proviso that when there are two or more substituents D, they are independent to each other) as R4 of Formula (1) is the same as defined above. The "C1-C6 haloalkyl group having a phenyl group" is preferably a 2,2,2-trifluoro-1-phenylethyl group or a 2,2-difluoro-1-phenylethyl group, and more preferably a 2,2,2-trifluoro-1-phenylethyl group. When substituent D is present, any hydrogen atom in the phenyl group is substituted with substituent D.

Each of the terms for the "Rc-L-" (wherein Rc represents a C1-C6 alkyl group or a C1-C6 haloalkyl group, and L represents S, SO or $SO_2$) as R4 of Formula (1) is the same as defined above. The "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group or a trifluoromethanesulfonyl group, more preferably a methylthio group, a methanesulfinyl group, a methanesulfonyl group, an ethylthio group, an ethanesulfinyl group or an ethanesulfonyl group, and particularly preferably an ethanesulfonyl group.

Each of the terms for the "ReC(═O)—" (wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— (wherein Ra and Rb are the same as defined above)) as R4 of Formula (1) is the same as defined above. Re is preferably a C1-C6 alkyl group optionally substituted with substituent B, a C1-C6 haloalkyl group, a C1-C6 alkoxy group, a C1-C6 haloalkoxy group or C3-C8 cycloalkoxy group, more preferably a C1-C6 alkyl group optionally substituted with substituent B or C1-C6 alkoxy group. The "ReC(═O)—" is preferably a formyl group, an acetyl group, a propionyl group, a 2-methylpropionyl group, a 2,2-dimethylpropionyl group, a butanoyl group, a methoxyacetyl group, a cyanoacetyl group, a difluoroacetyl group, a trifluoroacetyl group, a cyclopropanecarbonyl group, a propenoyl group, a 2-butenoyl group, a 3,3-dichloropropenoyl group, a 3,3-difluoropropenoyl group, a propynoyl group, a 2-butynoyl group, a 4,4,4-trifluoro-2-butynoyl group, a methoxycarbonyl group, an ethoxycarbonyl group, a propyloxycarbonyl group, an isopropyloxycarbonyl group, a butyloxycarbonyl group, an isobutyloxycarbonyl group, a t-butyloxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, a vinyloxycarbonyl group, a allyloxycarbonyl group, a 3,3-difluoroallyloxycarbonyl group, a propargyloxycarbonyl group, a 4,4,4-trifluoro-2-butynyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl (methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl-(methyl)aminocarbonyl group, a pyrrolidinylcarbonyl group or a piperidinylcarbonyl group, more preferably an acetyl group, a methoxyacetyl group, a cyanoacetyl group, a difluoroacetyl group, a trifluoroacetyl group, a methoxycarbonyl group, an ethoxycarbonyl group, a propyloxycarbonyl group, an isopropyloxycarbonyl group, a butyloxycarbonyl group, an isobutyloxycarbonyl group or a t-butyloxycarbonyl group, and particularly preferably an acetyl group, a methoxycarbonyl group or a t-butyloxycarbonyl group.

R3 and R4 in Formula (1) are independent to each other, and may be the same or different.

When Ra and Rb in Formula (1) in combination with the nitrogen atom to which they are bonded form the "aziridinyl group optionally substituted with substituent E" having substituent E, any hydrogen atom in the aziridinyl group is substituted with substituent E.

When Ra and Rb in Formula (1) in combination with the nitrogen atom to which they are bonded form the "azetidinyl group optionally substituted with substituent E" having substituent E, any hydrogen atom in the azetidinyl group is substituted with substituent E.

When Ra and Rb in Formula (1) in combination with the nitrogen atom to which they are bonded form the "pyrrolidinyl group optionally substituted with substituent E" having substituent E, any hydrogen atom in the pyrrolidinyl group is substituted with substituent E. Substituent E for the "pyrrolidinyl group optionally substituted with substituent E" is preferably an oxo group, a C1-C6 alkyl group or a C1-C6 alkoxy group, more preferably an oxo group.

The "pyrrolidinyl group optionally substituted with substituent E" is preferably a pyrrolidinyl group, a 2-oxopyrrolidinyl group, a 2-methyl-pyrrolidinyl group, a 2-methoxy-pyrrolidinyl group, a 3-oxopyrrolidinyl group, a 3-methyl-pyrrolidinyl group or 3-methoxy-pyrrolidinyl group, more preferably a pyrrolidinyl group, a 2-oxopyrrolidinyl group, a 2-methyl-pyrrolidinyl group or a 2-methoxy-pyrrolidinyl group, and particularly preferably a pyrrolidinyl group or a 2-oxopyrrolidinyl group.

When Ra and Rb in Formula (1) in combination with the nitrogen atom to which they are bonded form the "piperidinyl group optionally substituted with substituent E" having substituent E, any hydrogen atom in the piperidinyl group is substituted with substituent E. Substituent E for the "piperidinyl group optionally substituted with substituent E" is preferably an oxo group, a C1-C6 alkyl group or a C1-C6 alkoxy group, more preferably an oxo group or a C1-C6 alkyl group. The "piperidinyl group optionally substituted with substituent E" is preferably a piperidinyl group, a 2-oxopiperidinyl group, a 2-methyl-piperidinyl group, a 2-methoxy-piperidinyl group, a 3-oxopiperidinyl group, a 3-methyl-piperidinyl group, a 3-methoxy-piperidinyl group, a 4-oxopiperidinyl group, a 4-methyl-piperidinyl group or a 4-methoxy-piperidinyl group, more preferably a piperidinyl group, a 2-oxopiperidinyl group, a 4-oxopiperidinyl group, a 4-methyl-piperidinyl group or a 4-methoxy-piperidinyl group, and particularly preferably a piperidinyl group, a 2-oxopiperidinyl group or a 4-methyl-piperidinyl group.

When Ra and Rb in Formula (1) in combination with the nitrogen atom to which they are bonded form the "homopiperidinyl group optionally substituted with substituent E" having substituent E, any hydrogen atom in the homopiperidinyl group is substituted with substituent E.

When Ra and Rb in Formula (1) in combination with the nitrogen atom to which they are bonded form the "azocanyl group optionally substituted with substituent E" having substituent E, any hydrogen atom in the azocanyl group is substituted with substituent E.

When Ra and Rb in Formula (1) in combination with the nitrogen atom to which they are bonded form the "morpholinyl group optionally substituted with substituent E" having substituent E, any hydrogen atom in the morpholinyl group is substituted with substituent E. The "morpholinyl group optionally substituted with substituent E" is preferably a morpholinyl group, a 2-methyl-morpholinyl group, a 2-methoxymorpholinyl group, a 2-oxomorpholinyl group, a 3-methyl-morpholinyl group, a 3-methoxy-morpholinyl group or a 3-oxomorpholinyl group, more preferably a morpholinyl group, a 3-methyl-morpholinyl group, a 3-methoxy-morpholinyl group or a 3-oxomorpholinyl group, and particularly preferably a morpholinyl group.

The C1-C6 alkylidene group for the "C1-C6 alkylidene group optionally substituted with substituent F" formed by R3 and R4 in Formula (1) is the same as defined above, and preferably a methylidene group, an ethylidene group, a 1-methylethylidene group or a propylidene group, more preferably a methylidene group or an ethylidene group. When substituent F is present, any hydrogen atom in the alkylidene group is substituted with substituent F. Substituent F for the "C1-C6 alkylidene group optionally substituted with substituent F" is preferably an RaRbN— (wherein Ra and Rb are the same as defined above) or an RdC(═O)— (wherein Rd is the same as defined above). The "C1-C6 alkylidene group optionally substituted with substituent F" is preferably a dimethylformimidamide group, an ethylmethylformimidamide group, a diethylformimidamide group, an ethylpropyl-formimidamide group, a dipropylformimidamide group, a 1-(pyrrolidin-1-yl)methaneimino group, a 1-(piperidin-1-yl)methaneimino group, a methyl iminoacetate group, an ethyl iminoacetate group or a propyl iminoacetate group, more preferably a dimethylformimidamide group, an ethylmethylformimidamide group, a diethylformimidamide group, a 1-(pyrrolidin-1-yl)methaneimino group, a methyl iminoacetate group or an ethyl iminoacetate group, and particularly preferably a dimethylformimidamide group, an ethylmethylformimidamide group, a 1-(pyrrolidin-1-yl)methaneimino group or an ethyl iminoacetate group.

X in Formula (1) represents an oxygen atom or a sulfur atom. Preferred X is an oxygen atom.

Y in Formula (1) represents a phenyl group optionally substituted with 0 to 5 R5 (with the proviso that when there are two or more R5, they are independent to each other), a pyridyl group optionally substituted with 0 to 4 R5 (with the proviso that when there are two or more R5, they are independent to each other), a pyridazinyl group optionally substituted with 0 to 3 R5 (with the proviso that when there are two or more R5, they are independent to each other), a pyrimidinyl group optionally substituted with 0 to 3 R5 (with the proviso that when there are two or more R5, they are independent to each other), a pyradinyl group optionally substituted with 0 to 3 R5 (with the proviso that when there are two or more R5, they are independent to each other), a triazinyl group optionally substituted with 0 to 2 R5 (with the proviso that when there are two R5, they are independent to each other), a tetrazinyl group optionally substituted with R5, a thienyl group optionally substituted with 0 to 3 R5 (with the proviso that when there are two or more R5, they are independent to each other), a thiazolyl group optionally substituted with 0 to 2 R5 (with the proviso that when there are two R5, they are independent to each other), an isothiazolyl group optionally substituted with 0 to 2 R5 (with the proviso that when there are two R5, they are independent to each other) or a thiadiazolyl group optionally substituted with R5.

Among them, Y is preferably a phenyl group optionally substituted with 0 to 5 R5 (with the proviso that when there are two or more R5, they are independent to each other) or a pyridyl group optionally substituted with 0 to 4 R5 (with the proviso that when there are two or more R5, they are independent to each other), particularly preferably a phenyl group optionally substituted with 0 to 5 R5 (with the proviso that when there are two or more R5, they are independent to each other).

The "phenyl group optionally substituted with 0 to 5 R5" (with the proviso that when there are two or more R5, they are independent to each other) as Y of Formula (1) refers to the partial structure represented by Formula (a) shown below.

(a)

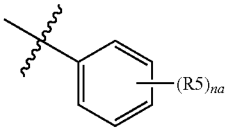

In Formula (a), na represents an integer of 0 to 5 and, when na is 2 or more, the substituents which two or more R5's represent are independent to each other and may be the same or different and arbitrarily selected.

Preferred arrangement of substituent(s) on Formula (a) is represented by the partial structure of Formula (a-1), Formula (a-2), Formula (a-3), Formula (a-4), Formula (a-5), Formula (a-6), Formula (a-7), Formula (a-8), Formula (a-9), Formula (a-10), Formula (a-11) or Formula (a-12):

(a-1)

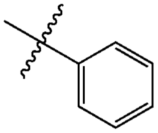

(a-2)

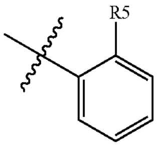

(a-3)

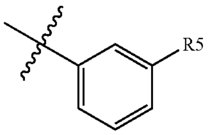

(a-4)

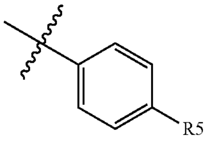

(a-5)

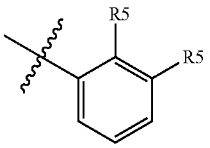

(a-6)

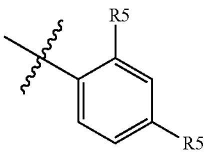

(a-7)

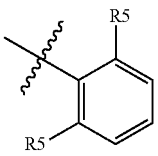

-continued (a-8)

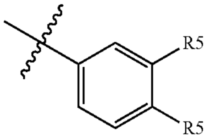

(a-9)

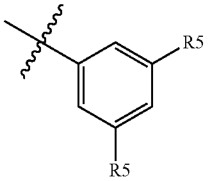

(a-10)

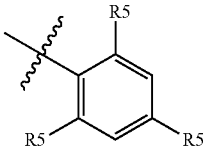

(a-11)

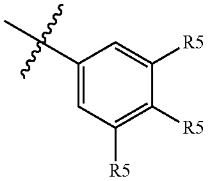

(a-12)

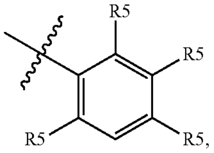

and more preferred arrangement of substituent(s) is represented by a partial structure of Formula (a-1), Formula (a-2), Formula (a-4), Formula (a-6), Formula (a-7), Formula (a-8), Formula (a-9) or Formula (a-10):

(a-1)

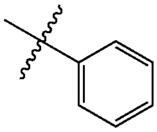

(a-2)

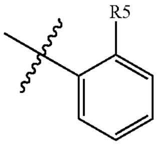

(a-4)

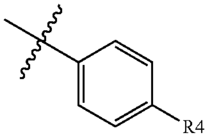

-continued (a-6)

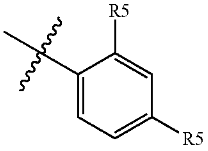

(a-7)

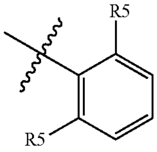

(a-8)

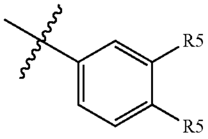

(a-9)

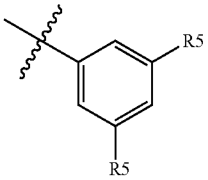

(a-10)

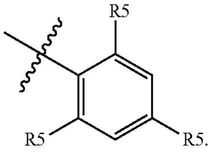

The "pyridyl group optionally substituted with 0 to 4 R5" (with the proviso that when there are two or more R5, they are independent to each other) as Y of Formula (1) refers to the partial structure represented by one formula selected from the group consisting of Formula (b-1), Formula (b-2) and Formula (b-3) shown below.

(b-1)

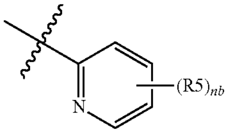

(b-2)

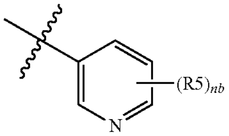

(b-3)

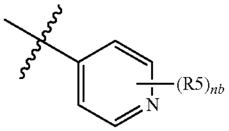

In each of Formula (b-1), Formula (b-2) and Formula (b-3), nb represents an integer of 0 to 4 and, when nb is 2 or more, the substituents which two or more R5's represent are independent to each other and may be the same or different and arbitrarily selected.

The “pyridazinyl group optionally substituted with 0 to 3 R5” (with the proviso that when there are two or more R5, they are independent to each other) as Y of Formula (1) refers to the partial structure represented by one formula selected from the group consisting of Formula (c-1), Formula (c-2) and Formula (c-3) shown below.

(c-1)

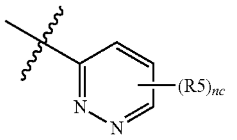

(c-2)

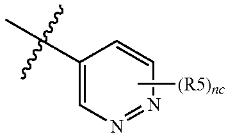

(c-3)

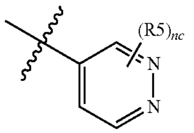

In each of Formula (c-1), Formula (c-2) and Formula (c-3), nc represents an integer of 0 to 3 and, when nc is 2 or more, the substituents which two or more R5’s represent are independent to each other and may be the same or different and arbitrarily selected.

The “pyrimidinyl group optionally substituted with 0 to 3 R5” (with the proviso that when there are two or more R5, they are independent to each other) as Y of Formula (1) refers to the partial structure represented by one formula selected from the group consisting of Formula (d-1), Formula (d-2) and Formula (d-3) shown below.

(d-1)

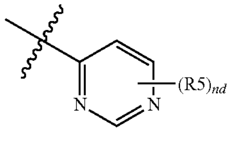

(d-2)

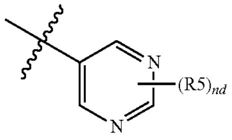

(d-3)

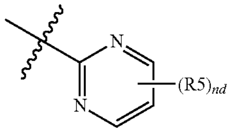

In each of Formula (d-1), Formula (d-2) and Formula (d-3), nd represents an integer of 0 to 3 and, when nd is 2 or more, the substituents which two or more R5’s represent are independent to each other and may be the same or different and arbitrarily selected.

The “pyradinyl group optionally substituted with 0 to 3 R5 (with the proviso that when there are two or more R5, they are independent to each other)” as Y of Formula (1) refers to the partial structure represented by Formula (e) shown below.

(e)

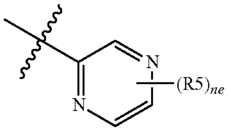

In Formula (e), ne represents an integer of 0 to 3 and, when ne is 2 or more, the substituents which two or more R5’s represent are independent to each other and may be the same or different and arbitrarily selected.

The “triazinyl group optionally substituted with 0 to 2 R5” (with the proviso that when there are two R5, they are independent to each other) as Y of Formula (1) refers to the partial structure represented by one formula selected from the group consisting of Formula (f-1), Formula (f-2), Formula (f-3), Formula (f-4) and Formula (f-5) shown below.

(f-1)

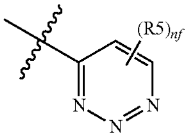

(f-2)

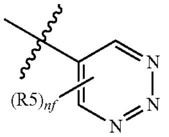

(f-3)

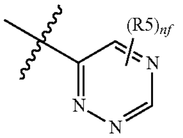

(f-4)

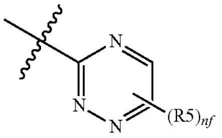

(f-5)

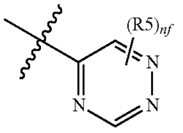

In each of Formula (f-1), Formula (f-2), Formula (f-3), Formula (f-4) and Formula (f-5), nf represents an integer of 0 to 2 and, when nf is 2, the substituents which two R5’s represent are independent to each other and may be the same or different and arbitrarily selected.

The “tetrazinyl group optionally substituted with R5” as Y of Formula (1) refers to the partial structure represented by one formula selected from the group consisting of Formula (g-1), Formula (g-2) and Formula (g-3) shown below.

(g-1)

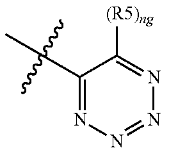

(g-2)

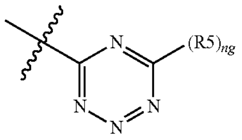

(g-3)

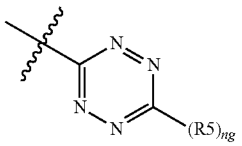

In each of Formula (g-1), Formula (g-2) and Formula (g-3), ng represents an integer of 0 to 1.

The "thienyl group optionally substituted with 0 to 3 R5" (with the proviso that when there are two or more R5, they are independent to each other) as Y of Formula (1) refers to the partial structure represented by one formula selected from the group consisting of Formula (h-1) and Formula (h-2) shown below.

(h-1)

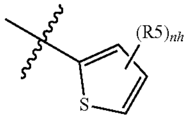

(h-2)

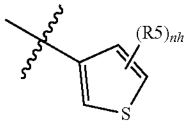

In each of Formula (h-1) and Formula (h-2), nh represents an integer of 0 to 3 and, when nh is 2 or more, the substituents which two or more R5's represent are independent to each other and may be the same or different and arbitrarily selected.

The "thiazolyl group optionally substituted with 0 to 2 R5" (with the proviso that when there are two R5, they are independent to each other) as Y of Formula (1) refers to the partial structure represented by one formula selected from the group consisting of Formula (i-1), Formula (i-2) and Formula (i-3) shown below.

(i-1)

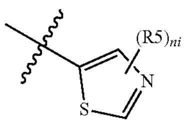

-continued (i-2)

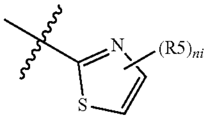

(i-3)

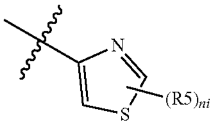

In each of Formula (i-1), Formula (i-2) and Formula (i-3), ni represents an integer of 0 to 2 and, when ni is 2, the substituents which two R5's represent are independent to each other and may be the same or different and arbitrarily selected.

The "isothiazolyl group optionally substituted with 0 to 2 R5" (with the proviso that when there are two R5, they are independent to each other) as Y of Formula (1) refers to the partial structure represented by one formula selected from the group consisting of Formula (j-1), Formula (j-2) and Formula (j-3) shown below.

(j-1)

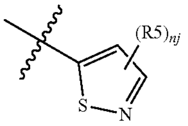

(j-2)

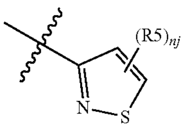

(j-3)

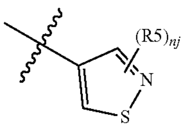

In each of Formula (j-1), Formula (j-2) and Formula (j-3), nj represents an integer of 0 to 2 and, when nj is 2, the substituents which two R5's represent are independent to each other and may be the same or different and arbitrarily selected.

The "thiadiazolyl group optionally substituted with R5" as Y of Formula (1) refers to the partial structure represented by one formula selected from the group consisting of Formula (k-1), Formula (k-2), Formula (k-3), Formula (k-4), Formula (k-5) and Formula (k-6) shown below.

(k-1)

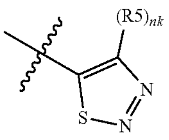

-continued (k-2)

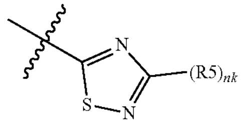

(k-3)

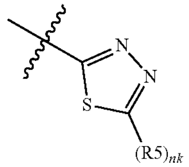

(k-4)

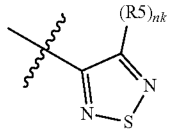

(k-5)

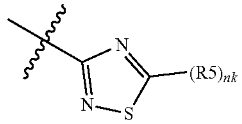

(k-6)

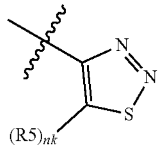

In each of Formula (k-1), Formula (k-2), Formula (k-3), Formula (k-4), Formula (k-5) and Formula (k-6), nk represents an integer of 0 to 1.

R5 in Formula (1) represents a hydroxyl group, a cyano group, a nitro group, a halogen atom, a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G, a C2-C6 haloalkenyl group, a C2-C6 alkynyl group optionally substituted with substituent G, a C2-C6 haloalkynyl group, a C1-C6 alkoxy group optionally substituted with substituent G, a C1-C6 haloalkoxy group, a C3-C8 cycloalkoxy group optionally substituted with substituent G, a C2-C6 alkenyloxy group optionally substituted with substituent G, a C2-C6 haloalkenyloxy group, a C3-C6 alkynyloxy group optionally substituted with substituent G, a C3-C6 haloalkynyloxy group, an RdC(═O)— (wherein Rd is the same as defined above), an RdC(═O)O— (wherein Rd is the same as defined above), an Rc-L- (wherein Rc and L are the same as defined above) or an RaRbN— (wherein Ra and Rb are the same as defined above).

Among them, R5 is preferably a hydroxyl group, a cyano group, a halogen atom, a C1-C6 alkyl group optionally substituted with substituent G, a C1-C6 alkoxy group optionally substituted with substituent G, a C1-C6 haloalkoxy group, a C2-C6 alkenyloxy group optionally substituted with substituent G, a C2-C6 haloalkenyloxy group, a C3-C6 alkynyloxy group optionally substituted with substituent G, a C3-C6 haloalkynyloxy group or an RdC(═O)O— (wherein Rd is the same as defined above), R5 is particularly preferably a hydroxyl group, a cyano group, a halogen atom, a C1-C6 alkyl group optionally substituted with substituent G, a C1-C6 alkoxy group optionally substituted with substituent G, a C2-C6 alkenyloxy group optionally substituted with substituent G or a C3-C6 alkynyloxy group optionally substituted with substituent G, and R5 is further preferably a cyano group, a halogen atom, a C1-C6 alkyl group optionally substituted with substituent G, a C1-C6 alkoxy group optionally substituted with substituent G or a C3-C6 alkynyloxy group optionally substituted with substituent G.

In R5 of Formula (1), a hydroxyl group, a cyano group and a nitro group are included.

The halogen atom as R5 of Formula (1) is the same as defined above, and preferably a fluorine atom, a chlorine atom, a bromine atom or an iodine atom, more preferably a fluorine atom, a chlorine atom or a bromine atom.

The C1-C6 alkyl group for the "C1-C6 alkyl group optionally substituted with the substituent G" as R5 of Formula (1) is the same as defined above, and preferably a methyl group, an ethyl group, a propyl group, an isopropyl group, a butyl group or an isobutyl group, more preferably a methyl group, an ethyl group, a propyl group or an isopropyl group, particularly preferably a methyl group. When substituent G is present, any hydrogen atom in the C1-C6 alkyl group is substituted with substituent G.

The "C1-C6 haloalkyl group" as R5 of Formula (1) is the same as defined above, and preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group, a trifluoromethyl group, a 2,2-difluoroethyl group or a 2,2,2-trifluoroethyl group.

The C3-C8 cycloalkyl group for the "C3-C8 cycloalkyl group optionally substituted with the substituent G" as R5 of Formula (1) is the same as defined above, and preferably a cyclopropyl group, a cyclobutyl group, a cyclopentyl group or a cyclohexyl group, more preferably a cyclopropyl group or a cyclobutyl group. When substituent G is present, any hydrogen atom in the C3-C8 cycloalkyl group is substituted with substituent G.

The C2-C6 alkenyl group for the "C2-C6 alkenyl group optionally substituted with the substituent G" as R5 of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group. When substituent G is present, any hydrogen atom in the C2-C6 alkenyl group is substituted with substituent G.

The "C2-C6 haloalkenyl group" as R5 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent G" as R5 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group. When substituent G is present, any hydrogen atom in the C2-C6 alkynyl group is substituted with substituent G.

The "C2-C6 haloalkynyl group" as R5 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxy group optionally substituted with substituent G" as R5 of Formula (1) is the same as defined above, and preferably a methoxy group, an ethoxy group, a propyloxy group, an isopropyloxy group, a butoxy group, an isobutoxy group or a pentyloxy group, more preferably a methoxy group, an ethoxy group, a propyloxy group, an isopropyloxy group or a butoxy group, particularly preferably a methoxy group or an ethoxy group. When substituent G is present, any hydrogen atom in the C1-C6 alkoxy group is substituted with substituent G. Substituent G is preferably a cyano group, a C3-C8 cycloalkyl group, a C1-C6 alkoxy group, a C1-C6 haloalkoxy group, a C2-C6 alkoxyalkoxy group, an Rc-L-(wherein Rc and L are the same as defined above), an RdC(═O)— (wherein Rd is the same as defined above) or a group of a 3-6 membered ring containing 1-2 oxygen atoms, more preferably a cyano group, a C1-C6 alkoxy group or an Rc-L-(wherein Rc and L are the same as defined above), and particularly preferably a C1-C6 alkoxy group. The "C1-C6 alkoxy group optionally substituted with the substituent G" is preferably a cyanomethoxy group, a 2-cyanoethoxy group, a methoxymethoxy group, a 2-methoxyethoxy group, an ethoxymethoxy group or a 2-ethoxyethoxy group, more preferably a cyanomethoxy group, a methoxymethoxy group or 2-methoxyethoxy group, and particularly preferably a 2-methoxyethoxy group.

The "C1-C6 haloalkoxy group" as R5 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with the substituent G" as R5 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent G is present, any hydrogen atom in the C3-C8 cycloalkoxy group is substituted with substituent G.

The C2-C6 alkenyloxy group for the "C2-C6 alkenyloxy group optionally substituted with the substituent G" as R5 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent G is present, any hydrogen atom in the C2-C6 alkenyloxy group is substituted with substituent G.

The "C2-C6 haloalkenyloxy group" as R5 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent G" as R5 of Formula (1) is the same as defined above, and preferably a propargyloxy group, a 2-butynyloxy group or a 3-butynyloxy group, more preferably a propargyloxy group. When substituent G is present, any hydrogen atom in the C3-C6 alkynyloxy group is substituted with substituent G.

The "C3-C6 haloalkynyloxy group" as R5 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

Rd for the "RdC(═O)—" as R5 of Formula (1) is the same as defined above. The "RdC(═O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)-methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl(methyl)aminocarbonyl group, a pyrrolidinyl carbonyl group or a piperidinylcarbonyl group, more preferably an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethyl(methyl)aminocarbonyl group or a diethylaminocarbonyl group.

Rd for the "RdC(═O)O—" as R5 of Formula (1) is the same as defined above. The "RdC(═O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyl oxy group, a (cyanomethyl)aminocarbonyloxy group, a (2-cyanoethyl)aminocarbonyloxy group, a dimethylaminocarbonyloxy group, a ethyl (methyl)aminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyl oxy group, a cyclopropylaminocarbonyloxy group, a cyclopropyl(methyl)aminocarbonyloxy group, a pyrrolidinylcarbonyloxy group or a piperidinylcarbonyloxy group, more preferably an acetyloxy group, a methoxyacetyloxy group, a cyanoacetyloxy group, a difluoroacetyloxy group, a trifluoroacetyloxy group, a methoxycarbonyloxy group, an ethoxycarbonyloxy group, an aminocarbonyloxy group, a dimethylaminocarbonyloxy group, an ethyl(methyl)aminocarbonyloxy group or a diethylaminocarbonyloxy group.

Rc and L for the "Rc-L-" as R5 of Formula (1) are the same as defined above. The "Rc-L-" is preferably a methylthio group, a methanesulfinyl group, a methanesulfonyl group, a trifluoromethylthio group, a trifluoromethanesulfinyl group or a trifluoromethanesulfonyl group, more preferably a methylthio group, a methanesulfinyl group or a methanesulfonyl group.

Ra and Rb for the "RaRbN—" as R5 of Formula (1) are the same as defined above. The "RaRbN—" is preferably an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl)amino group, a (methoxymethyl)-methylamino group, a (2-methoxyethyl)methylamino group, a (cyanomethyl)methylamino group, a (2-cyanoethyl)methylamino group, a diethylamino group, an ethyl-(propyl)amino group, an ethyl (isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group or a piperidinyl group, more preferably a dimethylamino group, an ethyl(methyl) amino group, an isopropyl(methyl)amino group, a diethylamino group or an ethyl(isopropyl)amino group.

Substituent A represents at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— (wherein Ra and Rb are the same as defined above) and an Rc-L- (wherein Rc and L are the same as defined above).

Among them, the substituent A is preferably a cyano group, a C1-C6 alkoxy group or an Rc-L- (wherein Rc and L are the same as defined above), particularly preferably a cyano group or a C1-C6 alkoxy group.

Each of the terms for substituent A is the same as defined above.

Preferred specific examples of substituent A include:

a hydroxyl group;

a cyano group;

a cyclopropyl group, a cyclobutyl group, a cyclopentyl group and a cyclohexyl group as the C3-C8 cycloalkyl group;

a methoxy group, an ethoxy group, a propyloxy group and an isopropyloxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group;

a cyclopropyloxy group, a cyclobutoxy group, a cyclopentyloxy group and a cyclohexyloxy group as the C3-C8 cycloalkoxy group;

an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl) amino group, a (methoxymethyl)methylamino group, a (2-methoxyethyl)methylamino group, a (cyanomethyl)methylamino group, a (2-cyanoethyl)methylamino group, a diethylamino group, an ethyl(propyl)amino group, an ethyl (isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined above); and a methylthio group, a methanesulfinyl group, a methanesulfonyl group, a trifluoromethylthio group, a trifluoromethanesulfinyl group and a trifluoromethanesulfonyl group as the Rc-L- (wherein Rc and L are the same as defined above).

More preferred specific examples of substituent A include:

a hydroxyl group;

a cyano group;

a cyclopropyl group and a cyclobutyl group as the C3-C8 cycloalkyl group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group;

a cyclopropyloxy group and a cyclobutoxy group as the C3-C8 cycloalkoxy group;

a dimethylamino group, an ethyl(methyl)amino group and a diethylamino group as the RaRbN— (wherein Ra and Rb are the same as defined above); and a methylthio group, a methanesulfinyl group and a methanesulfonyl group as the Rc-L- (wherein Rc and L are the same as defined above).

Substituent B is at least one member selected from the group consisting of a cyano group, a C1-C6 alkoxy group, a C1-C6 haloalkoxy group and a C3-C8 cycloalkoxy group.

Among them, substituent B is preferably a cyano group or a C1-C6 alkoxy group.

Each of the terms for substituent B is the same as defined above.

Preferred specific examples of substituent B include:

a cyano group;

a methoxy group, an ethoxy group, a propyloxy group and an isopropyloxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group; and a cyclopropyloxy group, a cyclobutoxy group, a cyclopentyloxy group and a cyclohexyloxy group as the C3-C8 cycloalkoxy group.

More preferred specific examples of substituent B include:

a cyano group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group; and a cyclopropyloxy group and a cyclobutoxy group as the C3-C8 cycloalkoxy group.

Substituent C is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group and an Rc-L- (wherein Rc and L are the same as defined above).

Among them, substituent C is preferably a hydroxyl group, a cyano group, a C3-C8 cycloalkyl group, a C1-C6 alkoxy group, a C1-C6 haloalkoxy group, a C3-C8 cycloalkoxy group, a C2-C6 alkenyloxy group, a C3-C6 alkynyloxy group or an Rc-L-(wherein Rc and L are the same as defined above), particularly preferably a cyano group, a C3-C8 cycloalkyl group, a C1-C6 alkoxy group, a C1-C6 haloalkoxy group or an Rc-L- (wherein Rc and L are the same as defined above).

Each of the terms for substituent C is the same as defined above.

Preferred specific examples of substituent C include:

a hydroxyl group;

a cyano group;

a cyclopropyl group, a cyclobutyl group, a cyclopentyl group and a cyclohexyl group as the C3-C8 cycloalkyl group;

a methoxy group, an ethoxy group, a propyloxy group and an isopropyloxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group;

a cyclopropyloxy group, a cyclobutoxy group, a cyclopentyloxy group and a cyclohexyloxy group as the C3-C8 cycloalkoxy group;

a vinyloxy group, a 1-propenyloxy group, an allyloxy group, a 1-butenyloxy group, a 2-butenyloxy group and a 3-butenyloxy group as the C2-C6 alkenyloxy group;

a 2-fluorovinyloxy group, a 2,2-difluorovinyloxy group, a 2,2-dichlorovinyloxy group, a 3-fluoroallyloxy group, a 3,3-difluoroallyloxy group and 3,3-dichloroallyloxy group as the C2-C6 haloalkenyloxy group;

a propargyloxy group, a 2-butynyloxy group and a 3-butynyloxy group as the C3-C6 alkynyloxy group;

a 4,4-difluoro-2-butynyloxy group, a 4-chloro-4,4-difluoro-2-butynyloxy group, a 4-bromo-4,4-difluoro-2-butynyloxy group and a 4,4,4-trifluoro-2-butynyloxy group as the C3-C6 haloalkynyloxy group; and a methylthio group, a methanesulfinyl group, a methanesulfonyl group, a trifluoromethylthio group, a trifluoromethanesulfinyl group and a trifluoromethanesulfonyl group as the an Rc-L- (wherein Rc and L are the same as defined above).

More preferred specific examples of substituent C include:

a hydroxyl group;

a cyano group;

a cyclopropyl group and a cyclobutyl group as the C3-C8 cycloalkyl group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group;

a cyclopropyloxy group and a cyclobutoxy group as the C3-C8 cycloalkoxy group;

a vinyloxy group, a 1-propenyloxy group and allyloxy group as the C2-C6 alkenyloxy group;

2-fluorovinyloxy group and 2,2-difluorovinyloxy group as the C2-C6 haloalkenyloxy group;

a propargyloxy group as the C3-C6 alkynyloxy group;

a 4,4-difluoro-2-butynyloxy group and a 4,4,4-trifluoro-2-butynyloxy group as the C3-C6 haloalkynyloxy group; and a methylthio group, a methanesulfinyl group and a methanesulfonyl group as the Rc-L- (wherein Rc and L are the same as defined above).

Substituent D is at least one member selected from the group consisting of a hydroxyl group, a cyano group, a nitro group, a halogen atom, a C1-C6 alkyl group optionally substituted with substituent B, a C1-C6 haloalkyl group, a C3-C8 cycloalkyl group, a C1-C6 alkoxy group, a C1-C6 haloalkoxy group and a C3-C8 cycloalkoxy group.

Among them, substituent D is preferably a cyano group, a halogen atom, a C1-C6 alkyl group optionally substituted with substituent B, a C1-C6 haloalkyl group, a C1-C6 alkoxy group or a C1-C6 haloalkoxy group, in particular, it is preferably a halogen atom, a C1-C6 alkyl group optionally substituted with substituent B or a C1-C6 alkoxy group.

Each of the terms for substituent D is the same as defined above. With regard to the "C1-C6 alkyl group optionally substituted with substituent B", when substituent B is present, any hydrogen atom in the C1-C6 alkyl group is substituted with substituent B.

Preferred specific examples of substituent D include:

a hydroxyl group;

a cyano group;

a nitro group;

a fluorine atom, a chlorine atom, a bromine atom and an iodine atom as the halogen atom;

a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, an isopropyl group, a butyl group and an isobutyl group as the C1-C6 alkyl group optionally substituted with substituent B;

a difluoromethyl group, a trifluoromethyl group, a 2,2-difluoroethyl group, a 2,2,2-trifluoroethyl group, a 3,3-difluoropropyl group and a 3,3,3-trifluoropropyl group as the C1-C6 haloalkyl group;

a cyclopropyl group, a cyclobutyl group, a cyclopentyl group and a cyclohexyl group as the C3-C8 cycloalkyl group;

a methoxy group, an ethoxy group, a propyloxy group, an isopropyloxy group, a butoxy group, an isobutoxy group and a t-butoxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group; and a cyclopropyloxy group, a cyclobutoxy group, a cyclopentyloxy group and a cyclohexyloxy group as the C3-C8 cycloalkoxy group.

More preferred specific examples of substituent D include:

a hydroxyl group;

a cyano group;

a nitro group;

a fluorine atom, a chlorine atom and a bromine atom as the halogen atom;

a methyl group, a methoxymethyl group, an ethoxymethyl group, a cyanomethyl group, an ethyl group, a 2-methoxyethyl group, a 2-ethoxyethyl group and a 2-cyanoethyl group as the C1-C6 alkyl group optionally substituted with substituent B; a difluoromethyl group, a trifluoromethyl group, a 2,2-difluoroethyl group and a 2,2,2-trifluoroethyl group as the C1-C6 haloalkyl group;

a cyclopropyl group and a cyclobutyl group as the C3-C8 cycloalkyl group;

a methoxy group, an ethoxy group, a propyloxy group and an isopropyloxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group; and a cyclopropyloxy group and a cyclobutoxy group as the C3-C8 cycloalkoxy group.

Substituent E is at least one member selected from the group consisting of an oxo group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group.

Among them, substituent E is preferably an oxo group, a halogen atom, a C1-C6 alkyl group or a C1-C6 alkoxy group, particularly preferably an oxo group or a C1-C6 alkyl group.

Each of the terms for substituent E is the same as defined above.

Preferred specific examples of substituent E include:

an oxo group;

a fluorine atom, a chlorine atom, a bromine atom and an iodine atom as the halogen atom;

a methyl group, an ethyl group, a propyl group and isopropyl group as the C1-C6 alkyl group;

a difluoromethyl group, a trifluoromethyl group, a 2,2-difluoroethyl group, a 2,2,2-trifluoroethyl group, 3,3-difluoropropyl group and a 3,3,3-trifluoropropyl group as the C1-C6 haloalkyl group;

a cyclopropyl group, a cyclobutyl group, a cyclopentyl group and a cyclohexyl group as the C3-C8 cycloalkyl group;

a methoxy group, an ethoxy group, a propyloxy group and an isopropyloxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group; and a cyclopropyloxy group, a cyclobutoxy group, a cyclopentyloxy group and a cyclohexyloxy group as the C3-C8 cycloalkoxy group.

More preferred specific examples of substituent E include:

an oxo group;

a fluorine atom as the halogen atom;

a methyl group and an ethyl group as the C1-C6 alkyl group;

a difluoromethyl group and a trifluoromethyl group as the C1-C6 haloalkyl group;

a cyclopropyl group and a cyclobutyl group as the C3-C8 cycloalkyl group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group; and a cyclopropyloxy group and a cyclobutoxy group as the C3-C8 cycloalkoxy group.

Substituent F is at least one member selected from the group consisting of a C1-C6 alkoxy group, an RaRbN— (wherein Ra and Rb are the same as defined above) and an RdC(=O)— (wherein Rd is the same as defined above).

Among them, substituent F is preferably an RaRbN— (wherein Ra and Rb are the same as defined above) or an RdC(=O)— (wherein Rd is the same as defined above).

Each of the terms for substituent F is the same as defined above.

Preferred specific examples of substituent F include:

a methoxy group, an ethoxy group, a propyloxy group and an isopropyloxy group as the C1-C6 alkoxy group;

an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl-(methyl)amino group, a (methoxymethyl)methylamino group, a (2-methoxyethyl)methylamino group, a (cyanomethyl)methylamino group, a (2-cyanoethyl)methylamino group, a diethylamino group, an ethyl(propyl)amino group, an ethyl(isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined above); and a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl(methyl)aminocarbonyl group, a pyrrolidinylcarbonyl group and a piperidinylcarbonyl group as the RdC(=O)— (wherein Rd is the same as defined above).

More preferred specific examples of substituent F include:

a methoxy group and an ethoxy group as the C1-C6 alkoxy group;

a dimethylamino group, an ethyl(methyl)amino group, a methyl(propyl)amino group, an isopropyl(methyl)amino group, a diethylamino group, an ethyl(propyl)amino group, an ethyl(isopropyl)amino group, a pyrrolidinyl group and a piperidinyl group as the RaRbN— (wherein Ra and Rb are the same as defined above); and a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group and a cyclopropyloxycarbonyl group as the RdC(=O)— (wherein Rd is the same as defined above).

Substituent G is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an RaRbN— (wherein Ra and Rb are the same as defined above), an Rc-L- (wherein Rc and L are the same as defined above), an RdC(=O)— (wherein Rd is the same as defined above), an RdC(=O)O— (wherein Rd is the same as defined above) and a group of a 3-6 membered ring containing 1-2 oxygen atoms.

Among them, substituent G is preferably a hydroxyl group, a cyano group, a C3-C8 cycloalkyl group, a C1-C6 alkoxy group, a C1-C6 haloalkoxy group, a C3-C8 cycloalkoxy group, an Rc-L- (wherein Rc and L are the same as defined above), an RdC(=O)— (wherein Rd is the same as defined above) or an RdC(=O)O— (wherein Rd is the same as defined above), in particular, it is preferably a hydroxyl group, a cyano group, a C3-C8 cycloalkyl group, a C1-C6 alkoxy group or an Rc-L- (wherein Rc and L are the same as defined above).

Each of the terms for substituent G is the same as defined above.

Preferred specific examples of substituent G include:

a hydroxyl group; a cyano group;

a cyclopropyl group, a cyclobutyl group, a cyclopentyl group and a cyclohexyl group as the C3-C8 cycloalkyl group;

a methoxy group, an ethoxy group, a propyloxy group, an isopropyloxy group, a butoxy group, an isobutoxy group and t-butoxy group as the C1-C6 alkoxy group;

a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group;

a cyclopropyloxy group, a cyclobutoxy group, a cyclopentyloxy group and a cyclohexyloxy group as the C3-C8 cycloalkoxy group;

a methoxymethoxy group, an ethoxymethoxy group, an methoxyethoxy group, an ethoxyethoxy group and a methoxypropyloxy group as the C2-C6 alkoxyalkoxy group;

an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl) amino group, a (methoxymethyl)methylamino group, a (2-methoxyethyl)methylamino group, a (cyanomethyl)methylamino group, a (2-cyano-ethyl)methylamino group, a diethylamino group, an ethyl(propyl)amino group, an ethyl (isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined above);

a methylthio group, a methanesulfinyl group, a methanesulfonyl group, a trifluoromethylthio group, a trifluoromethanesulfinyl group and a trifluoromethanesulfonyl group as the Rc-L- (wherein Rc and L are the same as defined above);

a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl) methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group and a piperidinylcarbonyl group as the RdC(=O)— (wherein Rd is the same as defined above);

a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, a ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl) aminocarbonyloxy group, a (2-cyanoethyl)aminocarbonyloxy group, a dimethylaminocarbonyloxy group, a ethyl (methyl)aminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoro-ethylaminocarbonyloxy group, a cyclopropylaminocarbonyloxy group, a cyclopropyl-(methyl)aminocarbonyloxy group, a pyrrolidinylcarbonyloxy group and a piperidinylcarbonyloxy group as the RdC(=O)O— (wherein Rd is the same as defined above); and a group of a 3-6 membered ring containing 1-2 oxygen atoms may be mentioned an oxolanyl group, an oxanyl group, a 1,3-dioxolanyl group and a 1,3-dioxanyl group.

More preferred specific examples of substituent G include:

a hydroxyl group;

a cyano group;

a cyclopropyl group and a cyclobutyl group as the C3-C8 cycloalkyl group;

a methoxy group and an ethoxy group as the C1-C6 alkoxy group;

a difluoromethoxy group, a trifluoromethoxy group, a 2,2-difluoroethoxy group and a 2,2,2-trifluoroethoxy group as the C1-C6 haloalkoxy group;

a cyclopropyloxy group and a cyclobutoxy group as the C3-C8 cycloalkoxy group;

a methoxymethoxy group, an ethoxymethoxy group, an methoxyethoxy group and an ethoxyethoxy group as the C2-C6 alkoxyalkoxy group;

a dimethylamino group, an ethyl(methyl)amino group and a diethylamino group as the RaRbN— (wherein Ra and Rb are the same as defined above);

a methylthio group, a methanesulfinyl group and a methanesulfonyl group as the Rc-L- (wherein Rc and L are the same as defined above);

a formyl group, an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethyl(methyl)aminocarbonyl group and a diethylaminocarbonyl group as the RdC(=O)— (wherein Rd is the same as defined above);

an acetyloxy group, a difluoroacetyloxy group and a trifluoroacetyloxy group as the RdC(=O)O— (wherein Rd is the same as defined above); and a 1,3-dioxolanyl group and a 1,3-dioxanyl group as the group of a 3-6 membered ring containing 1-2 oxygen atoms.

The compound represented by Formula (1) may have axial chirality. There is no particular limitation with respect to the ratio of isomers related to this matter, and the compound may be present as a single isomer or a mixture of isomers of any ratio.

The compound represented by Formula (1) or Formula (2) may contain an asymmetric atom. There is no particular limitation with respect to the ratio of isomers related to this matter, and the compound may be present as a single isomer or a mixture of isomers of any ratio.

The compound represented by Formula (1) or Formula (2) may contain a geometric isomer. There is no particular limitation with respect to the ratio of isomers related to this matter, and the compound may be present as a single isomer or a mixture of isomers of any ratio.

The compound represented by Formula (1) or Formula (2) may form a salt. Examples of such salts include a salt with an acid, such as hydrochloric acid, sulfuric acid, acetic acid, fumaric acid and maleic acid; and a salt with a metal, such as sodium, potassium and calcium. There is no particular limitation with respect to the salt as long as the salt can be used as an agricultural and horticultural fungicide.

A compound within the scope of compounds obtainable by arbitrarily combining the above-explained R1, R2, R3, R4, R5, X, Y, substituent A, substituent B, substituent C, substituent D, substituent E, substituent F and substituent G each within the preferable scope is regarded as being described herein as a compound within the scope of the compound of the present invention represented by Formula (1) or Formula (2).

Next, specific compounds of the present invention are shown as combinations of the structural formulae given in Table 1 (P-1 to P-60, wherein X in the structural formulae is an oxygen atom or a sulfur atom and Z represents R3R4N—), Ys given in Table 2 (Y-1 to Y-456) and Zs given in Table 3 (Z-1 to Z-7854).

These compounds are shown only for illustrative purpose and the present invention is not limited to these compounds.

TABLE 1

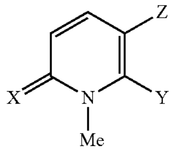
P-1

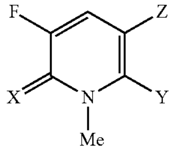
P-2

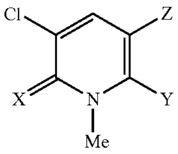
P-3

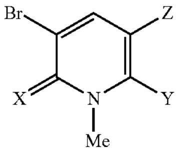
P-4

TABLE 1-continued

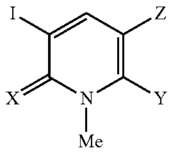
P-5

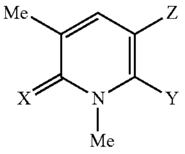
P-6

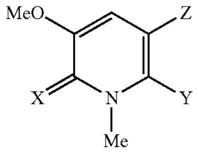
P-7

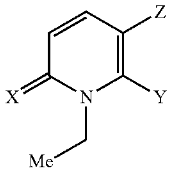
P-8

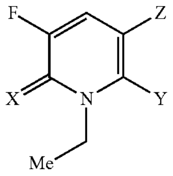
P-9

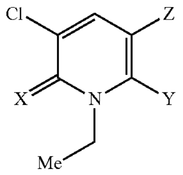
P-10

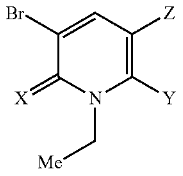
P-11

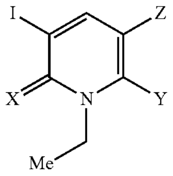
P-12

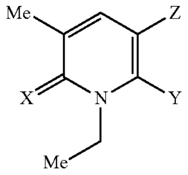
P-13

TABLE 1-continued
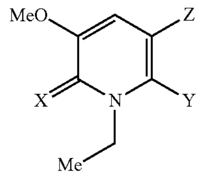
P-14
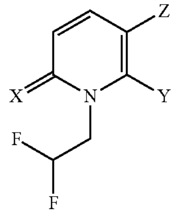
P-15
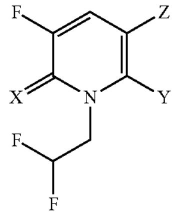
P-16
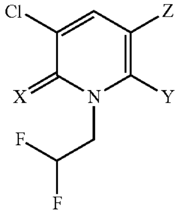
P-17
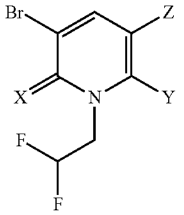
P-18
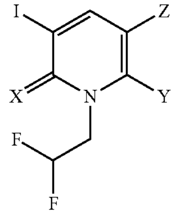
P-19
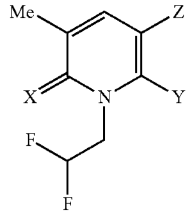
P-20
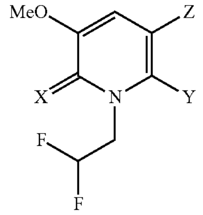
P-21
TABLE 1-continued
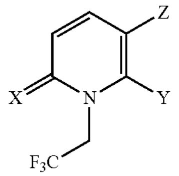
P-22
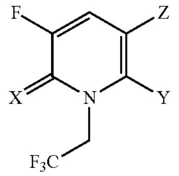
P-23
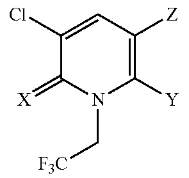
P-24
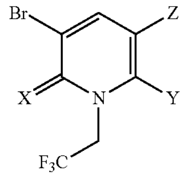
P-25
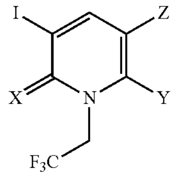
P-26
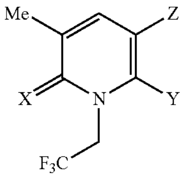
P-27
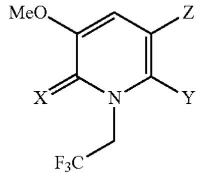
P-28
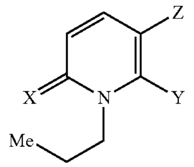
P-29
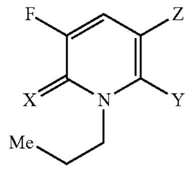
P-30

TABLE 1-continued
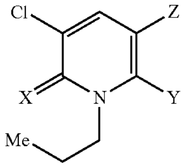
P-31
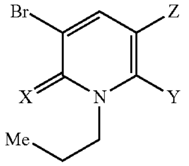
P-32
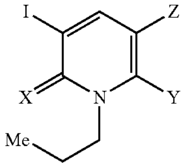
P-33
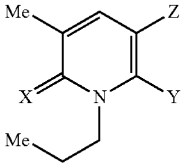
P-34
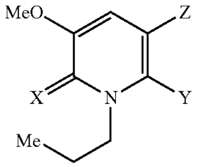
P-35
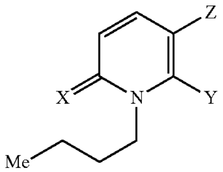
P-36
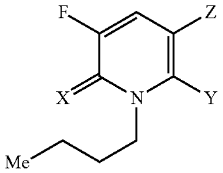
P-37
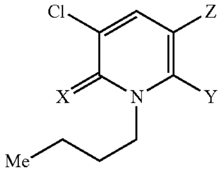
P-38
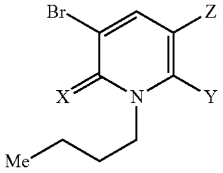
P-39
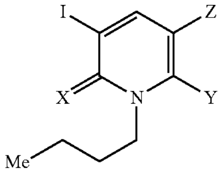
P-40
TABLE 1-continued
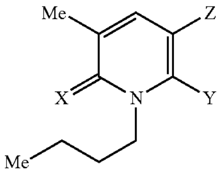
P-41
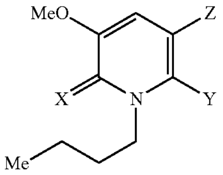
P-42
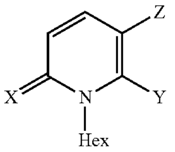
P-43
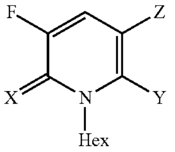
P-44
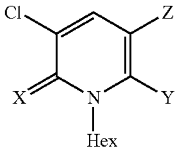
P-45
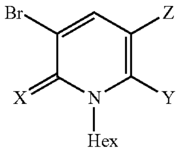
P-46
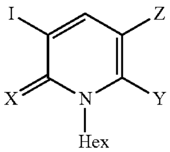
P-47
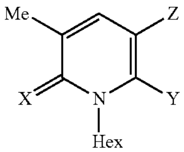
P-48
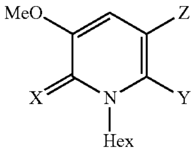
P-49
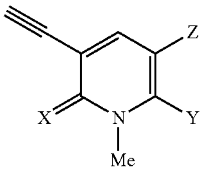
P-50

TABLE 1-continued
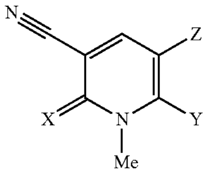
P-51
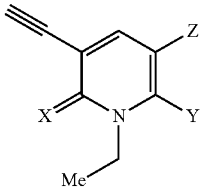
P-52
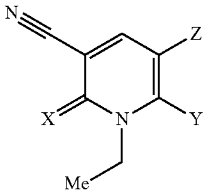
P-53
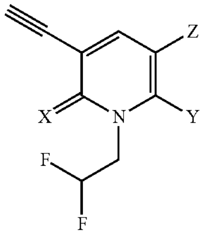
P-54
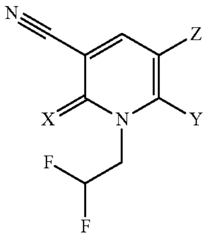
P-55
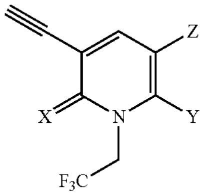
P-56
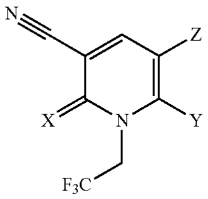
P-57
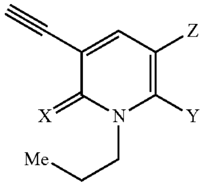
P-58
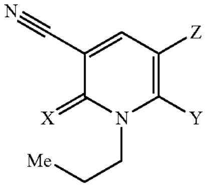
P-59
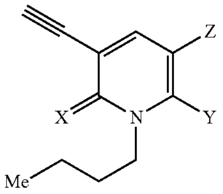
P-60
TABLE 2
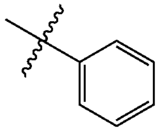 [SMILES: *c1ccccc1]
Y-1
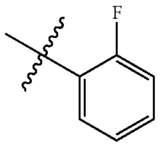 [SMILES: *c1ccccc1F]
Y-2
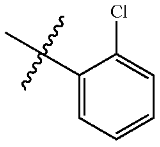
Y-3
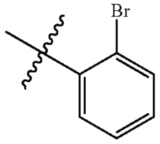
Y-4
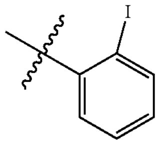 [SMILES: *c1ccccc1I]
Y-5
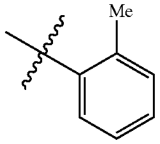 [SMILES: *c1ccccc1C]
Y-6
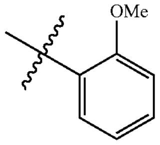 [SMILES: *c1ccccc1OC]
Y-7
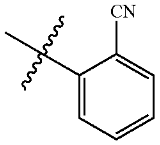 [SMILES: *c1ccccc1C#N]
Y-8

TABLE 2-continued
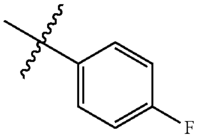 [SMILES: *c1ccc(F)cc1]
Y-9
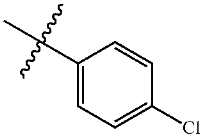 [SMILES: *c1ccc(Cl)cc1]
Y-10
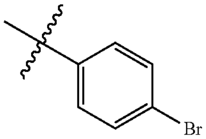 [SMILES: *c1ccc(Br)cc1]
Y-11
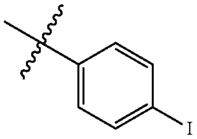 [SMILES: *c1ccc(I)cc1]
Y-12
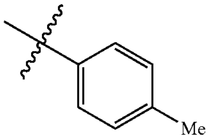 [SMILES: *c1ccc(C)cc1]
Y-13
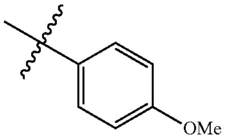 [SMILES: *c1ccc(OC)cc1]
Y-14
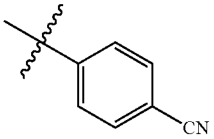 [SMILES: *c1ccc(C#N)cc1]
Y-15
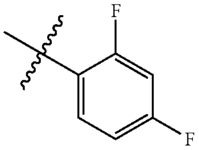 [SMILES: *c1ccc(F)cc1F]
Y-16
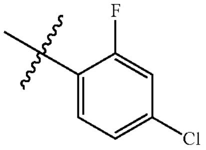 [SMILES: *c1ccc(Cl)cc1F]
Y-17
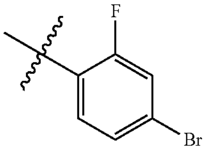 [SMILES: *c1ccc(Br)cc1F]
Y-18
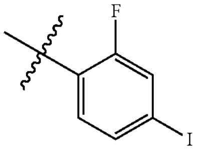 [SMILES: *c1ccc(I)cc1F]
Y-19
TABLE 2-continued
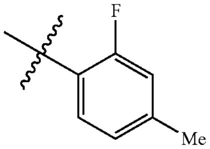 [SMILES: *c1ccc(C)cc1F]
Y-20
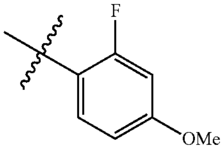 [SMILES: *c1ccc(OC)cc1F]
Y-21
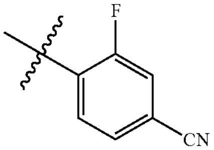 [SMILES: *c1ccc(C#N)cc1F]
Y-22
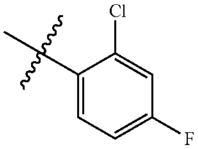 [SMILES: *c1ccc(F)cc1Cl]
Y-23
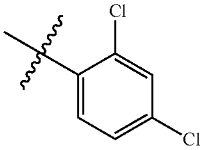 [SMILES: *c1ccc(Cl)cc1Cl]
Y-24
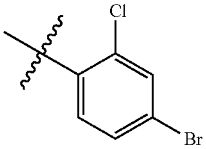 [SMILES: *c1ccc(Br)cc1Cl]
Y-25
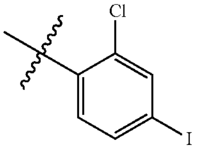 [SMILES: *c1ccc(I)cc1Cl]
Y-26
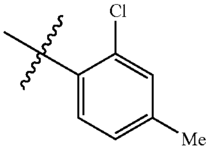 [SMILES: *c1ccc(C)cc1Cl]
Y-27
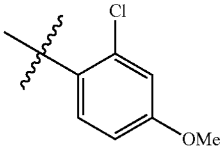 [SMILES: *c1ccc(OC)cc1Cl]
Y-28
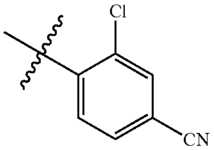 [SMILES: *c1ccc(C#N)cc1Cl]
Y-29
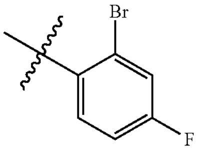
Y-30

TABLE 2-continued
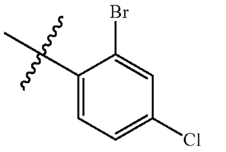 [SMILES: *c1ccc(Cl)cc1Br]
Y-31
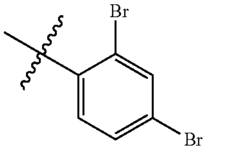 [SMILES: *c1ccc(Br)cc1Br]
Y-32
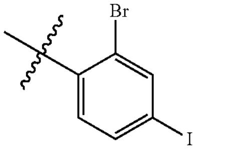 [SMILES: *c1ccc(I)cc1Br]
Y-33
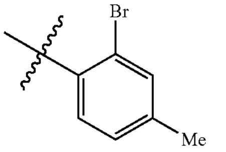 [SMILES: *c1ccc(C)cc1Br]
Y-34
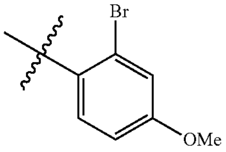 [SMILES: *c1ccc(OC)cc1Br]
Y-35
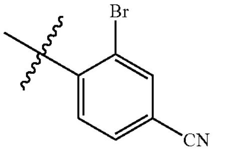 [SMILES: *c1ccc(C#N)cc1Br]
Y-36
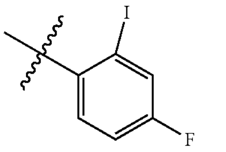 [SMILES: *c1ccc(F)cc1I]
Y-37
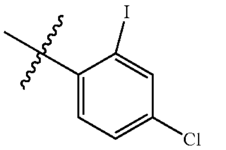 [SMILES: *c1ccc(Cl)cc1I]
Y-38
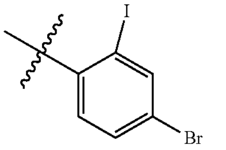 [SMILES: *c1ccc(Br)cc1I]
Y-39
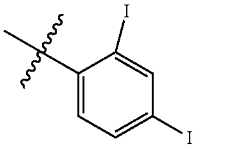 [SMILES: *c1ccc(I)cc1I]
Y-40
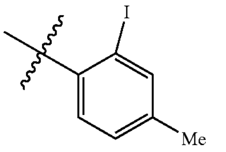 [SMILES: *c1ccc(C)cc1I]
Y-41
TABLE 2-continued
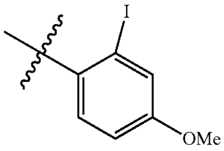 [SMILES: *c1ccc(OC)cc1I]
Y-42
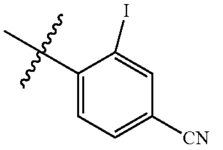 [SMILES: *c1ccc(C#N)cc1I]
Y-43
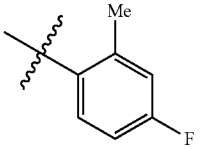 [SMILES: *c1ccc(F)cc1C]
Y-44
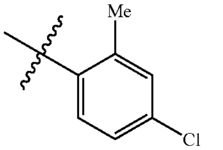
Y-45
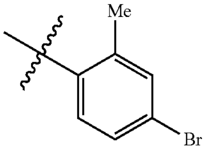 [SMILES: *c1ccc(Br)cc1C]
Y-46
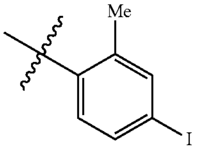 [SMILES: *c1ccc(I)cc1C]
Y-47
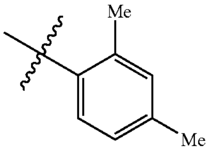 [SMILES: *c1ccc(C)cc1C]
Y-48
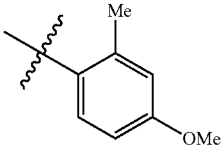 [SMILES: *c1ccc(OC)cc1C]
Y-49
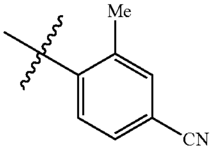 [SMILES: *c1ccc(C#N)cc1C]
Y-50
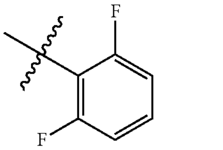 [SMILES: *c1c(F)cccc1F]
Y-51
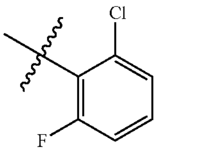
Y-52

TABLE 2-continued
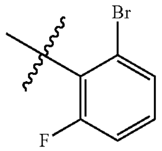
Y-53
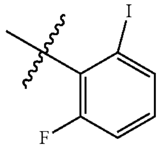
Y-54
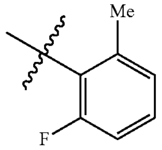
Y-55
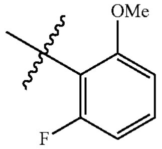
Y-56
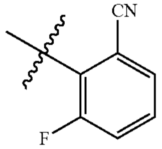
Y-57
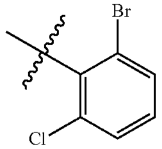 [SMILES: *c1c(Cl)cccc1Br]
Y-58
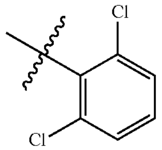 [SMILES: *c1c(Cl)cccc1Cl]
Y-59
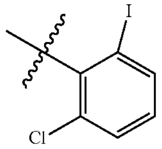
Y-60
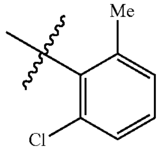
Y-61
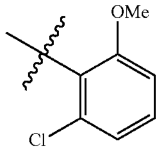
Y-62
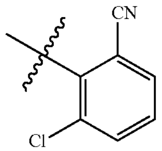
Y-63
TABLE 2-continued
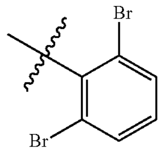
Y-64
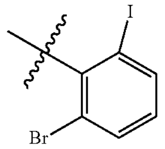 [SMILES: *c1c(Cl)cccc1I]
Y-65
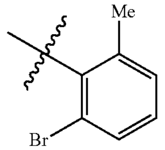 [SMILES: *c1c(C)cccc1Cl]
Y-66
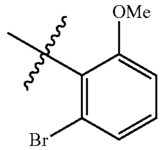 [SMILES: *c1c(Cl)cccc1OC]
Y-67
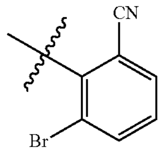 [SMILES: *c1c(Cl)cccc1C#N]
Y-68
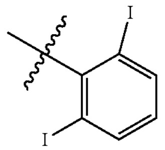 [SMILES: *c1c(I)cccc1I]
Y-69
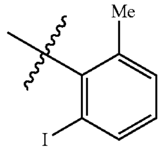 [SMILES: *c1c(C)cccc1I]
Y-70
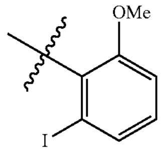 [SMILES: *c1c(I)cccc1OC]
Y-71
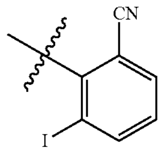 [SMILES: *c1c(I)cccc1C#N]
Y-72
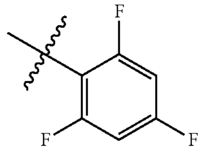 [SMILES: *c1c(F)cc(F)cc1F]
Y-73
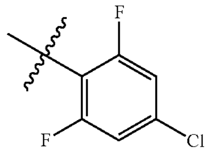 [SMILES: *c1c(F)cc(Cl)cc1F]
Y-74

TABLE 2-continued
Y-75
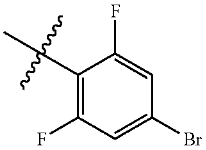 [SMILES: *c1c(F)cc(Br)cc1F]
Y-76
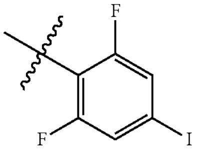 [SMILES: *c1c(F)cc(I)cc1F]
Y-77
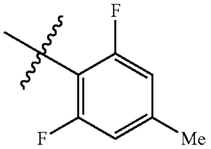 [SMILES: *c1c(F)cc(C)cc1F]
Y-78
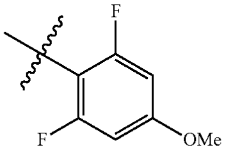 [SMILES: *c1c(F)cc(OC)cc1F]
Y-79
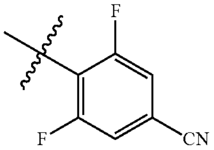 [SMILES: *c1c(F)cc(C#N)cc1F]
Y-80
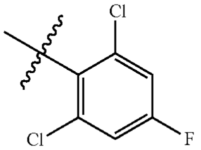 [SMILES: *c1c(Cl)cc(F)cc1Cl]
Y-81
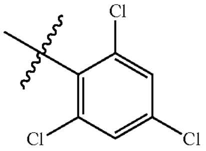 [SMILES: *c1c(Cl)cc(Cl)cc1Cl]
Y-82
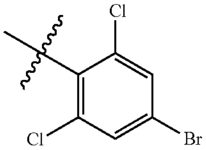 [SMILES: *c1c(Cl)cc(Br)cc1Cl]
Y-83
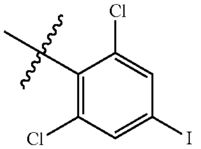 [SMILES: *c1c(Cl)cc(I)cc1Cl]
Y-84
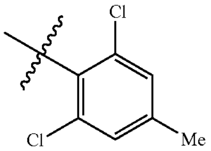 [SMILES: *c1c(Cl)cc(C)cc1Cl]
Y-85
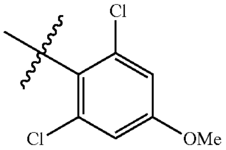 [SMILES: *c1c(Cl)cc(OC)cc1Cl]
TABLE 2-continued
Y-86
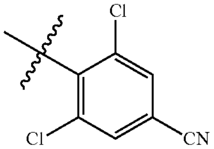 [SMILES: *c1c(Cl)cc(C#N)cc1Cl]
Y-87
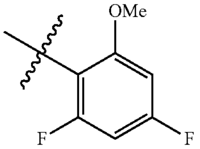 [SMILES: *c1c(F)cc(F)cc1OC]
Y-88
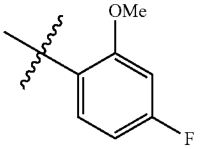 [SMILES: *c1ccc(F)cc1OC]
Y-89
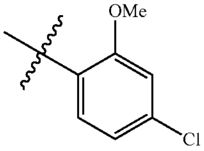 [SMILES: *c1ccc(Cl)cc1OC]
Y-90
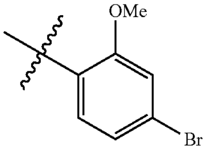 [SMILES: *c1ccc(Br)cc1OC]
Y-91
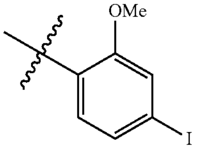 [SMILES: *c1ccc(I)cc1OC]
Y-92
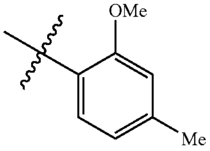 [SMILES: *c1ccc(C)cc1OC]
Y-93
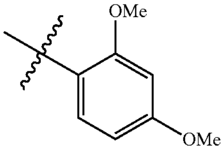 [SMILES: *c1ccc(OC)cc1OC]
Y-94
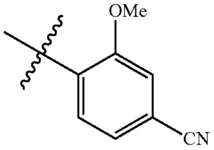 [SMILES: *c1ccc(C#N)cc1OC]
Y-95
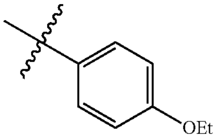 [SMILES: *c1ccc(OCC)cc1]
Y-96
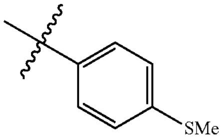 [SMILES: *c1ccc(SC)cc1]

TABLE 2-continued
Y-97
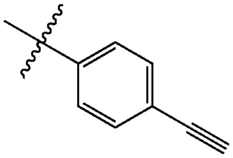 [SMILES: *c1ccc(C#C)cc1]
Y-98
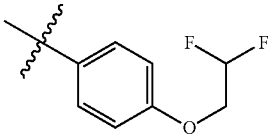 [SMILES: *c1ccc(OCC(F)F)cc1]
Y-99
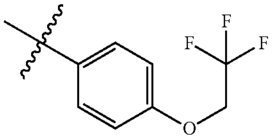 [SMILES: *c1ccc(OCC(F)(F)F)cc1]
Y-100
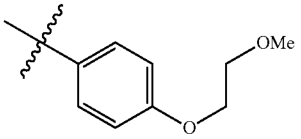 [SMILES: *c1ccc(OCCOC)cc1]
Y-101
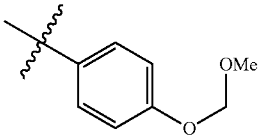 [SMILES: *c1ccc(OCOC)cc1]
Y-102
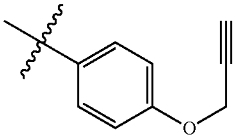 [SMILES: *c1ccc(OCC#C)cc1]
Y-103
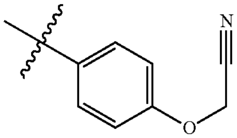 [SMILES: *c1ccc(OCC#N)cc1]
Y-104
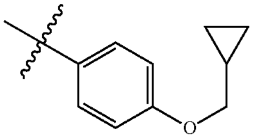 [SMILES: *c1ccc(OCC2CC2)cc1]
Y-105
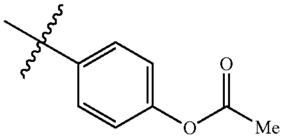 [SMILES: *c1ccc(OC(C)=O)cc1]
Y-106
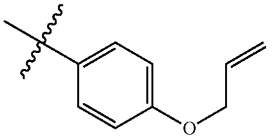 [SMILES: *c1ccc(OCC=C)cc1]
Y-107
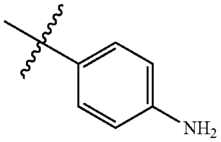 [SMILES: *c1ccc(N)cc1]
Y-108
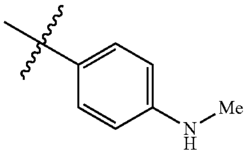 [SMILES: *c1ccc(NC)cc1]
TABLE 2-continued
Y-109
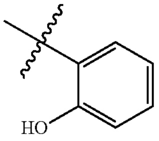 [SMILES: *c1ccccc1O]
Y-110
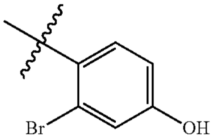
Y-111
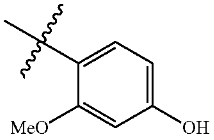 [SMILES: *c1ccc(O)cc1OC]
Y-112
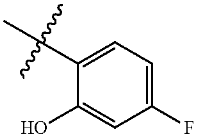
Y-113
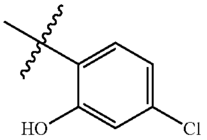 [SMILES: *c1ccc(Cl)cc1O]
Y-114
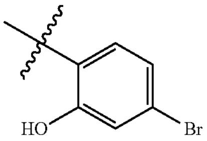 [SMILES: *c1ccc(Br)cc1O]
Y-115
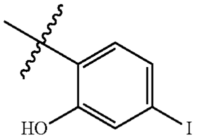
Y-116
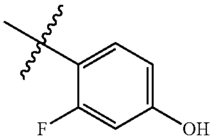
Y-117
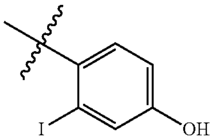 [SMILES: *c1ccc(O)cc1I]
Y-118
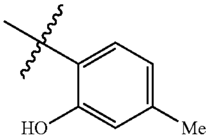 [SMILES: *c1ccc(C)cc1O]
Y-119
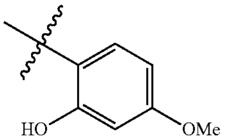
Y-120
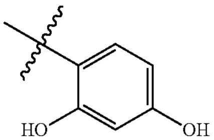

TABLE 2-continued
Y-121
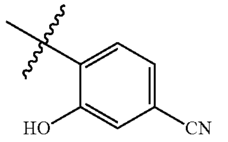
Y-122
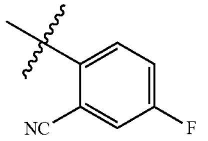 [SMILES: *c1ccc(F)cc1C#N]
Y-123
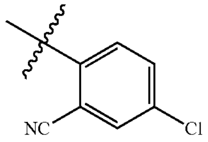 [SMILES: *c1ccc(Cl)cc1C#N]
Y-124
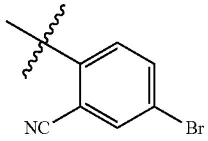 [SMILES: *c1ccc(Br)cc1C#N]
Y-125
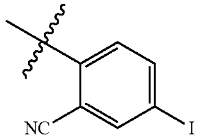 [SMILES: *c1ccc(I)cc1C#N]
Y-126
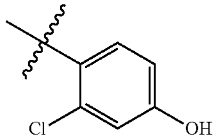 [SMILES: *c1ccc(O)cc1Cl]
Y-127
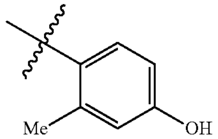 [SMILES: *c1ccc(O)cc1C]
Y-128
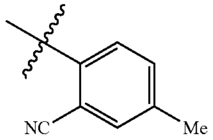 [SMILES: *c1ccc(C)cc1C#N]
Y-129
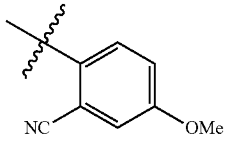 [SMILES: *c1ccc(OC)cc1C#N]
Y-130
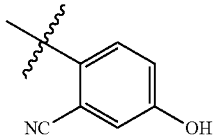 [SMILES: *c1ccc(O)cc1C#N]
Y-131
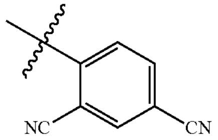 [SMILES: *c1ccc(C#N)cc1C#N]
Y-132
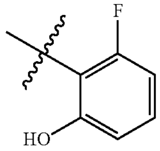 [SMILES: *c1c(O)cccc1F]
TABLE 2-continued
Y-133
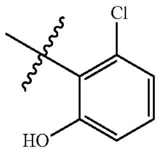
Y-134
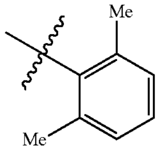 [SMILES: *c1c(C)cccc1C]
Y-135
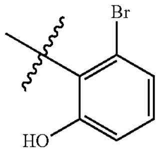 [SMILES: *c1c(O)cccc1Br]
Y-136
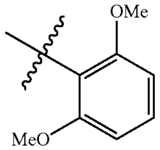 [SMILES: *c1c(OC)cccc1OC]
Y-137
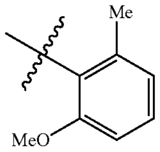 [SMILES: *c1c(C)cccc1OC]
Y-138
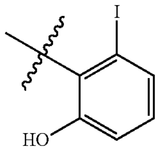 [SMILES: *c1c(O)cccc1I]
Y-139
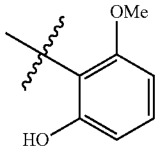
Y-140
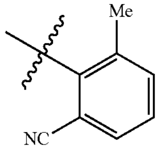 [SMILES: *c1c(C)cccc1C#N]
Y-141
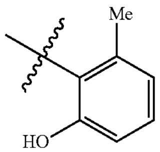
Y-142
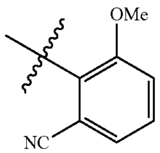
Y-143
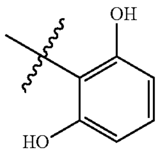

TABLE 2-continued
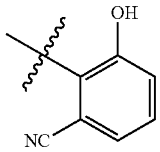 [SMILES: *c1c(O)cccc1C#N]
Y-144
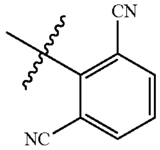 [SMILES: *c1c(C#N)cccc1C#N]
Y-145
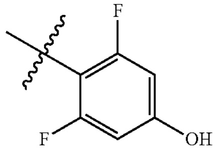 [SMILES: *c1c(F)cc(O)cc1F]
Y-146
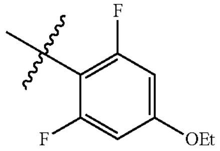 [SMILES: *c1c(F)cc(OCC)cc1F]
Y-147
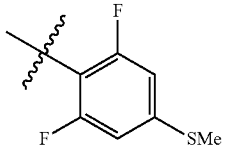 [SMILES: *c1c(F)cc(SC)cc1F]
Y-148
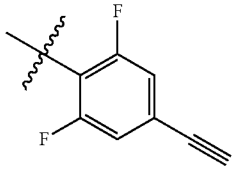 [SMILES: *c1c(F)cc(C#C)cc1F]
Y-149
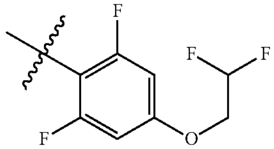 [SMILES: *c1c(F)cc(OCC(F)F)cc1F]
Y-150
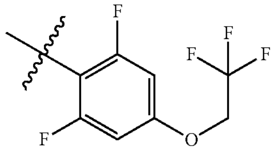 [SMILES: *c1c(F)cc(OCC(F)(F)F)cc1F]
Y-151
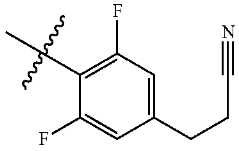 [SMILES: *c1c(F)cc(CCC#N)cc1F]
Y-152
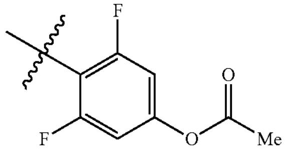 [SMILES: *c1c(F)cc(OC(C)=O)cc1F]
Y-153
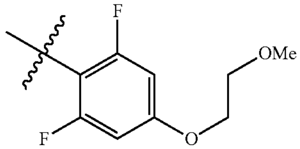 [SMILES: *c1c(F)cc(OCCOC)cc1F]
Y-154
TABLE 2-continued
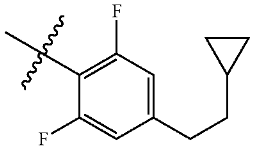 [SMILES: *c1c(F)cc(CCC2CC2)cc1F]
Y-155
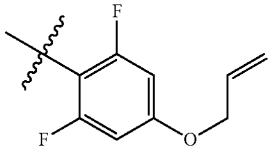 [SMILES: *c1c(F)cc(OCC=C)cc1F]
Y-156
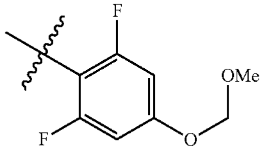 [SMILES: *c1c(F)cc(OCOC)cc1F]
Y-157
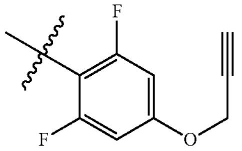 [SMILES: *c1c(F)cc(OCC#C)cc1F]
Y-158
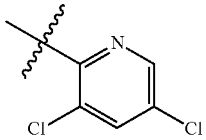 [SMILES: *c1ncc(Cl)cc1Cl]
Y-159
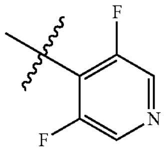
Y-160
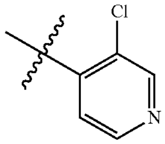
Y-161
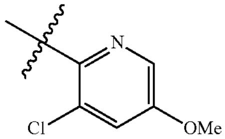 [SMILES: *c1ncc(OC)cc1Cl]
Y-162
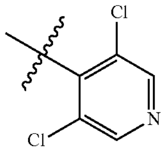
Y-163
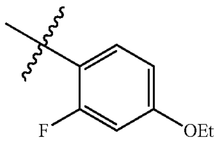
Y-164
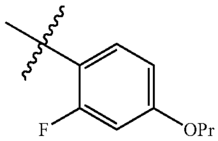 [SMILES: *c1ccc(OCC)cc1F]
Y-165

TABLE 2-continued
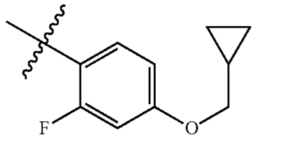 [SMILES: *c1ccc(OCC2CC2)cc1F]
Y-166
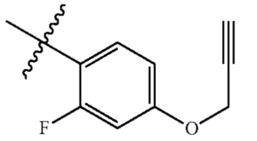
Y-167
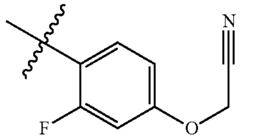
Y-168
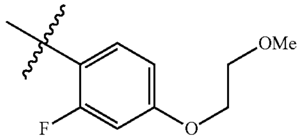
Y-169
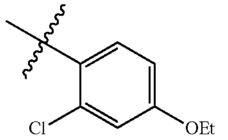 [SMILES: *c1ccc(OCC)cc1Cl]
Y-170
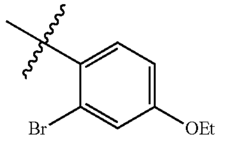 [SMILES: *c1ccc(OCC)cc1Br]
Y-171
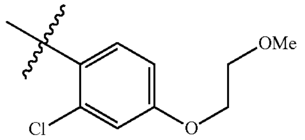 [SMILES: *c1ccc(OCCOC)cc1Cl]
Y-172
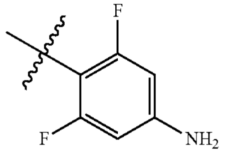
Y-173
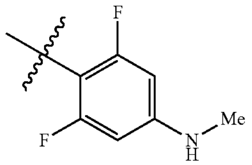 [SMILES: *c1c(F)cc(NC)cc1F]
Y-174
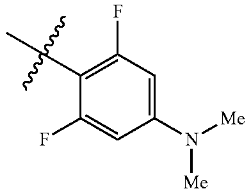
Y-175
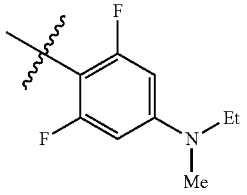
Y-176
TABLE 2-continued
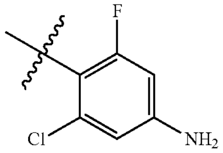 [SMILES: *c1c(F)cc(N)cc1Cl]
Y-177
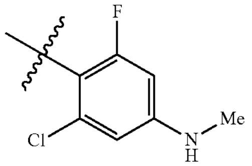 [SMILES: *c1c(F)cc(NC)cc1Cl]
Y-178
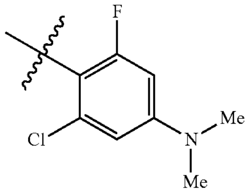 [SMILES: *c1c(F)cc(N(C)C)cc1Cl]
Y-179
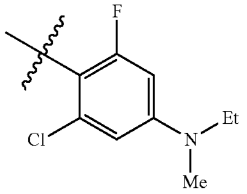 [SMILES: *c1c(F)cc(N(C)CC)cc1Cl]
Y-180
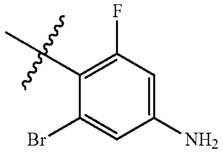 [SMILES: *c1c(F)cc(N)cc1Br]
Y-181
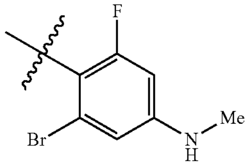 [SMILES: *c1c(F)cc(NC)cc1Br]
Y-182
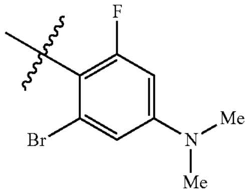 [SMILES: *c1c(F)cc(N(C)C)cc1Br]
Y-183
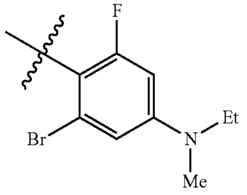 [SMILES: *c1c(F)cc(N(C)CC)cc1Br]
Y-184
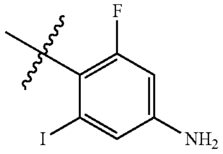 [SMILES: *c1c(F)cc(N)cc1I]
Y-185

TABLE 2-continued
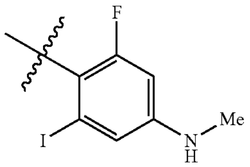 [SMILES: *c1c(F)cc(NC)cc1I]
Y-186
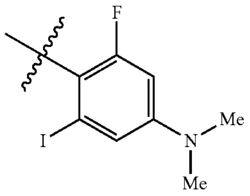 [SMILES: *c1c(F)cc(N(C)C)cc1I]
Y-187
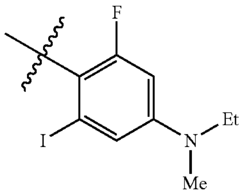 [SMILES: *c1c(F)cc(N(C)CC)cc1I]
Y-188
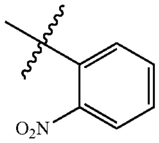 [SMILES: *c1ccccc1[N+](=O)[O-]]
Y-189
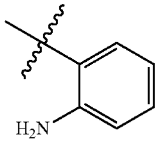
Y-190
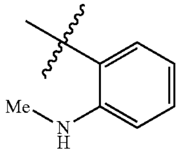 [SMILES: *c1ccccc1NC]
Y-191
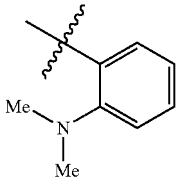 [SMILES: *c1ccccc1N(C)C]
Y-192
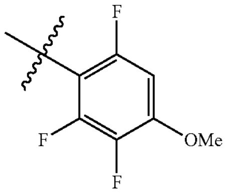 [SMILES: *c1c(F)cc(OC)c(F)c1F]
Y-193
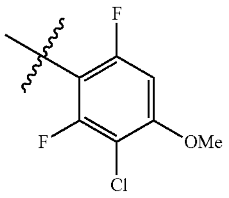 [SMILES: *c1c(F)cc(OC)c(Cl)c1F]
Y-194
TABLE 2-continued
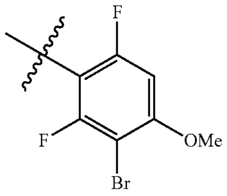 [SMILES: *c1c(F)cc(OC)c(Br)c1F]
Y-195
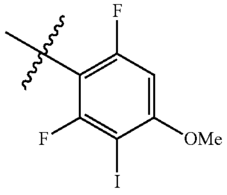 [SMILES: *c1c(F)cc(OC)c(I)c1F]
Y-196
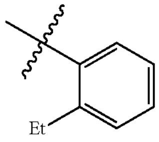 [SMILES: *c1ccccc1CC]
Y-197
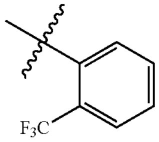
Y-198
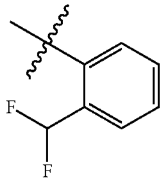 [SMILES: *c1ccccc1C(F)F]
Y-199
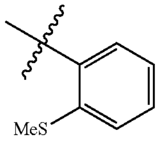 [SMILES: *c1ccccc1SC]
Y-200
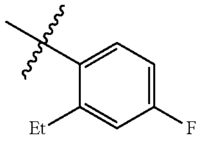 [SMILES: *c1ccc(F)cc1CC]
Y-201
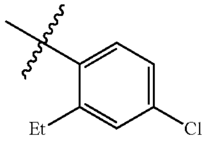 [SMILES: *c1ccc(Cl)cc1CC]
Y-202
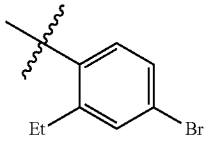 [SMILES: *c1ccc(Br)cc1CC]
Y-203
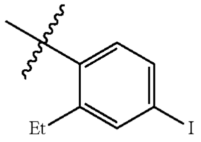 [SMILES: *c1ccc(I)cc1CC]
Y-204
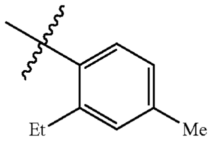 [SMILES: *c1ccc(C)cc1CC]
Y-205

TABLE 2-continued
Y-206
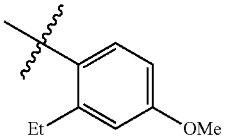 [SMILES: *c1ccc(OC)cc1CC]
Y-207
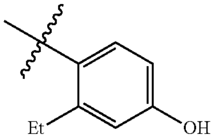
Y-208
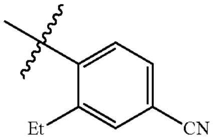 [SMILES: *c1ccc(C#N)cc1CC]
Y-209
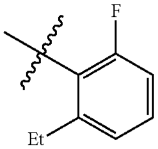 [SMILES: *c1c(F)cccc1CC]
Y-210
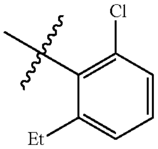 [SMILES: *c1c(Cl)cccc1CC]
Y-211
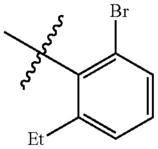 [SMILES: *c1c(Br)cccc1CC]
Y-212
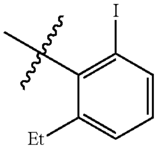 [SMILES: *c1c(I)cccc1CC]
Y-213
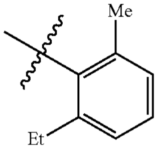 [SMILES: *c1c(C)cccc1CC]
Y-214
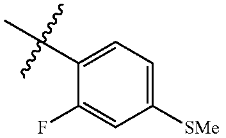
Y-215
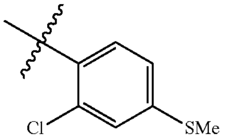
Y-216
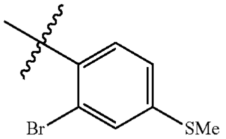 [SMILES: *c1ccc(SC)cc1Br]
TABLE 2-continued
Y-217
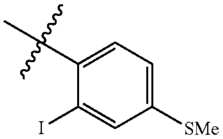 [SMILES: *c1ccc(SC)cc1I]
Y-218
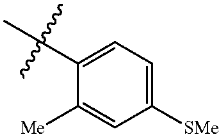 [SMILES: *c1ccc(SC)cc1C]
Y-219
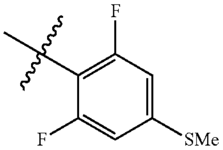 [SMILES: *c1c(F)cc(SC)cc1F]
Y-220
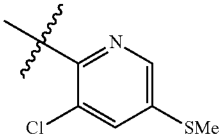 [SMILES: *c1ncc(SC)cc1Cl]
Y-221
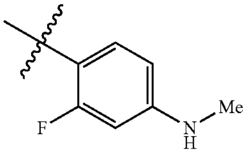
Y-222
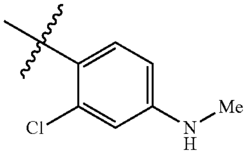 [SMILES: *c1ccc(NC)cc1Cl]
Y-223
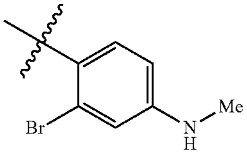
Y-224
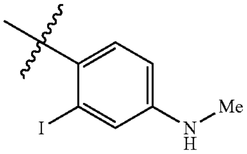 [SMILES: *c1ccc(NC)cc1I]
Y-225
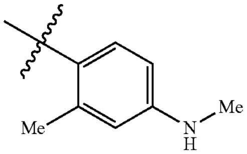
Y-226
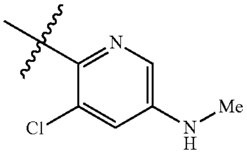 [SMILES: *c1ncc(NC)cc1Cl]
Y-227
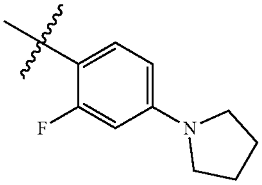

TABLE 2-continued
Y-228
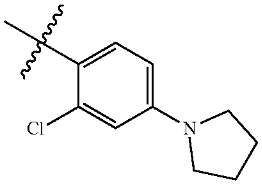
Y-229
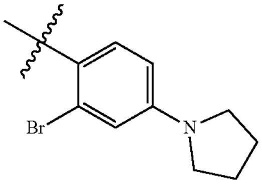 [SMILES: *c1ccc(N2CCCC2)cc1Br]
Y-230
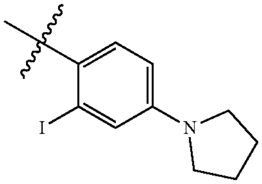 [SMILES: *c1ccc(N2CCCC2)cc1I]
Y-231
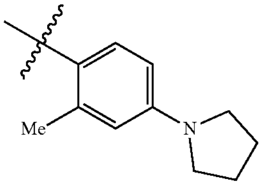 [SMILES: *c1ccc(N2CCCC2)cc1C]
Y-232
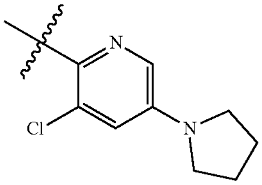 [SMILES: *c1ncc(N2CCCC2)cc1Cl]
Y-233
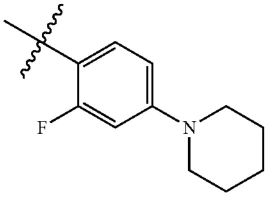
Y-234
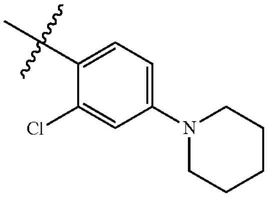 [SMILES: *c1ccc(N2CCCCC2)cc1Cl]
Y-235
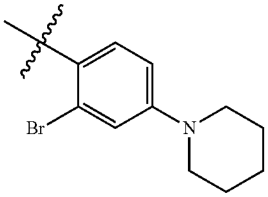 [SMILES: *c1ccc(N2CCCCC2)cc1Br]
Y-236
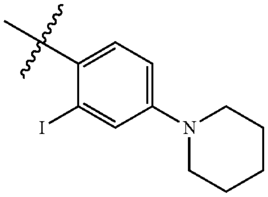 [SMILES: *c1ccc(N2CCCCC2)cc1I]
TABLE 2-continued
Y-237
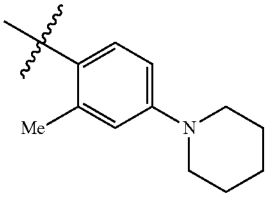 [SMILES: *c1ccc(N2CCCCC2)cc1C]
Y-238
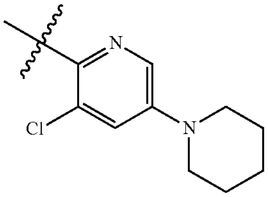 [SMILES: *c1ncc(N2CCCCC2)cc1Cl]
Y-239
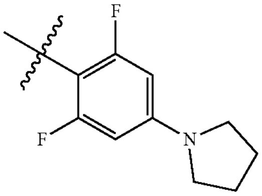 [SMILES: *c1c(F)cc(N2CCCC2)cc1F]
Y-240
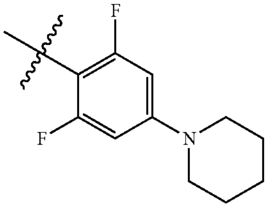 [SMILES: *c1c(F)cc(N2CCCCC2)cc1F]
Y-241
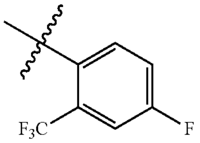 [SMILES: *c1ccc(F)cc1C(F)(F)F]
Y-242
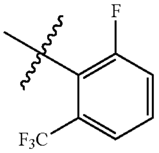 [SMILES: *c1c(F)cccc1C(F)(F)F]
Y-243
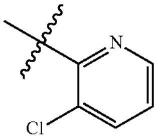
Y-244
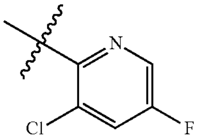 [SMILES: *c1ncc(F)cc1Cl]
Y-245
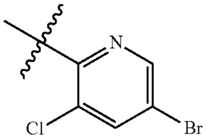 [SMILES: *c1ncc(Br)cc1Cl]
Y-246
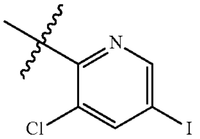 [SMILES: *c1ncc(I)cc1Cl]

TABLE 2-continued
Y-247
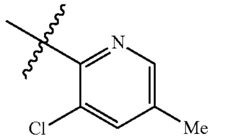 [SMILES: *c1ncc(C)cc1Cl]
Y-248
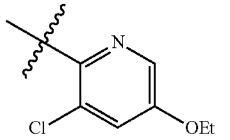 [SMILES: *c1ncc(OCC)cc1Cl]
Y-249
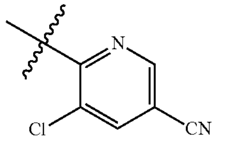 [SMILES: *c1ncc(C#N)cc1Cl]
Y-250
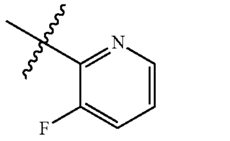 [SMILES: *c1ncccc1F]
Y-251
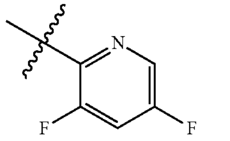 [SMILES: *c1ncc(F)cc1F]
Y-252
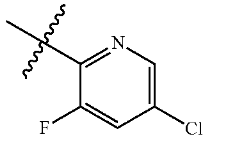 [SMILES: *c1ncc(Cl)cc1F]
Y-253
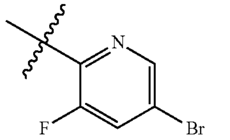 [SMILES: *c1ncc(Br)cc1F]
Y-254
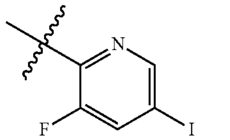 [SMILES: *c1ncc(I)cc1F]
Y-255
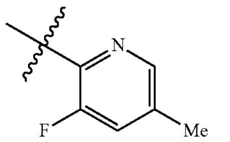 [SMILES: *c1ncc(C)cc1F]
Y-256
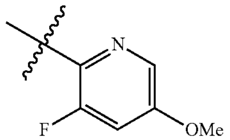 [SMILES: *c1ncc(OC)cc1F]
Y-257
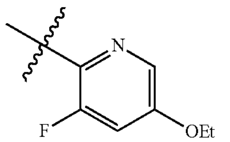
Y-258
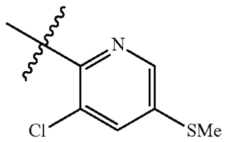 [SMILES: *c1ncc(SC)cc1Cl]
TABLE 2-continued
Y-259
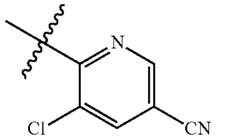 [SMILES: *c1ncc(C#N)cc1Cl]
Y-260
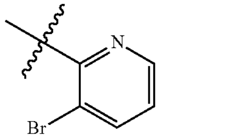 [SMILES: *c1ncccc1Br]
Y-261
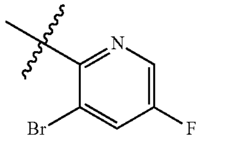 [SMILES: *c1ncc(F)cc1Br]
Y-262
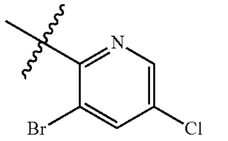
Y-263
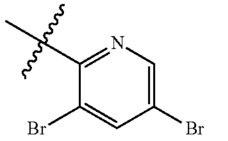 [SMILES: *c1ncc(Br)cc1Br]
Y-264
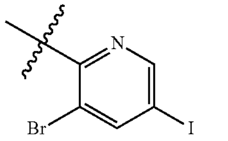 [SMILES: *c1ncc(I)cc1Br]
Y-265
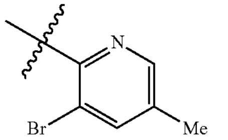 [SMILES: *c1ncc(C)cc1Br]
Y-266
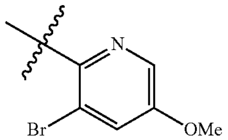
Y-267
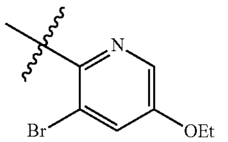
Y-268
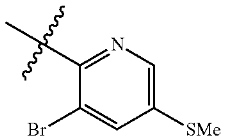
Y-269
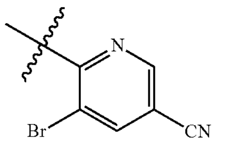
Y-270
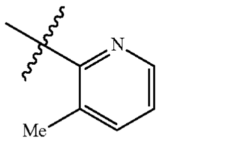 [SMILES: *c1ncccc1C]

TABLE 2-continued
Y-271
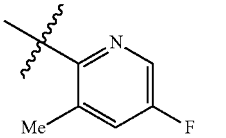 [SMILES: *c1ncc(F)cc1C]
Y-272
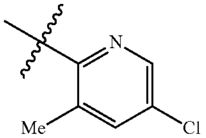 [SMILES: *c1ncc(Cl)cc1C]
Y-273
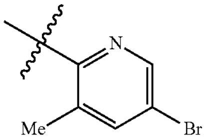 [SMILES: *c1ncc(Br)cc1C]
Y-274
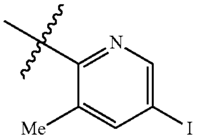 [SMILES: *c1ncc(I)cc1C]
Y-275
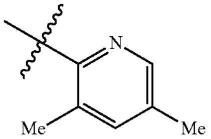 [SMILES: *c1ncc(C)cc1C]
Y-276
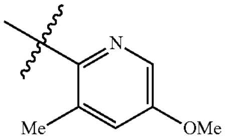 [SMILES: *c1ncc(OC)cc1C]
Y-277
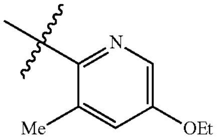 [SMILES: *c1ncc(OCC)cc1C]
Y-278
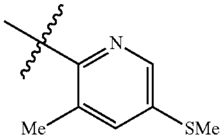 [SMILES: *c1ncc(SC)cc1C]
Y-279
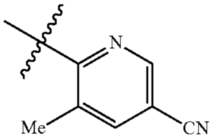
Y-280
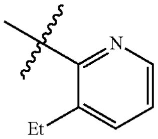 [SMILES: *c1ncccc1CC]
Y-281
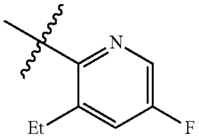 [SMILES: *c1ncc(F)cc1CC]
Y-282
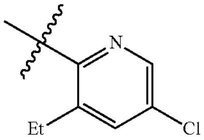 [SMILES: *c1ncc(Cl)cc1CC]
TABLE 2-continued
Y-283
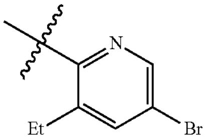 [SMILES: *c1ncc(Br)cc1CC]
Y-284
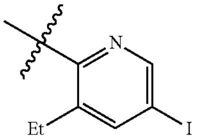
Y-285
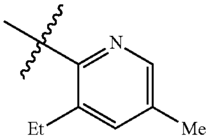 [SMILES: *c1ncc(C)cc1CC]
Y-286
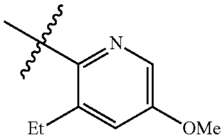 [SMILES: *c1ncc(OC)cc1CC]
Y-287
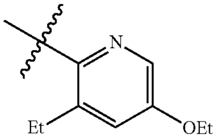
Y-288
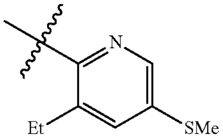
Y-289
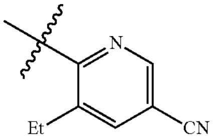 [SMILES: *c1ncc(C#N)cc1CC]
Y-290
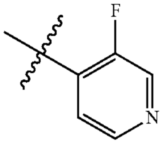 [SMILES: *c1ccncc1F]
Y-291
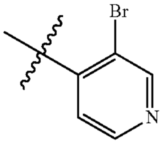
Y-292
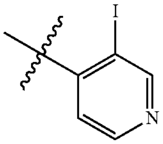 [SMILES: *c1ccncc1I]
Y-293
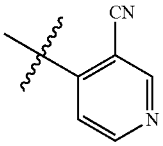 [SMILES: *c1ccncc1C#N]
Y-294
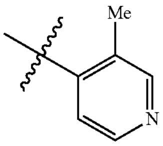 [SMILES: *c1ccncc1C]

TABLE 2-continued
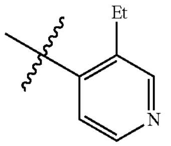 [SMILES: *c1ccncc1CC]
Y-295
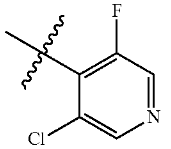 [SMILES: *c1c(F)cncc1Cl]
Y-296
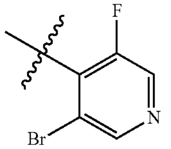
Y-297
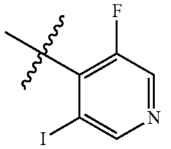
Y-298
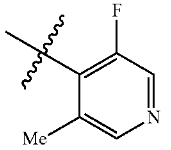
Y-299
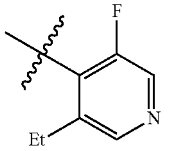
Y-300
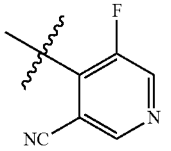
Y-301
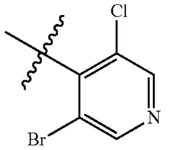
Y-302
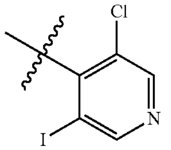 [SMILES: *c1c(Cl)cncc1I]
Y-303
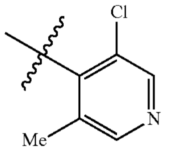 [SMILES: *c1c(C)cncc1Cl]
Y-304
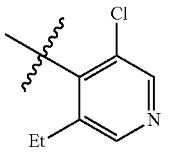
Y-305
TABLE 2-continued
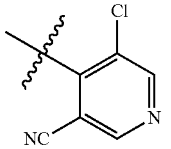 [SMILES: *c1c(Cl)cncc1C#N]
Y-306
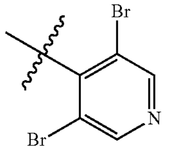
Y-307
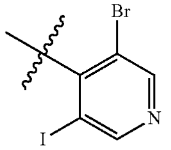 [SMILES: *c1c(Br)cncc1I]
Y-308
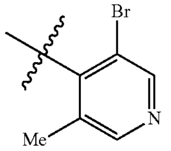 [SMILES: *c1c(C)cncc1Br]
Y-309
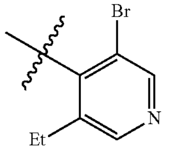 [SMILES: *c1c(Br)cncc1CC]
Y-310
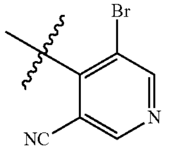 [SMILES: *c1c(Br)cncc1C#N]
Y-311
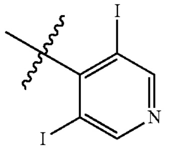 [SMILES: *c1c(I)cncc1I]
Y-312
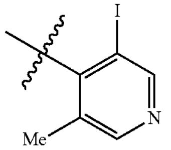 [SMILES: *c1c(C)cncc1I]
Y-313
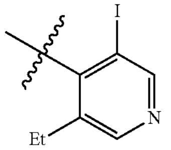 [SMILES: *c1c(I)cncc1CC]
Y-314
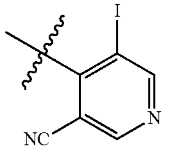 [SMILES: *c1c(I)cncc1C#N]
Y-315
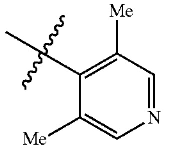 [SMILES: *c1c(C)cncc1C]
Y-316

TABLE 2-continued
Y-317
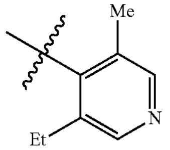 [SMILES: *c1c(C)cncc1CC]
Y-318
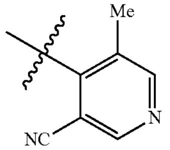 [SMILES: *c1c(C)cncc1C#N]
Y-319
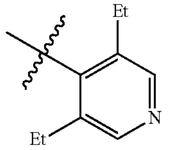
Y-320
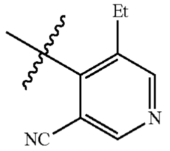 [SMILES: *c1c(C#N)cncc1CC]
Y-321
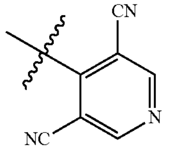 [SMILES: *c1c(C#N)cncc1C#N]
Y-322
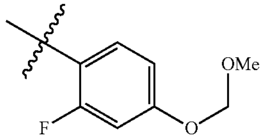 [SMILES: *c1ccc(OCOC)cc1F]
Y-323
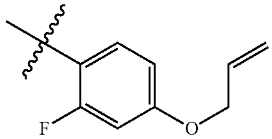
Y-324
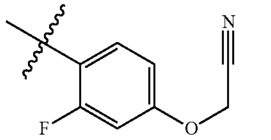
Y-325
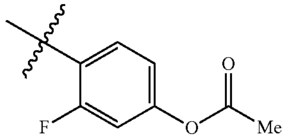
Y-326
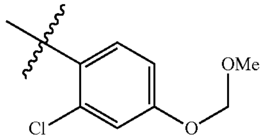 [SMILES: *c1ccc(OCOC)cc1Cl]
Y-327
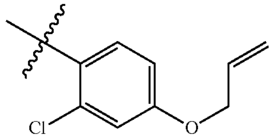 [SMILES: *c1ccc(OCC=C)cc1Cl]
Y-328
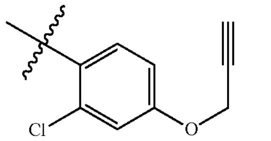 [SMILES: *c1ccc(OCC#C)cc1Cl]
TABLE 2-continued
Y-329
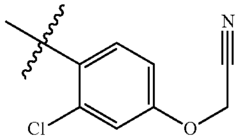 [SMILES: *c1ccc(OCC#N)cc1Cl]
Y-330
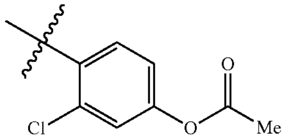 [SMILES: *c1ccc(OC(C)=O)cc1Cl]
Y-331
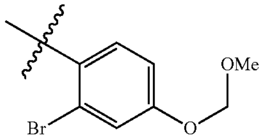 [SMILES: *c1ccc(OCOC)cc1Br]
Y-332
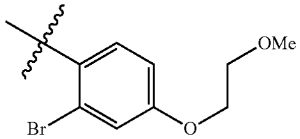
Y-333
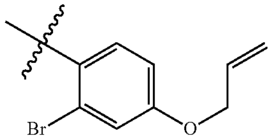 [SMILES: *c1ccc(OCC=C)cc1Br]
Y-334
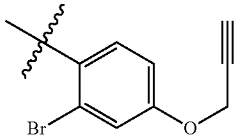 [SMILES: *c1ccc(OCC#C)cc1Br]
Y-335
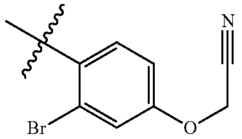 [SMILES: *c1ccc(OCC#N)cc1Br]
Y-336
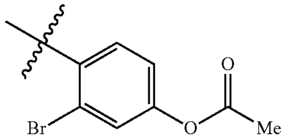 [SMILES: *c1ccc(OC(C)=O)cc1Br]
Y-337
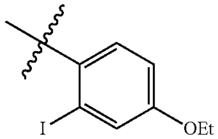 [SMILES: *c1ccc(OCC)cc1I]
Y-338
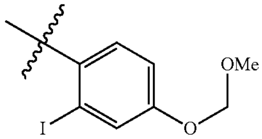 [SMILES: *c1ccc(OCOC)cc1I]
Y-339
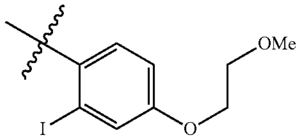 [SMILES: *c1ccc(OCCOC)cc1I]
Y-340
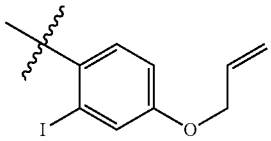 [SMILES: *c1ccc(OCC=C)cc1I]

TABLE 2-continued
Y-341
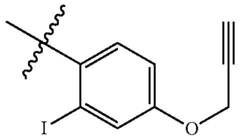
Y-342
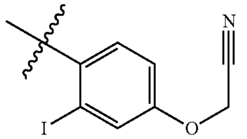 [SMILES: *c1ccc(OCC#N)cc1I]
Y-343
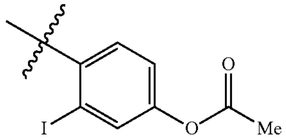 [SMILES: *c1ccc(OC(C)=O)cc1I]
Y-344
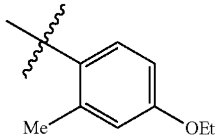
Y-345
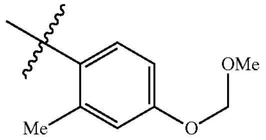 [SMILES: *c1ccc(OCOC)cc1C]
Y-346
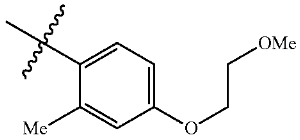 [SMILES: *c1ccc(OCCOC)cc1C]
Y-347
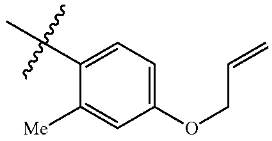 [SMILES: *c1ccc(OCC=C)cc1C]
Y-348
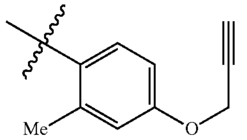 [SMILES: *c1ccc(OCC#C)cc1C]
Y-349
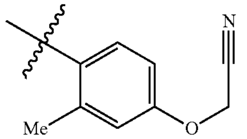 [SMILES: *c1ccc(OCC#N)cc1C]
Y-350
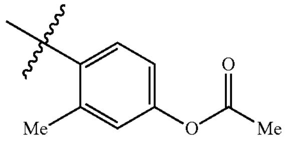 [SMILES: *c1ccc(OC(C)=O)cc1C]
Y-351
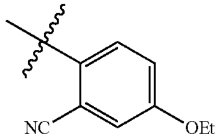
Y-352
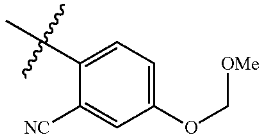 [SMILES: *c1ccc(OCOC)cc1C#N]
TABLE 2-continued
Y-353
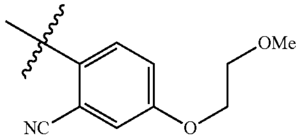 [SMILES: *c1ccc(OCCOC)cc1C#N]
Y-354
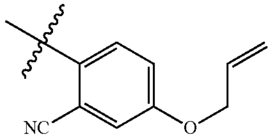 [SMILES: *c1ccc(OCC=C)cc1C#N]
Y-355
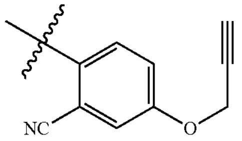
Y-356
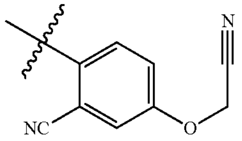 [SMILES: *c1ccc(OCC#N)cc1C#N]
Y-357
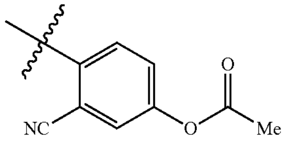 [SMILES: *c1ccc(OC(C)=O)cc1C#N]
Y-358
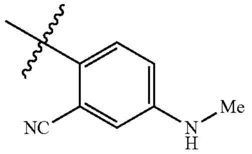 [SMILES: *c1ccc(NC)cc1C#N]
Y-359
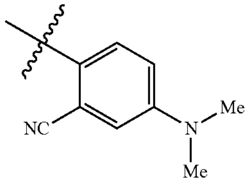 [SMILES: *c1ccc(N(C)C)cc1C#N]
Y-360
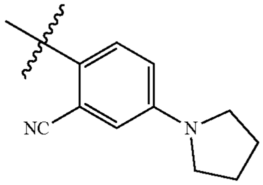 [SMILES: *c1ccc(N2CCCC2)cc1C#N]
Y-361
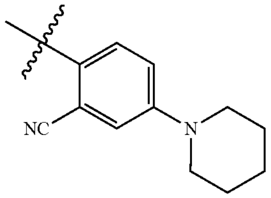 [SMILES: *c1ccc(N2CCCCC2)cc1C#N]
Y-362
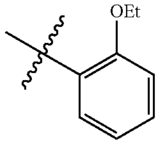 [SMILES: *c1ccccc1OCC]
Y-363
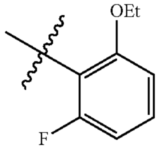

TABLE 2-continued
Y-364
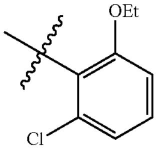 [SMILES: *c1c(Cl)cccc1OCC]
Y-365
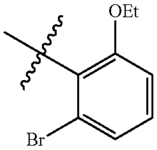 [SMILES: *c1c(Br)cccc1OCC]
Y-366
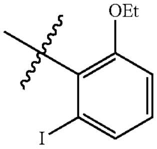 [SMILES: *c1c(I)cccc1OCC]
Y-367
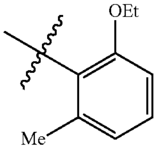 [SMILES: *c1c(C)cccc1OCC]
Y-368
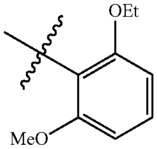 [SMILES: *c1c(OC)cccc1OCC]
Y-369
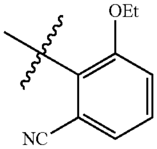
Y-370
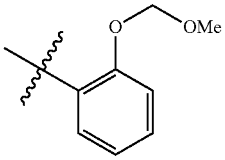 [SMILES: *c1ccccc1OCOC]
Y-371
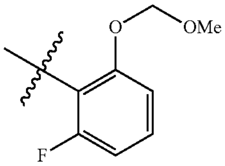
Y-372
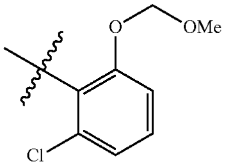 [SMILES: *c1c(Cl)cccc1OCOC]
Y-373
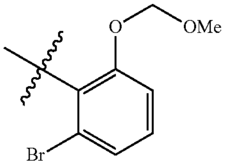 [SMILES: *c1c(Br)cccc1OCOC]
Y-374
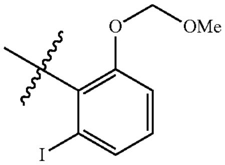 [SMILES: *c1c(I)cccc1OCOC]
TABLE 2-continued
Y-375
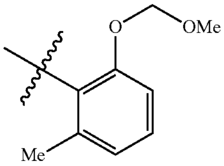 [SMILES: *c1c(C)cccc1OCOC]
Y-376
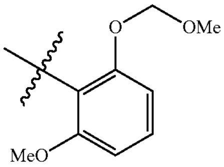 [SMILES: *c1c(OC)cccc1OCOC]
Y-377
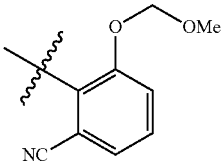 [SMILES: *c1c(C#N)cccc1OCOC]
Y-378
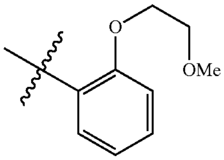 [SMILES: *c1ccccc1OCCOC]
Y-379
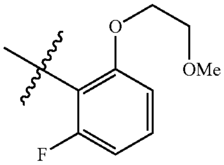
Y-380
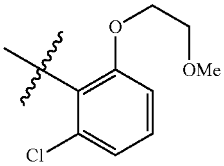 [SMILES: *c1c(Cl)cccc1OCCOC]
Y-381
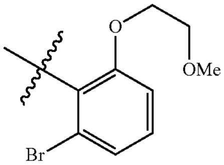 [SMILES: *c1c(Br)cccc1OCCOC]
Y-382
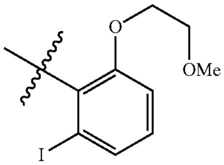 [SMILES: *c1c(I)cccc1OCCOC]
Y-383
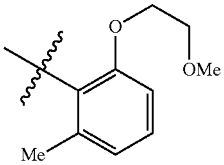 [SMILES: *c1c(C)cccc1OCCOC]
Y-384
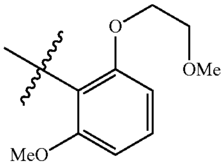 [SMILES: *c1c(OC)cccc1OCCOC]

TABLE 2-continued
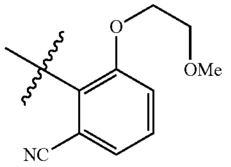 [SMILES: *c1c(C#N)cccc1OCCOC]
Y-385
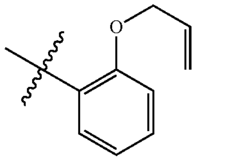 [SMILES: *c1ccccc1OCC=C]
Y-386
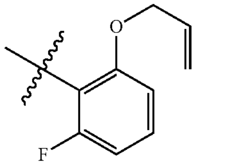 [SMILES: *c1c(F)cccc1OCC=C]
Y-387
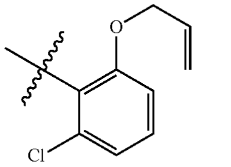 [SMILES: *c1c(Cl)cccc1OCC=C]
Y-388
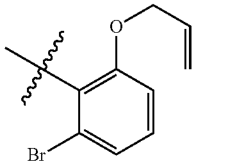 [SMILES: *c1c(Br)cccc1OCC=C]
Y-389
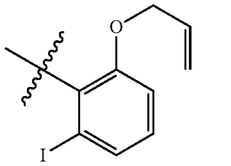 [SMILES: *c1c(I)cccc1OCC=C]
Y-390
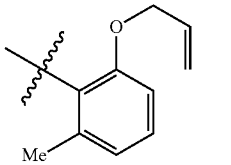 [SMILES: *c1c(C)cccc1OCC=C]
Y-391
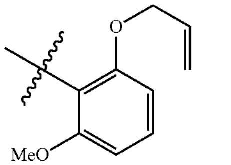 [SMILES: *c1c(OC)cccc1OCC=C]
Y-392
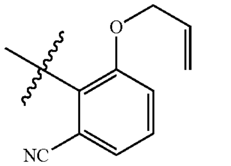 [SMILES: *c1c(C#N)cccc1OCC=C]
Y-393
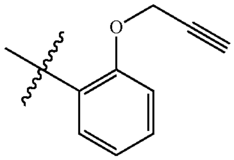 [SMILES: *c1ccccc1OCC#C]
Y-394
TABLE 2-continued
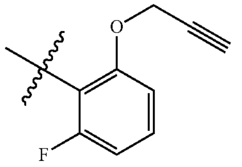
Y-395
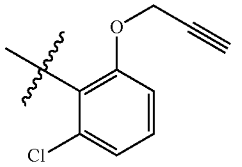 [SMILES: *c1c(Cl)cccc1OCC#C]
Y-396
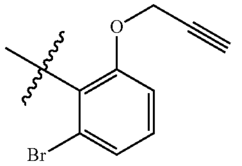 [SMILES: *c1c(Br)cccc1OCC#C]
Y-397
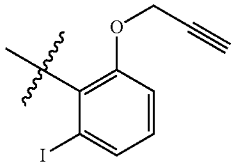 [SMILES: *c1c(I)cccc1OCC#C]
Y-398
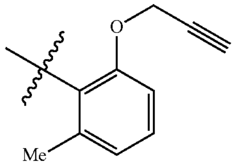 [SMILES: *c1c(C)cccc1OCC#C]
Y-399
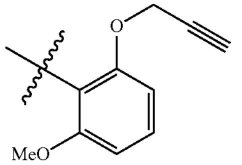 [SMILES: *c1c(OC)cccc1OCC#C]
Y-400
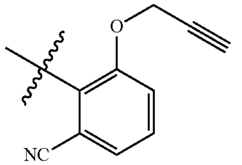 [SMILES: *c1c(C#N)cccc1OCC#C]
Y-401
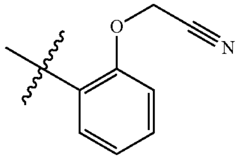 [SMILES: *c1ccccc1OCC#N]
Y-402
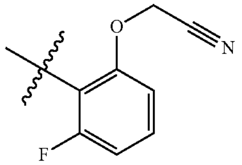
Y-403
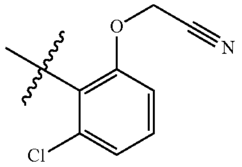 [SMILES: *c1c(Cl)cccc1OCC#N]
Y-404

TABLE 2-continued
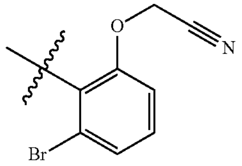 [SMILES: *c1c(Br)cccc1OCC#N]
Y-405
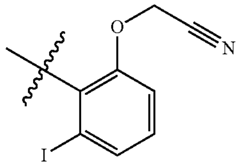 [SMILES: *c1c(I)cccc1OCC#N]
Y-406
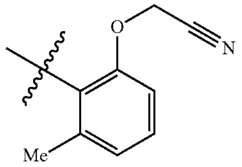 [SMILES: *c1c(C)cccc1OCC#N]
Y-407
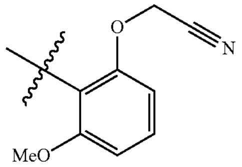 [SMILES: *c1c(OC)cccc1OCC#N]
Y-408
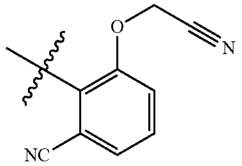 [SMILES: *c1c(C#N)cccc1OCC#N]
Y-409
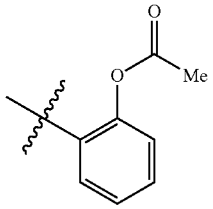 [SMILES: *c1ccccc1OC(C)=O]
Y-410
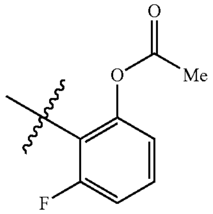
Y-411
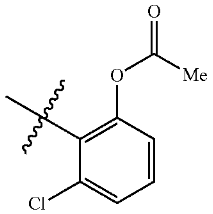 [SMILES: *c1c(Cl)cccc1OC(C)=O]
Y-412
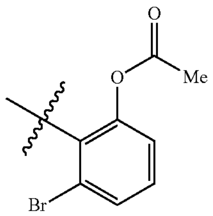
Y-413
TABLE 2-continued
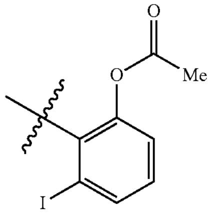 [SMILES: *c1c(I)cccc1OC(C)=O]
Y-414
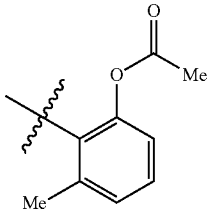 [SMILES: *c1c(C)cccc1OC(C)=O]
Y-415
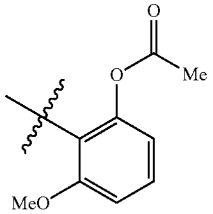 [SMILES: *c1c(OC)cccc1OC(C)=O]
Y-416
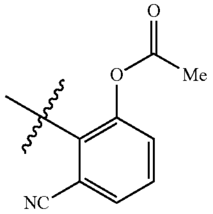 [SMILES: *c1c(C#N)cccc1OC(C)=O]
Y-417
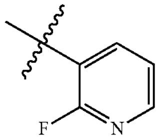
Y-418
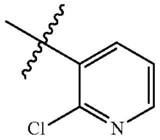 [SMILES: *c1cccnc1Cl]
Y-419
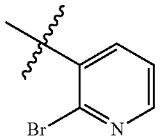 [SMILES: *c1cccnc1Br]
Y-420
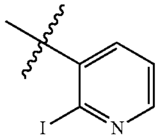 [SMILES: *c1cccnc1I]
Y-421
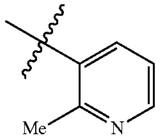 [SMILES: *c1cccnc1C]
Y-422
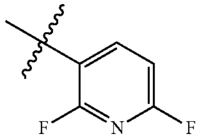 [SMILES: *c1ccc(F)nc1F]
Y-423

TABLE 2-continued
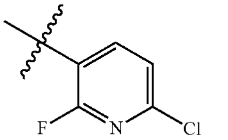 [SMILES: *c1ccc(Cl)nc1F]
Y-424
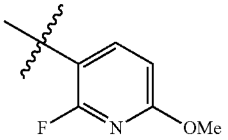 [SMILES: *c1ccc(OC)nc1F]
Y-425
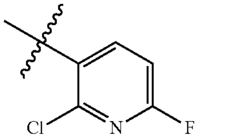 [SMILES: *c1ccc(F)nc1Cl]
Y-426
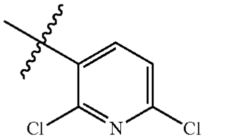 [SMILES: *c1ccc(Cl)nc1Cl]
Y-427
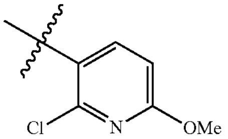 [SMILES: *c1ccc(OC)nc1Cl]
Y-428
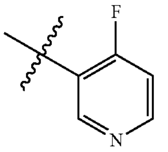 [SMILES: *c1cnccc1F]
Y-429
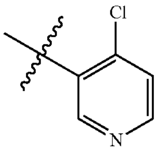
Y-430
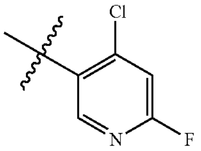
Y-431
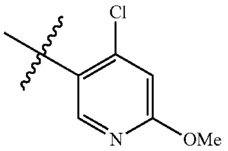 [SMILES: *c1cnc(OC)cc1Cl]
Y-432
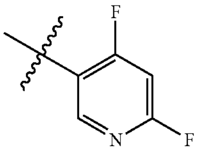 [SMILES: *c1cnc(F)cc1F]
Y-433
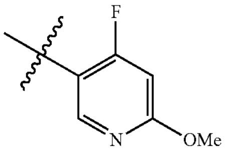 [SMILES: *c1cnc(OC)cc1F]
Y-434
TABLE 2-continued
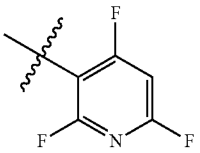 [SMILES: *c1c(F)cc(F)nc1F]
Y-435
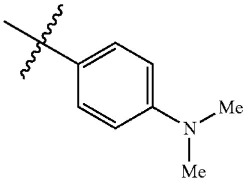 [SMILES: *c1ccc(N(C)C)cc1]
Y-436
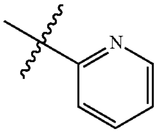 [SMILES: *c1ccccn1]
Y-437
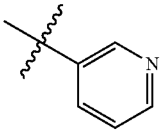 [SMILES: *c1cccnc1]
Y-438
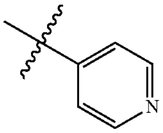 [SMILES: *c1ccncc1]
Y-439
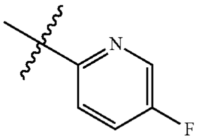 [SMILES: *c1ccc(F)cn1]
Y-440
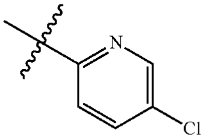 [SMILES: *c1ccc(Cl)cn1]
Y-441
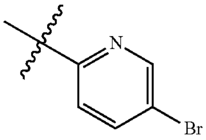 [SMILES: *c1ccc(Br)cn1]
Y-442
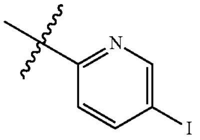 [SMILES: *c1ccc(I)cn1]
Y-443
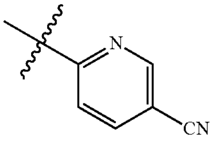 [SMILES: *c1ccc(C#N)cn1]
Y-444
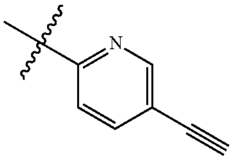 [SMILES: *c1ccc(C#C)cn1]
Y-445

TABLE 2-continued
Y-446
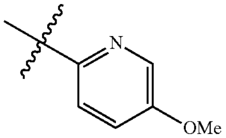 [SMILES: *c1ccc(OC)cn1]
Y-447
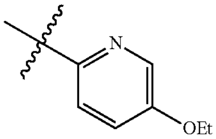 [SMILES: *c1ccc(OCC)cn1]
Y-448
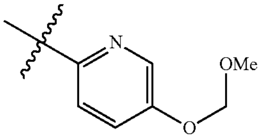 [SMILES: *c1ccc(OCOC)cn1]
Y-449
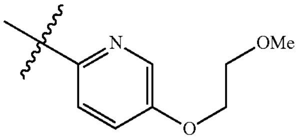 [SMILES: *c1ccc(OCCOC)cn1]
Y-450
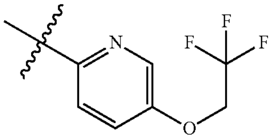 [SMILES: *c1ccc(OCC(F)(F)F)cn1]
Y-451
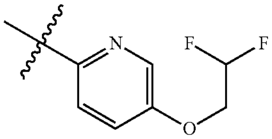 [SMILES: *c1ccc(OCC(F)F)cn1]
TABLE 2-continued
Y-452
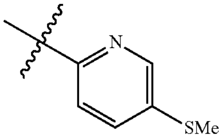 [SMILES: *c1ccc(SC)cn1]
Y-453
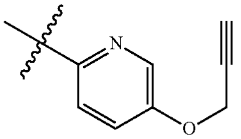 [SMILES: *c1ccc(OCC#C)cn1]
Y-454
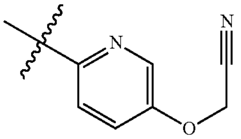 [SMILES: *c1ccc(OCC#N)cn1]
Y-455
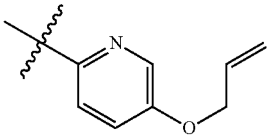 [SMILES: *c1ccc(OCC=C)cn1]
Y-456
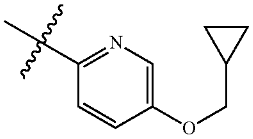 [SMILES: *c1ccc(OCC2CC2)cn1]

TABLE 3

| Z | R3 | R4 | Z | R3 | R4 | Z | R3 | R4 |
|---|---|---|---|---|---|---|---|---|
| Z-1 | H | H | Z-2 | H | 4-Br—Ph | Z-3 | H | 4-Cl—PhCH2— |
| Z-4 | H | Me | Z-5 | H | 2-I—Ph | Z-6 | H | 2-Br—PhCH2— |
| Z-7 | H | Et | Z-8 | H | 3-I—Ph | Z-9 | H | 3-Br—PhCH2— |
| Z-10 | H | Pr | Z-11 | H | 4-I—Ph | Z-12 | H | 4-Br—PhCH2— |
| Z-13 | H | i-Pr | Z-14 | H | 2-Me—Ph | Z-15 | H | 2-I—PhCH2— |
| Z-16 | H | Bn | Z-17 | H | 3-Me—Ph | Z-18 | H | 3-I—PhCH2— |
| Z-19 | H | i-Bu | Z-20 | H | 4-Me—Ph | Z-21 | H | 4-I—PhCH2— |
| Z-22 | H | sec-Bu | Z-23 | H | 2-MeO—Ph | Z-24 | H | 2-Me—PhCH2— |
| Z-25 | H | Pent | Z-26 | H | 3-MeO—Ph | Z-27 | H | 3-Me—PhCH2— |
| Z-28 | H | Hex | Z-29 | H | 4-MeO—Ph | Z-30 | H | 4-Me—PhCH2— |
| Z-31 | H | (CH3)2CH(CH3)CH— | Z-32 | H | 2,3-di-F—Ph | Z-33 | H | 2-MeO—PhCH2— |
| Z-34 | H | MeOCH2— | Z-35 | H | 2,4-di-F—Ph | Z-36 | H | 3-MeO—PhCH2— |
| Z-37 | H | MeOCH2CH2— | Z-38 | H | 2,5-di-F—Ph | Z-39 | H | 4-MeO—PhCH2— |
| Z-40 | H | EtOCH2— | Z-41 | H | 2,6-di-F—Ph | Z-42 | H | 2,3-di-F—PhCH2— |
| Z-43 | H | EtOCH2CH2— | Z-44 | H | 2-Cl-3-F—Ph | Z-45 | H | 2,4-di-F—PhCH2— |
| Z-46 | H | N≡CCH2— | Z-47 | H | 2-Cl-4-F—Ph | Z-48 | H | 2,5-di-F—PhCH2— |
| Z-49 | H | N≡CCH2CH2— | Z-50 | H | 2-Cl-5-F—Ph | Z-51 | H | 2,6-di-F—PhCH2— |
| Z-52 | H | c-Pr—CH2— | Z-53 | H | 2-Cl-6-F—Ph | Z-54 | H | 2-Cl-3-F—PhCH2— |
| Z-55 | H | c-Bu—CH2— | Z-56 | H | 2-Br-3-F—Ph | Z-57 | H | 2-Cl-4-F—PhCH2— |
| Z-58 | H | c-Pent-CH2— | Z-59 | H | 2-Br-4-F—Ph | Z-60 | H | 2-Cl-5-F—PhCH2— |
| Z-61 | H | c-Hex—CH2— | Z-62 | H | 2-Br-5-F—Ph | Z-63 | H | 2-Cl-6-F—PhCH2— |
| Z-64 | H | F3C— | Z-65 | H | 2-Br-6-F—Ph | Z-66 | H | 2-Br-3-F—PhCH2— |
| Z-67 | H | F2CH— | Z-68 | H | 2-F-3-MeO—Ph | Z-69 | H | 2-Br-4-F—PhCH2— |
| Z-70 | H | F3CCH2— | Z-71 | H | 2-FM—MeO—Ph | Z-72 | H | 2-Br-5-F—PhCH2— |
| Z-73 | H | F2CHCH2— | Z-74 | H | 2-F-5-MeO—Ph | Z-75 | H | 2-Br-6-F—PhCH2— |
| Z-76 | H | F3CF2C— | Z-77 | H | 2-F-6-MeO—Ph | Z-78 | H | 2-F-3-MeO—PhCH2— |
| Z-79 | H | F2CHF2C— | Z-80 | H | 2-Cl-3-MeO—Ph | Z-81 | H | 2-F-4-MeO—PhCH2— |
| Z-82 | H | (F3C)2FC— | Z-83 | H | 2-Cl-4-MeO—Ph | Z-84 | H | 2-F-5-MeO—PhCH2— |
| Z-85 | H | F3CF2C(F3C)FC— | Z-86 | H | 2-Cl-5-MeO—Ph | Z-87 | H | 2-F-6-MeO—PhCH2— |
| Z-88 | H | c-Pr | Z-89 | H | 2-Cl-6-MeO—Ph | Z-90 | H | 2-Cl-3-MeO—PhCH2— |
| Z-91 | H | c-Bu | Z-92 | H | 2-Br-3-MeO—Ph | Z-93 | H | 2-Cl-4-MeO—PhCH2— |
| Z-94 | H | c-Pent | Z-95 | H | 2-Br-4-MeO—Ph | Z-96 | H | 2-Cl-5-MeO—PhCH2— |
| Z-97 | H | c-Hex | Z-98 | H | 2-Br-5-MeO—Ph | Z-99 | H | 2-Cl-6-MeO—PhCH2— |
| Z-100 | H | H2C═CH— | Z-101 | H | 2-Br-6-MeO—Ph | Z-102 | H | 2-Br-3-MeO—PhCH2— |
| Z-103 | H | H3CCH═CH— | Z-104 | H | 2,3,4-tri-F—Ph | Z-105 | H | 2-Br-4-MeO—PhCH2— |
| Z-106 | H | H2C═CHCH2— | Z-107 | H | 2,3,5-tri-F—Ph | Z-108 | H | 2-Br-5-MeO—PhCH2— |
| Z-109 | H | F2C═CH— | Z-110 | H | 2,3,6-tri-F—Ph | Z-111 | H | 2-Br-6-MeO—PhCH2— |
| Z-112 | H | F2C═CHCH2— | Z-113 | H | 2-Br-3,4-di-F—Ph | Z-114 | H | 2,3,4-tri-F—PhCH2— |
| Z-115 | H | HC═C— | Z-116 | H | 2-Br-3,5-di-F—Ph | Z-117 | H | 2,3,5-tri-F—PhCH2— |
| Z-118 | H | HC≡CCH2— | Z-119 | H | 2-Br-3,6-di-F—Ph | Z-120 | H | 2,3,6-tri-F—PhCH2— |
| Z-121 | H | HC≡CCH2CH2— | Z-122 | H | 2-F-3,4-di-MeO—Ph | Z-123 | H | 2-Br-3,4-di-F—PhCH2— |
| Z-124 | H | H3CC≡CCH2— | Z-125 | H | 2-F-3,5-di-MeO—Ph | Z-126 | H | 2-Br-3,5-di-F—PhCH2— |
| Z-127 | H | FC═C— | Z-128 | H | 2-F-3,6-di-MeO—Ph | Z-129 | H | 2-Br-3,6-di-F—PhCH2— |
| Z-130 | H | FC≡CCF2— | Z-131 | H | 2-Cl-3,4-di-MeO—Ph | Z-132 | H | 2-F-3,4-di-MeO—PhCH2— |
| Z-133 | H | FC≡CCF2CF2— | Z-134 | H | 2-Cl-3,5-di-MeO—Ph | Z-135 | H | 2-F-3,5-di-MeO—PhCH2— |
| Z-136 | H | F3CC≡CCF2— | Z-137 | H | 2-Cl-3,6-di-MeO—Ph | Z-138 | H | 2-F-3,6-di-MeO—PhCH2— |
| Z-139 | H | Ph | Z-140 | H | 2-Br-3,4-di-MeO—Ph | Z-141 | H | 2-Cl-3,4-di-MeO—PhCH2— |
| Z-142 | H | 2-F—Ph | Z-143 | H | 2-Br-3,5-di-MeO—Ph | Z-144 | H | 2-Cl-3,5-di-MeO—PhCH2— |
| Z-145 | H | 3-F—Ph | Z-146 | H | 2-Br-3,6-di-MeO—Ph | Z-147 | H | 2-Cl-3,6-di-MeO—PhCH2— |

TABLE 3-continued

| Z | R3 | R4 | Z | R3 | R4 | Z | R3 | R4 |
|---|---|---|---|---|---|---|---|---|
| Z-148 | H | 4-F—Ph | Z-149 | H | PhCH2— | Z-150 | H | 2-Br-3,4-di-MeO—PhCH2— |
| Z-151 | H | 2-Cl—Ph | Z-152 | H | 2-F—PhCH2— | Z-153 | H | 2-Br-3,5-di-MeO—PhCH2— |
| Z-154 | H | 3-Cl—Ph | Z-155 | H | 3-F—PhCH2— | Z-156 | H | 2-Br-3,6-di-MeO—PhCH2— |
| Z-157 | H | 4-Cl—Ph | Z-158 | H | 4-F—PhCH2— | Z-159 | H | MeS— |
| Z-160 | H | 2-Br—Ph | Z-161 | H | 2-Cl—PhCH2— | Z-162 | H | MeS(═O)— |
| Z-163 | H | 3-Br—Ph | Z-164 | H | 3-Cl—PhCH2— | Z-165 | H | MeS(═O)2— |
| Z-166 | H | EtS— | Z-167 | Me | HC≡C— | Z-168 | Me | 2-Br-3,5-di-F—Ph |
| Z-169 | H | EtS(═O)— | Z-170 | Me | HC≡CCH2— | Z-171 | Me | 2-Br-3,6-di-F—Ph |
| Z-172 | H | EtS(═O)2— | Z-173 | Me | HC≡CCH2CH2— | Z-174 | Me | 2-F-3,4-di-MeO—Ph |
| Z-175 | H | PrS— | Z-176 | Me | H3CC≡CCH2— | Z-177 | Me | 2-F-3,5-di-MeO—Ph |
| Z-178 | H | PrS(═O)— | Z-179 | Me | FC≡C— | Z-180 | Me | 2-F-3,6-di-MeO—Ph |
| Z-181 | H | PrS(—O)2— | Z-182 | Me | FC≡CCF2— | Z-183 | Me | 2-Cl-3,4-di-MeO—Ph |
| Z-184 | H | Ac | Z-185 | Me | FC≡CCF2CF2— | Z-186 | Me | 2-Cl-3,5-di-MeO—Ph |
| Z-187 | H | OHC— | Z-188 | Me | F3CC≡CCF2— | Z-189 | Me | 2-Cl-3,6-di-MeO—Ph |
| Z-190 | H | Et(C═O)— | Z-191 | Me | Ph | Z-192 | Me | 2-Br-3,4-di-MeO—Ph |
| Z-193 | H | Pr(C═O)— | Z-194 | Me | 2-F—Ph | Z-195 | Me | 2-Br-3,5-di-MeO—Ph |
| Z-196 | H | i-Pr(C═O)— | Z-197 | Me | 3-F—Ph | Z-198 | Me | 2-Br-3,6-di-MeO—Ph |
| Z-199 | H | Bu(C═O)— | Z-200 | Me | 4-F—Ph | Z-201 | Me | PhCH2— |
| Z-202 | H | MeO(C═O)— | Z-203 | Me | 2-Cl—Ph | Z-204 | Me | 2-F—PhCH2— |
| Z-205 | H | EtO(C═O)— | Z-206 | Me | 3-Cl—Ph | Z-207 | Me | 3-F—PhCH2— |
| Z-208 | H | PrO(C═O)— | Z-209 | Me | 4-Cl—Ph | Z-210 | Me | 4-F—PhCH2— |
| Z-211 | H | i-PrO(C═O)— | Z-212 | Me | 2-Br—Ph | Z-213 | Me | 2-Cl—PhCH2— |
| Z-214 | H | BuO(C═O)— | Z-215 | Me | 3-Br—Ph | Z-216 | Me | 3-Cl—PhCH2— |
| Z-217 | H | t-BuOC(═O)— | Z-218 | Me | 4-Br—Ph | Z-219 | Me | 4-Cl—PhCH2— |
| Z-220 | Me | Me | Z-221 | Me | 2-I—Ph | Z-222 | Me | 2-Br—PhCH2— |
| Z-223 | Me | Et | Z-224 | Me | 3-I—Ph | Z-225 | Me | 3-Br—PhCH2— |
| Z-226 | Me | Pr | Z-227 | Me | 4-I—Ph | Z-228 | Me | 4-Br—PhCH2— |
| Z-229 | Me | i-Pr | Z-230 | Me | 2-Me—Ph | Z-231 | Me | 2-I—PhCH2— |
| Z-232 | Me | Bu | Z-233 | Me | 3-Me—Ph | Z-234 | Me | 3-I—PhCH2— |
| Z-235 | Me | i-Bu | Z-236 | Me | 4-Me—Ph | Z-237 | Me | 4-I—PhCH2— |
| Z-238 | Me | sec-Bu | Z-239 | Me | 2-MeO—Ph | Z-240 | Me | 2-Me—PhCH2— |
| Z-241 | Me | Pent | Z-242 | Me | 3-MeO—Ph | Z-243 | Me | 3-Me—PhCH2— |
| Z-244 | Me | Hex | Z-245 | Me | 4-MeO—Ph | Z-246 | Me | 4-Me—PhCH2— |
| Z-247 | Me | (CH3)2CH(CH3)CH— | Z-248 | Me | 2,3-di-F—Ph | Z-249 | Me | 2-MeO—PhCH2— |
| Z-250 | Me | MeOCH2— | Z-251 | Me | 2,4-di-F—Ph | Z-252 | Me | 3-MeO—PhCH2— |
| Z-253 | Me | MeOCH2CH2— | Z-254 | Me | 2,5-di-F—Ph | Z-255 | Me | 4-MeO—PhCH2— |
| Z-256 | Me | EtOCH2— | Z-257 | Me | 2,6-di-F—Ph | Z-258 | Me | 2,3-di-F—PhCH2— |
| Z-259 | Me | EtOCH2CH2— | Z-260 | Me | 2-Cl-3-F—Ph | Z-261 | Me | 2,4-di-F—PhCH2— |
| Z-262 | Me | N≡CCH2— | Z-263 | Me | 2-Cl-4-F—Ph | Z-264 | Me | 2,5-di-F—PhCH2— |
| Z-265 | Me | N≡CCH2CH2— | Z-266 | Me | 2-Cl-5-F—Ph | Z-267 | Me | 2,6-di-F—PhCH2— |
| Z-268 | Me | c-Pr—CH2— | Z-269 | Me | 2-Cl-6-F—Ph | Z-270 | Me | 2-Cl-3-F—PhCH2— |
| Z-271 | Me | c-Bu—CH2— | Z-272 | Me | 2-Br-3-F—Ph | Z-273 | Me | 2-Cl-4-F—PhCH2— |
| Z-274 | Me | c-Pent-CH2— | Z-275 | Me | 2-Br-4-F—Ph | Z-276 | Me | 2-Cl-5-F—PhCH2— |
| Z-277 | Me | c-Hex—CH2— | Z-278 | Me | 2-Br-5-F—Ph | Z-279 | Me | 2-Cl-6-F—PhCH2— |
| Z-280 | Me | F3C— | Z-281 | Me | 2-Br-6-F—Ph | Z-282 | Me | 2-Br-3-F—PhCH2— |
| Z-283 | Me | F2CH— | Z-284 | Me | 2-F-3-MeO—Ph | Z-285 | Me | 2-Br-4-F—PhCH2— |
| Z-286 | Me | F3CCH2— | Z-287 | Me | 2-F-4-MeO—Ph | Z-288 | Me | 2-Br-5-F—PhCH2— |
| Z-289 | Me | F2CHCH2— | Z-290 | Me | 2-F-5-MeO—Ph | Z-291 | Me | 2-Br-6-F—PhCH2— |
| Z-292 | Me | F3CF2C— | Z-293 | Me | 2-F-6-MeO—Ph | Z-294 | Me | 2-F-3-MeO—PhCH2— |
| Z-295 | Me | F2CHF2C— | Z-296 | Me | 2-Cl-3-MeO—Ph | Z-297 | Me | 2-F-4-MeO—PhCH2— |
| Z-298 | Me | (F3C)2FC— | Z-299 | Me | 2-Cl-4-MeO—Ph | Z-300 | Me | 2-F-5-MeO—PhCH2— |

TABLE 3-continued

| Z | R3 | R4 | Z | R3 | R4 | Z | R3 | R4 |
|---|---|---|---|---|---|---|---|---|
| Z-301 | Me | F3CF2C(F3C)FC— | Z-302 | Me | 2-Cl-5-MeO—Ph | Z-303 | Me | 2-F-6-MeO—PhCH2— |
| Z-304 | Me | c-Pr | Z-305 | Me | 2-Cl-6-MeO—Ph | Z-306 | Me | 2-Cl-3-MeO—PhCH2— |
| Z-307 | Me | c-Bu | Z-308 | Me | 2-Br-3-MeO—Ph | Z-309 | Me | 2-Cl-4-MeO—PhCH2— |
| Z-310 | Me | c-Pent | Z-311 | Me | 2-Br-4-MeO—Ph | Z-312 | Me | 2-Cl-5-MeO—PhCH2— |
| Z-313 | Me | c-Hex | Z-314 | Me | 2-Br-5-MeO—Ph | Z-315 | Me | 2-Cl-6-MeO—PhCH2— |
| Z-316 | Me | H2C═CH— | Z-317 | Me | 2-Br-6-MeO—Ph | Z-318 | Me | 2-Br-3-MeO—PhCH2— |
| Z-319 | Me | H3CCH═CH— | Z-320 | Me | 2,3,4-tri-F—Ph | Z-321 | Me | 2-Br-4-MeO—PhCH2— |
| Z-322 | Me | H2C═CHCH2— | Z-323 | Me | 2,3,5-tri-F—Ph | Z-324 | Me | 2-Br-5-MeO—PhCH2— |
| Z-325 | Me | F2C═CH— | Z-326 | Me | 2,3,6-tri-F—Ph | Z-327 | Me | 2-Br-6-MeO—PhCH2— |
| Z-328 | Me | F2C═CHCH2— | Z-329 | Me | 2-Br-3,4-di-F—Ph | Z-330 | Me | 2,3,4-tri-F—PhCH2— |
| Z-331 | Me | 2,3,5-tri-F—PhCH2— | Z-332 | Et | F2CH— | Z-333 | Et | 2-F-3-MeO—Ph |
| Z-334 | Me | 2,3,6-tri-F—PhCH2— | Z-335 | Et | F3CCH2— | Z-336 | Et | 2-F-4-MeO—Ph |
| Z-337 | Me | 2-Br-3,4-di-F—PhCH2— | Z-338 | Et | F2CHCH2— | Z-339 | Et | 2-F-5-MeO—Ph |
| Z-340 | Me | 2-Br-3,5-di-F—PhCH2— | Z-341 | Et | F3CF2C— | Z-342 | Et | 2-F-6-MeO—Ph |
| Z-343 | Me | 2-Br-3,6-di-F—PhCH2— | Z-344 | Et | F2CHF2C— | Z-345 | Et | 2-Cl-3-MeO—Ph |
| Z-346 | Me | 2-F-3,4-di-MeO—PhCH2— | Z-347 | Et | (F3C)2FC— | Z-348 | Et | 2-Cl-4-MeO—Ph |
| Z-349 | Me | 2-F-3,5-di-MeO—PhCH2— | Z-350 | Et | F3CF2C(F3C)FC— | Z-351 | Et | 2-Cl-5-MeO—Ph |
| Z-352 | Me | 2-F-3,6-di-MeO—PhCH2— | Z-353 | Et | c-Pr | Z-354 | Et | 2-Cl-6-MeO—Ph |
| Z-355 | Me | 2-Cl-3,4-di-MeO—PhCH2— | Z-356 | Et | c-Bu | Z-357 | Et | 2-Br-3-MeO—Ph |
| Z-358 | Me | 2-Cl-3,5-di-MeO—PhCH2— | Z-359 | Et | c-Pent | Z-360 | Et | 2-Br-4-MeO—Ph |
| Z-361 | Me | 2-Cl-3,6-di-MeO—PhCH2— | Z-362 | Et | c-Hex | Z-363 | Et | 2-Br-5-MeO—Ph |
| Z-364 | Me | 2-Br-3,4-di-MeO—PhCH2— | Z-365 | Et | H2C═CH— | Z-366 | Et | 2-Br-6-MeO—Ph |
| Z-367 | Me | 2-Br-3,5-di-MeO—PhCH2— | Z-368 | Et | H3CCH═CH— | Z-369 | Et | 2,3,4-tri-F—Ph |
| Z-370 | Me | 2-Br-3,6-di-MeO—PhCH2— | Z-371 | Et | H2C═CHCH2— | Z-372 | Et | 2,3,5-tri-F—Ph |
| Z-373 | Me | MeS— | Z-374 | Et | F2C═CH— | Z-375 | Et | 2,3,6-tri-F—Ph |
| Z-376 | Me | MeS(═O)— | Z-377 | Et | F2C═CHCH2— | Z-378 | Et | 2-Br-3,4-di-F—Ph |
| Z-379 | Me | MeS(═O)2— | Z-380 | Et | HC≡C— | Z-381 | Et | 2-Br-3,5-di-F—Ph |
| Z-382 | Me | EtS— | Z-383 | Et | HC≡CCH2— | Z-384 | Et | 2-Br-3,6-di-F—Ph |
| Z-385 | Me | EtS(═O)— | Z-386 | Et | HC≡CCH2CH2— | Z-387 | Et | 2-F-3,4-di-MeO—Ph |
| Z-388 | Me | EtS(═O)2— | Z-389 | Et | H3CC≡CCH2— | Z-390 | Et | 2-F-3,5-di-MeO—Ph |
| Z-391 | Me | PrS— | Z-392 | Et | FC≡C— | Z-393 | Et | 2-F-3,6-di-MeO—Ph |
| Z-394 | Me | PrS(═O)— | Z-395 | Et | FC≡CCF2— | Z-396 | Et | 2-Cl-3,4-di-MeO—Ph |
| Z-397 | Me | PrS(═O)2— | Z-398 | Et | FC≡CCF2CF2— | Z-399 | Et | 2-Cl-3,5-di-MeO—Ph |
| Z-400 | Me | Ac | Z-401 | Et | F3CC≡CCF2— | Z-402 | Et | 2-Cl-3,6-di-MeO—Ph |
| Z-403 | Me | OHC— | Z-404 | Et | Ph | Z-405 | Et | 2-Br-3,4-di-MeO—Ph |
| Z-406 | Me | Et(C═O)— | Z-407 | Et | 2-F—Ph | Z-408 | Et | 2-Br-3,5-di-MeO—Ph |
| Z-409 | Me | Pr(C═O)— | Z-410 | Et | 3-F—Ph | Z-411 | Et | 2-Br-3,6-di-MeO—Ph |
| Z-412 | Me | i-Pr(C═O)— | Z-413 | Et | 4-F—Ph | Z-414 | Et | PhCH2— |
| Z-415 | Me | Bu(C═O)— | Z-416 | Et | 2-Cl—Ph | Z-417 | Et | 2-F—PhCH2— |
| Z-418 | Me | MeO(C═O)— | Z-419 | Et | 3-Cl—Ph | Z-420 | Et | 3-F—PFCH2— |
| Z-421 | Me | EtO(C═O)— | Z-422 | Et | 4-Cl—Ph | Z-423 | Et | 4-F—PhCH2— |
| Z-424 | Me | PrO(C═O)— | Z-425 | Et | 2-Br—Ph | Z-426 | Et | 2-Cl—PhCH2— |
| Z-427 | Me | i-PrO(C═O)— | Z-428 | Et | 3-Br—Ph | Z-429 | Et | 3-Cl—PhCH2— |
| Z-430 | Me | BuO(C═O)— | Z-431 | Et | 4-Br—Ph | Z-432 | Et | 4-Cl—PhCH2— |
| Z-433 | Me | t-BuOC(═O)— | Z-434 | Et | 2-I—Ph | Z-435 | Et | 2-Br—PhCH2— |
| Z-436 | Et | Et | Z-437 | Et | 3-I—Ph | Z-438 | Et | 3-Br—PhCH2— |
| Z-439 | Et | Pr | Z-440 | Et | 4-I—Ph | Z-441 | Et | 4-Br—PhCH2— |
| Z-442 | Et | i-Pr | Z-443 | Et | 2-Me—Ph | Z-444 | Et | 2-I—PhCH2— |
| Z-445 | Et | Bu | Z-446 | Et | 3-Me—Ph | Z-447 | Et | 3-I—PhCH2— |
| Z-448 | Et | i-Bu | Z-449 | Et | 4-Me—Ph | Z-450 | Et | 4-I—PhCH2— |
| Z-451 | Et | sec-Bu | Z-452 | Et | 2-MeO—Ph | Z-453 | Et | 2-Me—PhCH2— |

TABLE 3-continued

| Z | R3 | R4 | Z | R3 | R4 | Z | R3 | R4 |
|---|---|---|---|---|---|---|---|---|
| Z-454 | Et | Pent | Z-455 | Et | 3-MeO—Ph | Z-456 | Et | 3-Me—PhCH2— |
| Z-457 | Et | Hex | Z-458 | Et | 4-MeO—Ph | Z-459 | Et | 4-Me—PhCH2— |
| Z-460 | Et | (CH3)2CH(CH3)CH— | Z-461 | Et | 2,3-di-F—Ph | Z-462 | Et | 2-MeO—PhCH2— |
| Z-463 | Et | MeOCH2— | Z-464 | Et | 2,4-di-F—Ph | Z-465 | Et | 3-MeO—PhCH2— |
| Z-466 | Et | MeOCH2CH2— | Z-467 | Et | 2,5-di-F—Ph | Z-468 | Et | 4-MeO—PhCH2— |
| Z-469 | Et | EtOCH2— | Z-470 | Et | 2,6-di-F—Ph | Z-471 | Et | 2,3-di-F—PhCH2— |
| Z-472 | Et | EtOCH2CH2— | Z-473 | Et | 2-Cl-3-F—Ph | Z-474 | Et | 2,4-di-F—PhCH2— |
| Z-475 | Et | N≡CCH2— | Z-476 | Et | 2-Cl-4-F—Ph | Z-477 | Et | 2,5-di-F—PhCH2— |
| Z-478 | Et | N≡CCH2CH2— | Z-479 | Et | 2-Cl-5-F—Ph | Z-480 | Et | 2,6-di-F—PhCH2— |
| Z-481 | Et | c-Pr—CH2— | Z-482 | Et | 2-Cl-6-F—Ph | Z-483 | Et | 2-Cl-3-F—PhCH2— |
| Z-484 | Et | c-Bu—CH2— | Z-485 | Et | 2-Br-3-F—Ph | Z-486 | Et | 2-Cl-4-F—PhCH2— |
| Z-487 | Et | c-Pent-CH2— | Z-488 | Et | 2-Br-4-E—Ph | Z-489 | Et | 2-Cl-5-F—PhCH2— |
| Z-490 | Et | c-Hex—CH2— | Z-491 | Et | 2-Br-5-F—Ph | Z-492 | Et | 2-Cl-6-F—PhCH2— |
| Z-493 | Et | F3C— | Z-494 | Et | 2-Br-6-F—Ph | Z-495 | Et | 2-Br-3-F—PhCH2— |
| Z-496 | Et | 2-Br-4-F—PhCH2— | Z-497 | Pr | sec-Bu | Z-498 | Pr | 2-MeO—Ph |
| Z-499 | Et | 2-Br-5-F—PhCH2— | Z-500 | Pr | Pent | Z-501 | Pr | 3-MeO—Ph |
| Z-502 | Et | 2-Br-6-F—PhCH2— | Z-503 | Pr | Hex | Z-504 | Pr | 4-MeO—Ph |
| Z-505 | Et | 2-F-3-MeO—PhCH2— | Z-506 | Pr | (CH3)2CH(CH3)CH— | Z-507 | Pr | 2,3-di-F—Ph |
| Z-508 | Et | 2-F-4-MeO—PhCH2— | Z-509 | Pr | MeOCH2— | Z-510 | Pr | 2,4-di-F—Ph |
| Z-511 | Et | 2-F-5-MeO—PhCH2— | Z-512 | Pr | MeOCH2CH2— | Z-513 | Pr | 2,5-di-F—Ph |
| Z-514 | Et | 2-F-6-MeO—PhCH2— | Z-515 | Pr | EtOCH2— | Z-516 | Pr | 2,6-di-F—Ph |
| Z-517 | Et | 2-Cl-3-MeO—PhCH2— | Z-518 | Pr | EtOCH2CH2— | Z-519 | Pr | 2-Cl-3-F—Ph |
| Z-520 | Et | 2-Cl-4-MeO—PhCH2— | Z-521 | Pr | N≡CCH2— | Z-522 | Pr | 2-Cl-4-F—Ph |
| Z-523 | Et | 2-Cl-5-MeO—PhCH2— | Z-524 | Pr | N≡CCH2CH2— | Z-525 | Pr | 2-Cl-5-F—Ph |
| Z-526 | Et | 2-Cl-6-MeO—PhCH2— | Z-527 | Pr | c-Pr—CH2— | Z-528 | Pr | 2-Cl-6-F—Ph |
| Z-529 | Et | 2-Br-3-MeO—PhCH2— | Z-530 | Pr | c-Bu—CH2— | Z-531 | Pr | 2-Br-3-F—Ph |
| Z-532 | Et | 2-Br-4-MeO—PhCH2— | Z-533 | Pr | c-Pent-CH2— | Z-534 | Pr | 2-Br-4-F—Ph |
| Z-535 | Et | 2-Br-5-MeO—PhCH2— | Z-536 | Pr | c-Hex—CH2— | Z-537 | Pr | 2-Br-5-F—Ph |
| Z-538 | Et | 2-Br-6-MeO—PhCH2— | Z-539 | Pr | F3C— | Z-540 | Pr | 2-Br-6-F—Ph |
| Z-541 | Et | 2,3,4-tri-F—PhCH2— | Z-542 | Pr | F2CH— | Z-543 | Pr | 2-F-3-MeO—Ph |
| Z-544 | Et | 2,3,5-tri-F—PhCH2— | Z-545 | Pr | F3CCH2— | Z-546 | Pr | 2-F-4-MeO—Ph |
| Z-547 | Et | 2,3,6-tri-F—PhCH2— | Z-548 | Pr | F2CHCH2— | Z-549 | Pr | 2-F-5-MeO—Ph |
| Z-550 | Et | 2-Br-3,4-di-F—PhCH2— | Z-551 | Pr | F3CF2C— | Z-552 | Pr | 2-F-6-MeO—Ph |
| Z-553 | Et | 2-Br-3,5-di-F—PhCH2— | Z-554 | Pr | F2CHF2C— | Z-555 | Pr | 2-Cl-3-MeO—Ph |
| Z-556 | Et | 2-Br-3,6-di-F—PhCH2— | Z-557 | Pr | (F3C)2FC— | Z-558 | Pr | 2-Cl-4-MeO—Ph |
| Z-559 | Et | 2-F-3,4-di-MeO—PhCH2— | Z-560 | Pr | F3CF2C(F3C)FC— | Z-561 | Pr | 2-Cl-5-MeO—Ph |
| Z-562 | Et | 2-F-3,5-di-MeO—PhCH2— | Z-563 | Pr | c-Pr | Z-564 | Pr | 2-Cl-6-MeO—Ph |
| Z-565 | Et | 2-F-3,6-di-MeO—PhCH2— | Z-566 | Pr | c-Bu | Z-567 | Pr | 2-Br-3-MeO—Ph |
| Z-568 | Et | 2-Cl-3,4-di-MeO—PhCH2— | Z-569 | Pr | c-Pent | Z-570 | Pr | 2-Br-4-MeO—Ph |
| Z-571 | Et | 2-Cl-3,5-di-MeO—PhCH2— | Z-572 | Pr | c-Hex | Z-573 | Pr | 2-Br-5-MeO—Ph |
| Z-574 | Et | 2-Cl-3,6-di-MeO—PhCH2— | Z-575 | Pr | H2C═CH— | Z-576 | Pr | 2-Br-6-MeO—Ph |
| Z-577 | Et | 2-Br-3,4-di-MeO—PhCH2— | Z-578 | Pr | H3CCH═CH— | Z-579 | Pr | 2,3,4-tri-F—Ph |
| Z-580 | Et | 2-Br-3,5-di-MeO—PhCH2— | Z-581 | Pr | H2C═CHCH2— | Z-582 | Pr | 2,3,5-tri-F—Ph |
| Z-583 | Et | 2-Br-3,6-di-MeO—PhCH2— | Z-584 | Pr | F2C═CH— | Z-585 | Pr | 2,3,6-tri-F—Ph |
| Z-586 | Et | MeS— | Z-587 | Pr | F2C═CHCH2— | Z-588 | Pr | 2-Br-3,4-di-F—Ph |
| Z-589 | Et | MeS(═O)— | Z-590 | Pr | HC≡C— | Z-591 | Pr | 2-Br-3,5-di-F—Ph |
| Z-592 | Et | MeS(═O)2— | Z-593 | Pr | HC≡CCH2— | Z-594 | Pr | 2-Br-3,6-di-F—Ph |
| Z-595 | Et | EtS— | Z-596 | Pr | HC≡CCH2CH2— | Z-597 | Pr | 2-F-3,4-di-MeO—Ph |
| Z-598 | Et | EtS(═O)— | Z-599 | Pr | H3CC≡CCH2— | Z-600 | Pr | 2-F-3,5-di-MeO—Ph |
| Z-601 | Et | EtS(═O)2— | Z-602 | Pr | FC≡C— | Z-603 | Pr | 2-F-3,6-di-MeO—Ph |
| Z-604 | Et | PrS— | Z-605 | Pr | FC≡CCF2— | Z-606 | Pr | 2-Cl-3,4-di-MeO—Ph |

TABLE 3-continued

| Z | R3 | R4 | Z | R3 | R4 | Z | R3 | R4 |
|---|---|---|---|---|---|---|---|---|
| Z-607 | Et | PrS(═O)— | Z-608 | Pr | FC≡CCF2CF2— | Z-609 | Pr | 2-Cl-3,5-di-MeO—Ph |
| Z-610 | Et | PrS(═O)2— | Z-611 | Pr | F3CC≡CCF2— | Z-612 | Pr | 2-Cl-3,6-di-MeO—Ph |
| Z-613 | Et | Ac | Z-614 | Pr | Ph | Z-615 | Pr | 2-Br-3,4-di-MeO—Ph |
| Z-616 | Et | OHC— | Z-617 | Pr | 2-F—Ph | Z-618 | Pr | 2-Br-3,5-di-MeO—Ph |
| Z-619 | Et | Et(C═O)— | Z-620 | Pr | 3-F—Ph | Z-621 | Pr | 2-Br-3,6-di-MeO—Ph |
| Z-622 | Et | Pr(C═O)— | Z-623 | Pr | 4-F—Ph | Z-624 | Pr | PhCH2— |
| Z-625 | Et | i-Pr(C═O)— | Z-626 | Pr | 2-Cl—Ph | Z-627 | Pr | 2-F—PhCH2— |
| Z-628 | Et | Bu(C═O)— | Z-629 | Pr | 3-Cl—Ph | Z-630 | Pr | 3-F—PhCH2— |
| Z-631 | Et | MeO(C═O)— | Z-632 | Pr | 4-Cl—Ph | Z-633 | Pr | 4-F—PhCH2— |
| Z-634 | Et | EtO(C═O)— | Z-635 | Pr | 2-Br—Ph | Z-636 | Pr | 2-Cl—PhCH2— |
| Z-637 | Et | PrO(C═O)— | Z-638 | Pr | 3-Br—Ph | Z-639 | Pr | 3-Cl—PhCH2— |
| Z-640 | Et | i-PrO(C═O)— | Z-641 | Pr | 4-Br—Ph | Z-642 | Pr | 4-Cl—PhCH2— |
| Z-643 | Et | BuO(C═O)— | Z-644 | Pr | 2-I—Ph | Z-645 | Pr | 2-Br—PhCH2— |
| Z-646 | Et | t-BuOC(═O)— | Z-647 | Pr | 3-I—Ph | Z-648 | Pr | 3-Br—PhCH2— |
| Z-649 | Pr | Pr | Z-650 | Pr | 4-I—Pb | Z-651 | Pr | 4-Br—PhCH2— |
| Z-652 | Pr | i-Pr | Z-653 | Pr | 2-Me—Ph | Z-654 | Pr | 2-I—PhCH2— |
| Z-655 | Pr | Bu | Z-656 | Pr | 3-Me—Ph | Z-657 | Pr | 3-I—PhCH2— |
| Z-658 | Pr | i-Bu | Z-659 | Pr | 4-Me—Ph | Z-660 | Pr | 4-I—PhCH2— |
| Z-661 | Pr | 2-Me—PhCH2— | Z-662 | Pr | OHC— | Z-663 | i-Pr | 3-F—Ph |
| Z-664 | Pr | 3-Me—PhCH2— | Z-665 | Pr | Et(C═O)— | Z-666 | i-Pr | 4-F—Ph |
| Z-667 | Pr | 4-Me—PhCH2— | Z-668 | Pr | Pr(C═O)— | Z-669 | i-Pr | 2-Cl—Ph |
| Z-670 | Pr | 2-MeO—PhCH2— | Z-671 | Pr | i-Pr(C═O)— | Z-672 | i-Pr | 3-Cl—Ph |
| Z-673 | Pr | 3-MeO—PhCH2— | Z-674 | Pr | Bu(C═O)— | Z-675 | i-Pr | 4-Cl—Ph |
| Z-676 | Pr | 4-MeO—PhCH2— | Z-677 | Pr | MeO(C═O)— | Z-678 | i-Pr | 2-Br—Ph |
| Z-679 | Pr | 2,3-di-F—PhCH2— | Z-680 | Pr | EtO(C═O)— | Z-681 | i-Pr | 3-Br—Ph |
| Z-682 | Pr | 2,4-di-F—PhCH2— | Z-683 | Pr | PrO(C═O)— | Z-684 | i-Pr | 4-Br—Ph |
| Z-685 | Pr | 2,5-di-F—PhCH2— | Z-686 | Pr | i-PrO(C═O) | Z-687 | i-Pr | 2-I—Ph |
| Z-688 | Pr | 2,6-di-F—PhCH2— | Z-689 | Pr | BuO(C═O)— | Z-690 | i-Pr | 3-I—Ph |
| Z-691 | Pr | 2-Cl-3-F—PhCH2— | Z-692 | Pr | t-BuOC(═O)— | Z-693 | i-Pr | 4-I—Ph |
| Z-694 | Pr | 2-Cl-4-F—PhCH2— | Z-695 | i-Pr | i-Pr | Z-696 | i-Pr | 2-Me—Ph |
| Z-697 | Pr | 2-Cl-5-F—PhCH2— | Z-698 | i-Pr | Bu | Z-699 | i-Pr | 3-Me—Ph |
| Z-700 | Pr | 2-Cl-6-F—PhCH2— | Z-701 | i-Pr | i-Bu | Z-702 | i-Pr | 4-Me—Ph |
| Z-703 | Pr | 2-Br-3-F—PhCH2— | Z-704 | i-Pr | sec-Bu | Z-705 | i-Pr | 2-MeO—Ph |
| Z-706 | Pr | 2-Br-4-F—PhCH2— | Z-707 | i-Pr | Pent | Z-708 | i-Pr | 3-MeO—Ph |
| Z-709 | Pr | 2-Br-5-F—PhCH2— | Z-710 | i-Pr | Hex | Z-711 | i-Pr | 4-MeO—Ph |
| Z-712 | Pr | 2-Br-6-F—PhCH2— | Z-713 | i-Pr | (CH3)2CH(CH3)CH— | Z-714 | i-Pr | 2,3-di-F—Ph |
| Z-715 | Pr | 2-F-3-MeO—PhCH2— | Z-716 | i-Pr | MeOCH2— | Z-717 | i-Pr | 2,4-di-F—Ph |
| Z-718 | Pr | 2-F-4-MeO—PhCH2— | Z-719 | i-Pr | MeOCH2CH2— | Z-720 | i-Pr | 2,5-di-F—Ph |
| Z-721 | Pr | 2-F-5-MeO—PhCH2— | Z-722 | i-Pr | EtOCH2— | Z-723 | i-Pr | 2,6-di-F—Ph |
| Z-724 | Pr | 2-F-6-MeO—PhCH2— | Z-725 | i-Pr | EtOCH2CH2— | Z-726 | i-Pr | 2-Cl-3-F—Ph |
| Z-727 | Pr | 2-Cl-3-MeO—PhCH2— | Z-728 | i-Pr | N≡CCH2— | Z-729 | i-Pr | 2-Cl-4-F—PF |
| Z-730 | Pr | 2-Cl-4-MeO—PhCH2— | Z-731 | i-Pr | N≡CH2CH2— | Z-732 | i-Pr | 2-Cl-5-F—PE |
| Z-733 | Pr | 2-Cl-5-MeO—PhCH2— | Z-734 | i-Pr | c-Pr—CH2— | Z-735 | i-Pr | 2-Cl-6-F—Ph |
| Z-736 | Pr | 2-Cl-6-MeO—PhCH2— | Z-737 | i-Pr | c-Bu—CH2— | Z-738 | i-Pr | 2-Br-3-F—Ph |
| Z-739 | Pr | 2-Br-3-MeO—PhCH2— | Z-740 | i-Pr | c-Pent-CH2— | Z-741 | i-Pr | 2-Br-4-F—Ph |
| Z-742 | Pr | 2-Br-4-MeO—PhCH2— | Z-743 | i-Pr | c-Hex—CH2— | Z-744 | i-Pr | 2-Br-5-F—Ph |
| Z-745 | Pr | 2-Br-5-MeO—PhCH2— | Z-746 | i-Pr | F3C— | Z-747 | i-Pr | 2-Br-6-F—Ph |
| Z-748 | Pr | 2-Br-6-MeO—PhCH2— | Z-749 | i-Pr | F2CH— | Z-750 | i-Pr | 2-F-3-MeO—Ph |
| Z-751 | Pr | 2,3,4-tri-F—PhCH2— | Z-752 | i-Pr | F3CCH2— | Z-753 | i-Pr | 2-F-4-MeO—Ph |
| Z-754 | Pr | 2,3,5-tri-F—PhCH2— | Z-755 | i-Pr | F2CHCH2— | Z-756 | i-Pr | 2-F-5-MeO—Ph |
| Z-757 | Pr | 2,3,6-tri-F—PhCH2— | Z-758 | i-Pr | F3CF2C— | Z-759 | i-Pr | 2-F-6-MeO—Ph |

TABLE 3-continued

| Z | R3 | R4 | Z | R3 | R4 | Z | R3 | R4 |
|---|---|---|---|---|---|---|---|---|
| Z-760 | Pr | 2-Br-3,4-di-F—PhCH2— | Z-761 | i-Pr | F2CHF2C— | Z-762 | i-Pr | 2-Cl-3-MeO—Ph |
| Z-763 | Pr | 2-Br-3,5-di-F—PhCH2— | Z-764 | i-Pr | (F3C)2FC— | Z-765 | i-Pr | 2-Cl-4-MeO—Ph |
| Z-766 | Pr | 2-Br-3,6-di-F—PhCH2— | Z-767 | i-Pr | F3CF2C(F3C)FC— | Z-768 | i-Pr | 2-Cl-5-MeO—Ph |
| Z-769 | Pr | 2-F-3,4-di-MeO—PhCH2— | Z-770 | i-Pr | c-Pr | Z-771 | i-Pr | 2-Cl-6-MeO—Ph |
| Z-772 | Pr | 2-F-3,5-di-MeO—PhCH2— | Z-773 | i-Pr | c-Bu | Z-774 | i-Pr | 2-Br-3-MeO—Ph |
| Z-775 | Pr | 2-F-3,6-di-MeO—PhCH2— | Z-776 | i-Pr | c-Pent | Z-777 | i-Pr | 2-Br-4-MeO—Ph |
| Z-778 | Pr | 2-Cl-3,4-di-MeO—PhCH2— | Z-779 | i-Pr | c-Hex | Z-780 | i-Pr | 2-Br-5-MeO—Ph |
| Z-781 | Pr | 2-Cl-3,5-di-MeO—PhCH2— | Z-782 | i-Pr | H2C═CH— | Z-783 | i-Pr | 2-Br-6-MeO—Ph |
| Z-784 | Pr | 2-Cl-3,6-di-MeO—PhCH2— | Z-785 | i-Pr | H3CCH═CH— | Z-786 | i-Pr | 2,3,4-tri-F—Ph |
| Z-787 | Pr | 2-Br-3,4-di-MeO—PhCH2— | Z-788 | i-Pr | H2C═CHCH2— | Z-789 | i-Pr | 2,3,5-tri-F—Ph |
| Z-790 | Pr | 2-Br-3,5-di-MeO—PhCH2— | Z-791 | i-Pr | F2C═CH— | Z-792 | i-Pr | 2,3,6-tri-F—Ph |
| Z-793 | Pr | 2-Br-3,6-di-MeO—PhCH2— | Z-794 | i-Pr | F2C═CHCH2— | Z-795 | i-Pr | 2-Br-3,4-di-F—Ph |
| Z-796 | Pr | MeS— | Z-797 | i-Pr | HC≡C— | Z-798 | i-Pr | 2-Br-3,5-di-F—Ph |
| Z-799 | Pr | MeS(═O)— | Z-800 | i-Pr | HC≡CCH2— | Z-801 | i-Pr | 2-Br-3,6-di-F—Ph |
| Z-802 | Pr | MeS(═O)2— | Z-803 | i-Pr | HC≡CCH2CH2— | Z-804 | i-Pr | 2-F-3,4-di-MeO—Ph |
| Z-805 | Pr | EtS— | Z-806 | i-Pr | H3CC≡CCH2— | Z-807 | i-Pr | 2-F-3,5-di-MeO—Ph |
| Z-808 | Pr | EtS(═O)— | Z-809 | i-Pr | FC≡C— | Z-810 | i-Pr | 2-F-3,6-di-MeO—Ph |
| Z-811 | Pr | EtS(—O)2— | Z-812 | i-Pr | FC≡CCF2— | Z-813 | i-Pr | 2-Cl-3,4-di-MeO—Ph |
| Z-814 | Pr | PrS— | Z-815 | i-Pr | FC≡CCF2CF2— | Z-816 | i-Pr | 2-Cl-3,5-di-MeO—Ph |
| Z-817 | Pr | PrS(═O)— | Z-818 | i-Pr | F3CC≡CCF2— | Z-819 | i-Pr | 2-Cl-3,6-di-MeO—Ph |
| Z-820 | Pr | PrS(═O)2— | Z-821 | i-Pr | Ph | Z-822 | i-Pr | 2-Br-3,4-di-MeO—Ph |
| Z-823 | Pr | Ac | Z-824 | i-Pr | 2-F—Ph | Z-825 | i-Pr | 2-Br-3,5-di-MeO—Ph |
| Z-826 | i-Pr | 2-Br-3,6-di-MeO—Ph | Z-827 | i-Pr | 2-Cl-3,6-di-MeO—PhCH2— | Z-828 | Bu | H2C═CHCH2— |
| Z-829 | i-Pr | PhCH2— | Z-830 | i-Pr | 2-Br-3,4-di-MeO—PhCH2— | Z-831 | Bu | F2C═CH— |
| Z-832 | i-Pr | 2-F—PhCH2— | Z-833 | i-Pr | 2-Br-3,5-di-MeO—PhCH2— | Z-834 | Bu | F2C═CHCH2— |
| Z-835 | i-Pr | 3-F—PhCH2— | Z-836 | i-Pr | 2-Br-3,6-di-MeO—PhCH2— | Z-837 | Bu | HC≡C— |
| Z-838 | i-Pr | 4-F—PhCH2— | Z-839 | i-Pr | MeS— | Z-840 | Bu | HC≡CCH2— |
| Z-841 | i-Pr | 2-Cl—PhCH2— | Z-842 | i-Pr | MeS(═O)— | Z-843 | Bu | HC≡CCH2CH2— |
| Z-844 | i-Pr | 3-Cl—PhCH2— | Z-845 | i-Pr | MeS(═O)2— | Z-846 | Bu | H3CC≡CCH2— |
| Z-847 | i-Pr | 4-Cl—PhCH2— | Z-848 | i-Pr | EtS— | Z-849 | Bu | FC≡C— |
| Z-850 | i-Pr | 2-Br—PhCH2— | Z-851 | i-Pr | EtS(═O)— | Z-852 | Bu | FC≡CCF2— |
| Z-853 | i-Pr | 3-Br—PhCH2— | Z-854 | i-Pr | EtS(═O)2— | Z-855 | Bu | FC≡CCF2CF2— |
| Z-856 | i-Pr | 4-Br—PhCH2— | Z-857 | i-Pr | PrS— | Z-858 | Bu | F3CC≡CCF2— |
| Z-859 | i-Pr | 2-I—PhCH2— | Z-860 | i-Pr | PrS(═O)— | Z-861 | Bu | Ph |
| Z-862 | i-Pr | 3-I—PhCH2— | Z-863 | i-Pr | PrS(═O)2— | Z-864 | Bu | 2-F—Ph |
| Z-865 | i-Pr | 4-I—PhCH2— | Z-866 | i-Pr | Ac | Z-867 | Bu | 3-F—Ph |
| Z-868 | i-Pr | 2-Me—PhCH2— | Z-869 | i-Pr | OHC— | Z-870 | Bu | 4-F—Ph |
| Z-871 | i-Pr | 3-Me—PhCH2— | Z-872 | i-Pr | Et(C═O)— | Z-873 | Bu | 2-Cl—Ph |
| Z-874 | i-Pr | 4-Me—PhCH2— | Z-875 | i-Pr | Pr(C═O)— | Z-876 | Bu | 3-Cl—Ph |
| Z-877 | i-Pr | 2-MeO—PhCH2— | Z-878 | i-Pr | i-Pr(C═O)— | Z-879 | Bu | 4-Cl—Ph |
| Z-880 | i-Pr | 3-MeO—PhCH2— | Z-881 | i-Pr | Bu(C═())— | Z-882 | Bu | 2-Br—Ph |
| Z-883 | i-Pr | 4-MeO—PhCH2— | Z-884 | i-Pr | MeO(C═O)— | Z-885 | Bu | 3-Br—Ph |
| Z-886 | i-Pr | 2,3-di-F—PhCH2— | Z-887 | i-Pr | EtO(C═O)— | Z-888 | Bu | 4-Br—Ph |
| Z-889 | i-Pr | 2,4-di-F—PhCH2— | Z-890 | i-Pr | PrO(C═O)— | Z-891 | Bu | 2-I—Ph |
| Z-892 | i-Pr | 2,5-di-F—PhCH2— | Z-893 | i-Pr | i-PrO(C═O) | Z-894 | Bu | 3-I—Ph |
| Z-895 | i-Pr | 2,6-di-F—PhCH2— | Z-896 | i-Pr | BuO(C═O)— | Z-897 | Bu | 4-I—Ph |
| Z-898 | i-Pr | 2-Cl-3-F—PhCH2— | Z-899 | i-Pr | t-BuOC(═O)— | Z-900 | Bu | 2-Me—Ph |
| Z-901 | i-Pr | 2-Cl-4-F—PhCH2— | Z-902 | Bu | Bu | Z-903 | Bu | 3-Me—Ph |
| Z-904 | i-Pr | 2-Cl-5-F—PhCH2— | Z-905 | Bu | i-Bu | Z-906 | Bu | 4-Me—Ph |
| Z-907 | i-Pr | 2-Cl-6-F—PhCH2— | Z-908 | Bu | sec-Bu | Z-909 | Bu | 2-MeO—Ph |
| Z-910 | i-Pr | 2-Br-3-F—PhCH2— | Z-911 | Bu | Pent | Z-912 | Bu | 3-MeO—Ph |

TABLE 3-continued

| Z | R3 | R4 | Z | R3 | R4 | Z | R3 | R4 |
|---|---|---|---|---|---|---|---|---|
| Z-913 | i-Pr | 2-Br-4-F—PhCH2— | Z-914 | Bu | Hex | Z-915 | Bu | 4-MeO—Ph |
| Z-916 | i-Pr | 2-Br-5-F—PhCH2— | Z-917 | Bu | (CH3)2CH(CH3)CH— | Z-918 | Bu | 2,3-di-F—Ph |
| Z-919 | i-Pr | 2-Br-6-F—PhCH2— | Z-920 | Bu | MeOCH2— | Z-921 | Bu | 2,4-di-F—Ph |
| Z-922 | i-Pr | 2-F-3-MeO—PhCH2— | Z-923 | Bu | MeOCH2CH2— | Z-924 | Bu | 2,5-di-F—Ph |
| Z-925 | i-Pr | 2-F-4-MeO—PhCH2— | Z-926 | Bu | EtOCH2— | Z-927 | Bu | 2,6-di-F—Ph |
| Z-928 | i-Pr | 2-F-5-MeO—PhCH2— | Z-929 | Bu | EtOCH2CH2— | Z-930 | Bu | 2-Cl-3-F—Ph |
| Z-931 | i-Pr | 2-F-6-MeO—PhCH2— | Z-932 | Bu | N≡CCH2— | Z-933 | Bu | 2-Cl-4-F—Ph |
| Z-934 | i-Pr | 2-Cl-3-MeO—PhCH2— | Z-935 | Bu | N≡CCH2CH2— | Z-936 | Bu | 2-Cl-5-F—Ph |
| Z-937 | i-Pr | 2-Cl-4-MeO—PhCH2— | Z-938 | Bu | c-Pr—CH2— | Z-939 | Bu | 2-Cl-6-F—Ph |
| Z-940 | i-Pr | 2-Cl-5-MeO—PhCH2— | Z-941 | Bu | c-Bu—CH2— | Z-942 | Bu | 2-Br-3-F—Ph |
| Z-943 | i-Pr | 2-Cl-6-MeO—PhCH2— | Z-944 | Bu | c-Pent-CH2— | Z-945 | Bu | 2-Br-4-F—Ph |
| Z-946 | i-Pr | 2-Br-3-MeO—PhCH2— | Z-947 | Bu | c-Hex—CH2— | Z-948 | Bu | 2-Br-5-F—Ph |
| Z-949 | i-Pr | 2-Br-4-MeO—PhCH2— | Z-950 | Bu | F3C— | Z-951 | Bu | 2-Br-6-F—Ph |
| Z-952 | i-Pr | 2-Br-5-MeO—PhCH2— | Z-953 | Bu | F2CH— | Z-954 | Bu | 2-F-3-MeO—Ph |
| Z-955 | i-Pr | 2-Br-6-MeO—PhCH2— | Z-956 | Bu | F3CCH2— | Z-957 | Bu | 2-F-4-MeO—Ph |
| Z-958 | i-Pr | 2,3,4-tri-F—PhCH2— | Z-959 | Bu | F2CHCH2— | Z-960 | Bu | 2-F-5-MeO—Ph |
| Z-961 | i-Pr | 2,3,5-tri-F—PhCH2— | Z-962 | Bu | F3CF2C— | Z-963 | Bu | 2-F-6-MeO—Ph |
| Z-964 | i-Pr | 2,3,6-tri-F—PhCH2— | Z-965 | Bu | F2CHF2C— | Z-966 | Bu | 2-Cl-3-MeO—Ph |
| Z-967 | i-Pr | 2-Br-3,4-di-F—PhCH2— | Z-968 | Bu | (F3C)2FC— | Z-969 | Bu | 2-Cl-4-MeO—Ph |
| Z-970 | i-Pr | 2-Br-3,5-di-F—PhCH2— | Z-971 | Bu | F3CF2C(F3C)FC— | Z-972 | Bu | 2-Cl-5-MeO—Ph |
| Z-973 | i-Pr | 2-Br-3,6-di-F—PhCH2— | Z-974 | Bu | c-Pr | Z-975 | Bu | 2-Cl-6-MeO—Ph |
| Z-976 | i-Pr | 2-F-3,4-di-MeO—PhCH2— | Z-977 | Bu | c-Bu | Z-978 | Bu | 2-Br-3-MeO—Ph |
| Z-979 | i-Pr | 2-F-3,5-di-MeO—PhCH2— | Z-980 | Bu | c-Pent | Z-981 | Bu | 2-Br-4-MeO—Ph |
| Z-982 | i-Pr | 2-F-3,6-di-MeO—PhCH2— | Z-983 | Bu | c-Hex | Z-984 | Bu | 2-Br-5-MeO—Ph |
| Z-985 | i-Pr | 2-Cl-3,4-di-MeO—PhCH2— | Z-986 | Bu | H2C═CH— | Z-987 | Bu | 2-Br-6-MeO—Ph |
| Z-988 | i-Pr | 2-Cl-3,5-di-MeO—PhCH2— | Z-989 | Bu | H3CCH═CH— | Z-990 | Bu | 2,3,4-tri-F—Ph |
| Z-991 | Bu | 2,3,5-tri-F—Ph | Z-992 | Bu | 2-Br-5-MeO—PhCH2— | Z-993 | i-Bu | F3CCH2— |
| Z-994 | Bu | 2,3,6-tri-F—Ph | Z-995 | Bu | 2-Br-6-MeO—PhCH2— | Z-996 | i-Bu | F2CHCH2— |
| Z-997 | Bu | 2-Br-3,4-di-F—Ph | Z-998 | Bu | 2,3,4-tri-F—PhCH2— | Z-999 | i-Bu | F3CF2C— |
| Z-1000 | Bu | 2-Br-3,5-di-F—Ph | Z-1001 | Bu | 2,3,5-tri-F—PhCH2— | Z-1002 | i-Bu | F2CHF2C— |
| Z-1003 | Bu | 2-Br-3,6-di-F—Ph | Z-1004 | Bu | 2,3,6-tri-F—PhCH2— | Z-1005 | i-Bu | (F3C)2FC— |
| Z-1006 | Bu | 2-F-3,4-di-MeO—Ph | Z-1007 | Bu | 2-Br-3,4-di-F—PhCH2— | Z-1008 | i-Bu | F3CF2C(F3C)FC— |
| Z-1009 | Bu | 2-F-3,5-di-MeO—Ph | Z-1010 | Bu | 2-Br-3,5-di-F—PhCH2— | Z-1011 | i-Bu | c-Pr |
| Z-1012 | Bu | 2-F-3,6-di-MeO—Ph | Z-1013 | Bu | 2-Br-3,6-di-F—PhCH2— | Z-1014 | i-Bu | c-Bu |
| Z-1015 | Bu | 2-Cl-3,4-di-MeO—Ph | Z-1016 | Bu | 2-F-3,4-di-MeO—PhCH2— | Z-1017 | i-Bu | c-Pent |
| Z-1018 | Bu | 2-Cl-3,5-di-MeO—Ph | Z-1019 | Bu | 2-F-3,5-di-MeO—PhCH2— | Z-1020 | i-Bu | c-Hex |
| Z-1021 | Bu | 2-Cl-3,6-di-MeO—Ph | Z-1022 | Bu | 2-F-3,6-di-MeO—PhCH2— | Z-1023 | i-Bu | H2C═CH— |
| Z-1024 | Bu | 2-Br-3,4-di-MeO—Ph | Z-1025 | Bu | 2-Cl-3,4-di-MeO—PhCH2— | Z-1026 | i-Bu | H3CCH═CH— |
| Z-1027 | Bu | 2-Br-3,5-di-MeO—Ph | Z-1028 | Bu | 2-Cl-3,5-di-MeO—PhCH2— | Z-1029 | i-Bu | H2C═CHCH2— |
| Z-1030 | Bu | 2-Br-3,6-di-MeO—Ph | Z-1031 | Bu | 2-Cl-3,6-di-MeO—PhCH2— | Z-1032 | i-Bu | F2C═CH— |
| Z-1033 | Bu | PhCH2— | Z-1034 | Bu | 2-Br-3,4-di-MeO—PhCH2— | Z-1035 | i-Bu | F2C═CHCH2— |
| Z-1036 | Bu | 2-F—PhCH2— | Z-1037 | Bu | 2-Br-3,5-di-MeO—PhCH2— | Z-1038 | i-Bu | HC≡C— |
| Z-1039 | Bu | 3-F—PhCH2— | Z-1040 | Bu | 2-Br-3,6-di-MeO—PhCH2— | Z-1041 | i-Bu | HC≡CCH2— |
| Z-1042 | Bu | 4-F—PhCH2— | Z-1043 | Bu | MeS— | Z-1044 | i-Bu | HC≡CCH2CH2— |
| Z-1045 | Bu | 2-Cl—PhCH2— | Z-1046 | Bu | MeS(═O)— | Z-1047 | i-Bu | H3CC≡CCH2— |
| Z-1048 | Bu | 3-Cl—PhCH2— | Z-1049 | Bu | MeS(═O)2— | Z-1050 | i-Bu | FC≡C— |
| Z-1051 | Bu | 4-Cl—PhCH2— | Z-1052 | Bu | EtS— | Z-1053 | i-Bu | FC≡CCF2— |
| Z-1054 | Bu | 2-Br—PhCH2— | Z-1055 | Bu | EtS(═O)— | Z-1056 | i-Bu | FC≡CCF2CF2— |
| Z-1057 | Bu | 3-Br—PhCH2— | Z-1058 | Bu | EtS(═O)2— | Z-1059 | i-Bu | F3CC≡CCF2— |
| Z-1060 | Bu | 4-Br—PhCH2— | Z-1061 | Bu | PrS— | Z-1062 | i-Bu | Ph |
| Z-1063 | Bu | 2-I—PhCH2— | Z-1064 | Bu | PrS(═O)— | Z-1065 | i-Bu | 2-F—Ph |

TABLE 3-continued

| Z | R3 | R4 | Z | R3 | R4 | Z | R3 | R4 |
|---|---|---|---|---|---|---|---|---|
| Z-1066 | Bu | 3-I—PhCH2— | Z-1067 | Bu | PrS(═O)2— | Z-1068 | i-Bu | 3-F—Ph |
| Z-1069 | Bu | 4-I—PhCH2— | Z-1070 | Bu | Ac | Z-1071 | i-Bu | 4-F—Ph |
| Z-1072 | Bu | 2-Me—PhCH2— | Z-1073 | Bu | OHC— | Z-1074 | i-Bu | 2-Cl—Ph |
| Z-1075 | Bu | 3-Me—PhCH2— | Z-1076 | Bu | Et(C═O)— | Z-1077 | i-Bu | 3-Cl—Ph |
| Z-1078 | Bu | 4-Me—PhCH2— | Z-1079 | Bu | Pr(C═O)— | Z-1080 | i-Bu | 4-Cl—Ph |
| Z-1081 | Bu | 2-MeO—PhCH2— | Z-1082 | Bu | i-Pr(C═O)— | Z-1083 | i-Bu | 2-Br—Ph |
| Z-1084 | Bu | 3-MeO—PhCH2— | Z-1085 | Bu | Bu(C═O)— | Z-1086 | i-Bu | 3-Br—Ph |
| Z-1087 | Bu | 4-MeO—PhCH2— | Z-1088 | Bu | MeO(C═O)— | Z-1089 | i-Bu | 4-Br—Ph |
| Z-1090 | Bu | 2,3-di-F—PhCH2— | Z-1091 | Bu | EtO(C═O)— | Z-1092 | i-Bu | 2-I—Ph |
| Z-1093 | Bu | 2,4-di-F—PhCH2— | Z-1094 | Bu | PrO(C═O)— | Z-1095 | i-Bu | 3-I—Ph |
| Z-1096 | Bu | 2,5-di-F—PhCH2— | Z-1097 | Bu | i-PrO(C═O) | Z-1098 | i-Bu | 4-I—Ph |
| Z-1099 | Bu | 2,6-di-F—PhCH2— | Z-1100 | Bu | BuO(C═O)— | Z-1101 | i-Bu | 2-Me—Ph |
| Z-1102 | Bu | 2-Cl-3-F—PhCH2— | Z-1103 | Bu | t-BuOC(═O)— | Z-1104 | i-Bu | 3-Me—Ph |
| Z-1105 | Bu | 2-Cl-4-F—PhCH2— | Z-1106 | i-Bu | i-Bu | Z-1107 | i-Bu | 4-Me—Ph |
| Z-1108 | Bu | 2-Cl-5-F—PhCH2— | Z-1109 | i-Bu | sec-Bu | Z-1110 | i-Bu | 2-MeO—Ph |
| Z-1111 | Bu | 2-Cl-6-F—PhCH2— | Z-1112 | i-Bu | Pent | Z-1113 | i-Bu | 3-MeO—Ph |
| Z-1114 | Bu | 2-Br-3-F—PhCH2— | Z-1115 | i-Bu | Hex | Z-1116 | i-Bu | 4-MeO—Ph |
| Z-1117 | Bu | 2-Br-4-F—PhCH2— | Z-1118 | i-Bu | (CH3)2CH(CH3)CH— | Z-1119 | i-Bu | 2,3-di-F—Ph |
| Z-1120 | Bu | 2-Br-5-F—PhCH2— | Z-1121 | i-Bu | MeOCH2— | Z-1122 | i-Bu | 2,4-di-F—Ph |
| Z-1123 | Bu | 2-Br-6-F—PhCH2— | Z-1124 | i-Bu | MeOCH2CH2— | Z-1125 | i-Bu | 2,5-di-F—Ph |
| Z-1126 | Bu | 2-F-3-MeO—PhCH2— | Z-1127 | i-Bu | EtOCH2— | Z-1128 | i-Bu | 2,6-di-F—Ph |
| Z-1129 | Bu | 2-F-4-MeO—PhCH2— | Z-1130 | i-Bu | EtOCH2CH2— | Z-1131 | i-Bu | 2-Cl-3-F—Ph |
| Z-1132 | Bu | 2-F-5-MeO—PhCH2— | Z-1133 | i-Bu | N≡CCH2— | Z-1134 | i-Bu | 2-Cl-4-F—Ph |
| Z-1135 | Bu | 2-F-6-MeO—PhCH2— | Z-1136 | i-Bu | N≡CCH2CH2— | Z-1137 | i-Bu | 2-Cl-5-F—Ph |
| Z-1138 | Bu | 2-Cl-3-MeO—PhCH2— | Z-1139 | i-Bu | c-Pr—CH2— | Z-1140 | i-Bu | 2-Cl-6-F—Ph |
| Z-1141 | Bu | 2-Cl-4-MeO—PhCH2— | Z-1142 | i-Bu | c-Bu—CH2— | Z-1143 | i-Bu | 2-Br-3-F—Ph |
| Z-1144 | Bu | 2-Cl-5-MeO—PhCH2— | Z-1145 | i-Bu | c-Pent-CH2— | Z-1146 | i-Bu | 2-Br-4-F—Ph |
| Z-1147 | Bu | 2-Cl-6-MeO—PhCH2— | Z-1148 | i-Bu | c-Hex—CH2— | Z-1149 | i-Bu | 2-Br-5-F—Ph |
| Z-1150 | Bu | 2-Br-3-MeO—PhCH2— | Z-1151 | i-Bu | F3C— | Z-1152 | i-Bu | 2-Bi-6-F—Ph |
| Z-1153 | Bu | 2-Br-4-MeO—PhCH2— | Z-1154 | i-Bu | F2CH— | Z-1155 | i-Bu | 2-F-3-MeO—Ph |
| Z-1156 | i-Bu | 2-F-4-MeO—Ph | Z-1157 | i-Bu | 2-Br-5-F—PhCH2— | Z-1158 | sec-Bu | MeOCH2CH2— |
| Z-1159 | i-Bu | 2-F-5-MeO—Ph | Z-1160 | i-Bu | 2-Br-6-F—PhCH2— | Z-1161 | sec-Bu | EtOCH2— |
| Z-1162 | i-Bu | 2-F-6-MeO—Ph | Z-1163 | i-Bu | 2-F-3-MeO—PhCH2— | Z-1164 | sec-Bu | EtOCH2CH2— |
| Z-1165 | i-Bu | 2-Cl-3-MeO—Ph | Z-1166 | i-Bu | 2-F-4-MeO—PhCH2— | Z-1167 | sec-Bu | N≡CCH2— |
| Z-1168 | i-Bu | 2-Cl-4-MeO—Ph | Z-1169 | i-Bu | 2-F-5-MeO—PhCH2— | Z-1170 | sec-Bu | N≡CCH2CH2— |
| Z-1171 | i-Bu | 2-Cl-5-MeO—Ph | Z-1172 | i-Bu | 2-F-6-MeO—PhCH2— | Z-1173 | sec-Bu | c-Pr—CH2— |
| Z-1174 | i-Bu | 2-Cl-6-MeO—Ph | Z-1175 | i-Bu | 2-Cl-3-MeO—PhCH2— | Z-1176 | sec-Bu | c-Bu—CH2— |
| Z-1177 | i-Bu | 2-Br-3-MeO—Ph | Z-1178 | i-Bu | 2-Cl-4-MeO—PhCH2— | Z-1179 | sec-Bu | c-Pent-CH2— |
| Z-1180 | i-Bu | 2-Br-4-MeO—Ph | Z-1181 | i-Bu | 2-Cl-5-MeO—PhCH2— | Z-1182 | sec-Bu | c-Hex—CH2— |
| Z-1183 | i-Bu | 2-Br-5-MeO—Ph | Z-1184 | i-Bu | 2-Cl-6-MeO—PhCH2— | Z-1185 | sec-Bu | F3C— |
| Z-1186 | i-Bu | 2-Br-6-MeO—Ph | Z-1187 | i-Bu | 2-Br-3-MeO—PhCH2— | Z-1188 | sec-Bu | F2CH— |
| Z-1189 | i-Bu | 2,3,4-tri-F—Ph | Z-1190 | i-Bu | 2-Br-4-MeO—PhCH2— | Z-1191 | sec-Bu | F3CCH2— |
| Z-1192 | i-Bu | 2,3,5-tri-F—Ph | Z-1193 | i-Bu | 2-Br-5-MeO—PhCH2— | Z-1194 | sec-Bu | F2CHCH2— |
| Z-1195 | i-Bu | 2,3,6-tri-F—Ph | Z-1196 | i-Bu | 2-Br-6-MeO—PhCH2— | Z-1197 | sec-Bu | F3CF2C— |
| Z-1198 | i-Bu | 2-Br-3,4-di-F—Ph | Z-1199 | i-Bu | 2,3,4-tri-F—PhCH2— | Z-1200 | sec-Bu | F2CHF2C— |
| Z-1201 | i-Bu | 2-Br-3,5-di-F—Ph | Z-1202 | i-Bu | 2,3,5-tri-F—PhCH2— | Z-1203 | sec-Bu | (F3C)2FC— |
| Z-1204 | i-Bu | 2-Br-3,6-di-F—Ph | Z-1205 | i-Bu | 2,3,6-tri-F—PhCH2— | Z-1206 | sec-Bu | F3CF2C(F3C)FC— |
| Z-1207 | i-Bu | 2-F-3,4-di-MeO—Ph | Z-1208 | i-Bu | 2-Br-3,4-di-F—PhCH2— | Z-1209 | sec-Bu | c-Pr |
| Z-1210 | i-Bu | 2-F-3,5-di-MeO—Ph | Z-1211 | i-Bu | 2-Br-3,5-di-F—PhCH2— | Z-1212 | sec-Bu | c-Bu |
| Z-1213 | i-Bu | 2-F-3,6-di-MeO—Ph | Z-1214 | i-Bu | 2-Br-3,6-di-F—PhCB2— | Z-1215 | sec-Bu | c-Pent |
| Z-1216 | i-Bu | 2-Cl-3,4-di-MeO—Ph | Z-1217 | i-Bu | 2-F-3,4-di-MeO—PhCH2— | Z-1218 | sec-Bu | c-Hex |

TABLE 3-continued

| Z | R3 | R4 | Z | R3 | R4 | Z | R3 | R4 |
|---|---|---|---|---|---|---|---|---|
| Z-1219 | i-Bu | 2-Cl-3,5-di-MeO—Ph | Z-1220 | i-Bu | 2-F-3,5-di-MeO—PhCH2— | Z-1221 | sec-Bu | H2C═CH— |
| Z-1222 | i-Bu | 2-Cl-3,6-di-MeO—Ph | Z-1223 | i-Bu | 2-F-3,6-di-MeO—PhCH2— | Z-1224 | sec-Bu | H3CCH═CH— |
| Z-1225 | i-Bu | 2-Br-3,4-di-MeO—Ph | Z-1226 | i-Bu | 2-Cl-3,4-di-MeO—PhCH2— | Z-1227 | sec-Bu | H2C═CHCH2— |
| Z-1228 | i-Bu | 2-Br-3,5-di-MeO—Ph | Z-1229 | i-Bu | 2-Cl-3,5-di-MeO—PhCH2— | Z-1230 | sec-Bu | F2C═CH— |
| Z-1231 | i-Bu | 2-Br-3,6-di-MeO—Ph | Z-1232 | i-Bu | 2-Cl-3,6-di-MeO—PhCH2— | Z-1233 | sec-Bu | F2C═CHCH2— |
| Z-1234 | i-Bu | PhCH2— | Z-1235 | i-Bu | 2-Br-3,4-di-MeO—PhCH2— | Z-1236 | sec-Bu | HC═C— |
| Z-1237 | i-Bu | 2-F—PhC—H2- | Z-1238 | i-Bu | 2-Br-3,5-di-MeO—PhCH2— | Z-1239 | sec-Bu | HC≡CCH2— |
| Z-1240 | i-Bu | 3-F—PhCH2— | Z-1241 | i-Bu | 2-Br-3,6-di-MeO—PhCH2— | Z-1242 | sec-Bu | HC≡CCH2CH2— |
| Z-1243 | i-Bu | 4-F—PhCH2— | Z-1244 | i-Bu | MeS— | Z-1245 | sec-Bu | H3CC≡CCH2— |
| Z-1246 | i-Bu | 2-Cl—PhCH2— | Z-1247 | i-Bu | MeS(═O)— | Z-1248 | sec-Bu | FC≡C— |
| Z-1249 | i-Bu | 3-Cl—PhCH2— | Z-1250 | i-Bu | MeS(═O)2— | Z-1251 | sec-Bu | FC≡CCF2— |
| Z-1252 | i-Bu | 4-Cl—PhCH2— | Z-1253 | i-Bu | EtS— | Z-1254 | sec-Bu | FC≡CCF2CF2— |
| Z-1255 | i-Bu | 2-Br—PhCH2— | Z-1256 | i-Bu | EtS(═O)— | Z-1257 | sec-Bu | F3CC≡CCF2— |
| Z-1258 | i-Bu | 3-Br—PhCH2— | Z-1259 | i-Bu | EtS(═O)2— | Z-1260 | sec-Bu | Ph |
| Z-1261 | i-Bu | 4-Br—PhCH2— | Z-1262 | i-Bu | PrS— | Z-1263 | sec-Bu | 2-F—Ph |
| Z-1264 | i-Bu | 2-I—PhCH2— | Z-1265 | i-Bu | PrS(═O)— | Z-1266 | sec-Bu | 3-F—Ph |
| Z-1267 | i-Bu | 3-I—PhCH2— | Z-1268 | i-Bu | PrS(═O)2— | Z-1269 | sec-Bu | 4-F—Ph |
| Z-1270 | i-Bu | 4-I—PhCH2— | Z-1271 | i-Bu | Ac | Z-1272 | sec-Bu | 2-Cl—Ph |
| Z-1273 | i-Bu | 2-Me—PhCH2— | Z-1274 | i-Bu | OHC— | Z-1275 | sec-Bu | 3-Cl—Ph |
| Z-1276 | i-Bu | 3-Me—PhCH2— | Z-1277 | i-Bu | Et(C═O)— | Z-1278 | sec-Bu | 4-Cl—Ph |
| Z-1279 | i-Bu | 4-Me—PhCH2— | Z-1280 | i-Bu | Pr(C═O)— | Z-1281 | sec-Bu | 2-Br—Ph |
| Z-1282 | i-Bu | 2-MeO—PhCH2— | Z-1283 | i-Bu | i-Pr(C═O)— | Z-1284 | sec-Bu | 3-Br—Ph |
| Z-1285 | i-Bu | 3-MeO—PhCH2— | Z-1286 | i-Bu | Bu(C═O)— | Z-1287 | sec-Bu | 4-Br—Ph |
| Z-1288 | i-Bu | 4-MeO—PhCH2— | Z-1289 | i-Bu | MeO(C═O)— | Z-1290 | sec-Bu | 2-I—Ph |
| Z-1291 | i-Bu | 2,3-di-F—PhCH2— | Z-1292 | i-Bu | EtO(C═O)— | Z-1293 | sec-Bu | 3-I—Ph |
| Z-1294 | i-Bu | 2,4-di-F—PhCH2— | Z-1295 | i-Bu | PrO(C═O)— | Z-1296 | sec-Bu | 4-I—Ph |
| Z-1297 | i-Bu | 2,5-di-F—PhCH2— | Z-1298 | i-Bu | i-Pro(C═O)— | Z-1299 | sec-Bu | 2-Me—Ph |
| Z-1300 | i-Bu | 2,6-di-F—PhCH2— | Z-1301 | i-Bu | BuO(C═O)— | Z-1302 | sec-Bu | 3-Me—Ph |
| Z-1303 | i-Bu | 2-Cl-3-F—PhCH2— | Z-1304 | i-Bu | t-BuOC(═O)— | Z-1305 | sec-Bu | 4-Me—Ph |
| Z-1306 | i-Bu | 2-Cl-4-F—PhCH2— | Z-1307 | sec-Bu | sec-Bu | Z-1308 | sec-Bu | 2-MeO—Ph |
| Z-1309 | i-Bu | 2-Cl-5-F—PhCH2— | Z-1310 | sec-Bu | Pent | Z-1311 | sec-Bu | 3-MeO—Ph |
| Z-1312 | i-Bu | 2-Cl-6-F—PhCH2— | Z-1313 | sec-Bu | Hex | Z-1314 | sec-Bu | 4-MeO—Ph |
| Z-1315 | i-Bu | 2-Br-3-F—PhCH2— | Z-1316 | sec-Bu | (CH3)2CH(CH3)CH— | Z-1317 | sec-Bu | 2,3-di-F—Ph |
| Z-1318 | i-Bu | 2-Br-4-F—PhCH2— | Z-1319 | sec-Bu | MeOCH2— | Z-1320 | sec-Bu | 2,4-di-F—Ph |
| Z-1321 | sec-Bu | 2,5-di-F—Ph | Z-1322 | sec-Bu | 4-MeO—PhCH2— | Z-1323 | sec-Bu | MeO(C═O)— |
| Z-1324 | sec-Bu | 2,6-di-F—Ph | Z-1325 | sec-Bu | 2,3-di-F—PhCH2— | Z-1326 | sec-Bu | EtO(C═O)— |
| Z-1327 | sec-Bu | 2-Cl-3-F—Ph | Z-1328 | sec-Bu | 2,4-di-F—PhCH2— | Z-1329 | sec-Bu | PrO(C═O)— |
| Z-1330 | sec-Bu | 2-Cl-4-F—Ph | Z-1331 | sec-Bu | 2,5-di-F—PhCH2— | Z-1332 | sec-Bu | i-PrO(C═O)— |
| Z-1333 | sec-Bu | 2-Cl-5-F—Ph | Z-1334 | sec-Bu | 2,6-di-F—PhCH2— | Z-1335 | sec-Bu | BuO(C═O)— |
| Z-1336 | sec-Bu | 2-Cl-6-F—Ph | Z-1337 | sec-Bu | 2-Cl-3-F—PFCH2— | Z-1338 | sec-Bu | t-BuOC(═O)— |
| Z-1339 | sec-Bu | 2-Br-3-F—Ph | Z-1340 | sec-Bu | 2-Cl-4-F—PhCH2— | Z-1341 | Pent | Pent |
| Z-1342 | sec-Bu | 2-Br-4-F—Ph | Z-1343 | sec-Bu | 2-Cl-5-F—PhCH2— | Z-1344 | Pent | Hex |
| Z-1345 | sec-Bu | 2-Br-5-F—Ph | Z-1346 | sec-Bu | 2-Cl-6-F—PhCH2— | Z-1347 | Pent | (CH3)2CH(CH3)CH— |
| Z-1348 | sec-Bu | 2-Br-6-F—Ph | Z-1349 | sec-Bu | 2-Br-3-F—PhCH2— | Z-1350 | Pent | MeOCH2— |
| Z-1351 | sec-Bu | 2-F-3-MeO—Ph | Z-1352 | sec-Bu | 2-Br-4-F—PhCH2— | Z-1353 | Pent | MeOCH2CH2— |
| Z-1354 | sec-Bu | 2-F-4-MeO—Ph | Z-1355 | sec-Bu | 2-Br-5-F—PFCH2— | Z-1356 | Pent | EtOCH2— |
| Z-1357 | sec-Bu | 2-F-5-MeO—Ph | Z-1358 | sec-Bu | 2-Br-6-F—PhCH2— | Z-1359 | Pent | EtOCH2CH2— |
| Z-1360 | sec-Bu | 2-F-6-MeO—Ph | Z-1361 | sec-Bu | 2-F-3-MeO—PhCH2— | Z-1362 | Pent | N≡CCH2— |
| Z-1363 | sec-Bu | 2-Cl-3-MeO—Ph | Z-1364 | sec-Bu | 2-F-4-MeO—PhCH2— | Z-1365 | Pent | N≡CCH2CH2— |
| Z-1366 | sec-Bu | 2-Cl-4-MeO—Ph | Z-1367 | sec-Bu | 2-F-5-MeO—PhCH2— | Z-1368 | Pent | c-Pr—CH2— |
| Z-1369 | sec-Bu | 2-Cl-5-MeO—Ph | Z-1370 | sec-Bu | 2-F-6-MeO—PhCH2— | Z-1371 | Pent | c-Bu—CH2— |

TABLE 3-continued

| Z | R3 | R4 | Z | R3 | R4 | Z | R3 | R4 |
|---|---|---|---|---|---|---|---|---|
| Z-1372 | sec-Bu | 2-Cl-6-MeO—Ph | Z-1373 | sec-Bu | 2-Cl-3-MeO—PhCH2— | Z-1374 | Pent | c-Pent-CH2— |
| Z-1375 | sec-Bu | 2-Br-3-MeO—Ph | Z-1376 | sec-Bu | 2-Cl-4-MeO—PhCH2— | Z-1377 | Pent | c-Hex—CH2— |
| Z-1378 | sec-Bu | 2-Br-4-MeO—Ph | Z-1379 | sec-Bu | 2-Cl-5-MeO—PhCH2— | Z-1380 | Pent | F3C— |
| Z-1381 | sec-Bu | 2-Br-5-MeO—Ph | Z-1382 | sec-Bu | 2-Cl-6-MeO—PhCH2— | Z-1383 | Pent | F2CH— |
| Z-1384 | sec-Bu | 2-Br-6-MeO—Ph | Z-1385 | sec-Bu | 2-Br-3-MeO—PhCH2— | Z-1386 | Pent | F3CCH2— |
| Z-1387 | sec-Bu | 2,3,4-tri-F—Ph | Z-1388 | sec-Bu | 2-Br-4-MeO—PhCH2— | Z-1389 | Pent | F2CHCH2— |
| Z-1390 | sec-Bu | 2,3,5-tri-F—Ph | Z-1391 | sec-Bu | 2-Br-5-MeO—PhCH2— | Z-1392 | Pent | F3CF2C— |
| Z-1393 | sec-Bu | 2,3,6-tri-F—Ph | Z-1394 | sec-Bu | 2-Br-6-MeO—PhCH2— | Z-1395 | Pent | F2CHF2C— |
| Z-1396 | sec-Bu | 2-Br-3,4-di-F—Ph | Z-1397 | sec-Bu | 2,3,4-tri-F—PhCH2— | Z-1398 | Pent | (F3C)2FC— |
| Z-1399 | sec-Bu | 2-Br-3,5-di-F—Ph | Z-1400 | sec-Bu | 2,3,5-tri-F—PhCH2— | Z-1401 | Pent | F3CF2C(F3C)FC— |
| Z-1402 | sec-Bu | 2-Br-3,6-di-F—Ph | Z-1403 | sec-Bu | 2,3,6-tri-F—PhCH2— | Z-1404 | Pent | c-Pr |
| Z-1405 | sec-Bu | 2-F-3,4-di-MeO—Ph | Z-1406 | sec-Bu | 2-Br-3,4-di-F—PhCH2— | Z-1407 | Pent | c-Bu |
| Z-1408 | sec-Bu | 2-F-3,5-di-MeO—Ph | Z-1409 | sec-Bu | 2-Br-3,5-di-F—PhCH2— | Z-1410 | Pent | c-Pent |
| Z-1411 | sec-Bu | 2-F-3,6-di-MeO—Ph | Z-1412 | sec-Bu | 2-Br-3,6-di-F—PhCH2— | Z-1413 | Pent | c-Hex |
| Z-1414 | sec-Bu | 2-Cl-3,4-di-MeO—Ph | Z-1415 | sec-Bu | 2-F-3,4-di-MeO—PhCH2— | Z-1416 | Pent | H2C═CH— |
| Z-1417 | sec-Bu | 2-Cl-3,5-di-MeO—Ph | Z-1418 | sec-Bu | 2-F-3,5-di-MeO—PhCH2— | Z-1419 | Pent | H3CCH═CH— |
| Z-1420 | sec-Bu | 2-Cl-3,6-di-MeO—Ph | Z-1421 | sec-Bu | 2-F-3,6-di-MeO—PhCH2— | Z-1422 | Pent | H2C═CHCH2— |
| Z-1423 | sec-Bu | 2-Br-3,4-di-MeO—Ph | Z-1424 | sec-Bu | 2-Cl-3,4-di-MeO—PhCH2— | Z-1425 | Pent | F2C═CH— |
| Z-1426 | sec-Bu | 2-Br-3,5-di-MeO—Ph | Z-1427 | sec-Bu | 2-Cl-3,5-di-MeO—PhCH2— | Z-1428 | Pent | F2C═CHCH2— |
| Z-1429 | sec-Bu | 2-Br-3,6-di-MeO—Ph | Z-1430 | sec-Bu | 2-Cl-3,6-di-MeO—PhCH2— | Z-1431 | Pent | HC≡C— |
| Z-1432 | sec-Bu | PhCH2— | Z-1433 | sec-Bu | 2-Br-3,4-di-MeO—PhCH2— | Z-1434 | Pent | HC≡CCH2— |
| Z-1435 | sec-Bu | 2-F—PhCH2— | Z-1436 | sec-Bu | 2-Br-3,5-di-MeO—PhCH2— | Z-1437 | Pent | HC≡CCH2CH2— |
| Z-1438 | sec-Bu | 3-F—PhCH2— | Z-1439 | sec-Bu | 2-Br-3,6-di-MeO—PhCH2— | Z-1440 | Pent | H3CC≡CCH2— |
| Z-1441 | sec-Bu | 4-F—PhCH2— | Z-1442 | sec-Bu | MeS— | Z-1443 | Pent | FC≡C— |
| Z-1444 | sec-Bu | 2-Cl—PhCH2— | Z-1445 | sec-Bu | MeS(═O)— | Z-1446 | Pent | FC≡CCF2— |
| Z-1447 | sec-Bu | 3-Cl—PhCH2— | Z-1448 | sec-Bu | MeS(═O)2— | Z-1449 | Pent | FC≡CCF2CF2— |
| Z-1450 | sec-Bu | 4-Cl—PhCH2— | Z-1451 | sec-Bu | EtS— | Z-1452 | Pent | F3CC≡CCF2— |
| Z-1453 | sec-Bu | 2-Br—PhCH2— | Z-1454 | sec-Bu | EtS(═O)— | Z-1455 | Pent | Ph |
| Z-1456 | sec-Bu | 3-Br—PhCH2— | Z-1457 | sec-Bu | EtS(═O)2— | Z-1458 | Pent | 2-F—Ph |
| Z-1459 | sec-Bu | 4-Br—PhCH2— | Z-1460 | sec-Bu | PrS— | Z-1461 | Pent | 3-F—Ph |
| Z-1462 | sec-Bu | 2-I—PhCH2— | Z-1463 | sec-Bu | PrS(═O)— | Z-1464 | Pent | 4-F—Ph |
| Z-1465 | sec-Bu | 3-I—PhCH2— | Z-1466 | sec-Bu | PrS(═O)2— | Z-1467 | Pent | 2-Cl—Ph |
| Z-1468 | sec-Bu | 4-I—PhCH2— | Z-1469 | sec-Bu | Ac | Z-1470 | Pent | 3-Cl—Ph |
| Z-1471 | sec-Bu | 2-Me—PhCH2— | Z-1472 | sec-Bu | OHC— | Z-1473 | Pent | 4-Cl—Ph |
| Z-1474 | sec-Bu | 3-Me—PhCH2— | Z-1475 | sec-Bu | Et(C═O)— | Z-1476 | Pent | 2-Br—Ph |
| Z-1477 | sec-Bu | 4-Me—PhCH2— | Z-1478 | sec-Bu | Pr(C═O)— | Z-1479 | Pent | 3-Br—Ph |
| Z-1480 | sec-Bu | 2-MeO—PhCH2— | Z-1481 | sec-Bu | i-Pr(C═O)— | Z-1482 | Pent | 4-Br—Ph |
| Z-1483 | sec-Bu | 3-MeO—PhCH2— | Z-1484 | sec-Bu | Bu(C═O)— | Z-1485 | Pent | 2-I—Ph |
| Z-1486 | Pent | 3-I—Ph | Z-1487 | Pent | 3-Br—PhCH2— | Z-1488 | Pent | EtS(═O)2— |
| Z-1489 | Pent | 4-I—Ph | Z-1490 | Pent | 4-Br—PhCH2— | Z-1491 | Pent | PrS— |
| Z-1492 | Pent | 2-Me—Ph | Z-1493 | Pent | 2-I—PhCH2— | Z-1494 | Pent | PrS(═O)— |
| Z-1495 | Pent | 3-Me—Ph | Z-1496 | Pent | 3-I—PhCH2— | Z-1497 | Pent | PrS(═O)2— |
| Z-1498 | Pent | 4-Me—Ph | Z-1499 | Pent | 4-I—PhCH2— | Z-1500 | Pent | Ac |
| Z-1501 | Pent | 2-MeO—Ph | Z-1502 | Pent | 2-Me—PhCH2— | Z-1503 | Pent | OHC— |
| Z-1504 | Pent | 3-MeO—Ph | Z-1505 | Pent | 3-Me—PhCH2— | Z-1506 | Pent | Et(C═O)— |
| Z-1507 | Pent | 4-MeO—Ph | Z-1508 | Pent | 4-Me—PhCH2— | Z-1509 | Pent | Pr(C═O)— |
| Z-1510 | Pent | 2,3-di-F—Ph | Z-1511 | Pent | 2-MeO—PhCH2— | Z-1512 | Pent | i-Pr(C═O)— |
| Z-1513 | Pent | 2,4-di-F—Ph | Z-1514 | Pent | 3-MeO—PhCH2— | Z-1515 | Pent | Bu(C═O)— |
| Z-1516 | Pent | 2,5-di-F—Ph | Z-1517 | Pent | 4-MeO—PhCH2— | Z-1518 | Pent | MeO(C═O)— |
| Z-1519 | Pent | 2,6-di-F—Ph | Z-1520 | Pent | 2,3-di-F—PhCH2— | Z-1521 | Pent | EtO(C═O)— |
| Z-1522 | Pent | 2-Cl-3-F—Ph | Z-1523 | Pent | 2,4-di-F—PhCH2— | Z-1524 | Pent | PrO(C═O)— |

TABLE 3-continued

| Z | R3 | R4 | Z | R3 | R4 | Z | R3 | R4 |
|---|---|---|---|---|---|---|---|---|
| Z-1525 | Pent | 2-Cl-4-F—Ph | Z-1526 | Pent | 2,5-di-F—PhCH2— | Z-1527 | Pent | i-PrO(C═O)— |
| Z-1528 | Pent | 2-Cl-5-F—Ph | Z-1529 | Pent | 2,6-di-F—PhCH2— | Z-1530 | Pent | BuO(C═O)— |
| Z-1531 | Pent | 2-Cl-6-F—Ph | Z-1532 | Pent | 2-Cl-3-F—PhCH2— | Z-1533 | Pent | t-BuOC(═O)— |
| Z-1534 | Pent | 2-Br-3-F—Ph | Z-1535 | Pent | 2-Cl-4-F—PhCH2— | Z-1536 | Hex | Hex |
| Z-1537 | Pent | 2-Br-4-F—Ph | Z-1538 | Pent | 2-Cl-5-F—PhCH2— | Z-1539 | Hex | (CH3)2CH(CH3)CH— |
| Z-1540 | Pent | 2-Br-5-F—Ph | Z-1541 | Pent | 2-Cl-6-F—PhCH2— | Z-1542 | Hex | MeOCH2— |
| Z-1543 | Pent | 2-Br-6-F—Ph | Z-1544 | Pent | 2-Br-3-F—PhCH2— | Z-1545 | Hex | MeOCH2CH2— |
| Z-1546 | Pent | 2-F-3-MeO—Ph | Z-1547 | Pent | 2-Br-4-F—PFCH2— | Z-1548 | Hex | EtOCH2— |
| Z-1549 | Pent | 2-F-4-MeO—Ph | Z-1550 | Pent | 2-Br-5-F—PhCH2— | Z-1551 | Hex | EtOCH2CH2— |
| Z-1552 | Pent | 2-F-5-MeO—Ph | Z-1553 | Pent | 2-Br-6-F—PhCH2— | Z-1554 | Hex | N≡CCH2— |
| Z-1555 | Pent | 2-F-6-MeO—Ph | Z-1556 | Pent | 2-F-3-MeO—PhCH2— | Z-1557 | Hex | N≡CCH2CH2— |
| Z-1558 | Pent | 2-Cl-3-MeO—Ph | Z-1559 | Pent | 2-F-4-MeO—PhCH2— | Z-1560 | Hex | c-Pr—CH2— |
| Z-1561 | Pent | 2-Cl-4-MeO—Ph | Z-1562 | Pent | 2-F-5-MeO—PhCH2— | Z-1563 | Hex | c-Bu—CH2— |
| Z-1564 | Pent | 2-Cl-5-MeO—Ph | Z-1565 | Pent | 2-F-6-MeO—PhCH2— | Z-1566 | Hex | c-Pent-CH2— |
| Z-1567 | Pent | 2-Cl-6-MeO—Ph | Z-1568 | Pent | 2-Cl-3-MeO—PhCH2— | Z-1569 | Hex | c-Hex—CH2— |
| Z-1570 | Pent | 2-Br-3-MeO—Ph | Z-1571 | Pent | 2-Cl-4-MeO—PhCH2— | Z-1572 | Hex | F3C— |
| Z-1573 | Pent | 2-Br-4-MeO—Ph | Z-1574 | Pent | 2-Cl-5-MeO—PhCH2— | Z-1575 | Hex | F2CH— |
| Z-1576 | Pent | 2-Br-5-MeO—Ph | Z-1577 | Pent | 2-Cl-6-MeO—PhCH2— | Z-1578 | Hex | F3CCH2— |
| Z-1579 | Pent | 2-Br-6-MeO—Ph | Z-1580 | Pent | 2-Br-3-MeO—PhCH2— | Z-1581 | Hex | F2CHCH2— |
| Z-1582 | Pent | 2,3,4-tri-F—Ph | Z-1583 | Pent | 2-Br-4-MeO—PhCH2— | Z-1584 | Hex | F3CF2C— |
| Z-1585 | Pent | 2,3,5-tri-F—Ph | Z-1586 | Pent | 2-Br-5-MeO—PhCH2— | Z-1587 | Hex | F2CHF2C— |
| Z-1588 | Pent | 2,3,6-tri-F—Ph | Z-1589 | Pent | 2-Br-6-MeO—PhCH2— | Z-1590 | Hex | (F3C)2FC— |
| Z-1591 | Pent | 2-Br-3,4-di-F—Ph | Z-1592 | Pent | 2,3,4-tri-F—PhCH2— | Z-1593 | Hex | F3CF2C(F3C)FC— |
| Z-1594 | Pent | 2-Br-3,5-di-F—Ph | Z-1595 | Pent | 2,3,5-tri-F—PhCH2— | Z-1596 | Hex | c-Pr |
| Z-1597 | Pent | 2-Br-3,6-di-F—Ph | Z-1598 | Pent | 2,3,6-tri-F—PhCH2— | Z-1599 | Hex | c-Bu |
| Z-1600 | Pent | 2-F-3,4-di-MeO—Ph | Z-1601 | Pent | 2-Br-3,4-di-F—PhCH2— | Z-1602 | Hex | c-Pent |
| Z-1603 | Pent | 2-F-3,5-di-MeO—Ph | Z-1604 | Pent | 2-Br-3,5-di-F—PhCH2— | Z-1605 | Hex | c-Hex |
| Z-1606 | Pent | 2-F-3,6-di-MeO—Ph | Z-1607 | Pent | 2-Br-3,6-di-F—PhCH2— | Z-1608 | Hex | H2C═CH— |
| Z-1609 | Pent | 2-Cl-3,4-di-MeO—Ph | Z-1610 | Pent | 2-F-3,4-di-MeO—PhCH2— | Z-1611 | Hex | H3CCH═CH— |
| Z-1612 | Pent | 2-Cl-3,5-di-MeO—Ph | Z-1613 | Pent | 2-F-3,5-di-MeO—PhCH2— | Z-1614 | Hex | H2C═CHCH2— |
| Z-1615 | Pent | 2-Cl-3,6-di-MeO—Ph | Z-1616 | Pent | 2-F-3,6-di-MeO—PhCH2— | Z-1617 | Hex | F2C═CH— |
| Z-1618 | Pent | 2-Br-3,4-di-MeO—Ph | Z-1619 | Pent | 2-Cl-3,4-di-MeO—PhCH2— | Z-1620 | Hex | F2C═CHCH2— |
| Z-1621 | Pent | 2-Br-3,5-di-MeO—Ph | Z-1622 | Pent | 2-Cl-3,5-di-MeO—PhCH2— | Z-1623 | Hex | HC≡C— |
| Z-1624 | Pent | 2-Br-3,6-di-MeO—Ph | Z-1625 | Pent | 2-Cl-3,6-di-MeO—PhCH2— | Z-1626 | Hex | HC≡CCH2— |
| Z-1627 | Pent | PhCH2— | Z-1628 | Pent | 2-Br-3,4-di-MeO—PhCH2— | Z-1629 | Hex | HC≡CCH2CH2— |
| Z-1630 | Pent | 2-F—PhCH2— | Z-1631 | Pent | 2-Br-3,5-di-MeO—PhCH2— | Z-1632 | Hex | H3CC≡CCH2— |
| Z-1633 | Pent | 3-F—PhCH2— | Z-1634 | Pent | 2-Br-3,6-di-MeO—PhCH2— | Z-1635 | Hex | FC≡C— |
| Z-1636 | Pent | 4-F—PhCH2— | Z-1637 | Pent | MeS— | Z-1638 | Hex | FC≡CCF2— |
| Z-1639 | Pent | 2-Cl—PhCH2— | Z-1640 | Pent | MeS(═O)— | Z-1641 | Hex | FC≡CCF2CF2— |
| Z-1642 | Pent | 3-Cl—PhCH2— | Z-1643 | Pent | MeS(═O)2— | Z-1644 | Hex | F3CC≡CCF2— |
| Z-1645 | Pent | 4-Cl—PhCH2— | Z-1646 | Pent | EtS— | Z-1647 | Hex | Ph |
| Z-1648 | Pent | 2-Br—PhCH2— | Z-1649 | Pent | EtS(═O)— | Z-1650 | Hex | 2-F—Ph |
| Z-1651 | Hex | 3-F—Ph | Z-1652 | Hex | 2-Br-3,6-di-MeO—Ph | Z-1653 | Hex | 2-Cl-3,6-di-MeO—PhCH2— |
| Z-1654 | Hex | 4-F—Ph | Z-1655 | Hex | PhCH2— | Z-1656 | Hex | 2-Br-3,4-di-MeO—PhCH2— |
| Z-1657 | Hex | 2-Cl—Ph | Z-1658 | Hex | 2-F—PKCH2— | Z-1659 | Hex | 2-Br-3,5-di-MeO—PhCH2— |
| Z-1660 | Hex | 3-Cl—Ph | Z-1661 | Ilex | 3-F—PhCH2— | Z-1662 | Hex | 2-Br-3,6-di-MeO—PhCH2— |
| Z-1663 | Hex | 4-Cl—Ph | Z-1664 | Hex | 4-F—PhCH2— | Z-1665 | Hex | MeS— |
| Z-1666 | Hex | 2-Br—Ph | Z-1667 | Hex | 2-Cl—PhCH2— | Z-1668 | Hex | MeS(═O)— |
| Z-1669 | Hex | 3-Br—Ph | Z-1670 | Hex | 3-Cl—PhCH2— | Z-1671 | Hex | MeS(═O)2— |
| Z-1672 | Hex | 4-Br—Ph | Z-1673 | Hex | 4-Cl—PhCH2— | Z-1674 | Hex | EtS— |
| Z-1675 | Hex | 2-I—Ph | Z-1676 | Hex | 2-Br—PhCH2— | Z-1677 | Hex | EtS(═O)— |

TABLE 3-continued

| Z | R3 | R4 | Z | R3 | R4 | Z | R3 | R4 |
|---|---|---|---|---|---|---|---|---|
| Z-1678 | Hex | 3-I—Ph | Z-1679 | Hex | 3-Br—PhCH2— | Z-1680 | Hex | EtS(═O)2— |
| Z-1681 | Hex | 4-I—Ph | Z-1682 | Hex | 4-Br—PhCH2— | Z-1683 | Hex | PrS— |
| Z-1684 | Hex | 2-Me—Ph | Z-1685 | Hex | 2-I—PhCH2— | Z-1686 | Hex | PrS(═O)— |
| Z-1687 | Hex | 3-Me—Ph | Z-1688 | Hex | 3-I—PhCH2— | Z-1689 | Hex | PrS(═O)2— |
| Z-1690 | Hex | 4-Me—Ph | Z-1691 | Hex | 4-I—PhCH2— | Z-1692 | Hex | Ac |
| Z-1693 | Hex | 2-MeO—Ph | Z-1694 | Hex | 2-Me—PhCH2— | Z-1695 | Hex | OHC— |
| Z-1696 | Hex | 3-MeO—Ph | Z-1697 | Hex | 3-Me—PhCH2— | Z-1698 | Hex | Et(C═O)— |
| Z-1699 | Hex | 4-MeO—Ph | Z-1700 | Hex | 4-Me—PhCH2— | Z-1701 | Hex | Pr(C═O)— |
| Z-1702 | Hex | 2,3-di-F—Ph | Z-1703 | Hex | 2-MeO—PhCH2— | Z-1704 | Hex | i-Pr(C═O)— |
| Z-1705 | Hex | 2,4-di-F—Ph | Z-1706 | Hex | 3-MeO—PhCH2— | Z-1707 | Hex | Bu(C═O)— |
| Z-1708 | Hex | 2,5-di-F—Ph | Z-1709 | Hex | 4-MeO—PhCH2— | Z-1710 | Hex | MeO(C═O)— |
| Z-1711 | Hex | 2,6-di-F—Ph | Z-1712 | Hex | 2,3-di-F—PhCH2— | Z-1713 | Hex | EtO(C═O)— |
| Z-1714 | Hex | 2-Cl-3-F—Ph | Z-1715 | Hex | 2,4-di-F—PhCH2— | Z-1716 | Hex | PrO(C═O)— |
| Z-1717 | Hex | 2-Cl-4-F—Ph | Z-1718 | Hex | 2,5-di-F—PhCH2— | Z-1719 | Hex | i-PrO(C═O)— |
| Z-1720 | Hex | 2-Cl-5-F—Ph | Z-1721 | Hex | 2,6-di-F—PhCH2— | Z-1722 | Hex | BuO(C═O)— |
| Z-1723 | Hex | 2-Cl-6-F—Ph | Z-1724 | Hex | 2-Cl-3-F—PhCH2— | Z-1725 | Hex | t-BuOC(═O)— |
| Z-1726 | Hex | 2-Br-3-F—Ph | Z-1727 | Hex | 2-Cl-4-F—PhCH2— | Z-1728 | MeOCH2— | MeOCH2— |
| Z-1729 | Hex | 2-Br-4-F—Ph | Z-1730 | Hex | 2-Cl-5-F—PhCH2— | Z-1731 | MeOCH2— | MeOCH2CH2— |
| Z-1732 | Hex | 2-Br-5-F—Ph | Z-1733 | Hex | 2-Cl-6-F—PhCH2— | Z-1734 | MeOCH2— | EtOCH2— |
| Z-1735 | Hex | 2-Br-6-F—Ph | Z-1736 | Hex | 2-Br-3-F—PhCH2— | Z-1737 | MeOCH2— | EtOCH2CH2— |
| Z-1738 | Hex | 2-F-3-MeO—Ph | Z-1739 | Hex | 2-Br-4-F—PhCH2— | Z-1740 | MeOCH2— | N≡CCH2— |
| Z-1741 | Hex | 2-F-4-MeO—Ph | Z-1742 | Hex | 2-Br-5-F—PhCH2— | Z-1743 | MeOCH2— | N≡CCH2CH2— |
| Z-1744 | Hex | 2-F-5-MeO—Ph | Z-1745 | Hex | 2-Br-6-F—PhCH2— | Z-1746 | MeOCH2— | c-Pr—CH2— |
| Z-1747 | Hex | 2-F-6-MeO—Ph | Z-1748 | Hex | 2-F-3-MeO—PhCH2 | Z-1749 | MeOCH2— | c-Bu—CH2— |
| Z-1750 | Hex | 2-Cl-3-MeO—Ph | Z-1751 | Hex | 2-F-4-MeO—PhCH2— | Z-1752 | MeOCH2— | c-Pent-CH2— |
| Z-1753 | Hex | 2-Cl-4-MeO—Ph | Z-1754 | Hex | 2-F-5-MeO—PhCH2— | Z-1755 | MeOCH2— | c-Hex—CH2— |
| Z-1756 | Hex | 2-Cl-5-MeO—Ph | Z-1757 | Hex | 2-F-6-MeO—PhCH2— | Z-1758 | MeOCH2— | F3C— |
| Z-1759 | Hex | 2-Cl-6-MeO—Ph | Z-1760 | Hex | 2-Cl-3-MeO—PhCH2— | Z-1761 | MeOCH2— | F2CH— |
| Z-1762 | Hex | 2-Br-3-MeO—Ph | Z-1763 | Hex | 2-Cl-4-MeO—PhCH2— | Z-1764 | MeOCH2— | F3CCH2— |
| Z-1765 | Hex | 2-Br-4-MeO—Ph | Z-1766 | Hex | 2-Cl-5-MeO—PhCH2— | Z-1767 | MeOCH2— | F2CHCH2— |
| Z-1768 | Hex | 2-Br-5-MeO—Ph | Z-1769 | Hex | 2-Cl-6-MeO—PhCH2— | Z-1770 | MeOCH2— | F3CF2C— |
| Z-1771 | Hex | 2-Br-6-MeO—Ph | Z-1772 | Hex | 2-Br-3-MeO—PhCH2— | Z-1773 | MeOCH2— | F2CHF2C— |
| Z-1774 | Hex | 2,3,4-tri-F—Ph | Z-1775 | Hex | 2-Br-4-MeO—PhCH2— | Z-1776 | MeOCH2— | (F3C)2FC— |
| Z-1777 | Hex | 2,3,5-tri-F—Ph | Z-1778 | Hex | 2-Br-5-MeO—PhCH2— | Z-1779 | MeOCH2— | F3CF2C(F3C)FC— |
| Z-1780 | Hex | 2,3,6-tri-F—Ph | Z-1781 | Hex | 2-Br-6-MeO—PhCH2— | Z-1782 | MeOCH2— | c-Pr |
| Z-1783 | Hex | 2-Br-3,4-di-F—Ph | Z-1784 | Hex | 2,3,4-tri-F—PhCH2— | Z-1785 | MeOCH2— | c-Bu |
| Z-1786 | Hex | 2-Br-3,5-di-F—Ph | Z-1787 | Hex | 2,3,5-tri-F—PhCH2— | Z-1788 | MeOCH2— | c-Pent |
| Z-1789 | Hex | 2-Br-3,6-di-F—Ph | Z-1790 | Hex | 2,3,6-tri-F—PhCH2— | Z-1791 | MeOCH2— | c-Hex |
| Z-1792 | Hex | 2-F-3,4-di-MeO—Ph | Z-1793 | Hex | 2-Br-3,4-di-F—PhCH2— | Z-1794 | MeOCH2— | 2-Br-3-MeO—PhCH2— |
| Z-1795 | Hex | 2-F-3,5-di-MeO—Ph | Z-1796 | Hex | 2-Br-3,5-di-F—PhCH2— | Z-1797 | MeOCH2— | 2-Br-4-MeO—PhCH2— |
| Z-1798 | Hex | 2-F-3,6-di-MeO—Ph | Z-1799 | Hex | 2-Br-3,6-di-F—PhCH2— | Z-1800 | MeOCH2— | 2-Br-5-MeO—PhCH2— |
| Z-1801 | Hex | 2-Cl-3,4-di-MeO—Ph | Z-1802 | Hex | 2-F-3,4-di-MeO—PhCH2— | Z-1803 | MeOCH2— | 2-Br-6-MeO—PhCH2— |
| Z-1804 | Hex | 2-Cl-3,5-di-MeO—Ph | Z-1805 | Hex | 2-F-3,5-di-MeO—PhCH2— | Z-1806 | MeOCH2— | 2,3,4-tri-F—PhCH2— |
| Z-1807 | Hex | 2-Cl-3,6-di-MeO—Ph | Z-1808 | Hex | 2-F-3,6-di-MeO—PhCH2— | Z-1809 | MeOCH2— | 2,3,5-tri-F—PhCH2— |
| Z-1810 | Hex | 2-Br-3,4-di-MeO—Ph | Z-1811 | Hex | 2-Cl-3,4-di-MeO—PhCH2— | Z-1812 | MeOCH2— | 2,3,6-tri-F—PhCH2— |
| Z-1813 | Hex | 2-Br-3,5-di-MeO—Ph | Z-1814 | Hex | 2-Cl-3,5-di-MeO—PhCH2— | Z-1815 | MeOCH2— | 2-Br-3,4-di-F—PhCH2— |
| Z-1816 | MeOCH2— | H2C═CH— | Z-1817 | MeOCH2— | 2-Br-6-MeO—Ph | Z-1818 | MeOCH2— | 2-Br-3,5-di-F—PhCH2— |
| Z-1819 | MeOCH2— | H3CCH═CH— | Z-1820 | MeOCH2— | 2,3,4-tri-F—Ph | Z-1821 | MeOCH2— | 2-Br-3,6-di-F—PhCH2— |
| Z-1822 | MeOCH2— | H2C═CHCH2— | Z-1823 | MeOCH2— | 2,3,5-tri-F—Ph | Z-1824 | MeOCH2— | 2-F-3,4-di-MeO—PhCH2— |
| Z-1825 | MeOCH2— | F2C═CH— | Z-1826 | MeOCH2— | 2,3,6-tri-F—Ph | Z-1827 | MeOCH2— | 2-F-3,5-di-MeO—PhCH2— |
| Z-1828 | MeOCH2— | F2C═CHCH2— | Z-1829 | MeOCH2— | 2-Br-3,4-di-F—Ph | Z-1830 | MeOCH2— | 2-F-3,6-di-MeO—PhCH2— |

TABLE 3-continued

| Z | R3 | R4 | Z | R3 | R4 | Z | R3 | R4 |
|---|---|---|---|---|---|---|---|---|
| Z-1831 | MeOCH2— | HC≡C— | Z-1832 | MeOCH2— | 2-Br-3,5-di-F—Ph | Z-1833 | MeOCH2— | 2-Cl-3,4-di-MeO—PhCH2— |
| Z-1834 | MeOCH2— | HC≡CCH2— | Z-1835 | MeOCH2— | 2-Br-3,6-di-F—Ph | Z-1836 | MeOCH2— | 2-Cl-3,5-di-MeO—PhCH2— |
| Z-1837 | MeOCH2— | HC≡CCH2CH2— | Z-1838 | MeOCH2— | 2-F-3,4-di-MeO—Ph | Z-1839 | MeOCH2— | 2-Cl-3,6-di-MeO—PhCH2— |
| Z-1840 | MeOCH2— | H3CC≡CCH2— | Z-1841 | MeOCH2— | 2-F-3,5-di-MeO—Ph | Z-1842 | MeOCH2— | 2-Br-3,4-di-MeO—PhCH2— |
| Z-1843 | MeOCH2— | FC≡C— | Z-1844 | MeOCH2— | 2-F-3,6-di-MeO—Ph | Z-1845 | MeOCH2— | 2-Br-3,5-di-MeO—PhCH2— |
| Z-1846 | MeOCH2— | FC≡CCF2— | Z-1847 | MeOCH2— | 2-Cl-3,4-di-MeO—Ph | Z-1848 | MeOCH2— | 2-Br-3,6-di-MeO—PhCH2— |
| Z-1849 | MeOCH2— | FC≡CCF2CF2— | Z-1850 | MeOCH2— | 2-Cl-3,5-di-MeO—Ph | Z-1851 | MeOCH2— | MeS— |
| Z-1852 | MeOCH2— | F3CC≡CCF2— | Z-1853 | MeOCH2— | 2-Cl-3,6-di-MeO—Ph | Z-1854 | MeOCH2— | MeS(═O)— |
| Z-1855 | MeOCH2— | Ph | Z-1856 | MeOCH2— | 2-Br-3,4-di-MeO—Ph | Z-1857 | MeOCH2— | MeS(═O)2— |
| Z-1858 | MeOCH2— | 2-F—Ph | Z-1859 | MeOCH2— | 2-Br-3,5-di-MeO—Ph | Z-1860 | MeOCH2— | EtS— |
| Z-1861 | MeOCH2— | 3-F—Ph | Z-1862 | MeOCH2— | 2-Br-3,6-di-MeO—Ph | Z-1863 | MeOCH2— | EtS(═O)— |
| Z-1864 | MeOCH2— | 4-F—Ph | Z-1865 | MeOCH2— | PhCH2— | Z-1866 | MeOCH2— | EtS(═O)2— |
| Z-1867 | MeOCH2— | 2-Cl—Ph | Z-1868 | MeOCH2— | 2-F—PhCH2— | Z-1869 | MeOCH2— | PrS— |
| Z-1870 | MeOCH2— | 3-Cl—Ph | Z-1871 | MeOCH2— | 3-F—PFCH2— | Z-1872 | MeOCH2— | PrS(═O)— |
| Z-1873 | MeOCH2— | 4-Cl—Ph | Z-1874 | MeOCH2— | 4-F—PFCH2— | Z-1875 | MeOCH2— | PrS(═O)2— |
| Z-1876 | MeOCH2— | 2-Br—Ph | Z-1877 | MeOCH2— | 2-Cl—PhCH2— | Z-1878 | MeOCH2— | Au |
| Z-1879 | MeOCH2— | 3-Br—Ph | Z-1880 | MeOCH2— | 3-Cl—PhCH2— | Z-1881 | MeOCH2— | OHC— |
| Z-1882 | MeOCH2— | 4-Br—Ph | Z-1883 | MeOCH2— | 4-Cl—PhCH2— | Z-1884 | MeOCH2— | Et(C═O)— |
| Z-1885 | MeOCH2— | 2-I—Ph | Z-1886 | MeOCH2— | 2-Br—PhCH2— | Z-1887 | MeOCH2— | Pr(C═O)— |
| Z-1888 | MeOCH2— | 3-I—Ph | Z-1889 | MeOCH2— | 3-Br—PhCH2— | Z-1890 | MeOCH2— | i-Pr(C═O)— |
| Z-1891 | MeOCH2— | 4-I—Ph | Z-1892 | MeOCH2— | 4-Br—PhCH2— | Z-1893 | MeOCH2— | Bu(C═O)— |
| Z-1894 | MeOCH2— | 2-Me—Ph | Z-1895 | MeOCH2— | 2-I—PhCH2— | Z-1896 | MeOCH2— | MeO(C═O)— |
| Z-1897 | MeOCH2— | 3-Me—Ph | Z-1898 | MeOCH2— | 3-I—PhCH2— | Z-1899 | MeOCH2— | EtO(C═O)— |
| Z-1900 | MeOCH2— | 4-Me—Ph | Z-1901 | MeOCH2— | 4-I—PhCH2— | Z-1902 | MeOCH2— | PrO(C═O)— |
| Z-1903 | MeOCH2— | 2-MeO—Ph | Z-1904 | MeOCH2— | 2-Me—PhCH2— | Z-1905 | MeOCH2— | i-PrO(C═O)— |
| Z-1906 | MeOCH2— | 3-MeO—Ph | Z-1907 | MeOCH2— | 3-Me—PhCH2— | Z-1908 | MeOCH2— | BuO(C═O)— |
| Z-1909 | MeOCH2— | 4-MeO—Ph | Z-1910 | MeOCH2— | 4-Me—PhCH2— | Z-1911 | MeOCH2— | t-BuOC(═O)— |
| Z-1912 | MeOCH2— | 2,3-di-F—Ph | Z-1913 | MeOCH2— | 2-MeO—PhCH2— | Z-1914 | MeOCH2CH2— | MeOCH2CH2— |
| Z-1915 | MeOCH2— | 2,4-di-F—Ph | Z-1916 | MeOCH2— | 3-MeO—PhCH2— | Z-1917 | MeOCH2CH2— | EtOCH2— |
| Z-1918 | MeOCH2— | 2,5-di-F—Ph | Z-1919 | MeOCH2— | 4-MeO—PhCH2— | Z-1920 | MeOCH2CH2— | EtOCH2CH2— |
| Z-1921 | MeOCH2— | 2,6-di-F—Ph | Z-1922 | MeOCH2— | 2,3-di-F—PhCH2— | Z-1923 | MeOCH2CH2— | N≡CCH2— |
| Z-1924 | MeOCH2— | 2-Cl-3-F—Ph | Z-1925 | MeOCH2— | 2,4-di-F—PhCH2— | Z-1926 | MeOCH2CH2— | N≡CCH2CH2— |
| Z-1927 | MeOCH2— | 2-Cl-4-F—Ph | Z-1928 | MeOCH2— | 2,5-di-F—PhCH2— | Z-1929 | MeOCH2CH2— | c-Pr—CH2— |
| Z-1930 | MeOCH2— | 2-Cl-5-F—Ph | Z-1931 | MeOCH2— | 2,6-di-F—PhCH2— | Z-1932 | MeOCH2CH2— | c-Bu—CH2— |
| Z-1933 | MeOCH2— | 2-Cl-6-F—Ph | Z-1934 | MeOCH2— | 2-Cl-3-F—PhCH2— | Z-1935 | MeOCH2CH2— | c-Pent-CH2— |
| Z-1936 | MeOCH2— | 2-Br-3-F—Ph | Z-1937 | MeOCH2— | 2-Cl-4-F—PhCH2— | Z-1938 | MeOCH2CH2— | c-Hex—CH2— |
| Z-1939 | MeOCH2— | 2-Br-4-F—Ph | Z-1940 | MeOCH2— | 2-Cl-5-F—PhCH2— | Z-1941 | MeOCH2CH2— | F3C— |
| Z-1942 | MeOCH2— | 2-Br-5-F—Ph | Z-1943 | MeOCH2— | 2-Cl-6-F—PhCH2— | Z-1944 | MeOCH2CH2— | F2CH— |
| Z-1945 | MeOCH2— | 2-Br-6-F—Ph | Z-1946 | MeOCH2— | 2-Br-3-F—PhCH2— | Z-1947 | MeOCH2CH2— | F3CCH2— |
| Z-1948 | MeOCH2— | 2-F-3-MeO—Ph | Z-1949 | MeOCH2— | 2-Br-4-F—PhCH2— | Z-1950 | MeOCH2CH2— | F2CHCH2— |
| Z-1951 | MeOCH2— | 2-F-4-MeO—Ph | Z-1952 | MeOCH2— | 2-Br-5-F—PhCH2— | Z-1953 | MeOCH2CH2— | F3CF2C— |
| Z-1954 | MeOCH2— | 2-F-5-MeO—Ph | Z-1955 | MeOCH2— | 2-Br-6-F—PhCH2— | Z-1956 | MeOCH2CH2— | F2CHF2C— |
| Z-1957 | MeOCH2— | 2-F-6-MeO—Ph | Z-1958 | MeOCH2— | 2-F-3-MeO—PhCH2— | Z-1959 | MeOCH2CH2— | 2-F-5-MeO—PhCH2— |
| Z-1960 | MeOCH2— | 2-Cl-3-MeO—Ph | Z-1961 | MeOCH2— | 2-F-4-MeO—PhCH2— | Z-1962 | MeOCH2CH2— | 2-F-6-MeO—PhCH2— |
| Z-1963 | MeOCH2— | 2-Cl-4-MeO—Ph | Z-1964 | MeOCH2— | 2-F-5-MeO—PhCH2— | Z-1965 | MeOCH2CH2— | 2-Cl-3-MeO—PhCH2— |
| Z-1966 | MeOCH2— | 2-Cl-5-MeO—Ph | Z-1967 | MeOCH2— | 2-F-6-MeO—PhCH2— | Z-1968 | MeOCH2CH2— | 2-Cl-4-MeO—PhCH2— |
| Z-1969 | MeOCH2— | 2-Cl-6-MeO—Ph | Z-1970 | MeOCH2— | 2-Cl-3-MeO—PhCH2— | Z-1971 | MeOCH2CH2— | 2-Cl-5-MeO—PhCH2— |
| Z-1972 | MeOCH2— | 2-Br-3-MeO—Ph | Z-1973 | MeOCH2— | 2-Cl-4-MeO—PhCH2— | Z-1974 | MeOCH2CH2— | 2-Cl-6-MeO—PhCH2— |
| Z-1975 | MeOCH2— | 2-Br-4-MeO—Ph | Z-1976 | MeOCH2— | 2-Cl-5-MeO—PhCH2— | Z-1977 | MeOCH2CH2— | 2-Br-3-MeO—PhCH2— |
| Z-1978 | MeOCH2— | 2-Br-5-MeO—Ph | Z-1979 | MeOCH2— | 2-Cl-6-MeO—PhCH2— | Z-1980 | MeOCH2CH2— | 2-Br-4-MeO—PhCH2— |
| Z-1981 | MeOCH2CH2— | (F3C)2FC— | Z-1982 | MeOCH2CH2— | 2-Cl-4-MeO—Ph | Z-1983 | MeOCH2CH2— | 2-Br-5-MeO—PhCH2— |

TABLE 3-continued

| Z | R3 | R4 | Z | R3 | R4 | Z | R3 | R4 |
|---|---|---|---|---|---|---|---|---|
| Z-1984 | MeOCH2CH2— | F3CF2C(F3C)FC— | Z-1985 | MeOCH2CH2— | 2-Cl-5-MeO—Ph | Z-1986 | MeOCH2CH2— | 2-Br-6-MeO—PhCH2— |
| Z-1987 | MeOCH2CH2— | c-Pr | Z-1988 | MeOCH2CH2— | 2-Cl-6-MeO—Ph | Z-1989 | MeOCH2CH2— | 2,3,4-tri-F—PhCH2— |
| Z-1990 | MeOCH2CH2— | c-Bu | Z-1991 | MeOCH2CH2— | 2-Br-3-MeO—Ph | Z-1992 | MeOCH2CH2— | 2,3,5-tri-F—PhCH2— |
| Z-1993 | MeOCH2CH2— | c-Pent | Z-1994 | MeOCH2CH2— | 2-Br-4-MeO—Ph | Z-1995 | MeOCH2CH2— | 2,3,6-tri-F—PhCH2— |
| Z-1996 | MeOCH2CH2— | c-Hex | Z-1997 | MeOCH2CH2— | 2-Br-5-MeO—Ph | Z-1998 | MeOCH2CH2— | 2-Br-3,4-di-F—PhCH2— |
| Z-1999 | MeOCH2CH2— | H2C═CH— | Z-2000 | MeOCH2CH2— | 2-Br-6-MeO—Ph | Z-2001 | MeOCH2CH2— | 2-Br-3,5-di-F—PhCH2— |
| Z-2002 | MeOCH2CH2— | H3CCH═CH— | Z-2003 | MeOCH2CH2— | 2,3,4-tri-F—Ph | Z-2004 | MeOCH2CH2— | 2-Br-3,6-di-F—PhCH2— |
| Z-2005 | MeOCH2CH2— | H2C═CHCH2— | Z-2006 | MeOCH2CH2— | 2,3,5-tri-F—Ph | Z-2007 | MeOCH2CH2— | 2-F-3,4-di-MeO—PhCH2— |
| Z-2008 | MeOCH2CH2— | F2C═CH— | Z-2009 | MeOCH2CH2— | 2,3,6-tri-F—Ph | Z-2010 | MeOCH2CH2— | 2-F-3,5-di-MeO—PhCH2— |
| Z-2011 | MeOCH2CH2— | F2C═CHCH2— | Z-2012 | MeOCH2CH2— | 2-Br-3,4-di-F—Ph | Z-2013 | MeOCH2CH2— | 2-F-3,6-di-MeO—PhCH2— |
| Z-2014 | MeOCH2CH2— | HC≡C— | Z-2015 | MeOCH2CH2— | 2-Br-3,5-di-F—Ph | Z-2016 | MeOCH2CH2— | 2-Cl-3,4-di-MeO—PhCH2— |
| Z-2017 | MeOCH2CH2— | HC≡CCH2— | Z-2018 | MeOCH2CH2— | 2-Br-3,6-di-F—Ph | Z-2019 | MeOCH2CH2— | 2-Cl-3,5-di-MeO—PhCH2— |
| Z-2020 | MeOCH2CH2— | HC≡CCH2CH2— | Z-2021 | MeOCH2CH2— | 2-F-3,4-di-MeO—Ph | Z-2022 | MeOCH2CH2— | 2-Cl-3,6-di-MeO—PhCH2— |
| Z-2023 | MeOCH2CH2— | H3CC≡CCH2— | Z-2024 | MeOCH2CH2— | 2-F-3,5-di-MeO—Ph | Z-2025 | MeOCH2CH2— | 2-Br-3,4-di-MeO—PhCH2— |
| Z-2026 | MeOCH2CH2— | FC≡C— | Z-2027 | MeOCH2CH2— | 2-F-3,6-di-MeO—Ph | Z-2028 | MeOCH2CH2— | 2-Br-3,5-di-MeO—PhCH2— |
| Z-2029 | MeOCH2CH2— | FC≡CCF2— | Z-2030 | MeOCH2CH2— | 2-Cl-3,4-di-MeO—Ph | Z-2031 | MeOCH2CH2— | 2-Br-3,6-di-MeO—PhCH2— |
| Z-2032 | MeOCH2CH2— | FC≡CCF2CF2— | Z-2033 | MeOCH2CH2— | 2-Cl-3,5-di-MeO—Ph | Z-2034 | MeOCH2CH2— | MeS— |
| Z-2035 | MeOCH2CH2— | F3CC≡CCF2— | Z-2036 | MeOCH2CH2— | 2-Cl-3,6-di-MeO—Ph | Z-2037 | MeOCH2CH2— | MeS(═O)— |
| Z-2038 | MeOCH2CH2— | Ph | Z-2039 | MeOCH2CH2— | 2-Br-3,4-di-MeO—Ph | Z-2040 | MeOCH2CH2— | MeS(═O)2— |
| Z-2041 | MeOCH2CH2— | 2-F—Ph | Z-2042 | MeOCH2CH2— | 2-Br-3,5-di-MeO—Ph | Z-2043 | MeOCH2CH2— | EtS— |
| Z-2044 | MeOCH2CH2— | 3-F—Ph | Z-2045 | MeOCH2CH2— | 2-Br-3,6-di-MeO—Ph | Z-2046 | MeOCH2CH2— | EtS(═O)— |
| Z-2047 | MeOCH2CH2— | 4-F—Ph | Z-2048 | MeOCH2CH2— | PhCH2— | Z-2049 | MeOCH2CH2— | EtS(═O)2— |
| Z-2050 | MeOCH2CH2— | 2-Cl—Ph | Z-2051 | MeOCH2CH2— | 2-F—PhCH2— | Z-2052 | MeOCH2CH2— | PrS— |
| Z-2053 | MeOCH2CH2— | 3-Cl—Ph | Z-2054 | MeOCH2CH2— | 3-F—PhCH2— | Z-2055 | MeOCH2CH2— | PrS(═O)— |
| Z-2056 | MeOCH2CH2— | 4-Cl—Ph | Z-2057 | MeOCH2CH2— | 4-F—PhCH2— | Z-2058 | MeOCH2CH2— | PrS(═O)2— |
| Z-2059 | MeOCH2CH2— | 2-Br—Ph | Z-2060 | MeOCH2CH2— | 2-Cl—PhCH2— | Z-2061 | MeOCH2CH2— | Ac |
| Z-2062 | MeOCH2CH2— | 3-Br—Ph | Z-2063 | MeOCH2CH2— | 3-Cl—PhCH2— | Z-2064 | MeOCH2CH2— | OHC— |
| Z-2065 | MeOCH2CH2— | 4-Br—Ph | Z-2066 | MeOCH2CH2— | 4-Cl—PhCH2— | Z-2067 | MeOCH2CH2— | Et(C═O)— |
| Z-2068 | MeOCH2CH2— | 2-I—Ph | Z-2069 | MeOCH2CH2— | 2-Br—PhCH2— | Z-2070 | MeOCH2CH2— | Pr(C═O)— |
| Z-2071 | MeOCH2CH2— | 3-I—Ph | Z-2072 | MeOCH2CH2— | 3-Br—PhCH2— | Z-2073 | MeOCH2CH2— | i-Pr(C═O)— |
| Z-2074 | MeOCH2CH2— | 4-I—Ph | Z-2075 | MeOCH2CH2— | 4-Br—PhCH2— | Z-2076 | MeOCH2CH2— | Bu(C═O)— |
| Z-2077 | MeOCH2CH2— | 2-Me—Ph | Z-2078 | MeOCH2CH2— | 2-I—PhCH2— | Z-2079 | MeOCH2CH2— | MeO(C═O)— |
| Z-2080 | MeOCH2CH2— | 3-Me—Ph | Z-2081 | MeOCH2CH2— | 3-I—PhCH2— | Z-2082 | MeOCH2CH2— | EtO(C═O)— |
| Z-2083 | MeOCH2CH2— | 4-Me—Ph | Z-2084 | MeOCH2CH2— | 4-I—PhCH2— | Z-2085 | MeOCH2CH2— | PrO(C═O)— |
| Z-2086 | MeOCH2CH2— | 2-MeO—Ph | Z-2087 | MeOCH2CH2— | 2-Me—PhCH2— | Z-2088 | MeOCH2CH2— | i-PrO(C═O)— |
| Z-2089 | MeOCH2CH2— | 3-MeO—Ph | Z-2090 | MeOCH2CH2— | 3-Me—PhCH2— | Z-2091 | MeOCH2CH2— | BuO(C═O)— |
| Z-2092 | MeOCH2CH2— | 4-MeO—Ph | Z-2093 | MeOCH2CH2— | 4-Me—PhCH2— | Z-2094 | MeOCH2CH2— | t-BuOC(═O)— |
| Z-2095 | MeOCH2CH2— | 2,3-di-F—Ph | Z-2096 | MeOCH2CH2— | 2-MeO—PhCH2— | Z-2097 | EtOCH2— | EtOCH2— |
| Z-2098 | MeOCH2CH2— | 2,4-di-F—Ph | Z-2099 | MeOCH2CH2— | 3-MeO—PhCH2— | Z-2100 | EtOCH2— | EtOCH2CH2— |
| Z-2101 | MeOCH2CH2— | 2,5-di-F—Ph | Z-2102 | MeOCH2CH2— | 4-MeO—PhCH2— | Z-2103 | EtOCH2— | N≡CCH2— |
| Z-2104 | MeOCH2CH2— | 2,6-di-F—Ph | Z-2105 | MeOCH2CH2— | 2,3-di-F—PhCH2— | Z-2106 | EtOCH2— | N≡CCH2CH2— |
| Z-2107 | MeOCH2CH2— | 2-Cl-3-F—Ph | Z-2108 | MeOCH2CH2— | 2,4-di-F—PhCH2 | Z-2109 | EtOCH2— | c-Pr—CH2— |
| Z-2110 | MeOCH2CH2— | 2-Cl-4-F—Ph | Z-2111 | MeOCH2CH2— | 2,5-di-F—PhCH2— | Z-2112 | EtOCH2— | c-Bu—CH2— |
| Z-2113 | MeOCH2CH2— | 2-Cl-5-F—Ph | Z-2114 | MeOCH2CH2— | 2,6-di-F—PhCH2— | Z-2115 | EtOCH2— | c-Pent-CH2— |
| Z-2116 | MeOCH2CH2— | 2-Cl-6-F—Ph | Z-2117 | MeOCH2CH2— | 2-Cl-3-F—PhCH2— | Z-2118 | EtOCH2— | c-Hex—CH2— |
| Z-2119 | MeOCH2CH2— | 2-Br-3-F—Ph | Z-2120 | MeOCH2CH2— | 2-Cl-4-F—PhCH2— | Z-2121 | EtOCH2— | F3C— |
| Z-2122 | MeOCH2CH2— | 2-Br-4-F—Ph | Z-2123 | MeOCH2CH2— | 2-Cl-5-F—PhCH2— | Z-2124 | EtOCH2— | 2-Br-4-F—PhCH2— |
| Z-2125 | MeOCH2CH2— | 2-Br-5-F—Ph | Z-2126 | MeOCH2CH2— | 2-Cl-6-F—PhCH2— | Z-2127 | EtOCH2— | 2-Br-5-F—PhCH2— |
| Z-2128 | MeOCH2CH2— | 2-Br-6-F—Ph | Z-2129 | MeOCH2CH2— | 2-Br-3-F—PhCH2— | Z-2130 | EtOCH2— | 2-Br-6-F—PhCH2— |
| Z-2131 | MeOCH2CH2— | 2-F-3-MeO—Ph | Z-2132 | MeOCH2CH2— | 2-Br-4-F—PhCH2— | Z-2133 | EtOCH2— | 2-F-3-MeO—PhCH2— |
| Z-2134 | MeOCH2CH2— | 2-F-4-MeO—Ph | Z-2135 | MeOCH2CH2— | 2-Br-5-F—PhCH2— | Z-2136 | EtOCH2— | 2-F-4-MeO—PhCH2— |

TABLE 3-continued

| Z | R3 | R4 | Z | R3 | R4 | Z | R3 | R4 |
|---|---|---|---|---|---|---|---|---|
| Z-2137 | MeOCH2CH2— | 2-F-5-MeO—Ph | Z-2138 | MeOCH2CH2— | 2-Br-6-F—PhCH2— | Z-2139 | EtOCH2— | 2-F-5-MeO—PhCH2— |
| Z-2140 | MeOCH2CH2— | 2-F-6-MeO—Ph | Z-2141 | MeOCH2CH2— | 2-F-3-MeO—PhCH2— | Z-2142 | EtOCH2— | 2-F-6-MeO—PhCH2— |
| Z-2143 | MeOCH2CH2— | 2-Cl-3-MeO—Ph | Z-2144 | MeOCH2CH2— | 2-F-4-MeO—PhCH2— | Z-2145 | EtOCH2— | 2-Cl-3-MeO—PhCH2— |
| Z-2146 | EtOCH2— | F2CH— | Z-2147 | EtOCH2— | 2-F-3-MeO—Ph | Z-2148 | EtOCH2— | 2-Cl-4-MeO—PhCH2— |
| Z-2149 | EtOCH2— | F3CCH2— | Z-2150 | EtOCH2— | 2-F-4-MeO—Ph | Z-2151 | EtOCH2— | 2-Cl-5-MeO—PhCH2— |
| Z-2152 | EtOCH2— | F2CHCH2— | Z-2153 | EtOCH2— | 2-F-5-MeO—Ph | Z-2154 | EtOCH2— | 2-Cl-6-MeO—PhCH2— |
| Z-2155 | EtOCH2— | F3CF2C— | Z-2156 | EtOCH2— | 2-F-6-MeO—Ph | Z-2157 | EtOCH2— | 2-Br-3-MeO—PhCH2— |
| Z-2158 | EtOCH2— | F2CHF2C— | Z-2159 | EtOCH2— | 2-Cl-3-MeO—Ph | Z-2160 | EtOCH2— | 2-Br-4-MeO—PhCH2— |
| Z-2161 | EtOCH2— | (F3C)2FC— | Z-2162 | EtOCH2— | 2-Cl-4-MeO—Ph | Z-2163 | EtOCH2— | 2-Br-5-MeO—PhCH2— |
| Z-2164 | EtOCH2— | F3CF2C(F3C)FC— | Z-2165 | EtOCH2— | 2-Cl-5-MeO—Ph | Z-2166 | EtOCH2— | 2-Br-6-MeO—PhCH2— |
| Z-2167 | EtOCH2— | c-Pr | Z-2168 | EtOCH2— | 2-Cl-6-MeO—Ph | Z-2169 | EtOCH2— | 2,3,4-tri-F—PhCH2— |
| Z-2170 | EtOCH2— | c-Bu | Z-2171 | EtOCH2— | 2-Br-3-MeO—Ph | Z-2172 | EtOCH2— | 2,3,5-tri-F—PhCH2— |
| Z-2173 | EtOCH2— | c-Pent | Z-2174 | EtOCH2— | 2-Br-4-MeO—Ph | Z-2175 | EtOCH2— | 2,3,6-tri-F—PhCH2— |
| Z-2176 | EtOCH2— | c-Hex | Z-2177 | EtOCH2— | 2-Br-5-MeO—Ph | Z-2178 | EtOCH2— | 2-Br-3,4-di-F—PhCH2— |
| Z-2179 | EtOCH2— | H2C═CH— | Z-2180 | EtOCH2— | 2-Br-6-MeO—Ph | Z-2181 | EtOCH2— | 2-Br-3,5-di-F—PhCH2— |
| Z-2182 | EtOCH2— | H3CCH═CH— | Z-2183 | EtOCH2— | 2,3,4-tri-F—Ph | Z-2184 | EtOCH2— | 2-Br-3,6-di-F—PhCH2— |
| Z-2185 | EtOCH2— | H2C═CHCH2— | Z-2186 | EtOCH2— | 2,3,5-tri-F—Ph | Z-2187 | EtOCH2— | 2-F-3,4-di-MeO—PhCH2— |
| Z-2188 | EtOCH2— | F2C═CH— | Z-2189 | EtOCH2— | 2,3,6-tri-F—Ph | Z-2190 | EtOCH2— | 2-F-3,5-di-MeO—PhCH2— |
| Z-2191 | EtOCH2— | F2C═CHCH2— | Z-2192 | EtOCH2— | 2-Br-3,4-di-F—Ph | Z-2193 | EtOCH2— | 2-F-3,6-di-MeO—PhCH2— |
| Z-2194 | EtOCH2— | HC≡C— | Z-2195 | EtOCH2— | 2-Br-3,5-di-F—Ph | Z-2196 | EtOCH2— | 2-Cl-3,4-di-MeO—PhCH2— |
| Z-2197 | EtOCH2— | HC≡CCH2— | Z-2198 | EtOCH2— | 2-Br-3,6-di-F—Ph | Z-2199 | EtOCH2— | 2-Cl-3,5-di-MeO—PhCH2— |
| Z-2200 | EtOCH2— | HC≡CCH2CH2— | Z-2201 | EtOCH2— | 2-F-3,4-di-MeO—Ph | Z-2202 | EtOCH2— | 2-Cl-3,6-di-MeO—PhCH2— |
| Z-2203 | EtOCH2— | H3CC≡CCH2— | Z-2204 | EtOCH2— | 2-F-3,5-di-MeO—Ph | Z-2205 | EtOCH2— | 2-Br-3,4-di-MeO—PhCH2— |
| Z-2206 | EtOCH2— | FC≡C— | Z-2207 | EtOCH2— | 2-F-3,6-di-MeO—Ph | Z-2208 | EtOCH2— | 2-Br-3,5-di-MeO—PhCH2— |
| Z-2209 | EtOCH2— | FC≡CCF2— | Z-2210 | EtOCH2— | 2-Cl-3,4-di-MeO—Ph | Z-2211 | EtOCH2— | 2-Br-3,6-di-MeO—PhCH2— |
| Z-2212 | EtOCH2— | FC≡CCF2CF2— | Z-2213 | EtOCH2— | 2-Cl-3,5-di-MeO—Ph | Z-2214 | EtOCH2— | MeS— |
| Z-2215 | EtOCH2— | F3CC≡CCF2— | Z-2216 | EtOCH2— | 2-Cl-3,6-di-MeO—Ph | Z-2217 | EtOCH2— | MeS(═O)— |
| Z-2218 | EtOCH2— | Ph | Z-2219 | EtOCH2— | 2-Br-3,4-di-MeO—Ph | Z-2220 | EtOCH2— | MeS(═O)2— |
| Z-2221 | EtOCH2— | 2-F—Ph | Z-2222 | EtOCH2— | 2-Br-3,5-di-MeO—Ph | Z-2223 | EtOCH2— | EtS— |
| Z-2224 | EtOCH2— | 3-F—Ph | Z-2225 | EtOCH2— | 2-Br-3,6-di-MeO—Ph | Z-2226 | EtOCH2— | EtS(═O)— |
| Z-2227 | EtOCH2— | 4-F—Ph | Z-2228 | EtOCH2— | PhCH2— | Z-2229 | EtOCH2— | EtS(═O)2— |
| Z-2230 | EtOCH2— | 2-Cl—Ph | Z-2231 | EtOCH2— | 2-F—PhCH2— | Z-2232 | EtOCH2— | PrS— |
| Z-2233 | EtOCH2— | 3-Cl—Ph | Z-2234 | EtOCH2— | 3-F—PhCH2— | Z-2235 | EtOCH2— | PrS(═O)— |
| Z-2236 | EtOCH2— | 4-Cl—Ph | Z-2237 | EtOCH2— | 4-F—PhCH2— | Z-2238 | EtOCH2— | PrS(═O)2— |
| Z-2239 | EtOCH2— | 2-Br—Ph | Z-2240 | EtOCH2— | 2-Cl—PhCH2— | Z-2241 | EtOCH2— | Ac |
| Z-2242 | EtOCH2— | 3-Br—Ph | Z-2243 | EtOCH2— | 3-Cl—PhCH2— | Z-2244 | EtOCH2— | OHC— |
| Z-2245 | EtOCH2— | 4-Br—Ph | Z-2246 | EtOCH2— | 4-Cl—PhCH2— | Z-2247 | EtOCH2— | Et(C═O)— |
| Z-2248 | EtOCH2— | 2-I—Ph | Z-2249 | EtOCH2— | 2-Br—PhCH2— | Z-2250 | EtOCH2— | Pr(C═O)— |
| Z-2251 | EtOCH2— | 3-I—Ph | Z-2252 | EtOCH2— | 3-Br—PhCH2— | Z-2253 | EtOCH2— | i-Pr(C═O)— |
| Z-2254 | EtOCH2— | 4-I—Ph | Z-2255 | EtOCH2— | 4-Br—PhCH2— | Z-2256 | EtOCH2— | Bu(C═O)— |
| Z-2251 | EtOCH2— | 2-Me—Ph | Z-2258 | EtOCH2— | 2-I—PhCH2— | Z-2259 | EtOCH2— | MeO(C═O)— |
| Z-2260 | EtOCH2— | 3-Me—Ph | Z-2261 | EtOCH2— | 3-I—PhCH2— | Z-2262 | EtOCH2— | EtO(C═O)— |
| Z-2263 | EtOCH2— | 4-Me—Ph | Z-2264 | EtOCH2— | 4-I—PhCH2— | Z-2265 | EtOCH2— | PrO(C═O)— |
| Z-2266 | EtOCH2— | 2-MeO—Ph | Z-2267 | EtOCH2— | 2-Me—PhCH2— | Z-2268 | EtOCH2— | i-PrO(C═O)— |
| Z-2269 | EtOCH2— | 3-MeO—Ph | Z-2270 | EtOCH2— | 3-Me—PhCH2— | Z-2271 | EtOCH2— | BuO(C═O)— |
| Z-2272 | EtOCH2— | 4-MeO—Ph | Z-2273 | EtOCH2— | 4-Me—PhCH2— | Z-2274 | EtOCH2— | t-BuOC(═O)— |
| Z-2275 | EtOCH2— | 2,3-di-F—Ph | Z-2276 | EtOCH2— | 2-MeO—PhCH2— | Z-2211 | N≡CCH2— | 2,5-di-F—PhCH2— |
| Z-2278 | EtOCH2— | 2,4-di-F—Ph | Z-2279 | EtOCH2— | 3-MeO—PhCH2— | Z-2280 | N≡CCH2— | 2,6-di-F—PhCH2— |
| Z-2281 | EtOCH2— | 2,5-di-F—Ph | Z-2282 | EtOCH2— | 4-MeO—PhCH2— | Z-2283 | N≡CCH2— | 2-Cl-3-F—PhCH2— |
| Z-2284 | EtOCH2— | 2,6-di-F—Ph | Z-2285 | EtOCH2— | 2,3-di-F—PhCH2— | Z-2286 | N≡CCH2— | 2-Cl-4-F—PhCH2— |
| Z-2287 | EtOCH2— | 2-Cl-3-F—Ph | Z-2288 | EtOCH2— | 2,1-di-F—PhCH2— | Z-2289 | N≡CCH2— | 2-Cl-5-F—PhCH2— |

TABLE 3-continued

| Z | R3 | R4 | Z | R3 | R4 | Z | R3 | R4 |
|---|---|---|---|---|---|---|---|---|
| Z-2290 | EtOCH2— | 2-Cl-4-F—Ph | Z-2291 | EtOCH2— | 2,5-di-F—PhCH2— | Z-2292 | N≡CCH2— | 2-Cl-6-F—PhCH2— |
| Z-2293 | EtOCH2— | 2-Cl-5-F—Ph | Z-2294 | EtOCH2— | 2,6-di-F—PhCH2— | Z-2295 | N≡CCH2— | 2-Br-3-F—PhCH2— |
| Z-2296 | EtOCH2— | 2-Cl-6-F—Ph | Z-2291 | EtOCH2— | 2-Cl-3-F—PhCH2— | Z-2298 | N≡CCH2— | 2-Br-4-F—PhCH2— |
| Z-2299 | EtOCH2— | 2-Br-3-F—Ph | Z-2300 | EtOCH2— | 2-Cl-4-F—PhCH2— | Z-2301 | N≡CCH2— | 2-Br-5-F—PhCH2— |
| Z-2302 | EtOCH2— | 2-Br-4-F—Ph | Z-2303 | EtOCH2— | 2-Cl-5-F—PhCH2— | Z-2304 | N≡CCH2— | 2-Br-6-F—PhCH2— |
| Z-2305 | EtOCH2— | 2-Br-5-F—Ph | Z-2306 | EtOCH2— | 2-Cl-6-F—PhCH2— | Z-2307 | N≡CCH2— | 2-F-3-MeO—PhCH2— |
| Z-2308 | EtOCH2— | 2-Br-6-F—Ph | Z-2309 | EtOCH2— | 2-Br-3-F—PhCH2— | Z-2310 | N≡CCH2— | 2-F-4-MeO—PhCH2— |
| Z-2311 | N≡CCH2— | N≡CCH2— | Z-2312 | N≡CCH2— | 2-Cl-4-F—Ph | Z-2313 | N≡CCH2— | 2-F-5-MeO—PhCH2— |
| Z-2314 | N≡CCH2— | N≡CCH2CH2— | Z-2315 | N≡CCH2— | 2-Cl-5-F—Ph | Z-2316 | N≡CCH2— | 2-F-6-MeO—PhCH2— |
| Z-2317 | N≡CCH2— | c-Pr—CH2— | Z-2318 | N≡CCH2— | 2-Cl-6-F—Ph | Z-2319 | N≡CCH2— | 2-Cl-3-MeO—PhCH2— |
| Z-2320 | N≡CCH2— | c-Bu—CH2— | Z-2321 | N≡CCH2— | 2-Br-3-F—Ph | Z-2322 | N≡CCH2— | 2-Cl-4-MeO—PhCH2— |
| Z-2323 | N≡CCH2— | c-Pent-CH2— | Z-2324 | N≡CCH2— | 2-Br-4-F—Ph | Z-2325 | N≡CCH2— | 2-Cl-5-MeO—PhCH2— |
| Z-2326 | N≡CCH2— | c-Hex—CH2— | Z-2327 | N≡CCH2— | 2-Br-5-F—Ph | Z-2328 | N≡CCH2— | 2-Cl-6-MeO—PhCH2— |
| Z-2329 | N≡CCH2— | F3C— | Z-2330 | N≡CCH2— | 2-Br-6-F—Ph | Z-2331 | N≡CCH2— | 2-Br-3-MeO—PhCH2— |
| Z-2332 | N≡CCH2— | F2CH— | Z-2333 | N≡CCH2— | 2-F-3-MeO—Ph | Z-2334 | N≡CCH2— | 2-Br-4-MeO—PhCH2— |
| Z-2335 | N≡CCH2— | F3CCH2— | Z-2336 | N≡CCH2— | 2-F-4-MeO—Ph | Z-2331 | N≡CCH2— | 2-Br-5-MeO—PhCH2— |
| Z-2338 | N≡CCH2— | F2CHCH2— | Z-2339 | N≡CCH2— | 2-F-5-MeO—Ph | Z-2340 | N≡CCH2— | 2-Br-6-MeO—PhCH2— |
| Z-2341 | N≡CCH2— | F3CF2C— | Z-2342 | N≡CCH2— | 2-F-6-MeO—Ph | Z-2343 | N≡CCH2— | 2,3,4-tri-F—PhCH2— |
| Z-2344 | N≡CCH2— | F2CHF2C— | Z-2345 | N≡CCH2— | 2-Cl-3-MeO—Ph | Z-2346 | N≡CCH2— | 2,3,5-tri-F—PhCH2— |
| Z-2347 | N≡CCH2— | (F3C)2FC— | Z-2348 | N≡CCH2— | 2-Cl-4-MeO—Ph | Z-2349 | N≡CCH2— | 2,3,6-tri-F—PhCH2— |
| Z-2350 | N≡CCH2— | F3CF2C(F3C)FC— | Z-2351 | N≡CCH2— | 2-Cl-5-MeO—Ph | Z-2352 | N≡CCH2— | 2-Br-3,4-di-F—PhCH2— |
| Z-2353 | N≡CCH2— | c-Pr | Z-2354 | N≡CCH2— | 2-Cl-6-MeO—Ph | Z-2355 | N≡CCH2— | 2-Br-3,5-di-F—PhCH2— |
| Z-2356 | N≡CCH2— | c-Bu | Z-2357 | N≡CCH2— | 2-Br-3-MeO—Ph | Z-2358 | N≡CCH2— | 2-Br-3,6-di-F—PhCH2— |
| Z-2359 | N≡CCH2— | c-Pent | Z-2360 | N≡CCH2— | 2-Br-4-MeO—Ph | Z-2361 | N≡CCH2— | 2-F-3,4-di-MeO—PhCH2— |
| Z-2362 | N≡CCH2— | c-Hex | Z-2363 | N≡CCH2— | 2-Br-5-MeO—Ph | Z-2364 | N≡CCH2— | 2-F-3,5-di-MeO—PhCH2— |
| Z-2365 | N≡CCH2— | H2C=CH— | Z-2366 | N≡CCH2— | 2-Br-6-MeO—Ph | Z-2367 | N≡CCH2— | 2-F-3,6-di-MeO—PhCH2— |
| Z-2368 | N≡CCH2— | H3CCH=CH— | Z-2369 | N≡CCH2— | 2,3,4-tri-F—Ph | Z-2370 | N≡CCH2— | 2-Cl-3,4-di-MeO—PhCH2— |
| Z-2371 | N≡CCH2— | H2C=CHCH2— | Z-2372 | N≡CCH2— | 2,3,5-tri-F—Ph | Z-2373 | N≡CCH2— | 2-Cl-3,5-di-MeO—PhCH2— |
| Z-2374 | N≡CCH2— | F2C=CH— | Z-2375 | N≡CCH2— | 2,3,6-tri-F—Ph | Z-2376 | N≡CCH2— | 2-Cl-3,6-di-MeO—PhCH2— |
| Z-2377 | N≡CCH2— | F2C=CHCH2— | Z-2378 | N≡CCH2— | 2-Br-3,4-di-F—Ph | Z-2379 | N≡CCH2— | 2-Br-3,4-di-MeO—PhCH2— |
| Z-2380 | N≡CCH2— | HC≡C— | Z-2381 | N≡CCH2— | 2-Br-3,5-di-F—Ph | Z-2382 | N≡CCH2— | 2-Br-3,5-di-MeO—PhCH2— |
| Z-2383 | N≡CCH2— | HC≡CCH2— | Z-2384 | N≡CCH2— | 2-Br-3,6-di-F—Ph | Z-2385 | N≡CCH2— | 2-Br-3,6-di-MeO—PhCH2— |
| Z-2386 | N≡CCH2— | HC≡CCH2CH2— | Z-2387 | N≡CCH2— | 2-F-3,4-di-MeO—Ph | Z-2388 | N≡CCH2— | MeS— |
| Z-2389 | N≡CCH2— | H3CC≡CCH2— | Z-2390 | N≡CCH2— | 2-F-3,5-di-MeO—Ph | Z-2391 | N≡CCH2— | MeS(=O)— |
| Z-2392 | N≡CCH2— | FC≡C— | Z-2393 | N≡CCH2— | 2-F-3,6-di-MeO—Ph | Z-2394 | N≡CCH2— | MeS(=O)2— |
| Z-2395 | N≡CCH2— | FC≡CCF2— | Z-2396 | N≡CCH2— | 2-Cl-3,4-di-MeO—Ph | Z-2397 | N≡CCH2— | EtS— |
| Z-2398 | N≡CCH2— | FC≡CCF2CF2— | Z-2399 | N≡CCH2— | 2-Cl-3,5-di-MeO—Ph | Z-2400 | N≡CCH2— | EtS(=O)— |
| Z-2401 | N≡CCH2— | F3CC≡CCF2— | Z-2402 | N≡CCH2— | 2-Cl-3,6-di-MeO—Ph | Z-2403 | N≡CCH2— | EtS(=O)2— |
| Z-2404 | N≡CCH2— | Ph | Z-2405 | N≡CCH2— | 2-Br-3,4-di-MeO—Ph | Z-2406 | N≡CCH2— | PrS— |
| Z-2407 | N≡CCH2— | 2-F—Ph | Z-2408 | N≡CCH2— | 2-Br-3,5-di-MeO—Ph | Z-2409 | N≡CCH2— | PrS(=O)— |
| Z-2410 | N≡CCH2— | 3-F—Ph | Z-2411 | N≡CCH2— | 2-Br-3,6-di-MeO—Ph | Z-2412 | N≡CCH2— | PrS(=O)2— |
| Z-2413 | N≡CCH2— | 4-F—Ph | Z-2414 | N≡CCH2— | PhCH2— | Z-2415 | N≡CCH2— | Ac |
| Z-2416 | N≡CCH2— | 2-Cl—Ph | Z-2417 | N≡CCH2— | 2-F—PhCH2— | Z-2418 | N≡CCH2— | OHC— |
| Z-2419 | N≡CCH2— | 3-Cl—Ph | Z-2420 | N≡CCH2— | 3-F—PhCH2— | Z-2421 | N≡CCH2— | Et(C=O)— |
| Z-2422 | N≡CCH2— | 4-Cl—Ph | Z-2423 | N≡CCH2— | 4-F—PhCH2— | Z-2424 | N≡CCH2— | Pr(C=O)— |
| Z-2425 | N≡CCH2— | 2-Br—Ph | Z-2426 | N≡CCH2— | 2-Cl—PhCH2— | Z-2427 | N≡CCH2— | i-Pr(C=O)— |
| Z-2428 | N≡CCH2— | 3-Br—Ph | Z-2429 | N≡CCH2— | 3-Cl—PhCH2— | Z-2430 | N≡CCH2— | Bu(C=O)— |
| Z-2431 | N≡CCH2— | 4-Br—Ph | Z-2432 | N≡CCH2— | 4-Cl—PhCH2— | Z-2433 | N≡CCH2— | MeO(C=O)— |
| Z-2434 | N≡CCH2— | 2-I—Ph | Z-2435 | N≡CCH2— | 2-Br—PhCH2— | Z-2436 | N≡CCH2— | EtO(C=O)— |
| Z-2437 | N≡CCH2— | 3-I—Ph | Z-2438 | N≡CCH2— | 3-Br—PhCH2— | Z-2439 | N≡CCH2— | PrO(C=O)— |
| Z-2440 | N≡CCH2— | 4-I—Ph | Z-2441 | N≡CCH2— | 4-Br—PhCH2— | Z-2442 | c-Pr—CH2— | 4-MeO—PhCH2— |

TABLE 3-continued

| Z | R3 | R4 | Z | R3 | R4 | Z | R3 | R4 |
|---|---|---|---|---|---|---|---|---|
| Z-2443 | N≡CCH2— | 2-Me—Ph | Z-2444 | N≡CCH2— | 2-I—PhCH2— | Z-2445 | c-Pr—CH2— | 2,3-di-F—PhCH2— |
| Z-2446 | N≡CCH2— | 3-Me—Ph | Z-2447 | N≡CCH2— | 3-I—PhCH2— | Z-2448 | c-Pr—CH2— | 2,4-di-F—PhCH2— |
| Z-2449 | N≡CCH2— | 4-Me—Ph | Z-2450 | N≡CCH2— | 4-I—PhCH2— | Z-2451 | c-Pr—CH2— | 2,5-di-F—PhCH2— |
| Z-2452 | N≡CCH2— | 2-MeO—Ph | Z-2453 | N≡CCH2— | 2-Me—PhCH2— | Z-2454 | c-Pr—CH2— | 2,6-di-F—PhCH2— |
| Z-2455 | N≡CCH2— | 3-MeO—Ph | Z-2456 | N≡CCH2— | 3-Me—PhCH2— | Z-2457 | c-Pr—CH2— | 2-Cl-3-F—PhCH2— |
| Z-2458 | N≡CCH2— | 4-MeO—Ph | Z-2459 | N≡CCH2— | 4-Me—PhCH2— | Z-2460 | c-Pr—CH2— | 2-Cl-4-F—PhCH2— |
| Z-2461 | N≡CCH2— | 2,3-di-F—Ph | Z-2462 | N≡CCH2— | 2-MeO—PhCH2— | Z-2463 | c-Pr—CH2— | 2-Cl-5-F—PhCH2— |
| Z-2464 | N≡CCH2— | 2,4-di-F—Ph | Z-2465 | N≡CCH2— | 3-MeO—PhCH2— | Z-2466 | c-Pr—CH2— | 2-Cl-6-F—PhCH2— |
| Z-2467 | N≡CCH2— | 2,5-di-F—Ph | Z-2468 | N≡CCH2— | 4-MeO—PhCH2— | Z-2469 | c-Pr—CH2— | 2-Br-3-F—PhCH2— |
| Z-2470 | N≡CCH2— | 2,6-di-F—Ph | Z-2471 | N≡CCH2— | 2,3-di-F—PhCH2— | Z-2472 | c-Pr—CH2— | 2-Br-4-F—PhCH2— |
| Z-2473 | N≡CCH2— | 2-Cl-3-F—Ph | Z-2474 | N≡CCH2— | 2,4-di-F—PhCH2— | Z-2473 | c-Pr—CH2— | 2-Br-5-F—PhCH2— |
| Z-2476 | N≡CCH2— | i-PrO(C═O)— | Z-2477 | c-Pr—CH2— | 2,5-di-F—Ph | Z-2478 | c-Pr—CH2— | 2-Br-6-F—PhCH2— |
| Z-2479 | N≡CCH2— | BuO(C═O)— | Z-2480 | c-Pr—CH2— | 2,6-di-F—Ph | Z-2481 | c-Pr—CH2— | 2-F-3-MeO—PhCH2— |
| Z-2482 | N≡CCH2— | t-BuOC(═O)— | Z-2483 | c-Pr—CH2— | 2-Cl-3-F—Ph | Z-2484 | c-Pr—CH2— | 2-F-4-MeO—PhCH2— |
| Z-2485 | c-Pr—CH2— | c-Pr—CH2— | Z-2486 | c-Pr—CH2— | 2-Cl-4-F—Ph | Z-2487 | c-Pr—CH2— | 2-F-5-MeO—PhCH2— |
| Z-2488 | c-Pr—CH2— | c-Bu—CH2— | Z-2489 | c-Pr—CH2— | 2-Cl-5-F—PH | Z-2490 | c-Pr—CH2— | 2-F-6-MeO—PhCH2— |
| Z-2491 | c-Pr—CH2— | c-Pent-CH2— | Z-2492 | c-Pr—CH2— | 2-Cl-6-F—Ph | Z-2493 | c-Pr—CH2— | 2-Cl-3-MeO—PhCH2— |
| Z-2494 | c-Pr—CH2— | c-Hex—CH2— | Z-2495 | c-Pr—CH2— | 2-Br-3-F—Ph | Z-2496 | c-Pr—CH2— | 2-Cl-4-MeO—PhCH2— |
| Z-2497 | c-Pr—CH2— | F3C— | Z-2498 | c-Pr—CH2— | 2-Br-4-F—Ph | Z-2499 | c-Pr—CH2— | 2-Cl-5-MeO—PhCH2— |
| Z-2500 | c-Pr—CH2— | F2CH— | Z-2501 | c-Pr—CH2— | 2-Br-5-F—Ph | Z-2502 | c-Pr—CH2— | 2-Cl-6-MeO—PhCH2— |
| Z-2503 | c-Pr—CH2— | F3CCH2— | Z-2504 | c-Pr—CH2— | 2-Br-6-F—Ph | Z-2505 | c-Pr—CH2— | 2-Br-3-MeO—PhCH2— |
| Z-2506 | c-Pr—CH2— | F2CHCH2— | Z-2507 | c-Pr—CH2— | 2-F-3-MeO—Ph | Z-2508 | c-Pr—CH2— | 2-Br-4-MeO—PhCH2— |
| Z-2509 | c-Pr—CH2— | F3CF2C— | Z-2510 | c-Pr—CH2— | 2-F-4-MeO—Ph | Z-2511 | c-Pr—CH2— | 2-Br-5-MeO—PhCH2— |
| Z-2512 | c-Pr—CH2— | F2CHF2C— | Z-2513 | c-Pr—CH2— | 2-F-5-MeO—Ph | Z-2514 | c-Pr—CH2— | 2-Br-6-MeO—PhCH2— |
| Z-2515 | c-Pr—CH2— | (F3C)2FC— | Z-2516 | c-Pr—CH2— | 2-F-6-MeO—Ph | Z-2517 | c-Pr—CH2— | 2,3,4-tri-F—PhCH2— |
| Z-2318 | c-Pr—CH2— | F3CF2C(F3C)FC— | Z-2519 | c-Pr—CH2— | 2-Cl-3-MeO—Ph | Z-2520 | c-Pr—CH2— | 2,3,5-tri-F—PhCH2— |
| Z-2521 | c-Pr—CH2— | c-Pr | Z-2522 | c-Pr—CH2— | 2-Cl-4-MeO—Ph | Z-2523 | c-Pr—CH2— | 2,3,6-tri-F—PhCH2— |
| Z-2524 | c-Pr—CH2— | c-Bu | Z-2525 | c-Pr—CH2— | 2-Cl-5-MeO—Ph | Z-2526 | c-Pr—CH2— | 2-Br-3,4-di-F—PhCH2— |
| Z-2527 | c-Pr—CH2— | c-Pent | Z-2528 | c-Pr—CH2— | 2-Cl-6-MeO—Ph | Z-2529 | c-Pr—CH2— | 2-Br-3,5-di-F—PhCH2— |
| Z-253C | c-Pr—CH2— | c-Hex | Z-2531 | c-Pr—CH2— | 2-Br-3-MeO—Ph | Z-2532 | c-Pr—CH2— | 2-Br-3,6-di-F—PhCH2— |
| Z-2533 | c-Pr—CH2— | H2C═CH— | Z-2534 | c-Pr—CH2— | 2-Br-4-MeO—Ph | Z-2535 | c-Pr—CH2— | 2-F-3,4-di-MeO—PhCH2— |
| Z-2536 | c-Pr—CH2— | H3CCH═CH— | Z-2537 | c-Pr—CH2— | 2-Br-5-MeO—Ph | Z-2538 | c-Pr—CH2— | 2-F-3,5-di-MeO—PhCH2— |
| Z-2539 | c-Pr—CH2— | H2C═CHCH2— | Z-2540 | c-Pr—CH2— | 2-Br-6-MeO—Ph | Z-2541 | c-Pr—CH2— | 2-F-3,6-di-MeO—PhCH2— |
| Z-2542 | c-Pr—CH2— | F2C═CH— | Z-2543 | c-Pr—CH2— | 2,3,4-tri-F—Ph | Z-2544 | c-Pr—CH2— | 2-Cl-3,4-di-MeO—PhCH2— |
| Z-2545 | c-Pr—CH2— | F2C═CHCH2— | Z-2546 | c-Pr—CH2— | 2,3,5-tri-F—Ph | Z-2547 | c-Pr—CH2— | 2-Cl-3,5-di-MeO—PhCH2— |
| Z-2548 | c-Pr—CH2— | HC≡C— | Z-2549 | c-Pr—CH2— | 2,3,6-tri-F—Ph | Z-2550 | c-Pr—CH2— | 2-Cl-3,6-di-MeO—PhCH2— |
| Z-2551 | c-Pr—CH2— | HC≡CCH2— | Z-2552 | c-Pr—CH2— | 2-Br-3,4-di-F—Ph | Z-2553 | c-Pr—CH2— | 2-Br-3,4-di-MeO—PhCH2— |
| Z-2554 | c-Pr—CH2— | HC≡CCH2CH2— | Z-2555 | c-Pr—CH2— | 2-Br-3,5-di-F—Ph | Z-2556 | c-Pr—CH2— | 2-Br-3,5-di-MeO—PhCH2— |
| Z-2557 | c-Pr—CH2— | H3CC≡CCH2— | Z-2558 | c-Pr—CH2— | 2-Br-3,6-di-F—Ph | Z-2559 | c-Pr—CH2— | 2-Br-3,6-di-MeO—PhCH2— |
| Z-2560 | c-Pr—CH2— | FC≡C— | Z-2561 | c-Pr—CH2— | 2-F-3,4-di-MeO—Ph | Z-2562 | c-Pr—CH2— | MeS— |
| Z-2563 | c-Pr—CH2— | FC≡CCF2— | Z-2564 | c-Pr—CH2— | 2-F-3,5-di-MeO—Ph | Z-2565 | c-Pr—CH2— | MeS(═O)— |
| Z-2566 | c-Pr—CH2— | FC≡CCF2CF2— | Z-2567 | c-Pr—CH2— | 2-F-3,6-di-MeO—Ph | Z-2568 | c-Pr—CH2— | MeS(═O)2— |
| Z-2569 | c-Pr—CH2— | F3CC≡CCF2— | Z-2570 | c-Pr—CH2— | 2-Cl-3,4-di-MeO—Ph | Z-2571 | c-Pr—CH2— | EtS— |
| Z-2572 | c-Pr—CH2— | Ph | Z-2573 | c-Pr—CH2— | 2-Cl-3,5-di-MeO—Ph | Z-2574 | c-Pr—CH2— | EtS(═O)— |
| Z-2575 | c-Pr—CH2— | 2-F—Ph | Z-2576 | c-Pr—CH2— | 2-Cl-3,6-di-MeO—Ph | Z-2577 | c-Pr—CH2— | EtS(═O)2— |
| Z-2578 | c-Pr—CH2— | 3-F—Ph | Z-2579 | c-Pr—CH2— | 2-Br-3,4-di-MeO—Ph | Z-2580 | c-Pr—CH2— | PrS— |
| Z-2581 | c-Pr—CH2— | 4-F—Ph | Z-2582 | c-Pr—CH2— | 2-Br-3,5-di-MeO—Ph | Z-2583 | c-Pr—CH2— | PrS(═O)— |
| Z-2584 | c-Pr—CH2— | 2-Cl—Ph | Z-2585 | c-Pr—CH2— | 2-Br-3,6-di-MeO—Ph | Z-2586 | c-Pr—CH2— | PrS(═O)2— |
| Z-2587 | c-Pr—CH2— | 3-Cl—Ph | Z-2588 | c-Pr—CH2— | PhCH2— | Z-2589 | c-Pr—CH2— | Ac |
| Z-2590 | c-Pr—CH2— | 4-Cl—Ph | Z-2591 | c-Pr—CH2— | 2-F—PhCH2— | Z-2592 | c-Pr—CH2— | OHC— |
| Z-2593 | c-Pr—CH2— | 2-Br—Ph | Z-2594 | c-Pr—CH2— | 3-F—PhCH2— | Z-2595 | c-Pr—CH2— | Et(C═O)— |

TABLE 3-continued

| Z | R3 | R4 | Z | R3 | R4 | Z | R3 | R4 |
|---|---|---|---|---|---|---|---|---|
| Z-2596 | c-Pr—CH2— | 3-Br—Ph | Z-2597 | c-Pr—CH2— | 4-F—PhCH2— | Z-2598 | c-Pr—CH2— | Pr(C═O)— |
| Z-2599 | c-Pr—CH2— | 4-Br—Ph | Z-2600 | c-Pr—CH2— | 2-Cl—PhCH2— | Z-2601 | c-Pr—CH2— | i-Pr(C═O)— |
| Z-2602 | c-Pr—CH2— | 2-I—Ph | Z-2603 | c-Pr—CH2— | 3-Cl—PhCH2— | Z-2604 | c-Pr—CH2— | Bu(C═O)— |
| Z-2605 | c-Pr—CH2— | 3-I—Ph | Z-2606 | c-Pr—CH2— | 4-Cl—PhCH2— | Z-2607 | c-Pent-CH2— | 2,3-di-F—PhCH2— |
| Z-2608 | c-Pr—CH2— | 4-I—Ph | Z-2609 | c-Pr—CH2— | 2-Br—PhCH2— | Z-2610 | c-Pent-CH2— | 2,4-di-F—PhCH2— |
| Z-2611 | c-Pr—CH2— | 2-Me—Ph | Z-2612 | c-Pr—CH2— | 3-Br—PhCH2— | Z-2613 | c-Pent-CH2— | 2,5-di-F—PhCH2— |
| Z-2614 | c-Pr—CH2— | 3-Me—Ph | Z-2615 | c-Pr—CH2— | 4-Br—PhCH2— | Z-2616 | c-Pent-CH2— | 2,6-di-F—PhCH2— |
| Z-2617 | c-Pr—CH2— | 4-Me—Ph | Z-2618 | c-Pr—CH2— | 2-I—PhCH2— | Z-2619 | c-Pent-CH2— | 2-Cl-3-F—PFCH2— |
| Z-2620 | c-Pr—CH2— | 2-MeO—Ph | Z-2621 | c-Pr—CH2— | 3-I—PhCH2— | Z-2622 | c-Pent-CH2— | 2-Cl-4-F—PhCH2— |
| Z-2623 | c-Pr—CH2— | 3-MeO—Ph | Z-2624 | c-Pr—CH2— | 4-I—PhCH2— | Z-2625 | c-Pent-CH2— | 2-Cl-5-F—PhCH2— |
| Z-2626 | c-Pr—CH2— | 4-MeO—Ph | Z-2627 | c-Pr—CH2— | 2-Me—PhCH2— | Z-2628 | c-Pent-CH2— | 2-Cl-6-F—PhCH2— |
| Z-2629 | c-Pr—CH2— | 2,3-di-F—Ph | Z-2630 | c-Pr—CH2— | 3-Me—PhCH2— | Z-2631 | c-Pent-CH2— | 2-Br-3-F—PhCH2— |
| Z-2632 | c-Pr—CH2— | 2,4-di-F—Ph | Z-2633 | c-Pr—CH2— | 4-Me—PhCH2— | Z-2634 | c-Pent-CH2— | 2-Br-4-F—PhCH2— |
| Z-2635 | c-Pr—CH2— | MeO(C═O)— | Z-2636 | c-Pr—CH2— | 2-MeO—PhCH2— | Z-2637 | c-Pent-CH2— | 2-Br-5-F—PhCH2— |
| Z-2638 | c-Pr—CH2— | EtO(C═O)— | Z-2639 | c-Pr—CH2— | 3-MeO—PhCH2— | Z-2640 | c-Pent-CH2— | 2-Br-6-F—PhCH2— |
| Z-2641 | c-Pr—CH2— | PrO(C═O)— | Z-2642 | c-Pent-CH2— | 2,6-di-F—Ph | Z-2643 | c-Pent-CH2— | 2-F-3-MeO—PhCH2— |
| Z-2644 | c-Pr—CH2— | i-PrO(C═O)— | Z-2645 | c-Pent-CH2— | 2-Cl-3-F—Ph | Z-2646 | c-Pent-CH2— | 2-F-4-MeO—PhCH2— |
| Z-2647 | c-Pr—CH2— | BuO(C═O)— | Z-2648 | c-Pent-CH2— | 2-Cl-4-F—Ph | Z-2649 | c-Pent-CH2— | 2-F-5-MeO—PhCH2— |
| Z-2650 | c-Pr—CH2— | t-BuOC(═O)— | Z-2651 | c-Pent-CH2— | 2-Cl-5-F—Ph | Z-2652 | c-Pent-CH2— | 2-F-6-MeO—PhCH2— |
| Z-2653 | c-Pent-CH2— | c-Pent-CH2— | Z-2654 | c-Pent-CH2— | 2-Cl-6-F—Ph | Z-2655 | c-Pent-CH2— | 2-Cl-3-MeO—PhCH2— |
| Z-2656 | c-Pent-CH2— | c-Hex—CH2— | Z-2657 | c-Pent-CH2— | 2-Br-3-F—Ph | Z-2658 | c-Pent-CH2— | 2-Cl-4-MeO—PhCH2— |
| Z-2659 | c-Pent-CH2— | F3C— | Z-2660 | c-Pent-CH2— | 2-Br-4-F—Ph | Z-2661 | c-Pent-CH2— | 2-Cl-5-MeO—PhCH2— |
| Z-2662 | c-Pent-CH2— | F2CH— | Z-2663 | c-Pent-CH2— | 2-Br-5-F—Ph | Z-2664 | c-Pent-CH2— | 2-Cl-6-MeO—PhCH2— |
| Z-2665 | c-Pent-CH2— | F3CCH2— | Z-2666 | c-Pent-CH2— | 2-Br-6-F—Ph | Z-2667 | c-Pent-CH2— | 2-Br-3-MeO—PhCH2— |
| Z-2668 | c-Pent-CH2— | F2CHCH2— | Z-2669 | c-Pent-CH2— | 2-F-3-MeO—Ph | Z-2670 | c-Pent-CH2— | 2-Br-4-MeO—PhCH2— |
| Z-2671 | c-Pent-CH2— | F3CF2C— | Z-2672 | c-Pent-CH2— | 2-F-4-MeO—Ph | Z-2673 | c-Pent-CH2— | 2-Br-5-MeO—PhCH2— |
| Z-2674 | c-Pent-CH2— | F2CHF2C— | Z-2675 | c-Pent-CH2— | 2-F-5-MeO—Ph | Z-2676 | c-Pent-CH2— | 2-Br-6-MeO—PhCH2— |
| Z-2677 | c-Pent-CH2— | (F3C)2FC— | Z-2678 | c-Pent-CH2— | 2-F-6-MeO—Ph | Z-2679 | c-Pent-CH2— | 2,3,4-tri-F—PhCH2— |
| Z-2680 | c-Pent-CH2— | F3CF2C(F3C)FC— | Z-2681 | c-Pent-CH2— | 2-Cl-3-MeO—Ph | Z-2682 | c-Pent-CH2— | 2,3,5-tri-F—PhCH2— |
| Z-2683 | c-Pent-CH2— | c-Pr | Z-2684 | c-Pent-CH2— | 2-Cl-4-MeO—Ph | Z-2685 | c-Pent-CH2— | 2,3,6-tri-F—PhCH2— |
| Z-2686 | c-Pent-CH2— | c-Bu | Z-2687 | c-Pent-CH2— | 2-Cl-5-MeO—Ph | Z-2688 | c-Pent-CH2— | 2-Br-3,4-di-F—PhCH2— |
| Z-2689 | c-Pent-CH2— | c-Pent | Z-2690 | c-Pent-CH2— | 2-Cl-6-MeO—Ph | Z-2691 | c-Pent-CH2— | 2-Br-3,5-di-F—PhCH2— |
| Z-2692 | c-Pent-CH2— | c-Hex | Z-2693 | c-Pent-CH2— | 2-Br-3-MeO—Ph | Z-2694 | c-Pent-CH2— | 2-Br-3,6-di-F—PhCH2— |
| Z-2695 | c-Pent-CH2— | H2C═CH— | Z-2696 | c-Pent-CH2— | 2-Br-4-MeO—Ph | Z-2697 | c-Pent-CH2— | 2-F-3,4-di-MeO—PhCH2— |
| Z-2698 | c-Pent-CH2— | H3CCH═CH— | Z-2699 | c-Pent-CH2— | 2-Br-5-MeO—Ph | Z-2700 | c-Pent-CH2— | 2-F-3,5-di-MeO—PhCH2— |
| Z-2701 | c-Pent-CH2— | H2C═CHCH2— | Z-2702 | c-Pent-CH2— | 2-Br-6-MeO—Ph | Z-2703 | c-Pent-CH2— | 2-F-3,6-di-MeO—PhCH2— |
| Z-2704 | c-Pent-CH2— | F2C═CH— | Z-2705 | c-Pent-CH2— | 2,3,4-tri-F—Ph | Z-2706 | c-Pent-CH2— | 2-Cl-3,4-di-MeO—PhCH2— |
| Z-2707 | c-Pent-CH2— | F2C═CHCH2— | Z-2708 | c-Pent-CH2— | 2,3,5-tri-F—Ph | Z-2709 | c-Pent-CH2— | 2-Cl-3,5-di-MeO—PhCH2— |
| Z-2710 | c-Pent-CH2— | HC≡C— | Z-2711 | c-Pent-CH2— | 2,3,6-tri-F—Ph | Z-2712 | c-Pent-CH2— | 2-Cl-3,6-di-MeO—PhCH2— |
| Z-2713 | c-Pent-CH2— | HC≡CCH2— | Z-2714 | c-Pent-CH2— | 2-Br-3,4-di-F—Ph | Z-2715 | c-Pent-CH2— | 2-Br-3,4-di-MeO—PhCH2— |
| Z-2716 | c-Pent-CH2— | HC≡CCH2CH2— | Z-2717 | c-Pent-CH2— | 2-Br-3,5-di-F—Ph | Z-2718 | c-Pent-CH2— | 2-Br-3,5-di-MeO—PhCH2— |
| Z-2719 | c-Pent-CH2— | H3CC≡CCH2— | Z-2720 | c-Pent-CH2— | 2-Br-3,6-di-F—Ph | Z-2721 | c-Pent-CH2— | 2-Br-3,6-di-MeO—PhCH2— |
| Z-2722 | c-Pent-CH2— | FC≡C— | Z-2723 | c-Pent-CH2— | 2-F-3,4-di-MeO—Ph | Z-2724 | c-Pent-CH2— | MeS— |
| Z-2725 | c-Pent-CH2— | FC≡CCF2— | Z-2726 | c-Pent-CH2— | 2-F-3,5-di-MeO—Ph | Z-2727 | c-Pent-CH2— | MeS(═O)— |
| Z-2728 | c-Pent-CH2— | FC≡CCF2CF2— | Z-2729 | c-Pent-CH2— | 2-F-3,6-di-MeO—Ph | Z-2730 | c-Pent-CH2— | MeS(═O)2— |
| Z-2731 | c-Pent-CH2— | F3CC≡CCF2— | Z-2732 | c-Pent-CH2— | 2-Cl-3,4-di-MeO—Ph | Z-2733 | c-Pent-CH2— | EtS— |
| Z-2734 | c-Pent-CH2— | Ph | Z-2735 | c-Pent-CH2— | 2-Cl-3,5-di-MeO—Ph | Z-2736 | c-Pent-CH2— | EtS(═O)— |
| Z-2737 | c-Pent-CH2— | 2-F—Ph | Z-2738 | c-Pent-CH2— | 2-Cl-3,6-di-MeO—Ph | Z-2739 | c-Pent-CH2— | EtS(═O)2— |
| Z-2740 | c-Pent-CH2— | 3-F—Ph | Z-2741 | c-Pent-CH2— | 2-Br-3,4-di-MeO—Ph | Z-2742 | c-Pent-CH2— | PrS— |
| Z-2743 | c-Pent-CH2— | 4-F—Ph | Z-2744 | c-Pent-CH2— | 2-Br-3,5-di-MeO—Ph | Z-2743 | c-Pent-CH2— | PrS(═O)— |
| Z-2746 | c-Pent-CH2— | 2-Cl—Ph | Z-2747 | c-Pent-CH2— | 2-Br-3,6-di-MeO—Ph | Z-2748 | c-Pent-CH2— | PrS(═O)2— |

TABLE 3-continued

| Z | R3 | R4 | Z | R3 | R4 | Z | R3 | R4 |
|---|---|---|---|---|---|---|---|---|
| Z-2749 | c-Pent-CH2— | 3-Cl—Ph | Z-2750 | c-Pent-CH2— | PhCH2— | Z-2751 | c-Pent-CH2— | Ac |
| Z-2752 | c-Pent-CH2— | 4-Cl—Ph | Z-2753 | c-Pent-CH2— | 2-F—PhCH2— | Z-2754 | c-Pent-CH2— | OHC— |
| Z-2755 | c-Pent-CH2— | 2-Br—Ph | Z-2756 | c-Pent-CH2— | 3-F—PhCH2— | Z-2757 | c-Pent-CH2— | Et(C═O)— |
| Z-2758 | c-Pent-CH2— | 3-Br—Ph | Z-2759 | c-Pent-CH2— | 4-F—PhCH2— | Z-2760 | c-Pent-CH2— | Pr(C═O)— |
| Z-2761 | c-Pent-CH2— | 4-Br—Ph | Z-2762 | c-Pent-CH2— | 2-Cl—PhCH2— | Z-2763 | c-Pent-CH2— | i-Pr(C═O)— |
| Z-2764 | c-Pent-CH2— | 2-I—Ph | Z-2765 | c-Pent-CH2— | 3-Cl—PhCH2— | Z-2766 | c-Pent-CH2— | Bu(C═O)— |
| Z-2767 | c-Pent-CH2— | 3-I—Ph | Z-2768 | c-Pent-CH2— | 4-Cl—PhCH2— | Z-2769 | c-Pent-CH2— | MeO(C═O)— |
| Z-2770 | c-Pent-CH2— | 4-I—Ph | Z-2771 | c-Pent-CH2— | 2-Br—PhCH2— | Z-2772 | c-Hex—CH2— | 2,5-di-F—PhCH2— |
| Z-2773 | c-Pent-CH2— | 2-Me—Ph | Z-2774 | c-Pent-CH2— | 3-Br—PhCH2— | Z-2775 | c-Hex—CH2— | 2,6-di-F—PhCH2— |
| Z-2776 | c-Pent-CH2— | 3-Me—Ph | Z-2777 | c-Pent-CH2— | 4-Br—PhCH2— | Z-2778 | c-Hex—CH2— | 2-Cl-3-F—PhCH2— |
| Z-2779 | c-Pent-CH2— | 4-Me—Ph | Z-2780 | c-Pent-CH2— | 2-I—PhCH2— | Z-2781 | c-Hex—CH2— | 2-Cl-4-F—PhCH2— |
| Z-2782 | c-Pent-CH2— | 2-MeO—Ph | Z-2783 | c-Pent-CH2— | 3-I—PhCH2— | Z-2784 | c-Hex—CH2— | 2-Cl-5-F—PhCH2— |
| Z-2785 | c-Pent-CH2— | 3-MeO—Ph | Z-2786 | c-Pent-CH2— | 4-I—PhCH2— | Z-2787 | c-Hex—CH2— | 2-Cl-6-F—PhCH2— |
| Z-2788 | c-Pent-CH2— | 4-MeO—Ph | Z-2789 | c-Pent-CH2— | 2-Me—PhCH2— | Z-2790 | c-Hex—CH2— | 2-Br-3-F—PhCH2— |
| Z-2791 | c-Pent-CH2— | 2,3-di-F—Ph | Z-2792 | c-Pent-CH2— | 3-Me—PhCH2— | Z-2793 | c-Hex—CH2— | 2-Br-4-F—PhCH2— |
| Z-2794 | c-Pent-CH2— | 2,4-di-F—Ph | Z-2795 | c-Pent-CH2— | 4-Me—PhCH2— | Z-2796 | c-Hex—CH2— | 2-Br-5-F—PhCH2— |
| Z-2797 | c-Pent-CH2— | 2,5-di-F—Ph | Z-2798 | c-Pent-CH2— | 2-MeO—PhCH2— | Z-2799 | c-Hex—CH2— | 2-Br-6-F—PhCH2— |
| Z-2800 | c-Pent-CH2— | EtO(C═O)— | Z-2801 | c-Pent-CH2— | 3-MeO—PhCH2— | Z-2802 | c-Hex—CH2— | 2-F-3-MeO—PhCH2— |
| Z-2803 | c-Pent-CH2— | PrO(C═O)— | Z-2804 | c-Pent-CH2— | 4-MeO—PhCH2— | Z-2805 | c-Hex—CH2— | 2-F-4-MeO—PhCH2— |
| Z-2806 | c-Pent-CH2— | i-PrO(C═O)— | Z-2807 | c-Hex—CH2— | 2-Cl-4-F—PH | Z-2808 | c-Hex—CH2— | 2-F-5-MeO—PhCH2— |
| Z-2809 | c-Pent-CH2— | BuO(C═O)— | Z-2810 | c-Hex—CH2— | 2-Cl-5-F—Ph | Z-2811 | c-Hex—CH2— | 2-F-6-MeO—PhCH2— |
| Z-2812 | c-Pent-CH2— | t-BuOC(═O)— | Z-2813 | c-Hex—CH2— | 2-Cl-6-F—Ph | Z-2814 | c-Hex—CH2— | 2-Cl-3-MeO—PhCH2— |
| Z-2815 | c-Hex—CH2— | c-Hex—CH2— | Z-2816 | c-Hex—CH2— | 2-Br-3-F—Ph | Z-2817 | c-Hex—CH2— | 2-Cl-4-MeO—PhCH2— |
| Z-2818 | c-Hex—CH2— | F3C— | Z-2819 | c-Hex—CH2— | 2-Br-4-F—Ph | Z-2820 | c-Hex—CH2— | 2-Cl-5-MeO—PhCH2— |
| Z-2821 | c-Hex—CH2— | F2CH— | Z-2822 | c-Hex—CH2— | 2-Br-5-F—Ph | Z-2823 | c-Hex—CH2— | 2-Cl-6-MeO—PhCH2— |
| Z-2824 | c-Hex—CH2— | F3CCH2— | Z-2825 | c-Hex—CH2— | 2-Br-6-F—Ph | Z-2826 | c-Hex—CH2— | 2-Br-3-MeO—PhCH2— |
| Z-2827 | c-Hex—CH2— | F2CHCH2— | Z-2828 | c-Hex—CH2— | 2-F-3-MeO—Ph | Z-2829 | c-Hex—CH2— | 2-Br-4-MeO—PhCH2— |
| Z-2830 | c-Hex—CH2— | F3CF2C— | Z-2831 | c-Hex—CH2— | 2-F-4-MeO—Ph | Z-2832 | c-Hex—CH2— | 2-Br-5-MeO—PhCH2— |
| Z-2833 | c-Hex—CH2— | F2CHF2C— | Z-2834 | c-Hex—CH2— | 2-F-5-MeO—Ph | Z-2835 | c-Hex—CH2— | 2-Br-6-MeO—PhCH2— |
| Z-2836 | c-Hex—CH2— | (F3C)2FC— | Z-2837 | c-Hex—CH2— | 2-F-6-MeO—Ph | Z-2838 | c-Hex—CH2— | 2,3,4-tri-F—PhCH2— |
| Z-2839 | c-Hex—CH2— | F3CF2C(F3C)FC— | Z-2840 | c-Hex—CH2— | 2-Cl-3-MeO—Ph | Z-2841 | c-Hex—CH2— | 2,3,5-tri-F—PhCH2— |
| Z-2842 | c-Hex—CH2— | c-Pr | Z-2843 | c-Hex—CH2— | 2-Cl-4-MeO—Ph | Z-2844 | c-Hex—CH2— | 2,3,6-tri-F—PhCH2— |
| Z-2845 | c-Hex—CH2— | c-Bu | Z-2846 | c-Hex—CH2— | 2-Cl-5-MeO—Ph | Z-2847 | c-Hex—CH2— | 2-Br-3,4-di-F—PhCH2— |
| Z-2848 | c-Hex—CH2— | c-Pent | Z-2849 | c-Hex—CH2— | 2-Cl-6-MeO—Ph | Z-2850 | c-Hex—CH2— | 2-Br-3,5-di-F—PhCH2— |
| Z-2851 | c-Hex—CH2— | c-Hex | Z-2852 | c-Hex—CH2— | 2-Br-3-MeO—Ph | Z-2853 | c-Hex—CH2— | 2-Br-3,6-di-F—PhCH2— |
| Z-2854 | c-Hex—CH2— | H2C═CH— | Z-2855 | c-Hex—CH2— | 2-Br-4-MeO—Ph | Z-2856 | c-Hex—CH2— | 2-F-3,4-di-MeO—PhCH2— |
| Z-2857 | c-Hex—CH2— | H3CCH═CH— | Z-2858 | c-Hex—CH2— | 2-Br-5-MeO—Ph | Z-2859 | c-Hex—CH2— | 2-F-3,5-di-MeO—PhCH2— |
| Z-2860 | c-Hex—CH2— | H2C═CHCH2— | Z-2861 | c-Hex—CH2— | 2-Br-6-MeO—Ph | Z-2862 | c-Hex—CH2— | 2-F-3,6-di-MeO—PhCH2— |
| Z-2863 | c-Hex—CH2— | F2C═CH— | Z-2864 | c-Hex—CH2— | 2,3,4-tri-F—Ph | Z-2865 | c-Hex—CH2— | 2-Cl-3,4-di-MeO—PhCH2— |
| Z-2866 | c-Hex—CH2— | F2C═CHCH2— | Z-2867 | c-Hex—CH2— | 2,3,5-tri-F—Ph | Z-2868 | c-Hex—CH2— | 2-Cl-3,5-di-MeO—PhCH2— |
| Z-2869 | c-Hex—CH2— | HC≡C— | Z-2870 | c-Hex—CH2— | 2,3,6-tri-F—Ph | Z-2871 | c-Hex—CH2— | 2-Cl-3,6-di-MeO—PhCH2— |
| Z-2872 | c-Hex—CH2— | HC≡CCH2— | Z-2873 | c-Hex—CH2— | 2-Br-3,4-di-F—Ph | Z-2874 | c-Hex—CH2— | 2-Br-3,4-di-MeO—PhCH2— |
| Z-2875 | c-Hex—CH2— | HC≡CCH2CH2— | Z-2876 | c-Hex—CH2— | 2-Br-3,5-di-F—Ph | Z-2877 | c-Hex—CH2— | 2-Br-3,5-di-MeO—PhCH2— |
| Z-2878 | c-Hex—CH2— | H3CC≡CCH2— | Z-2879 | c-Hex—CH2— | 2-Br-3,6-di-F—Ph | Z-2880 | c-Hex—CH2— | 2-Br-3,6-di-MeO—PhCH2— |
| Z-2881 | c-Hex—CH2— | FC≡C— | Z-2882 | c-Hex—CH2— | 2-F-3,4-di-MeO—Ph | Z-2883 | c-Hex—CH2— | MeS— |
| Z-2884 | c-Hex—CH2— | FC≡CCF2— | Z-2885 | c-Hex—CH2— | 2-F-3,5-di-MeO—Ph | Z-2886 | c-Hex—CH2— | MeS(═O)— |
| Z-2887 | c-Hex—CH2— | FC≡CCF2CF2— | Z-2888 | c-Hex—CH2— | 2-F-3,6-di-MeO—Ph | Z-2889 | c-Hex—CH2— | MeS(═O)2— |
| Z-2890 | c-Hex—CH2— | F3CC≡CCF2— | Z-2891 | c-Hex—CH2— | 2-Cl-3,4-di-MeO—Ph | Z-2892 | c-Hex—CH2— | EtS— |
| Z-2893 | c-Hex—CH2— | Ph | Z-2894 | c-Hex—CH2— | 2-Cl-3,5-di-MeO—Ph | Z-2895 | c-Hex—CH2— | EtS(═O)— |
| Z-2896 | c-Hex—CH2— | 2-F—Ph | Z-2897 | c-Hex—CH2— | 2-Cl-3,6-di-MeO—Ph | Z-2898 | c-Hex—CH2— | EtS(═O)2— |
| Z-2899 | c-Hex—CH2— | 3-F—Ph | Z-2900 | c-Hex—CH2— | 2-Br-3,4-di-MeO—Ph | Z-2901 | c-Hex—CH2— | PrS— |

TABLE 3-continued

| Z | R3 | R4 | Z | R3 | R4 | Z | R3 | R4 |
|---|---|---|---|---|---|---|---|---|
| Z-2902 | c-Hex—CH2— | 4-F—Ph | Z-2903 | c-Hex—CH2— | 2-Br-3,5-di-MeO—Ph | Z-2904 | c-Hex—CH2— | PrS(═O)— |
| Z-2905 | c-Hex—CH2— | 2-Cl—Ph | Z-2906 | c-Hex—CH2— | 2-Br-3,6-di-MeO—Ph | Z-2907 | c-Hex—CH2— | PrS(═O)2— |
| Z-2908 | c-Hex—CH2— | 3-Cl—Ph | Z-2909 | c-Hex—CH2— | PhCH2— | Z-2910 | c-Hex—CH2— | Ac |
| Z-2911 | c-Hex—CH2— | 4-Cl—Ph | Z-2912 | c-Hex—CH2— | 2-F—PhCH2— | Z-2913 | c-Hex—CH2— | OHC— |
| Z-2914 | c-Hex—CH2— | 2-Br—Ph | Z-2915 | c-Hex—CH2— | 3-F—PhCH2— | Z-2916 | c-Hex—CH2— | Et(C═O)— |
| Z-2917 | c-Hex—CH2— | 3-Br—Ph | Z-2918 | c-Hex—CH2— | 4-F—PhCH2— | Z-2919 | c-Hex—CH2— | Pr(C═O)— |
| Z-2920 | c-Hex—CH2— | 4-Br—Ph | Z-2921 | c-Hex—CH2— | 2-Cl—PhCH2— | Z-2922 | c-Hex—CH2— | i-Pr(C═O)— |
| Z-2923 | c-Hex—CH2— | 2-I—Ph | Z-2924 | c-Hex—CH2— | 3-Cl—PhCH2— | Z-2925 | c-Hex—CH2— | Bu(C═O)— |
| Z-2926 | c-Hex—CH2— | 3-I—Ph | Z-2927 | c-Hex—CH2— | 4-Cl—PhCH2— | Z-2928 | c-Hex—CH2— | MeO(C═O)— |
| Z-2929 | c-Hex—CH2— | 4-I—Ph | Z-2930 | c-Hex—CH2— | 2-Br—PhCH2— | Z-2931 | c-Hex—CH2— | EtO(C═O)— |
| Z-2932 | c-Hex—CH2— | 2-Me—Ph | Z-2933 | c-Hex—CH2— | 3-Br—PhCH2— | Z-2934 | c-Hex—CH2— | PrO(C═O)— |
| Z-2935 | c-Hex—CH2— | 3-Me—Ph | Z-2936 | c-Hex—CH2— | 4-Br—PhCH2— | Z-2937 | F3C— | 2-Cl-4-F—PhCH2— |
| Z-2938 | c-Hex—CH2— | 4-Me—Ph | Z-2939 | c-Hex—CH2— | 2-I—PhCH2— | Z-2940 | F3C— | 2-Cl-5-F—PhCH2— |
| Z-2941 | c-Hex—CH2— | 2-MeO—Ph | Z-2942 | c-Hex—CH2— | 3-I—PhCH2— | Z-2943 | F3C— | 2-Cl-6-F—PhCH2— |
| Z-2944 | c-Hex—CH2— | 3-MeO—Ph | Z-2945 | c-Hex—CH2— | 4-I—PhCH2— | Z-2946 | F3C— | 2-Br-3-F—PhCH2— |
| Z-2947 | c-Hex—CH2— | 4-MeO—Ph | Z-2948 | c-Hex—CH2— | 2-Me—PhCH2— | Z-2949 | F3C— | 2-Br-4-F—PhCH2— |
| Z-2950 | c-Hex—CH2— | 2,3-di-F—Ph | Z-2951 | c-Hex—CH2— | 3-Me—PhCH2— | Z-2952 | F3C— | 2-Br-5-F—PhCH2— |
| Z-2953 | c-Hex—CH2— | 2,4-di-F—Ph | Z-2954 | c-Hex—CH2— | 4-Me—PhCH2— | Z-2955 | F3C— | 2-Br-6-F—PhCH2— |
| Z-2956 | c-Hex—CH2— | 2,5-di-F—Ph | Z-2957 | c-Hex—CH2— | 2-MeO—PhCH2— | Z-2958 | F3C— | 2-F-3-MeO—PhCH2— |
| Z-2959 | c-Hex—CH2— | 2,6-di-F—Ph | Z-2960 | c-Hex—CH2— | 3-MeO—PhCH2— | Z-2961 | F3C— | 2-F-4-MeO—PhCH2— |
| Z-2962 | c-Hex—CH2— | 2-Cl-3-F—Ph | Z-2963 | c-Hex—CH2— | 4-MeO—PhCH2— | Z-2964 | F3C— | 2-F-5-MeO—PhCH2— |
| Z-2965 | c-Hex—CH2— | i-PrO(C═O)— | Z-2966 | c-Hex—CH2— | 2,3-di-F—PhCH2— | Z-2967 | F3C— | 2-F-6-MeO—PhCH2— |
| Z-2968 | c-Hex—CH2— | BuO(C═O)— | Z-2969 | c-Hex—CH2— | 2,4-di-F—PhCH2— | Z-2970 | F3C— | 2-Cl-3-MeO—PhCH2— |
| Z-2971 | c-Hex—CH2— | t-BuOC(═O)— | Z-2972 | F3C— | 2-Br-3-F—Ph | Z-2973 | F3C— | 2-Cl-4-MeO—PhCH2— |
| Z-2974 | F3C— | F3C— | Z-2975 | F3C— | 2-Br-4-F—Ph | Z-2976 | F3C— | 2-Cl-5-MeO—PhCH2— |
| Z-2977 | F3C— | F2CH— | Z-2978 | F3C— | 2-Br-5-F—Ph | Z-2979 | F3C— | 2-Cl-6-MeO—PhCH2— |
| Z-2980 | F3C— | F3CCH2— | Z-2981 | F3C— | 2-Br-6-F—Ph | Z-2982 | F3C— | 2-Br-3-MeO—PhCH2— |
| Z-2983 | F3C— | F2CHCH2— | Z-2984 | F3C— | 2-F-3-MeO—Ph | Z-2985 | F3C— | 2-Br-4-MeO—PhCH2— |
| Z-2986 | F3C— | F3CF2C— | Z-2987 | F3C— | 2-F-4-MeO—Ph | Z-2988 | F3C— | 2-Br-5-MeO—PhCH2— |
| Z-2989 | F3C— | F2CHF2C— | Z-2990 | F3C— | 2-F-5-MeO—Ph | Z-2991 | F3C— | 2-Br-6-MeO—PhCH2— |
| Z-2992 | F3C— | (F3C)2FC— | Z-2993 | F3C— | 2-F-6-MeO—Ph | Z-2994 | F3C— | 2,3,4-tri-F—PhCH2— |
| Z-2995 | F3C— | F3CF2C(F3C)FC— | Z-2996 | F3C— | 2-Cl-3-MeO—Ph | Z-2997 | F3C— | 2,3,5-tri-F—PhCH2— |
| Z-2998 | F3C— | c-Pr | Z-2999 | F3C— | 2-Cl-4-MeO—Ph | Z-3000 | F3C— | 2,3,6-tri-F—PhCH2— |
| Z-3001 | F3C— | c-Bu | Z-3002 | F3C— | 2-Cl-5-MeO—Ph | Z-3003 | F3C— | 2-Br-3,4-di-F—PhCH2— |
| Z-3004 | F3C— | c-Pent | Z-3005 | F3C— | 2-Cl-6-MeO—Ph | Z-3006 | F3C— | 2-Br-3,5-di-F—PhCH2— |
| Z-3007 | F3C— | c-Hex | Z-3008 | F3C— | 2-Br-3-MeO—Ph | Z-3009 | F3C— | 2-Br-3,6-di-F—PhCH2— |
| Z-3010 | F3C— | H2C═CH— | Z-3011 | F3C— | 2-Br-4-MeO—Ph | Z-3012 | F3C— | 2-F-3,4-di-MeO—PhCH2— |
| Z-3013 | F3C— | H3CCH═CH— | Z-3014 | F3C— | 2-Br-5-MeO—Ph | Z-3015 | F3C— | 2-F-3,5-di-MeO—PhCH2— |
| Z-3016 | F3C— | H2C═CHCH2— | Z-3017 | F3C— | 2-Br-6-MeO—Ph | Z-3018 | F3C— | 2-F-3,6-di-MeO—PhCH2— |
| Z-3019 | F3C— | F2C═CH— | Z-3020 | F3C— | 2,3,4-tri-F—Ph | Z-3021 | F3C— | 2-Cl-3,4-di-MeO—PhCH2— |
| Z-3022 | F3C— | F2C═CHCH2— | Z-3023 | F3C— | 2,3,5-tri-F—Ph | Z-3024 | F3C— | 2-Cl-3,5-di-MeO—PhCH2— |
| Z-3025 | F3C— | HC≡C— | Z-3026 | F3C— | 2,3,6-tri-F—Ph | Z-3027 | F3C— | 2-Cl-3,6-di-MeO—PhCH2— |
| Z-3028 | F3C— | HC≡CCH2— | Z-3029 | F3C— | 2-Br-3,4-di-F—Ph | Z-3030 | F3C— | 2-Br-3,4-di-MeO—PhCH2— |
| Z-3031 | F3C— | HC≡CCH2CH2— | Z-3032 | F3C— | 2-Br-3,5-di-F—Ph | Z-3033 | F3C— | 2-Br-3,5-di-MeO—PhCH2— |
| Z-3034 | F3C— | H3CC≡CCH2— | Z-3035 | F3C— | 2-Br-3,6-di-F—Ph | Z-3036 | F3C— | 2-Br-3,6-di-MeO—PhCH2— |
| Z-3037 | F3C— | FC≡C— | Z-3038 | F3C— | 2-F-3,4-di-MeO—Ph | Z-3039 | F3C— | MeS— |
| Z-3040 | F3C— | FC≡CCF2— | Z-3041 | F3C— | 2-F-3,5-di-MeO—Ph | Z-3042 | F3C— | MeS(═O)— |
| Z-3043 | F3C— | FC≡CCF2CF2— | Z-3044 | F3C— | 2-F-3,6-di-MeO—Ph | Z-3045 | F3C— | MeS(═O)2— |
| Z-3046 | F3C— | F3CC≡CCF2— | Z-3047 | F3C— | 2-Cl-3,4-di-MeO—Ph | Z-3048 | F3C— | EtS— |
| Z-3049 | F3C— | Ph | Z-3050 | F3C— | 2-Cl-3,5-di-MeO—Ph | Z-3051 | F3C— | EtS(═O)— |
| Z-3052 | F3C— | 2-F—Ph | Z-3053 | F3C— | 2-Cl-3,6-di-MeO—Ph | Z-3054 | F3C— | ELS(═O)2— |

TABLE 3-continued

| Z | R3 | R4 | Z | R3 | R4 | Z | R3 | R4 |
|---|---|---|---|---|---|---|---|---|
| Z-3055 | F3C— | 3-F—Ph | Z-3056 | F3C— | 2-Br-3,4-di-MeO—Ph | Z-3057 | F3C— | PrS— |
| Z-3058 | F3C— | 4-F—Ph | Z-3059 | F3C— | 2-Br-3,5-di-MeO—Ph | Z-3060 | F3C— | PrS(═O)— |
| Z-3061 | F3C— | 2-Cl—Ph | Z-3062 | F3C— | 2-Br-3,6-di-MeO—Ph | Z-3063 | F3C— | PrS(═O)2— |
| Z-3064 | F3C— | 3-Cl—Ph | Z-3065 | F3C— | PFCH2— | Z-3066 | F3C— | Au |
| Z-3067 | F3C— | 4-Cl—Ph | Z-3068 | F3C— | 2-F—PhCH2— | Z-3069 | F3C— | OHC— |
| Z-3070 | F3C— | 2-Br—Ph | Z-3071 | F3C— | 3-F—PhCH2— | Z-3072 | F3C— | Et(C═O)— |
| Z-3073 | F3C— | 3-Br—Ph | Z-3074 | F3C— | 4-F—PhCH2— | Z-3075 | F3C— | Pr(C═O)— |
| Z-3076 | F3C— | 4-Br—Ph | Z-3077 | F3C— | 2-Cl—PhCH2— | Z-3078 | F3C— | i-Pr(C═O)— |
| Z-3079 | F3C— | 2-I—Ph | Z-3080 | F3C— | 3-Cl—PhCH2— | Z-3081 | F3C— | Bu(C═O)— |
| Z-3082 | F3C— | 3-I—Ph | Z-3083 | F3C— | 4-Cl—PhCH2— | Z-3084 | F3C— | MeO(C═O)— |
| Z-3085 | F3C— | 4-I—Ph | Z-3086 | F3C— | 2-Br—PhCH2— | Z-3087 | F3C— | EtO(C═O)— |
| Z-3088 | F3C— | 2-Me—Ph | Z-3089 | F3C— | 3-Br—PhCH2— | Z-3090 | F3C— | PrO(C═O)— |
| Z-3091 | F3C— | 3-Me—Ph | Z-3092 | F3C— | 4-Br—PhCH2— | Z-3093 | F3C— | i-PrO(C═O)— |
| Z-3094 | F3C— | 4-Me—Ph | Z-3095 | F3C— | 2-I—PhCH2— | Z-3096 | F3C— | BuO(C═O)— |
| Z-3097 | F3C— | 2-MeO—Ph | Z-3098 | F3C— | 3-I—PhCH2— | Z-3099 | F3C— | t-BuOC(═O)— |
| Z-3100 | F3C— | 3-MeO—Ph | Z-3101 | F3C— | 4-I—PhCH2— | Z-3102 | F2CH— | 2-Br-4-F—PhCH2— |
| Z-3103 | F3C— | 4-MeO—Ph | Z-3104 | F3C— | 2-Me—PhCH2— | Z-3105 | F2CH— | 2-Br-5-F—PhCH2— |
| Z-3106 | F3C— | 2,3-di-F—Ph | Z-3107 | F3C— | 3-Me—PhCH2— | Z-3108 | F2CH— | 2-Br-6-F—PhCH2— |
| Z-3109 | F3C— | 2,4-di-F—Ph | Z-3110 | F3C— | 4-Me—PhCH2— | Z-3111 | F2CH— | 2-F-3-MeO—PhCH2— |
| Z-3112 | F3C— | 2,5-di-F—Ph | Z-3113 | F3C— | 2-MeO—PhCH2— | Z-3114 | F2CH— | 2-F-4-MeO—PhCH2— |
| Z-3115 | F3C— | 2,6-di-F—Ph | Z-3116 | F3C— | 3-MeO—PhCH2— | Z-3117 | F2CH— | 2-F-5-MeO—PhCH2— |
| Z-3118 | F3C— | 2-Cl-3-F—Ph | Z-3119 | F3C— | 4-MeO—PhCH2— | Z-3120 | F2CH— | 2-F-6-MeO—PhCH2— |
| Z-3121 | F3C— | 2-Cl-4-F—Ph | Z-3122 | F3C— | 2,3-di-F—PhCH2— | Z-3123 | F2CH— | 2-Cl-3-MeO—PhCH2— |
| Z-3124 | F3C— | 2-Cl-5-F—Ph | Z-3125 | F3C— | 2,4-di-F—PhCH2— | Z-3126 | F2CH— | 2-Cl-4-MeO—PhCH2— |
| Z-3127 | F3C— | 2-Cl-6-F—Ph | Z-3128 | F3C— | 2,5-di-F—PhCH2— | Z-3129 | F2CH— | 2-Cl-5-MeO—PhCH2— |
| Z-3130 | F2CH— | F2CH— | Z-3131 | F3C— | 2,6-di-F—PhCH2— | Z-3132 | F2CH— | 2-Cl-6-MeO—PhCH2— |
| Z-3133 | F2CH— | F3CCH2— | Z-3134 | F3C— | 2-Cl-3-F—PhCH2— | Z-3135 | F2CH— | 2-Br-3-MeO—PhCH2— |
| Z-3136 | F2CH— | F2CHCH2— | Z-3137 | F2CH— | 2-F-3-MeO—Ph | Z-3138 | F2CH— | 2-Br-4-MeO—PhCH2— |
| Z-3139 | F2CH— | F3CF2C— | Z-3140 | F2CH— | 2-F-4-MeO—Ph | Z-3141 | F2CH— | 2-Br-5-MeO—PhCH2— |
| Z-3142 | F2CH— | F2CHF2C— | Z-3143 | F2CH— | 2-F-5-MeO—Ph | Z-3144 | F2CH— | 2-Br-6-MeO—PhCH2— |
| Z-3145 | F2CH— | (F3C)2FC— | Z-3146 | F2CH— | 2-F-6-MeO—Ph | Z-3147 | F2CH— | 2,3,4-tri-F—PhCH2— |
| Z-3148 | F2CH— | F3CF2C(F3C)FC— | Z-3149 | F2CH— | 2-Cl-3-MeO—Ph | Z-3150 | F2CH— | 2,3,5-tri-F—PhCH2— |
| Z-3151 | F2CH— | c-Pr | Z-3152 | F2CH— | 2-Cl-4-MeO—Ph | Z-3153 | F2CH— | 2,3,6-tri-F—PhCH2— |
| Z-3154 | F2CH— | c-Bu | Z-3155 | F2CH— | 2-Cl-5-MeO—Ph | Z-3156 | F2CH— | 2-Br-3,4-di-F—PhCH2— |
| Z-3157 | F2CH— | c-Pent | Z-3158 | F2CH— | 2-Cl-6-MeO—Ph | Z-3159 | F2CH— | 2-Br-3,5-di-F—PhCH2— |
| Z-3160 | F2CH— | c-Hex | Z-3161 | F2CH— | 2-Br-3-MeO—Ph | Z-3162 | F2CH— | 2-Br-3,6-di-F—PhCH2— |
| Z-3163 | F2CH— | H2C═CH— | Z-3164 | F2CH— | 2-Br-4-MeO—Ph | Z-3165 | F2CH— | 2-F-3,4-di-MeO—PhCH2— |
| Z-3166 | F2CH— | H3CCH═CH— | Z-3167 | F2CH— | 2-Br-5-MeO—Ph | Z-3168 | F2CH— | 2-F-3,5-di-MeO—PhCH2— |
| Z-3169 | F2CH— | H2C═CHCH2— | Z-3170 | F2CH— | 2-Br-6-MeO—Ph | Z-3171 | F2CH— | 2-F-3,6-di-MeO—PhCH2— |
| Z-3172 | F2CH— | F2C═CH— | Z-3173 | F2CH— | 2,3,4-tri-F—Ph | Z-3174 | F2CH— | 2-Cl-3,4-di-MeO—PhCH2— |
| Z-3175 | F2CH— | F2C═CHCH2— | Z-3176 | F2CH— | 2,3,5-tri-F—Ph | Z-3177 | F2CH— | 2-Cl-3,5-di-MeO—PhCH2— |
| Z-3178 | F2CH— | HC≡C— | Z-3179 | F2CH— | 2,3,6-tri-F—Ph | Z-3180 | F2CH— | 2-Cl-3,6-di-MeO—PhCH2— |
| Z-3181 | F2CH— | HC≡CCH2— | Z-3182 | F2CH— | 2-Br-3,4-di-F—Ph | Z-3183 | F2CH— | 2-Br-3,4-di-MeO—PhCH2— |
| Z-3184 | F2CH— | HC≡CCH2CH2— | Z-3185 | F2CH— | 2-Br-3,5-di-F—Ph | Z-3186 | F2CH— | 2-Br-3,5-di-MeO—PhCH2— |
| Z-3187 | F2CH— | H3CC≡CCH2— | Z-3188 | F2CH— | 2-Br-3,6-di-F—Ph | Z-3189 | F2CH— | 2-Br-3,6-di-MeO—PhCH2— |
| Z-3190 | F2CH— | FC≡C— | Z-3191 | F2CH— | 2-F-3,4-di-MeO—Ph | Z-3192 | F2CH— | MeS— |
| Z-3193 | F2CH— | FC≡CCF2— | Z-3194 | F2CH— | 2-F-3,5-di-MeO—Ph | Z-3195 | F2CH— | MeS(═O)— |
| Z-3196 | F2CH— | FC≡CCF2CF2— | Z-3197 | F2CH— | 2-F-3,6-di-MeO—Ph | Z-3198 | F2CH— | MeS(═O)2— |
| Z-3199 | F2CH— | F3CC≡CCF2— | Z-3200 | F2CH— | 2-Cl-3,4-di-MeO—Ph | Z-3201 | F2CH— | EtS— |
| Z-3202 | F2CH— | Ph | Z-3203 | F2CH— | 2-Cl-3,5-di-MeO—Ph | Z-3204 | F2CH— | EtS(═O)— |
| Z-3205 | F2CH— | 2-F—Ph | Z-3206 | F2CH— | 2-Cl-3,6-di-MeO—Ph | Z-3207 | F2CH— | EtS(═O)2— |

TABLE 3-continued

| Z | R3 | R4 | Z | R3 | R4 | Z | R3 | R4 |
|---|---|---|---|---|---|---|---|---|
| Z-3208 | F2CH— | 3-F—Ph | Z-3209 | F2CH— | 2-Br-3,4-di-MeO—Ph | Z-3210 | F2CH— | PrS— |
| Z-3211 | F2CH— | 4-F—Ph | Z-3212 | F2CH— | 2-Br-3,5-di-MeO—Ph | Z-3213 | F2CH— | PrS(═O)— |
| Z-3214 | F2CH— | 2-Cl—Ph | Z-3215 | F2CH— | 2-Br-3,6-di-MeO—Ph | Z-3216 | F2CH— | PrS(═O)2— |
| Z-3217 | F2CH— | 3-Cl—Ph | Z-3218 | F2CH— | PhCH2— | Z-3219 | F2CH— | Au |
| Z-3220 | F2CH— | 4-Cl—Ph | Z-3221 | F2CH— | 2-F—PhCH2— | Z-3222 | F2CH— | OHC— |
| Z-3223 | F2CH— | 2-Br—Ph | Z-3224 | F2CH— | 3-F—PhCH2— | Z-3225 | F2CH— | Et(C═O)— |
| Z-3226 | F2CH— | 3-Br—Ph | Z-3227 | F2CH— | 4-F—PhCH2— | Z-3228 | F2CH— | Pr(C═O)— |
| Z-3229 | F2CH— | 4-Br—Ph | Z-3230 | F2CH— | 2-Cl—PhCH2— | Z-3231 | F2CH— | i-Pr(C═O)— |
| Z-3232 | F2CH— | 2-I—Ph | Z-3233 | F2CH— | 3-Cl—PhCH2— | Z-3234 | F2CH— | Bu(C═O)— |
| Z-3235 | F2CH— | 3-I—Ph | Z-3236 | F2CH— | 4-Cl—PhCH2— | Z-3237 | F2CH— | MeO(C═O)— |
| Z-3238 | F2CH— | 4-I—Ph | Z-3239 | F2CH— | 2-Br—PhCH2— | Z-3240 | F2CH— | EtO(C═O)— |
| Z-3241 | F2CH— | 2-Me—Ph | Z-3242 | F2CH— | 3-Br—PhCH2— | Z-3243 | F2CH— | PrO(C═O)— |
| Z-3244 | F2CH— | 3-Me—Ph | Z-3245 | F2CH— | 4-Br—PhCH2— | Z-3246 | F2CH— | i-PrO(C═O)— |
| Z-3247 | F2CH— | 4-Me—Ph | Z-3248 | F2CH— | 2-I—PhCH2— | Z-3249 | F2CH— | BuO(C═O)— |
| Z-3250 | F2CH— | 2-MeO—Ph | Z-3251 | F2CH— | 3-I—PhCH2— | Z-3252 | F2CH— | r—BuOC(═O)— |
| Z-3253 | F2CH— | 3-MeO—Ph | Z-3254 | F2CH— | 4-I—PhCH2— | Z-3255 | F3CCH2— | F3CCH2— |
| Z-3256 | F2CH— | 4-MeO—Ph | Z-3257 | F2CH— | 2-Me—PhCH2— | Z-3258 | F3CCH2— | F2CHCH2— |
| Z-3259 | F2CH— | 2,3-di-F—Ph | Z-3260 | F2CH— | 3-Me—PhCH2— | Z-3261 | F3CCH2— | F3CF2C— |
| Z-3262 | F2CH— | 2,4-di-F—Ph | Z-3263 | F2CH— | 4-Me—PhCH2— | Z-3264 | F3CCH2— | F2CHF2C— |
| Z-3265 | F2CH— | 2,5-di-F—Ph | Z-3266 | F2CH— | 2-MeO—PhCH2— | Z-3267 | F3CCH2— | 2-F-5-MeO—PhCH2— |
| Z-3268 | F2CH— | 2,6-di-F—Ph | Z-3269 | F2CH— | 3-MeO—PhCH2— | Z-3270 | F3CCH2— | 2-F-6-MeO—PhCH2— |
| Z-3271 | F2CH— | 2-Cl-3-F—Ph | Z-3272 | F2CH— | 4-MeO—PhCH2— | Z-3273 | F3CCH2— | 2-Cl-3-MeO—PhCH2— |
| Z-3274 | F2CH— | 2-Cl-4-F—Ph | Z-3275 | F2CH— | 2,3-di-F—PhCH2— | Z-3276 | F3CCH2— | 2-Cl-4-MeO—PhCH2— |
| Z-3277 | F2CH— | 2-Cl-5-F—Ph | Z-3278 | F2CH— | 2,1-di-F—PhCH2 | Z-3279 | F3CCH2— | 2-Cl-5-MeO—PhCH2— |
| Z-3280 | F2CH— | 2-Cl-6-F—Ph | Z-3281 | F2CH— | 2,5-di-F—PhCH2— | Z-3282 | F3CCH2— | 2-Cl-6-MeO—PhCH2— |
| Z-3283 | F2CH— | 2-Br-3-F—Ph | Z-3284 | F2CH— | 2,6-di-F—PhCH2— | Z-3285 | F3CCH2— | 2-Br-3-MeO—PhCH2— |
| Z-3286 | F2CH— | 2-Br-4-F—Ph | Z-3287 | F2CH— | 2-Cl-3-F—PhCH2— | Z-3288 | F3CCH2— | 2-Br-4-MeO—PhCH2— |
| Z-3289 | F2CH— | 2-Br-5-F—Ph | Z-3290 | F2CH— | 2-Cl-4-F—PhCH2— | Z-3291 | F3CCH2— | 2-Br-5-MeO—PhCH2— |
| Z-3292 | F2CH— | 2-Br-6-F—Ph | Z-3293 | F2CH— | 2-Cl-5-F—PhCH2— | Z-3294 | F3CCH2— | 2-Br-6-MeO—PhCH2— |
| Z-3295 | F3CCH2— | (F3C)2FC— | Z-3296 | F2CH— | 2-Cl-6-F—PhCH2— | Z-3297 | F3CCH2— | 2,3,4-tri-F—PhCH2— |
| Z-3298 | F3CCH2— | F3CF2C(F3C)FC— | Z-3299 | F2CH— | 2-Br-3-F—PhCH2— | Z-3300 | F3CCH2— | 2,3,5-tri-F—PhCH2— |
| Z-3301 | F3CCH2— | c-Pr | Z-3302 | F3CCH2— | 2-Cl-4-MeO—Ph | Z-3303 | F3CCH2— | 2,3,6-tri-F—PhCH2— |
| Z-3304 | F3CCH2— | c-Bu | Z-3305 | F3CCH2— | 2-Cl-5-MeO—Ph | Z-3306 | F3CCH2— | 2-Br-3,4-di-F—PhCH2— |
| Z-3307 | F3CCH2— | c-Pent | Z-3308 | F3CCH2— | 2-Cl-6-MeO—Ph | Z-3309 | F3CCH2— | 2-Br-3,5-di-F—PhCH2— |
| Z-3310 | F3CCH2— | c-Hex | Z-3311 | F3CCH2— | 2-Br-3-MeO—Ph | Z-3312 | F3CCH2— | 2-Br-3,6-di-F—PhCH2— |
| Z-3313 | F3CCH2— | H2C═CH— | Z-3314 | F3CCH2— | 2-Br-4-MeO—Ph | Z-3315 | F3CCH2— | 2-F-3,4-di-MeO—PhCH2— |
| Z-3316 | F3CCH2— | H3CCH═CH— | Z-3317 | F3CCH2— | 2-Br-5-MeO—Ph | Z-3318 | F3CCH2— | 2-F-3,5-di-MeO—PhCH2— |
| Z-3319 | F3CCH2— | H2C═CHCH2— | Z-3320 | F3CCH2— | 2-Br-6-MeO—Ph | Z-3321 | F3CCH2— | 2-F-3,6-di-MeO—PhCH2— |
| Z-3322 | F3CCH2— | F2C═CH— | Z-3323 | F3CCH2— | 2,3,4-tri-F—Ph | Z-3324 | F3CCH2— | 2-Cl-3,4-di-MeO—PhCH2— |
| Z-3325 | F3CCH2— | F2C═CHCH2— | Z-3326 | F3CCH2— | 2,3,5-tri-F—Ph | Z-3327 | F3CCH2— | 2-Cl-3,5-di-MeO—PhCH2— |
| Z-3328 | F3CCH2— | HC≡C— | Z-3329 | F3CCH2— | 2,3,6-tri-F—Ph | Z-3330 | F3CCH2— | 2-Cl-3,6-di-MeO—PhCH2— |
| Z-3331 | F3CCH2— | HC≡CCH2— | Z-3332 | F3CCH2— | 2-Br-3,4-di-F—Ph | Z-3333 | F3CCH2— | 2-Br-3,4-di-MeO—PhCH2— |
| Z-3334 | F3CCH2— | HC≡CCH2CH2— | Z-3335 | F3CCH2— | 2-Br-3,5-di-F—Ph | Z-3336 | F3CCH2— | 2-Br-3,5-di-MeO—PhCH2— |
| Z-3337 | F3CCH2— | H3CC≡CCH2— | Z-3338 | F3CCH2— | 2-Br-3,6-di-F—Ph | Z-3339 | F3CCH2— | 2-Br-3,6-di-MeO—PhCH2— |
| Z-3340 | F3CCH2— | FC≡C— | Z-3341 | F3CCH2— | 2-F-3,4-di-MeO—Ph | Z-3342 | F3CCH2— | MeS— |
| Z-3343 | F3CCH2— | FC≡CCF2— | Z-3344 | F3CCH2— | 2-F-3,5-di-MeO—Ph | Z-3345 | F3CCH2— | MeS(═O)— |
| Z-3346 | F3CCH2— | FC≡CCF2CF2— | Z-3347 | F3CCH2— | 2-F-3,6-di-MeO—Ph | Z-3348 | F3CCH2— | MeS(═O)2— |
| Z-3349 | F3CCH2— | F3CC≡CCF2— | Z-3350 | F3CCH2— | 2-Cl-3,4-di-MeO—Ph | Z-3351 | F3CCH2— | EtS— |
| Z-3352 | F3CCH2— | Ph | Z-3353 | F3CCH2— | 2-Cl-3,5-di-MeO—Ph | Z-3354 | F3CCH2— | EtS(═O)— |
| Z-3355 | F3CCH2— | 2-F—Ph | Z-3356 | F3CCH2— | 2-Cl-3,6-di-MeO—Ph | Z-3357 | F3CCH2— | EtS(═O)2— |
| Z-3358 | F3CCH2— | 3-F—Ph | Z-3359 | F3CCH2— | 2-Br-3,4-di-MeO—Ph | Z-3360 | F3CCH2— | PrS— |

TABLE 3-continued

| Z | R3 | R4 | Z | R3 | R4 | Z | R3 | R4 |
|---|---|---|---|---|---|---|---|---|
| Z-3361 | F3CCH2— | 4-F—Ph | Z-3362 | F3CCH2— | 2-Br-35-di-MeO—Ph | Z-3363 | F3CCH2— | PrS(═O)— |
| Z-3364 | F3CCH2— | 2-Cl—Ph | Z-3365 | F3CCH2— | 2-Br-3,6-di-MeO—Ph | Z-3366 | F3CCH2— | PrS(═O)2— |
| Z-3367 | F3CCH2— | 3-Cl—Ph | Z-3368 | F3CCH2— | PhCH2— | Z-3369 | F3CCH2— | Ac |
| Z-3370 | F3CCH2— | 4-Cl—Ph | Z-3371 | F3CCH2— | 2-F—PhCH2— | Z-3372 | F3CCH2— | NHC— |
| Z-3373 | F3CCH2— | 2-Br—Ph | Z-3374 | F3CCH2— | 3-F—PhCH2— | Z-3375 | F3CCH2— | Et(C═O)— |
| Z-3376 | F3CCH2— | 3-Br—Ph | Z-3377 | F3CCH2— | 4-F—PhCH2— | Z-3378 | F3CCH2— | Pr(C═O)— |
| Z-3379 | F3CCH2— | 4-Br—Ph | Z-3380 | F3CCH2— | 2-Cl—PhCH2— | Z-3381 | F3CCH2— | i-Pr(C═O)— |
| Z-3382 | F3CCH2— | 2-I—Ph | Z-3383 | F3CCH2— | 3-Cl—PhCH2— | Z-3384 | F3CCH2— | Bu(C═O)— |
| Z-3385 | F3CCH2— | 3-I—Ph | Z-3386 | F3CCH2— | 4-Cl—PhCH2— | Z-3387 | F3CCH2— | MeO(C═O)— |
| Z-3388 | F3CCH2— | 4-I—Ph | Z-3389 | F3CCH2— | 2-Br—PhCH2— | Z-3390 | F3CCH2— | EtO(C═O)— |
| Z-3391 | F3CCH2— | 2-Me—Ph | Z-3392 | F3CCH2— | 3-Br—PhCH2— | Z-3393 | F3CCH2— | PrO(C═O)— |
| Z-3394 | F3CCH2— | 3-Me—Ph | Z-3395 | F3CCH2— | 4-Br—PhCH2— | Z-3396 | F3CCH2— | i-PrO(C═O)— |
| Z-3397 | F3CCH2— | 4-Me—Ph | Z-3398 | F3CCH2— | 2-I—PhCH2— | Z-3399 | F3CCH2— | BuO(C═O)— |
| Z-3400 | F3CCH2— | 2-MeO—Ph | Z-3401 | F3CCH2— | 3-I—PhCH2— | Z-3402 | F3CCH2— | t-BuOC(═O)— |
| Z-3403 | F3CCH2— | 3-MeO—Ph | Z-3404 | F3CCH2— | 4-I—PhCH2— | Z-3405 | F2CHCH2— | F2CHCH2— |
| Z-3406 | F3CCH2— | 4-MeO—Ph | Z-3407 | F3CCH2— | 2-Me—PhCH2— | Z-3408 | F2CHCH2— | F3CF2C— |
| Z-3409 | F3CCH2— | 2,3-di-F—Ph | Z-3410 | F3CCH2— | 3-Me—PhCH2— | Z-3411 | F2CHCH2— | F2CHF2C— |
| Z-3412 | F3CCH2— | 2,4-di-F—Ph | Z-3413 | F3CCH2— | 4-Me—PhCH2— | Z-3414 | F2CHCH2— | (F3C)2FC— |
| Z-3415 | F3CCH2— | 2,5-di-F—Ph | Z-3416 | F3CCH2— | 2-MeO—PhCH2— | Z-3417 | F2CHCH2— | F3CF2C(F3C)FC— |
| Z-3418 | F3CCH2— | 2,6-di-F—Ph | Z-3419 | F3CCH2— | 3-MeO—PhCH2— | Z-3420 | F2CHCH2— | c-Pr |
| Z-3421 | F3CCH2— | 2-Cl-3-F—Ph | Z-3422 | F3CCH2— | 4-MeO—PhCH2— | Z-3423 | F2CHCH2— | c-Bu |
| Z-3424 | F3CCH2— | 2-Cl-4-F—Ph | Z-3425 | F3CCH2— | 2,3-di-F—PhCH2— | Z-3426 | F2CHCH2— | c-Pent |
| Z-3427 | F3CCH2— | 2-Cl-5-F—Ph | Z-3428 | F3CCH2— | 2,4-di-F—PhCH2— | Z-3429 | F2CHCH2— | c-Hex |
| Z-3430 | F3CCH2— | 2-Cl-6-F—Ph | Z-3431 | F3CCH2— | 2,5-di-F—PhCH2— | Z-3432 | F2CHCH2— | 2-Br-3-MeO—PhCH2— |
| Z-3433 | F3CCH2— | 2-Br-3-F—Ph | Z-3434 | F3CCH2— | 2,6-di-F—PhCH2— | Z-3435 | F2CHCH2— | 2-Br-4-MeO—PhCH2— |
| Z-3436 | F3CCH2— | 2-Br-4-F—Ph | Z-3437 | F3CCH2— | 2-Cl-3-F—PhCH2— | Z-3438 | F2CHCH2— | 2-Br-5-MeO—PhCH2— |
| Z-3439 | F3CCH2— | 2-Br-5-F—Ph | Z-3440 | F3CCH2— | 2-Cl-4-F—PhCH2— | Z-3441 | F2CHCH2— | 2-Br-6-MeO—PhCH2— |
| Z-3442 | F3CCH2— | 2-Br-6-F—Ph | Z-3443 | F3CCH2— | 2-Cl-5-F—PhCH2— | Z-3444 | F2CHCH2— | 2,3,4-tri-F—PhCH2— |
| Z-3445 | F3CCH2— | 2-F-3-MeO—Ph | Z-3446 | F3CCH2— | 2-Cl-6-F—PhCH2— | Z-3447 | F2CHCH2— | 2,3,5-tri-F—PhCH2— |
| Z-3448 | F3CCH2— | 2-F-4-MeO—Ph | Z-3449 | F3CCH2— | 2-Br-3-F—PhCH2— | Z-3450 | F2CHCH2— | 2,3,6-tri-F—PhCH2— |
| Z-3451 | F3CCH2— | 2-F-5-MeO—Ph | Z-3452 | F3CCH2— | 2-Br-4-F—PhCH2— | Z-3453 | F2CHCH2— | 2-Br-3,4-di-F—PhCH2— |
| Z-3454 | F3CCH2— | 2-F-6-MeO—Ph | Z-3455 | F3CCH2— | 2-Br-5-F—PhCH2— | Z-3456 | F2CHCH2— | 2-Br-3,5-di-F—PhCH2— |
| Z-3457 | F3CCH2— | 2-Cl-3-MeO—Ph | Z-3458 | F3CCH2— | 2-Br-6-F—PhCH2— | Z-3459 | F2CHCH2— | 2-Br-3,6-di-F—PhCH2 |
| Z-3460 | F2CHCH2— | H2C═CH— | Z-3461 | F3CCH2— | 2-F-3-MeO—PhCH2— | Z-3462 | F2CHCH2— | 2-F-3,4-di-MeO—PhCH2— |
| Z-3463 | F2CHCH2— | H3CCH═CH— | Z-3464 | F3CCH2— | 2-F-4-MeO—PhCH2— | Z-3465 | F2CHCH2— | 2-F-3,5-di-MeO—PhCH2— |
| Z-3466 | F2CHCH2— | H2C═CHCH2— | Z-3467 | F2CHCH2— | 2-Br-6-MeO—Ph | Z-3468 | F2CHCH2— | 2-F-3,6-di-MeO—PhCH2— |
| Z-3469 | F2CHCH2— | F2C═CH— | Z-3470 | F2CHCH2— | 2,3,4-tri-F—Ph | Z-3471 | F2CHCH2— | 2-Cl-3,4-di-MeO—PhCH2— |
| Z-3472 | F2CHCH2— | F2C═CHCH2— | Z-3473 | F2CHCH2— | 2,3,5-tri-F—Ph | Z-3474 | F2CHCH2— | 2-Cl-3,5-di-MeO—PhCH2— |
| Z-3475 | F2CHCH2— | HC≡C— | Z-3476 | F2CHCH2— | 2,3,6-tri-F—Ph | Z-3477 | F2CHCH2— | 2-Cl-3,6-di-MeO—PhCH2— |
| Z-3478 | F2CHCH2— | HC≡CCH2— | Z-3479 | F2CHCH2— | 2-Br-3,4-di-F—Ph | Z-3480 | F2CHCH2— | 2-Br-3,4-di-MeO—PhCH2— |
| Z-3481 | F2CHCH2— | HC≡CCH2CH2— | Z-3482 | F2CHCH2— | 2-Br-3,5-di-F—Ph | Z-3483 | F2CHCH2— | 2-Br-3,5-di-MeO—PhCH2— |
| Z-3484 | F2CHCH2— | H3CC≡CCH2— | Z-3485 | F2CHCH2— | 2-Br-3,6-di-F—Ph | Z-3486 | F2CHCH2— | 2-Br-3,6-di-MeO—PhCH2— |
| Z-3487 | F2CHCH2— | FC≡C— | Z-3488 | F2CHCH2— | 2-F-3,4-di-MeO—Ph | Z-3489 | F2CHCH2— | MeS— |
| Z-3490 | F2CHCH2— | FC≡CCF2— | Z-3491 | F2CHCH2— | 2-F-3,5-di-MeO—Ph | Z-3492 | F2CHCH2— | MeS(═O)— |
| Z-3493 | F2CHCH2— | FC≡CCF2CF2— | Z-3494 | F2CHCH2— | 2-F-3,6-di-MeO—Ph | Z-3495 | F2CHCH2— | MeS(═O)2— |
| Z-3496 | F2CHCH2— | F3CC≡CCF2— | Z-3497 | F2CHCH2— | 2-Cl-3,4-di-MeO—Ph | Z-3498 | F2CHCH2— | EtS— |
| Z-3499 | F2CHCH2— | Ph | Z-3500 | F2CHCH2— | 2-Cl-3,5-di-MeO—Ph | Z-3501 | F2CHCH2— | EtS(═O)— |
| Z-3502 | F2CHCH2— | 2-F—Ph | Z-3503 | F2CHCH2— | 2-Cl-3,6-di-MeO—Ph | Z-3504 | F2CHCH2— | EtS(═O)2— |
| Z-3505 | F2CHCH2— | 3-F—Ph | Z-3506 | F2CHCH2— | 2-Br-3,4-di-MeO—Ph | Z-3507 | F2CHCH2— | PrS— |
| Z-3508 | F2CHCH2— | 4-F—Ph | Z-3509 | F2CHCH2— | 2-Br-3,5-di-MeO—Ph | Z-3510 | F2CHCH2— | PrS(═O)— |
| Z-3511 | F2CHCH2— | 2-Cl—Ph | Z-3512 | F2CHCH2— | 2-Br-3,6-di-MeO—Ph | Z-3513 | F2CHCH2— | PrS(═O)2— |

TABLE 3-continued

| Z | R3 | R4 | Z | R3 | R4 | Z | R3 | R4 |
|---|---|---|---|---|---|---|---|---|
| Z-3514 | F2CHCH2— | 3-Cl—Ph | Z-3515 | F2CHCH2— | PhCH2— | Z-3516 | F2CHCH2— | Au |
| Z-3517 | F2CHCH2— | 4-Cl—Ph | Z-3518 | F2CHCH2— | 2-F—PhCH2— | Z-3519 | F2CHCH2— | OHC— |
| Z-3520 | F2CHCH2— | 2-Br—Ph | Z-3521 | F2CHCH2— | 3-F—PhCH2— | Z-3522 | F2CHCH2— | Et(C═O)— |
| Z-3523 | F2CHCH2— | 3-Br—Ph | Z-3524 | F2CHCH2— | 4-F—PhCH2— | Z-3525 | F2CHCH2— | Pr(C═O)— |
| Z-3526 | F2CHCH2— | 4-Br—Ph | Z-3527 | F2CHCH2— | 2-Cl—PhCH2— | Z-3528 | F2CHCH2— | i-Pr(C═O)— |
| Z-3529 | F2CHCH2— | 2-I—Ph | Z-3530 | F2CHCH2— | 3-Cl—PhCH2— | Z-3531 | F2CHCH2— | Bu(C═O)— |
| Z-3532 | F2CHCH2— | 3-I—Ph | Z-3533 | F2CHCH2— | 4-Cl—PhCH2— | Z-3534 | F2CHCH2— | MeO(C═O)— |
| Z-3535 | F2CHCH2— | 4-I—Ph | Z-3536 | F2CHCH2— | 2-Br—PhCH2— | Z-3537 | F2CHCH2— | EtO(C═O)— |
| Z-3538 | F2CHCH2— | 2-Me—Ph | Z-3539 | F2CHCH2— | 3-Br—PhCH2— | Z-3540 | F2CHCH2— | PrO(C═O)— |
| Z-3541 | F2CHCH2— | 3-Me—Ph | Z-3542 | F2CHCH2— | 4-Br—PhCH2— | Z-3543 | F2CHCH2— | i-PrO(C═O)— |
| Z-3544 | F2CHCH2— | 4-Me—Ph | Z-3545 | F2CHCH2— | 2-I—PhCH2— | Z-3546 | F2CHCH2— | BuO(C═O)— |
| Z-3547 | F2CHCH2— | 2-MeO—Ph | Z-3548 | F2CHCH2— | 3-I—PhCH2— | Z-3549 | F2CHCH2— | t-BuOC(═O)— |
| Z-3550 | F2CHCH2— | 3-MeO—Ph | Z-3551 | F2CHCH2— | 4-I—PhCH2— | Z-3552 | F3CF2C— | F3CF2C— |
| Z-3553 | F2CHCH2— | 4-MeO—Ph | Z-3554 | F2CHCH2— | 2-Me—PhCH2— | Z-3555 | F3CF2C— | F2CHF2C— |
| Z-3556 | F2CHCH2— | 2,3-di-F—Ph | Z-3557 | F2CHCH2— | 3-Me—PhCH2— | Z-3558 | F3CF2C— | (F3C)2FC— |
| Z-3559 | F2CHCH2— | 2,4-di-F—Ph | Z-3560 | F2CHCH2— | 4-Me—PhCH2— | Z-3561 | F3CF2C— | F3CF2C(F3C)FC— |
| Z-3562 | F2CHCH2— | 2,5-di-F—Ph | Z-3563 | F2CHCH2— | 2-MeO—PhCH2— | Z-3564 | F3CF2C— | c-Pr |
| Z-3565 | F2CHCH2— | 2,6-di-F—Ph | Z-3566 | F2CHCH2— | 3-MeO—PhCH2— | Z-3567 | F3CF2C— | c-Bu |
| Z-3568 | F2CHCH2— | 2-Cl-3-F—Ph | Z-3569 | F2CHCH2— | 4-MeO—PhCH2— | Z-3570 | F3CF2C— | c-Pent |
| Z-3571 | F2CHCH2— | 2-Cl-4-F—Ph | Z-3572 | F2CHCH2— | 2,3-di-F—PhCH2— | Z-3573 | F3CF2C— | c-Hex |
| Z-3574 | F2CHCH2— | 2-Cl-5-F—Ph | Z-3575 | F2CHCH2— | 2,4-di-F—PhCH2— | Z-3576 | F3CF2C— | H2C═CH— |
| Z-3577 | F2CHCH2— | 2-Cl-6-F—Ph | Z-3578 | F2CHCH2— | 2,5-di-F—PhCH2— | Z-3579 | F3CF2C— | H3CCH═CH— |
| Z-3580 | F2CHCH2— | 2-Br-3-F—Ph | Z-3581 | F2CHCH2— | 2,6-di-F—PhCH2— | Z-3582 | F3CF2C— | H2C═CHCH2— |
| Z-3583 | F2CHCH2— | 2-Br-4-F—Ph | Z-3584 | F2CHCH2— | 2-Cl-3-F—PhCH2— | Z-3585 | F3CF2C— | F2C═CH— |
| Z-3586 | F2CHCH2— | 2-Br-5-F—Ph | Z-3587 | F2CHCH2— | 2-Cl-4-F—PhCH2— | Z-3588 | F3CF2C— | F2C═CHCH2— |
| Z-3589 | F2CHCH2— | 2-Br-6-F—Ph | Z-3590 | F2CHCH2— | 2-Cl-5-F—PhCH2— | Z-3591 | F3CF2C— | HC≡C— |
| Z-3592 | F2CHCH2— | 2-F-3-MeO—Ph | Z-3593 | F2CHCH2— | 2-Cl-6-F—PhCH2— | Z-3594 | F3CF2C— | HC≡CCH2— |
| Z-3595 | F2CHCH2— | 2-F-4-MeO—Ph | Z-3596 | F2CHCH2— | 2-Br-3-F—PhCH2— | Z-3597 | F3CF2C— | 2-Br-3,4-di-F—PhCH2— |
| Z-3598 | F2CHCH2— | 2-F-5-MeO—Ph | Z-3599 | F2CHCH2— | 2-Br-4-F—PhCH2— | Z-3600 | F3CF2C— | 2-Br-3,5-di-F—PhCH2— |
| Z-3601 | F2CHCH2— | 2-F-6-MeO—Ph | Z-3602 | F2CHCH2— | 2-Br-5-F—PhCH2— | Z-3603 | F3CF2C— | 2-Br-3,6-di-F—PhCH2— |
| Z-3604 | F2CHCH2— | 2-Cl-3-MeO—Ph | Z-3605 | F2CHCH2— | 2-Br-6-F—PhCH2— | Z-3606 | F3CF2C— | 2-F-3,4-di-MeO—PhCH2— |
| Z-3607 | F2CHCH2— | 2-Cl-4-MeO—Ph | Z-3608 | F2CHCH2— | 2-F-3-MeO—PhCH2— | Z-3609 | F3CF2C— | 2-F-3,5-di-MeO—PhCH2— |
| Z-3610 | F2CHCH2— | 2-Cl-5-MeO—Ph | Z-3611 | F2CHCH2— | 2-F-4-MeO—PhCH2— | Z-3612 | F3CF2C— | 2-F-3,6-di-MeO—PhCH2— |
| Z-3613 | F2CHCH2— | 2-Cl-6-MeO—Ph | Z-3614 | F2CHCH2— | 2-F-5-MeO—PhCH2— | Z-3615 | F3CF2C— | 2-Cl-3,4-di-MeO—PhCH2— |
| Z-3616 | F2CHCH2— | 2-Br-3-MeO—Ph | Z-3617 | F2CHCH2— | 2-F-6-MeO—PhCH2— | Z-3618 | F3CF2C— | 2-Cl-3,5-di-MeO—PhCH2— |
| Z-3619 | F2CHCH2— | 2-Br-4-MeO—Ph | Z-3620 | F2CHCH2— | 2-Cl-3-MeO—PhCH2— | Z-3621 | F3CF2C— | 2-Cl-3,6-di-MeO—PhCH2— |
| Z-3622 | F2CHCH2— | 2-Br-5-MeO—Ph | Z-3623 | F2CHCH2— | 2-Cl-4-MeO—PhCH2— | Z-3624 | F3CF2C— | 2-Br-3,4-di-MeO—PhCH2— |
| Z-3625 | F3CF2C— | HC═CCH2CH2— | Z-3626 | F2CHCH2— | 2-Cl-5-MeO—PhCH2— | Z-3627 | F3CF2C— | 2-Br-3,5-di-MeO—PhCH2— |
| Z-3628 | F3CF2C— | H3CC≡CCH2— | Z-3629 | F2CHCH2— | 2-Cl-6-MeO—PhCH2— | Z-3630 | F3CF2C— | 2-Br-3,6-di-MeO—PhCH2— |
| Z-3631 | F3CF2C— | FC≡C— | Z-3632 | F3CF2C— | 2-F-3,4-di-MeO—Ph | Z-3633 | F3CF2C— | MeS— |
| Z-3634 | F3CF2C— | FC≡CCF2— | Z-3635 | F3CF2C— | 2-F-3,5-di-MeO—Ph | Z-3636 | F3CF2C— | MeS(═O)— |
| Z-3637 | F3CF2C— | FC═CCF2CF2— | Z-3638 | F3CF2C— | 2-F-3,6-di-MeO—Ph | Z-3639 | F3CF2C— | MeS(═O)2— |
| Z-3640 | F3CF2C— | F3CC≡CCF2— | Z-3641 | F3CF2C— | 2-Cl-3,4-di-MeO—Ph | Z-3642 | F3CF2C— | EtS— |
| Z-3643 | F3CF2C— | Ph | Z-3644 | F3CF2C— | 2-Cl-3,5-di-MeO—Ph | Z-3645 | F3CF2C— | EtS(═O)— |
| Z-3646 | F3CF2C— | 2-F—Ph | Z-3647 | F3CF2C— | 2-Cl-3,6-di-MeO—Ph | Z-3648 | F3CF2C— | EtS(═O)2— |
| Z-3649 | F3CF2C— | 3-F—Ph | Z-3650 | F3CF2C— | 2-Br-3,4-di-MeO—Ph | Z-3651 | F3CF2C— | PrS— |
| Z-3652 | F3CF2C— | 4-F—Ph | Z-3653 | F3CF2C— | 2-Br-3,5-di-MeO—Ph | Z-3654 | F3CF2C— | PrS(═O)— |
| Z-3655 | F3CF2C— | 2-Cl—Ph | Z-3656 | F3CF2C— | 2-Br-3,6-di-MeO—Ph | Z-3657 | F3CF2C— | PrS(═O)2— |
| Z-3658 | F3CF2C— | 3-Cl—Ph | Z-3659 | F3CF2C— | PhCH2— | Z-3660 | F3CF2C— | Ac |
| Z-3661 | F3CF2C— | 4-Cl—Ph | Z-3662 | F3CF2C— | 2-F—PhCH2— | Z-3663 | F3CF2C— | OHC— |
| Z-3664 | F3CF2C— | 2-Br—Ph | Z-3665 | F3CF2C— | 3-F—PhCH2— | Z-3666 | F3CF2C— | Et(C═O)— |

TABLE 3-continued

| Z | R3 | R4 | Z | R3 | R4 | Z | R3 | R4 |
|---|---|---|---|---|---|---|---|---|
| Z-3667 | F3CF2C— | 3-Br—Ph | Z-3668 | F3CF2C— | 4-F—PhCH2— | Z-3669 | F3CF2C— | Pr(C═O)— |
| Z-3670 | F3CF2C— | 4-Br—Ph | Z-3671 | F3CF2C— | 2-Cl—PhCH2— | Z-3672 | F3CF2C— | i-Pr(C═O)— |
| Z-3673 | F3CF2C— | 2-I—Ph | Z-3674 | F3CF2C— | 3-Cl—PhCH2— | Z-3675 | F3CF2C— | Bu(C═O)— |
| Z-3676 | F3CF2C— | 3-I—Ph | Z-3677 | F3CF2C— | 4-Cl—PhCH2— | Z-3678 | F3CF2C— | MeO(C═O)— |
| Z-3679 | F3CF2C— | 4-I—Ph | Z-3680 | F3CF2C— | 2-Br—PhCH2— | Z-3681 | F3CF2C— | EtO(C═O)— |
| Z-3682 | F3CF2C— | 2-Me—Ph | Z-3683 | F3CF2C— | 3-Br—PhCH2— | Z-3684 | F3CF2C— | PrO(C═O)— |
| Z-3685 | F3CF2C— | 3-Me—Ph | Z-3686 | F3CF2C— | 4-Br—PhCH2— | Z-3687 | F3CF2C— | i-PrO(C═O)— |
| Z-3688 | F3CF2C— | 4-Me—Ph | Z-3689 | F3CF2C— | 2-I—PhCH2— | Z-3690 | F3CF2C— | BuO(C═O)— |
| Z-3691 | F3CF2C— | 2-MeO—Ph | Z-3692 | F3CF2C— | 3-I—PhCH2— | Z-3693 | F3CF2C— | t-BuOC(═O)— |
| Z-3694 | F3CF2C— | 3-MeO—Ph | Z-3695 | F3CF2C— | 4-I—PhCH2— | Z-3696 | F2CHF2C— | F2CHF2C— |
| Z-3697 | F3CF2C— | 4-MeO—Ph | Z-3698 | F3CF2C— | 2-Me—PhCH2— | Z-3699 | F2CHF2C— | (F3C)2FC— |
| Z-3700 | F3CF2C— | 2,3-di-F—Ph | Z-3701 | F3CF2C— | 3-Me—PhCH2— | Z-3702 | F2CHF2C— | F3CF2C(F3C)FC— |
| Z-3703 | F3CF2C— | 2,4-di-F—Ph | Z-3704 | F3CF2C— | 4-Me—PhCH2— | Z-3705 | F2CHF2C— | c-Pr |
| Z-3706 | F3CF2C— | 2,5-di-F—Ph | Z-3707 | F3CF2C— | 2-MeO—PhCH2— | Z-3708 | F2CHF2C— | c-Bu |
| Z-3709 | F3CF2C— | 2,6-di-F—Ph | Z-3710 | F3CF2C— | 3-MeO—PhCH2— | Z-3711 | F2CHF2C— | c-Pent |
| Z-3712 | F3CF2C— | 2-Cl-3-F—Ph | Z-3713 | F3CF2C— | 4-MeO—PhCH2— | Z-3714 | F2CHF2C— | c-Hex |
| Z-3715 | F3CF2C— | 2-Cl-4-F—Ph | Z-3716 | F3CF2C— | 2,3-di-F—PhCH2— | Z-3717 | F2CHF2C— | H2C═CH— |
| Z-3718 | F3CF2C— | 2-Cl-5-F—Ph | Z-3719 | F3CF2C— | 2,4-di-F—PhCH2— | Z-3720 | F2CHF2C— | H3CCH═CH— |
| Z-3721 | F3CF2C— | 2-Cl-6-F—Ph | Z-3722 | F3CF2C— | 2,5-di-F—PhCH2— | Z-3723 | F2CHF2C— | H2C═CHCH2— |
| Z-3724 | F3CF2C— | 2-Br-3-F—Ph | Z-3725 | F3CF2C— | 2,6-di-F—PhCH2— | Z-3726 | F2CHF2C— | F2C═CH— |
| Z-3727 | F3CF2C— | 2-Br-4-F—Ph | Z-3728 | F3CF2C— | 2-Cl-3-F—PhCH2 | Z-3729 | F2CHF2C— | F2C═CHCH2— |
| Z-3730 | F3CF2C— | 2-Br-5-F—Ph | Z-3731 | F3CF2C— | 2-Cl-4-F—PhCH2— | Z-3732 | F2CHF2C— | HC≡C— |
| Z-3733 | F3CF2C— | 2-Br-6-F—Ph | Z-3734 | F3CF2C— | 2-Cl-5-F—PhCH2— | Z-3735 | F2CHF2C— | HC≡CCH2— |
| Z-3736 | F3CF2C— | 2-F-3-MeO—Ph | Z-3737 | F3CF2C— | 2-Cl-6-F—PhCH2— | Z-3738 | F2CHF2C— | HC≡CCH2CH2— |
| Z-3739 | F3CF2C— | 2-F-4-MeO—Ph | Z-3740 | F3CF2C— | 2-Br-3-F—PhCH2— | Z-3741 | F2CHF2C— | H3CC≡CCH2— |
| Z-3742 | F3CF2C— | 2-F-5-MeO—Ph | Z-3743 | F3CF2C— | 2-Br-4-F—PhCH2— | Z-3744 | F2CHF2C— | FC≡C— |
| Z-3745 | F3CF2C— | 2-F-6-MeO—Ph | Z-3746 | F3CF2C— | 2-Br-5-F—PhCH2— | Z-3747 | F2CHF2C— | FC≡CCF2— |
| Z-3748 | F3CF2C— | 2-Cl-3-MeO—Ph | Z-3749 | F3CF2C— | 2-Br-6-F—PhCH2— | Z-3750 | F2CHF2C— | FC≡CCF2CF2— |
| Z-3751 | F3CF2C— | 2-Cl-4-MeO—Ph | Z-3752 | F3CF2C— | 2-F-3-MeO—PhCH2— | Z-3753 | F2CHF2C— | F3CC≡CCF2— |
| Z-3754 | F3CF2C— | 2-Cl-5-MeO—Ph | Z-3755 | F3CF2C— | 2-F-4-MeO—PhCH2— | Z-3756 | F2CHF2C— | Ph |
| Z-3757 | F3CF2C— | 2-Cl-6-MeO—Ph | Z-3758 | F3CF2C— | 2-F-5-MeO—PhCH2— | Z-3759 | F2CHF2C— | 2-F—Ph |
| Z-3760 | F3CF2C— | 2-Br-3-MeO—Ph | Z-3761 | F3CF2C— | 2-F-6-MeO—PhCH2— | Z-3762 | F2CHF2C— | 2-Cl-3,6-di-MeO—PhCH2— |
| Z-3763 | F3CF2C— | 2-Br-4-MeO—Ph | Z-3764 | F3CF2C— | 2-Cl-3-MeO—PhCH2— | Z-3765 | F2CHF2C— | 2-Br-3,4-di-MeO—PhCH2— |
| Z-3766 | F3CF2C— | 2-Br-5-MeO—Ph | Z-3767 | F3CF2C— | 2-Cl-4-MeO—PhCH2— | Z-3768 | F2CHF2C— | 2-Br-3,5-di-MeO—PhCH2— |
| Z-3769 | F3CF2C— | 2-Br-6-MeO—Ph | Z-3770 | F3CF2C— | 2-Cl-5-MeO—PhCH2— | Z-3771 | F2CHF2C— | 2-Br-3,6-di-MeO—PhCH2— |
| Z-3772 | F3CF2C— | 2,3,4-tri-F—Ph | Z-3773 | F3CF2C— | 2-Cl-6-MeO—PhCH2— | Z-3774 | F2CHF2C— | MeS— |
| Z-3775 | F3CF2C— | 2,3,5-tri-F—Ph | Z-3776 | F3CF2C— | 2-Br-3-MeO—PhCH2— | Z-3777 | F2CHF2C— | MeS(═O)— |
| Z-3778 | F3CF2C— | 2,3,6-tri-F—Ph | Z-3779 | F3CF2C— | 2-Br-4-MeO—PhCH2— | Z-3780 | F2CHF2C— | MeS(═O)2— |
| Z-3781 | F3CF2C— | 2-Br-3,4-di-F—Ph | Z-3782 | F3CF2C— | 2-Br-5-MeO—PhCH2— | Z-3783 | F2CHF2C— | EtS— |
| Z-3784 | F3CF2C— | 2-Br-3,5-di-F—Ph | Z-3785 | F3CF2C— | 2-Br-6-MeO—PhCH2— | Z-3786 | F2CHF2C— | EtS(═O)— |
| Z-3787 | F3CF2C— | 2-Br-3,6-di-F—Ph | Z-3788 | F3CF2C— | 2,3,4-tri-F—PhCH2— | Z-3789 | F2CHF2C— | EtS(═O)2— |
| Z-3790 | F2CHF2C— | 3-F—Ph | Z-3791 | F3CF2C— | 2,3,5-tri-F—PhCH2— | Z-3792 | F2CHF2C— | PrS— |
| Z-3793 | F2CHF2C— | 4-F—Ph | Z-3794 | F3CF2C— | 2,3,6-tri-F—PhCH2— | Z-3795 | F2CHF2C— | PrS(═O)— |
| Z-3796 | F2CHF2C— | 2-Cl—Ph | Z-3797 | F2CHF2C— | 2-Br-3,6-di-MeO—Ph | Z-3798 | F2CHF2C— | PrS(═O)2— |
| Z-3799 | F2CHF2C— | 3-Cl—Ph | Z-3800 | F2CHF2C— | PhCH2— | Z-3801 | F2CHF2C— | Ac |
| Z-3802 | F2CHF2C— | 4-Cl—Ph | Z-3803 | F2CHF2C— | 2-F—PhCH2— | Z-3804 | F2CHF2C— | OHC— |
| Z-3805 | F2CHF2C— | 2-Br—Ph | Z-3806 | F2CHF2C— | 3-F—PhCH2— | Z-3807 | F2CHF2C— | Et(C═O)— |
| Z-3808 | F2CHF2C— | 3-Br—Ph | Z-3809 | F2CHF2C— | 4-F—PhCH2— | Z-3810 | F2CHF2C— | Pr(C═O)— |
| Z-3811 | F2CHF2C— | 4-Br—Ph | Z-3812 | F2CHF2C— | 2-Cl—PhCH2— | Z-3813 | F2CHF2C— | i-Pr(C═O)— |
| Z-3814 | F2CHF2C— | 2-I—Ph | Z-3815 | F2CHF2C— | 3-Cl—PhCH2— | Z-3816 | F2CHF2C— | Bu(C═O)— |
| Z-3817 | F2CHF2C— | 3-I—Ph | Z-3818 | F2CHF2C— | 4-Cl—PhCH2— | Z-3819 | F2CHF2C— | MeO(C═O)— |

TABLE 3-continued

| Z | R3 | R4 | Z | R3 | R4 | Z | R3 | R4 |
|---|---|---|---|---|---|---|---|---|
| Z-3820 | F2CHF2C— | 4-I—Ph | Z-3821 | F2CHF2C— | 2-Br—PhCH2— | Z-3822 | F2CHF2C— | EtO(C═O)— |
| Z-3823 | F2CHF2C— | 2-Me—Ph | Z-3824 | F2CHF2C— | 3-Br—PhCH2— | Z-3825 | F2CHF2C— | PrO(C═O)— |
| Z-3826 | F2CHF2C— | 3-Me—Ph | Z-3827 | F2CHF2C— | 4-Br—PhCH2— | Z-3828 | F2CHF2C— | i-PrO(C═O)— |
| Z-3829 | F2CHF2C— | 4-Me—Ph | Z-3830 | F2CHF2C— | 2-I—PhCH2— | Z-3831 | F2CHF2C— | BuO(C═O)— |
| Z-3832 | F2CHF2C— | 2-MeO—Ph | Z-3833 | F2CHF2C— | 3-I—PhCH2— | Z-3834 | F2CHF2C— | i-BuOC(═O)— |
| Z-3835 | F2CHF2C— | 3-MeO—Ph | Z-3836 | F2CHF2C— | 4-I—PhCH2— | Z-3837 | (F3C)2FC— | (F3C)2FC— |
| Z-3838 | F2CHF2C— | 4-MeO—Ph | Z-3839 | F2CHF2C— | 2-Me—PhCH2— | Z-3840 | (F3C)2FC— | F3CF2C(F3C)FC— |
| Z-3841 | F2CHF2C— | 2,3-di-F—Ph | Z-3842 | F2CHF2C— | 3-Me—PhCH2— | Z-3843 | (F3C)2FC— | c-Pr |
| Z-3844 | F2CHF2C— | 2,4-di-F—Ph | Z-3845 | F2CHF2C— | 4-Me—PhCH2— | Z-3846 | (F3C)2FC— | c-Bu |
| Z-3847 | F2CHF2C— | 2,5-di-F—Ph | Z-3848 | F2CHF2C— | 2-MeO—PhCH2— | Z-3849 | (F3C)2FC— | c-Pent |
| Z-3850 | F2CHF2C— | 2,6-di-F—Ph | Z-3851 | F2CHF2C— | 3-MeO—PhCH2— | Z-3852 | (F3C)2FC— | c-Hex |
| Z-3853 | F2CHF2C— | 2-Cl-3-F—Ph | Z-3854 | F2CHF2C— | 4-MeO—PhCH2— | Z-3855 | (F3C)2FC— | H2C═CH— |
| Z-3856 | F2CHF2C— | 2-Cl-4-F—Ph | Z-3857 | F2CHF2C— | 2,3-di-F—PhCH2— | Z-3858 | (F3C)2FC— | H3CCH═CH— |
| Z-3859 | F2CHF2C— | 2-Cl-5-F—Ph | Z-3860 | F2CHF2C— | 2,4-di-F—PhCH2— | Z-3861 | (F3C)2FC— | H2C═CHCH2— |
| Z-3862 | F2CHF2C— | 2-Cl-6-F—Ph | Z-3863 | F2CHF2C— | 2,5-di-F—PhCH2— | Z-3864 | (F3C)2FC— | F2C═CH— |
| Z-3865 | F2CHF2C— | 2-Br-3-F—Ph | Z-3866 | F2CHF2C— | 2,6-di-F—PhCH2— | Z-3867 | (F3C)2FC— | F2C═CHCH2— |
| Z-3868 | F2CHF2C— | 2-Br-4-F—Ph | Z-3869 | F2CHF2C— | 2-Cl-3-F—PhCH2— | Z-3870 | (F3C)2FC— | HC≡C— |
| Z-3871 | F2CHF2C— | 2-Br-5-F—Ph | Z-3872 | F2CHF2C— | 2-Cl-4-F—PhCH2— | Z-3873 | (F3C)2FC— | HC≡CCH2— |
| Z-3874 | F2CHF2C— | 2-Br-6-F—Ph | Z-3875 | F2CHF2C— | 2-Cl-5-F—PhCH2— | Z-3876 | (F3C)2FC— | HC≡CCH2CH2— |
| Z-3877 | F2CHF2C— | 2-F-3-MeO—Ph | Z-3878 | F2CHF2C— | 2-Cl-6-F—PhCH2— | Z-3879 | (F3C)2FC— | H3CC≡CCH2— |
| Z-3880 | F2CHF2C— | 2-F-4-MeO—Ph | Z-3881 | F2CHF2C— | 2-Br-3-F—PhCH2— | Z-3882 | (F3C)2FC— | FC≡C— |
| Z-3883 | F2CHF2C— | 2-F-5-MeO—Ph | Z-3884 | F2CHF2C— | 2-Br-4-F—PhCH2— | Z-3885 | (F3C)2FC— | FC≡CCF2— |
| Z-3886 | F2CHF2C— | 2-F-6-MeO—Ph | Z-3887 | F2CHF2C— | 2-Br-5-F—PhCH2— | Z-3888 | (F3C)2FC— | FC≡CCF2CF2— |
| Z-3889 | F2CHF2C— | 2-Cl-3-MeO—Ph | Z-3890 | F2CHF2C— | 2-Br-6-F—PhCH2— | Z-3891 | (F3C)2FC— | F3CC≡CCF2— |
| Z-3892 | F2CHF2C— | 2-Cl-4-MeO—Ph | Z-3893 | F2CHF2C— | 2-F-3-MeO—PhCH2— | Z-3894 | (F3C)2FC— | Ph |
| Z-3895 | F2CHF2C— | 2-Cl-5-MeO—Ph | Z-3896 | F2CHF2C— | 2-F-4-MeO—PhCH2— | Z-3897 | (F3C)2FC— | 2-F—Ph |
| Z-3898 | F2CHF2C— | 2-Cl-6-MeO—Ph | Z-3899 | F2CHF2C— | 2-F-5-MeO—PhCH2— | Z-3900 | (F3C)2FC— | 3-F—Ph |
| Z-3901 | F2CHF2C— | 2-Br-3-MeO—Ph | Z-3902 | F2CHF2C— | 2-F-6-MeO—PhCH2— | Z-3903 | (F3C)2FC— | 4-F—Ph |
| Z-3904 | F2CHF2C— | 2-Br-4-MeO—Ph | Z-3905 | F2CHF2C— | 2-Cl-3-MeO—PhCH2— | Z-3906 | (F3C)2FC— | 2-Cl—Ph |
| Z-3907 | F2CHF2C— | 2-Br-5-MeO—Ph | Z-3908 | F2CHF2C— | 2-Cl-4-MeO—PhCH2— | Z-3909 | (F3C)2FC— | 3-Cl—Ph |
| Z-3910 | F2CHF2C— | 2-Br-6-MeO—Ph | Z-3911 | F2CHF2C— | 2-Cl-5-MeO—PhCH2— | Z-3912 | (F3C)2FC— | 4-Cl—Ph |
| Z-3913 | F2CHF2C— | 2,3,4-tri-F—Ph | Z-3914 | F2CHF2C— | 2-Cl-6-MeO—PhCH2— | Z-3915 | (F3C)2FC— | 2-Br—Ph |
| Z-3916 | F2CHF2C— | 2,3,5-tri-F—Ph | Z-3917 | F2CHF2C— | 2-Br-3-MeO—PhCH2— | Z-3918 | (F3C)2FC— | 3-Br—Ph |
| Z-3919 | F2CHF2C— | 2,3,6-tri-F—Ph | Z-3920 | F2CHF2C— | 2-Br-4-MeO—PhCH2— | Z-3921 | (F3C)2FC— | 4-Br—Ph |
| Z-3922 | F2CHF2C— | 2-Br-3,4-di-F—Ph | Z-3923 | F2CHF2C— | 2-Br-5-MeO—PhCH2— | Z-3924 | (F3C)2FC— | 2-I—Ph |
| Z-3925 | F2CHF2C— | 2-Br-3,5-di-F—Ph | Z-3926 | F2CHF2C— | 2-Br-6-MeO—PhCH2— | Z-3927 | (F3C)2FC— | EtS(═O)2— |
| Z-3928 | F2CHF2C— | 2-Br-3,6-di-F—Ph | Z-3929 | F2CHF2C— | 2,3,4-tri-F—PhCH2— | Z-3930 | (F3C)2FC— | PrS— |
| Z-3931 | F2CHF2C— | 2-F-3,4-di-MeO—Ph | Z-3932 | F2CHF2C— | 2,3,5-tri-F—PhCH2— | Z-3933 | (F3C)2FC— | PrS(═O)— |
| Z-3934 | F2CHF2C— | 2-F-3,5-di-MeO—Ph | Z-3935 | F2CHF2C— | 2,3,6-tri-F—PhCH2— | Z-3936 | (F3C)2FC— | PrS(═O)2— |
| Z-3937 | F2CHF2C— | 2-F-3,6-di-MeO—Ph | Z-3938 | F2CHF2C— | 2-Br-3,4-di-F—PhCH2— | Z-3939 | (F3C)2FC— | Ac |
| Z-3940 | F2CHF2C— | 2-Cl-3,4-di-MeO—Ph | Z-3941 | F2CHF2C— | 2-Br-3,5-di-F—PhCH2— | Z-3942 | (F3C)2FC— | OHC— |
| Z-3943 | F2CHF2C— | 2-Cl-3,5-dt-MeO—Ph | Z-3944 | F2CHF2C— | 2-Br-3,6-di-F—PhCH2— | Z-3945 | (F3C)2FC— | Et(C═O)— |
| Z-3946 | F2CHF2C— | 2-Cl-3,6-di-MeO—Ph | Z-3947 | F2CHF2C— | 2-F-3,4-di-MeO—PhCH2— | Z-3948 | (F3C)2FC— | Pr(C═O)— |
| Z-3949 | F2CHF2C— | 2-Br-3,4-di-MeO—Ph | Z-3950 | F2CHF2C— | 2-F-3,5-di-MeO—PhCH2— | Z-3951 | (F3C)2FC— | i-Pr(C═O)— |
| Z-3952 | F2CHF2C— | 2-Br-3,5-di-MeO—Ph | Z-3953 | F2CHF2C— | 2-F-3,6-di-MeO—PhCH2— | Z-3954 | (F3C)2FC— | Bu(C═O)— |
| Z-3955 | (F3C)2FC— | 3-I—Ph | Z-3956 | F2CHF2C— | 2-Cl-3,4-di-MeO—PhCH2— | Z-3957 | (F3C)2FC— | MeO(C═O)— |
| Z-3958 | (F3C)2FC— | 4-I—Ph | Z-3959 | F2CHF2C— | 2-Cl-3,5-di-MeO—PhCH2— | Z-3960 | (F3C)2FC— | EtO(C═O)— |
| Z-3961 | (F3C)2FC— | 2-Me—Ph | Z-3962 | (F3C)2FC— | 3-Br—PhCH2— | Z-3963 | (F3C)2FC— | PrO(C═O)— |
| Z-3964 | (F3C)2FC— | 3-Me—Ph | Z-3965 | (F3C)2FC— | 4-Br—PhCH2— | Z-3966 | (F3C)2FC— | i-PrO(C═O)— |
| Z-3967 | (F3C)2FC— | 4-Me—Ph | Z-3968 | (F3C)2FC— | 2-I—PhCH2— | Z-3969 | (F3C)2FC— | BuO(C═O)— |
| Z-3970 | (F3C)2FC— | 2-MeO—Ph | Z-3971 | (F3C)2FC— | 3-I—PhCH2— | Z-3972 | (F3C)2FC— | t-BuOC(═O)— |

TABLE 3-continued

| Z | R3 | R4 | Z | R3 | R4 | Z | R3 | R4 |
|---|---|---|---|---|---|---|---|---|
| Z-3973 | (F3C)2FC— | 3-MeO—Ph | Z-3974 | (F3C)2FC— | 4-I—PhCH2— | Z-3975 | c-Pr | c-Pr |
| Z-3976 | (F3C)2FC— | 4-MeO—Ph | Z-3977 | (F3C)2FC— | 2-Me—PhCH2— | Z-3978 | c-Pr | c-Bu |
| Z-3979 | (F3C)2FC— | 2,3-di-F—Ph | Z-3980 | (F3C)2FC— | 3-Me—PhCH2— | Z-3981 | c-Pr | c-Pent |
| Z-3982 | (F3C)2FC— | 2,4-di-F—Ph | Z-3983 | (F3C)2FC— | 4-Me—PhCH2— | Z-3984 | c-Pr | c-Hex |
| Z-3985 | (F3C)2FC— | 2,5-di-F—Ph | Z-3986 | (F3C)2FC— | 2-MeO—PhCH2— | Z-3987 | c-Pr | H2C═CH— |
| Z-3988 | (F3C)2FC— | 2,6-di-F—Ph | Z-3989 | (F3C)2FC— | 3-MeO—PhCH2— | Z-3990 | c-Pr | H3CCH═CH— |
| Z-3991 | (F3C)2FC— | 2-Cl-3-F—Ph | Z-3992 | (F3C)2FC— | 4-MeO—PhCH2— | Z-3993 | c-Pr | H2C═CHCH2— |
| Z-3994 | (F3C)2FC— | 2-Cl-4-F—Ph | Z-3995 | (F3C)2FC— | 2,3-di-F—PhCH2— | Z-3996 | c-Pr | F2C═CH— |
| Z-3997 | (F3C)2FC— | 2-Cl-5-F—Ph | Z-3998 | (F3C)2FC— | 2,1-di-F—PhCH2— | Z-3999 | c-Pr | F2C═CHCH2— |
| Z-4000 | (F3C)2FC— | 2-Cl-6-F—Ph | Z-4001 | (F3C)2FC— | 2,5-di-F—PhCH2— | Z-4002 | c-Pr | HC≡C— |
| Z-4003 | (F3C)2FC— | 2-Br-3-F—Ph | Z-4004 | (F3C)2FC— | 2,6-di-F—PhCH2— | Z-4005 | c-Pr | HC≡CCH2— |
| Z-4006 | (F3C)2FC— | 2-Br-4-F—Ph | Z-4007 | (F3C)2FC— | 2-Cl-3-F—PhCH2— | Z-4008 | c-Pr | HC≡CCH2CH2— |
| Z-4009 | (F3C)2FC— | 2-Br-5-F—Ph | Z-4010 | (F3C)2FC— | 2-Cl-4-F—PhCH2— | Z-4011 | c-Pr | H3CC≡CCH2— |
| Z-4012 | (F3C)2FC— | 2-Br-6-F—Ph | Z-4013 | (F3C)2FC— | 2-Cl-5-F—PhCH2— | Z-4014 | c-Pr | FC≡C— |
| Z-4015 | (F3C)2FC— | 2-F-3-MeO—Ph | Z-4016 | (F3C)2FC— | 2-Cl-6-F—PhCH2— | Z-4017 | c-Pr | FC≡CCF2— |
| Z-4018 | (F3C)2FC— | 2-F-4-MeO—Ph | Z-4019 | (F3C)2FC— | 2-Br-3-F—PhCH2— | Z-4020 | c-Pr | FC≡CCF2CF2— |
| Z-4021 | (F3C)2FC— | 2-F-5-MeO—Ph | Z-4022 | (F3C)2FC— | 2-Br-4-F—PhCH2— | Z-4023 | c-Pr | F3CC≡CCF2— |
| Z-4024 | (F3C)2FC— | 2-F-6-MeO—Ph | Z-4025 | (F3C)2FC— | 2-Br-5-F—PhCH2— | Z-4026 | c-Pr | Ph |
| Z-4027 | (F3C)2FC— | 2-Cl-3-MeO—Ph | Z-4028 | (F3C)2FC— | 2-Br-6-F—PhCH2— | Z-4029 | c-Pr | 2-F—Ph |
| Z-4030 | (F3C)2FC— | 2-Cl-4-MeO—Ph | Z-4031 | (F3C)2FC— | 2-F-3-MeO—PhCH2— | Z-4032 | c-Pr | 3-F—Ph |
| Z-4033 | (F3C)2FC— | 2-Cl-5-MeO—Ph | Z-4034 | (F3C)2FC— | 2-F-4-MeO—PhCH2— | Z-4035 | c-Pr | 4-F—Ph |
| Z-4036 | (F3C)2FC— | 2-Cl-6-MeO—Ph | Z-4037 | (F3C)2FC— | 2-F-5-MeO—PhCH2— | Z-4038 | c-Pr | 2-Cl—Ph |
| Z-4039 | (F3C)2FC— | 2-Br-3-MeO—Ph | Z-4040 | (F3C)2FC— | 2-F-6-MeO—PhCH2— | Z-4041 | c-Pr | 3-Cl—Ph |
| Z-4042 | (F3C)2FC— | 2-Br-4-MeO—Ph | Z-4043 | (F3C)2FC— | 2-Cl-3-MeO—PhCH2— | Z-4044 | c-Pr | 4-Cl—Ph |
| Z-4045 | (F3C)2FC— | 2-Br-5-MeO—Ph | Z-4046 | (F3C)2FC— | 2-Cl-4-MeO—PhCH2— | Z-4047 | c-Pr | 2-Br—Ph |
| Z-4048 | (F3C)2FC— | 2-Br-6-MeO—Ph | Z-4049 | (F3C)2FC— | 2-Cl-5-MeO—PhCH2— | Z-4050 | c-Pr | 3-Br—Ph |
| Z-4051 | (F3C)2FC— | 2,3-4-tri-F—Ph | Z-4052 | (F3C)2FC— | 2-Cl-6-MeO—PhCH2— | Z-4053 | c-Pr | 4-Br—Ph |
| Z-4054 | (F3C)2FC— | 2,3,5-tri-F—Ph | Z-4055 | (F3C)2FC— | 2-Br-3-MeO—PhCH2— | Z-4056 | c-Pr | 2-I—Ph |
| Z-4057 | (F3C)2FC— | 2,3,6-tri-F—Ph | Z-4058 | (F3C)2FC— | 2-Br-4-MeO—PhCH2— | Z-4059 | c-Pr | 3-I—Ph |
| Z-4060 | (F3C)2FC— | 2-Br-3,4-di-F—Ph | Z-4061 | (F3C)2FC— | 2-Br-5-MeO—PhCH2— | Z-4062 | c-Pr | 4-I—Ph |
| Z-4063 | (F3C)2FC— | 2-Br-3,5-di-F—Ph | Z-4064 | (F3C)2FC— | 2-Br-6-MeO—PhCH2— | Z-4065 | c-Pr | 2-Me—Ph |
| Z-4066 | (F3C)2FC— | 2-Br-3,6-di-F—Ph | Z-4067 | (F3C)2FC— | 2,3,4-tri-F—PhCH2— | Z-4068 | c-Pr | 3-Me—Ph |
| Z-4069 | (F3C)2FC— | 2-F-3,4-di-MeO—Ph | Z-4070 | (F3C)2FC— | 2,3,5-tri-F—PhCH2— | Z-4071 | c-Pr | 4-Me—Ph |
| Z-4072 | (F3C)2FC— | 2-F-3,5-di-MeO—Ph | Z-4073 | (F3C)2FC— | 2,3,6-tri-F—PhCH2— | Z-4074 | c-Pr | 2-MeO—Ph |
| Z-4075 | (F3C)2FC— | 2-F-3,6-di-MeO—Ph | Z-4076 | (F3C)2FC— | 2-Br-3,4-di-F—PhCH2— | Z-4077 | c-Pr | 3-MeO—Ph |
| Z-4078 | (F3C)2FC— | 2-Cl-3,4-di-MeO—Ph | Z-4079 | (F3C)2FC— | 2-Br-3,5-di-F—PhCH2— | Z-4080 | c-Pr | 4-MeO—Ph |
| Z-4081 | (F3C)2FC— | 2-Cl-3,5-di-MeO—Ph | Z-4082 | (F3C)2FC— | 2-Br-3,6-di-F—PhCH2— | Z-4083 | c-Pr | 2,3-di-F—Ph |
| Z-4084 | (F3C)2FC— | 2-Cl-3,6-di-MeO—Ph | Z-4085 | (F3C)2FC— | 2-F-3,4-di-MeO—PhCH2— | Z-4086 | c-Pr | 2,4-di-F—Ph |
| Z-4087 | (F3C)2FC— | 2-Br-3,4-di-MeO—Ph | Z-4088 | (F3C)2FC— | 2-F-3,5-di-MeO—PhCH2— | Z-4089 | c-Pr | 2,5-di-F—Ph |
| Z-4090 | (F3C)2FC— | 2-Br-3,5-di-MeO—Ph | Z-4091 | (F3C)2FC— | 2-F-3,6-di-MeO—PhCH2— | Z-4092 | c-Pr | 2,6-di-F—Ph |
| Z-4093 | (F3C)2FC— | 2-Br-3,6-di-MeO—Ph | Z-4004 | (F3C)2FC— | 2-Cl-3,4-di-MeO—PhCH2— | Z-4095 | c-Pr | 2-Cl-3-F—Ph |
| Z-4096 | (F3C)2FC— | PhCH2— | Z-4097 | (F3C)2FC— | 2-Cl-3,5-di-MeO—PhCH2— | Z-4098 | c-Pr | 2-Cl-4-F—Ph |
| Z-4099 | (F3C)2FC— | 2-F—PhCH2— | Z-4100 | (F3C)2FC— | 2-Cl-3,6-di-MeO—PhCH2— | Z-4101 | c-Pr | 2-Cl-5-F—Ph |
| Z-4102 | (F3C)2FC— | 3-F—PhCH2— | Z-4103 | (F3C)2FC— | 2-Br-3,4-di-MeO—PhCH2— | Z-4104 | c-Pr | 2-Cl-6-F—Ph |
| Z-4105 | (F3C)2FC— | 4-F—PhCH2— | Z-4106 | (F3C)2FC— | 2-Br-3,5-di-MeO—PhCH2— | Z-4107 | c-Pr | 2-Br-3-F—Ph |
| Z-4108 | (F3C)2FC— | 2-Cl—PhCH2— | Z-4109 | (F3C)2FC— | 2-Br-3,6-di-MeO—PhCH2— | Z-4110 | c-Pr | 2-Br-4-F—Ph |
| Z-4111 | (F3C)2FC— | 3-Cl—PhCH2— | Z-4112 | (F3C)2FC— | MeS— | Z-4113 | c-Pr | 2-Br-5-F—Ph |
| Z-4114 | (F3C)2FC— | 4-Cl—PhCH2— | Z-4115 | (F3C)2FC— | MeS(═O)— | Z-4116 | c-Pr | 2-Br-6-F—Ph |
| Z-4117 | (F3C)2FC— | 2-Br—PhCH2— | Z-4118 | (F3C)2FC— | MeS(═O)2— | Z-4119 | c-Pr | 2-F-3-MeO—Ph |
| Z-4120 | c-Pr | 2-F-4-MeO—Ph | Z-4121 | (F3C)2FC— | EtS— | Z-4122 | c-Bu | H2C═CHCH2— |
| Z-4123 | c-Pr | 2-F-5-MeO—Ph | Z-4124 | (F3C)2FC— | EtS(═O)— | Z-4125 | c-Bu | F2C═CH— |

TABLE 3-continued

| Z | R3 | R4 | Z | R3 | R4 | Z | R3 | R4 |
|---|---|---|---|---|---|---|---|---|
| Z-4126 | c-Pr | 2-F-6-MeO—Ph | Z-4127 | c-Pr | 2-Br-5-F—PhCH2— | Z-4128 | c-Bu | F2C═CHCH2— |
| Z-4129 | c-Pr | 2-Cl-3-MeO—Ph | Z-4130 | c-Pr | 2-Br-6-F—PhCH2— | Z-4131 | c-Bu | HC≡C— |
| Z-4132 | c-Pr | 2-Cl-4-MeO—Ph | Z-4133 | c-Pr | 2-F-3-MeO—PhCH2— | Z-4134 | c-Bu | HC≡CCH2— |
| Z-4135 | c-Pr | 2-Cl-5-MeO—Ph | Z-4136 | c-Pr | 2-F-4-MeO—PhCH2— | Z-4137 | c-Bu | HC≡CCH2CH2— |
| Z-4138 | c-Pr | 2-Cl-6-MeO—Ph | Z-4139 | c-Pr | 2-F-5-MeO—PhCH2— | Z-4140 | c-Bu | H3CC≡CCH2— |
| Z-4141 | c-Pr | 2-Br-3-MeO—Ph | Z-4142 | c-Pr | 2-F-6-MeO—PhCH2— | Z-4143 | c-Bu | FC≡C— |
| Z-4144 | c-Pr | 2-Br-4-MeO—Ph | Z-4145 | c-Pr | 2-Cl-3-MeO—PhCH2— | Z-4146 | c-Bu | FC≡CCF2— |
| Z-4147 | c-Pr | 2-Br-5-MeO—Ph | Z-4148 | c-Pr | 2-Cl-4-MeO—PhCH2— | Z-4149 | c-Bu | FC≡CCF2CF2— |
| Z-4150 | c-Pr | 2-Br-6-MeO—Ph | Z-4151 | c-Pr | 2-Cl-5-MeO—PhCH2— | Z-4152 | c-Bu | F3CC≡CCF2— |
| Z-4153 | c-Pr | 2,3,4-tri-F—Ph | Z-4154 | c-Pr | 2-Cl-6-MeO—PhCH2— | Z-4155 | c-Bu | Ph |
| Z-4156 | c-Pr | 2,3,5-tri-F—Ph | Z-4157 | c-Pr | 2-Br-3-MeO—PhCH2— | Z-4158 | c-Bu | 2-F—Ph |
| Z-4159 | c-Pr | 2,3,6-tri-F—Ph | Z-4160 | c-Pr | 2-Br-4-MeO—PhCH2— | Z-4161 | c-Bu | 3-F—Ph |
| Z-4162 | c-Pr | 2-Br-3,4-di-F—Ph | Z-4163 | c-Pr | 2-Br-5-MeO—PhCH2— | Z-4164 | c-Bu | 4-F—Ph |
| Z-4165 | c-Pr | 2-Br-3,5-di-F—Ph | Z-4166 | c-Pr | 2-Br-6-MeO—PhCH2— | Z-4167 | c-Bu | 2-Cl—Ph |
| Z-4168 | c-Pr | 2-Br-3,6-di-F—Ph | Z-4169 | c-Pr | 2,3,4-tri-F—PhCH2— | Z-4170 | c-Bu | 3-Cl—Ph |
| Z-4171 | c-Pr | 2-F-3,4-di-MeO—Ph | Z-4172 | c-Pr | 2,3,5-tri-F—PhCH2— | Z-4173 | c-Bu | 4-Cl—Ph |
| Z-4174 | c-Pr | 2-F-3,5-di-MeO—Ph | Z-4175 | c-Pr | 2,3,6-tri-F—PhCH2— | Z-4176 | c-Bu | 2-Br—Ph |
| Z-4177 | c-Pr | 2-F-3,6-di-MeO—Ph | Z-4178 | c-Pr | 2-Br-3,4-di-F—PhCH2— | Z-4179 | c-Bu | 3-Br—Ph |
| Z-4180 | c-Pr | 2-Cl-3,4-di-MeO—Ph | Z-4181 | c-Pr | 2-Br-3,5-di-F—PhCH2— | Z-4182 | c-Bu | 4-Br—Ph |
| Z-4183 | c-Pr | 2-Cl-3,5-di-MeO—Ph | Z-4184 | c-Pr | 2-Br-3,6-di-F—PhCH2— | Z-4185 | c-Bu | 2-I—Ph |
| Z-4186 | c-Pr | 2-Cl-3,6-di-MeO—Ph | Z-4187 | c-Pr | 2-F-3,4-di-MeO—PhCH2— | Z-4188 | c-Bu | 3-I—Ph |
| Z-4189 | c-Pr | 2-Br-3,4-di-MeO—Ph | Z-4190 | c-Pr | 2-F-3,5-di-MeO—PhCH2— | Z-4191 | c-Bu | 4-I—Ph |
| Z-4192 | c-Pr | 2-Br-3,5-di-MeO—Ph | Z-4193 | c-Pr | 2-F-3,6-di-MeO—PhCH2— | Z-4194 | c-Bu | 2-Me—Ph |
| Z-4195 | c-Pr | 2-Br-3,6-di-MeO—Ph | Z-4196 | c-Pr | 2-Cl-3,4-di-MeO—PhCH2— | Z-4197 | c-Bu | 3-Me—Ph |
| Z-4198 | c-Pr | PhCH2— | Z-4199 | c-Pr | 2-Cl-3,5-di-MeO—PhCH2— | Z-4200 | c-Bu | 4-Me—Ph |
| Z-4201 | c-Pr | 2-F—PhCH2— | Z-4202 | c-Pr | 2-Cl-3,6-di-MeO—PhCH2— | Z-4203 | c-Bu | 2-MeO—Ph |
| Z-4204 | c-Pr | 3-F—PhCH2— | Z-4205 | c-Pr | 2-Br-3,4-di-MeO—PhCH2— | Z-4206 | c-Bu | 3-MeO—Ph |
| Z-4207 | c-Pr | 4-F—PhCH2— | Z-4208 | c-Pr | 2-Br-3,5-di-MeO—PhCH2— | Z-4209 | c-Bu | 4-MeO—Ph |
| Z-4210 | c-Pr | 2-Cl—PhCH2— | Z-4211 | c-Pr | 2-Br-3,6-di-MeO—PhCH2— | Z-4212 | c-Bu | 2,3-di-F—Ph |
| Z-4213 | c-Pr | 3-Cl—PhCH2— | Z-4214 | c-Pr | MeS— | Z-4215 | c-Bu | 2,4-di-F—Ph |
| Z-4216 | c-Pr | 4-Cl—PhCH2— | Z-4217 | c-Pr | MeS(═O)— | Z-4218 | c-Bu | 2,5-di-F—Ph |
| Z-4219 | c-Pr | 2-Br—PhCH2— | Z-4220 | c-Pr | MeS(═O)2— | Z-4221 | c-Bu | 2,6-di-F—Ph |
| Z-4222 | c-Pr | 3-Br—PhCH2— | Z-4223 | c-Pr | EtS— | Z-4224 | c-Bu | 2-Cl-3-F—Ph |
| Z-4225 | c-Pr | 4-Br—PhCH2— | Z-4226 | c-Pr | EtS(═O)— | Z-4227 | c-Bu | 2-Cl-4-F—Ph |
| Z-4228 | c-Pr | 2-I—PhCH2— | Z-4229 | c-Pr | EtS(═O)2— | Z-4230 | c-Bu | 2-Cl-5-F—Ph |
| Z-4231 | c-Pr | 3-I—PhCH2— | Z-4232 | c-Pr | PrS— | Z-4233 | c-Bu | 2-Cl-6-F—Ph |
| Z-4234 | c-Pr | 4-I—PhCH2— | Z-4235 | c-Pr | PrS(═O)— | Z-4236 | c-Bu | 2-Br-3-F—Ph |
| Z-4237 | c-Pr | 2-Me—PhCH2— | Z-4238 | c-Pr | PrS(═O)2— | Z-4239 | c-Bu | 2-Br-4-F—Ph |
| Z-4240 | c-Pr | 3-Me—PhCH2— | Z-4241 | c-Pr | Ac | Z-4242 | c-Bu | 2-Br-5-F—Ph |
| Z-4243 | c-Pr | 4-Me—PhCH2— | Z-4244 | c-Pr | OHC— | Z-4245 | c-Bu | 2-Br-6-F—Ph |
| Z-4246 | c-Pr | 2-MeO—PhCH2— | Z-4247 | c-Pr | Et(C═O)— | Z-4248 | c-Bu | 2-F-3-MeO—Ph |
| Z-4249 | c-Pr | 3-MeO—PhCH2— | Z-4250 | c-Pr | Pr(C═O)— | Z-4251 | c-Bu | 2-F-4-MeO—Ph |
| Z-4252 | c-Pr | 4-MeO—PhCH2— | Z-4253 | c-Pr | i-Pr(C═O)— | Z-4254 | c-Bu | 2-F-5-MeO—Ph |
| Z-4255 | c-Pr | 2,3-di-F—PhCH2— | Z-4256 | c-Pr | Bu(C═C))— | Z-4257 | c-Bu | 2-F-6-MeO—Ph |
| Z-4258 | c-Pr | 2,4-di-F—PhCH2— | Z-4259 | c-Pr | MeO(C═O)— | Z-4260 | c-Bu | 2-Cl-3-MeO—Ph |
| Z-4261 | c-Pr | 2,5-di-F—PhCH2— | Z-4262 | c-Pr | EtO(C═O)— | Z-4263 | c-Bu | 2-Cl-4-MeO—Ph |
| Z-4264 | c-Pr | 2,6-di-F—PhCH2— | Z-4265 | c-Pr | PrO(C═O)— | Z-4266 | c-Bu | 2-Cl-5-MeO—Ph |
| Z-4267 | c-Pr | 2-Cl-3-F—PhCH2— | Z-4268 | c-Pr | i═PrO(C═O) | Z-4269 | c-Bu | 2-Cl-6-MeO—Ph |
| Z-4270 | c-Pr | 2-Cl-4-F—PhCH2— | Z-4271 | c-Pr | BuO(C═O)— | Z-4272 | c-Bu | 2-Br-3-MeO—Ph |
| Z-4273 | c-Pr | 2-Cl-5-F—PhCH2— | Z-4274 | c-Pr | t-BuOC(═O)— | Z-4275 | c-Bu | 2-Br-4-MeO—Ph |
| Z-4276 | c-Pr | 2-Cl-6-F—PhCH2— | Z-4277 | c-Bu | c-Bu | Z-4278 | c-Bu | 2-Br-5-MeO—Ph |

TABLE 3-continued

| Z | R3 | R4 | Z | R3 | R4 | Z | R3 | R4 |
|---|---|---|---|---|---|---|---|---|
| Z-4279 | c-Pr | 2-Br-3-F—PhCH2— | Z-4280 | c-Bu | c-Pent | Z-4281 | c-Bu | 2-Br-6-MeO—Ph |
| Z-4282 | c-Pr | 2-Br-4-F—PhCH2— | Z-4283 | c-Bu | c-Hex | Z-4284 | c-Bu | 2,3,4-tri-F—Ph |
| Z-4285 | c-Bu | 2,3,5-tri-F—Ph | Z-4286 | c-Bu | H2C═CH— | Z-4287 | c-Pent | 3-F—Ph |
| Z-4288 | c-Bu | 2,3,6-tri-F—Ph | Z-4289 | c-Bu | H3CCH═CH— | Z-4290 | c-Pent | 4-F—Ph |
| Z-4291 | c-Bu | 2-Br-3,4-di-F—Ph | Z-4292 | c-Bu | 2-Br-5-MeO—PhCH2— | Z-4293 | c-Pent | 2-Cl—Ph |
| Z-4294 | c-Bu | 2-Br-3,5-di-F—Ph | Z-4295 | c-Bu | 2-Br-6-MeO—PhCH2— | Z-4296 | c-Pent | 3-Cl—Ph |
| Z-4297 | c-Bu | 2-Br-3,6-di-F—Ph | Z-4298 | c-Bu | 2,3,4-tri-F—PhCH2— | Z-4299 | c-Pent | 4-Cl—Ph |
| Z-4300 | c-Bu | 2-F-3,4-di-MeO—Ph | Z-4301 | c-Bu | 2,3,5-tri-F—PhCH2— | Z-4302 | c-Pent | 2-Br—Ph |
| Z-4303 | c-Bu | 2-F-3,5-di-MeO—Ph | Z-4304 | c-Bu | 2,3,6-tri-F—PhCH2— | Z-4305 | c-Pent | 3-Br—Ph |
| Z-4306 | c-Bu | 2-F-3,6-di-MeO—Ph | Z-4307 | c-Bu | 2-Br-3,4-di-F—PhCH2— | Z-4308 | c-Pent | 4-Br—Ph |
| Z-4309 | c-Bu | 2-Cl-3,4-di-MeO—Ph | Z-4310 | c-Bu | 2-Br-3,5-di-F—PhCH2— | Z-4311 | c-Pent | 2-I—Ph |
| Z-4312 | c-Bu | 2-Cl-3,5-di-MeO—Ph | Z-4313 | c-Bu | 2-Br-3,6-di-F—PhCH2— | Z-4314 | c-Pent | 3-I—Ph |
| Z-4315 | c-Bu | 2-Cl-3,6-di-MeO—Ph | Z-4316 | c-Bu | 2-F-3,4-di-MeO—PhCH2— | Z-4317 | c-Pent | 4-I—Ph |
| Z-4318 | c-Bu | 2-Br-3,4-di-MeO—Ph | Z-4319 | c-Bu | 2-F-3,5-di-MeO—PhCH2— | Z-4320 | c-Pent | 2-Me—Ph |
| Z-4321 | c-Bu | 2-Br-3,5-di-MeO—Ph | Z-4322 | c-Bu | 2-F-3,6-di-MeO—PhCH2— | Z-4323 | c-Pent | 3-Me—Ph |
| Z-4324 | c-Bu | 2-Br-3,6-di-MeO—Ph | Z-4325 | c-Bu | 2-Cl-3,4-di-MeO—PhCH2— | Z-4326 | c-Pent | 4-Me—Ph |
| Z-4327 | c-Bu | PhCH2— | Z-4328 | c-Bu | 2-Cl-3,5-di-MeO—PhCH2— | Z-4329 | c-Pent | 2-MeO—Ph |
| Z-4330 | c-Bu | 2-F—PhCH2— | Z-4331 | c-Bu | 2-Cl-3,6-di-MeO—PhCH2— | Z-4332 | c-Pent | 3-MeO—Ph |
| Z-4333 | c-Bu | 3-F—PhCH2— | Z-4334 | c-Bu | 2-Br-3,4-di-MeO—PhCH2— | Z-4335 | c-Pent | 4-MeO—Ph |
| Z-4336 | c-Bu | 4-F—PhCH2— | Z-4337 | c-Bu | 2-Br-3,5-di-MeO—PhCH2— | Z-4338 | c-Pent | 2,3-di-F—Ph |
| Z-4339 | c-Bu | 2-Cl—PhCH2— | Z-4340 | c-Bu | 2-Br-3,6-di-MeO—PhCH2— | Z-4341 | c-Pent | 2,4-di-F—Ph |
| Z-4342 | c-Bu | 3-Cl—PhCH2— | Z-4343 | c-Bu | MeS— | Z-4344 | c-Pent | 2,5-di-F—Ph |
| Z-4345 | c-Bu | 4-Cl—PhCH2— | Z-4346 | c-Bu | MeS(═O)— | Z-4347 | c-Pent | 2,6-di-F—Ph |
| Z-4348 | c-Bu | 2-Br—PhCH2— | Z-4349 | c-Bu | MeS(═O)2— | Z-4350 | c-Pent | 2-Cl-3-F—Ph |
| Z-4351 | c-Bu | 3-Br—PhCH2— | Z-4352 | c-Bu | EtS— | Z-4353 | c-Pent | 2-Cl-4-F—Ph |
| Z-4354 | c-Bu | 4-Br—PhCH2— | Z-4355 | c-Bu | EtS(═O)— | Z-4356 | c-Pent | 2-Cl-5-F—Ph |
| Z-4357 | c-Bu | 2-I—PhCH2— | Z-4358 | c-Bu | EtS(═O)2— | Z-4359 | c-Pent | 2-Cl-6-F—Ph |
| Z-4360 | c-Bu | 3-I—PhCH2— | Z-4361 | c-Bu | PrS— | Z-4362 | c-Pent | 2-Br-3-F—Ph |
| Z-4363 | c-Bu | 4-I—PhCH2— | Z-4364 | c-Bu | PrS(═O)— | Z-4365 | c-Pent | 2-Br-4-F—Ph |
| Z-4366 | c-Bu | 2-Me—PhCH2— | Z-4367 | c-Bu | PrS(═O)2— | Z-4368 | c-Pent | 2-Br-5-F—Ph |
| Z-4369 | c-Bu | 3-Me—PhCH2— | Z-4370 | c-Bu | Ac | Z-4371 | c-Pent | 2-Br-6-F—Ph |
| Z-4372 | c-Bu | 4-Me—PhCH2— | Z-4373 | c-Bu | OHC— | Z-4374 | c-Pent | 2-F-3-MeO—Ph |
| Z-4375 | c-Bu | 2-MeO—PhCH2— | Z-4376 | c-Bu | Et(C═O)— | Z-4377 | c-Pent | 2-F-4-MeO—Ph |
| Z-4378 | c-Bu | 3-MeO—PhCH2— | Z-4379 | c-Bu | Pr(C═O)— | Z-4380 | c-Pent | 2-F-5-MeO—Ph |
| Z-4381 | c-Bu | 4-MeO—PhCH2— | Z-4382 | c-Bu | i-Pr(C═O)— | Z-4383 | c-Pent | 2-F-6-MeO—Ph |
| Z-4384 | c-Bu | 2,3-di-F—PhCH2— | Z-4385 | c-Bu | Bu(C═O)— | Z-4386 | c-Pent | 2-Cl-3-MeO—Ph |
| Z-4387 | c-Bu | 2,4-di-F—PhCH2— | Z-4388 | c-Bu | MeO(C═O)— | Z-4389 | c-Pent | 2-Cl-4-MeO—Ph |
| Z-4390 | c-Bu | 2,5-di-F—PhCH2— | Z-4391 | c-Bu | EtO(C═O)— | Z-4392 | c-Pent | 2-Cl-5-MeO—Ph |
| Z-4393 | c-Bu | 2,6-di-F—PhCH2— | Z-4394 | c-Bu | PrO(C═O)— | Z-4395 | c-Pent | 2-Cl-6-MeO—Ph |
| Z-4396 | c-Bu | 2-Cl-3-F—PhCH2— | Z-4397 | c-Bu | i-PrO(C═O)— | Z-4398 | c-Pent | 2-Br-3-MeO—Pb |
| Z-4399 | c-Bu | 2-Cl-4-F—PhCH2— | Z-4400 | c-Bu | BuO(C═O)— | Z-4401 | c-Pent | 2-Br-4-MeO—Ph |
| Z-4402 | c-Bu | 2-Cl-5-F—PhCH2— | Z-4403 | c-Bu | t-BuOC(═O)— | Z-4404 | c-Pent | 2-Br-5-MeO—Ph |
| Z-4405 | c-Bu | 2-Cl-6-F—PhCH2— | Z-4406 | c-Pent | c-Pent | Z-4407 | c-Pent | 2-Br-6-MeO—Ph |
| Z-4408 | c-Bu | 2-Br-3-F—PhCH2— | Z-4409 | c-Pent | c-Hex | Z-4410 | c-Pent | 2,3,4-tri-F—Ph |
| Z-4411 | c-Bu | 2-Br-4-F—PhCH2— | Z-4412 | c-Pent | H2C═CH— | Z-4413 | c-Pent | 2,3,5-tri-F—Ph |
| Z-4414 | c-Bu | 2-Br-5-F—PhCH2— | Z-4415 | c-Pent | H3CCH═CH— | Z-4416 | c-Pent | 2,3,6-tri-F—Ph |
| Z-4417 | c-Bu | 2-Br-6-F—PhCH2— | Z-4418 | c-Pent | H2C═CHCH2— | Z-4419 | c-Pent | 2-Br-3,4-di-r—Ph |
| Z-4420 | c-Bu | 2-F-3-MeO—PhCH2— | Z-4421 | c-Pent | F2C═CH— | Z-4422 | c-Pent | 2-Br-3,5-di-F—Ph |
| Z-4423 | c-Bu | 2-F-4-MeO—PhCH2— | Z-4424 | c-Pent | F2C═CHCH2— | Z-4425 | c-Pent | 2-Br-3,6-di-F—Ph |
| Z-4426 | c-Bu | 2-F-5-MeO—PhCH2— | Z-4427 | c-Pent | HC≡C— | Z-4428 | c-Pent | 2-F-3,4-di-MeO—Ph |
| Z-4429 | c-Bu | 2-F-6-MeO—PhCH2— | Z-4430 | c-Pent | HC≡CCH2— | Z-4431 | c-Pent | 2-F-3,5-di-MeO—Ph |

TABLE 3-continued

| Z | R3 | R4 | Z | R3 | R4 | Z | R3 | R4 |
|---|---|---|---|---|---|---|---|---|
| Z-4432 | c-Bu | 2-Cl-3-MeO—PhCH2— | Z-4433 | c-Pent | HC≡CCH2CH2— | Z-4434 | c-Pent | 2-F-3,6-di-MeO—Ph |
| Z-4435 | c-Bu | 2-Cl-4-MeO—PhCH2— | Z-4436 | c-Pent | H3CC≡CCH2— | Z-4437 | c-Pent | 2-Cl-3,4-di-MeO—Ph |
| Z-4438 | c-Bu | 2-Cl-5-MeO—PhCH2— | Z-4439 | c-Pent | FC≡C— | Z-4440 | c-Pent | 2-Cl-3,5-di-MeO—Ph |
| Z-4441 | c-Bu | 2-Cl-6-MeO—PhCH2— | Z-4442 | c-Pent | FC≡CCF2— | Z-4443 | c-Pent | 2-Cl-3,6-di-MeO—Ph |
| Z-4444 | c-Bu | 2-Br-3-MeO—PhCH2— | Z-4445 | c-Pent | FC≡CCF2CF2— | Z-4446 | c-Pent | 2-Br-3,4-di-MeO—Ph |
| Z-4447 | c-Bu | 2-Br-4-MeO—PhCH2— | Z-4448 | c-Pent | F3CC≡CCF2— | Z-4449 | c-Pent | 2-Br-3,5-di-MeO—Ph |
| Z-4450 | c-Pent | 2-Br-3,6-di-MeO—Ph | Z-4451 | c-Pent | Ph | Z-4452 | c-Hex | 2-MeO—Ph |
| Z-4453 | c-Pent | PhCH2— | Z-4454 | c-Pent | 2-F—Ph | Z-4455 | c-Hex | 3-MeO—Ph |
| Z-4456 | c-Pent | 2-F—PhCH2— | Z-4457 | c-Pent | 2-Cl-3,6-di-MeO—PhCH2— | Z-4458 | c-Hex | 4-MeO—Ph |
| Z-4459 | c-Pent | 3-F—PhCH2— | Z-4460 | c-Pent | 2-Br-3,4-di-MeO—PhCH2— | Z-4461 | c-Hex | 2,3-di-F—Ph |
| Z-4462 | c-Pent | 4-F—PhCH2— | Z-4463 | c-Pent | 2-Br-3,5-di-MeO—PhCH2— | Z-4464 | c-Hex | 2,4-di-F—Ph |
| Z-4465 | c-Pent | 2-Cl—PhCH2— | Z-4466 | c-Pent | 2-Br-3,6-di-MeO—PhCH2— | Z-4467 | c-Hex | 2,5-di-F—Ph |
| Z-4468 | c-Pent | 3-Cl—PhCH2— | Z-4469 | c-Pent | MeS— | Z-4470 | c-Hex | 2,6-di-F—Ph |
| Z-4471 | c-Pent | 4-Cl—PhCH2— | Z-4472 | c-Pent | MeS(=O)— | Z-4473 | c-Hex | 2-Cl-3-F—Ph |
| Z-4474 | c-Pent | 2-Br—PhCH2— | Z-4475 | c-Pent | MeS(=O)2— | Z-4476 | c-Hex | 2-Cl-4-F—Ph |
| Z-4477 | c-Pent | 3-Br—PhCH2— | Z-4478 | c-Pent | EtS— | Z-4479 | c-Hex | 2-Cl-5-F—Ph |
| Z-4480 | c-Pent | 4-Br—PhCH2— | Z-4481 | c-Pent | EtS(=O)— | Z-4482 | c-Hex | 2-Cl-6-F—Ph |
| Z-4483 | c-Pent | 2-I—PhCH2— | Z-4484 | c-Pent | EtS(=O)2— | Z-4485 | c-Hex | 2-Br-3-F—Ph |
| Z-4486 | c-Pent | 3-I—PhCH2— | Z-4487 | c-Pent | PrS— | Z-4488 | c-Hex | 2-Rr-4-F—Ph |
| Z-4489 | c-Pent | 4-I—PhCH2— | Z-4490 | c-Pent | PrS(=O)— | Z-4491 | c-Hex | 2-Br-5-F—Ph |
| Z-4492 | c-Pent | 2-Me—PhCH2— | Z-4493 | c-Pent | PrS(=O)2— | Z-4494 | c-Hex | 2-Br-6-F—Ph |
| Z-4495 | c-Pent | 3-Me—PhCH2— | Z-4496 | c-Pent | Ac | Z-4497 | c-Hex | 2-F-3-MeO—Ph |
| Z-4498 | c-Pent | 4-Me—PhCH2— | Z-4499 | c-Pent | OHC— | Z-4500 | c-Hex | 2-F-4-MeO—Ph |
| Z-4501 | c-Pent | 2-MeO—PhCH2— | Z-4502 | c-Pent | Et(C=O)— | Z-4503 | c-Hex | 2-F-5-MeO—Ph |
| Z-4504 | c-Pent | 3-MeO—PhCH2— | Z-4505 | c-Pent | Pr(C=O)— | Z-4506 | c-Hex | 2-F-6-MeO—Ph |
| Z-4507 | c-Pent | 4-MeO—PhCH2— | Z-4508 | c-Pent | i-Pr(C=O)— | Z-4509 | c-Hex | 2-Cl-3-MeO—Ph |
| Z-4510 | c-Pent | 2,3-di-F—PhCH2— | Z-4511 | c-Pent | Bu(C=O)— | Z-4512 | c-Hex | 2-Cl-4-MeO—Ph |
| Z-4513 | c-Pent | 2,4-di-F—PhCH2— | Z-4514 | c-Pent | MeO(C=O)— | Z-4515 | c-Hex | 2-Cl-5-MeO—Ph |
| Z-4516 | c-Pent | 2,5-di-F—PhCH2— | Z-4517 | c-Pent | EtO(C=O)— | Z-4518 | c-Hex | 2-Cl-6-MeO—Ph |
| Z-4519 | c-Pent | 2,6-di-F—PhCH2— | Z-4520 | c-Pent | PrO(C=O)— | Z-4521 | c-Hex | 2-Br-3-MeO—Ph |
| Z-4522 | c-Pent | 2-Cl-3-F—PhCH2— | Z-4523 | c-Pent | i-PrO(C=O) | Z-4524 | c-Hex | 2-Br-4-MeO—Ph |
| Z-4525 | c-Pent | 2-Cl-4-F—PhCH2— | Z-4526 | c-Pent | BuO(C=O)— | Z-4527 | c-Hex | 2-Br-5-MeO—Ph |
| Z-4528 | c-Pent | 2-Cl-5-F—PhCH2— | Z-4529 | c-Pent | t-BuOC(=O)— | Z-4530 | c-Hex | 2-Br-6-MeO—Ph |
| Z-4531 | c-Pent | 2-Cl-6-F—PhCH2— | Z-4532 | c-Hex | c-Hex | Z-4533 | c-Hex | 2,3,4-tri-F—Ph |
| Z-4534 | c-Pent | 2-Br-3-F—PhCH2— | Z-4535 | c-Hex | H2C=CH— | Z-4536 | c-Hex | 2,3,5-tri-F—Ph |
| Z-4537 | c-Pent | 2-Br-4-F—PhCH2— | Z-4538 | c-Hex | H3CCH=CH— | Z-4539 | c-Hex | 2,3,6-tri-F—Ph |
| Z-4540 | c-Pent | 2-Br-5-F—PhCH2— | Z-4541 | c-Hex | H2C=CHCH2— | Z-4542 | c-Hex | 2-Br-3,4-di-F—Ph |
| Z-4543 | c-Pent | 2-Br-6-F—PhCH2— | Z-4544 | c-Hex | F2C=CH— | Z-4545 | c-Hex | 2-Br-3,5-di-F—Ph |
| Z-4546 | c-Pent | 2-F-3-MeO—PhCH2— | Z-4547 | c-Hex | F2C=CHCH2— | Z-4548 | c-Hex | 2-Br-3,6-di-F—Ph |
| Z-4549 | c-Pent | 2-F-4-MeO—PhCH2— | Z-4550 | c-Hex | HC≡C— | Z-4551 | c-Hex | 2-F-3,4-di-MeO—Ph |
| Z-4552 | c-Pent | 2-F-5-MeO—PhCH2— | Z-4553 | c-Hex | HC≡CCH2— | Z-4554 | c-Hex | 2-F-3,5-di-MeO—Ph |
| Z-4555 | c-Pent | 2-F-6-MeO—PhCH2— | Z-4556 | c-Hex | HC≡CCH2CH2— | Z-4557 | c-Hex | 2-F-3,6-di-MeO—Ph |
| Z-4558 | c-Pent | 2-Cl-3-MeO—PhCH2— | Z-4559 | c-Hex | H3CC≡CCH2— | Z-4560 | c-Hex | 2-Cl-3,4-di-MeO—Ph |
| Z-4561 | c-Pent | 2-Cl-4-MeO—PhCH2— | Z-4562 | c-Hex | FC≡C— | Z-4563 | c-Hex | 2-Cl-3,5-di-MeO—Ph |
| Z-4564 | c-Pent | 2-Cl-5-MeO—PhCH2— | Z-4565 | c-Hex | FC≡CCF2— | Z-4566 | c-Hex | 2-Cl-3,6-di-MeO—Ph |
| Z-4567 | c-Pent | 2-Cl-6-MeO—PhCH2— | Z-4568 | c-Hex | FC≡CCF2CF2— | Z-4569 | c-Hex | 2-Br-3,4-di-MeO—Ph |
| Z-4570 | c-Pent | 2-Br-3-MeO—PhCH2— | Z-4571 | c-Hex | F3CC≡CCF2— | Z-4572 | c-Hex | 2-Br-3,5-di-MeO—Ph |
| Z-4573 | c-Pent | 2-Br-4-MeO—PhCH2— | Z-4574 | c-Hex | Ph | Z-4575 | c-Hex | 2-Br-3,6-di-MeO—Ph |
| Z-4576 | c-Pent | 2-Br-5-MeO—PhCH2— | Z-4577 | c-Hex | 2-F—Ph | Z-4578 | c-Hex | PhCH2— |
| Z-4579 | c-Pent | 2-Br-6-MeO—PhCH2— | Z-4580 | c-Hex | 3-F—Ph | Z-4581 | c-Hex | 2-F—PhCH2— |
| Z-4582 | c-Pent | 2,3,4-tri-F—PhCH2— | Z-4583 | c-Hex | 4-F—Ph | Z-4584 | c-Hex | 3-F—PhCH2— |

TABLE 3-continued

| Z | R3 | R4 | Z | R3 | R4 | Z | R3 | R4 |
|---|---|---|---|---|---|---|---|---|
| Z-4585 | c-Pent | 2,3,5-tri-F—PhCH2— | Z-4586 | c-Hex | 2-Cl—Ph | Z-4587 | c-Hex | 4-F—PhCH2— |
| Z-4588 | c-Pent | 2,3,6-tri-F—PhCH2— | Z-4589 | c-Hex | 3-Cl—Ph | Z-4590 | c-Hex | 2-Cl—PhCH2— |
| Z-4591 | c-Pent | 2-Br-3,4-di-F—PhCH2— | Z-4592 | c-Hex | 4-Cl—Ph | Z-4593 | c-Hex | 3-Cl—PhCH2— |
| Z-4594 | c-Pent | 2-Br-3,5-di-F—PhCH2— | Z-4595 | c-Hex | 2-Br—Ph | Z-4596 | c-Hex | 4-Cl—PhCH2— |
| Z-4597 | c-Pent | 2-Br-3,6-di-F—PhCH2— | Z-4598 | c-Hex | 3-Br—Ph | Z-4599 | c-Hex | 2-Br—PhCH2— |
| Z-4600 | c-Pent | 2-F-3,4-di-MeO—PhCH2— | Z-4601 | c-Hex | 4-Br—Ph | Z-4602 | c-Hex | 3-Br—PhCH2— |
| Z-4603 | c-Pent | 2-F-3,5-di-MeO—PhCH2— | Z-4604 | c-Hex | 2-I—Ph | Z-4605 | c-Hex | 4-Br—PhCH2— |
| Z-4606 | c-Pent | 2-F-3,6-di-MeO—PhCH2— | Z-4607 | c-Hex | 3-I—Ph | Z-4608 | c-Hex | 2-I—PhCH2— |
| Z-4609 | c-Pent | 2-Cl-3,4-di-MeO—PhCH2— | Z-4610 | c-Hex | 4-I—Pb | Z-4611 | c-Hex | 3-I—PhCH2— |
| Z-4612 | c-Pent | 2-Cl-3,5-di-MeO—PhCH2— | Z-4613 | c-Hex | 2-Me—Ph | Z-4614 | c-Hex | 4-I—PhCH2— |
| Z-4615 | c-Hex | 2-Me—PhCH2— | Z-4616 | c-Hex | 3-Me—Ph | Z-4617 | H2C═CH— | 2-F-3-MeO—Ph |
| Z-4618 | c-Hex | 3-Me—PhCH2— | Z-4619 | c-Hex | 4-Me—Ph | Z-4620 | H2C═CH— | 2-F-4-MeO—Ph |
| Z-4621 | c-Hex | 4-Me—PhCH2— | Z-4622 | c-Hex | OHC— | Z-4623 | H2C═CH— | 2-F-5-MeO—Ph |
| Z-4624 | c-Hex | 2-MeO—PhCH2— | Z-4625 | c-Hex | Et(C═O)— | Z-4626 | H2C═CH— | 2-F-6-MeO—Ph |
| Z-4627 | c-Hex | 3-MeO—PhCH2— | Z-4628 | c-Hex | Pr(C═O)— | Z-4629 | H2C═CH— | 2-Cl-3-MeO—Ph |
| Z-4630 | c-Hex | 4-MeO—PhCH2— | Z-4631 | c-Hex | i-Pr(C═O)— | Z-4632 | H2C═CH— | 2-Cl-4-MeO—Ph |
| Z-4633 | c-Hex | 2,3-di-F—PhCH2— | Z-4634 | c-Hex | Bu(C═O)— | Z-4635 | H2C═CH— | 2-Cl-5-MeO—Ph |
| Z-4636 | c-Hex | 2,4-di-F—PhCH2— | Z-4637 | c-Hex | MeO(C═O)— | Z-4638 | H2C═CH— | 2-Cl-6-MeO—Ph |
| Z-4639 | c-Hex | 2,5-di-F—PhCH2— | Z-4640 | c-Hex | EtO(C═O)— | Z-4641 | H2C═CH— | 2-Br-3-MeO—Ph |
| Z-4642 | c-Hex | 2,6-di-F—PhCH2— | Z-4643 | c-Hex | PrO(C═O)— | Z-4644 | H2C═CH— | 2-Br-4-MeO—Ph |
| Z-4645 | c-Hex | 2-Cl-3-F—PhCH2— | Z-4646 | c-Hex | i-PrO(C═O) | Z-4647 | H2C═CH— | 2-Br-5-MeO—Ph |
| Z-4648 | c-Hex | 2-Cl-4-F—PhCH2— | Z-4649 | c-Hex | BuO(C═O)— | Z-4650 | H2C═CH— | 2-Br-6-MeO—Ph |
| Z-4651 | c-Hex | 2-Cl-5-F—PhCH2— | Z-4652 | c-Hex | t-BuOC(═O)— | Z-4653 | H2C═CH— | 2,3,4-tri-F—Ph |
| Z-4654 | c-Hex | 2-Cl-6-F—PhCH2— | Z-4655 | H2C═CH— | H2C═CH— | Z-4656 | H2C═CH— | 7,3,5-tri-F—Ph |
| Z-4657 | c-Hex | 2-Br-3-F—PhCH2— | Z-4658 | H2C═CH— | H3CCH═CH— | Z-4659 | H2C═CH— | 2,3,6-tri-F—Ph |
| Z-4660 | c-Hex | 2-Br-4-F—PhCH2— | Z-4661 | H2C═CH— | H2C═CHCH2— | Z-4662 | H2C═CH— | 2-Br-3,4-di-F—Ph |
| Z-4663 | c-Hex | 2-Br-5-F—PhCH2— | Z-4664 | H2C═CH— | F2C═CH— | Z-4665 | H2C═CH— | 2-Br-3,5-di-F—Ph |
| Z-4666 | c-Hex | 2-Rr-6-F—PhCH2— | Z-4667 | H2C═CH— | F2C═CHCH2— | Z-4668 | H2C═CH— | 2-Br-3,6-di-F—Ph |
| Z-4669 | c-Hex | 2-F-3-MeO—PhCH2— | Z-4670 | H2C═CH— | HC≡C— | Z-4671 | H2C═CH— | 2-F-3,4-di-MeO—Ph |
| Z-4672 | c-Hex | 2-F-4-MeO—PhCH2— | Z-4673 | H2C═CH— | HC≡CCH2— | Z-4674 | H2C═CH— | 2-F-3,5-di-MeO—Ph |
| Z-4675 | c-Hex | 2-F-5-MeO—PhCH2— | Z-4676 | H2C═CH— | HC≡CCH2CH2— | Z-4677 | H2C═CH— | 2-F-3,6-di-MeO—Ph |
| Z-4678 | c-Hex | 2-F-6-MeO—PhCH2— | Z-4679 | H2C═CH— | H3CC≡CCH2— | Z-4680 | H2C═CH— | 2-Cl-3,4-di-MeO—Ph |
| Z-4681 | c-Hex | 2-Cl-3-MeO—PhCH2— | Z-4682 | H2C═CH— | FC≡C— | Z-4683 | H2C═CH— | 2-Cl-3,5-di-MeO—Ph |
| Z-4684 | c-Hex | 2-Cl-4-MeO—PhCH2— | Z-4685 | H2C═CH— | FC≡CCF2— | Z-4686 | H2C═CH— | 2-Cl-3,6-di-MeO—Ph |
| Z-4687 | c-Hex | 2-Cl-5-MeO—PhCH2— | Z-4688 | H2C═CH— | FC≡CCF2CF2— | Z-4689 | H2C═CH— | 2-Br-3,4-di-MeO—Ph |
| Z-4690 | c-Hex | 2-Cl-6-MeO—PhCH2— | Z-4691 | H2C═CH— | F3CC≡CCF2— | Z-4692 | H2C═CH— | 2-Br-3,5-di-MeO—Ph |
| Z-4693 | c-Hex | 2-Br-3-MeO—PhCH2— | Z-4694 | H2C═CH— | Ph | Z-4695 | H2C═CH— | 2-Br-3,6-di-MeO—Ph |
| Z-4696 | c-Hex | 2-Br-4-MeO—PhCH2— | Z-4697 | H2C═CH— | 2-F—Ph | Z-4698 | H2C═CH— | PhCH2— |
| Z-4699 | c-Hex | 2-Br-5-MeO—PhCH2— | Z-4700 | H2C═CH— | 3-F—Ph | Z-4701 | H2C═CH— | 2-F—PhCH2— |
| Z-4702 | c-Hex | 2-Br-6-MeO—PhCH2— | Z-4703 | H2C═CH— | 4-F—Ph | Z-4704 | H2C═CH— | 3-F—PhCH2— |
| Z-4705 | c-Hex | 2,3,4-tri-F—PhCH2— | Z-4706 | H2C═CH— | 2-Cl—Ph | Z-4707 | H2C═CH— | 4-F—PhCH2— |
| Z-4708 | c-Hex | 2,3,5-tri-F—PhCH2— | Z-4709 | H2C═CH— | 3-Cl—Ph | Z-4710 | H2C═CH— | 2-Cl—PhCH2— |
| Z-4711 | c-Hex | 2,3,6-tri-F—PhCH2— | Z-4712 | H2C═CH— | 4-Cl—Ph | Z-4713 | H2C═CH— | 3-Cl—PhCH2— |
| Z-4714 | c-Hex | 2-Br-3,4-di-F—PhCH2— | Z-4715 | H2C═CH— | 2-Br—Ph | Z-4716 | H2C═CH— | 4-Cl—PhCH2— |
| Z-4717 | c-Hex | 2-Br-3,5-di-F—PhCH2 | Z-4718 | H2C═CH— | 3-Br—Ph | Z-4719 | H2C═CH— | 2-Br—PhCH2— |
| Z-4720 | c-Hex | 2-Br-3,6-di-F—PhCH2— | Z-4721 | H2C═CH— | 4-Br—Ph | Z-4722 | H2C═CH— | 3-Br—PhCH2— |
| Z-4723 | c-Hex | 2-F-3,4-di-MeO—PhCH2— | Z-4724 | H2C═CH— | 2-I—Ph | Z-4725 | H2C═CH— | 4-Br—PhCH2— |
| Z-4726 | c-Hex | 2-F-3,5-di-MeO—PhCH2— | Z-4727 | H2C═CH— | 3-I—Ph | Z-4728 | H2C═CH— | 2-I—PhCH2— |
| Z-4729 | c-Hex | 2-F-3,6-di-MeO—PhCH2— | Z-4730 | H2C═CH— | 4-I—Ph | Z-4731 | H2C═CH— | 3-I—PhCH2— |
| Z-4732 | c-Hex | 2-Cl-3,4-di-MeO—PhCH2— | Z-4733 | H2C═CH— | 2-Me—Ph | Z-4734 | H2C═CH— | 4-I—PhCH2— |
| Z-4735 | c-Hex | 2-Cl-3,5-di-MeO—PhCH2— | Z-4736 | H2C═CH— | 3-Me—Ph | Z-4737 | H2C═CH— | 2-Me—PhCH2— |

TABLE 3-continued

| Z | R3 | R4 | Z | R3 | R4 | Z | R3 | R4 |
|---|---|---|---|---|---|---|---|---|
| Z-4738 | c-Hex | 2-Cl-3,6-di-MeO—PhCH2— | Z-4739 | H2C═CH— | 4-Me—Ph | Z-4746 | H2C═CH— | 3-Me—PhCH2— |
| Z-4741 | c-Hex | 2-Br-3,4-di-MeO—PhCH2— | Z-4742 | H2C═CH— | 2-MeO—Ph | Z-4743 | H2C═CH— | 4-Me—PhCH2— |
| Z-4744 | c-Hex | 2-Br-3,5-di-MeO—PhCH2— | Z-4745 | H2C═CH— | 3-MeO—Ph | Z-4746 | H2C═CH— | 2-MeO—PhCH2— |
| Z-4747 | c-Hex | 2-Br-3,6-di-MeO—PhCH2— | Z-4748 | H2C═CH— | 4-MeO—Ph | Z-4749 | H2C═CH— | 3-MeO—PhCH2— |
| Z-4750 | c-Hex | MeS— | Z-4751 | H2C═CH— | 2,3-di-F—Ph | Z-4752 | H2C═CH— | 4-MeO—PhCH2— |
| Z-4753 | c-Hex | MeS(═O)— | Z-4754 | H2C═CH— | 2,4-di-F—Ph | Z-4755 | H2C═CH— | 2,3-di-F—PhCH2— |
| Z-4756 | c-Hex | MeS(═O)2— | Z-4757 | H2C═CH— | 2,5-di-F—Ph | Z-4758 | H2C═CH— | 2,4-di-F—PhCH2— |
| Z-4759 | c-Hex | EtS— | Z-4766 | H2C═CH— | 2,6-di-F—Ph | Z-4761 | H2C═CH— | 2,5-di-F—PhCH2— |
| Z-4762 | c-Hex | EtS(═O)— | Z-4763 | H2C═CH— | 2-Cl-3-F—Ph | Z-4764 | H2C═CH— | 2,6-di-F—PhCH2— |
| Z-4765 | c-Hex | EtS(═O)2— | Z-4766 | H2C═CH— | 2-Cl-4-F—PH | Z-4767 | H2C═CH— | 2-Cl-3-F—PhCH2— |
| Z-4768 | c-Hex | PrS— | Z-4769 | H2C═CH— | 2-Cl-5-F—Ph | Z-4770 | H2C═CH— | 2-Cl-4-F—PhCH2— |
| Z-4771 | c-Hex | PrS(═O)— | Z-4772 | H2C═CH— | 2-Cl-6-F—Ph | Z-4773 | H2C═CH— | 2-Cl-5-F—PhCH2— |
| Z-4774 | c-Hex | PrS(═O)2— | Z-4775 | H2C═CH— | 2-Br-3-F—Ph | Z-4776 | H2C═CH— | 2-Cl-6-F—PhCH2— |
| Z-4777 | c-Hex | Ac | Z-4778 | H2C═CH— | 2-Br-4-F—Ph | Z-4779 | H2C═CH— | 2-Br-3-F—PhCH2— |
| Z-4780 | H2C═CH— | 2-Br-4-F—PhCH2— | Z-4781 | H2C═CH— | 2-Br-5-F—Ph | Z-4782 | H2C═CHCH2— | 4-Cl—PhCH2— |
| Z-4783 | H2C═CH— | 2-Br-5-F—PhCH2— | Z-4784 | H2C═CH— | 2-Br-6-F—Ph | Z-4785 | H2C═CHCH2— | 2-Br—PhCH2— |
| Z-4786 | H2C═CH— | 2-Br-6-F—PhCH2— | Z-4787 | H2C═CHCH2— | 4-Br—Ph | Z-4788 | H2C═CHCH2— | 3-Br—PhCH2— |
| Z-4789 | H2C═CH— | 2-F-3-MeO—PhCH2— | Z-4790 | H2C═CHCH2— | 2-I—Pb | Z-4791 | H2C═CHCH2— | 4-Br—PhCH2— |
| Z-4792 | H2C═CH— | 2-F-4-MeO—PhCH2— | Z-4793 | H2C═CHCH2— | 3-I—Ph | Z-4794 | H2C═CHCH2— | 2-I—PhCH2— |
| Z-4795 | H2C═CH— | 2-F-5-MeO—PhCH2— | Z-4796 | H2C═CHCH2— | 4-I—Ph | Z-4797 | H2C═CHCH2— | 3-I—PhCH2— |
| Z-4798 | H2C═CH— | 2-F-6-MeO—PhCH2— | Z-4799 | H2C═CHCH2— | 2-Me—Ph | Z-4800 | H2C═CHCH2— | 4-I—PhCH2— |
| Z-4801 | H2C═CH— | 2-Cl-3-MeO—PhCH2— | Z-4802 | H2C═CHCH2— | 3-Me—Ph | Z-4803 | H2C═CHCH2— | 2-Me—PhCH2— |
| Z-4804 | H2C═CH— | 2-Cl-4-MeO—PhCH2— | Z-4805 | H2C═CHCH2— | 4-Me—Ph | Z-4806 | H2C═CHCH2— | 3-Me—PhCH2— |
| Z-4807 | H2C═CH— | 2-Cl-5-MeO—PhCH2— | Z-4808 | H2C═CHCH2— | 2-MeO—Ph | Z-4809 | H2C═CHCH2— | 4-Me—PhCH2— |
| Z-4810 | H2C═CH— | 2-Cl-6-MeO—PhCH2— | Z-4811 | H2C═CHCH2— | 3-MeO—Ph | Z-4812 | H2C═CHCH2— | 2-MeO—PhCH2— |
| Z-4813 | H2C═CH— | 2-Br-3-MeO—PhCH2— | Z-4814 | H2C═CHCH2— | 4-MeO—Ph | Z-4815 | H2C═CHCH2— | 3-MeO—PhCH2— |
| Z-4816 | H2C═CH— | 2-Br-4-MeO—PhCH2— | Z-4817 | H2C═CHCH2— | 2,3-di-F—Ph | Z-4818 | H2C═CHCH2— | 4-MeO—PhCH2— |
| Z-4819 | H2C═CH— | 2-Br-5-MeO—PhCH2— | Z-4820 | H2C═CHCH2— | 2,4-di-F—Ph | Z-4821 | H2C═CHCH2— | 2,3-di-F—PhCH2— |
| Z-4822 | H2C═CH— | 2-Br-6-MeO—PhCH2— | Z-4823 | H2C═CHCH2— | 2,5-di-F—Ph | Z-4824 | H2C═CHCH2— | 2,4-di-F—PhCH2— |
| Z-4825 | H2C═CH— | 2,3,4-tri-F—PhCH2— | Z-4826 | H2C═CHCH2— | 2,6-di-F—Ph | Z-4827 | H2C═CHCH2— | 2,5-di-F—PhCH2— |
| Z-4828 | H2C═CH— | 2,3,5-tri-F—PhCH2— | Z-4829 | H2C═CHCH2— | 2-Cl-3-F—Ph | Z-4830 | H2C═CHCH2— | 2,6-di-F—PhCH2— |
| Z-4831 | H2C═CH— | 2,3,6-tri-F—PhCH2— | Z-4832 | H2C═CHCH2— | 2-Cl-4-F—Ph | Z-4833 | H2C═CHCH2— | 2-Cl-3-F—PhCH2— |
| Z-4834 | H2C═CH— | 2-Br-3,4-di-F—PhCH2— | Z-4835 | H2C═CHCH2— | 2-Cl-5-F—Ph | Z-4836 | H2C═CHCH2— | 2-Cl-4-F—PhCH2— |
| Z-4837 | H2C═CH— | 2-Br-3,5-di-F—PhCH2— | Z-4838 | H2C═CHCH2— | 2-Cl-6-F—Ph | Z-4839 | H2C═CHCH2— | 2-Cl-5-F—PhCH2— |
| Z-4840 | H2C═CH— | 2-Br-3,6-di-F—PhCH2— | Z-4841 | H2C═CHCH2— | 2-Br-3-F—Ph | Z-4842 | H2C═CHCH2— | 2-Cl-6-F—PhCH2— |
| Z-4843 | H2C═CH— | 2-F-3,4-di-MeO—PhCH2— | Z-4844 | H2C═CHCH2— | 2-Br-4-F—Ph | Z-4845 | H2C═CHCH2— | 2-Br-3-F—PhCH2— |
| Z-4846 | H2C═CH— | 2-F-3,5-di-MeO—PhCH2— | Z-4847 | H2C═CHCH2— | 2-Br-5-F—Ph | Z-4848 | H2C═CHCH2— | 2-Br-4-F—PhCH2— |
| Z-4849 | H2C═CH— | 2-F-3,6-di-MeO—PhCH2— | Z-4850 | H2C═CHCH2— | 2-Br-6-F—Pb | Z-4851 | H2C═CHCH2— | 2-Br-5-F—PhCH2— |
| Z-4852 | H2C═CH— | 2-Cl-3,4-di-MeO—PhCH2— | Z-4853 | H2C═CHCH2— | 2-F-3-MeO—Ph | Z-4854 | H2C═CHCH2— | 2-Br-6-F—PhCH2— |
| Z-4855 | H2C═CH— | 2-Cl-3,5-di-MeO—PhCH2— | Z-4856 | H2C═CHCH2— | 2-F-4-MeO—Ph | Z-4857 | H2C═CHCH2— | 2-F-3-MeO—PhCH2— |
| Z-4858 | H2C═CH— | 2-Cl-3,6-di-MeO—PhCH2— | Z-4859 | H2C═CHCH2— | 2-F-5-MeO—Ph | Z-4860 | H2C═CHCH2— | 2-F-4-MeO—PhCH2— |
| Z-4861 | H2C═CH— | 2-Br-3,4-di-MeO—PhCH2— | Z-4862 | H2C═CHCH2— | 2-F-6-MeO—Ph | Z-4863 | H2C═CHCH2— | 2-F-5-MeO—PhCH2— |
| Z-4864 | H2C═CH— | 2-Br-3,5-di-MeO—PhCH2— | Z-4865 | H2C═CHCH2— | 2-Cl-3-MeO—Ph | Z-4866 | H2C═CHCH2— | 2-F-6-MeO—PhCH2— |
| Z-4867 | H2C═CH— | 2-Br-3,6-di-MeO—PhCH2— | Z-4868 | H2C═CHCH2— | 2-Cl-4-MeO—Ph | Z-4869 | H2C═CHCH2— | 2-Cl-3-MeO—PhCH2— |
| Z-4870 | H2C═CH— | MeS— | Z-4871 | H2C═CHCH2— | 2-Cl-5-MeO—Ph | Z-4872 | H2C═CHCH2— | 2-Cl-4-MeO—PhCH2— |
| Z-4873 | H2C═CH— | MeS(═O)— | Z-4874 | H2C═CHCH2— | 2-Cl-6-MeO—Ph | Z-4875 | H2C═CHCH2— | 2-Cl-5-MeO—PhCH2— |
| Z-4876 | H2C═CH— | MeS(═O)2— | Z-4877 | H2C═CHCH2— | 2-Br-3-MeO—Ph | Z-4878 | H2C═CHCH2— | 2-Cl-6-MeO—PhCH2— |
| Z-4879 | H2C═CH— | EtS— | Z-4880 | H2C═CHCH2— | 2-Br-4-MeO—Ph | Z-4881 | H2C═CHCH2— | 2-Br-3-MeO—PhCH2— |
| Z-4882 | H2C═CH— | EtS(═O)— | Z-4883 | H2C═CHCH2— | 2-Br-5-MeO—Ph | Z-4884 | H2C═CHCH2— | 2-Br-4-MeO—PhCH2— |
| Z-4885 | H2C═CH— | EtS(═O)2— | Z-4886 | H2C═CHCH2— | 2-Br-6-MeO—Ph | Z-4887 | H2C═CHCH2— | 2-Br-5-MeO—PhCH2— |
| Z-4888 | H2C═CH— | PrS— | Z-4889 | H2C═CHCH2— | 2,3,4-tri-F—Ph | Z-4890 | H2C═CHCH2— | 2-Br-6-MeO—PhCH2— |

TABLE 3-continued

| Z | R3 | R4 | Z | R3 | R4 | Z | R3 | R4 |
|---|---|---|---|---|---|---|---|---|
| Z-4891 | H2C═CH— | PrS(═O)— | Z-4892 | H2C═CHCH2— | 2,3,5-tri-F—Ph | Z-4893 | H2C═CHCH2— | 2,3,4-tri-F—PhCH2— |
| Z-4894 | H2C═CH— | PrS(═O)2— | Z-4895 | H2C═CHCH2— | 2,3,6-tri-F—Ph | Z-4896 | H2C═CHCH2— | 2,3,5-tri-F—PhCH2— |
| Z-4897 | H2C═CH— | Ac | Z-4898 | H2C═CHCH2— | 2-Br-3,4-di-F—Ph | Z-4899 | H2C═CHCH2— | 2,3,6-tri-F—PhCH2— |
| Z-4900 | H2C═CH— | OHC— | Z-4901 | H2C═CHCH2— | 2-Br-3,5-di-F—Ph | Z-4902 | H2C═CHCH2— | 2-Br-3,4-di-F—PhCH2— |
| Z-4903 | H2C═CH— | Et(C═O)— | Z-4904 | H2C═CHCH2— | 2-Br-3,6-di-F—Ph | Z-4905 | H2C═CHCH2— | 2-Br-3,5-di-F—PhCH2— |
| Z-4906 | H2C═CH— | Pr(C═O)— | Z-4907 | H2C═CHCH2— | 2-F-3,4-di-MeO—Ph | Z-4908 | H2C═CHCH2— | 2-Br-3,6-di-F—PhCH2— |
| Z-4909 | H2C═CH— | i-Pr(C═O)— | Z-4910 | H2C═CHCH2— | 2-F-3,5-di-MeO—Ph | Z-4911 | H2C═CHCH2— | 2-F-3,4-di-MeO—PhCH2— |
| Z-4912 | H2C═CH— | Bu(C═O)— | Z-4913 | H2C═CHCH2— | 2-F-3,6-di-MeO—Ph | Z-4914 | H2C═CHCH2— | 2-F-3,5-di-MeO—PhCH2— |
| Z-4915 | H2C═CH— | MeO(C═O)— | Z-4916 | H2C═CHCH2— | 2-Cl-3,4-di-MeO—Ph | Z-4917 | H2C═CHCH2— | 2-F-3,6-di-MeO—PhCH2— |
| Z-4918 | H2C═CH— | EtO(C═O)— | Z-4919 | H2C═CHCH2— | 2-Cl-3,5-di-MeO—Ph | Z-4920 | H2C═CHCH2— | 2-Cl-3,4-di-MeO—PhCH2— |
| Z-4921 | H2C═CH— | PrO(C═O)— | Z-4922 | H2C═CHCH2— | 2-Cl-3,6-di-MeO—Ph | Z-4923 | H2C═CHCH2— | 2-Cl-3,5-di-MeO—PhCH2— |
| Z-4924 | H2C═CH— | i-PrO(C═O)— | Z-4925 | H2C═CHCH2— | 2-Br-3,4-di-MeO—Ph | Z-4926 | H2C═CHCH2— | 2-Cl-3,6-di-MeO—PhCH2— |
| Z-4927 | H2C═CH— | BuO(C═O)— | Z-4928 | H2C═CHCH2— | 2-Br-3,5-di-MeO—Ph | Z-4929 | H2C═CHCH2— | 2-Br-3,4-di-MeO—PhCH2— |
| Z-4930 | H2C═CH— | t-BuOC(═O)— | Z-4931 | H2C═CHCH2— | 2-Br-3,6-di-MeO—Ph | Z-4932 | H2C═CHCH2— | 2-Br-3,5-di-MeO—PhCH2— |
| Z-4933 | H2C═CHCH2— | H2C═CHCH2— | Z-4934 | H2C═CHCH2— | PhCH2— | Z-4935 | H2C═CHCH2— | 2-Br-3,6-di-MeO—PhCH2— |
| Z-4936 | H2C═CHCH2— | F2C═CH— | Z-4937 | H2C═CHCH2— | 2-F—PhCH2— | Z-4938 | H2C═CHCH2— | MeS— |
| Z-4939 | H2C═CHCH2— | F2C═CHCH2— | Z-4940 | H2C═CHCH2— | 3-F—PhCH2— | Z-4941 | H2C═CHCH2— | MeS(═O)— |
| Z-4942 | H2C═CHCH2— | HC≡C— | Z-4943 | H2C═CHCH2— | 4-F—PhCH2— | Z-4944 | H2C═CHCH2— | MeS(═O)2— |
| Z-4945 | H2C═CHCH2— | HC≡CCH2— | Z-4946 | H2C═CHCH2— | 2-Cl—PhCH2— | Z-4947 | F2C═CHCH2— | 2,3,4-tri-F—PhCH2— |
| Z-4948 | H2C═CHCH2— | HC≡CCH2CH2— | Z-4949 | H2C═CHCH2— | 3-Cl—PhCH2— | Z-4950 | F2C═CHCH2— | 2,3,5-tri-F—PhCH2— |
| Z-4951 | H2C═CHCH2— | H3CC≡CCH2— | Z-4952 | F2C═CHCH2— | 2-Br-3,4-di-F—Ph | Z-4953 | F2C═CHCH2— | 2,3,6-tri-F—PhCH2— |
| Z-4954 | H2C═CHCH2— | FC≡C— | Z-4955 | F2C═CHCH2— | 2-Br-3,5-di-F—Ph | Z-4956 | F2C═CHCH2— | 2-Br-3,4-di-F—PhCH2— |
| Z-4957 | H2C═CHCH2— | FC≡CCF2— | Z-4958 | F2C═CHCH2— | 2-Br-3,6-di-F—Ph | Z-4959 | F2C═CHCH2— | 2-Br-3,5-di-F—PhCH2— |
| Z-4960 | H2C═CHCH2— | FC≡CCF2CF2— | Z-4961 | F2C═CHCH2— | 2-F-3,4-di-MeO—Ph | Z-4962 | F2C═CHCH2— | 2-Br-3,6-di-F—PhCH2— |
| Z-4963 | H2C═CHCH2— | F3CC≡CCF2— | Z-4964 | F2C═CHCH2— | 2-F-3,5-di-MeO—Ph | Z-4965 | F2C═CHCH2— | 2-F-3,4-di-MeO—PhCH2— |
| Z-4966 | H2C═CHCH2— | Ph | Z-4967 | F2C═CHCH2— | 2-F-3,6-di-MeO—Ph | Z-4968 | F2C═CHCH2— | 2-F-3,5-di-MeO—PhCH2— |
| Z-4969 | H2C═CHCH2— | 2-F—Ph | Z-4970 | F2C═CHCH2— | 2-Cl-3,4-di-MeO—Ph | Z-4971 | F2C═CHCH2— | 2-F-3,6-di-MeO—PhCH2— |
| Z-4972 | H2C═CHCH2— | 3-F—Ph | Z-4973 | F2C═CHCH2— | 2-Cl-3,5-di-MeO—Ph | Z-4974 | F2C═CHCH2— | 2-Cl-3,4-di-MeO—PhCH2— |
| Z-4975 | H2C═CHCH2— | 4-F—Ph | Z-4976 | F2C═CHCH2— | 2-Cl-3,6-di-MeO—Ph | Z-4977 | F2C═CHCH2— | 2-Cl-3,5-di-MeO—PhCH2— |
| Z-4978 | H2C═CHCH2— | 2-Cl—Ph | Z-4979 | F2C═CHCH2— | 2-Br-3,4-di-MeO—Ph | Z-4980 | F2C═CHCH2— | 2-Cl-3,6-di-MeO—PhCH2— |
| Z-4981 | H2C═CHCH2— | 3-Cl—Ph | Z-4982 | F2C═CHCH2— | 2-Br-3,5-di-MeO—Ph | Z-4983 | F2C═CHCH2— | 2-Br-3,4-di-MeO—PhCH2— |
| Z-4984 | H2C═CHCH2— | 4-Cl—Ph | Z-4985 | F2C═CHCH2— | 2-Br-3,6-di-MeO—Ph | Z-4986 | F2C═CHCH2— | 2-Br-3,5-di-MeO—PhCH2— |
| Z-4987 | H2C═CHCH2— | 2-Br—Ph | Z-4988 | F2C═CHCH2— | PhCH2— | Z-4989 | F2C═CHCH2— | 2-Br-3,6-di-MeO—PhCH2— |
| Z-4990 | H2C═CHCH2— | 3-Br—Ph | Z-4991 | F2C═CHCH2— | 2-F—PhCH2— | Z-4992 | F2C═CHCH2— | MeS— |
| Z-4993 | H2C═CHCH2— | EtS— | Z-4994 | F2C═CHCH2— | 3-F—PhCH2— | Z-4995 | F2C═CHCH2— | MeS(═O)— |
| Z-4996 | H2C═CHCH2— | EtS(═O)— | Z-4997 | F2C═CHCH2— | 4-F—PhCH2— | Z-4998 | F2C═CHCH2— | MeS(═O)2— |
| Z-4999 | H2C═CHCH2— | EtS(═O)2— | Z-5000 | F2C═CHCH2— | 2-Cl—PhCH2— | Z-5001 | F2C═CHCH2— | EtS— |
| Z-5002 | H2C═CHCH2— | PrS— | Z-5003 | F2C═CHCH2— | 3-Cl—PhCH2— | Z-5004 | F2C═CHCH2— | EtS(═O)— |
| Z-5005 | H2C═CHCH2— | PrS(═O)— | Z-5006 | F2C═CHCH2— | 4-Cl—PhCH2— | Z-5007 | F2C═CHCH2— | EtS(═O)2— |
| Z-5008 | H2C═CHCH2— | PrS(═O)2— | Z-5009 | F2C═CHCH2— | 2-Br—PhCH2— | Z-5010 | F2C═CHCH2— | PrS— |
| Z-5011 | H2C═CHCH2— | Ac | Z-5012 | F2C═CHCH2— | 3-Br—PhCH2— | Z-5013 | F2C═CHCH2— | PrS(═O)— |
| Z-5014 | H2C═CHCH2— | OHC— | Z-5015 | F2C═CHCH2— | 4-Br—PhCH2— | Z-5016 | F2C═CHCH2— | PrS(═O)2— |
| Z-5017 | H2C═CHCH2— | Et(C═O)— | Z-5018 | F2C═CHCH2— | 2-I—PhCH2— | Z-5019 | F2C═CHCH2— | Ac |
| Z-5020 | H2C═CHCH2— | Pr(C═O)— | Z-5021 | F2C═CHCH2— | 3-I—PhCH2— | Z-5922 | F2C═CHCH2— | OHC— |
| Z-5023 | H2C═CHCH2— | i-Pr(C═O)— | Z-5024 | F2C═CHCH2— | 4-I—PhCH2— | Z-5025 | F2C═CHCH2— | Et(C═O)— |
| Z-5026 | H2C═CHCH2— | Bu(C═O)— | Z-5027 | F2C═CHCH2— | 2-Me—PhCH2— | Z-5028 | F2C═CHCH2— | Pr(C═O)— |
| Z-5029 | H2C═CHCH2— | MeO(C═O)— | Z-5030 | F2C═CHCH2— | 3-Me—PhCH2— | Z-5031 | F2C═CHCH2— | i-Pr(C═O)— |
| Z-5032 | H2C═CHCH2— | EtO(C═O)— | Z-5033 | F2C═CHCH2— | 4-Me—PhCH2— | Z-5034 | F2C═CHCH2— | Bu(C═O)— |
| Z-5035 | H2C═CHCH2— | PrO(C═O)— | Z-5036 | F2C═CHCH2— | 2-MeO—PhCH2— | Z-5037 | F2C═CHCH2— | MeO(C═O)— |
| Z-5038 | H2C═CHCH2— | i-PrO(C═O)— | Z-5039 | F2C═CHCH2— | 3-MeO—PhCH2— | Z-5040 | F2C═CHCH2— | EtO(C═O)— |
| Z-5041 | H2C═CHCH2— | BuO(C═O)— | Z-5042 | F2C═CHCH2— | 4-MeO—PhCH2— | Z-5043 | F2C═CHCH2— | PrO(C═O)— |

TABLE 3-continued

| Z | R3 | R4 | Z | R3 | R4 | Z | R3 | R4 |
|---|---|---|---|---|---|---|---|---|
| Z-5044 | H2C═CHCH2— | t-BuOC(═O)— | Z-5045 | F2C═CHCH2— | 2,3-di-F—PhCH2— | Z-5046 | F2C═CHCH2— | i-PrO(C═O)— |
| Z-5047 | F2C═CHCH2— | F2C═CHCH2— | Z-5048 | F2C═CHCH2— | 2,4-di-F—PhCH2— | Z-5049 | F2C═CHCH2— | BuO(C═O)— |
| Z-5050 | F2C═CHCH2— | HC≡C— | Z-5051 | F2C═CHCH2— | 2,5-di-F—PhCH2— | Z-5052 | F2C═CHCH2— | t-BuOC(═O)— |
| Z-5053 | F2C═CHCH2— | HC≡CCH2— | Z-5054 | F2C═CHCH2— | 2,6-di-F—PhCH2— | Z-5055 | HC≡C— | HC≡C— |
| Z-5056 | F2C═CHCH2— | HC≡CCH2CH2— | Z-5057 | F2C═CHCH2— | 2-Cl-3-F—PhCH2— | Z-5058 | HC≡C— | HC≡CCH2— |
| Z-5059 | F2C═CHCH2— | H3CC≡CCH2— | Z-5060 | F2C═CHCH2— | 2-Cl-4-F—PhCH2— | Z-5061 | HC≡C— | HC≡CCH2CH2— |
| Z-5062 | F2C═CHCH2— | FC≡C— | Z-5063 | F2C═CHCH2— | 2-Cl-5-F—PhCH2— | Z-5064 | HC≡C— | H3CC≡CCH2— |
| Z-5065 | F2C═CHCH2— | FC≡CCF2— | Z-5066 | F2C═CHCH2— | 2-Cl-6-F—PhCH2— | Z-5067 | HC≡C— | FC≡C— |
| Z-5068 | F2C═CHCH2— | FC≡CCF2CF2— | Z-5069 | F2C═CHCH2— | 2-Br-3-F—PhCH2— | Z-5070 | HC≡C— | FC≡CCF2— |
| Z-5071 | F2C═CHCH2— | F3CC≡CCF2— | Z-5072 | F2C═CHCH2— | 2-Br-4-F—PhCH2— | Z-5073 | HC≡C— | FC≡CCF2CF2— |
| Z-5074 | F2C═CHCH2— | Ph | Z-5075 | F2C═CHCH2— | 2-Br-5-F—PhCH2— | Z-5076 | HC≡C— | F3CC≡CCF2— |
| Z-5077 | F2C═CHCH2— | 2-F—Ph | Z-5078 | F2C═CHCH2— | 2-Br-6-F—PhCH2— | Z-5079 | HC≡C— | Ph |
| Z-5080 | F2C═CHCH2— | 3-F—Ph | Z-5081 | F2C═CHCH2— | 2-F-3-MeO—PhCH2— | Z-5082 | HC≡C— | 2-F—Ph |
| Z-5083 | F2C═CHCH2— | 4-F—Ph | Z-5084 | F2C═CHCH2— | 2-F-4-MeO—PhCH2— | Z-5085 | HC≡C— | 3-F—Ph |
| Z-5086 | F2C═CHCH2— | 2-Cl—Ph | Z-5087 | F2C═CHCH2— | 2-F-5-MeO—PhCH2— | Z-5088 | HC≡C— | 4-F—Ph |
| Z-5089 | F2C═CHCH2— | 3-Cl—Ph | Z-5090 | F2C═CHCH2— | 2-F-6-MeO—PhCH2— | Z-5091 | HC≡C— | 2-Cl—Ph |
| Z-5092 | F2C═CHCH2— | 4-Cl—Ph | Z-5093 | F2C═CHCH2— | 2-Cl-3-MeO—PhCH2— | Z-5094 | HC≡C— | 3-Cl—Ph |
| Z-5095 | F2C═CHCH2— | 2-Br—Ph | Z-5096 | F2C═CHCH2— | 2-Cl-4-MeO—PhCH2— | Z-5097 | HC≡C— | 4-Cl—Ph |
| Z-5098 | F2C═CHCH2— | 3-Br—Ph | Z-5099 | F2C═CHCH2— | 2-Cl-5-MeO—PhCH2— | Z-5100 | HC≡C— | 2-Br—Ph |
| Z-5101 | F2C═CHCH2— | 4-Br—Ph | Z-5102 | F2C═CHCH2— | 2-Cl-6-MeO—PhCH2— | Z-5103 | HC≡C— | 3-Br—Ph |
| Z-5104 | F2C═CHCH2— | 2-I—Ph | Z-5105 | F2C═CHCH2— | 2-Br-3-MeO—PhCH2— | Z-5106 | HC≡C— | 4-Br—Ph |
| Z-5107 | F2C═CHCH2— | 3-I—Ph | Z-5108 | F2C═CHCH2— | 2-Br-4-MeO—PhCH2— | Z-5109 | HC≡C— | 2-I—Ph |
| Z-5110 | F2C═CHCH2— | 4-I—Ph | Z-5111 | F2C═CHCH2— | 2-Br-5-MeO—PhCH2— | Z-5112 | HC≡C— | EtS(═O)2— |
| Z-5113 | F2C═CHCH2— | 2-Me—Ph | Z-5114 | F2C═CHCH2— | 2-Br-6-MeO—PhCH2— | Z-5115 | HC≡C— | PrS— |
| Z-5116 | F2C═CHCH2— | 3-Me—Ph | Z-5117 | HC≡C— | 3-Br—PhCH2— | Z-5118 | HC≡C— | PrS(═O)— |
| Z-5119 | F2C═CHCH2— | 4-Me—Ph | Z-5120 | HC≡C— | 4-Br—PhCH2— | Z-5121 | HC≡C— | PrS(═O)2— |
| Z-5122 | F2C═CHCH2— | 2-MeO—Ph | Z-5123 | HC≡C— | 2-I—PhCH2— | Z-5124 | HC≡C— | Ac |
| Z-5125 | F2C═CHCH2— | 3-MeO—Ph | Z-5126 | HC≡C— | 3-I—PhCH2— | Z-5127 | HC≡C— | OHC— |
| Z-5128 | F2C═CHCH2— | 4-MeO—Ph | Z-5129 | HC≡C— | 4-I—PhCH2— | Z-5130 | HC≡C— | Et(C═O)— |
| Z-5131 | F2C═CHCH2— | 2,3-di-F—Ph | Z-5132 | HC≡C— | 2-Me—PhCH2— | Z-5133 | HC≡C— | Pr(C═O)— |
| Z-5134 | F2C═CHCH2— | 2,4-di-F—Ph | Z-5135 | HC≡C— | 3-Me—PhCH2— | Z-5136 | HC≡C— | i-Pr(C═O)— |
| Z-5137 | F2C═CHCH2— | 2,5-di-F—Ph | Z-5138 | HC≡C— | 4-Me—PhCH2— | Z-5139 | HC≡C— | Bu(C═O)— |
| Z-5140 | F2C═CHCH2— | 2,6-di-F—Ph | Z-5141 | HC≡C— | 2-MeO—PhCH2— | Z-5142 | HC≡C— | MeO(C═O)— |
| Z-5143 | F2C═CHCH2— | 2-Cl-3-F—Ph | Z-5144 | HC≡C— | 3-MeO—PhCH2— | Z-5145 | HC≡C— | EtO(C═O)— |
| Z-5146 | F2C═CHCH2— | 2-Cl-4-F—Ph | Z-5147 | HC≡C— | 4-MeO—PhCH2— | Z-5148 | HC≡C— | PrO(C═O)— |
| Z-5149 | F2C═CHCH2— | 2-Cl-5-F—Ph | Z-5150 | HC≡C— | 2,3-di-F—PhCH2— | Z-5151 | HC≡C— | i-PrO(C═O)— |
| Z-5152 | F2C═CHCH2— | 2-Cl-6-F—Ph | Z-5153 | HC≡C— | 2,4-di-F—PhCH2— | Z-5154 | HC≡C— | BuO(C═O)— |
| Z-5155 | F2C═CHCH2— | 2-Br-3-F—Ph | Z-5156 | HC≡C— | 2,5-di-F—PhCH2— | Z-5157 | HC≡C— | t-BuOC(═O)— |
| Z-5158 | F2C═CHCH2— | 2-Br-4-F—Ph | Z-5159 | HC≡C— | 2,6-di-F—PhCH2— | Z-5160 | HC≡CCH2— | HC≡CCH2— |
| Z-5161 | F2C═CHCH2— | 2-Br-5-F—Ph | Z-5162 | HC≡C— | 2-Cl-3-F—PhCH2— | Z-5163 | HC≡CCH2— | HC≡CCH2CH2— |
| Z-5164 | F2C═CHCH2— | 2-Br-6-F—Ph | Z-5165 | HC≡C— | 2-Cl-4-F—PhCH2— | Z-5166 | HC≡CCH2— | H3CC≡CCH2— |
| Z-5167 | F2C═CHCH2— | 2-F-3-MeO—Ph | Z-5168 | HC≡C— | 2-Cl-5-F—PhCH2 | Z-5169 | HC≡CCH2— | FC≡C— |
| Z-5170 | F2C═CHCH2— | 2-F-4-MeO—Ph | Z-5171 | HC≡C— | 2-Cl-6-F—PhCH2— | Z-5172 | HC≡CCH2— | FC≡CCF2— |
| Z-5173 | F2C═CHCH2— | 2-F-5-MeO—Ph | Z-5174 | HC≡C— | 2-Br-3-F—PhCH2— | Z-5175 | HC≡CCH2— | FC≡CCF2CF2— |
| Z-5176 | F2C═CHCH2— | 2-F-6-MeO—Ph | Z-5177 | HC≡C— | 2-Br-4-F—PhCH2— | Z-5178 | HC≡CCH2— | F3CC≡CCF2— |
| Z-5179 | F2C═CHCH2— | 2-Cl-3-MeO—Ph | Z-5180 | HC≡C— | 2-Br-5-F—PhCH2— | Z-5181 | HC≡CCH2— | Ph |
| Z-5182 | F2C═CHCH2— | 2-Cl-4-MeO—Ph | Z-5183 | HC≡C— | 2-Br-6-F—PhCH2— | Z-5184 | HC≡CCH2— | 2-F—Ph |
| Z-5185 | F2C═CHCH2— | 2-Cl-5-MeO—Ph | Z-5186 | HC≡C— | 2-F-3-MeO—PhCH2— | Z-5187 | HC≡CCH2— | 3-F—Ph |
| Z-5188 | F2C═CHCH2— | 2-Cl-6-MeO—Ph | Z-5189 | HC≡C— | 2-F-4-MeO—PhCH2— | Z-5190 | HC≡CCH2— | 4-F—Ph |
| Z-5191 | F2C═CHCH2— | 2-Br-3-MeO—Ph | Z-5192 | HC≡C— | 2-F-5-MeO—PhCH2— | Z-5193 | HC≡CCH2— | 2-Cl—Ph |
| Z-5194 | F2C═CHCH2— | 2-Br-4-MeO—Ph | Z-5195 | HC≡C— | 2-F-6-MeO—PhCH2— | Z-5196 | HC≡CCH2— | 3-Cl—Ph |

TABLE 3-continued

| Z | R3 | R4 | Z | R3 | R4 | Z | R3 | R4 |
|---|---|---|---|---|---|---|---|---|
| Z-5197 | F2C═CHCH2— | 2-Br-5-MeO—Ph | Z-5198 | HC≡C— | 2-Cl-3-MeO—PhCH2— | Z-5199 | HC≡CCH2— | 4-Cl—Ph |
| Z-5200 | F2C═CHCH2— | 2-Br-6-MeO—Ph | Z-5201 | HC≡C— | 2-Cl-4-MeO—PhCH2— | Z-5202 | HC≡CCH2— | 2-Br—Ph |
| Z-5203 | F2C═CHCH2— | 2,3,4-tri-F—Ph | Z-5204 | HC≡C— | 2-Cl-5-MeO—PhCH2— | Z-5205 | HC≡CCH2— | 3-Br—Ph |
| Z-5206 | F2C═CHCH2— | 2,3,5-tri-F—Ph | Z-5207 | HC≡C— | 2-Cl-6-MeO—PhCH2— | Z-5208 | HC≡CCH2— | 4-Br—Ph |
| Z-5209 | F2C═CHCH2— | 2,3,6-tri-F—Ph | Z-5210 | HC≡C— | 2-Br-3-MeO—PhCH2— | Z-5211 | HC≡CCH2— | 2-I—Ph |
| Z-5212 | HC≡C— | 3-I—Ph | Z-5213 | HC≡C— | 2-Br-4-MeO—PhCH2— | Z-5214 | HC≡CCH2— | 3-I—Ph |
| Z-5215 | HC≡C— | 4-I—Ph | Z-5216 | HC≡C— | 2-Br-5-MeO—PhCH2— | Z-5217 | HC≡CCH2— | 4-I—Ph |
| Z-5218 | HC≡C— | 2-Me—Ph | Z-5219 | HC≡C— | 2-Br-6-MeO—PhCH2— | Z-5220 | HC≡CCH2— | 2-Me—Ph |
| Z-5221 | HC≡C— | 3-Me—Ph | Z-5222 | HC≡C— | 2,3,4-tri-F—PhCH2— | Z-5223 | HC≡CCH2— | 3-Me—Ph |
| Z-5224 | HC≡C— | 4-Me—Ph | Z-5225 | HC≡C— | 2,3,5-tri-F—PhCH2— | Z-5226 | HC≡CCH2— | 4-Me—Ph |
| Z-5227 | HC≡C— | 2-MeO—Ph | Z-5228 | HC≡C— | 2,3,6-tri-F—PhCH2— | Z-5229 | HC≡CCH2— | 2-MeO—Ph |
| Z-5230 | HC≡C— | 3-MeO—Ph | Z-5231 | HC≡C— | 2-Br-3,4-di-F—PhCH2— | Z-5232 | HC≡CCH2— | 3-MeO—Ph |
| Z-5233 | HC≡C— | 4-MeO—Ph | Z-5234 | HC≡C— | 2-Br-3,5-di-F—PhCH2— | Z-5235 | HC≡CCH2— | 4-MeO—Ph |
| Z-5236 | HC≡C— | 2,3-di-F—Ph | Z-5237 | HC≡C— | 2-Br-3,6-di-F—PhCH2— | Z-5238 | HC≡CCH2— | 2,3-di-F—Ph |
| Z-5239 | HC≡C— | 2,4-di-F—Ph | Z-5240 | HC≡C— | 2-F-3,4-di-MeO—PhCH2— | Z-5241 | HC≡CCH2— | 2,4-di-F—Ph |
| Z-5242 | HC≡C— | 2,5-di-F—Ph | Z-5243 | HC≡C— | 2-F-3,5-di-MeO—PhCH2— | Z-5244 | HC≡CCH2— | 2,5-di-F—Ph |
| Z-5245 | HC≡C— | 2,6-di-F—Ph | Z-5246 | HC≡C— | 2-F-3,6-di-MeO—PhCH2— | Z-5247 | HC≡CCH2— | 2,6-di-f—Ph |
| Z-5248 | HC≡C— | 2-Cl-3-F—Ph | Z-5249 | HC≡C— | 2-Cl-3,4-di-MeO—PhCH2— | Z-5250 | HC≡CCH2— | 2-Cl-3-F—Ph |
| Z-5251 | HC≡C— | 2-Cl-4-F—Ph | Z-5252 | HC≡C— | 2-Cl-3,5-di-MeO—PhCH2— | Z-5253 | HC≡CCH2— | 2-Cl-4-F—Ph |
| Z-5254 | HC≡C— | 2-Cl-5-F—Ph | Z-5255 | HC≡C— | 2-Cl-3,6-di-MeO—PhCH2— | Z-5256 | HC≡CCH2— | 2-Cl-5-F—Ph |
| Z-5257 | HC≡C— | 2-Cl-6-F—Ph | Z-5258 | HC≡C— | 2-Br-3,4-di-MeO—PhCH2— | Z-5259 | HC≡CCH2— | 2-Cl-6-F—Ph |
| Z-5260 | HC≡C— | 2-Br-3-F—Ph | Z-5261 | HC≡C— | 2-Br-3,5-di-MeO—PhCH2— | Z-5262 | HC≡CCH2— | 2-Br-3-F—Ph |
| Z-5263 | HC≡C— | 2-Br-4-F—Ph | Z-5264 | HC≡C— | 2-Br-3,6-di-MeO—PhCH2— | Z-5265 | HC≡CCH2— | 2-Br-4-F—Ph |
| Z-5266 | HC≡C— | 2-Br-5-F—Ph | Z-5267 | HC≡C— | MeS— | Z-5268 | HC≡CCH2— | 2-Br-5-F—Ph |
| Z-5269 | HC≡C— | 2-Br-6-F—Ph | Z-5270 | HC≡C— | MeS(═O)— | Z-5271 | HC≡CCH2— | 2-Br-6-F—Ph |
| Z-5272 | HC≡C— | 2-F-3-MeO—Ph | Z-5273 | HC≡C— | MeS(═O)2— | Z-5274 | HC≡CCH2— | 2-F-3-MeO—Ph |
| Z-5275 | HC≡C— | 2-F-4-MeO—Ph | Z-5276 | HC≡C— | EtS— | Z-5271 | H3CC≡CCH2— | 2,6-di-F—Ph |
| Z-5278 | HC≡C— | 2-F-5-MeO—Ph | Z-5279 | HC≡C— | EtS(═O)— | Z-5280 | H3CC≡CCH2— | 2-Cl-3-F—Ph |
| Z-5281 | HC≡C— | 2-F-6-MeO—Ph | Z-5282 | HC≡CCH2— | 2-Br-5-F—PhCH2— | Z-5283 | H3CC≡CCH2— | 2-Cl-4-F—Ph |
| Z-5284 | HC≡C— | 2-Cl-3-MeO—Ph | Z-5285 | HC≡CCH2— | 2-Br-6-F—PhCH2— | Z-5286 | H3CC≡CCH2— | 2-Cl-5-F—Ph |
| Z-5287 | HC≡C— | 2-Cl-4-MeO—Ph | Z-5288 | HC≡CCH2— | 2-F-3-MeO—PhCH2— | Z-5289 | H3CC≡CCH2— | 2-Cl-6-F—Ph |
| Z-5290 | HC≡C— | 2-Cl-5-MeO—Ph | Z-5291 | HC≡CCH2— | 2-F-4-MeO—PhCH2— | Z-5292 | H3CC≡CCH2— | 2-Br-3-F—Ph |
| Z-5293 | HC≡C— | 2-Cl-6-MeO—Ph | Z-5294 | HC≡CCH2— | 2-F-5-MeO—PhCH2— | Z-5295 | H3CC≡CCH2— | 2-Br-4-F—Ph |
| Z-5296 | HC≡C— | 2-Br-3-MeO—Ph | Z-5297 | HC≡CCH2— | 2-F-6-MeO—PhCH2— | Z-5298 | H3CC≡CCH2— | 2-Br-5-F—Ph |
| Z-5299 | HC≡C— | 2-Br-4-MeO—Ph | Z-5300 | HC≡CCH2— | 2-Cl-3-MeO—PhCH2— | Z-5301 | H3CC≡CCH2— | 2-Br-6-F—Ph |
| Z-5302 | HC≡C— | 2-Br-5-MeO—Ph | Z-5303 | HC≡CCH2— | 2-Cl-4-MeO—PhCH2— | Z-5304 | H3CC≡CCH2— | 2-F-3-MeO—Ph |
| Z-5305 | HC≡C— | 2-Br-6-MeO—Ph | Z-5306 | HC≡CCH2— | 2-Cl-5-MeO—PhCH2— | Z-5307 | H3CC≡CCH2— | 2-F-4-MeO—Ph |
| Z-5308 | HC≡C— | 2,3,4-tri-F—Ph | Z-5309 | HC≡CCH2— | 2-Cl-6-MeO—PhCH2— | Z-5310 | H3CC≡CCH2— | 2-F-5-MeO—Ph |
| Z-5311 | HC≡C— | 2,3,5-tri-F—Ph | Z-5312 | HC≡CCH2— | 2-Br-3-MeO—PhCH2— | Z-5313 | H3CC≡CCH2— | 2-F-6-MeO—Ph |
| Z-5314 | HC≡C— | 2,3,6-tri-F—Ph | Z-5315 | HC≡CCH2— | 2-Br-4-MeO—PhCH2— | Z-5316 | H3CC≡CCH2— | 2-Cl-3-MeO—Ph |
| Z-5317 | HC≡C— | 2-Br-3,4-di-F—Ph | Z-5318 | HC≡CCH2— | 2-Br-5-MeO—PhCH2— | Z-5319 | H3CC≡CCH2— | 2-Cl-4-MeO—Ph |
| Z-5320 | HC≡C— | 2-Br-3,5-di-F—Ph | Z-5321 | HC≡CCH2— | 2-Br-6-MeO—PhCH2— | Z-5322 | H3CC≡CCH2— | 2-Cl-5-MeO—Ph |
| Z-5323 | HC≡C— | 2-Br-3,6-di-F—Ph | Z-5324 | HC≡CCH2— | 2,3,4-tri-F—PhCH2— | Z-5325 | H3CC≡CCH2— | 2-Cl-6-MeO—Ph |
| Z-5326 | HC≡C— | 2-F-3,4-di-MeO—Ph | Z-5327 | HC≡CCH2— | 2,3,5-tri-F—PhCH2— | Z-5328 | H3CC≡CCH2— | 2-Br-3-MeO—Ph |
| Z-5329 | HC≡C— | 2-F-3,5-di-MeO—Ph | Z-5330 | HC≡CCH2— | 2,3,6-tri-F—PhCH2— | Z-5331 | H3CC≡CCH2— | 2-Br-4-MeO—Ph |
| Z-5332 | HC≡C— | 2-F-3,6-di-MeO—Ph | Z-5333 | HC≡CCH2— | 2-Br-3,4-di-F—PhCH2— | Z-5334 | H3CC≡CCH2— | 2-Br-5-MeO—Ph |
| Z-5335 | HC≡C— | 2-Cl-3,4-di-MeO—Ph | Z-5336 | HC≡CCH2— | 2-Br-3,5-di-F—PhCH2— | Z-5337 | H3CC≡CCH2— | 2-Br-6-MeO—Ph |
| Z-5338 | HC≡C— | 2-Cl-3,5-di-MeO—Ph | Z-5339 | HC≡CCH2— | 2-Br-3,6-di-F—PhCH2— | Z-5340 | H3CC≡CCH2— | 2,3,4-tri-F—Ph |
| Z-5341 | HC≡C— | 2-Cl-3,6-di-MeO—Ph | Z-5342 | HC≡CCH2— | 2-F-3,4-di-MeO—PhCH2— | Z-5343 | H3CC≡CCH2— | 2,3-5-tri-F—Ph |
| Z-5344 | HC≡C— | 2-Br-3,4-di-MeO—Ph | Z-5345 | HC≡CCH2— | 2-F-3,5-di-MeO—PhCH2— | Z-5346 | H3CC≡CCH2— | 2,3,6-tri-F—Ph |
| Z-5347 | HC≡C— | 2-Br-3,5-di-MeO—Ph | Z-5348 | HC≡CCH2— | 2-F-3,6-di-MeO—PhCH2— | Z-5349 | H3CC≡CCH2— | 2-Br-3,4-di-F—Ph |

TABLE 3-continued

| Z | R3 | R4 | Z | R3 | R4 | Z | R3 | R4 |
|---|---|---|---|---|---|---|---|---|
| Z-5350 | HC≡C— | 2-Br-3,6-di-MeO—Ph | Z-5351 | HC≡CCH2— | 2-Cl-3,4-di-MeO—PhCH2— | Z-5352 | H3CC≡CCH2— | 2-Br-3,5-di-F—Ph |
| Z-5353 | HC≡C— | PhCH2— | Z-5354 | HC≡CCH2— | 2-Cl-3,5-di-MeO—PhCH2— | Z-5355 | H3CC≡CCH2— | 2-Br-3,6-di-F—Ph |
| Z-5356 | HC≡C— | 2-F—PhCH2— | Z-5357 | HC≡CCH2— | 2-Cl-3,6-di-MeO—PhCH2— | Z-5358 | H3CC≡CCH2— | 2-F-3,4-di-MeO—Ph |
| Z-5359 | HC≡C— | 3-F—PhCH2— | Z-5360 | HC≡CCH2— | 2-Br-3,4-di-MeO—PhCH2— | Z-5361 | H3CC≡CCH2— | 2-F-3,5-di-MeO—Ph |
| Z-5362 | HC≡C— | 4-F—PhCH2— | Z-5363 | HC≡CCH2— | 2-Br-3,5-di-MeO—PhCH2— | Z-5364 | H3CC≡CCH2— | 2-F-3,6-di-MeO—Ph |
| Z-5365 | HC≡C— | 2-Cl—PhCH2— | Z-5366 | HC≡CCH2— | 2-Br-3,6-di-MeO—PhCH2— | Z-5367 | H3CC≡CCH2— | 2-Cl-3,4-di-MeO—Ph |
| Z-5368 | HC≡C— | 3-Cl—PhCH2— | Z-5369 | HC≡CCH2— | MeS— | Z-5370 | H3CC≡CCH2— | 2-Cl-3,5-di-MeO—Ph |
| Z-5371 | HC≡C— | 4-Cl—PhCH2— | Z-5372 | HC≡CCH2— | MeS(=O)— | Z-5373 | H3CC≡CCH2— | 2-Cl-3,6-di-MeO—Ph |
| Z-5374 | HC≡C— | 2-Br—PhCH2— | Z-5375 | HC≡CCH2— | MeS(=O)2— | Z-5376 | H3CC≡CCH2— | 2-Br-3,4-di-MeO—Ph |
| Z-5377 | HC≡CCH2— | 2-F-4-MeO—Ph | Z-5378 | HC≡CCH2— | EtS— | Z-5379 | H3CC≡CCH2— | 2-Br-3,5-di-MeO—Ph |
| Z-5380 | HC≡CCH2— | 2-F-5-MeO—Ph | Z-5381 | HC≡CCH2— | EtS(=O)— | Z-5382 | H3CC≡CCH2— | 2-Br-3,6-di-MeO—Ph |
| Z-5383 | HC≡CCH2— | 2-F-6-MeO—Ph | Z-5384 | HC≡CCH2— | EtS(=O)2— | Z-5385 | H3CC≡CCH2— | PhCH2— |
| Z-5386 | HC≡CCH2— | 2-Cl-3-MeO—Ph | Z-5387 | HC≡CCH2— | PrS— | Z-5388 | H3CC≡CCH2— | 2-F—PhCH2— |
| Z-5389 | HC≡CCH2— | 2-Cl-4-MeO—Ph | Z-5390 | HC≡CCH2— | PrS(=O)— | Z-5391 | H3CC≡CCH2— | 3-F—PhCH2— |
| Z-5392 | HC≡CCH2— | 2-Cl-5-MeO—Ph | Z-5393 | HC≡CCH2— | PrS(=O)2— | Z-5394 | H3CC≡CCH2— | 4-F—PhCH2— |
| Z-5395 | HC≡CCH2— | 2-Cl-6-MeO—Ph | Z-5396 | HC≡CCH2— | Ac | Z-5397 | H3CC≡CCH2— | 2-Cl—PhCH2— |
| Z-5398 | HC≡CCH2— | 2-Br-3-MeO—Ph | Z-5399 | HC≡CCH2— | OHC— | Z-5400 | H3CC≡CCH2— | 3-Cl—PhCH2— |
| Z-5401 | HC≡CCH2— | 2-Br-4-MeO—Ph | Z-5402 | HC≡CCH2— | Et(C=O)— | Z-5403 | H3CC≡CCH2— | 4-Cl—PhCH2— |
| Z-5414 | HC≡CCH2— | 2-Br-5-MeO—Ph | Z-5405 | HC≡CCH2— | Pr(C=O)— | Z-5406 | H3CC≡CCH2— | 2-Br—PhCH2— |
| Z-5407 | HC≡CCH2— | 2-Br-6-MeO—Ph | Z-5408 | HC≡CCH2— | i-Pr(C=O)— | Z-5409 | H3CC≡CCH2— | 3-Br—PhCH2— |
| Z-5410 | HC≡CCH2— | 2,3,4-tri-F—Ph | Z-5411 | HC≡CCH2— | Bu(C=O)— | Z-5412 | H3CC≡CCH2— | 4-Br—PhCH2— |
| Z-5413 | HC≡CCH2— | 2,3,5-tri-F—Ph | Z-5414 | HC≡CCH2— | MeO(C=O)— | Z-5415 | H3CC≡CCH2— | 2-I—PhCH2— |
| Z-5416 | HC≡CCH2— | 2,3,6-tri-F—Ph | Z-5417 | HC≡CCH2— | EtO(C=O)— | Z-5418 | H3CC≡CCH2— | 3-I—PhCH2— |
| Z-5419 | HC≡CCH2— | 2-Br-3,4-di-F—Ph | Z-5420 | HC≡CCH2— | PrO(C=O)— | Z-5421 | H3CC≡CCH2— | 4-I—PhCH2— |
| Z-5422 | HC≡CCH2— | 2-Br-3,5-di-F—Ph | Z-5423 | HC≡CCH2— | i-PrO(C=O) | Z-5424 | H3CC≡CCH2— | 2-Me—PhCH2— |
| Z-5425 | HC≡CCH2— | 2-Br-3,6-di-F—Ph | Z-5426 | HC≡CCH2— | BuO(C=O)— | Z-5427 | H3CC≡CCH2— | 3-Me—PhCH2— |
| Z-5428 | HC≡CCH2— | 2-F-3,4-di-MeO—Ph | Z-5429 | HC≡CCH2— | t-BuOC(=O)— | Z-5430 | H3CC≡CCH2— | 4-Me—PhCH2— |
| Z-5431 | HC≡CCH2— | 2-F-3,5-di-MeO—Ph | Z-5432 | H3CC≡CCH2— | H3CC≡CCH2— | Z-5433 | H3CC≡CCH2— | 2-MeO—PhCH2— |
| Z-5434 | HC≡CCH2— | 2-F-3,6-di-MeO—Ph | Z-5435 | H3CC≡CCH2— | FC≡C— | Z-5436 | H3CC≡CCH2— | 3-MeO—PhCH2— |
| Z-5437 | HC≡CCH2— | 2-Cl-3,4-di-MeO—Ph | Z-5438 | H3CC≡CCH2— | FC≡CCF2— | Z-5439 | H3CC≡CCH2— | 4-MeO—PhCH2— |
| Z-5440 | HC≡CCH2— | 2-Cl-3,5-di-MeO—Ph | Z-5441 | H3CC≡CCH2— | FC≡CCF2CF2— | Z-5442 | MeS— | Ph |
| Z-5443 | HC≡CCH2— | 2-Cl-3,6-di-MeO—Ph | Z-5444 | H3CC≡CCH2— | F3CC≡CCF2— | Z-5445 | MeS— | 2-F—Ph |
| Z-5446 | HC≡CCH2— | 2-Br-3,4-di-MeO—Ph | Z-5447 | H3CC≡CCH2— | Ph | Z-5448 | MeS— | 3-F—Ph |
| Z-5449 | HC≡CCH2— | 2-Br-3,5-di-MeO—Ph | Z-5450 | H3CC≡CCH2— | 2-F—Ph | Z-5451 | MeS— | 4-F—Ph |
| Z-5452 | HC≡CCH2— | 2-Br-3,6-di-MeO—Ph | Z-5453 | H3CC≡CCH2— | 3-F—Ph | Z-5454 | MeS— | 2-Cl—Ph |
| Z-5455 | HC≡CCH2— | PhCH2— | Z-5456 | H3CC≡CCH2— | 4-F—Ph | Z-5457 | MeS— | 3-Cl—Ph |
| Z-5458 | HC≡CCH2— | 2-F—PhCH2— | Z-5459 | H3CC≡CCH2— | 2-Cl—Ph | Z-5460 | MeS— | 4-Cl—Ph |
| Z-5461 | HC≡CCH2— | 3-F—PhCH2— | Z-5462 | H3CC≡CCH2— | 3-Cl—Ph | Z-5463 | MeS— | 2-Br—Ph |
| Z-5464 | HC≡CCH2— | 4-F—PhCH2— | Z-5465 | H3CC≡CCH2— | 4-Cl—Ph | Z-5466 | MeS— | 3-Br—Ph |
| Z-5467 | HC≡CCH2— | 2-Cl—PhCH2— | Z-5468 | H3CC≡CCH2— | 2-Br—Ph | Z-5469 | MeS— | 4-Br—Ph |
| Z-5470 | HC≡CCH2— | 3-Cl—PhCH2— | Z-5471 | H3CC≡CCH2— | 3-Br—Ph | Z-5472 | MeS— | 2-I—Ph |
| Z-5473 | HC≡CCH2— | 4-Cl—PhCH2— | Z-5474 | H3CC≡CCH2— | 4-Br—Ph | Z-5475 | MeS— | 3-I—Ph |
| Z-5476 | HC≡CCH2— | 2-Br—PhCH2— | Z-5477 | H3CC≡CCH2— | 2-I—Ph | Z-5478 | MeS— | 4-I—Ph |
| Z-5479 | HC≡CCH2— | 3-Br—PhCH2— | Z-5480 | H3CC≡CCH2— | 3-I—Ph | Z-5481 | MeS— | 2-Me—Ph |
| Z-5482 | HC≡CCH2— | 4-Br—PhCH2— | Z-5483 | H3CC≡CCH2— | 4-I—Ph | Z-5484 | MeS— | 3-Me—Ph |
| Z-5485 | HC≡CCH2— | 2-I—PhCH2— | Z-5486 | H3CC≡CCH2— | 2-Me—Ph | Z-5487 | MeS— | 4-Me—Ph |
| Z-5488 | HC≡CCH2— | 3-I—PhCH2— | Z-5489 | H3CC≡CCH2— | 3-Me—Ph | Z-5490 | MeS— | 2-MeO—Ph |
| Z-5491 | HC≡CCH2— | 4-I—PhCH2— | Z-5492 | H3CC≡CCH2— | 4-Me—Ph | Z-5493 | MeS— | 3-MeO—Ph |
| Z-5494 | HC≡CCH2— | 2-Me—PhCH2— | Z-5495 | H3CC≡CCH2— | 2-MeO—Ph | Z-5496 | MeS— | 4-MeO—Ph |
| Z-5497 | HC≡CCH2— | 3-Me—PhCH2— | Z-5498 | H3CC≡CCH2— | 3-MeO—Ph | Z-5499 | MeS— | 2,3-di-F—Ph |
| Z-5500 | HC≡CCH2— | 4-Me—PhCH2— | Z-5501 | H3CC≡CCH2— | 4-MeO—Ph | Z-5502 | MeS— | 2,4-di-F—Ph |

TABLE 3-continued

| Z | R3 | R4 | Z | R3 | R4 | Z | R3 | R4 |
|---|---|---|---|---|---|---|---|---|
| Z-5503 | HC≡CCH2— | 2-MeO—PhCH2— | Z-5504 | H3CC≡CCH2— | 2,3-di-F—Ph | Z-5505 | MeS— | 2,5-di-F—Ph |
| Z-5506 | HC≡CCH2— | 3-MeO—PhCH2— | Z-5507 | H3CC≡CCH2— | 2,4-di-F—Ph | Z-5508 | MeS— | 2,6-di-F—Ph |
| Z-5509 | HC≡CCH2— | 4-MeO—PhCH2— | Z-5510 | H3CC≡CCH2— | 2,5-di-F—Ph | Z-5511 | MeS— | 2-Cl-3-F—Ph |
| Z-5512 | HC≡CCH2— | 2,3-di-F—PhCH2— | Z-5513 | H3CC≡CCH2— | EtO(C═O)— | Z-5514 | MeS— | 2-Cl-4-F—Ph |
| Z-5515 | HC≡CCH2— | 2,4-di-F—PhCH2— | Z-5516 | H3CC≡CCH2— | PrO(C═O)— | Z-5517 | MeS— | 2-Cl-5-F—Ph |
| Z-5518 | HC≡CCH2— | 2,5-di-F—PhCH2— | Z-5519 | H3CC≡CCH2— | i-PrO(C═O)— | Z-5520 | MeS— | 2-Cl-6-F—Ph |
| Z-5521 | HC≡CCH2— | 2,6-di-F—PhCH2— | Z-5522 | H3CC≡CCH2— | BuO(C═O)— | Z-5523 | MeS— | 2-Br-3-F—Ph |
| Z-5524 | HC≡CCH2— | 2-Cl-3-F—PhCH2— | Z-5525 | H3CC≡CCH2— | t-BuOC(═O)— | Z-5526 | MeS— | 2-Br-4-F—Ph |
| Z-5527 | HC≡CCH2— | 2-Cl-4-F—PhCH2— | Z-5528 | MeS— | 2-Br-3-MeO—PhCH2— | Z-5529 | MeS— | 2-Br-5-F—Ph |
| Z-5530 | HC≡CCH2— | 2-Cl-5-F—PhCH2— | Z-5531 | MeS— | 2-Br-4-MeO—PhCH2— | Z-5532 | MeS— | 2-Br-6-F—Ph |
| Z-5533 | HC≡CCH2— | 2-Cl-6-F—PhCH2— | Z-5534 | MeS— | 2-Br-5-MeO—PhCH2— | Z-5535 | MeS— | 2-F-3-MeO—Ph |
| Z-5536 | HC≡CCH2— | 2-Br-3-F—PhCH2— | Z-5537 | MeS— | 2-Br-6-MeO—PhCH2— | Z-5538 | MeS— | 2-F-4-MeO—Ph |
| Z-5539 | HC≡CCH2— | 2-Br-4-F—PhCH2— | Z-5540 | MeS— | 2,3,4-tri-F—PhCH2— | Z-5541 | MeS— | 2-F-5-MeO—Ph |
| Z-5542 | H3CC≡CCH2— | 2,3-di-F—PhCH2— | Z-5543 | MeS— | 2,3,5-tri-F—PhCH2— | Z-5544 | MeS— | 2-F-6-MeO—Ph |
| Z-5545 | H3CC≡CCH2— | 2,4-di-F—PhCH2— | Z-5546 | MeS— | 2,3,6-tri-F—PhCH2— | Z-5547 | MeS— | 2-Cl-3-MeO—Ph |
| Z-5548 | H3CC≡CCH2— | 2,5-di-F—PhCH2— | Z-5549 | MeS— | 2-Br-3,4-di-F—PhCH2— | Z-5550 | MeS— | 2-Cl-4-MeO—Ph |
| Z-5551 | H3CC≡CCH2— | 2,6-di-F—PhCH2— | Z-5552 | MeS— | 2-Br-3,5-di-F—PhCH2— | Z-5553 | MeS— | 2-Cl-5-MeO—Ph |
| Z-5554 | H3CC≡CCH2— | 2-Cl-3-F—PhCH2— | Z-5555 | MeS— | 2-Br-3,6-di-F—PhCH2— | Z-5556 | MeS— | 2-Cl-6-MeO—Ph |
| Z-5557 | H3CC≡CCH2— | 2-Cl-4-F—PhCH2— | Z-5558 | MeS— | 2-F-3,4-di-MeO—PhCH2— | Z-5559 | MeS— | 2-Br-3-MeO—Ph |
| Z-5560 | H3CC≡CCH2— | 2-Cl-5-F—PhCH2— | Z-5561 | MeS— | 2-F-3,5-di-MeO—PhCH2— | Z-5562 | MeS— | 2-Br-4-MeO—Ph |
| Z-5563 | H3CC≡CCH2— | 2-Cl-6-F—PhCH2— | Z-5564 | MeS— | 2-F-3,6-di-MeO—PhCH2— | Z-5565 | MeS— | 2-Br-5-MeO—Ph |
| Z-5566 | H3CC≡CCH2— | 2-Br-3-F—PhCH2— | Z-5567 | MeS— | 2-Cl-3,4-di-MeO—PhCH2— | Z-5568 | MeS(═O)— | 4-Me—Ph |
| Z-5569 | H3CC≡CCH2— | 2-Br-4-F—PhCH2— | Z-5570 | MeS— | 2-Cl-3,5-di-MeO—PhCH2— | Z-5571 | MeS(═O)— | 2-MeO—Ph |
| Z-5572 | H3CC≡CCH2— | 2-Br-5-F—PhCH2— | Z-5573 | MeS— | 2-Cl-3,6-di-MeO—PhCH2— | Z-5574 | MeS(═O)— | 3-MeO—Ph |
| Z-5575 | H3CC≡CCH2— | 2-Br-6-F—PhCH2— | Z-5576 | MeS— | 2-Br-3,4-di-MeO—PhCH2— | Z-5577 | MeS(═O)— | 4-MeO—Ph |
| Z-5578 | H3CC≡CCH2— | 2-F-3-MeO—PhCH2— | Z-5579 | MeS— | 2-Br-3,5-di-MeO—PhCH2— | Z-5580 | MeS(═O)— | 2,3-di-F—Ph |
| Z-5581 | H3CC≡CCH2— | 2-F-4-MeO—PhCH2— | Z-5582 | MeS— | 2-Br-3,6-di-MeO—PhCH2— | Z-5583 | MeS(═O)— | 2,4-di-F—Ph |
| Z-5584 | H3CC≡CCH2— | 2-F-5-MeO—PhCH2— | Z-5585 | MeS— | MeS— | Z-5586 | MeS(═O)— | 2,5-di-F—Ph |
| Z-5587 | H3CC≡CCH2— | 2-F-6-MeO—PhCH2— | Z-5588 | MeS— | MeS(═O)— | Z-5589 | MeS(═O)— | 2,6-di-F—Ph |
| Z-5596 | H3CC≡CCH2— | 2-Cl-3-MeO—PhCH2— | Z-5591 | MeS— | MeS(═O)2— | Z-5592 | MeS(═O)— | 2-Cl-3-F—Ph |
| Z-5593 | H3CC≡CCH2— | 2-Cl-4-MeO—PhCH2— | Z-5594 | MeS— | EtS— | Z-5595 | MeS(═O)— | 2-Cl-4-F—Ph |
| Z-5596 | H3CC≡CCH2— | 2-Cl-5-MeO—PhCH2— | Z-5597 | MeS— | EtS(═O)— | Z-5598 | MeS(═O)— | 2-Cl-5-F—Ph |
| Z-5599 | H3CC≡CCH2— | 2-Cl-6-MeO—PhCH2— | Z-5600 | MeS— | EtS(═O)2— | Z-5601 | MeS(═O)— | 2-Cl-6-F—Ph |
| Z-5602 | H3CC≡CCH2— | 2-Br-3-MeO—PhCH2— | Z-5603 | MeS— | PrS— | Z-5604 | MeS(═O)— | 2-Br-3-F—Ph |
| Z-5605 | H3CC≡CCH2— | 2-Br-4-MeO—PhCH2— | Z-5606 | MeS— | PrS(═O)— | Z-5607 | MeS(═O)— | 2-Br-4-F—Ph |
| Z-5608 | H3CC≡CCH2— | 2-Br-5-MeO—PhCH2— | Z-5609 | MeS— | PrS(═O)2— | Z-5610 | MeS(═O)— | 2-Br-5-F—Ph |
| Z-5611 | H3CC≡CCH2— | 2-Br-6-MeO—PhCH2— | Z-5612 | MeS— | Ac | Z-5613 | MeS(═O)— | 2-Br-6-F—Ph |
| Z-5614 | H3CC≡CCH2— | 2,3,4-tri-F—PhCH2— | Z-5615 | MeS— | OHC— | Z-5616 | MeS(═O)— | 2-F-3-MeO—Ph |
| Z-5617 | H3CC≡CCH2— | 2,3,5-tri-F—PhCH2— | Z-5618 | MeS— | Et(C═O)— | Z-5619 | MeS(═O)— | 2-F-4-MeO—Ph |
| Z-5620 | H3CC≡CCH2— | 2,3,6-tri-F—PhCH2— | Z-5621 | MeS— | Pr(C═O)— | Z-5622 | MeS(═O)— | 2-F-5-MeO—Ph |
| Z-5623 | H3CC≡CCH2— | 2-Br-3,4-di-F—PhCH2— | Z-5624 | MeS— | i-Pr(C═O)— | Z-5625 | MeS(═O)— | 2-F-6-MeO—Ph |
| Z-5626 | H3CC≡CCH2— | 2-Br-3,5-di-F—PhCH2— | Z-5627 | MeS— | Bu(C═O)— | Z-5628 | MeS(═O)— | 2-Cl-3-MeO—Ph |
| Z-5629 | H3CC≡CCH2— | 2-Br-3,6-di-F—PhCH2— | Z-5630 | MeS— | MeO(C═O)— | Z-5631 | MeS(═O)— | 2-Cl-4-MeO—Ph |
| Z-5632 | H3CC≡CCH2— | 2-F-3,4-di-MeO—PhCH2— | Z-5633 | MeS— | EtO(C═O)— | Z-5634 | MeS(═O)— | 2-Cl-5-MeO—Ph |
| Z-5635 | H3CC≡CCH2— | 2-F-3,5-di-MeO—PhCH2— | Z-5636 | MeS— | PrO(C═O)— | Z-5637 | MeS(═O)— | 2-Cl-6-MeO—Ph |
| Z-5638 | H3CC≡CCH2— | 2-F-3,6-di-MeO—PhCH2— | Z-5639 | MeS— | i-PrO(C═O)— | Z-5640 | MeS(═O)— | 2-Br-3-MeO—Ph |
| Z-5641 | H3CC≡CCH2— | 2-Cl-3,4-di-MeO—PhCH2— | Z-5642 | MeS— | BuO(C═O)— | Z-5643 | MeS(═O)— | 2-Br-4-MeO—Ph |
| Z-5644 | H3CC≡CCH2— | 2-Cl-3,5-di-MeO—PhCH2— | Z-5645 | MeS— | t-BuOC(═O)— | Z-5646 | MeS(═O)— | 2-Br-5-MeO—Ph |
| Z-5647 | H3CC≡CCH2— | 2-Cl-3,6-di-MeO—PhCH2— | Z-5648 | MeS(═O)— | Ph | Z-5649 | MeS(═O)— | 2-Br-6-MeO—Ph |
| Z-5650 | H3CC≡CCH2— | 2-Br-3,4-di-MeO—PhCH2— | Z-5651 | MeS(═O)— | 2-F—Ph | Z-5652 | MeS(═O)— | 2,3,4-tri-F—Ph |
| Z-5653 | H3CC≡CCH2— | 2-Br-3,5-di-MeO—PhCH2— | Z-5654 | MeS(═O)— | 3-F—Ph | Z-5655 | MeS(═O)— | 2,3,5-tri-F—Ph |

TABLE 3-continued

| Z | R3 | R4 | Z | R3 | R4 | Z | R3 | R4 |
|---|---|---|---|---|---|---|---|---|
| Z-5656 | H3CC≡CCH2— | 2-Br-3,6-di-MeO—PhCH2— | Z-5657 | MeS(═O)— | 4-F—Ph | Z-5658 | MeS(═O)— | 2,3,6-tri-F—Ph |
| Z-5659 | H3CC≡CCH2— | MeS— | Z-5660 | MeS(═O)— | 2-Cl—Ph | Z-5661 | MeS(═O)— | 2-Br-3,4-di-F—Ph |
| Z-5662 | H3CC≡CCH2— | MeS(═O)— | Z-5663 | MeS(═O)— | 3-Cl—Ph | Z-5664 | MeS(═O)— | 2-Br-3,5-di-F—Ph |
| Z-5665 | H3CC≡CCH2— | MeS(═O)2— | Z-5666 | MeS(═O)— | 4-Cl—Ph | Z-5667 | MeS(═O)— | 2-Br-3,6-di-F—Ph |
| Z-5668 | H3CC≡CCH2— | EtS— | Z-5669 | MeS(═O)— | 2-Br—Ph | Z-5670 | MeS(═O)— | 2-F-3,4-di-MeO—Ph |
| Z-5671 | H3CC≡CCH2— | EtS(═O)— | Z-5672 | MeS(═O)— | 3-Br—Ph | Z-5673 | MeS(═O)— | 2-F-3,5-di-MeO—Ph |
| Z-5674 | H3CC≡CCH2— | EtS(═O)2— | Z-5675 | MeS(═O)— | 4-Br—Ph | Z-5676 | MeS(═O)— | 2-F-3,6-di-MeO—Ph |
| Z-5677 | H3CC≡CCH2— | PrS— | Z-5678 | MeS(═O)— | 2-I—Ph | Z-5679 | MeS(═O)— | 2-Cl-3,4-di-MeO—Ph |
| Z-5680 | H3CC≡CCH2— | PrS(═O)— | Z-5681 | MeS(═O)— | 3-I—Ph | Z-5682 | MeS(═O)— | 2-Cl-3,5-di-MeO—Ph |
| Z-5683 | H3CC≡CCH2— | PrS(═O)2— | Z-5684 | MeS(═O)— | 4-I—Ph | Z-5685 | MeS(═O)— | 2-Cl-3,6-di-MeO—Ph |
| Z-5686 | H3CC≡CCH2— | Ac | Z-5687 | MeS(═O)— | 2-Me—Ph | Z-5688 | MeS(═O)— | 2-Br-3,4-di-MeO—Ph |
| Z-5689 | H3CC≡CCH2— | OHC— | Z-5690 | MeS(═O)— | 3-Me—Ph | Z-5691 | MeS(═O)— | 2-Br-3,5-di-MeO—Ph |
| Z-5692 | H3CC≡CCH2— | Et(C═O)— | Z-5693 | MeS(═O)— | OHC— | Z-5694 | MeS(═O)— | 2-Br-3,6-di-MeO—Ph |
| Z-5695 | H3CC≡CCH2— | Pr(C═O)— | Z-5696 | MeS(═O)— | Et(C═O)— | Z-5697 | MeS(═O)— | PhCH2— |
| Z-5698 | H3CC≡CCH2— | i-Pr(C═O)— | Z-5699 | MeS(═O)— | Pr(C═O)— | Z-5700 | MeS(═O)— | 2-F—PhCH2— |
| Z-5701 | H3CC≡CCH2— | Bu(C═O)— | Z-5702 | MeS(═O)— | i-Pr(C═O)— | Z-5703 | MeS(═O)— | 3-F—PhCH2— |
| Z-5704 | H3CC≡CCH2— | MeO(C═O)— | Z-5705 | MeS(═O)— | Bu(C═O)— | Z-5706 | MeS(═O)— | 4-F—PhCH2— |
| Z-5707 | MeS— | 2-Br-6-MeO—Ph | Z-5708 | MeS(═O)— | MeO(C═O)— | Z-5709 | MeS(═O)— | 2-Cl—PhCH2— |
| Z-5710 | MeS— | 2,3,4-tri-F—Ph | Z-5711 | MeS(═O)— | EtO(C═O)— | Z-5712 | MeS(═O)— | 3-Cl—PhCH2— |
| Z-5713 | MeS— | 2,3,5-tri-F—Ph | Z-5714 | MeS(═O)— | PrO(C═O)— | Z-5715 | MeS(═O)— | 4-Cl—PhCH2— |
| Z-5716 | MeS— | 2,3,6-tri-F—Ph | Z-5717 | MeS(═O)— | i-PrO(C═O)— | Z-5718 | MeS(═O)— | 2-Br—PhCH2— |
| Z-5719 | MeS— | 2-Br-3,4-di-F—Ph | Z-5720 | MeS(═O)— | BuO(C═O)— | Z-5721 | MeS(═O)— | 3-Br—PhCH2— |
| Z-5722 | MeS— | 2-Br-3,5-di-F—Ph | Z-5723 | MeS(═O)— | t-BuOC(═O)— | Z-5724 | MeS(═O)— | 4-Br—PhCH2— |
| Z-5725 | MeS— | 2-Br-3,6-di-F—Ph | Z-5726 | MeS(═O)2— | Ph | Z-5727 | MeS(═O)— | 2-I—PhCH2— |
| Z-5728 | MeS— | 2-F-3,4-di-MeO—Ph | Z-5729 | MeS(═O)2— | 2-F—Ph | Z-5730 | MeS(═O)— | 3-I—PhCH2— |
| Z-5731 | MeS— | 2-F-3,5-di-MeO—Ph | Z-5732 | MeS(═O)2— | 3-F—Ph | Z-5733 | MeS(═O)2— | 2,3,5-tri-F—Ph |
| Z-5734 | MeS— | 2-F-3,6-di-MeO—Ph | Z-5735 | MeS(═O)2— | 4-F—Ph | Z-5736 | MeS(═O)2— | 2,3,6-tri-F—Ph |
| Z-5737 | MeS— | 2-Cl-3,4-di-MeO—Ph | Z-5738 | MeS(═O)2— | 2-Cl—Ph | Z-5739 | MeS(═O)2— | 2-Br-3,4-di-F—Ph |
| Z-5740 | MeS— | 2-Cl-3,5-di-MeO—Ph | Z-5741 | MeS(═O)2— | 3-Cl—Ph | Z-5742 | MeS(═O)2— | 2-Br-3,5-di-F—Ph |
| Z-5743 | MeS— | 2-Cl-3,6-di-MeO—Ph | Z-5744 | MeS(═O)2— | 4-Cl—Ph | Z-5745 | MeS(═O)2— | 2-Br-3,6-di-F—Ph |
| Z-5746 | MeS— | 2-Br-3,4-di-MeO—Ph | Z-5747 | MeS(═O)2— | 2-Br—Ph | Z-5748 | MeS(═O)2— | 2-F-3,4-di-MeO—Ph |
| Z-5749 | MeS— | 2-Br-3,5-di-MeO—Ph | Z-5750 | MeS(═O)2— | 3-Br—Ph | Z-5751 | MeS(═O)2— | 2-F-3,5-di-MeO—Ph |
| Z-5752 | MeS— | 2-Br-3,6-di-MeO—Ph | Z-5753 | MeS(═O)2— | 4-Br—Ph | Z-5754 | MeS(═O)2— | 2-F-3,6-di-MeO—Ph |
| Z-5755 | MeS— | PhCH2— | Z-5756 | MeS(═O)2— | 2-I—Ph | Z-5757 | MeS(═O)2— | 2-Cl-3,4-di-MeO—Ph |
| Z-5758 | MeS— | 2-F—PhCH2— | Z-5759 | MeS(═O)2— | 3-I—Ph | Z-5760 | MeS(═O)2— | 2-Cl-3,5-di-MeO—Ph |
| Z-5761 | MeS— | 3-F—PhCH2— | Z-5762 | MeS(═O)2— | 4-I—Ph | Z-5763 | MeS(═O)2— | 2-Cl-3,6-di-MeO—Ph |
| Z-5764 | MeS— | 4-F—PhCH2— | Z-5765 | MeS(═O)2— | 2-Me—Ph | Z-5766 | MeS(═O)2— | 2-Br-3,4-di-MeO—Ph |
| Z-5767 | MeS— | 2-Cl—PhCH2— | Z-5768 | MeS(═O)2— | 3-Me—Ph | Z-5769 | MeS(═O)2— | 2-Br-3,5-di-MeO—Ph |
| Z-5770 | MeS— | 3-Cl—PhCH2— | Z-5771 | MeS(═O)2— | 4-Me—Ph | Z-5772 | MeS(═O)2— | 2-Br-3,6-di-MeO—Ph |
| Z-5773 | MeS— | 4-Cl—PhCH2— | Z-5774 | MeS(═O)2— | 2-MeO—Ph | Z-5775 | MeS(═O)2— | PhCH2— |
| Z-5776 | MeS— | 2-Br—PhCH2— | Z-5777 | MeS(═O)2— | 3-MeO—Ph | Z-5778 | MeS(═O)2— | 2-F—PhCH2— |
| Z-5779 | MeS— | 3-Br—PhCH2— | Z-5780 | MeS(═O)2— | 4-MeO—Ph | Z-5781 | MeS(═O)2— | 3-F—PhCH2— |
| Z-5782 | MeS— | 4-Br—PhCH2— | Z-5783 | MeS(═O)2— | 2,3-di-F—Ph | Z-5784 | MeS(═O)2— | 4-F—PhCH2— |
| Z-5785 | MeS— | 2-I—PhCH2— | Z-5786 | MeS(═O)2— | 2,4-di-F—Ph | Z-5787 | MeS(═O)2— | 2-Cl—PhCH2— |
| Z-5788 | MeS— | 3-I—PhCH2— | Z-5789 | MeS(═O)2— | 2,5-di-F—Ph | Z-5790 | MeS(═O)2— | 3-Cl—PhCH2— |
| Z-5791 | MeS— | 4-I—PhCH2— | Z-5792 | MeS(═O)2— | 2,6-di-F—Ph | Z-5793 | MeS(═O)2— | 4-Cl—PhCH2— |
| Z-5794 | MeS— | 2-Me—PhCH2— | Z-5795 | MeS(═O)2— | 2-Cl-3-F—Ph | Z-5796 | MeS(═O)2— | 2-Br—PhCH2— |
| Z-5797 | MeS— | 3-Me—PhCH2— | Z-5798 | MeS(═O)2— | 2-Cl-4-F—Ph | Z-5799 | MeS(═O)2— | 3-Br—PhCH2— |
| Z-5800 | MeS— | 4-Me—PhCH2— | Z-5801 | MeS(═O)2— | 2-Cl-5-F—Ph | Z-5802 | MeS(═O)2— | 4-Br—PhCH2— |
| Z-5803 | MeS— | 2-MeO—PhCH2— | Z-5804 | MeS(═O)2— | 2-Cl-6-F—Ph | Z-5805 | MeS(═O)2— | 2-I—PhCH2— |
| Z-5806 | MeS— | 3-MeO—PhCH2— | Z-5807 | MeS(═O)2— | 2-Br-3-F—Ph | Z-5808 | MeS(═O)2— | 3-I—PhCH2— |

TABLE 3-continued

| Z | R3 | R4 | Z | R3 | R4 | Z | R3 | R4 |
|---|---|---|---|---|---|---|---|---|
| Z-5809 | MeS— | 4-MeO—PhCH2— | Z-5810 | MeS(═O)2— | 2-Br-4-F—Ph | Z-5811 | MeS(═O)2— | 4-I—PhCH2— |
| Z-5812 | MeS— | 2,3-di-F—PhCH2— | Z-5813 | MeS(═O)2— | 2-Br-5-F—Ph | Z-5814 | MeS(═O)2— | 2-Me—PhCH2— |
| Z-5815 | MeS— | 2,4-di-F—PhCH2— | Z-5816 | MeS(═O)2— | 2-Br-6-F—Ph | Z-5817 | MeS(═O)2— | 3-Me—PhCH2— |
| Z-5818 | MeS— | 2,5-di-F—PhCH2— | Z-5819 | MeS(═O)2— | 2-F-3-MeO—Ph | Z-5820 | MeS(═O)2— | 4-Me—PhCH2— |
| Z-5821 | MeS— | 2,6-di-F—PhCH2— | Z-5822 | MeS(═O)2— | 2-F-4-MeO—Ph | Z-5823 | MeS(═O)2— | 2-MeO—PhCH2— |
| Z-5824 | MeS— | 2-Cl-3-F—PhCH2— | Z-5825 | MeS(═O)2— | 2-F-5-MeO—Ph | Z-5826 | MeS(═O)2— | 3-MeO—PhCH2— |
| Z-5827 | MeS— | 2-Cl-4-F—PhCH2— | Z-5828 | MeS(═O)2— | 2-F-6-MeO—Ph | Z-5829 | MeS(═O)2— | 4-MeO—PhCH2— |
| Z-5830 | MeS— | 2-Cl-5-F—PhCH2— | Z-5831 | MeS(═O)2— | 2-Cl-3-MeO—Ph | Z-5832 | MeS(═O)2— | 2,3-di-F—PhCH2— |
| Z-5833 | MeS— | 2-Cl-6-F—PhCH2— | Z-5834 | MeS(═O)2— | 2-Cl-4-MeO—Ph | Z-5835 | MeS(═O)2— | 2,4-di-F—PhCH2— |
| Z-5836 | MeS— | 2-Br-3-F—PhCH2— | Z-5837 | MeS(═O)2— | 2-Cl-5-MeO—Ph | Z-5838 | MeS(═O)2— | 2,5-di-F—PhCH2— |
| Z-5839 | MeS— | 2-Br-4-F—PhCH2— | Z-5840 | MeS(═O)2— | 2-Cl-6-MeO—Ph | Z-5841 | MeS(═O)2— | 2,6-di-F—PhCH2— |
| Z-5842 | MeS— | 2-Br-5-F—PhCH2— | Z-5843 | MeS(═O)2— | 2-Br-3-MeO—Ph | Z-5844 | MeS(═O)2— | 2-Cl-3-F—PhCH2— |
| Z-5845 | MeS— | 2-Br-6-F—PhCH2— | Z-5846 | MeS(═O)2— | 2-Br-4-MeO—Ph | Z-5847 | MeS(═O)2— | 2-Cl-4-F—PhCH2— |
| Z-5848 | MeS— | 2-F-3-MeO—PhCH2— | Z-5849 | MeS(═O)2— | 2-Br-5-MeO—Ph | Z-5850 | MeS(═O)2— | 2-Cl-5-F—PhCH2— |
| Z-5851 | MeS— | 2-F-4-MeO—PhCH2— | Z-5852 | MeS(═O)2— | 2-Br-6-MeO—Ph | Z-5853 | MeS(═O)2— | 2-Cl-6-F—PhCH2— |
| Z-5854 | MeS— | 2-F-5-MeO—PhCH2— | Z-5855 | MeS(═O)2— | 2,3,4-tri-F—Ph | Z-5856 | MeS(═O)2— | 2-Br-3-F—PhCH2— |
| Z-5857 | MeS— | 2-F-6-MeO—PhCH2— | Z-5858 | EtS— | 2,3-di-F—Ph | Z-5859 | MeS(═O)2— | 2-Br-4-F—PhCH2— |
| Z-5860 | MeS— | 2-Cl-3-MeO—PhCH2— | Z-5861 | EtS— | 2,4-di-F—Ph | Z-5862 | MeS(═O)2— | 2-Br-5-F—PhCH2— |
| Z-5863 | MeS— | 2-Cl-4-MeO—PhCH2— | Z-5864 | EtS— | 2,5-di-F—Ph | Z-5865 | MeS(═O)2— | 2-Br-6-F—PhCH2— |
| Z-5866 | MeS— | 2-Cl-5-MeO—PhCH2— | Z-5867 | EtS— | 2,6-di-F—Ph | Z-5868 | MeS(═O)2— | 2-F-3-MeO—PhCH2— |
| Z-5869 | MeS— | 2-Cl-6-MeO—PhCH2— | Z-5870 | EtS— | 2-Cl-3-F—Ph | Z-5871 | MeS(═O)2— | 2-F-4-MeO—PhCH2— |
| Z-5872 | MeS(═O)— | 4-I—PhCH2— | Z-5873 | EtS— | 2-Cl-4-F—Ph | Z-5874 | MeS(═O)2— | 2-F-5-MeO—PhCH2— |
| Z-5875 | MeS(═O)— | 2-Me—PhCH2— | Z-5876 | EtS— | 2-Cl-5-F—Ph | Z-5877 | MeS(═O)2— | 2-F-6-MeO—PhCH2— |
| Z-5878 | MeS(═O)— | 3-Me—PhCH2— | Z-5879 | EtS— | 2-Cl-6-F—Ph | Z-5880 | MeS(═O)2— | 2-Cl-3-MeO—PhCH2— |
| Z-5881 | MeS(═O)— | 4-Me—PhCH2— | Z-5882 | EtS— | 2-Br-3-F—Ph | Z-5883 | MeS(═O)2— | 2-Cl-4-MeO—PhCH2— |
| Z-5884 | MeS(═O)— | 2-MeO—PhCH2— | Z-5885 | EtS— | 2-Br-4-F—Ph | Z-5886 | MeS(═O)2— | 2-Cl-5-MeO—PhCH2— |
| Z-5887 | MeS(═O)— | 3-MeO—PhCH2— | Z-5888 | EtS— | 2-Br-5-F—Ph | Z-5889 | MeS(═O)2— | 2-Cl-6-MeO—PhCH2— |
| Z-5890 | MeS(═O)— | 4-MeO—PhCH2— | Z-5891 | EtS— | 2-Br-6-F—Ph | Z-5892 | MeS(═O)2— | 2-Br-3-MeO—PhCH2— |
| Z-5893 | MeS(═O)— | 2,3-di-F—PhCH2— | Z-5894 | EtS— | 2-F-3-MeO—Ph | Z-5895 | MeS(═O)2— | 2-Br-4-MeO—PhCH2— |
| Z-5896 | MeS(═O)— | 2,4-di-F—PhCH2— | Z-5897 | EtS— | 2-F-4-MeO—Ph | Z-5898 | EtS— | 2-MeO—PhCH2— |
| Z-5899 | MeS(═O)— | 2,5-di-F—PhCH2— | Z-5900 | EtS— | 2-F-5-MeO—Ph | Z-5901 | EtS— | 3-MeO—PhCH2— |
| Z-5902 | MeS(═O)— | 2,6-di-F—PhCH2— | Z-5903 | EtS— | 2-F-6-MeO—Ph | Z-5904 | EtS— | 4-MeO—PhCH2— |
| Z-5905 | MeS(═O)— | 2-Cl-3-F—PhCH2— | Z-5906 | EtS— | 2-Cl-3-MeO—Ph | Z-5907 | EtS— | 2,3-di-F—PhCH2— |
| Z-5908 | MeS(═O)— | 2-Cl-4-F—PhCH2— | Z-5909 | EtS— | 2-Cl-4-MeO—Ph | Z-5910 | EtS— | 2,4-di-F—PhCH2— |
| Z-5911 | MeS(═O)— | 2-Cl-5-F—PhCH2— | Z-5912 | EtS— | 2-Cl-5-MeO—Ph | Z-5913 | EtS— | 2,5-di-F—PhCH2— |
| Z-5914 | MeS(═O)— | 2-Cl-6-F—PhCH2— | Z-5915 | EtS— | 2-Cl-6-MeO—Ph | Z-5916 | EtS— | 2,6-di-F—PhCH2— |
| Z-5917 | MeS(═O)— | 2-Br-3-F—PhCH2— | Z-5918 | EtS— | 2-Br-3-MeO—Ph | Z-5919 | EtS— | 2-Cl-3-F—PhCH2— |
| Z-5920 | MeS(═O)— | 2-Br-4-F—PhCH2— | Z-5921 | EtS— | 2-Br-4-MeO—Ph | Z-5922 | EtS— | 2-Cl-4-F—PhCH2— |
| Z-5923 | MeS(═O)— | 2-Br-5-F—PhCH2— | Z-5924 | EtS— | 2-Br-5-MeO—Ph | Z-5925 | EtS— | 2-Cl-5-F—PhCH2— |
| Z-5926 | MeS(═O)— | 2-Br-6-F—PhCH2— | Z-5927 | EtS— | 2-Br-6-MeO—Ph | Z-5928 | EtS— | 2-Cl-6-F—PhCH2— |
| Z-5929 | MeS(═O)— | 2-F-3-MeO—PhCH2— | Z-5930 | EtS— | 2,3,4-tri-F—Ph | Z-5931 | EtS— | 2-Br-3-F—PhCH2— |
| Z-5932 | MeS(═O)— | 2-F-4-MeO—PhCH2— | Z-5933 | EtS— | 2,3,5-tri-F—Ph | Z-5934 | EtS— | 2-Br-4-F—PhCH2— |
| Z-5935 | MeS(═O)— | 2-F-5-MeO—PhCH2— | Z-5936 | EtS— | 2,3,6-tri-F—Ph | Z-5937 | EtS— | 2-Br-5-F—PhCH2— |
| Z-5938 | MeS(═O)— | 2-F-6-MeO—PhCH2— | Z-5939 | EtS— | 2-Br-3,4-di-F—Ph | Z-5940 | EtS— | 2-Br-6-F—PhCH2— |
| Z-5941 | MeS(═O)— | 2-Cl-3-MeO—PhCH2— | Z-5942 | EtS— | 2-Br-3,5-di-F—Ph | Z-5943 | EtS— | 2-F-3-MeO—PhCH2— |
| Z-5944 | MeS(═O)— | 2-Cl-4-MeO—PhCH2— | Z-5945 | EtS— | 2-Br-3,6-di-F—Ph | Z-5946 | EtS— | 2-F-4-MeO—PhCH2— |
| Z-5947 | MeS(═O)— | 2-Cl-5-MeO—PhCH2— | Z-5948 | EtS— | 2-F-3,4-di-MeO—Ph | Z-5949 | EtS— | 2-F-5-MeO—PhCH2— |
| Z-5950 | MeS(═O)— | 2-Cl-6-MeO—PhCH2— | Z-5951 | EtS— | 2-F-3,5-di-MeO—Ph | Z-5952 | EtS— | 2-F-6-MeO—PhCH2— |
| Z-5953 | MeS(═O)— | 2-Br-3-MeO—PhCH2— | Z-5954 | EtS— | 2-F-3,6-di-MeO—Ph | Z-5955 | EtS— | 2-Cl-3-MeO—PhCH2— |
| Z-5956 | MeS(═O)— | 2-Br-4-MeO—PhCH2— | Z-5957 | EtS— | 2-Cl-3,4-di-MeO—Ph | Z-5958 | EtS— | 2-Cl-4-MeO—PhCH2— |
| Z-5959 | MeS(═O)— | 2-Br-5-MeO—PhCH2— | Z-5960 | EtS— | 2-Cl-3,5-di-MeO—Ph | Z-5961 | EtS— | 2-Cl-5-MeO—PhCH2— |

TABLE 3-continued

| Z | R3 | R4 | Z | R3 | R4 | Z | R3 | R4 |
|---|---|---|---|---|---|---|---|---|
| Z-5962 | MeS(═O)— | 2-Br-6-MeO—PhCH2— | Z-5963 | EtS— | 2-Cl-3,6-di-MeO—Ph | Z-5964 | EtS— | 2-Cl-6-MeO—PhCH2— |
| Z-5965 | MeS(═O)— | 2,3,4-tri-F—PhCH2— | Z-5966 | EtS— | 2-Br-3,4-di-MeO—Ph | Z-5967 | EtS— | 2-Br-3-MeO—PhCH2— |
| Z-5968 | MeS(═O)— | 2,3,5-tri-F—PhCH2— | Z-5969 | EtS— | 2-Br-3,5-di-MeO—Ph | Z-5970 | EtS— | 2-Br-4-MeO—PhCH2— |
| Z-5971 | MeS(═O)— | 2,3,6-tri-F—PhCH2— | Z-5972 | EtS— | 2-Br-3,6-di-MeO—Ph | Z-5973 | EtS— | 2-Br-5-MeO—PhCH2— |
| Z-5974 | MeS(═O)— | 2-Br-3,4-di-F—PhCH2— | Z-5975 | EtS— | PhCH2— | Z-5976 | EtS— | 2-Br-6-MeO—PhCH2— |
| Z-5977 | MeS(═O)— | 2-Br-3,5-di-F—PhCH2— | Z-5978 | EtS— | 2-F—PhCH2— | Z-5979 | EtS— | 2,3,4-tri-F—PhCH2— |
| Z-5980 | MeS(═O)— | 2-Br-3,6-di-F—PhCH2— | Z-5981 | EtS— | 3-F—PhCH2— | Z-5982 | EtS— | 2,3,5-tri-F—PhCH2— |
| Z-5983 | MeS(═O)— | 2-F-3,4-di-MeO—PhCH2— | Z-5984 | EtS— | 4-F—PhCH2— | Z-5985 | EtS— | 2,3,6-tri-F—PhCH2— |
| Z-5986 | MeS(═O)— | 2-F-3,5-di-MeO—PhCH2— | Z-5987 | EtS— | 2-Cl—PhCH2— | Z-5988 | EtS— | 2-Br-3,4-di-F—PhCH2— |
| Z-5989 | MeS(═O)— | 2-F-3,6-di-MeO—PhCH2— | Z-5990 | EtS— | 3-Cl—PhCH2— | Z-5991 | EtS— | 2-Br-3,5-di-F—PhCH2— |
| Z-5992 | MeS(═O)— | 2-Cl-3,4-di-MeO—PhCH2— | Z-5993 | EtS— | 4-Cl—PhCH2— | Z-5994 | EtS— | 2-Br-3,6-di-F—PhCH2— |
| Z-5995 | MeS(═O)— | 2-Cl-3,5-di-MeO—PhCH2— | Z-5996 | EtS— | 2-Br—PhCH2— | Z-5997 | EtS— | 2-F-3,4-di-MeO—PhCH2— |
| Z-5998 | MeS(═O)— | 2-Cl-3,6-di-MeO—PhCH2— | Z-5999 | EtS— | 3-Br—PhCH2— | Z-6000 | EtS— | 2-F-3,5-di-MeO—PhCH2— |
| Z-6001 | MeS(═O)— | 2-Br-3,4-di-MeO—PhCH2— | Z-6002 | EtS— | 4-Br—PhCH2— | Z-6003 | EtS— | 2-F-3,6-di-MeO—PhCH2— |
| Z-6004 | MeS(═O)— | 2-Br-3,5-di-MeO—PhCH2— | Z-6005 | EtS— | 2-I—PhCH2— | Z-6006 | EtS— | 2-Cl-3,4-di-MeO—PhCH2— |
| Z-6007 | MeS(═O)— | 2-Br-3,6-di-MeO—PhCH2— | Z-6008 | EtS— | 3-I—PhCH2— | Z-6009 | EtS— | 2-Cl-3,5-di-MeO—PhCH2— |
| Z-6010 | MeS(═O)— | MeS(═O)— | Z-6011 | EtS— | 4-I—PhCH2— | Z-6012 | EtS— | 2-Cl-3,6-di-MeO—PhCH2— |
| Z-6013 | MeS(═O)— | MeS(═O)2— | Z-6014 | EtS— | 2-Me—PhCH2— | Z-6015 | EtS— | 2-Br-3,4-di-MeO—PhCH2— |
| Z-6016 | MeS(═O)— | EtS— | Z-6017 | EtS— | 3-Me—PhCH2— | Z-6018 | EtS— | 2-Br-3,5-di-MeO—PhCH2— |
| Z-6019 | MeS(═O)— | EtS(═O)— | Z-6020 | EtS— | 4-Me—PhCH2— | Z-6021 | EtS— | 2-Br-3,6-di-MeO—PhCH2— |
| Z-6022 | MeS(═O)— | EtS(═O)2— | Z-6023 | EtS(═O)— | 2-F-3,5-di-MeO—Ph | Z-6024 | EtS— | EtS— |
| Z-6025 | MeS(═O)— | PrS— | Z-6026 | EtS(═O)— | 2-F-3,6-di-MeO—Ph | Z-6027 | EtS— | EtS(═O)— |
| Z-6028 | MeS(═O)— | PrS(═O)— | Z-6029 | EtS(═O)— | 2-Cl-3,4-di-MeO—Ph | Z-6030 | EtS— | EtS(═O)2— |
| Z-6031 | MeS(═O)— | PrS(═O)2— | Z-6032 | EtS(═O)— | 2-Cl-3,5-di-MeO—Ph | Z-6033 | EtS— | PrS— |
| Z-6034 | MeS(═O)— | Ac | Z-6035 | EtS(═O)— | 2-Cl-3,6-di-MeO—Ph | Z-6036 | EtS— | PrS(═O)— |
| Z-6037 | MeS(═O)2— | 2-Br-5-MeO—PhCH2— | Z-6038 | EtS(═O)— | 2-Br-3,4-di-MeO—Ph | Z-6039 | EtS— | PrS(═O)2— |
| Z-6040 | MeS(═O)2— | 2-Br-6-MeO—PhCH2— | Z-6041 | EtS(═O)— | 2-Br-3,5-di-MeO—Ph | Z-6042 | EtS— | Ac |
| Z-6043 | MeS(═O)2— | 2,3,4-tri-F—PhCH2— | Z-6044 | EtS(═O)— | 2-Br-3,6-di-MeO—Ph | Z-6045 | EtS— | OHC— |
| Z-6046 | MeS(═O)2— | 2,3,5-tri-F—PhCH2— | Z-6047 | EtS(═O)— | PhCH2— | Z-6048 | EtS— | Et(C═O)— |
| Z-6049 | MeS(═O)2— | 2,3,6-tri-F—PhCH2— | Z-6050 | EtS(═O)— | 2-F—PECH2— | Z-6051 | EtS— | Pr(C═O)— |
| Z-6052 | MeS(═O)2— | 2-Br-3,4-di-F—PhCH2— | Z-6053 | EtS(═O)— | 3-F—PhCH2— | Z-6054 | EtS— | i-Pr(C═O)— |
| Z-6055 | MeS(═O)2— | 2-Br-3,5-di-F—PhCH2— | Z-6056 | EtS(═O)— | 4-F—PhCH2— | Z-6057 | EtS— | Bu(C═O)— |
| Z-6058 | MeS(═O)2— | 2-Br-3,6-di-F—PhCH2— | Z-6059 | EtS(═O)— | 2-Cl—PhCH2— | Z-6060 | EtS— | MeO(C═O)— |
| Z-6061 | MeS(═O)2— | 2-F-3,4-di-MeO—PhCH2— | Z-6062 | EtS(═O)— | 3-Cl—PhCH2— | Z-6063 | EtS(═O)— | 2-Br-3,5-di-F—PhCH2— |
| Z-6064 | MeS(═O)2— | 2-F-3,5-di-MeO—PhCH2— | Z-6065 | EtS(═O)— | 4-Cl—PhCH2— | Z-6066 | EtS(═O)— | 2-Br-3,6-di-F—PhCH2— |
| Z-6067 | MeS(═O)2— | 2-F-3,6-di-MeO—PhCH2— | Z-6068 | EtS(═O)— | 2-Br—PhCH2— | Z-6069 | EtS(═O)— | 2-F-3,4-di-MeO—PhCH2— |
| Z-6070 | MeS(═O)2— | 2-Cl-3,4-di-MeO—PhCH2— | Z-6071 | EtS(═O)— | 3-Br—PhCH2— | Z-6072 | EtS(═O)— | 2-F-3,5-di-MeO—PhCH2— |
| Z-6073 | MeS(═O)2— | 2-Cl-3,5-di-MeO—PhCH2— | Z-6074 | EtS(═O)— | 4-Br—PhCH2— | Z-6075 | EtS(═O)— | 2-F-3,6-di-MeO—PhCH2— |
| Z-6076 | MeS(═O)2— | 2-Cl-3,6-di-MeO—PhCH2— | Z-6077 | EtS(═O)— | 2-I—PhCH2— | Z-6078 | EtS(═O)— | 2-Cl-3,4-di-MeO—PhCH2— |
| Z-6079 | MeS(═O)2— | 2-Br-3,4-di-MeO—PhCH2— | Z-6080 | EtS(═O)— | 3-I—PhCH2— | Z-6081 | EtS(═O)— | 2-Cl-3,5-di-MeO—PhCH2— |
| Z-6082 | MeS(═O)2— | 2-Br-3,5-di-MeO—PhCH2— | Z-6083 | EtS(═O)— | 4-I—PhCH2— | Z-6084 | EtS(═O)— | 2-Cl-3,6-di-MeO—PhCH2— |
| Z-6085 | MeS(═O)2— | 2-Br-3,6-di-MeO—PhCH2— | Z-6086 | EtS(═O)— | 2-Me—PhCH2— | Z-6087 | EtS(═O)— | 2-Br-3,4-di-MeO—PhCH2— |
| Z-6088 | MeS(═O)2— | MeS(═O)2— | Z-6089 | EtS(═O)— | 3-Me—PhCH2— | Z-6090 | EtS(═O)— | 2-Br-3,5-di-MeO—PhCH2— |
| Z-6091 | MeS(═O)2— | EtS— | Z-6092 | EtS(═O)— | 4-Me—PhCH2— | Z-6093 | EtS(═O)— | 2-Br-3,6-di-MeO—PhCH2— |
| Z-6094 | MeS(═O)2— | EtS(═O)— | Z-6095 | EtS(═O)— | 2-MeO—PhCH2— | Z-6096 | EtS(═O)— | EtS(═O)— |
| Z-6097 | MeS(═O)2— | EtS(═O)2— | Z-6098 | EtS(═O)— | 3-MeO—PhCH2— | Z-6099 | EtS(═O)— | EtS(═O)2— |
| Z-6100 | MeS(═O)2— | PrS— | Z-6101 | EtS(═O)— | 4-MeO—PhCH2— | Z-6102 | EtS(═O)— | PrS— |
| Z-6103 | MeS(═O)2— | PrS(═O)— | Z-6104 | EtS(═O)— | 2,3-di-F—PhCH2— | Z-6105 | EtS(═O)— | PrS(═O)— |
| Z-6106 | MeS(═O)2— | PrS(═O)2— | Z-6107 | EtS(═O)— | 2,4-di-F—PhCH2— | Z-6108 | EtS(═O)— | PrS(═O)2— |
| Z-6109 | MeS(═O)2— | Ac | Z-6110 | EtS(═O)— | 2,5-di-F—PhCH2— | Z-6111 | EtS(═O)— | Ac |
| Z-6112 | MeS(═O)2— | OHC— | Z-6113 | EtS(═O)— | 2,6-di-F—PhCH2— | Z-6114 | EtS(═O)— | OHC— |

TABLE 3-continued

| Z | R3 | R4 | Z | R3 | R4 | Z | R3 | R4 |
|---|---|---|---|---|---|---|---|---|
| Z-6115 | MeS(=O)2— | Et(C=O)— | Z-6116 | EtS(=O)— | 2-Cl-3-F—PhCH2— | Z-6117 | EtS(=O)— | Et(C=O)— |
| Z-6118 | MeS(=O)2— | Pr(C=O)— | Z-6119 | EtS(=O)— | 2-Cl-4-F—PhCH2— | Z-6120 | EtS(=O)— | Pr(C=O)— |
| Z-6121 | MeS(=O)2— | i-Pr(C=O)— | Z-6122 | EtS(=O)— | 2-Cl-5-F—PhCH2— | Z-6123 | EtS(=O)— | i-Pr(C=O)— |
| Z-6124 | MeS(=O)2— | Bu(C=O)— | Z-6125 | EtS(=O)— | 2-Cl-6-F—PhCH2— | Z-6126 | EtS(=O)— | Bu(C=O)— |
| Z-6127 | MeS(=O)2— | MeO(C=O)— | Z-6128 | EtS(=O)— | 2-Br-3-F—PhCH2— | Z-6129 | EtS(=O)— | MeO(C=O)— |
| Z-6130 | MeS(=O)2— | EtO(C=O)— | Z-6131 | EtS(=O)— | 2-Br-4-F—PhCH2— | Z-6132 | EtS(=O)— | EtO(C=O)— |
| Z-6133 | MeS(=O)2— | PrO(C=O)— | Z-6134 | EtS(=O)— | 2-Br-5-F—PhCH2— | Z-6135 | EtS(=O)— | PrO(C=O)— |
| Z-6136 | MeS(=O)2— | i-PrO(C=O)— | Z-6137 | EtS(=O)— | 2-Br-6-F—PhCH2— | Z-6138 | EtS(=O)— | i-PrO(C=O)— |
| Z-6139 | MeS(=O)2— | BuO(C=O)— | Z-6140 | EtS(=O)— | 2-F-3-MeO—PhCH2— | Z-6141 | EtS(=O)— | BuO(C=O)— |
| Z-6142 | MeS(=O)2— | t-BuOC(=O)— | Z-6143 | EtS(=O)— | 2-F-4-MeO—PhCH2— | Z-6144 | EtS(=O)— | t-BuOC(=O)— |
| Z-6145 | EtS— | Ph | Z-6146 | EtS(=O)— | 2-F-5-MeO—PhCH2— | Z-6147 | EtS(=O)2— | Ph |
| Z-6148 | EtS— | 2-F—Ph | Z-6149 | EtS(=O)— | 2-F-6-MeO—PhCH2— | Z-6150 | EtS(=O)2— | 2-F—Ph |
| Z-6151 | EtS— | 3-F—Ph | Z-6152 | EtS(=O)— | 2-Cl-3-MeO—PhCH2— | Z-6153 | EtS(=O)2— | 3-F—Ph |
| Z-6154 | EtS— | 4-F—Ph | Z-6155 | EtS(=O)— | 2-Cl-4-MeO—PhCH2— | Z-6156 | EtS(=O)2— | 4-F—Ph |
| Z-6157 | EtS— | 2-Cl—Ph | Z-6158 | EtS(=O)— | 2-Cl-5-MeO—PhCH2— | Z-6159 | EtS(=O)2— | 2-Cl—Ph |
| Z-6160 | EtS— | 3-Cl—Ph | Z-6161 | EtS(=O)— | 2-Cl-6-MeO—PhCH2— | Z-6162 | EtS(=O)2— | 3-Cl—Ph |
| Z-6163 | EtS— | 4-Cl—Ph | Z-6164 | EtS(=O)— | 2-Br-3-MeO—PhCH2— | Z-6165 | EtS(=O)2— | 4-Cl—Ph |
| Z-6166 | EtS— | 2-Br—Ph | Z-6167 | EtS(=O)— | 2-Br-4-MeO—PhCH2— | Z-6168 | EtS(=O)2— | 2-Br—Ph |
| Z-6169 | EtS— | 3-Br—Ph | Z-6170 | EtS(=O)— | 2-Br-5-MeO—PhCH2— | Z-6171 | EtS(=O)2— | 3-Br—Ph |
| Z-6172 | EtS— | 4-Br—Ph | Z-6173 | EtS(=O)— | 2-Br-6-MeO—PhCH2— | Z-6174 | EtS(=O)2— | 4-Br—Ph |
| Z-6175 | EtS— | 2-I—Ph | Z-6176 | EtS(=O)— | 2,3,4-tri-F—PhCH2— | Z-6177 | EtS(=O)2— | 2-I—Ph |
| Z-6178 | EtS— | 3-I—Ph | Z-6179 | EtS(=O)— | 2,3,5-tri-F—PhCH2— | Z-6180 | EtS(=O)2— | 3-I—Ph |
| Z-6181 | EtS— | 4-I—Ph | Z-6182 | EtS(=O)— | 2,3,6-tri-F—PhCH2— | Z-6183 | EtS(=O)2— | 4-I—Ph |
| Z-6184 | EtS— | 2-Me—Ph | Z-6185 | EtS(=O)— | 2-Br-3,4-di-F—PhCH2— | Z-6186 | EtS(=O)2— | 2-Me—Ph |
| Z-6187 | EtS— | 3-Me—Ph | Z-6188 | EtS(=O)2— | 2-Cl-4-F—PhCH2— | Z-6189 | EtS(=O)2— | 3-Me—Ph |
| Z-6190 | EtS— | 4-Me—Ph | Z-6191 | EtS(=O)2— | 2-Cl-5-F—PhCH2— | Z-6192 | EtS(=O)2— | 4-Me—Ph |
| Z-6193 | EtS— | 2-MeO—Ph | Z-6194 | EtS(=O)2— | 2-Cl-6-F—PhCH2— | Z-6195 | EtS(=O)2— | 2-MeO—Ph |
| Z-6196 | EtS— | 3-MeO—Ph | Z-6197 | EtS(=O)2— | 2-Br-3-F—PhCH2— | Z-6198 | EtS(=O)2— | 3-MeO—Ph |
| Z-6199 | EtS— | 4-MeO—Ph | Z-6200 | EtS(=O)2— | 2-Br-4-F—PhCH2— | Z-6201 | EtS(=O)2— | 4-MeO—Ph |
| Z-6202 | EtS— | EtO(C=O)— | Z-6203 | EtS(=O)2— | 2-Br-5-F—PhCH2— | Z-6204 | EtS(=O)2— | 2,3-di-F—Ph |
| Z-6205 | EtS— | PrO(C=O)— | Z-6206 | EtS(=O)2— | 2-Br-6-F—PhCH2— | Z-6207 | EtS(=O)2— | 2,4-di-F—Ph |
| Z-6208 | EtS— | i-PrO(C=O)— | Z-6209 | EtS(=O)2— | 2-F-3-MeO—PhCH2— | Z-6210 | EtS(=O)2— | 2,5-di-F—Ph |
| Z-6211 | EtS— | BuO(C=O)— | Z-6212 | EtS(=O)2— | 2-F-4-MeO—PhCH2— | Z-6213 | EtS(=O)2— | 2,6-di-F—Ph |
| Z-6214 | EtS— | t-BuOC(=O)— | Z-6215 | EtS(=O)2— | 2-F-5-MeO—PhCH2— | Z-6216 | EtS(=O)2— | 2-Cl-3-F—Ph |
| Z-6217 | EtS(=O)— | Ph | Z-6218 | EtS(=O)2— | 2-F-6-MeO—PhCH2— | Z-6219 | EtS(=O)2— | 2-Cl-4-F—Ph |
| Z-6220 | EtS(=O)— | 2-F—Ph | Z-6221 | EtS(=O)2— | 2-Cl-3-MeO—PhCH2— | Z-6222 | EtS(=O)2— | 2-Cl-5-F—Ph |
| Z-6223 | EtS(=O)— | 3-F—Ph | Z-6224 | EtS(=O)2— | 2-Cl-4-MeO—PhCH2— | Z-6225 | EtS(=O)2— | 2-Cl-6-F—Ph |
| Z-6226 | EtS(=O)— | 4-F—Ph | Z-6227 | EtS(=O)2— | 2-Cl-5-MeO—PhCH2— | Z-6228 | Ac | 2-MeO—PhCH2— |
| Z-6229 | EtS(=O)— | 2-Cl—Ph | Z-6230 | EtS(=O)2— | 2-Cl-6-MeO—PhCH2— | Z-6231 | Ac | 3-MeO—PhCH2— |
| Z-6232 | EtS(=O)— | 3-Cl—Ph | Z-6233 | EtS(=O)2— | 2-Br-3-MeO—PhCH2— | Z-6234 | Ac | 4-MeO—PhCH2— |
| Z-6235 | EtS(=O)— | 4-Cl—Ph | Z-6236 | EtS(=O)2— | 2-Br-4-MeO—PhCH2— | Z-6237 | Ac | 2,3-di-F—PhCH2— |
| Z-6238 | EtS(=O)— | 2-Br—Ph | Z-6239 | EtS(=O)2— | 2-Br-5-MeO—PhCH2— | Z-6240 | Ac | 2,4-di-F—PhCH2— |
| Z-6241 | EtS(=O)— | 3-Br—Ph | Z-6242 | EtS(=O)2— | 2-Br-6-MeO—PhCH2— | Z-6243 | Ac | 2,5-di-F—PhCH2— |
| Z-6244 | EtS(=O)— | 4-Br—Ph | Z-6245 | EtS(=O)2— | 2,3,4-tri-F—PhCH2— | Z-6246 | Ac | 2,6-di-F—PhCH2— |
| Z-6247 | EtS(=O)— | 2-I—Ph | Z-6248 | EtS(=O)2— | 2,3,5-tri-F—PhCH2— | Z-6249 | Ac | 2-Cl-3-F—PhCH2— |
| Z-6250 | EtS(=O)— | 3-I—Ph | Z-6251 | EtS(=O)2— | 2,3,6-tri-F—PhCH2— | Z-6252 | Ac | 2-Cl-4-F—PhCH2— |
| Z-6253 | EtS(=O)— | 4-I—Ph | Z-6254 | EtS(=O)2— | 2-Br-3,4-di-F—PhCH2— | Z-6255 | Ac | 2-Cl-5-F—PhCH2— |
| Z-6256 | EtS(=O)— | 2-Me—Ph | Z-6257 | EtS(=O)2— | 2-Br-3,5-di-F—PhCH2— | Z-6258 | Ac | 2-Cl-6-F—PhCH2— |
| Z-6259 | EtS(=O)— | 3-Me—Ph | Z-6260 | EtS(=O)2— | 2-Br-3,6-di-F—PhCH2— | Z-6261 | Ac | 2-Br-3-F—PhCH2— |
| Z-6262 | EtS(=O)— | 4-Me—Ph | Z-6263 | EtS(=O)2— | 2-F-3,4-di-MeO—PhCH2— | Z-6264 | Ac | 2-Br-4-F—PhCH2— |
| Z-6265 | EtS(=O)— | 2-MeO—Ph | Z-6266 | EtS(=O)2— | 2-F-3,5-di-MeO—PhCH2— | Z-6261 | Ac | 2-Br-5-F—PhCH2— |

TABLE 3-continued

| Z | R3 | R4 | Z | R3 | R4 | Z | R3 | R4 |
|---|---|---|---|---|---|---|---|---|
| Z-6268 | EtS(═O)— | 3-MeO—Ph | Z-6269 | EtS(═O)2— | 2-F-3,6-di-MeO—PhCH2— | Z-6270 | Ac | 2-Br-6-F—PhCH2— |
| Z-6271 | EtS(═O)— | 4-MeO—Ph | Z-6272 | EtS(═O)2— | 2-Cl-3,4-di-MeO—PhCH2— | Z-6273 | Ac | 2-F-3-MeO—PhCH2— |
| Z-6274 | EtS(═O)— | 2,3-di-F—Ph | Z-6275 | EtS(═O)2— | 2-Cl-3,5-di-MeO—PhCH2— | Z-6276 | Ac | 2-F-4-MeO—PhCH2— |
| Z-6277 | EtS(═O)— | 2,4-di-F—Ph | Z-6278 | EtS(═O)2— | 2-Cl-3,6-di-MeO—PhCH2— | Z-6279 | Ac | 2-F-5-MeO—PhCH2— |
| Z-6280 | EtS(═O)— | 2,5-di-F—Ph | Z-6281 | EtS(═O)2— | 2-Br-3,4-di-MeO—PhCH2— | Z-6282 | Ac | 2-F-6-MeO—PhCH2— |
| Z-6283 | EtS(═O)— | 2,6-di-F—Ph | Z-6284 | EtS(═O)2— | 2-Br-3,5-di-MeO—PhCH2— | Z-6285 | Ac | 2-Cl-3-MeO—PhCH2— |
| Z-6286 | EtS(═O)— | 2-Cl-3-F—Ph | Z-6287 | EtS(═O)2— | 2-Br-3,6-di-MeO—PhCH2— | Z-6288 | Ac | 2-Cl-4-MeO—PhCH2— |
| Z-6289 | EtS(═O)— | 2-Cl-4-F—Ph | Z-6290 | EtS(═O)2— | EtS(═O)2— | Z-6291 | Ac | 2-Cl-5-MeO—PhCH2— |
| Z-6292 | EtS(═O)— | 2-Cl-5-F—Ph | Z-6293 | EtS(═O)2— | PrS— | Z-6294 | Ac | 2-Cl-6-MeO—PhCH2— |
| Z-6295 | EtS(═O)— | 2-Cl-6-F—Ph | Z-6296 | EtS(═O)2— | PrS(═O)— | Z-6297 | Ac | 2-Br-3-MeO—PhCH2— |
| Z-6298 | EtS(═O)— | 2-Br-3-F—Ph | Z-6299 | EtS(═O)2— | PrS(═O)2— | Z-6300 | Ac | 2-Br-4-MeO—PhCH2— |
| Z-6301 | EtS(═O)— | 2-Br-4-F—Ph | Z-6302 | EtS(═O)2— | Ac | Z-6303 | Ac | 2-Br-5-MeO—PhCH2— |
| Z-6304 | EtS(═O)— | 2-Br-5-F—Ph | Z-6305 | EtS(═O)2— | OHC— | Z-6306 | Ac | 2-Br-6-MeO—PhCH2— |
| Z-6307 | EtS(═O)— | 2-Br-6-F—Ph | Z-6308 | EtS(═O)2— | Et(C═O)— | Z-6309 | Ac | 2,3,4-tri-F—PhCH2— |
| Z-6310 | EtS(═O)— | 2-F-3-MeO—Ph | Z-6311 | EtS(═O)2— | Pr(C═O)— | Z-6312 | Ac | 2,3,5-tri-F—PhCH2— |
| Z-6313 | EtS(═O)— | 2-F-4-MeO—Ph | Z-6314 | EtS(═O)2— | i-Pr(C═O)— | Z-6315 | Ac | 2,3,6-tri-F—PhCH2— |
| Z-6316 | EtS(═O)— | 2-F-5-MeO—Ph | Z-6317 | EtS(═O)2— | Bu(C═O)— | Z-6318 | Ac | 2-Br-3,4-di-F—PhCH2— |
| Z-6319 | EtS(═O)— | 2-F-6-MeO—Ph | Z-6320 | EtS(═O)2— | MeO(C═O)— | Z-6321 | Ac | 2-Br-3,5-di-F—PhCH2— |
| Z-6322 | EtS(═O)— | 2-Cl-3-MeO—Ph | Z-6323 | EtS(═O)2— | EtO(C═O)— | Z-6324 | Ac | 2-Br-3,6-di-F—PhCH2— |
| Z-6325 | EtS(═O)— | 2-Cl-4-MeO—Ph | Z-6326 | EtS(═O)2— | PrO(C═O)— | Z-6327 | Ac | 2-F-3,4-di-MeO—PhCH2— |
| Z-6328 | EtS(═O)— | 2-Cl-5-MeO—Ph | Z-6329 | EtS(═O)2— | i-PrO(C═O)— | Z-6330 | Ac | 2-F-3,5-di-MeO—PhCH2— |
| Z-6331 | EtS(═O)— | 2-Cl-6-MeO—Ph | Z-6332 | EtS(═O)2— | BuO(C═O)— | Z-6333 | Ac | 2-F-3,6-di-MeO—PhCH2— |
| Z-6334 | EtS(═O)— | 2-Br-3-MeO—Ph | Z-6335 | EtS(═O)2— | t-BuOC(═O)— | Z-6336 | Ac | 2-Cl-3,4-di-MeO—PhCH2— |
| Z-6337 | EtS(═O)— | 2-Br-4-MeO—Ph | Z-6338 | Ac | 2,3-di-F—Ph | Z-6339 | Ac | 2-Cl-3,5-di-MeO—PhCH2— |
| Z-6340 | EtS(═O)— | 2-Br-5-MeO—Ph | Z-6341 | Ac | 2,4-di-F—Ph | Z-6342 | Ac | 2-Cl-3,6-di-MeO—PhCH2— |
| Z-6343 | EtS(═O)— | 2-Br-6-MeO—Ph | Z-6344 | Ac | 2,5-di-F—Ph | Z-6345 | Ac | 2-Br-3,4-di-MeO—PhCH2— |
| Z-6346 | EtS(═O)— | 2,3,4-tri-F—Ph | Z-6347 | Ac | 2,6-di-F—Ph | Z-6348 | Ac | 2-Br-3,5-di-MeO—PhCH2— |
| Z-6349 | EtS(═O)— | 2,3,5-tri-F—Ph | Z-6350 | Ac | 2-Cl-3-F—Ph | Z-6351 | Ac | 2-Br-3,6-di-MeO—PhCH2— |
| Z-6352 | EtS(═O)— | 2,3,6-tri-F—Ph | Z-6353 | Ac | 2-Cl-4-F—Ph | Z-6354 | Ac | Ac |
| Z-6355 | EtS(═O)— | 2-Br-3,4-di-F—Ph | Z-6356 | Ac | 2-Cl-5-F—Ph | Z-6357 | Ac | OHC— |
| Z-6358 | EtS(═O)— | 2-Br-3,5-di-F—Ph | Z-6359 | Ac | 2-Cl-6-F—Ph | Z-6360 | Ac | Et(C═O)— |
| Z-6361 | EtS(═O)— | 2-Br-3,6-di-F—Ph | Z-6362 | Ac | 2-Br-3-F—Ph | Z-6363 | Ac | Pr(C═O)— |
| Z-6364 | EtS(═O)— | 2-F-3,4-di-MeO—Ph | Z-6365 | Ac | 2-Br-4-F—Ph | Z-6366 | Ac | i-Pr(C═O)— |
| Z-6367 | EtS(═O)2— | 2-Br-3-F—Ph | Z-6368 | Ac | 2-Br-5-F—Ph | Z-6369 | Ac | Bu(C═O)— |
| Z-6370 | EtS(═O)2— | 2-Br-4-F—Ph | Z-6371 | Ac | 2-Br-6-F—Ph | Z-6372 | Ac | MeO(C═O)— |
| Z-6373 | EtS(═O)2— | 2-Br-5-F—Ph | Z-6374 | Ac | 2-F-3-MeO—Ph | Z-6375 | Ac | EtO(C═O)— |
| Z-6376 | EtS(═O)2— | 2-Br-6-F—Ph | Z-6377 | Ac | 2-F-4-MeO—Ph | Z-6378 | Ac | PrO(C═O)— |
| Z-6379 | EtS(═O)2— | 2-F-3-MeO—Ph | Z-6380 | Ac | 2-F-5-MeO—Ph | Z-6381 | Ac | i-PrO(C═O)— |
| Z-6382 | EtS(═O)2— | 2-F-4-MeO—Ph | Z-6383 | Ac | 2-F-6-MeO—Ph | Z-6384 | Ac | BuO(C═O)— |
| Z-6385 | EtS(═O)2— | 2-F-5-MeO—Ph | Z-6386 | Ac | 2-Cl-3-MeO—Ph | Z-6387 | Ac | t-BuOC(═O)— |
| Z-6388 | EtS(═O)2— | 2-F-6-MeO—Ph | Z-6389 | Ac | 2-Cl-4-MeO—Ph | Z-6390 | OHC— | Ph |
| Z-6391 | EtS(═O)2— | 2-Cl-3-MeO—Ph | Z-6392 | Ac | 2-Cl-5-MeO—Ph | Z-6393 | OHC— | 2-Cl-3,5-di-MeO—PhCH2— |
| Z-6394 | EtS(═O)2— | 2-Cl-4-MeO—Ph | Z-6395 | Ac | 2-Cl-6-MeO—Ph | Z-6396 | OHC— | 2-Cl-3,6-di-MeO—PhCH2— |
| Z-6397 | EtS(═O)2— | 2-Cl-5-MeO—Ph | Z-6398 | Ac | 2-Br-3-MeO—Ph | Z-6399 | OHC— | 2-Br-3,4-di-MeO—PhCH2— |
| Z-6400 | EtS(═O)2— | 2-Cl-6-MeO—Ph | Z-6401 | Ac | 2-Br-4-MeO—Ph | Z-6402 | OHC— | 2-Br-3,5-di-MeO—PhCH2— |
| Z-6403 | EtS(═O)2— | 2-Br-3-MeO—Ph | Z-6404 | Ac | 2-Br-5-MeO—Ph | Z-6405 | OHC— | 2-Br-3,6-di-MeO—PhCH2— |
| Z-6406 | EtS(═O)2— | 2-Br—MeO—Ph | Z-6407 | Ac | 2-Br-6-MeO—Ph | Z-6408 | OHC— | OHC— |
| Z-6409 | EtS(═O)2— | 2-Br-5-MeO—Ph | Z-6410 | Ac | 2,3,4-tri-F—Ph | Z-6411 | OHC— | Et(C═O)— |
| Z-6412 | EtS(═O)2— | 2-Br-6-MeO—Ph | Z-6413 | Ac | 2,3,5-tri-F—Ph | Z-6414 | OHC— | Pr(C═O)— |
| Z-6415 | EtS(═O)2— | 2,3,4-tri-F—Ph | Z-6416 | Ac | 2,3,6-tri-F—Ph | Z-6417 | OHC— | i-Pr(C═O)— |
| Z-6418 | EtS(═O)2— | 2,3,5-tri-F—Ph | Z-6419 | Ac | 2-Br-3,4-di-F—Ph | Z-6420 | OHC— | Bu(C═O)— |

TABLE 3-continued

| Z | R3 | R4 | Z | R3 | R4 | Z | R3 | R4 |
|---|---|---|---|---|---|---|---|---|
| Z-6421 | EtS(═O)2— | 2,3,6-tri-F—Ph | Z-6422 | Ac | 2-Br-3,5-di-F—Ph | Z-6423 | OHC— | MeO(C═O)— |
| Z-6424 | EtS(═O)2— | 2-Br-3,4-di-F—Ph | Z-6425 | Ac | 2-Br-3,6-di-F—Ph | Z-6426 | OHC— | EtO(C═O)— |
| Z-6427 | EtS(═O)2— | 2-Br-3,5-di-F—Ph | Z-6428 | Ac | 2-F-3,4-di-MeO—Ph | Z-6429 | OHC— | PrO(C═O)— |
| Z-6430 | EtS(═O)2— | 2-Br-3,6-di-F—Ph | Z-6431 | Ac | 2-F-3,5-di-MeO—Ph | Z-6432 | OHC— | i-PrO(C═O)— |
| Z-6433 | EtS(═O)2— | 2-F-3,4-di-MeO—Ph | Z-6434 | Ac | 2-F-3,6-di-MeO—Ph | Z-6435 | OHC— | BuO(C═O)— |
| Z-6436 | EtS(═O)2— | 2-F-3,5-di-MeO—Ph | Z-6437 | Ac | 2-Cl-3,4-di-MeO—Ph | Z-6438 | OHC— | t-BuOC(═O)— |
| Z-6439 | EtS(═O)2— | 2-F-3,6-di-MeO—Ph | Z-6440 | Ac | 2-Cl-3,5-di-MeO—Ph | Z-6441 | Et(C═O)— | Ph |
| Z-6442 | EtS(═O)2— | 2-Cl-3,4-di-MeO—Ph | Z-6443 | Ac | 2-Cl-3,6-di-MeO—Ph | Z-6444 | Et(C═O)— | 2-F—Ph |
| Z-6445 | EtS(═O)2— | 2-Cl-3,5-di-MeO—Ph | Z-6446 | Ac | 2-Br-3,4-di-MeO—Ph | Z-6447 | Et(C═O)— | 3-F—Ph |
| Z-6448 | EtS(═O)2— | 2-Cl-3,6-di-MeO—Ph | Z-6449 | Ac | 2-Br-3,5-di-MeO—Ph | Z-6450 | Et(C═O)— | 4-F—Ph |
| Z-6451 | EtS(═O)2— | 2-Br-3,4-di-MeO—Ph | Z-6452 | Ac | 2-Br-3,6-di-MeO—Ph | Z-6453 | Et(C═O)— | 2-Cl—Ph |
| Z-6454 | EtS(═O)2— | 2-Br-3,5-di-MeO—Ph | Z-6455 | Ac | PhCH2— | Z-6456 | Et(C═O)— | 3-Cl—Ph |
| Z-6457 | EtS(═O)2— | 2-Br-3,6-di-MeO—Ph | Z-6458 | Ac | 2-F—PhCH2— | Z-6459 | Et(C═O)— | 4-Cl—Ph |
| Z-6460 | EtS(═O)2— | PhCH2— | Z-6461 | Ac | 3-F—PhCH2— | Z-6462 | Et(C═O)— | 2-Br—Ph |
| Z-6463 | EtS(═O)2— | 2-F—PhCH2— | Z-6464 | Ac | 4-F—PhCH2— | Z-6465 | Et(C═O)— | 3-Br—Ph |
| Z-6466 | EtS(═O)2— | 3-F—PhCH2— | Z-6467 | Ac | 2-Cl—PhCH2— | Z-6468 | Et(C═O)— | 4-Br—Ph |
| Z-6469 | EtS(═O)2— | 4-F—PhCH2— | Z-6470 | Ac | 3-Cl—PhCH2— | Z-6471 | Et(C═O)— | 2-I—Ph |
| Z-6472 | EtS(═O)2— | 2-Cl—PhCH2— | Z-6473 | Ac | 4-Cl—PhCH2— | Z-6474 | Et(C═O)— | 3-I—Ph |
| Z-6475 | EtS(═O)2— | 3-Cl—PhCH2— | Z-6476 | Ac | 2-Br—PhCH2— | Z-6477 | Et(C═O)— | 4-I—Ph |
| Z-6478 | EtS(═O)2— | 4-Cl—PhCH2— | Z-6479 | Ac | 3-Br—PhCH2— | Z-6480 | Et(C═O)— | 2-Me—Ph |
| Z-6481 | EtS(═O)2— | 2-Br—PhCH2— | Z-6482 | Ac | 4-Br—PhCH2— | Z-6483 | Et(C═O)— | 3-Me—Ph |
| Z-6484 | EtS(═O)2— | 3-Br—PhCH2— | Z-6485 | Ac | 2-I—PhCH2— | Z-6486 | Et(C═O)— | 4-Me—Ph |
| Z-6487 | EtS(═O)2— | 4-Br—PhCH2— | Z-6488 | Ac | 3-I—PhCH2— | Z-6489 | Et(C═O)— | 2-MeO—Ph |
| Z-6490 | EtS(═O)2— | 2-I—PhCH2— | Z-6491 | Ac | 4-I—PhCH2— | Z-6492 | Et(C═O)— | 3-MeO—Ph |
| Z-6493 | EtS(═O)2— | 3-I—PhCH2— | Z-6494 | Ac | 2-Me—PhCH2— | Z-6495 | Et(C═O)— | 4-MeO—Ph |
| Z-6496 | EtS(═O)2— | 4-I—PhCH2— | Z-6497 | Ac | 3-Me—PhCH2— | Z-6498 | Et(C═O)— | 2,3-di-F—Ph |
| Z-6499 | EtS(═O)2— | 2-Me—PhCH2— | Z-6500 | Ac | 4-Me—PhCH2— | Z-6501 | Et(C═O)— | 2,4-di-F—Ph |
| Z-6502 | EtS(═O)2— | 3-Me—PhCH2— | Z-6503 | OHC— | 2-Br-3,5-di-MeO—Ph | Z-6504 | Et(C═O)— | 2,5-di-F—Ph |
| Z-6505 | EtS(═O)2— | 4-Me—PhCH2— | Z-6506 | OHC— | 2-Br-3,6-di-MeO—Ph | Z-6507 | Et(C═O)— | 2,6-di-F—Ph |
| Z-6508 | EtS(═O)2— | 2-MeO—PhCH2— | Z-6509 | OHC— | PhCH2— | Z-6510 | Et(C═O)— | 2-Cl-3-F—Ph |
| Z-6511 | EtS(═O)2— | 3-MeO—PhCH2— | Z-6512 | OHC— | 2-F—PhCH2— | Z-6513 | Et(C═O)— | 2-Cl-4-F—Ph |
| Z-6514 | EtS(═O)2— | 4-MeO—PhCH2— | Z-6515 | OHC— | 3-F—PhCH2— | Z-6516 | Et(C═O)— | 2-Cl-5-F—Ph |
| Z-6517 | EtS(═O)2— | 2,3-di-F—PhCH2— | Z-6518 | OHC— | 4-F—PhCH2— | Z-6519 | Et(C═O)— | 2-Cl-6-F—Ph |
| Z-6520 | EtS(═O)2— | 2,4-di-F—PhCH2— | Z-6521 | OHC— | 2-Cl—PhCH2— | Z-6522 | Et(C═O)— | 2-Br-3-F—Ph |
| Z-6523 | EtS(═O)2— | 2,5-di-F—PhCH2— | Z-6524 | OHC— | 3-Cl—PhCH2— | Z-6525 | Et(C═O)— | 2-Br-4-F—Ph |
| Z-6526 | EtS(═O)2— | 2,6-di-F—PhCH2— | Z-6527 | OHC— | 4-Cl—PhCH2— | Z-6528 | Et(C═O)— | 2-Br-5-F—Ph |
| Z-6529 | EtS(═O)2— | 2-Cl-3-F—PhCH2— | Z-6530 | OHC— | 2-Br—PhCH2— | Z-6531 | Et(C═O)— | 2-Br-6-F—Ph |
| Z-6532 | Ac | Ph | Z-6533 | OHC— | 3-Br—PhCH2— | Z-6534 | Et(C═O)— | 2-F-3-MeO—Ph |
| Z-6535 | Ac | 2-F—Ph | Z-6536 | OHC— | 4-Br—PhCH2— | Z-6537 | Et(C═O)— | 2-F-4-MeO—Ph |
| Z-6538 | Ac | 3-F—Ph | Z-6539 | OHC— | 2-I—PhCH2— | Z-6540 | Et(C═O)— | 2-F-5-MeO—Ph |
| Z-6541 | Ac | 4-F—Ph | Z-6542 | OHC— | 3-I—PhCH2— | Z-6543 | Et(C═O)— | 2-F-6-MeO—Ph |
| Z-6544 | Ac | 2-Cl—Ph | Z-6545 | OHC— | 4-I—PhCH2— | Z-6546 | Et(C═O)— | 2-Cl-3-MeO—Ph |
| Z-6547 | Ac | 3-Cl—Ph | Z-6548 | OHC— | 2-Me—PhCH2— | Z-6549 | Et(C═O)— | 2-Cl-4-MeO—Ph |
| Z-6550 | Ac | 4-Cl—Ph | Z-6551 | OHC— | 3-Me—PhCH2— | Z-6552 | Et(C═O)— | 2-Cl-5-MeO—Ph |
| Z-6553 | Ac | 2-Br—Ph | Z-6554 | OHC— | 4-Me—PhCH2— | Z-6555 | Et(C═O)— | 2-Cl-6-MeO—Ph |
| Z-6556 | Ac | 3-Br—Ph | Z-6557 | OHC— | 2-MeO—PhCH2— | Z-6558 | Pr(C═O)— | 2-Cl-3-F—Ph |
| Z-6559 | Ac | 4-Br—Ph | Z-6560 | OHC— | 3-MeO—PhCH2— | Z-6561 | Pr(C═O)— | 2-Cl-4-F—Ph |
| Z-6562 | Ac | 2-I—Ph | Z-6563 | OHC— | 4-MeO—PhCH2— | Z-6564 | Pr(C═O)— | 2-Cl-5-F—Ph |
| Z-6565 | Ac | 3-I—Ph | Z-6566 | OHC— | 2,3-di-F—PhCH2— | Z-6567 | Pr(C═O)— | 2-Cl-6-F—Ph |
| Z-6568 | Ac | 4-I—Ph | Z-6569 | OHC— | 2,4-di-F—PhCH2— | Z-6570 | Pr(C═O)— | 2-Br-3-F—Ph |
| Z-6571 | Ac | 2-Me—Ph | Z-6572 | OHC— | 2,5-di-F—PhCH2— | Z-6573 | Pr(C═O)— | 2-Br-4-F—Ph |

TABLE 3-continued

| Z | R3 | R4 | Z | R3 | R4 | Z | R3 | R4 |
|---|---|---|---|---|---|---|---|---|
| Z-6574 | Ac | 3-Me—Ph | Z-6575 | OHC— | 2,6-di-F—PhCH2— | Z-6576 | Pr(C═O)— | 2-Br-5-F—Ph |
| Z-6577 | Ac | 4-Me—Ph | Z-6578 | OHC— | 2-Cl-3-F—PhCH2— | Z-6579 | Pr(C═O)— | 2-Br-6-F—Ph |
| Z-6580 | Ac | 2-MeO—Ph | Z-6581 | OHC— | 2-Cl-4-F—PhCH2— | Z-6582 | Pr(C═O)— | 2-F-3-MeO—Ph |
| Z-6583 | Ac | 3-MeO—Ph | Z-6584 | OHC— | 2-Cl-5-F—PhCH2— | Z-6585 | Pr(C═O)— | 2-F-4-MeO—Ph |
| Z-6586 | Ac | 4-MeO—Ph | Z-6587 | OHC— | 2-Cl-6-F—PhCH2— | Z-6588 | Pr(C═O)— | 2-F-5-MeO—Ph |
| Z-6589 | OHC— | 2-F—Ph | Z-6590 | OHC— | 2-Br-3-F—PhCH2— | Z-6591 | Pr(C═O)— | 2-F-6-MeO—Ph |
| Z-6592 | OHC— | 3-F—Ph | Z-6593 | OHC— | 2-Br-4-F—PhCH2— | Z-6594 | Pr(C═O)— | 2-Cl-3-MeO—Ph |
| Z-6595 | OHC— | 4-F—Ph | Z-6596 | OHC— | 2-Br-5-F—PhCH2— | Z-6597 | Pr(C═O)— | 2-Cl-4-MeO—Ph |
| Z-6598 | OHC— | 2-Cl—Ph | Z-6599 | OHC— | 2-Br-6-F—PhCH2— | Z-6600 | Pr(C═O)— | 2-Cl-5-MeO—Ph |
| Z-6601 | OHC— | 3-Cl—Ph | Z-6602 | OHC— | 2-F-3-MeO—PhCH2— | Z-6603 | Pr(C═O)— | 2-Cl-6-MeO—Ph |
| Z-6604 | OHC— | 4-Cl—Ph | Z-6605 | OHC— | 2-F-4-MeO—PhCH2— | Z-6606 | Pr(C═O)— | 2-Br-3-MeO—Ph |
| Z-6607 | OHC— | 2-Br—Ph | Z-6608 | OHC— | 2-F-5-MeO—PhCH2— | Z-6609 | Pr(C═O)— | 2-Br-4-MeO—Ph |
| Z-6610 | OHC— | 3-Br—Ph | Z-6611 | OHC— | 2-F-6-MeO—PhCH2— | Z-6612 | Pr(C═O)— | 2-Br-5-MeO—Ph |
| Z-6613 | OHC— | 4-Br—Ph | Z-6614 | OHC— | 2-Cl-3-MeO—PhCH2— | Z-6615 | Pr(C═O)— | 2-Br-6-MeO—Ph |
| Z-6616 | OHC— | 2-I—Ph | Z-6617 | OHC— | 2-Cl-4-MeO—PhCH2— | Z-6618 | Pr(C═O)— | 2,3,4-tri-F—Ph |
| Z-6619 | OHC— | 3-I—Ph | Z-6620 | OHC— | 2-Cl-5-MeO—PhCH2— | Z-6621 | Pr(C═O)— | 2,3,5-tri-F—Ph |
| Z-6622 | OHC— | 4-I—Ph | Z-6623 | OHC— | 2-Cl-6-MeO—PhCH2— | Z-6624 | Pr(C═O)— | 2,3,6-tri-F—Ph |
| Z-6625 | OHC— | 2-Me—Ph | Z-6626 | OHC— | 2-Br-3-MeO—PhCH2— | Z-6627 | Pr(C═O)— | 2-Br-3,4-di-F—Ph |
| Z-6628 | OHC— | 3-Me—Ph | Z-6629 | OHC— | 2-Br-4-MeO—PhCH2— | Z-6630 | Pr(C═O)— | 2-Br-3,5-di-F—Ph |
| Z-6631 | OHC— | 4-Me—Ph | Z-6632 | OHC— | 2-Br-5-MeO—PhCH2— | Z-6633 | Pr(C═O)— | 2-Br-3,6-di-F—Ph |
| Z-6634 | OHC— | 2-MeO—Ph | Z-6635 | OHC— | 2-Br-6-MeO—PhCH2— | Z-6636 | Pr(C═O)— | 2-F-3,4-di-MeO—Ph |
| Z-6637 | OHC— | 3-MeO—Ph | Z-6638 | OHC— | 2,3,4-tri-F—PhCH2— | Z-6639 | Pr(C═O)— | 2-F-3,5-di-MeO—Ph |
| Z-6640 | OHC— | 4-MeO—Ph | Z-6641 | OHC— | 2,3,5-tri-F—PhCH2— | Z-6642 | Pr(C═O)— | 2-F-3,6-di-MeO—Ph |
| Z-6643 | OHC— | 2,3-di-F—Ph | Z-6644 | OHC— | 2,3,6-tri-F—PhCH2— | Z-6645 | Pr(C═O)— | 2-Cl-3,4-di-MeO—Ph |
| Z-6646 | OHC— | 2,4-di-F—Ph | Z-6647 | OHC— | 2-Br-3,4-di-F—PhCH2— | Z-6648 | Pr(C═O)— | 2-Cl-3,5-di-MeO—Ph |
| Z-6649 | OHC— | 2,5-di-F—Ph | Z-6650 | OHC— | 2-Br-3,5-di-F—PhCH2— | Z-6651 | Pr(C═O)— | 2-Cl-3,6-di-MeO—Ph |
| Z-6652 | OHC— | 2,6-di-F—Ph | Z-6653 | OHC— | 2-Br-3,6-di-F—PhCH2— | Z-6654 | Pr(C═O)— | 2-Br-3,4-di-MeO—Ph |
| Z-6655 | OHC— | 2-Cl-3-F—Ph | Z-6656 | OHC— | 2-F-3,4-di-MeO—PhCH2— | Z-6657 | Pr(C═O)— | 2-Br-3,5-di-MeO—Ph |
| Z-6658 | OHC— | 2-Cl-4-F—Ph | Z-6659 | OHC— | 2-F-3,5-di-MeO—PhCH2— | Z-6660 | Pr(C═O)— | 2-Br-3,6-di-MeO—Ph |
| Z-6661 | OHC— | 2-Cl-5-F—Ph | Z-6662 | OHC— | 2-F-3,6-di-MeO—PhCH2— | Z-6663 | Pr(C═O)— | PhCH2— |
| Z-6664 | OHC— | 2-Cl-6-F—Ph | Z-6665 | OHC— | 2-Cl-3,4-di-MeO—PhCH2— | Z-6666 | Pr(C═O)— | 2-F—PhCH2— |
| Z-6667 | OHC— | 2-Br-3-F—Ph | Z-6668 | Et(C═O)— | 2-Cl-4-MeO—PhCH2— | Z-6669 | Pr(C═O)— | 3-F—PhCH2— |
| Z-6670 | OHC— | 2-Br-4-F—Ph | Z-6671 | Et(C═O)— | 2-Cl-5-MeO—PhCH2— | Z-6672 | Pr(C═O)— | 4-F—PhCH2— |
| Z-6673 | OHC— | 2-Br-5-F—Ph | Z-6674 | Et(C═O)— | 2-Cl-6-MeO—PhCH2— | Z-6675 | Pr(C═O)— | 2-Cl—PhCH2— |
| Z-6676 | OHC— | 2-Br-6-F—Ph | Z-6677 | Et(C═O)— | 2-Br-3-MeO—PhCH2— | Z-6678 | Pr(C═O)— | 3-Cl—PhCH2— |
| Z-6679 | OHC— | 2-F-3-MeO—Ph | Z-6680 | Et(C═O)— | 2-Br-4-MeO—PhCH2— | Z-6681 | Pr(C═O)— | 4-Cl—PhCH2— |
| Z-6682 | OHC— | 2-F-4-MeO—Ph | Z-6683 | Et(C═O)— | 2-Br-5-MeO—PhCH2— | Z-6684 | Pr(C═O)— | 2-Br—PhCH2— |
| Z-6685 | OHC— | 2-F-5-MeO—Ph | Z-6686 | Et(C═O)— | 2-Br-6-MeO—PhCH2— | Z-6687 | Pr(C═O)— | 3-Br—PhCH2— |
| Z-6688 | OHC— | 2-F-6-MeO—Ph | Z-6689 | Et(C═O)— | 2,3,4-tri-F—PhCH2— | Z-6690 | Pr(C═O)— | 4-Br—PhCH2— |
| Z-6691 | OHC— | 2-Cl-3-MeO—Ph | Z-6692 | Et(C═O)— | 2,3,5-tri-F—PhCH2— | Z-6693 | Pr(C═O)— | 2-I—PhCH2— |
| Z-6694 | OHC— | 2-Cl-4-MeO—Ph | Z-6695 | Et(C═O)— | 2,3,6-tri-F—PhCH2— | Z-6696 | Pr(C═O)— | 3-I—PhCH2— |
| Z-6697 | OHC— | 2-Cl-5-MeO—Ph | Z-6698 | Et(C═O)— | 2-Br-3,4-di-F—PhCH2— | Z-6699 | Pr(C═O)— | 4-I—PhCH2— |
| Z-6700 | OHC— | 2-Cl-6-MeO—Ph | Z-6701 | Et(C═O)— | 2-Br-3,5-di-F—PhCH2— | Z-6702 | Pr(C═O)— | 2-Me—PhCH2— |
| Z-6703 | OHC— | 2-Br-3-MeO—Ph | Z-6704 | Et(C═O)— | 2-Br-3,6-di-F—PhCH2— | Z-6705 | Pr(C═O)— | 3-Me—PhCH2— |
| Z-6706 | OHC— | 2-Br-4-MeO—Ph | Z-6707 | Et(C═O)— | 2-F-3,4-di-MeO—PhCH2— | Z-6708 | Pr(C═O)— | 4-Me—PhCH2— |
| Z-6709 | OHC— | 2-Br-5-MeO—Ph | Z-6710 | Et(C═O)— | 2-F-3,5-di-MeO—PhCH2— | Z-6711 | Pr(C═O)— | 2-MeO—PhCH2— |
| Z-6712 | OHC— | 2-Br-6-MeO—Ph | Z-6713 | Et(C═O)— | 2-F-3,6-di-MeO—PhCH2— | Z-6714 | Pr(C═O)— | 3-MeO—PhCH2— |
| Z-6715 | OHC— | 2,3,4-tri-F—Ph | Z-6716 | Et(C═O)— | 2-Cl-3,4-di-MeO—PhCH2— | Z-6717 | Pr(C═O)— | 4-MeO—PhCH2— |
| Z-6718 | OHC— | 2,3,5-tri-F—Ph | Z-6719 | Et(C═O)— | 2-Cl-3,5-di-MeO—PhCH2— | Z-6720 | Pr(C═O)— | 2,3-di-F—PhCH2— |
| Z-6721 | OHC— | 2,3,6-tri-F—Ph | Z-6722 | Et(C═O)— | 2-Cl-3,6-di-MeO—PhCH2— | Z-6723 | i-Pr(C═O)— | 3-Cl—PhCH2— |
| Z-6724 | OHC— | 2-Br-3,4-di-F—Ph | Z-6725 | Et(C═O)— | 2-Br-3,4-di-MeO—PhCH2— | Z-6726 | i-Pr(C═O)— | 4-Cl—PhCH2— |

TABLE 3-continued

| Z | R3 | R4 | Z | R3 | R4 | Z | R3 | R4 |
|---|---|---|---|---|---|---|---|---|
| Z-6727 | OHC— | 2-Br-3,5-di-F—Ph | Z-6728 | Et(C═O)— | 2-Br-3,5-di-MeO—PhCH2— | Z-6729 | i-Pr(C═O)— | 2-Br—PhCH2— |
| Z-6730 | OHC— | 2-Br-3,6-di-F—Ph | Z-6731 | Et(C═O)— | 2-Br-3,6-di-MeO—PhCH2— | Z-6732 | i-Pr(C═O)— | 3-Br—PhCH2— |
| Z-6733 | OHC— | 2-F-3,4-di-MeO—Ph | Z-6734 | Et(C═O)— | Et(C═O)— | Z-6735 | i-Pr(C═O)— | 4-Br—PhCH2— |
| Z-6736 | OHC— | 2-F-3,5-di-MeO—Ph | Z-6737 | Et(C═O)— | Pr(C═O)— | Z-6738 | i-Pr(C═O)— | 2-I—PhCH2— |
| Z-6739 | OHC— | 2-F-3,6-di-MeO—Ph | Z-6740 | Et(C═O)— | i-Pr(C═O)— | Z-6741 | i-Pr(C═O)— | 3-I—PhCH2— |
| Z-6742 | OHC— | 2-Cl-3,4-di-MeO—Ph | Z-6743 | Et(C═O)— | Bu(C═O)— | Z-6744 | i-Pr(C═O)— | 4-I—PhCH2— |
| Z-6745 | OHC— | 2-Cl-3,5-di-MeO—Ph | Z-6746 | Et(C═O)— | MeO(C═O)— | Z-6747 | i-Pr(C═O)— | 2-Me—PhCH2— |
| Z-6748 | OHC— | 2-Cl-3,6-di-MeO—Ph | Z-6749 | Et(C═O)— | EtO(C═O)— | Z-6750 | i-Pr(C═O)— | 3-Me—PhCH2— |
| Z-6751 | OHC— | 2-Br-3,4-di-MeO—Ph | Z-6752 | Et(C═O)— | PrO(C═O)— | Z-6753 | i-Pr(C═O)— | 4-Me—PhCH2— |
| Z-6754 | Et(C═O)— | 2-Br-3-MeO—Ph | Z-6755 | Et(C═O)— | i-PrO(C═O)— | Z-6756 | i-Pr(C═O)— | 2-MeO—PhCH2— |
| Z-6757 | Et(C═O)— | 2-Br-4-MeO—Ph | Z-6758 | Et(C═O)— | BuO(C═O)— | Z-6759 | i-Pr(C═O)— | 3-MeO—PhCH2— |
| Z-6766 | Et(C═O)— | 2-Br-5-MeO—Ph | Z-6761 | Et(C═O)— | t-BuOC(═O)— | Z-6762 | i-Pr(C═O)— | 4-MeO—PhCH2— |
| Z-6763 | Et(C═O)— | 2-Br-6-MeO—Ph | Z-6764 | Pr(C═O)— | Ph | Z-6765 | i-Pr(C═O)— | 2,3-di-F—PhCH2— |
| Z-6766 | Et(C═O)— | 2,3,4-tri-F—Ph | Z-6767 | Pr(C═O)— | 2-F—Ph | Z-6768 | i-Pr(C═O)— | 2,4-di-F—PhCH2— |
| Z-6769 | Et(C═O)— | 2,3,5-tri-F—Ph | Z-6770 | Pr(C═O)— | 3-F—Ph | Z-6771 | i-Pr(C═O)— | 2,5-di-F—PhCH2— |
| Z-6772 | Et(C═O)— | 2,3,6-tri-F—Ph | Z-6773 | Pr(C═O)— | 4-F—Ph | Z-6774 | i-Pr(C═O)— | 2,6-di-F—PhCH2— |
| Z-6775 | Et(C═O)— | 2-Br-3,4-di-F—Ph | Z-6776 | Pr(C═O)— | 2-Cl—Ph | Z-6777 | i-Pr(C═O)— | 2-Cl-3-F—PhCH2— |
| Z-6778 | Et(C═O)— | 2-Br-3,5-di-F—Ph | Z-6779 | Pr(C═O)— | 3-Cl—Ph | Z-6780 | i-Pr(C═O)— | 2-Cl-4-F—PhCH2— |
| Z-6781 | Et(C═O)— | 2-Br-3,6-di-F—Ph | Z-6782 | Pr(C═O)— | 4-Cl—Ph | Z-6783 | i-Pr(C═O)— | 2-Cl-5-F—PhCH2— |
| Z-6784 | Et(C═O)— | 2-F-3,4-di-MeO—Ph | Z-6785 | Pr(C═O)— | 2-Br—Ph | Z-6786 | i-Pr(C═O)— | 2-Cl-6-F—PhCH2— |
| Z-6787 | Et(C═O)— | 2-F-3,5-di-MeO—Ph | Z-6788 | Pr(C═O)— | 3-Br—Ph | Z-6789 | i-Pr(C═O)— | 2-Br-3-F—PhCH2— |
| Z-6790 | Et(C═O)— | 2-F-3,6-di-MeO—Ph | Z-6791 | Pr(C═O)— | 4-Br—Ph | Z-6792 | i-Pr(C═O)— | 2-Br-4-F—PhCH2— |
| Z-6793 | Et(C═O)— | 2-Cl-3,4-di-MeO—Ph | Z-6794 | Pr(C═O)— | 2-I—Ph | Z-6795 | i-Pr(C═O)— | 2-Br-5-F—PhCH2— |
| Z-6796 | Et(C═O)— | 2-Cl-3,5-di-MeO—Ph | Z-6797 | Pr(C═O)— | 3-I—Ph | Z-6798 | i-Pr(C═O)— | 2-Br-6-F—PhCH2— |
| Z-6799 | Et(C═O)— | 2-Cl-3,6-di-MeO—Ph | Z-6800 | Pr(C═O)— | 4-I—Ph | Z-6801 | i-Pr(C═O)— | 2-F-3-MeO—PhCH2— |
| Z-6802 | Et(C═O)— | 2-Br-3,4-di-MeO—Ph | Z-6803 | Pr(C═O)— | 2-Me—Ph | Z-6804 | i-Pr(C═O)— | 2-F-4-MeO—PhCH2— |
| Z-6805 | Et(C═O)— | 2-Br-3,5-di-MeO—Ph | Z-6806 | Pr(C═O)— | 3-Me—Ph | Z-6807 | i-Pr(C═O)— | 2-F-5-MeO—PhCH2— |
| Z-6808 | Et(C═O)— | 2-Br-3,6-di-MeO—Ph | Z-6809 | Pr(C═O)— | 4-Me—Ph | Z-6810 | i-Pr(C═O)— | 2-F-6-MeO—PhCH2— |
| Z-6811 | Et(C═O)— | PhCH2— | Z-6812 | Pr(C═O)— | 2-MeO—Ph | Z-6813 | i-Pr(C═O)— | 2-Cl-3-MeO—PhCH2— |
| Z-6814 | Et(C═O)— | 2-F—PhCH2— | Z-6815 | Pr(C═O)— | 3-MeO—Ph | Z-6816 | i-Pr(C═O)— | 2-Cl-4-MeO—PhCH2— |
| Z-6817 | Et(C═O)— | 3-F—PhCH2— | Z-6818 | Pr(C═O)— | 4-MeO—Ph | Z-6819 | i-Pr(C═O)— | 2-Cl-5-MeO—PhCH2— |
| Z-6820 | Et(C═O)— | 4-F—PhCH2— | Z-6821 | Pr(C═O)— | 2,3-di-F—Ph | Z-6822 | i-Pr(C═O)— | 2-Cl-6-MeO—PhCH2— |
| Z-6823 | Et(C═O)— | 2-Cl—PhCH2— | Z-6824 | Pr(C═O)— | 2,4-di-F—Ph | Z-6825 | i-Pr(C═O)— | 2-Br-3-MeO—PhCH2— |
| Z-6826 | Et(C═O)— | 3-Cl—PhCH2— | Z-6827 | Pr(C═O)— | 2,5-di-F—Ph | Z-6828 | i-Pr(C═O)— | 2-Br-4-MeO—PhCH2— |
| Z-6829 | Et(C═O)— | 4-Cl—PhCH2— | Z-6830 | Pr(C═O)— | 2,6-di-F—Ph | Z-6831 | i-Pr(C═O)— | 2-Br-5-MeO—PhCH2— |
| Z-6832 | Et(C═O)— | 2-Br—PhCH2— | Z-6833 | i-Pr(C═O)— | 3-Br—Ph | Z-6834 | i-Pr(C═O)— | 2-Br-6-MeO—PhCH2— |
| Z-6835 | Et(C═O)— | 3-Br—PhCH2— | Z-6836 | i-Pr(C═O)— | 4-Br—Ph | Z-6837 | i-Pr(C═O)— | 2,3,4-tri-F—PhCH2— |
| Z-6838 | Et(C═O)— | 4-Br—PhCH2— | Z-6839 | i-Pr(C═O)— | 2-I—Ph | Z-6840 | i-Pr(C═O)— | 2,3,5-tri-F—PhCH2— |
| Z-6841 | Et(C═O)— | 2-I—PhCH2— | Z-6842 | i-Pr(C═O)— | 3-I—Ph | Z-6843 | i-Pr(C═O)— | 2,3,6-tri-F—PhCH2— |
| Z-6844 | Et(C═O)— | 3-I—PhCH2— | Z-6845 | i-Pr(C═O)— | 4-I—Ph | Z-6846 | i-Pr(C═O)— | 2-Br-3,4-di-F—PhCH2— |
| Z-6847 | Et(C═O)— | 4-I—PhCH2— | Z-6848 | i-Pr(C═O)— | 2-Me—Ph | Z-6849 | i-Pr(C═O)— | 2-Br-3,5-di-F—PhCH2— |
| Z-6850 | Et(C═O)— | 2-Me—PhCH2— | Z-6851 | i-Pr(C═O)— | 3-Me—Ph | Z-6852 | i-Pr(C═O)— | 2-Br-3,6-di-F—PhCH2— |
| Z-6853 | Et(C═O)— | 3-Me—PhCH2— | Z-6854 | i-Pr(C═O)— | 4-Me—Ph | Z-6855 | i-Pr(C═O)— | 2-F-3,4-di-MeO—PhCH2— |
| Z-6856 | Et(C═O)— | 4-Me—PhCH2— | Z-6857 | i-Pr(C═O)— | 2-MeO—Ph | Z-6858 | i-Pr(C═O)— | 2-F-3,5-di-MeO—PhCH2— |
| Z-6859 | Et(C═O)— | 2-MeO—PhCH2— | Z-6860 | i-Pr(C═O)— | 3-MeO—Ph | Z-6861 | i-Pr(C═O)— | 2-F-3,6-di-MeO—PhCH2— |
| Z-6862 | Et(C═O)— | 3-MeO—PhCH2— | Z-6863 | i-Pr(C═O)— | 4-MeO—Ph | Z-6864 | i-Pr(C═O)— | 2-Cl-3,4-di-MeO—PhCH2— |
| Z-6865 | Et(C═O)— | 4-MeO—PhCH2— | Z-6866 | i-Pr(C═O)— | 2,3-di-F—Ph | Z-6867 | i-Pr(C═O)— | 2-Cl-3,5-di-MeO—PhCH2— |
| Z-6868 | Et(C═O)— | 2,3-di-F—PhCH2— | Z-6869 | i-Pr(C═O)— | 2,4-di-F—Ph | Z-6870 | i-Pr(C═O)— | 2-Cl-3,6-di-MeO—PhCH2— |
| Z-6871 | Et(C═O)— | 2,4-di-F—PhCH2— | Z-6872 | i-Pr(C═O)— | 2,5-di-F—Ph | Z-6873 | i-Pr(C═O)— | 2-Br-3,4-di-MeO—PhCH2— |
| Z-6874 | Et(C═O)— | 2,5-di-F—PhCH2— | Z-6875 | i-Pr(C═O)— | 2,6-di-F—Ph | Z-6876 | i-Pr(C═O)— | 2-Br-3,5-di-MeO—PhCH2— |
| Z-6877 | Et(C═O)— | 2,6-di-F—PhCH2— | Z-6878 | i-Pr(C═O)— | 2-Cl-3-F—Ph | Z-6879 | i-Pr(C═O)— | 2-Br-3,6-di-MeO—PhCH2— |

TABLE 3-continued

| Z | R3 | R4 | Z | R3 | R4 | Z | R3 | R4 |
|---|---|---|---|---|---|---|---|---|
| Z-6880 | Et(C═O)— | 2-Cl-3-F—PhCH2— | Z-6881 | i-Pr(C═O)— | 2-Cl-4-F—Ph | Z-6882 | i-Pr(C═O)— | i-Pr(C═O)— |
| Z-6883 | Et(C═O)— | 2-Cl-4-F—PhCH2— | Z-6884 | i-Pr(C═O)— | 2-Cl-5-F—Ph | Z-6885 | i-Pr(C═O)— | Bu(C═O)— |
| Z-6886 | Et(C═O)— | 2-Cl-5-F—PhCH2— | Z-6887 | i-Pr(C═O)— | 2-Cl-6-F—Ph | Z-6888 | Bu(C═O)— | 2-Br-3,4-di-F—PhCH2— |
| Z-6889 | Et(C═O)— | 2-Cl-6-F—PhCH2— | Z-6890 | i-Pr(C═O)— | 2-Br-3-F—Ph | Z-6891 | Bu(C═O)— | 2-Br-3,5-di-F—PhCH2— |
| Z-6892 | Et(C═O)— | 2-Br-3-F—PhCH2— | Z-6893 | i-Pr(C═O)— | 2-Br-4-F—Ph | Z-6894 | Bu(C═O)— | 2-Br-3,6-di-F—PhCH2— |
| Z-6895 | Et(C═O)— | 2-Br-4-F—PhCH2— | Z-6896 | i-Pr(C═O)— | 2-Br-5-F—Ph | Z-6897 | Bu(C═O)— | 2-F-3,4-di-MeO—PhCH2— |
| Z-6898 | Et(C═O)— | 2-Br-5-F—PhCH2— | Z-6899 | i-Pr(C═O)— | 2-Br-6-F—Ph | Z-6900 | Bu(C═O)— | 2-F-3,5-di-MeO—PhCH2— |
| Z-6901 | Et(C═O)— | 2-Br-6-F—PhCH2— | Z-6902 | i-Pr(C═O)— | 2-F-3-MeO—Ph | Z-6903 | Bu(C═O)— | 2-F-3,6-di-MeO—PhCH2— |
| Z-6904 | Et(C═O)— | 2-F-3-MeO—PhCH2— | Z-6905 | i-Pr(C═O)— | 2-F-4-MeO—Ph | Z-6906 | Bu(C═O)— | 2-Cl-3,4-di-MeO—PhCH2— |
| Z-6907 | Et(C═O)— | 2-F-4-MeO—PhCH2— | Z-6908 | i-Pr(C═O)— | 2-F-5-MeO—Ph | Z-6909 | Bu(C═O)— | 2-Cl-3,5-di-MeO—PhCH2— |
| Z-6910 | Et(C═O)— | 2-F-5-MeO—PhCH2— | Z-6911 | i-Pr(C═O)— | 2-F-6-MeO—Ph | Z-6912 | Bu(C═O)— | 2-Cl-3,6-di-MeO—PhCH2— |
| Z-6913 | Et(C═O)— | 2-F-6-MeO—PhCH2— | Z-6914 | i-Pr(C═O)— | 2-Cl-3-MeO—Ph | Z-6915 | Bu(C═O)— | 2-Br-3,4-di-MeO—PhCH2— |
| Z-6916 | Et(C═O)— | 2-Cl-3-MeO—PhCH2— | Z-6917 | i-Pr(C═O)— | 2-Cl-4-MeO—Ph | Z-6918 | Bu(C═O)— | 2-Br-3,5-di-MeO—PhCH2— |
| Z-6919 | Pr(C═O)— | 2,4-di-F—PhCH2— | Z-6920 | i-Pr(C═O)— | 2-Cl-5-MeO—Ph | Z-6921 | Bu(C═O)— | 2-Br-3,6-di-MeO—PhCH2— |
| Z-6922 | Pr(C═O)— | 2,5-di-F—PhCH2— | Z-6923 | i-Pr(C═O)— | 2-Cl-6-MeO—Ph | Z-6924 | Bu(C═O)— | Bu(C═O)— |
| Z-6925 | Pr(C═O)— | 2,6-di-F—PhCH2— | Z-6926 | i-Pr(C═O)— | 2-Br-3-MeO—Ph | Z-6927 | Bu(C═O)— | MeO(C═O)— |
| Z-6928 | Pr(C═O)— | 2-Cl-3-F—PhCH2— | Z-6929 | i-Pr(C═O)— | 2-Br-4-MeO—Ph | Z-6930 | Bu(C═O)— | EtO(C═O)— |
| Z-6931 | Pr(C═O)— | 2-Cl-4-F—PhCH2— | Z-6932 | i-Pr(C═O)— | 2-Br-5-MeO—Ph | Z-6933 | Bu(C═O)— | PrO(C═O)— |
| Z-6934 | Pr(C═O)— | 2-Cl-5-F—PhCH2— | Z-6935 | i-Pr(C═O)— | 2-Br-6-MeO—Ph | Z-6936 | Bu(C═O)— | i-PrO(C═O)— |
| Z-6937 | Pr(C═O)— | 2-Cl-6-F—PhCH2— | Z-6938 | i-Pr(C═O)— | 2,3,4-tri-F—Ph | Z-6939 | Bu(C═O)— | BuO(C═O)— |
| Z-6946 | Pr(C═O)— | 2-Br-3-F—PhCH2— | Z-6941 | i-Pr(C═O)— | 2,3,5-tri-F—Ph | Z-6942 | Bu(C═O)— | t-BuOC(═O)— |
| Z-6943 | Pr(C═O)— | 2-Br-4-F—PhCH2— | Z-6944 | i-Pr(C═O)— | 2,3,6-tri-F—Ph | Z-6945 | MeO(C═O)— | Ph |
| Z-6946 | Pr(C═O)— | 2-Br-5-F—PhCH2— | Z-6947 | i-Pr(C═O)— | 2-Br-3,4-di-F—Ph | Z-6948 | MeO(C═O)— | 2-F—Ph |
| Z-6949 | Pr(C═O)— | 2-Br-6-F—PhCH2— | Z-6950 | i-Pr(C═O)— | 2-Br-3,5-di-F—Ph | Z-6951 | MeO(C═O)— | 3-F—Ph |
| Z-6952 | Pr(C═O)— | 2-F-3-MeO—PhCH2— | Z-6953 | i-Pr(C═O)— | 2-Br-3,6-di-F—Ph | Z-6954 | MeO(C═O)— | 4-F—Ph |
| Z-6955 | Pr(C═O)— | 2-F-4-MeO—PhCH2— | Z-6956 | i-Pr(C═O)— | 2-F-3,4-di-MeO—Ph | Z-6957 | MeO(C═O)— | 2-Cl—Ph |
| Z-6958 | Pr(C═O)— | 2-F-5-MeO—PhCH2— | Z-6959 | i-Pr(C═O)— | 2-F-3,5-di-MeO—Ph | Z-6960 | MeO(C═O)— | 3-Cl—Ph |
| Z-6961 | Pr(C═O)— | 2-F-6-MeO—PhCH2— | Z-6962 | i-Pr(C═O)— | 2-F-3,6-di-MeO—Ph | Z-6963 | MeO(C═O)— | 4-Cl—Ph |
| Z-6964 | Pr(C═O)— | 2-Cl-3-MeO—PhCH2— | Z-6965 | i-Pr(C═O)— | 2-Cl-3,4-di-MeO—Ph | Z-6966 | MeO(C═O)— | 2-Br—Ph |
| Z-6967 | Pr(C═O)— | 2-Cl-4-MeO—PhCH2— | Z-6968 | i-Pr(C═O)— | 2-Cl-3,5-di-MeO—Ph | Z-6969 | MeO(C═O)— | 3-Br—Ph |
| Z-6970 | Pr(C═O)— | 2-Cl-5-MeO—PhCH2— | Z-6971 | i-Pr(C═O)— | 2-Cl-3,6-di-MeO—Ph | Z-6972 | MeO(C═O)— | 4-Br—Ph |
| Z-6973 | Pr(C═O)— | 2-Cl-6-MeO—PhCH2— | Z-6974 | i-Pr(C═O)— | 2-Br-3,4-di-MeO—Ph | Z-6975 | MeO(C═O)— | 2-I—Ph |
| Z-6976 | Pr(C═O)— | 2-Br-3-MeO—PhCH2— | Z-6977 | i-Pr(C═O)— | 2-Br-3,5-di-MeO—Ph | Z-6978 | MeO(C═O)— | 3-I—Ph |
| Z-6979 | Pr(C═O)— | 2-Br-4-MeO—PhCH2— | Z-6980 | i-Pr(C═O)— | 2-Br-3,6-di-MeO—Ph | Z-6981 | MeO(C═O)— | 4-I—Ph |
| Z-6982 | Pr(C═O)— | 2-Br-5-MeO—PhCH2— | Z-6983 | i-Pr(C═O)— | PhCH2— | Z-6984 | MeO(C═O)— | 2-Me—Ph |
| Z-6985 | Pr(C═O)— | 2-Br-6-MeO—PhCH2— | Z-6986 | i-Pr(C═O)— | 2-F—PhCH2— | Z-6987 | MeO(C═O)— | 3-Me—Ph |
| Z-6988 | Pr(C═O)— | 2,3,4-tri-F—PhCH2— | Z-6989 | i-Pr(C═O)— | 3-F—PFCH2— | Z-6990 | MeO(C═O)— | 4-Me—Ph |
| Z-6991 | Pr(C═O)— | 2,3,5-tri-F—PhCH2— | Z-6992 | i-Pr(C═O)— | 4-F—PhCH2— | Z-6993 | MeO(C═O)— | 2-MeO—Ph |
| Z-6994 | Pr(C═O)— | 2,3,6-tri-F—PhCH2— | Z-6995 | i-Pr(C═O)— | 2-Cl—PhCH2— | Z-6996 | MeO(C═O)— | 3-MeO—Ph |
| Z-6997 | Pr(C═O)— | 2-Br-3,4-di-F—PhCH2— | Z-6998 | Bu(C═O)— | 2-F-3,4-di-MeO—Ph | Z-6999 | MeO(C═O)— | 4-MeO—Ph |
| Z-7000 | Pr(C═O)— | 2-Br-3,5-di-F—PhCH2— | Z-7001 | Bu(C═O)— | 2-F-3,5-di-MeO—Ph | Z-7002 | MeO(C═O)— | 2,3-di-F—Ph |
| Z-7003 | Pr(C═O)— | 2-Br-3,6-di-F—PhCH2— | Z-7004 | Bu(C═O)— | 2-F-3,6-di-MeO—Ph | Z-7005 | MeO(C═O)— | 2,4-di-F—Ph |
| Z-7006 | Pr(C═O)— | 2-F-3,4-di-MeO—PhCH2— | Z-7007 | Bu(C═O)— | 2-Cl-3,4-di-MeO—Ph | Z-7008 | MeO(C═O)— | 2,5-di-F—Ph |
| Z-7009 | Pr(C═O)— | 2-F-3,5-di-MeO—PhCH2— | Z-7010 | Bu(C═O)— | 2-Cl-3,5-di-MeO—Ph | Z-7011 | MeO(C═O)— | 2,6-di-F—Ph |
| Z-7012 | Pr(C═O)— | 2-F-3,6-di-MeO—PhCH2— | Z-7013 | Bu(C═O)— | 2-Cl-3,6-di-MeO—Ph | Z-7014 | MeO(C═O)— | 2-Cl-3-F—Ph |
| Z-7015 | Pr(C═O)— | 2-Cl-3,4-di-MeO—PhCH2— | Z-7016 | Bu(C═O)— | 2-Br-3,4-di-MeO—Ph | Z-7017 | MeO(C═O)— | 2-Cl-4-F—Ph |
| Z-7018 | Pr(C═O)— | 2-Cl-3,5-di-MeO—PhCH2— | Z-7019 | Bu(C═O)— | 2-Br-3,5-di-MeO—Ph | Z-7020 | MeO(C═O)— | 2-Cl-5-F—Ph |
| Z-7021 | Pr(C═O)— | 2-Cl-3,6-di-MeO—PhCH2— | Z-7022 | Bu(C═O)— | 2-Br-3,6-di-MeO—Ph | Z-7023 | MeO(C═O)— | 2-Cl-6-F—Ph |
| Z-7024 | Pr(C═O)— | 2-Br-3,4-di-MeO—PhCH2— | Z-7025 | Bu(C═O)— | PhCH2— | Z-7026 | MeO(C═O)— | 2-Br-3-F—Ph |
| Z-7027 | Pr(C═O)— | 2-Br-3,5-di-MeO—PhCH2— | Z-7028 | Bu(C═O)— | 2-F—PhCH2— | Z-7029 | MeO(C═O)— | 2-Br-4-F—Ph |
| Z-7030 | Pr(C═O)— | 2-Br-3,6-di-MeO—PhCH2— | Z-7031 | Bu(C═O)— | 3-F—PhCH2— | Z-7032 | MeO(C═O)— | 2-Br-5-F—Ph |

TABLE 3-continued

| Z | R3 | R4 | Z | R3 | R4 | Z | R3 | R4 |
|---|---|---|---|---|---|---|---|---|
| Z-7033 | Pr(C═O)— | Pr(C═O)— | Z-7034 | Bu(C═O)— | 4-F—PhCH2— | Z-7035 | MeO(C═O)— | 2-Br-6-F—Ph |
| Z-7036 | Pr(C═O)— | i-Pr(C═O)— | Z-7037 | Bu(C═O)— | 2-Cl—PFCH2— | Z-7038 | MeO(C═O)— | 2-F-3-MeO—Ph |
| Z-7039 | Pr(C═O)— | Bu(C═O)— | Z-7040 | Bu(C═O)— | 3-Cl—PhCH2— | Z-7041 | MeO(C═O)— | 2-F-4-MeO—Ph |
| Z-7042 | Pr(C═O)— | MeO(C═O)— | Z-7043 | Bu(C═O)— | 4-Cl—PhCH2— | Z-7044 | MeO(C═O)— | 2-F-5-MeO—Ph |
| Z-7045 | Pr(C═O)— | EtO(C═O)— | Z-7046 | Bu(C═O)— | 2-Br—PhCH2— | Z-7047 | MeO(C═O)— | 2-F-6-MeO—Ph |
| Z-7048 | Pr(C═O)— | PrO(C═O)— | Z-7049 | Bu(C═O)— | 3-Br—PhCH2— | Z-7050 | MeO(C═O)— | 2-Cl-3-MeO—Ph |
| Z-7051 | Pr(C═O)— | i-PrO(C═O)— | Z-7052 | Bu(C═O)— | 4-Br—PhCH2— | Z-7053 | EtO(C═O)— | 2-Cl-4-F—Ph |
| Z-7054 | Pr(C═O)— | BuO(C═O)— | Z-7055 | Bu(C═O)— | 2-I—PhCH2— | Z-7056 | EtO(C═O)— | 2-Cl-5-F—Ph |
| Z-7057 | Pr(C═O)— | t-BuOC(═O)— | Z-7058 | Bu(C═O)— | 3-I—PhCH2— | Z-7059 | EtO(C═O)— | 2-Cl-6-F—Ph |
| Z-7060 | i-Pr(C═O)— | Ph | Z-7061 | Bu(C═O)— | 4-I—PhCH2— | Z-7062 | EtO(C═O)— | 2-Br-3-F—Ph |
| Z-7063 | i-Pr(C═O)— | 2-F—Ph | Z-7064 | Bu(C═O)— | 2-Me—PhCH2— | Z-7065 | EtO(C═O)— | 2-Br-4-F—Ph |
| Z-7066 | i-Pr(C═O)— | 3-F—Ph | Z-7067 | Bu(C═O)— | 3-Me—PhCH2— | Z-7068 | EtO(C═O)— | 2-Br-5-F—Ph |
| Z-7069 | i-Pr(C═O)— | 4-F—Ph | Z-7070 | Bu(C═O)— | 4-Me—PhCH2— | Z-7071 | EtO(C═O)— | 2-Br-6-F—Ph |
| Z-7072 | i-Pr(C═O)— | 2-Cl—Ph | Z-7073 | Bu(C═O)— | 2-MeO—PhCH2— | Z-7074 | EtO(C═O)— | 2-F-3-MeO—Ph |
| Z-7075 | i-Pr(C═O)— | 3-Cl—Ph | Z-7076 | Bu(C═O)— | 3-MeO—PhCH2— | Z-7077 | EtO(C═O)— | 2-F-4-MeO—Ph |
| Z-7078 | i-Pr(C═O)— | 4-Cl—Ph | Z-7079 | Bu(C═O)— | 4-MeO—PhCH2— | Z-7080 | EtO(C═O)— | 2-F-5-MeO—Ph |
| Z-7081 | i-Pr(C═O)— | 2-Br—Ph | Z-7082 | Bu(C═O)— | 2,3-di-F—PhCH2— | Z-7083 | EtO(C═O)— | 2-F-6-MeO—Ph |
| Z-7084 | i-Pr(C═O)— | MeO(C═O)— | Z-7085 | Bu(C═O)— | 2,4-di-F—PhCH2— | Z-7086 | EtO(C═O)— | 2-Cl-3-MeO—Ph |
| Z-7087 | i-Pr(C═O)— | EtO(C═O)— | Z-7088 | Bu(C═O)— | 2,5-di-F—PhCH2— | Z-7089 | EtO(C═O)— | 2-Cl-4-MeO—Ph |
| Z-7090 | i-Pr(C═O)— | PrO(C═O)— | Z-7091 | Bu(C═O)— | 2,6-di-F—PhCH2— | Z-7092 | EtO(C═O)— | 2-Cl-5-MeO—Ph |
| Z-7093 | i-Pr(C═O)— | i-PrO(C═O)— | Z-7094 | Bu(C═O)— | 2-Cl-3-F—PhCH2— | Z-7095 | EtO(C═O)— | 2-Cl-6-MeO—Ph |
| Z-7096 | i-Pr(C═O)— | BuO(C═O)— | Z-7097 | Bu(C═O)— | 2-Cl-4-F—PhCH2— | Z-7098 | EtO(C═O)— | 2-Br-3-MeO—Ph |
| Z-7099 | i-Pr(C═O)— | t-BuOC(═O)— | Z-7100 | Bu(C═O)— | 2-Cl-5-F—PhCH2— | Z-7101 | EtO(C═O)— | 2-Br-4-MeO—Ph |
| Z-7102 | Bu(C═O)— | Ph | Z-7103 | Bu(C═O)— | 2-Cl-6-F—PhCH2— | Z-7104 | EtO(C═O)— | 2-Br-5-MeO—Ph |
| Z-7105 | Bu(C═O)— | 2-F—Ph | Z-7106 | Bu(C═O)— | 2-Br-3-F—PhCH2— | Z-7107 | EtO(C═O)— | 2-Br-6-MeO—Ph |
| Z-7108 | Bu(C═O)— | 3-F—Ph | Z-7109 | Bu(C═O)— | 2-Br-4-F—PhCH2— | Z-7110 | EtO(C═O)— | 2,3,4-tri-F—Ph |
| Z-7111 | Bu(C═O)— | 4-F—Ph | Z-7112 | Bu(C═O)— | 2-Br-5-F—PhCH2— | Z-7113 | EtO(C═O)— | 2,3,5-tri-F—Ph |
| Z-7114 | Bu(C═O)— | 2-Cl—Ph | Z-7115 | Bu(C═O)— | 2-Br-6-F—PhCH2— | Z-7116 | EtO(C═O)— | 2,3,6-tri-F—Ph |
| Z-7117 | Bu(C═O)— | 3-Cl—Ph | Z-7118 | Bu(C═O)— | 2-F-3-MeO—PhCH2— | Z-7119 | EtO(C═O)— | 2-Br-3,4-di-F—Ph |
| Z-7120 | Bu(C═O)— | 4-Cl—Ph | Z-7121 | Bu(C═O)— | 2-F-4-MeO—PhCH2— | Z-7122 | EtO(C═O)— | 2-Br-3,5-di-F—Ph |
| Z-7123 | Bu(C═O)— | 2-Br—Ph | Z-7124 | Bu(C═O)— | 2-F-5-MeO—PhCH2— | Z-7125 | EtO(C═O)— | 2-Br-3,6-di-F—Ph |
| Z-7126 | Bu(C═O)— | 3-Br—Ph | Z-7127 | Bu(C═O)— | 2-F-6-MeO—PhCH2— | Z-7128 | EtO(C═O)— | 2-F-3,4-di-MeO—Ph |
| Z-7129 | Bu(C═O)— | 4-Br—Ph | Z-7130 | Bu(C═O)— | 2-Cl-3-MeO—PhCH2— | Z-7131 | EtO(C═O)— | 2-F-3,5-di-MeO—Ph |
| Z-7132 | Bu(C═O)— | 2-I—Ph | Z-7133 | Bu(C═O)— | 2-Cl-4-MeO—PhCH2— | Z-7134 | EtO(C═O)— | 2-F-3,6-di-MeO—Ph |
| Z-7135 | Bu(C═O)— | 3-I—Ph | Z-7136 | Bu(C═O)— | 2-Cl-5-MeO—PhCH2— | Z-7137 | EtO(C═O)— | 2-Cl-3,4-di-MeO—Ph |
| Z-7138 | Bu(C═O)— | 4-I—Ph | Z-7139 | Bu(C═O)— | 2-Cl-6-MeO—PhCH2— | Z-7140 | EtO(C═O)— | 2-Cl-3,5-di-MeO—Ph |
| Z-7141 | Bu(C═O)— | 2-Me—Ph | Z-7142 | Bu(C═O)— | 2-Br-3-MeO—PhCH2— | Z-7143 | EtO(C═O)— | 2-Cl-3,6-di-MeO—Ph |
| Z-7144 | Bu(C═O)— | 3-Me—Ph | Z-7145 | Bu(C═O)— | 2-Br-4-MeO—PhCH2— | Z-7146 | EtO(C═O)— | 2-Br-3,4-di-MeO—Ph |
| Z-7147 | Bu(C═O)— | 4-Me—Ph | Z-7148 | Bu(C═O)— | 2-Br-5-MeO—PhCH2— | Z-7149 | EtO(C═O)— | 2-Br-3,5-di-MeO—Ph |
| Z-7150 | Bu(C═O)— | 2-MeO—Ph | Z-7151 | Bu(C═O)— | 2-Br-6-MeO—PhCH2— | Z-7152 | EtO(C═O)— | 2-Br-3,6-di-MeO—Ph |
| Z-7153 | Bu(C═O)— | 3-MeO—Ph | Z-7154 | Bu(C═O)— | 2,3,4-tri-F—PhCH2— | Z-7155 | EtO(C═O)— | PhCH2— |
| Z-7156 | Bu(C═O)— | 4-MeO—Ph | Z-7157 | Bu(C═O)— | 2,3,5-tri-F—PhCH2— | Z-7158 | EtO(C═O)— | 2-F—PhCH2— |
| Z-7159 | Bu(C═O)— | 2,3-di-F—Ph | Z-7160 | Bu(C═O)— | 2,3,6-tri-F—PhCH2— | Z-7161 | EtO(C═O)— | 3-F—PhCH2— |
| Z-7162 | Bu(C═O)— | 2,4-di-F—Ph | Z-7163 | MeO(C═O)— | 2-F-5-MeO—PhCH2— | Z-7164 | EtO(C═O)— | 4-F—PhCH2— |
| Z-7165 | Bu(C═O)— | 2,5-di-F—Ph | Z-7166 | MeO(C═O)— | 2-F-6-MeO—PhCH2— | Z-7167 | EtO(C═O)— | 2-Cl—PhCH2— |
| Z-7168 | Bu(C═O)— | 2,6-di-F—Ph | Z-7169 | MeO(C═O)— | 2-Cl-3-MeO—PhCH2— | Z-7170 | EtO(C═O)— | 3-Cl—PhCH2— |
| Z-7171 | Bu(C═O)— | 2-Cl-3-F—Ph | Z-7172 | MeO(C═O)— | 2-Cl-4-MeO—PhCH2— | Z-7173 | EtO(C═O)— | 4-Cl—PhCH2— |
| Z-7174 | Bu(C═O)— | 2-Cl-4-F—Ph | Z-7175 | MeO(C═O)— | 2-Cl-5-MeO—PhCH2— | Z-7176 | EtO(C═O)— | 2-Br—PhCH2— |
| Z-7177 | Bu(C═O)— | 2-Cl-5-F—Ph | Z-7178 | MeO(C═O)— | 2-Cl-6-MeO—PhCH2— | Z-7179 | EtO(C═O)— | 3-Br—PhCH2— |
| Z-7180 | Bu(C═O)— | 2-Cl-6-F—Ph | Z-7181 | MeO(C═O)— | 2-Br-3-MeO—PhCH2— | Z-7182 | EtO(C═O)— | 4-Br—PhCH2— |
| Z-7183 | Bu(C═O)— | 2-Br-3-F—Ph | Z-7184 | MeO(C═O)— | 2-Br-4-MeO—PhCH2— | Z-7185 | EtO(C═O)— | 2-I—PhCH2— |

TABLE 3-continued

| Z | R3 | R4 | Z | R3 | R4 | Z | R3 | R4 |
|---|---|---|---|---|---|---|---|---|
| Z-7186 | Bu(C═O)— | 2-Br-4-F—Ph | Z-7187 | MeO(C═O)— | 2-Br-5-MeO—PhCH2— | Z-7188 | EtO(C═O)— | 3-I—PhCH2— |
| Z-7189 | Bu(C═O)— | 2-Br-5-F—Ph | Z-7190 | MeO(C═O)— | 2-Br-6-MeO—PhCH2— | Z-7191 | EtO(C═O)— | 4-I—PhCH2— |
| Z-7192 | Bu(C═O)— | 2-Br-6-F—Ph | Z-7193 | MeO(C═O)— | 2,3,4-tri-F—PhCH2— | Z-7194 | EtO(C═O)— | 2-Me—PhCH2— |
| Z-7195 | Bu(C═O)— | 2-F-3-MeO—Ph | Z-7196 | MeO(C═O)— | 2,3,5-tri-F—PhCH2— | Z-7197 | EtO(C═O)— | 3-Me—PhCH2— |
| Z-7198 | Bu(C═O)— | 2-F-4-MeO—Ph | Z-7199 | MeO(C═O)— | 2,3,6-tri-F—PhCH2— | Z-7200 | EtO(C═O)— | 4-Me—PhCH2— |
| Z-7201 | Bu(C═O)— | 2-F-5-MeO—Ph | Z-7202 | MeO(C═O)— | 2-Br-3,4-di-F—PhCH2— | Z-7203 | EtO(C═O)— | 2-MeO—PhCH2— |
| Z-7204 | Bu(C═O)— | 2-F-6-MeO—Ph | Z-7205 | MeO(C═O)— | 2-Br-3,5-di-F—PhCH2— | Z-7206 | EtO(00)— | 3-MeO—PhCH2— |
| Z-7207 | Bu(C═O)— | 2-Cl-3-MeO—Ph | Z-7208 | MeO(C═O)— | 2-Br-3,6-di-F—PhCH2— | Z-7209 | EtO(C═O)— | 4-MeO—PhCH2— |
| Z-7210 | Bu(C═O)— | 2-Cl-4-MeO—Ph | Z-7211 | MeO(C═O)— | 2-F-3,4-di-MeO—PhCH2— | Z-7212 | EtO(C═O)— | 2,3-di-F—PhCH2— |
| Z-7213 | Bu(C═O)— | 2-Cl-5-MeO—Ph | Z-7214 | MeO(C═O)— | 2-F-3,5-di-MeO—PhCH2— | Z-7215 | EtO(C═O)— | 2,4-di-F—PhCH2— |
| Z-7216 | Bu(C═O)— | 2-Cl-6-MeO—Ph | Z-7217 | MeO(C═O)— | 2-F-3,6-di-MeO—PhCH2— | Z-7218 | PrO(C═O)— | 2-I—PhCH2— |
| Z-7219 | Bu(C═O)— | 2-Br-3-MeO—Ph | Z-7220 | MeO(C═O)— | 2-Cl-3,4-di-MeO—PhCH2— | Z-7221 | PrO(C═O)— | 3-I—PhCH2— |
| Z-7222 | Bu(C═O)— | 2-Br-4-MeO—Ph | Z-7223 | MeO(C═O)— | 2-Cl-3,5-di-MeO—PhCH2— | Z-7224 | PrO(C═O)— | 4-I—PhCH2— |
| Z-7225 | Bu(C═O)— | 2-Br-5-MeO—Ph | Z-7226 | MeO(C═O)— | 2-Cl-3,6-di-MeO—PhCH2— | Z-7227 | PrO(C═O)— | 2-Me—PhCH2— |
| Z-7228 | Bu(C═O)— | 2-Br-6-MeO—Ph | Z-7229 | MeO(C═O)— | 2-Br-3,4-di-MeO—PhCH2— | Z-7230 | PrO(C═O)— | 3-Me—PhCH2— |
| Z-7231 | Bu(C═O)— | 2,3,4-tri-F—Ph | Z-7232 | MeO(C═O)— | 2-Br-3,5-di-MeO—PhCH2— | Z-7233 | PrO(C═O)— | 4-Me—PhCH2— |
| Z-7234 | Bu(C═O)— | 2,3,5-tri-F—Ph | Z-7235 | MeO(C═O)— | 2-Br-3,6-di-MeO—PhCH2— | Z-7236 | PrO(C═O)— | 2-MeO—PhCH2— |
| Z-7237 | Bu(C═O)— | 2,3,6-tri-F—Ph | Z-7238 | MeO(C═O)— | MeO(C═O)— | Z-7239 | PrO(C═O)— | 3-MeO—PhCH2— |
| Z-7240 | Bu(C═O)— | 2-Br-3,4-di-F—Ph | Z-7241 | MeO(C═O)— | EtO(C═O)— | Z-7242 | PrO(C═O)— | 4-MeO—PhCH2— |
| Z-7243 | Bu(C═O)— | 2-Br-3,5-di-F—Ph | Z-7244 | MeO(C═O)— | PrO(C═O)— | Z-7245 | PrO(C═O)— | 2,3-di-F—PhCH2— |
| Z-7246 | Bu(C═O)— | 2-Br-3,6-di-F—Ph | Z-7247 | MeO(C═O)— | i-PrO(C═O)— | Z-7248 | PrO(C═O)— | 2,4-di-F—PhCH2— |
| Z-7249 | MeO(C═O)— | 2-Cl-4-MeO—Ph | Z-7250 | MeO(C═O)— | BuO(C═O)— | Z-7251 | PrO(C═O)— | 2,5-di-F—PhCH2— |
| Z-7252 | MeO(C═O)— | 2-Cl-5-MeO—Ph | Z-7253 | MeO(C═O)— | t-BuOC(═O)— | Z-7254 | PrO(C═O)— | 2,6-di-F—PhCH2— |
| Z-7255 | MeO(C═O)— | 2-Cl-6-MeO—Ph | Z-7256 | EtO(C═O)— | Ph | Z-7257 | PrO(C═O)— | 2-Cl-3-F—PhCH2— |
| Z-7258 | MeO(C═O)— | 2-Br-3-MeO—Ph | Z-7259 | EtO(C═O)— | 2-F—Ph | Z-7260 | PrO(C═O)— | 2-Cl-4-F—PhCH2— |
| Z-7261 | MeO(C═O)— | 2-Br-4-MeO—Ph | Z-7262 | EtO(C═O)— | 3-F—Ph | Z-7263 | PrO(C═O)— | 2-Cl-5-F—PhCH2— |
| Z-7264 | MeO(C═O)— | 2-Br-5-MeO—Ph | Z-7265 | EtO(C═O)— | 4-F—Ph | Z-7266 | PrO(C═O)— | 2-Cl-6-F—PhCH2— |
| Z-7267 | MeO(C═O)— | 2-Br-6-MeO—Ph | Z-7268 | EtO(C═O)— | 2-Cl—Ph | Z-7269 | PrO(C═O)— | 2-Br-3-F—PhCH2— |
| Z-7279 | MeO(C═O)— | 2,3,4-tri-F—Ph | Z-7271 | EtO(C═O)— | 3-Cl—Ph | Z-7272 | PrO(C═O)— | 2-Br-4-F—PhCH2— |
| Z-7273 | MeO(C═O)— | 2,3,5-tri-F—Ph | Z-7274 | EtO(C═O)— | 4-Cl—Ph | Z-7275 | PrO(C═O)— | 2-Br-5-F—PhCH2— |
| Z-7276 | MeO(C═O)— | 2,3,6-tri-F—Ph | Z-7277 | EtO(C═O)— | 2-Br—Ph | Z-7278 | PrO(C═O)— | 2-Br-6-F—PhCH2— |
| Z-7270 | MeO(C═O)— | 2-Br-3,4-di-F—Ph | Z-7280 | EtO(C═O)— | 3-Br—Ph | Z-7281 | PrO(C═O)— | 2-F-3-MeO—PhCH2— |
| Z-7282 | MeO(C═O)— | 2-Br-3,5-di-F—Ph | Z-7283 | EtO(C═O)— | 4-Br—Ph | Z-7284 | PrO(C═O)— | 2-F-4-MeO—PhCH2— |
| Z-7285 | MeO(C═O)— | 2-Br-3,6-di-F—Ph | Z-7286 | EtO(C═O)— | 2-I—Ph | Z-7287 | PrO(C═O)— | 2-F-5-MeO—PhCH2— |
| Z-7288 | MeO(C═O)— | 2-F-3,4-di-MeO—Ph | Z-7289 | EtO(C═O)— | 3-I—Ph | Z-7290 | PrO(C═O)— | 2-F-6-MeO—PhCH2— |
| Z-7291 | MeO(C═O)— | 2-F-3,5-di-MeO—Ph | Z-7292 | EtO(C═O)— | 4-I—Ph | Z-7293 | PrO(C═O)— | 2-Cl-3-MeO—PhCH2— |
| Z-7294 | MeO(C═O)— | 2-F-3,6-di-MeO—Ph | Z-7295 | EtO(C═O)— | 2-Me—Ph | Z-7296 | PrO(C═O)— | 2-Cl-4-MeO—PhCH2— |
| Z-7297 | MeO(C═O)— | 2-Cl-3,4-di-MeO—Ph | Z-7298 | EtO(C═O)— | 3-Me—Ph | Z-7299 | PrO(C═O)— | 2-Cl-5-MeO—PhCH2— |
| Z-7300 | MeO(C═O)— | 2-Cl-3,5-di-MeO—Ph | Z-7301 | EtO(C═O)— | 4-Me—Ph | Z-7302 | PrO(C═O)— | 2-Cl-6-MeO—PhCH2— |
| Z-7303 | MeO(C═O)— | 2-Cl-3,6-di-MeO—Ph | Z-7304 | EtO(C═O)— | 2-MeO—Ph | Z-7305 | PrO(C═O)— | 2-Br-3-MeO—PhCH2— |
| Z-7306 | MeO(C═O)— | 2-Br-3,4-di-MeO—Ph | Z-7307 | EtO(C═O)— | 3-MeO—Ph | Z-7308 | PrO(C═O)— | 2-Br-4-MeO—PhCH2— |
| Z-7309 | MeO(C═O)— | 2-Br-3,5-di-MeO—Ph | Z-7310 | EtO(C═O)— | 4-MeO—Ph | Z-7311 | PrO(C═O)— | 2-Br-5-MeO—PhCH2— |
| Z-7312 | MeO(C═O)— | 2-Br-3,6-di-MeO—Ph | Z-7313 | EtO(C═O)— | 2,3-di-F—Ph | Z-7314 | PrO(C═O)— | 2-Br-6-MeO—PhCH2— |
| Z-7315 | MeO(C═O)— | PhCH2— | Z-7316 | EtO(C═O)— | 2,4-di-F—Ph | Z-7317 | PrO(C═O)— | 2,3,4-tri-F—PhCH2— |
| Z-7318 | MeO(C═O)— | 2-F—PhCH2— | Z-7319 | EtO(C═O)— | 2,5-di-F—Ph | Z-7320 | PrO(C═O)— | 2,3,5-tri-F—PbCH2— |
| Z-7321 | MeO(C═O)— | 3-F—PhCH2— | Z-7322 | EtO(C═O)— | 2,6-di-F—Ph | Z-7323 | PrO(C═O)— | 2,3,6-tri-F—PhCH2— |
| Z-7324 | MeO(C═O)— | 4-F—PbCH2— | Z-7325 | EtO(C═O)— | 2-Cl-3-F—Ph | Z-7326 | PrO(C═O)— | 2-Br-3,4-di-F—PhCH2— |
| Z-7327 | MeO(C═O)— | 2-Cl—PhCH2— | Z-7328 | PrO(C═O)— | 2-Me—Ph | Z-7329 | PrO(C═O)— | 2-Br-3,5-di-F—PhCH2— |
| Z-7330 | MeO(C═O)— | 3-Cl—PhCH2— | Z-7331 | PrO(C═O)— | 3-Me—Ph | Z-7332 | PrO(C═O)— | 2-Br-3,6-di-F—PhCH2— |
| Z-7333 | MeO(C═O)— | 4-Cl—PhCH2— | Z-7334 | PrO(C═O)— | 4-Me—Ph | Z-7335 | PrO(C═O)— | 2-F-3,4-di-MeO—PhCH2— |
| Z-7336 | MeO(C═O)— | 2-Br—PhCH2— | Z-7337 | PrO(C═O)— | 2-MeO—Ph | Z-7338 | PrO(C═O)— | 2-F-3,5-di-MeO—PhCH2— |

TABLE 3-continued

| Z | R3 | R4 | Z | R3 | R4 | Z | R3 | R4 |
|---|---|---|---|---|---|---|---|---|
| Z-7339 | MeO(C═O)— | 3-Br—PhCH2— | Z-7340 | PrO(C═O)— | 3-MeO—Ph | Z-7341 | PrO(C═O)— | 2-F-3,6-di-MeO—PhCH2— |
| Z-7342 | MeO(C═O)— | 4-Br—PhCH2— | Z-7343 | PrO(C═O)— | 4-MeO—Ph | Z-7344 | PrO(C═O)— | 2-Cl-3,4-di-MeO—PhCH2— |
| Z-7345 | MeO(C═O)— | 2-I—PhCH2— | Z-7346 | PrO(C═O)— | 2,3-di-F—Ph | Z-7347 | PrO(C═O)— | 2-Cl-3,5-di-MeO—PhCH2— |
| Z-7348 | MeO(C═O)— | 3-I—PhCH2— | Z-7349 | PrO(C═O)— | 2,4-di-F—Ph | Z-7350 | PrO(C═O)— | 2-Cl-3,6-di-MeO—PhCH2— |
| Z-7351 | MeO(C═O)— | 4-I—PhCH2— | Z-7352 | PrO(C═O)— | 2,5-di-F—Ph | Z-7353 | PrO(C═O)— | 2-Br-3,4-di-MeO—PhCH2— |
| Z-7354 | MeO(C═O)— | 2-Me—PhCH2— | Z-7355 | PrO(C═O)— | 2,6-di-F—Ph | Z-7356 | PrO(C═O)— | 2-Br-3,5-di-MeO—PhCH2— |
| Z-7357 | MeO(C═O)— | 3-Me—PhCH2— | Z-7358 | PrO(C═O)— | 2-Cl-3-F—Ph | Z-7359 | PrO(C═O)— | 2-Br-3,6-di-MeO—PhCH2— |
| Z-7360 | MeO(C═O)— | 4-Me—PhCH2— | Z-7361 | PrO(C═O)— | 2-Cl-4-F—Ph | Z-7362 | PrO(C═O)— | PrO(C═O)— |
| Z-7363 | MeO(C═O)— | 2-MeO—PhCH2— | Z-7364 | PrO(C═O)— | 2-Cl-5-F—Ph | Z-7365 | PrO(C═O)— | i-PrO(C═O)— |
| Z-7366 | MeO(C═O)— | 3-MeO—PhCH2— | Z-7367 | PrO(C═O)— | 2-Cl-6-F—Ph | Z-7368 | PrO(C═O)— | BuO(C═O)— |
| Z-7369 | MeO(C═O)— | 4-MeO—PhCH2— | Z-7370 | PrO(C═O)— | 2-Br-3-F—Ph | Z-7371 | PrO(C═O)— | t-BuOC(═O)— |
| Z-7372 | MeO(C═O)— | 2,3-di-F—PhCH2— | Z-7373 | PrO(C═O)— | 2-Br-4-F—Ph | Z-7374 | i-PrO(C═O)— | Ph |
| Z-7375 | MeO(C═O)— | 2,4-di-F—PhCH2— | Z-7376 | PrO(C═O)— | 2-Br-5-F—Ph | Z-7377 | i-PrO(C═O)— | 2-F—Ph |
| Z-7378 | MeO(C═O)— | 2,5-di-F—PhCH2— | Z-7379 | PrO(C═O)— | 2-Br-6-F—Ph | Z-7380 | i-PrO(C═O)— | 3-F—Ph |
| Z-7381 | MeO(C═O)— | 2,6-di-F—PhCH2— | Z-7382 | PrO(C═O)— | 2-F-3-MeO—Ph | Z-7383 | i-PrO(C═O)— | 2-Br-3,4-di-MeO—PhCH2— |
| Z-7384 | MeO(C═O)— | 2-Cl-3-F—PhCH2— | Z-7385 | PrO(C═O)— | 2-F-4-MeO—Ph | Z-7386 | i-PrO(C═O)— | 2-Br-3,5-di-MeO—PhCH2— |
| Z-7387 | MeO(C═O)— | 2-Cl-4-F—PhCH2— | Z-7388 | PrO(C═O)— | 2-F-5-MeO—Ph | Z-7389 | i-PrO(C═O)— | 2-Br-3,6-di-MeO—PhCH2— |
| Z-7390 | MeO(C═O)— | 2-Cl-5-F—PhCH2— | Z-7391 | PrO(C═O)— | 2-F-6-MeO—Ph | Z-7392 | i-PrO(C═O)— | i-PrO(C═O)— |
| Z-7393 | MeO(C═O)— | 2-Cl-6-F—PhCH2— | Z-7394 | PrO(C═O)— | 2-Cl-3-MeO—Ph | Z-7395 | i-PrO(C═O)— | BuO(C═O)— |
| Z-7396 | MeO(C═O)— | 2-Br-3-F—PhCH2— | Z-7397 | PrO(C═O)— | 2-Cl-4-MeO—Ph | Z-7398 | i-PrO(C═O)— | t-BuOC(═O)— |
| Z-7399 | MeO(C═O)— | 2-Br-4-F—PhCH2— | Z-7400 | PrO(C═O)— | 2-Cl-5-MeO—Ph | Z-7401 | BuO(C═O)— | Ph |
| Z-7402 | MeO(C═O)— | 2-Br-5-F—PhCH2— | Z-7403 | PrO(C═O)— | 2-Cl-6-MeO—Ph | Z-7404 | BuO(C═O)— | 2-F—Ph |
| Z-7405 | MeO(C═O)— | 2-Br-6-F—PhCH2— | Z-7406 | PrO(C═O)— | 2-Br-3-MeO—Ph | Z-7407 | BuO(C═O)— | 3-F—Ph |
| Z-7408 | MeO(C═O)— | 2-F-3-MeO—PhCH2— | Z-7409 | PrO(C═O)— | 2-Br-4-MeO—Ph | Z-7410 | BuO(C═O)— | 4-F—Ph |
| Z-7411 | MeO(C═O)— | 2-F-4-MeO—PhCH2— | Z-7412 | PrO(C═O)— | 2-Br-5-MeO—Ph | Z-7413 | BuO(C═O)— | 2-Cl—Ph |
| Z-7414 | EtO(C═O)— | 2,5-di-F—PhCH2— | Z-7415 | PrO(C═O)— | 2-Br-6-MeO—Ph | Z-7416 | BuO(C═O)— | 3-Cl—Ph |
| Z-7417 | EtO(C═O)— | 2,6-di-F—PhCH2— | Z-7418 | PrO(C═O)— | 2,3,4-tri-F—Ph | Z-7419 | BuO(C═O)— | 4-Cl—Ph |
| Z-7420 | EtO(C═O)— | 2-Cl-3-F—PhCH2— | Z-7421 | PrO(C═O)— | 2,3,5-tri-F—Ph | Z-7422 | BuO(C═O)— | 2-Br—Ph |
| Z-7423 | EtO(C═O)— | 2-Cl-4-F—PhCH2— | Z-7424 | PrO(C═O)— | 23,6-tri-F—Ph | Z-7425 | BuO(C═O)— | 3-Br—Ph |
| Z-7426 | EtO(C═O)— | 2-Cl-5-F—PhCH2— | Z-7427 | PrO(C═O)— | 2-Br-3,4-di-F—Ph | Z-7428 | BuO(C═O)— | 4-Br—Ph |
| Z-7429 | EtO(C═O)— | 2-Cl-6-F—PhCH2— | Z-7430 | PrO(C═O)— | 2-Br-3,5-di-F—Ph | Z-7431 | BuO(C═O)— | 2-I—Ph |
| Z-7432 | EtO(C═O)— | 2-Br-3-F—PhCH2— | Z-7433 | PrO(C═O)— | 2-Br-3,6-di-F—Ph | Z-7434 | BuO(C═O)— | 3-I—Ph |
| Z-7435 | EtO(C═O)— | 2-Br-4-F—PhCH2— | Z-7436 | PrO(C═O)— | 2-F-3,4-di-MeO—Ph | Z-7437 | BuO(C═O)— | 4-I—Ph |
| Z-7438 | EtO(C═O)— | 2-Br-5-F—PhCH2— | Z-7439 | PrO(C═O)— | 2-F-3,5-di-MeO—Ph | Z-7440 | BuO(C═O)— | 2-Me—Ph |
| Z-7441 | EtO(C═O)— | 2-Br-6-F—PhCH2— | Z-7442 | PrO(C═O)— | 2-F-3,6-di-MeO—Ph | Z-7443 | BuO(C═O)— | 3-Me—Ph |
| Z-7444 | EtO(C═O)— | 2-F-3-MeO—PhCH2— | Z-7445 | PrO(C═O)— | 2-Cl-3,4-di-MeO—Ph | Z-7446 | BuO(C═O)— | 4-Me—Ph |
| Z-7447 | EtO(C═O)— | 2-F-4-MeO—PhCH2— | Z-7448 | PrO(C═O)— | 2-Cl-3,5-di-MeO—Ph | Z-7449 | BuO(C═O)— | 2-MeO—Ph |
| Z-7450 | EtO(C═O)— | 2-F-5-MeO—PhCH2— | Z-7451 | PrO(C═O)— | 2-Cl-3,6-di-MeO—Ph | Z-7452 | BuO(C═O)— | 3-MeO—Ph |
| Z-7453 | EtO(C═O)— | 2-F-6-MeO—PhCH2— | Z-7454 | PrO(C═O)— | 2-Br-3,4-di-MeO—Ph | Z-7455 | BuO(C═O)— | 4-MeO—Ph |
| Z-7456 | EtO(C═O)— | 2-Cl-3-MeO—PhCH2— | Z-7457 | PrO(C═O)— | 2-Br-3,5-di-MeO—Ph | Z-7458 | BuO(C═O)— | 2,3-di-F—Ph |
| Z-7459 | EtO(C═O)— | 2-Cl-4-MeO—PhCH2— | Z-7460 | PrO(C═O)— | 2-Br-3,6-di-MeO—Ph | Z-7461 | BuO(C═O)— | 2,4-di-F—Ph |
| Z-7462 | EtO(C═O)— | 2-Cl-5-MeO—PhCH2— | Z-7463 | PrO(C═O)— | PhCH2— | Z-7464 | BuO(C═O)— | 2,5-di-F—Ph |
| Z-7465 | EtO(C═O)— | 2-Cl-6-MeO—PhCH2— | Z-7466 | PrO(C═O)— | 2-F—PhCH2— | Z-7467 | BuO(C═O)— | 2,6-di-F—Ph |
| Z-7468 | EtO(C═O)— | 2-Br-3-MeO—PhCH2— | Z-7469 | PrO(C═O)— | 3-F—PhCH2— | Z-7470 | BuO(C═O)— | 2-Cl-3-F—Ph |
| Z-7471 | EtO(C═O)— | 2-Br-4-MeO—PhCH2— | Z-7472 | PrO(C═O)— | 4-F—PhCH2— | Z-7473 | BuO(C═O)— | 2-Cl-4-F—Ph |
| Z-7474 | EtO(C═O)— | 2-Br-5-MeO—PhCH2— | Z-7475 | PrO(C═O)— | 2-Cl—PhCH2— | Z-7476 | BuO(C═O)— | 2-Cl-5-F—Ph |
| Z-7477 | EtO(C═O)— | 2-Br-6-MeO—PhCH2— | Z-7478 | PrO(C═O)— | 3-Cl—PhCH2— | Z-7479 | BuO(C═O)— | 2-Cl-6-F—Ph |
| Z-7480 | EtO(C═O)— | 2,3,4-tri-F—PhCH2— | Z-7481 | PrO(C═O)— | 4-Cl—PhCH2— | Z-7482 | BuO(C═O)— | 2-Br-3-F—Ph |
| Z-7483 | EtO(C═O)— | 2,3,5-tri-F—PhCH2— | Z-7484 | PrO(C═O)— | 2-Br—PhCH2— | Z-7485 | BuO(C═O)— | 2-Br-4-F—Ph |
| Z-7486 | EtO(C═O)— | 2,3,6-tri-F—PhCH2— | Z-7487 | PrO(C═O)— | 3-Br—PhCH2— | Z-7488 | BuO(C═O)— | 2-Br-5-F—Ph |
| Z-7489 | EtO(C═O)— | 2-Br-3,4-di-F—PhCH2— | Z-7490 | PrO(C═O)— | 4-Br—PhCH2— | Z-7491 | BuO(C═O)— | 2-Br-6-F—Ph |

TABLE 3-continued

| Z | R3 | R4 | Z | R3 | R4 | Z | R3 | R4 |
|---|---|---|---|---|---|---|---|---|
| Z-7492 | EtO(C═O)— | 2-Br-3,5-di-F—PhCH2— | Z-7493 | i-PrO(C═O)— | PhCH2— | Z-7494 | BuO(C═O)— | 2-F-3-MeO—Ph |
| Z-7495 | EtO(C═O)— | 2-Br-3,6-di-F—PhCH2— | Z-7496 | i-PrO(C═O)— | 2-F—PhCH2— | Z-7497 | BuO(C═O)— | 2-F-4-MeO—Ph |
| Z-7498 | EtO(C═O)— | 2-F-3,4-di-MeO—PhCH2— | Z-7499 | i-PrO(C═O)— | 3-F—PhCH2— | Z-7500 | BuO(C═O)— | 2-F-5-MeO—Ph |
| Z-7501 | EtO(C═O)— | 2-F-3,5-di-MeO—PhCH2— | Z-7502 | i-PrO(C═O)— | 4-F—PhCH2— | Z-7503 | BuO(C═O)— | 2-F-6-MeO—Ph |
| Z-7504 | EtO(C═O)— | 2-F-3,6-di-MeO—PhCH2— | Z-7505 | i-PrO(C═O)— | 2-Cl—PhCH2— | Z-7506 | BuO(C═O)— | 2-Cl-3-MeO—Ph |
| Z-7507 | EtO(C═O)— | 2-Cl-3,4-di-MeO—PhCH2— | Z-7508 | i-PrO(C═O)— | 3-Cl—PhCH2— | Z-7509 | BuO(C═O)— | 2-Cl-4-MeO—Ph |
| Z-7510 | EtO(C═O)— | 2-Cl-3,5-di-MeO—PhCH2— | Z-7511 | i-PrO(C═O)— | 4-Cl—PhCH2— | Z-7512 | BuO(C═O)— | 2-Cl-5-MeO—Ph |
| Z-7513 | EtO(C═O)— | 2-Cl-3,6-di-MeO—PhCH2— | Z-7514 | i-PrO(C═O)— | 2-Br—PhCH2— | Z-7515 | BuO(C═O)— | 2-Cl-6-MeO—Ph |
| Z-7516 | EtO(C═O)— | 2-Br-3,4-di-MeO—PhCH2— | Z-7517 | i-PrO(C═O)— | 3-Br—PhCH2— | Z-7518 | BuO(C═O)— | 2-Br-3-MeO—Ph |
| Z-7519 | EtO(C═O)— | 2-Br-3,5-di-MeO—PhCH2— | Z-7520 | i-PrO(C═O)— | 4-Br—PhCH2— | Z-7521 | BuO(C═O)— | 2-Br-4-MeO—Ph |
| Z-7522 | EtO(C═O)— | 2-Br-3,6-di-MeO—PhCH2— | Z-7523 | i-PrO(C═O)— | 2-I—PhCH2— | Z-7524 | BuO(C═O)— | 2-Br-5-MeO—Ph |
| Z-7525 | EtO(C═O)— | EtO(C═O)— | Z-7526 | i-PrO(C═O)— | 3-I—PhCH2— | Z-7527 | BuO(C═O)— | 2-Br-6-MeO—Ph |
| Z-7528 | EtO(C═O)— | PrO(C═O)— | Z-7529 | i-PrO(C═O)— | 4-I—PhCH2— | Z-7530 | BuO(C═O)— | 2,3,4-tri-F—Ph |
| Z-7531 | EtO(C═O)— | i-PrO(C═O)— | Z-7532 | i-PrO(C═O)— | 2-Me—PhCH2— | Z-7533 | BuO(C═O)— | 2,3,5-tri-F—Ph |
| Z-7534 | EtO(C═O)— | BuO(C═O)— | Z-7535 | i-PrO(C═O)— | 3-Me—PhCH2— | Z-7536 | BuO(C═O)— | 2,3,6-tri-F—Ph |
| Z-7537 | EtO(C═O)— | t-BuOC(═O)— | Z-7538 | i-PrO(C═O)— | 4-Me—PhCH2— | Z-7539 | BuO(C═O)— | 2-Br-3,4-di-F—Ph |
| Z-7540 | PrO(C═O)— | Ph | Z-7541 | i-PrO(C═O)— | 2-MeO—PhCH2— | Z-7542 | BuO(C═O)— | 2-Br-3,5-di-F—Ph |
| Z-7543 | PrO(C═O)— | 2-F—Ph | Z-7544 | i-PrO(C═O)— | 3-MeO—PhCH2— | Z-7545 | BuO(C═O)— | 2-Br-3,6-di-F—Ph |
| Z-7546 | PrO(C═O)— | 3-F—Ph | Z-7547 | i-PrO(C═O)— | 4-MeO—PhCH2— | Z-7548 | t-BuOC(═O)— | 2-Br-5-MeO—Ph |
| Z-7549 | PrO(C═O)— | 4-F—Ph | Z-7550 | i-PrO(C═O)— | 2,3-di-F—PhCH2— | Z-7551 | t-BuOC(═O)— | 2-Br-6-MeO—Ph |
| Z-7552 | PrO(C═O)— | 2-Cl—Ph | Z-7553 | i-PrO(C═O)— | 2,4-di-F—PhCH2— | Z-7554 | t-BuOC(═O)— | 2,3,4-tri-F—Ph |
| Z-7555 | PrO(C═O)— | 3-Cl—Ph | Z-7556 | i-PrO(C═O)— | 2,5-di-F—PhCH2— | Z-7557 | t-BuOC(═O)— | 2,3,5-tri-F—Ph |
| Z-7558 | PrO(C═O)— | 4-Cl—Ph | Z-7559 | i-PrO(C═O)— | 2,6-di-F—PhCH2— | Z-7560 | t-BuOC(═O)— | 2,3,6-tri-F—Ph |
| Z-7561 | PrO(C═O)— | 2-Br—Ph | Z-7562 | i-PrO(C═O)— | 2-Cl-3-F—PhCH2— | Z-7563 | t-BuOC(═O)— | 2-Br-3,4-di-F—Ph |
| Z-7564 | PrO(C═O)— | 3-Br—Ph | Z-7565 | i-PrO(C═O)— | 2-Cl-4-F—PhCH2— | Z-7566 | t-BuOC(═O)— | 2-Br-3,5-di-F—Ph |
| Z-7567 | PrO(C═O)— | 4-Br—Ph | Z-7568 | i-PrO(C═O)— | 2-Cl-5-F—PhCH2— | Z-7569 | t-BuOC(═O)— | 2-Br-3,6-di-F—Ph |
| Z-7570 | PrO(C═O)— | 2-I—Ph | Z-7571 | i-PrO(C═O)— | 2-Cl-6-F—PhCH2— | Z-7572 | t-BuOC(═O)— | 2-F-3,4-di-MeO—Ph |
| Z-7573 | PrO(C═O)— | 3-I—Ph | Z-7574 | i-PrO(C═O)— | 2-Br-3-F—PhCH2— | Z-7575 | t-BuOC(═O)— | 2-F-3,5-di-MeO—Ph |
| Z-7576 | PrO(C═O)— | 4-I—Ph | Z-7577 | i-PrO(C═O)— | 2-Br-4-F—PhCH2— | Z-7578 | t-BuOC(═O)— | 2-F-3,6-di-MeO—Ph |
| Z-7579 | i-PrO(C═O)— | 4-F—Ph | Z-7580 | i-PrO(C═O)— | 2-Br-5-F—PhCH2— | Z-7581 | t-BuOC(═O)— | 2-Cl-3,4-di-MeO—Ph |
| Z-7582 | i-PrO(C═O)— | 2-Cl—Ph | Z-7583 | i-PrO(C═O)— | 2-Br-6-F—PhCH2— | Z-7584 | t-BuOC(═O)— | 2-Cl-3,5-di-MeO—Ph |
| Z-7585 | i-PrO(C═O)— | 3-Cl—Ph | Z-7586 | i-PrO(C═O)— | 2-F-3-MeO—PhCH2— | Z-7587 | t-BuOC(═O)— | 2-Cl-3,6-di-MeO—Ph |
| Z-7588 | i-PrO(C═O)— | 4-Cl—Ph | Z-7589 | i-PrO(C═O)— | 2-F-4-MeO—PhCH2— | Z-7590 | t-BuOC(═O)— | 2-Br-3,4-di-MeO—Ph |
| Z-7591 | i-PrO(C═O)— | 2-Br—Ph | Z-7592 | i-PrO(C═O)— | 2-F-5-MeO—PhCH2— | Z-7593 | t-BuOC(═O)— | 2-Br-3,5-di-MeO—Ph |
| Z-7594 | i-PrO(C═O)— | 3-Br—Ph | Z-7595 | i-PrO(C═O)— | 2-F-6-MeO—PhCH2— | Z-7596 | t-BuOC(═O)— | 2-Br-3,6-di-MeO—Ph |
| Z-7597 | i-PrO(C═O)— | 4-Br—Ph | Z-7598 | i-PrO(C═O)— | 2-Cl-3-MeO—PhCH2— | Z-7599 | t-BuOC(═O)— | PhCH2— |
| Z-7600 | i-PrO(C═O)— | 2-I—Ph | Z-7601 | i-PrO(C═O)— | 2-Cl-4-MeO—PhCH2— | Z-7602 | t-BuOC(═O)— | 2-F—PhCH2— |
| Z-7603 | i-PrO(C═O)— | 3-I—Ph | Z-7604 | i-PrO(C═O)— | 2-Cl-5-MeO—PhCH2— | Z-7605 | t-BuOC(═O)— | 3-F—PhCH2— |
| Z-7606 | i-PrO(C═O)— | 4-I—Ph | Z-7607 | i-PrO(C═O)— | 2-Cl-6-MeO—PhCH2— | Z-7608 | t-BuOC(═O)— | 4-F—PhCH2— |
| Z-7609 | i-PrO(C═O)— | 2-Me—Ph | Z-7610 | i-PrO(C═O)— | 2-Br-3-MeO—PhCH2— | Z-7611 | t-BuOC(═O)— | 2-Cl—PhCH2— |
| Z-7612 | i-PrO(C═O)— | 3-Me—Ph | Z-7613 | i-PrO(C═O)— | 2-Br-4-MeO—PhCH2— | Z-7614 | t-BuOC(═O)— | 3-Cl—PhCH2— |
| Z-7615 | i-PrO(C═O)— | 4-Me—Ph | Z-7616 | i-PrO(C═O)— | 2-Br-5-MeO—PhCH2— | Z-7617 | t-BuOC(═O)— | 4-Cl—PhCH2— |
| Z-7618 | i-PrO(C═O)— | 2-MeO—Ph | Z-7619 | i-PrO(C═O)— | 2-Br-6-MeO—PhCH2— | Z-7620 | t-BuOC(═O)— | 2-Br—PhCH2— |
| Z-7621 | i-PrO(C═O)— | 3-MeO—Ph | Z-7622 | i-PrO(C═O)— | 2,3,4-tri-F—PhCH2— | Z-7623 | t-BuOC(═O)— | 3-Br—PhCH2— |
| Z-7624 | i-PrO(C═O)— | 4-MeO—Ph | Z-7625 | i-PrO(C═O)— | 2,3,5-tri-F—PhCH2— | Z-7626 | t-BuOC(═O)— | 4-Br—PhCH2— |
| Z-7627 | i-PrO(C═O)— | 2,3-di-F—Ph | Z-7628 | i-PrO(C═O)— | 2,3,6-tri-F—PhCH2— | Z-7629 | t-BuOC(═O)— | 2-I—PhCH2— |
| Z-7630 | i-PrO(C═O)— | 2,4-di-F—Ph | Z-7631 | i-PrO(C═O)— | 2-Br-3,4-di-F—PhCH2— | Z-7632 | t-BuOC(═O)— | 3-I—PhCH2— |
| Z-7633 | i-PrO(C═O)— | 2,5-di-F—Ph | Z-7634 | i-PrO(C═O)— | 2-Br-3,5-di-F—PhCH2— | Z-7635 | t-BuOC(═O)— | 4-I—PhCH2— |
| Z-7636 | i-PrO(C═O)— | 2,6-di-F—Ph | Z-7637 | i-PrO(C═O)— | 2-Br-3,6-di-F—PhCH2— | Z-7638 | t-BuOC(═O)— | 2-Me—PhCH2— |
| Z-7639 | i-PrO(C═O)— | 2-Cl-3-F—Ph | Z-7640 | i-PrO(C═O)— | 2-F-3,4-di-MeO—PhCH2— | Z-7641 | t-BuOC(═O)— | 3-Me—PhCH2— |
| Z-7642 | i-PrO(C═O)— | 2-Cl-4-F—Ph | Z-7643 | i-PrO(C═O)— | 2-F-3,5-di-MeO—PhCH2— | Z-7644 | t-BuOC(═O)— | 4-Me—PhCH2— |

TABLE 3-continued

| Z | R3 | R4 | Z | R3 | R4 | Z | R3 | R4 |
|---|---|---|---|---|---|---|---|---|
| Z-7645 | i-PrO(C═O)— | 2-Cl-5-F—Ph | Z-7646 | i-PrO(C═O)— | 2-F-3,6-di-MeO—PhCH2— | Z-7647 | t-BuOC(═O)— | 2-MeO—PhCH2— |
| Z-7648 | i-PrO(C═O)— | 2-Cl-6-F—Ph | Z-7649 | i-PrO(C═O)— | 2-Cl-3,4-di-MeO—PhCH2— | Z-7650 | t-BuOC(═O)— | 3-MeO—PhCH2— |
| Z-7651 | i-PrO(C═O)— | 2-Br-3-F—Ph | Z-7652 | i-PrO(C═O)— | 2-Cl-3,5-di-MeO—PhCH2— | Z-7653 | t-BuOC(═O)— | 4-MeO—PhCH2— |
| Z-7654 | i-PrO(C═O)— | 2-Br-4-F—Ph | Z-7655 | i-PrO(C═O)— | 2-Cl-3,6-di-MeO—PhCH2— | Z-7656 | t-BuOC(═O)— | 2,3-di-F—PhCH2— |
| Z-7657 | i-PrO(C═O)— | 2-Br-5-F—Ph | Z-7658 | BuO(C═O)— | 2-Br-3,4-di-F—PhCH2— | Z-7659 | t-BuOC(═O)— | 2,4-di-F—PhCH2— |
| Z-7660 | i-PrO(C═O)— | 2-Br-6-F—Ph | Z-7661 | BuO(C═O)— | 2-Br-3,5-di-F—PhCH2— | Z-7662 | t-BuOC(═O)— | 2,5-di-F—PhCH2— |
| Z-7663 | i-PrO(C═O)— | 2-F-3-MeO—Ph | Z-7664 | BuO(C═O)— | 2-Br-3,6-di-F—PhCH2— | Z-7665 | t-BuOC(═O)— | 2,6-di-F—PhCH2— |
| Z-7666 | i-PrO(C═O)— | 2-F-4-MeO—Ph | Z-7667 | BuO(C═O)— | 2-F-3,4-di-MeO—PhCH2— | Z-7668 | t-BuOC(═O)— | 2-Cl-3-F—PhCH2— |
| Z-7669 | i-PrO(C═O)— | 2-F-5-MeO—Ph | Z-7670 | BuO(C═O)— | 2-F-3,5-di-MeO—PhCH2— | Z-7671 | t-BuOC(═O)— | 2-Cl-4-F—PhCH2— |
| Z-7672 | i-PrO(C═O)— | 2-F-6-MeO—Ph | Z-7673 | BnO(C═O)— | 2-F-3,6-di-MeO—PhCH2— | Z-7674 | t-BuOC(═O)— | 2-Cl-5-F—PhCH2— |
| Z-7675 | i-PrO(C═O)— | 2-Cl-3-MeO—Ph | Z-7676 | BuO(C═O)— | 2-Cl-3,4-di-MeO—PhCH2— | Z-7677 | t-BuOC(═O)— | 2-Cl-6-F—PhCH2— |
| Z-7678 | i-PrO(C═O)— | 2-Cl-4-MeO—Ph | Z-7679 | BuO(C═O)— | 2-Cl-3,5-di-MeO—PhCH2— | Z-7680 | t-BuOC(═O)— | 2-Br-3-F—PhCH2— |
| Z-7681 | i-PrO(C═O)— | 2-Cl-5-MeO—Ph | Z-7682 | BuO(C═O)— | 2-Cl-3,6-di-MeO—PhCH2— | Z-7683 | t-BuOC(═O)— | 2-Br-4-F—PhCH2— |
| Z-7684 | i-PrO(C═O)— | 2-Cl-6-MeO—Ph | Z-7685 | BuO(C═O)— | 2-Br-3,4-di-MeO—PhCH2— | Z-7686 | t-BuOC(═O)— | 2-Br-5-F—PhCH2— |
| Z-7687 | i-PrO(C═O)— | 2-Br-3-MeO—Ph | Z-7688 | BuO(C═O)— | 2-Br-3,5-di-MeO—PhCH2— | Z-7689 | t-BuOC(═O)— | 2-Br-6-F—PhCH2— |
| Z-7690 | i-PrO(C═O)— | 2-Br-4-MeO—Ph | Z-7691 | BuO(C═O)— | 2-Br-3,6-di-MeO—PhCH2— | Z-7692 | t-BuOC(═O)— | 2-F-3-MeO—PhCH2— |
| Z-7693 | i-PrO(C═O)— | 2-Br-5-MeO—Ph | Z-7694 | BuO(C═O)— | BuO(C═O)— | Z-7695 | t-BuOC(═O)— | 2-F-4-MeO—PhCH2— |
| Z-7696 | i-PrO(C═O)— | 2-Br-6-MeO—Ph | Z-7697 | BuO(C═O)— | t-BuOC(═O)— | Z-7698 | t-BuOC(═O)— | 2-F-5-MeO—PhCH2— |
| Z-7699 | i-PrO(C═O)— | 2,3,4-tri-F—Ph | Z-7700 | t-BuOC(═O)— | Ph | Z-7701 | t-BuOC(═O)— | 2-F-6-MeO—PhCH2— |
| Z-7702 | i-PrO(C═O)— | 2,3,5-tri-F—Ph | Z-7703 | t-BuOC(═O)— | 2-F—Ph | Z-7704 | t-BuOC(═O)— | 2-Cl-3-MeO—PhCH2— |
| Z-7705 | i-PrO(C═O)— | 2,3,6-tri-F—Ph | Z-7706 | t-BuOC(═O)— | 3-F—Ph | Z-7707 | t-BuOC(═O)— | 2-Cl-4-MeO—PhCH2— |
| Z-7708 | i-PrO(C═O)— | 2-Br-3,4-di-F—Ph | Z-7709 | t-BuOC(═O)— | 4-F—Ph | Z-7710 | t-BuOC(═O)— | 2-Cl-5-MeO—PhCH2— |
| Z-7711 | i-PrO(C═O)— | 2-Br-3,5-di-F—Ph | Z-7712 | t-BuOC(═O)— | 2-Cl—Ph | Z-7713 | t-BuOC(═O)— | 2-F-3,4-di-MeO—PhCH2— |
| Z-7714 | i-PrO(C═O)— | 2-Br-3,6-di-F—Ph | Z-7715 | t-BuOC(═O)— | 3-Cl—Ph | Z-7716 | t-BuOC(═O)— | 2-Cl-3,4-di-MeO—PhCH2— |
| Z-7717 | i-PrO(C═O)— | 2-F-3,4-di-MeO—Ph | Z-7718 | t-BuOC(═O)— | 4-Cl—Ph | Z-7719 | t-BuOC(═O)— | 2-Br-3,4-di-MeO—PhCH2— |
| Z-7720 | i-PrO(C═O)— | 2-F-3,5-di-MeO—Ph | Z-7721 | t-BuOC(═O)— | 2-Br—Ph | Z-7722 | t-BuOC(═O)— | 2-Br-3,4-di-F—PhCH2— |
| Z-7723 | i-PrO(C═O)— | 2-F-3,6-di-MeO—Ph | Z-7724 | t-BuOC(═O)— | 3-Br—Ph | Z-7725 | t-BuOC(═O)— | 2-Br-3,5-di-F—PhCH2— |
| Z-7726 | i-PrO(C═O)— | 2-Cl-3,4-di-MeO—Ph | Z-7727 | t-BuOC(═O)— | 4-Br—Ph | Z-7728 | t-BuOC(═O)— | 2-Cl-3,5-di-MeO—PhCH2— |
| Z-7729 | i-PrO(C═O)— | 2-Cl-3,5-di-MeO—Ph | Z-7730 | t-BuOC(═O)— | 2-I—Ph | Z-7731 | t-BuOC(═O)— | 2,3,6-tri-F—PhCH2— |
| Z-7732 | i-PrO(C═O)— | 2-Cl-3,6-di-MeO—Ph | Z-7733 | t-BuOC(═O)— | 3-I—Ph | Z-7734 | BuO(C═O)— | 2-Br-4-F—PhCH2— |
| Z-7735 | i-PrO(C═O)— | 2-Br-3,4-di-MeO—Ph | Z-7736 | t-BuOC(═O)— | 4-I—Ph | Z-7737 | BuO(C═O)— | 2-Br-5-F—PhCH2— |
| Z-7738 | i-PrO(C═O)— | 2-Br-3,5-di-MeO—Ph | Z-7739 | t-BuOC(═O)— | 2-Me—Ph | Z-7740 | BuO(C═O)— | 2-Br-6-F—PhCH2— |
| Z-7741 | i-PrO(C═O)— | 2-Br-3,6-di-MeO—Ph | Z-7742 | t-BuOC(═O)— | 3-Me—Ph | Z-7743 | BuO(C═O)— | 2-F-3-MeO—PhCH2— |
| Z-7744 | BuO(C═O)— | 2-F-3,4-di-MeO—Ph | Z-7745 | t-BuOC(═O)— | 4-Me—Ph | Z-7746 | BuO(C═O)— | 2-F-4-MeO—PhCH2— |
| Z-7747 | BuO(C═O)— | 2-F-3,5-di-MeO—Ph | Z-7748 | t-BuOC(═O)— | 2-MeO—Ph | Z-7749 | BuO(C═O)— | 2-F-5-MeO—PhCH2— |
| Z-7750 | BuO(C═O)— | 2-F-3,6-di-MeO—Ph | Z-7751 | t-BuOC(═O)— | 3-MeO—Ph | Z-7752 | BuO(C═O)— | 2-F-6-MeO—PhCH2— |
| Z-7753 | BuO(C═O)— | 2-Cl-3,4-di-MeO—Ph | Z-7754 | t-BuOC(═O)— | 4-MeO—Ph | Z-7755 | BuO(C═O)— | 2-Cl-3-MeO—PhCH2— |
| Z-7756 | BuO(C═O)— | 2-Cl-3,5-di-MeO—Ph | Z-7757 | t-BuOC(═O)— | 2,3-di-F—Ph | Z-7758 | BuO(C═O)— | 2-Cl-4-MeO—PhCH2— |
| Z-7759 | BuO(C═O)— | 2-Cl-3,6-di-MeO—Ph | Z-7760 | t-BuOC(═O)— | 2,4-di-F—Ph | Z-7761 | BuO(C═O)— | 2-Cl-5-MeO—PhCH2— |
| Z-7762 | BuO(C═O)— | 2-Br-3,4-di-MeO—Ph | Z-7763 | t-BuOC(═O)— | 2,5-di-F—Ph | Z-7764 | BuO(C═O)— | 2-Cl-6-MeO—PhCH2— |
| Z-7765 | BuO(C═O)— | 2-Br-3,5-di-MeO—Ph | Z-7766 | t-BuOC(═O)— | 2,6-di-F—Ph | Z-7767 | BuO(C═O)— | 2-Br-3-MeO—PhCH2— |
| Z-7768 | BuO(C═O)— | 2-Br-3,6-di-MeO—Ph | Z-7769 | t-BuOC(═O)— | 2-Cl-3-F—Ph | Z-7770 | BuO(C═O)— | 2-Br-4-MeO—PhCH2— |
| Z-7771 | BuO(C═O)— | PhCH2— | Z-7772 | t-BuOC(═O)— | 2-Cl-4-F—Ph | Z-7773 | BuO(C═O)— | 2-Br-5-MeO—PhCH2— |
| Z-7774 | BuO(C═O)— | 2-F—PhCH2— | Z-7775 | t-BuOC(═O)— | 2-Cl-5-F—Ph | Z-7776 | BuO(C═O)— | 2-Br-6-MeO—PhCH2— |
| Z-7777 | BuO(C═O)— | 3-F—PhCH2— | Z-7778 | t-BuOC(═O)— | 2-Cl-6-F—Ph | Z-7779 | BuO(C═O)— | 2,3,4-tri-F—PhCH2— |
| Z-7780 | BuO(C═O)— | 4-F—PhCH2— | Z-7781 | t-BuOC(═O)— | 2-Br-3-F—Ph | Z-7782 | BuO(C═O)— | 2,3,5-tri-F—PhCH2— |
| Z-7783 | BuO(C═O)— | 2-Cl—PhCH2— | Z-7784 | t-BuOC(═O)— | 2-Br-4-F—Ph | Z-7785 | BuO(C═O)— | 2,3,6-tri-F—PhCH2— |
| Z-7786 | BuO(C═O)— | 3-Cl—PhCH2— | Z-7787 | t-BuOC(═O)— | 2-Br-5-F—Ph | Z-7788 | BuO(C═O)— | 4-MeO—PhCH2— |
| Z-7789 | BuO(C═O)— | 4-Cl—PhCH2— | Z-7790 | t-BuOC(═O)— | 2-Br-6-F—Ph | Z-7791 | BuO(C═O)— | 2,3-di-F—PhCH2— |
| Z-7792 | BuO(C═O)— | 2-Br—PhCH2— | Z-7793 | t-BuOC(═O)— | 2-F-3-MeO—Ph | Z-7794 | BuO(C═O)— | 2,4-di-F—PhCH2— |
| Z-7795 | BuO(C═O)— | 3-Br—PhCH2— | Z-7796 | t-BuOC(═O)— | 2-F-4-MeO—Ph | Z-7797 | BuO(C═O)— | 2,5-di-F—PhCH2— |

TABLE 3-continued

| Z | R3 | R4 | Z | R3 | R4 | Z | R3 | R4 |
|---|---|---|---|---|---|---|---|---|
| Z-7798 | BuO(C═O)— | 4-Br—PhCH2— | Z-7799 | t-BuOC(═O)— | 2-F-5-MeO—Ph | Z-7800 | BuO(C═O)— | 2,6-di-F—PhCH2— |
| Z-7801 | BuO(C═O)— | 2-I—PhCH2— | Z-7802 | t-BuOC(═O)— | 2-F-6-MeO—Ph | Z-7803 | BuO(C═O)— | 2-Cl-3-F—PhCH2— |
| Z-7804 | BuO(C═O)— | 3-I—PhCH2— | Z-7805 | t-BuOC(═O)— | 2-Cl-3-MeO—Ph | Z-7806 | BuO(C═O)— | 2-Cl-4-F—PhCH2— |
| Z-7807 | BuO(C═O)— | 4-I—PhCH2— | Z-7808 | t-BuOC(═O)— | 2-Cl-4-MeO—Ph | Z-7809 | BuO(C═O)— | 2-Cl-5-F—PhCH2— |
| Z-7810 | BuO(C═O)— | 2-Me—PhCH2— | Z-7811 | t-BuOC(═O)— | 2-Cl-5-MeO—Ph | Z-7812 | BuO(C═O)— | 2-Cl-6-F—PhCH2— |
| Z-7813 | BuO(C═O)— | 3-Me—PhCH2— | Z-7814 | t-BuOC(═O)— | 2-Cl-6-MeO—Ph | Z-7815 | BuO(C═O)— | 2-Br-3-F—PhCH2— |
| Z-7816 | BuO(C═O)— | 4-Me—PhCH2— | Z-7817 | t-BuOC(═O)— | 2-Br-3-MeO—Ph | Z-7818 | BuO(C═O)— | 3-MeO—PhCH2— |
| Z-7819 | BuO(C═O)— | 2-MeO—PhCH2— | Z-7820 | t-BuOC(═O)— | 2-Br-4-MeO—Ph | Z-7821 | t-BuOC(═O)— | t-BuOC(═O)— |
| Z-7822 | t-BuOC(═O)— | 2-Br-3,6-di-F—PhCH2— | Z-7823 | t-BuOC(═O)— | 2-Cl-3,6-di-MeO—PhCH2— | Z-7824 | t-BuOC(═O)— | 2-F-3,5-di-MeO—PhCH2— |
| Z-7825 | t-BuOC(═O)— | 2-F-3,6-di-MeO—PhCH2— | Z-7826 | t-BuOC(═O)— | 2-Br-3,6-di-MeO—PhCH2— | Z-7827 | t-BuOC(═O)— | 2-Br-3,5-di-MeO—PhCH2— |
| Z-7828 | t-BuOC(═O)— | 2-Cl-6-MeO—PhCH2— | Z-7829 | t-BuOC(═O)— | 2-Br-4-MeO—PhCH2— | Z-7830 | t-BuOC(═O)— | 2-Br-6-MeO—PhCH2— |
| Z-7831 | t-BuOC(═O)— | 2-Br-3-MeO—PhCH2— | Z-7832 | t-BuOC(═O)— | 2-Br-5-MeO—PhCH2— | Z-7833 | t-BuOC(═O)— | 2,3,4-tri-F—PhCH2— |
| Z-7834 | t-BuOC(═O)— | 2,3,5-tri-F—PhCH2— | Z-7835 | Me2N—CH— | | Z-7836 | i-PrOC(═O)—CH═ | |
| Z-7837 | Me(Et)N—CH═ | | Z-7838 | (pyrrolidin-1-yl)-CH═ | | Z-7839 | i-BuOC(═O)—CH═ | |
| Z-7840 | PrOC(═O)—CH═ | | Z-7841 | Et(Pr)N—CH═ | | Z-7842 | —CH2CH2CH(CH3)CH2CH2— | |
| Z-7843 | BuOC(═O)—CH═ | | Z-7844 | EtOC(═O)—CH═ | | Z-7845 | MeOC(═O)—CH═ | |
| Z-7846 | (pipelidin-1-yl)-CH | | Z-7847 | —(CH2)4—C(═O)— | | Z-7848 | —(CH2)4— | |
| Z-7849 | —(CH2)3—C(═O)— | | Z-7850 | —(CH2)2—O—(CH2)2— | | Z-7851 | —(CH2)5— | |
| Z-7852 | Et(Et)N—CH═ | | Z-7853 | Pr(Pr)N—CH═ | | Z-7854 | Pr(Bu)N—CH═ | |

Hereinbelow, the method for producing the compound represented by Formula (1) is illustrated. The method for producing the compound of the present invention is not limited to Production Method A to Production Method AB.

[Production Method A]

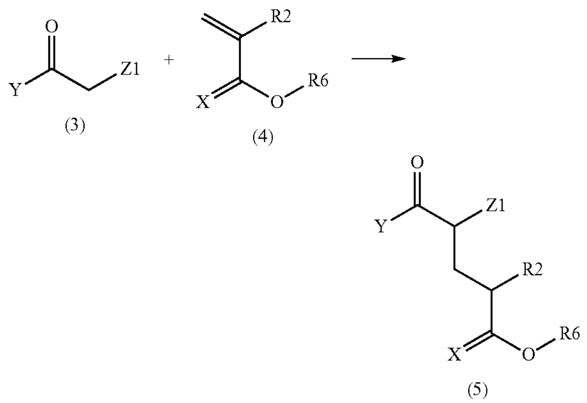

(3) (4) (5)

wherein Z1 represents a C1-C6 alkyl group, R6 represents a hydrogen atom or a C1-C6 alkyl group, and R2, X and Y are the same as defined above.

Production Method A is a method for obtaining a production intermediate represented by Formula (5), which comprises reacting a compound represented by Formula (3) with a compound represented by Formula (4) in a solvent in the presence of a base.

The compound represented by Formula (3) used in this reaction is commercially available or can be produced by a method of a Reference Example or a conventionally known method.

The compound represented by Formula (4) used in this reaction is commercially available or can be produced by a conventionally known method.

The amount of the compound represented by Formula (4) used in this reaction is not particularly limited as long as the amount is 1 equivalent or more relative to the compound represented by Formula (3) and the intended reaction proceeds. The amount is usually 1 equivalent or more and 3 equivalents or less.

Examples of the base used in this reaction include inorganic bases, such as sodium carbonate, potassium carbonate, cesium carbonate and tripotassium phosphate; metal alkoxides, such as sodium methoxide, sodium ethoxide, sodium t-butoxide and potassium t-butoxide; and the like.

The amount of the base used in this reaction is not particularly limited as long as the intended reaction proceeds. It is usually 0.01 equivalent or more and 3 equivalents or less relative to the compound represented by Formula (3).

Examples of the solvent used in this reaction include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less, relative to the compound represented by Formula (3).

The temperature for carrying out this reaction is not particularly limited as long as the intended reaction proceeds, and is usually −50° C. or higher and 150° C. or lower, or a boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, if necessary, it is possible to add a solvent which is immiscible with water such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride, a hydrocarbon solvent, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (5), may be dehydrated with a drying agent, such as sodium sulfate and magnesium sulfate, but this is not essential.

With respect to the reaction mixture obtained above, which contains the compound represented by Formula (5), the solvent may be evaporated under reduced pressure as long as the compound is not decomposed.

The reaction mixture obtained after the evaporation of the solvent, which contains the compound represented by Formula (5), may be purified by washing, reprecipitation, recrystallization, column chromatography and the like using an appropriate solvent. The purification method may be appropriately selected depending on the desired purity.

[Production Method B]

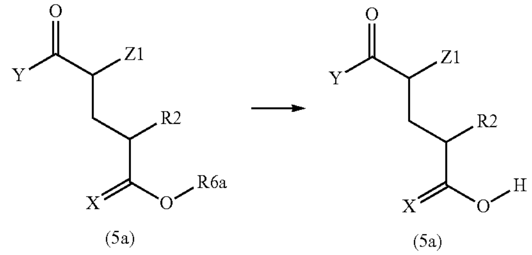

(5a) (5a)

wherein R6a represents a C1-C6 alkyl group, and R2, X, Y and Z1 are the same as defined above.

Production Method B is a method for obtaining a production intermediate represented by Formula (5b) among the compound represented by Formula (5), which comprises reacting a compound represented by Formula (5a) in a solvent under acidic conditions or basic conditions.

First, the reaction under acidic conditions is explained.

Examples of the acid used in this reaction include inorganic acids, such as hydrochloric acid, hydrobromic acid and phosphoric acid; and organic acids, such as acetic acid, methanesulfonic acid, p-toluenesulfonic acid and trifluoroacetic acid. The acid is not particularly limited as long as the intended reaction proceeds.

The amount of the acid used in this reaction is not particularly limited as long as the intended reaction proceeds, and may be a catalytic amount. The amount is usually 0.01 equivalent or more relative to the compound represented by Formula (5a). An acid in a liquid state can be used as a solvent.

The solvent used in this reaction is not particularly limited as long as the intended reaction proceeds, and examples of the solvent include water solvent; acidic solvents, such as acetic acid and methanesulfonic acid; ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (5a).

The temperature for carrying out this reaction is not particularly limited as long as the intended reaction proceeds, and is usually 0° C. or higher and 180° C. or lower, or the boiling point of the solvent or lower.

Next, the reaction under basic conditions is explained.

Examples of the base used in this reaction include inorganic bases, such as lithium hydroxide, sodium hydroxide and potassium hydroxide. The base is not particularly limited as long as the intended reaction proceeds.

The amount of the base used in this reaction is not particularly limited as long as the amount is 1 equivalent or more relative to the compound represented by Formula (5a) and the intended reaction proceeds. The amount is usually 1 equivalent or more and 30 equivalents or less.

The solvent used in this reaction is not particularly limited as long as the intended reaction proceeds, and examples of the solvent include water solvent; ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (5a).

The temperature for carrying out this reaction is not particularly limited as long as the intended reaction proceeds, and is usually −20° C. or higher and 180° C. or lower, or the boiling point of the solvent or lower.

In the reaction under acidic conditions and that under basic conditions, the post treatment of the reaction can be carried out in a common manner. It is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (5b), may be dehydrated with a drying agent, such as sodium sulfate and magnesium sulfate, but this is not essential.

With respect to the reaction mixture obtained above, which contains the compound represented by Formula (5b), the solvent may be evaporated under reduced pressure as long as the compound is not decomposed.

The reaction mixture obtained after the evaporation of the solvent, which contains the compound represented by Formula (5b), may be purified by washing, reprecipitation, recrystallization, column chromatography and the like using an appropriate solvent. The purification method may be appropriately selected depending on the desired purity.

The compound represented by Formula (5b) also includes an isomer represented by Formula (5b'):

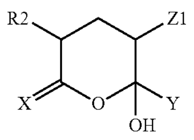

(5b')

(wherein R2, X, Y and Z1 are the same as defined above).

The compound represented by Formula (5b') can be handled in substantially the same manner as in the compound represented by Formula (5b) and, for example, adapt to Production Method C. In addition, the compound represented by Formula (5b') contains an asymmetric carbon and, with respect to the ratio of isomers in a mixture, this compound may consist of a single isomer or be a mixture of isomers in any ratio. Further, this compound may be a mixture of the compound represented by Formula (5b) and the compound represented by Formula (5b') and, with respect to the ratio of isomers in a mixture, this compound may consist of a single isomer or be a mixture of isomers in any ratio.

[Production Method C]

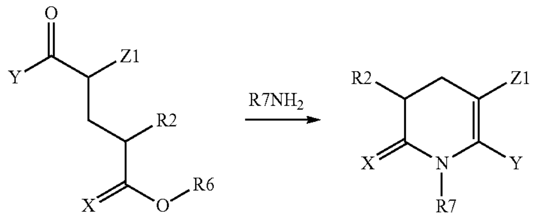

(5) (6)

wherein R7 represents a hydrogen atom, a hydroxyl group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group or an RaRbN— (wherein Ra and Rb are the same as defined above), and R2, R6, X, Y and Z1 are the same as defined above.

Production Method C is a method for obtaining a production intermediate represented by Formula (6), which comprises reacting a compound represented by Formula (5) with $R7NH_2$ in the presence of an acid.

The $R7NH_2$ used in this reaction is commercially available or can be produced by a conventionally known method. The $R7NH_2$ is not particularly limited as long as the intended reaction proceeds, and may be in the form of a salt with an acidic compound, such as hydrochloric acid and acetic acid.

The amount of the $R7NH_2$ used in this reaction is not particularly limited as long as the amount is 1 equivalent or more relative to the compound represented by Formula (5) and the intended reaction proceeds. The amount is usually 1 equivalent or more and 200 equivalents or less.

Examples of the acid used in this reaction include inorganic acids, such as hydrochloric acid and sulfuric acid; and organic acids, such as acetic acid, methanesulfonic acid and p-toluenesulfonic acid. The acid is not particularly limited as long as the intended reaction proceeds, and preferably acetic acid. In addition, when a salt of the $R7NH_2$ with an acidic compound is used, use of the acid is not essential.

The amount of the acid used in this reaction is not particularly limited as long as the amount is 1 equivalent or more relative to the $R7NH_2$ and the intended reaction proceeds. The amount is usually 1 equivalent or more and 200 equivalents or less. In addition, when the acid used is in a liquid form, the acid can be used as a solvent.

A solvent can be used in this reaction, but this is not essential.

The solvent used in this reaction is not particularly limited as long as the intended reaction proceeds, and examples of the solvent include acidic solvents, such as acetic acid and methanesulfonic acid; ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; and the like. These solvents may be used individually or in combination in any ratio. As preferred solvents, there can be mentioned acidic solvents and, as a more preferred solvent, there can be mentioned acetic acid.

The amount of the solvent used in this reaction is not particularly limited as long as the intended reaction proceeds. The amount is usually 3 times by weight or more and 200 times by weight or less relative to the compound represented by Formula (5).

The temperature for carrying out this reaction is not particularly limited as long as the intended reaction proceeds, and is usually 50° C. or higher and 180° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (6), may be dehydrated with a drying agent, such as sodium sulfate and magnesium sulfate, but this is not essential.

With respect to the reaction mixture obtained above, which contains the compound represented by Formula (6), the solvent may be evaporated under reduced pressure as long as the compound is not decomposed.

The reaction mixture obtained after the evaporation of the solvent, which contains the compound represented by Formula (6), may be purified by washing, reprecipitation, recrystallization, column chromatography and the like using an appropriate solvent. The purification method may be appropriately selected depending on the desired purity.

[Production Method D]

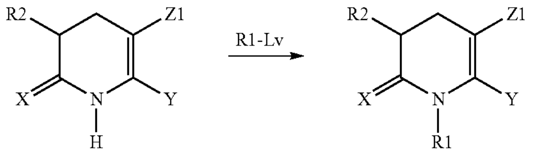

(6a) (6b)

wherein Lv represents a leaving group such as a methanesulfonyl group, a trifluoromethanesulfonyl group, a p-toluenesulfonyl group and a halogen atom, and R1, R2, X, Y and Z1 are the same as defined above.

Production Method D is a method for obtaining a production intermediate represented by Formula (6b), which comprises reacting a compound represented by Formula (6a) with R1-Lv in a solvent in the presence of a base.

The compound represented by Formula (6a), which is a starting material of the present invention, can be synthesized with reference to Production Method C or a non-patent literature, such as Journal of Heterocyclic Chemistry, vol. 20, pages 65-67 (1983) and the like.

The R1-Lv used in this reaction is commercially available or can be produced by a conventionally known method.

Examples of the base used in this reaction include inorganic bases, such as sodium hydroxide, potassium hydroxide, sodium carbonate, potassium carbonate, cesium carbonate and sodium hydride. The base is not particularly limited as long as the intended reaction proceeds.

The amount of the base used in this reaction is not particularly limited as long as the amount is 1 equivalent or more relative to the compound represented by Formula (6a) and the intended reaction proceeds. The amount is usually 1 equivalent or more and 10 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (6a).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (6b), may be dehydrated with a drying agent, such as sodium sulfate and magnesium sulfate, but this is not essential.

With respect to the reaction mixture obtained above, which contains the compound represented by Formula (6b), the solvent may be evaporated under reduced pressure as long as the compound is not decomposed.

The reaction mixture obtained after the evaporation of the solvent, which contains the compound represented by Formula (6b), may be purified by washing, reprecipitation, recrystallization, column chromatography and the like using an appropriate solvent. The purification method may be appropriately selected depending on the desired purity.

[Production Method E]

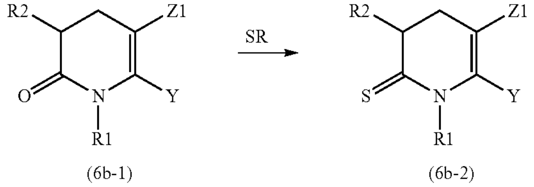

(6b-1) (6b-2)

wherein SR represents a sulfurizing agent, and R1, R2, Y and Z1 are the same as defined above.

Production Method E is a method for obtaining a compound represented by Formula (6b-2) among the compounds represented by Formula (6b), which comprises reacting a compound represented by Formula (6b-1) with a sulfurizing agent (SR) in a solvent.

As examples of the sulfurizing agent used in this reaction, there can be mentioned Lawesson's reagent (2,4-bis(4-methoxyphenyl)-1,3-dithia-2,4-diphosphetane-2,4-disulfide) and the like.

The amount of the sulfurizing agent used in this reaction is not particularly limited as long as the amount is 0.5 equivalent or more relative to the compound represented by Formula (6b-1) and the intended reaction proceeds. The amount is usually 1 equivalent or more and 10 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (6b-1).

The temperature for carrying out this reaction is not particularly limited as long as the intended reaction proceeds, and is usually 50° C. or higher and 180° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield. Further, in this reaction, the liquid separating operation is not essential.

The reaction mixture obtained above, which contains the compound represented by Formula (6b-2), may be dehydrated with a drying agent, such as sodium sulfate and magnesium sulfate, but this is not essential.

With respect to the reaction mixture obtained above, which contains the compound represented by Formula (6b-2), the solvent may be evaporated under reduced pressure as long as the compound is not decomposed.

The reaction mixture obtained after the evaporation of the solvent, which contains the compound represented by Formula (6b-2), may be purified by washing, reprecipitation, recrystallization, column chromatography and the like using an appropriate solvent. The purification method may be appropriately selected depending on the desired purity.

[Production Method F]

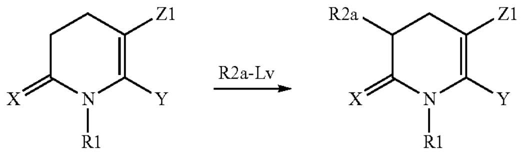

(6b-3) (6b-4)

wherein R2a represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group or RdC(═O)— (wherein Rd is the same as defined above), and R1, X, Y, Z1 and Lv are the same as defined above.

Production Method F is a method for obtaining, among the compounds represented by Formula (6b), a compound represented by Formula (6b-4) in which R2a is a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group or RdC(═O)— (wherein Rd is the same as defined above), which comprises reacting a compound represented by Formula (6b-3) with R2a-Lv in a solvent in the presence of a base.

The R2a-Lv used in this reaction is commercially available or can be produced by a conventionally known method.

The amount of the R2a-Lv used in this reaction is not particularly limited as long as the amount is 1 equivalent or more relative to the compound represented by Formula (6b-3) and the intended reaction proceeds. The amount is usually 1 equivalent or more and 1.8 equivalents or less.

Examples of the base used in this reaction include metal hydrides, such as sodium hydride; organolithiums, such as methyllithium, butyllithium, sec-butyllithium, t-butyllithium and hexyllithium; metal amides, such as lithium diisopropylamide, hexamethyldisilazane lithium, hexamethyldisilazane sodium and hexamethyldisilazane potassium.

The amount of the base used in this reaction is not particularly limited as long as the amount is 1 equivalent or more relative to the compound represented by Formula (6b-3) and the intended reaction proceeds. The amount is usually 1 equivalent or more and 10 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (6b-3).

The temperature for carrying out this reaction is not particularly limited as long as the intended reaction proceeds, and is usually −80° C. or higher and 100° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane and chloroform; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (6b-4), may be dehydrated with a drying agent, such as sodium sulfate and magnesium sulfate, but this is not essential.

With respect to the reaction mixture obtained above, which contains the compound represented by Formula (6b-4), the solvent may be evaporated under reduced pressure as long as the compound is not decomposed.

The reaction mixture obtained after the evaporation of the solvent, which contains the compound represented by Formula (6b-4), may be purified by washing, reprecipitation, recrystallization, column chromatography and the like using an appropriate solvent. The purification method may be appropriately selected depending on the desired purity.

[Production Method G]

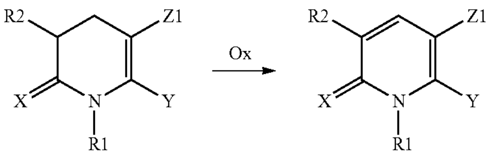

(6b) (7)

wherein Ox represents an oxidizing agent, and R1, R2, X, Y and Z1 are the same as defined above.

Production Method G is a method for obtaining a compound represented by Formula (7), a production intermediate for the compound of the present invention, which comprises reacting a compound represented by Formula (6b) with an oxidizing agent (Ox) in a solvent.

As the oxidizing agent for this reaction, it is possible to use metal oxides, such as manganese dioxide; benzoquinones, such as 2,3-dichloro-5,6-dicyano-p-benzoquinone; a combination of a radical initiator (such as azobisisobutyronitrile and benzoyl peroxide) and a halogenating agent (such as N-chlorosuccinimide, N-bromosuccinimide, N-iodosuccinimide, 1,3-dichloro-5,5-dimethylhydantoin, 1,3-dibromo-5,5-dimethylhydantoin and 1,3-diiodo-5,5-dimethylhydantoin); and the like.

A method in which the oxidizing agent is a metal oxide is explained below.

The amount of the oxidizing agent used in this reaction is not particularly limited as long as the amount is 1 equivalent or more relative to the compound represented by Formula (6b) and the intended reaction proceeds. The amount is usually 1 equivalent or more and 200 equivalents or less.

The solvent used in this reaction is not particularly limited as long as the intended reaction proceeds, and examples of the solvent include benzene-based solvents, such as benzene, toluene, xylene, mesitylene, chlorobenzene and dichlorobenzene; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (6b).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to remove undissolved metals by filtration. Further, it is also possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield. Further, in this reaction, the liquid separating operation is not essential.

The reaction mixture obtained above, which contains the compound represented by Formula (7), may be dehydrated with a drying agent, such as sodium sulfate and magnesium sulfate, but this is not essential.

With respect to the reaction mixture obtained above, which contains the compound represented by Formula (7), the solvent may be evaporated under reduced pressure as long as the compound is not decomposed.

The reaction mixture obtained after the evaporation of the solvent, which contains the compound represented by Formula (7), may be purified by washing, reprecipitation, recrystallization, column chromatography and the like using an appropriate solvent. The purification method may be appropriately selected depending on the desired purity.

A method in which the oxidizing agent is benzoquinones is explained below.

The amount of the oxidizing agent used in this reaction is not particularly limited as long as the amount is 1 equivalent or more relative to the compound represented by Formula (6b) and the intended reaction proceeds. The amount is usually 1 equivalent or more and 20 equivalents or less.

The solvent used in this reaction is not particularly limited as long as the intended reaction proceeds, and examples of the solvent include benzene-based solvents, such as benzene, toluene, xylene, mesitylene, chlorobenzene and dichlorobenzene; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (6b).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield. Further, in this reaction, the liquid separating operation is not essential.

The reaction mixture obtained above, which contains the compound represented by Formula (7), may be dehydrated with a drying agent, such as sodium sulfate and magnesium sulfate, but this is not essential.

With respect to the reaction mixture obtained above, which contains the compound represented by Formula (7), the solvent may be evaporated under reduced pressure as long as the compound is not decomposed.

The reaction mixture obtained after the evaporation of the solvent, which contains the compound represented by Formula (7), may be purified by washing, reprecipitation, recrystallization, column chromatography and the like using an appropriate solvent. The purification method may be appropriately selected depending on the desired purity.

A method in which the oxidizing agent is a combination of a radical initiator and a halogenating agent is explained below.

The amounts of the radical initiator and halogenating agent used in this reaction are not particularly limited as long as the amount of the former is 0.01 equivalent or more and the amount of the latter is 1 equivalent or more, relative to the compound represented by Formula (6b), and the intended reaction proceeds. The amount of the radical initiator is usually 0.01 equivalent or more and 1 equivalents or less, and the amount the halogenating agent is usually 1 equivalent or more and 3 equivalents or less.

The solvent used in this reaction is not particularly limited as long as the intended reaction proceeds, and examples of the solvent include halogenated benzene-based solvents, such as chlorobenzene and dichlorobenzene; ester solvents, such as ethyl acetate, isopropyl acetate and butyl acetate; halogen-based solvents, such as dichloromethane, dichloroethane, chloroform and carbon tetrachloride; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (6b).

The temperature for carrying out this reaction is not particularly limited as long as the intended reaction proceeds, and is usually 20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane and chloroform; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (7), may be dehydrated with a drying agent, such as sodium sulfate and magnesium sulfate, but this is not essential.

With respect to the reaction mixture obtained above, which contains the compound represented by Formula (7), the solvent may be evaporated under reduced pressure as long as the compound is not decomposed.

The reaction mixture obtained after the evaporation of the solvent, which contains the compound represented by Formula (7), may be purified by washing, reprecipitation, recrystallization, column chromatography and the like using an appropriate solvent. The purification method may be appropriately selected depending on the desired purity.

[Production Method H]

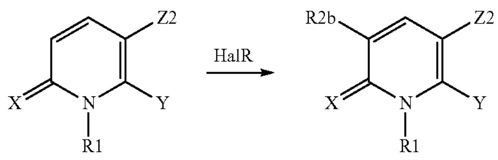

(7a) (7b)

wherein R2b represents a halogen atom, Z2 represents a C1-C6 alkyl group or R3R4N— (R3 and R4 are the same as defined above), HalR represents a halogenating agent, and R1, X and Y are the same as defined above.

Production Method H is a method for obtaining a compound represented by Formula (7b) wherein R2b represents a halogen atom, which comprises reacting a compound represented by Formula (7a) with a halogenating agent (HalR) in a solvent.

Examples of the halogenating agent used in this reaction include Selectfluor® (N-fluoro-N'-chloromethyl-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like.

The amount of the halogenating agent used in this reaction is not particularly limited as long as the amount is 1 equivalent or more relative to the compound represented by Formula (7a) and the intended reaction proceeds. The amount is usually 1 equivalent or more and 10 equivalents or less. However, with respect to the halogenating agent comprising a hydantoin compound, the amount of the halogenating agent is not particularly limited as long as the amount is 0.5 equivalent or more and the intended reaction proceeds. The amount is usually 1 equivalent or more and 5 equivalents or less.

When the halogenating agent used in this reaction is an iodinating agent, an acid, for example, an inorganic acid, such as hydrochloric acid and sulfuric acid; or an organic acid, such as acetic acid, trifluoroacetic acid, methanesulfonic acid and trifluoromethanesulfonic acid, can be added.

The amount of the acid used in the case wherein the halogenating agent used in this reaction is an iodinating agent is not particularly limited as long as the amount is 0.01 equivalent or more relative to the compound represented by Formula (7a) and the intended reaction proceeds. The amount is usually 0.1 equivalent or more and 3 equivalents or less.

The solvent used in this reaction is not particularly limited as long as the intended reaction proceeds, and examples of the solvent include acidic solvents, such as sulfuric acid, acetic acid, trifluoroacetic acid, methanesulfonic acid and trifluoromethanesulfonic acid; ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (7a).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (7b), may be dehydrated with a drying agent, such as sodium sulfate and magnesium sulfate, but this is not essential.

With respect to the reaction mixture obtained above, which contains the compound represented by Formula (7b), the solvent may be evaporated under reduced pressure as long as the compound is not decomposed.

The reaction mixture obtained after the evaporation of the solvent, which contains the compound represented by Formula (7b), may be purified by washing, reprecipitation, recrystallization, column chromatography and the like using an appropriate solvent. The purification method may be appropriately selected depending on the desired purity.

[Production Method I]

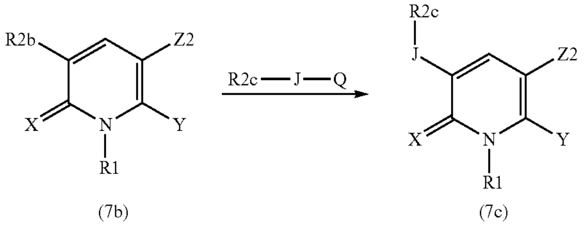

wherein J represents an oxygen atom or a sulfur atom, when J is an oxygen atom, R2c represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C3-C6 alkynyl group optionally substituted with substituent A or a C3-C6 haloalkynyl group, and when J is a sulfur atom, R2c represents a C1-C6 alkyl group or a C1-C6 haloalkyl group, Q represents a hydrogen atom or a metal, and R1, R2b, X, Y and Z2 are the same as defined above.

Production Method I is a method for obtaining a compound represented by Formula (7c) wherein J represents an oxygen atom or a sulfur atom, when J is an oxygen atom, R2c represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C3-C6 alkynyl group optionally substituted with substituent A or a C3-C6 haloalkynyl group, and when J is a sulfur atom, R2c represents a C1-C6 alkyl group or a C1-C6 haloalkyl group, which comprises obtaining it by a coupling reaction in which a compound represented by Formula (7b) is reacted with R2c-J-Q in the presence of a transition metal.

In the compounds represented by Formula (7b), preferred R2b is a chlorine atom, a bromine atom or an iodine atom.

The R2c-J-Q used in this reaction is commercially available or can be produced by a conventionally known method. Preferred Q is a hydrogen atom or alkali metals such as sodium and potassium.

The amount of R2c-J-Q used in this reaction is not particularly limited as long as the amount is 1 equivalent or more relative to the compound represented by Formula (7b) and the intended reaction proceeds. The R2c-J-Q can be used also as a solvent when Q is a hydrogen atom.

Examples of the transition metal used in this reaction, which may have a ligand, include, for example, a palladium compound, such as palladium acetate, [1,1'-bis(diphenylphosphino)ferrocene]palladium dichloride, tris(dibenzylideneacetone)-dipalladium, tetrakis(triphenylphosphine) palladium and bis(triphenylphosphine)-palladium dichloride.

The amount of the transition metal used in this reaction is usually 0.001 equivalent or more and 1 equivalent or less relative to the compound represented by Formula (7b) and not particularly limited as long as the intended reaction proceeds.

In order to efficiently proceed with this reaction, it is possible to add a phosphine ligand, such as triphenylphosphine, 1,1'-bis(diphenylphosphino)ferrocene, 2-dicyclohexylphosphino-2'4'6'-triisopropylbiphenyl and 2-di-t-butylphosphino-2'4'6'-triisopropylbiphenyl.

The amount of the phosphine ligand used in this reaction is usually 0.001 equivalent or more and 1 equivalent or less relative to the compound represented by Formula (7b) and not particularly limited as long as the intended reaction proceeds.

Examples of the base used in this reaction include an inorganic base, such as sodium carbonate, potassium carbonate and cesium carbonate; and an organic base, such as triethylamine, tributylamine and diisopropylethylamine.

The amount of the base used in this reaction is not particularly limited as long as the amount is 1 equivalent or more relative to the compound represented by Formula (7b) and the intended reaction proceeds. The amount is usually 1 equivalent or more and 50 equivalents or less.

The solvent used in this reaction is not particularly limited as long as the intended reaction proceeds, and examples of the solvent include alcohol solvents represented by the formula: R2c-J-H (wherein R2c is the same as defined above, and J is an oxygen atom); ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (7b).

The temperature for carrying out this reaction is not particularly limited as long as the intended reaction proceeds, and is usually 30° C. or higher and 200° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield. It is also possible to remove insoluble materials by carrying out filtration operation, but this is not essential.

The reaction mixture obtained above, which contains the compound represented by Formula (7c), may be dehydrated with a drying agent, such as sodium sulfate and magnesium sulfate, but this is not essential.

With respect to the reaction mixture obtained above, which contains the compound represented by Formula (7c), the solvent may be evaporated under reduced pressure as long as the compound is not decomposed.

The reaction mixture obtained after the evaporation of the solvent, which contains the compound represented by Formula (7c), may be purified by washing, reprecipitation, recrystallization, column chromatography and the like using an appropriate solvent. The purification method may be appropriately selected depending on the desired purity.

[Production Method J]

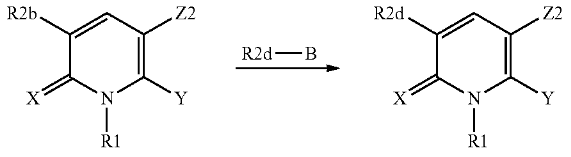

(7b) (7d)

wherein R2d represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A or a C2-C6 haloalkenyl group, R2d-B represents an organic boronic acid derivative, and R1, R2b, X, Y and Z2 are the same as defined above.

Production Method J is a method for obtaining a compound represented by Formula (7d) wherein R2d is a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A or a C2-C6 haloalkenyl group, which comprises obtaining it by Suzuki-Miyaura coupling in which a compound represented by Formula (7b) is reacted with an organic boronic acid derivative (R2d-B) in a solvent in the presence of a transition metal and a base.

Preferred R2b in Formula (7b) is a chlorine atom, a bromine atom or an iodine atom.

The R2d-B used in this reaction represents an organic boronic acid derivative, such as an organic boronic acid and an organic boronic acid ester, and is commercially available or can be produced by a conventionally known method.

The amount of R2d-B used in this reaction is not particularly limited as long as the amount is 1 equivalent or more relative to the compound represented by Formula (7b) and the intended reaction proceeds. The amount is usually 1 equivalent or more and 10 equivalents or less.

Examples of the transition metal used in this reaction, which may have a ligand, include palladium, nickel and ruthenium. As preferred examples, there can be mentioned palladium compounds, such as palladium acetate, [1,1'-bis(diphenyl-phosphino)ferrocene]palladium dichloride, tris(dibenzylideneacetone)dipalladium, tetrakis(triphenylphosphine)palladium, bis(triphenylphosphine)palladium dichloride and the like.

The amount of the transition metal used in this reaction is usually 0.001 equivalent or more and 1 equivalent or less relative to the compound represented by Formula (7b), and not particularly limited as long as the intended reaction proceeds.

In order to efficiently proceed with this reaction, it is possible to add a phosphine ligand, such as triphenylphosphine and tricyclohexylphosphine.

The amount of the phosphine ligand used in this reaction is usually 0.001 equivalent or more and 1 equivalent or less relative to the compound represented by Formula (7b), and not particularly limited as long as the intended reaction proceeds.

Examples of the base used in this reaction include an inorganic base, such as sodium carbonate, potassium carbonate, cesium carbonate and tripotassium phosphate; and a metal alkoxide, such as sodium methoxide, sodium ethoxide, sodium t-butoxide and potassium t-butoxide; and the like.

The amount of the base used in this reaction is not particularly limited as long as the amount is 1 equivalent or more relative to the compound represented by Formula (7b) and the intended reaction proceeds. The amount is usually 1 equivalent or more and 50 equivalents or less.

The solvent used in this reaction is not particularly limited as long as the intended reaction proceeds, and examples of the solvent include water solvent; ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (7b).

The temperature for carrying out this reaction is not particularly limited as long as the intended reaction proceeds, and is usually 30° C. or higher and 200° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield. It is also possible to remove insoluble materials by carrying out filtration operation, but this is not essential.

The reaction mixture obtained above, which contains the compound represented by Formula (7d), may be dehydrated with a drying agent, such as sodium sulfate and magnesium sulfate, but this is not essential.

With respect to the reaction mixture obtained above, which contains the compound represented by Formula (7d), the solvent may be evaporated under reduced pressure as long as the compound is not decomposed.

The reaction mixture obtained after the evaporation of the solvent, which contains the compound represented by Formula (7d), may be purified by washing, reprecipitation, recrystallization, column chromatography and the like using an appropriate solvent. The purification method may be appropriately selected depending on the desired purity.

[Production Method K]

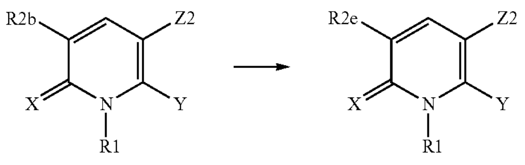

(7b) (7e)

wherein R2e represents a C2-C6 alkynyl group optionally substituted with substituent A or a C2-C6 haloalkynyl group, R1, R2b, X, Y and Z2 are the same as defined above.

Production Method K is a method for obtaining a compound represented by Formula (7e) wherein R2e is a C2-C6 alkynyl group optionally substituted with substituent A or a C2-C6 haloalkynyl group, which comprises obtaining it by Sonogashira coupling in which a compound represented by (7b) is reacted with a terminal-alkyne compound in a solvent in the presence of a transition metal and a base.

In Formula (7b), preferable R2b is a chlorine atom, a bromine atom or an iodine atom.

The terminal-alkyne compound used in this reaction is commercially available or can be produced by a conventionally known method. As the terminal-alkyne compound, trimethylsilylacetylene may be also used. In this case, after introducing trimethylsilylethynyl group into the compound represented by Formula (7b), it is necessary to conduct desilylation. The desilylation may be carried out with reference to non-patent documents, such as Journal of the American Chemical Society, vol. 131, No. 2, pp. 634-643 (2009) and Journal of Organometallic Chemistry, vol. 696, No. 25, pp. 4039-4045 (2011).

The amount of the terminal-alkyne compound used in this reaction is not particularly limited as long as the amount is 1 equivalent or more relative to the compound represented by Formula (7b) and the intended reaction proceeds. The amount is usually 1 equivalent or more and 10 equivalents or less.

Examples of the transition metal used in this reaction, which may have a ligand, include a palladium compound, such as palladium acetate, [1,1'-bis(diphenylphosphino)ferrocene]palladium dichloride, tris(dibenzylideneacetone)-dipalladium, tetrakis(triphenylphosphine)palladium, bis(triphenylphosphine)palladium dichloride and the like. In addition, a copper compound, such as copper chloride, copper bromide and copper iodide, is simultaneously used.

The amount of each of the transition metals used in this reaction is not particularly limited as long as, with respect to each of the palladium compounds and copper compounds, the amount is usually 0.001 equivalent or more relative to the compound represented by Formula (7b) and the intended reaction proceeds. The amount of each of these compounds is preferably 0.001 equivalent or more and 1 equivalent or less.

Examples of the base used in this reaction include organic amines, such as triethylamine, tributylamine, isopropylamine, diethylamine, diisopropylamine and diisopropylethylamine; inorganic bases, such as sodium carbonate, potassium carbonate and cesium carbonate; and the like.

The amount of the base used in this reaction is not particularly limited as long as the amount is 1 equivalent or more relative to the compound represented by Formula (7b) and the intended reaction proceeds. The amount is usually 1 equivalent or more and 50 equivalents or less. An organic base in a liquid state can be used as a solvent.

In order to efficiently proceed with this reaction, it is possible to add a phosphine ligand, such as tri-t-butylphosphine and 2-dicyclohexylphosphino-2'4'6'-triisopropylbiphenyl, but this is not essential.

The amount of the phosphine ligand used in this reaction is usually 0.001 equivalent or more and 1 equivalent or less relative to the compound represented by Formula (7b) and not particularly limited as long as the intended reaction proceeds.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; organic amine solvents, such as triethylamine, tributylamine, isopropylamine, diethylamine, diisopropylamine and diisopropylethylamine; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (7b).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield. It is also possible to remove insoluble materials by carrying out filtration operation, but this is not essential.

The reaction mixture obtained above, which contains the compound represented by Formula (7e), may be dehydrated with a drying agent, such as sodium sulfate and magnesium sulfate, but this is not essential.

With respect to the reaction mixture obtained above, which contains the compound represented by Formula (7e), the solvent may be evaporated under reduced pressure as long as the compound is not decomposed.

The reaction mixture obtained after the evaporation of the solvent, which contains the compound represented by Formula (7e), may be purified by washing, reprecipitation, recrystallization, column chromatography and the like using an appropriate solvent. The purification method may be appropriately selected depending on the desired purity.

[Production Method L]

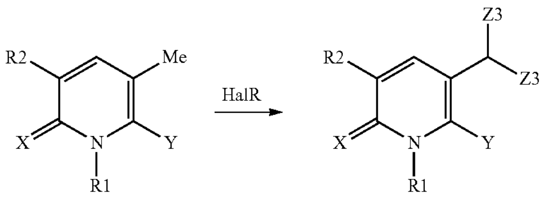

(7-1) (7f)

wherein Z3 represents a halogen atom, and HalR, R1, R2, X and Y are the same as defined above.

Production Method L is a method for obtaining a compound represented by Formula (7f) wherein Z3 is a halogen atom, which comprises subjecting a compound represented by Formula (7-1) to a reaction using a radical initiator and a halogenating agent (HalR).

In Formula (7f), preferable Z3 is a chlorine atom, a bromine atom or an iodine atom.

Examples of the radical initiator used in this reaction include azobisisobutyronitrile, benzoyl peroxide and the like.

The amount of the radical initiator used in this reaction is not particularly limited as long as the intended reaction proceeds. The amount is usually 0.01 equivalent or more and 1.0 equivalent or less relative to the compound represented by Formula (7-1).

Examples of the halogenating agent used in this reaction include N— chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin and the like.

The amount of the halogenating agent used in this reaction is not particularly limited as long as the amount is 2 equivalents or more relative to the compound represented by Formula (7-1) and the intended reaction proceeds. The amount is usually 2 equivalents or more and 2.8 equivalents or less.

The solvent used in this reaction is not particularly limited as long as the intended reaction proceeds, and examples of the solvent include halogenated benzene-based solvents, such as chlorobenzene and dichlorobenzene; ester solvents, such as ethyl acetate, isopropyl acetate and butyl acetate; halogen-based solvents, such as dichloromethane, dichloroethane, chloroform and carbon tetrachloride; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (7-1).

The temperature for carrying out this reaction is not particularly limited as long as the intended reaction proceeds, and is usually 20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane and chloroform; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (7f), may be dehydrated with a drying agent, such as sodium sulfate and magnesium sulfate, but this is not essential.

With respect to the reaction mixture obtained above, which contains the compound represented by Formula (7f), the solvent may be evaporated under reduced pressure as long as the compound is not decomposed.

The reaction mixture obtained after the evaporation of the solvent, which contains the compound represented by Formula (7f), may be purified by washing, reprecipitation, recrystallization, column chromatography and the like using an appropriate solvent. The purification method may be appropriately selected depending on the desired purity.

[Production Method M]

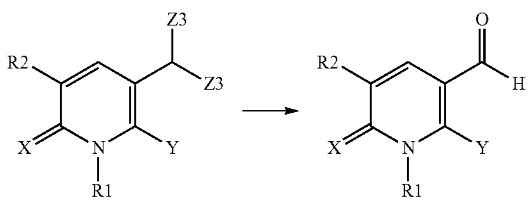

(7f) (7g)

wherein R1, R2, X, Y and Z3 are the same as defined above.

Production Method M is a method for obtaining a compound represented by Formula (7g), a production intermediate for the present invention, which comprises hydrolyzing a compound represented by Formula (7f) in the presence of water.

In Formula (7f), preferable Z3 is a chlorine atom, a bromine atom or an iodine atom.

Water is essential for this reaction. Further, silver nitrate may be used for smoothly proceeding with this reaction.

The amount of water used in this reaction is not particularly limited as long as the amount is 1 equivalent or more relative to the compound represented by Formula (7f) and the intended reaction proceeds. Water can be used as a solvent.

The amount of silver nitrate used in this reaction is not particularly limited as long as the amount is 2 equivalents or more relative to the compound represented by Formula (7f) and the intended reaction proceeds. The amount is usually 2 equivalents or more and 10 equivalents or less.

The solvent used in this reaction is not particularly limited as long as the intended reaction proceeds, and examples of the solvent include water solvent; ether solvents, such as diethyl ether, diisopropyl ether, methyl-t-butyl ether, dimethoxyethane, tetrahydrofuran and dioxane; nitrile-based solvent such as acetonitrile and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (7f).

The temperature for carrying out this reaction is not particularly limited as long as the intended reaction proceeds, and is usually −10° C. or higher and 100° C. or lower, or the boiling point of the solvent or lower.

As a post treatment after the reaction, it is possible to remove an undissolved metal by filtration. Further, it is also possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (7g), may be dehydrated with a drying agent, such as sodium sulfate and magnesium sulfate, but this is not essential.

With respect to the reaction mixture obtained above, which contains the compound represented by Formula (7g), the solvent may be evaporated under reduced pressure as long as the compound is not decomposed.

The reaction mixture obtained after the evaporation of the solvent, which contains the compound represented by Formula (7g), may be purified by washing, reprecipitation, recrystallization, column chromatography and the like using an appropriate solvent. The purification method may be appropriately selected depending on the desired purity.

[Production Method N]

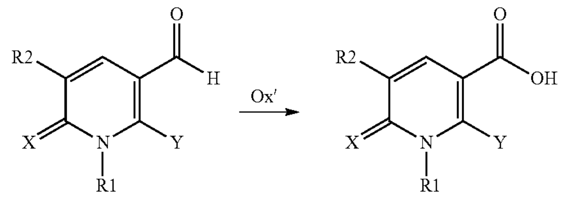

(7g) (2)

wherein Ox' represents an oxidizing agent, and R1, R2, X and Y are the same as defined above.

Production Method N is a method for obtaining a compound represented by Formula (2), a production intermediate for the present invention, which comprises reacting a compound represented by Formula (7g) with an oxidizing agent (Ox') in a solvent.

Examples of the oxidizing agent used in this reaction include sodium chlorite and the like.

The amount of the oxidizing agent used in this reaction is not particularly limited as long as the amount is 1 equivalent or more relative to the compound represented by Formula (7g) and the intended reaction proceeds. The amount is usually 1 equivalent or more and 20 equivalents or less.

In this reaction, phosphoric acid derivatives and/or olefin compounds can be added to suppress side reactions.

Examples of the phosphoric acid derivatives used in this reaction include sodium dihydrogen phosphate, potassium dihydrogen phosphate and the like.

The amount of the phosphoric acid derivatives used in this reaction is not particularly limited as long as the intended reaction proceeds and, for example, with respect to sodium dihydrogen phosphate, the amount is preferably 1 equivalent to 1.5 equivalents relative to the compound represented by Formula (7g).

Examples of the olefin compound used in this reaction include 2-methyl-2-butene and the like.

The amount of the olefin compound used in this reaction is not particularly limited as long as the amount is 1 equivalent or more relative to the compound represented by Formula (7g) and the intended reaction proceeds. The amount is usually 1 equivalent or more and 50 equivalents or less.

The solvent used in this reaction is not particularly limited as long as the intended reaction proceeds, and examples of the solvent include water solvent; ether solvents, such as diethyl ether, diisopropyl ether, methyl-t-butyl ether, dimethoxyethane, tetrahydrofuran and dioxane; alcohol solvents, such as tertiary butanol; and the like. These solvents may be used individually or in combination in any ratio.

The amount of the solvent used in this reaction is not particularly limited as long as the intended reaction proceeds. The amount is usually 3 times by weight or more and 300 times by weight or less relative to the compound represented by Formula (7g).

The temperature for carrying out this reaction is not particularly limited as long as the intended reaction proceeds, and is usually −20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (2), may be dehydrated with a drying agent, such as sodium sulfate and magnesium sulfate, but this is not essential.

With respect to the reaction mixture obtained above, which contains the compound represented by Formula (2), the solvent may be evaporated under reduced pressure as long as the compound is not decomposed.

The reaction mixture obtained after the evaporation of the solvent, which contains the compound represented by Formula (2), may be purified by washing, reprecipitation, recrystallization, column chromatography and the like using an appropriate solvent. The purification method may be appropriately selected depending on the desired purity.

The compound represented by Formula (2) can be a useful production intermediate for obtaining a compound represented by Formula (1), i.e., the compound of the present invention. The compound represented by Formula (1) can be obtained by subjecting the compound represented by Formula (2) to Crutius rearrangement.

Specific examples of the production intermediates represented by Formula (2) are shown as combinations of the structural formulae given in Table 4 (I-1 to I-60; wherein X in the formulae represents an oxygen atom or a sulfur atom) and Ys (Y-1 to Y-456) given in Table 2. These compounds are shown only for illustrative purpose and the present invention is not limited to these compounds.

TABLE 4

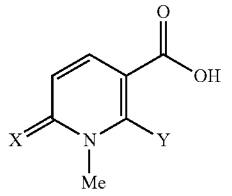

I-1

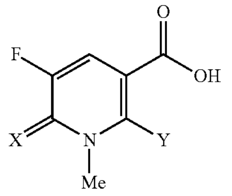

I-2

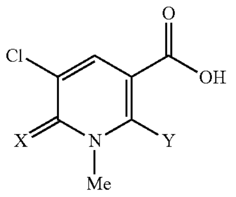

I-3

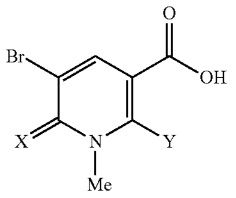

I-4

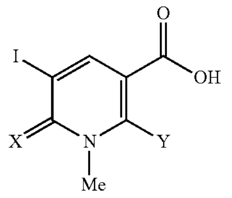

I-5

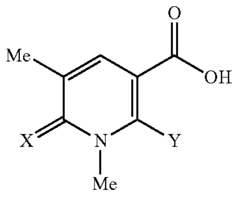

I-6

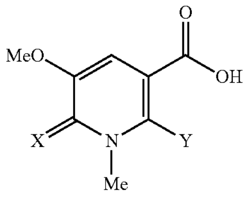

I-7

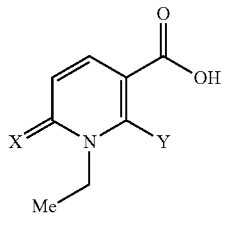

I-8

TABLE 4-continued
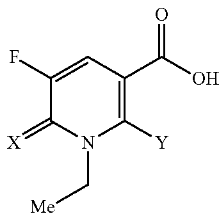
I-9
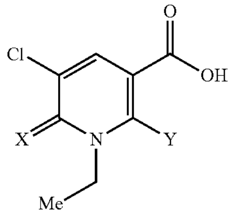
I-10
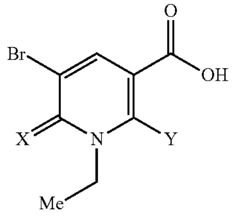
I-11
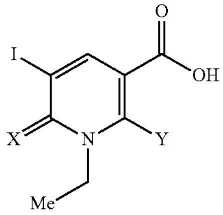
I-12
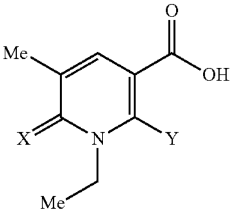
I-13
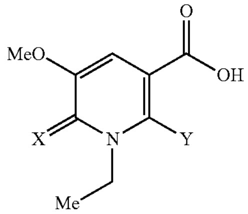
I-14
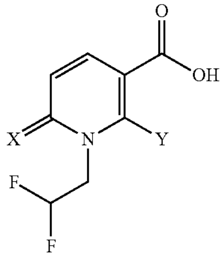
I-15
TABLE 4-continued
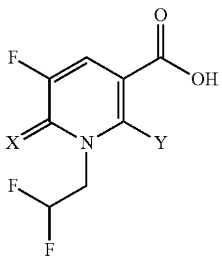
I-16
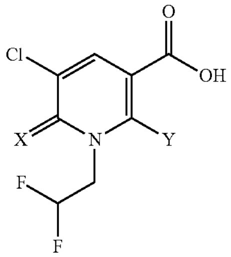
I-17
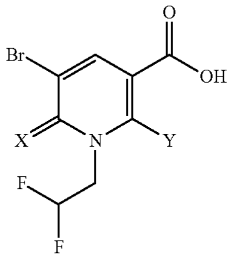
I-18
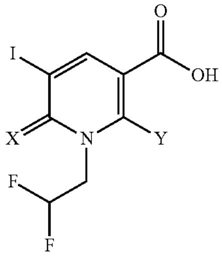
I-19
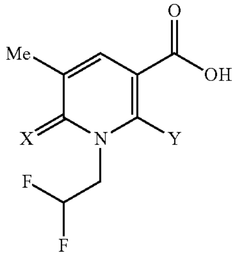
I-20
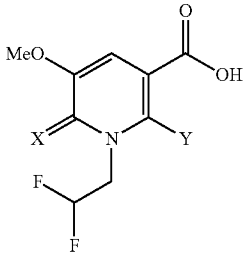
I-21

TABLE 4-continued
I-22
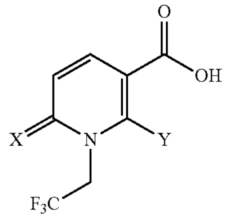
I-23
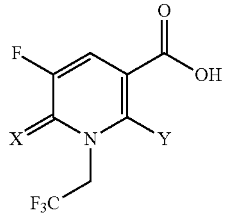
I-24
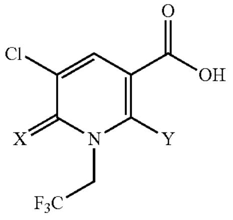
I-25
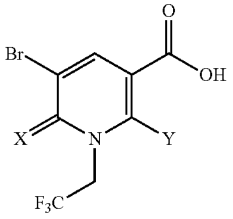
I-26
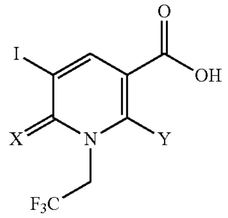
I-27
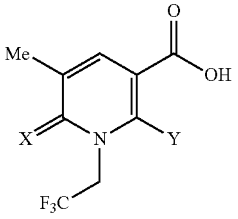
I-28
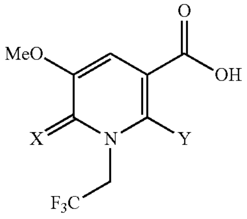
TABLE 4-continued
I-29
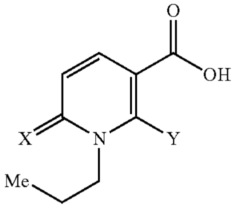
I-30
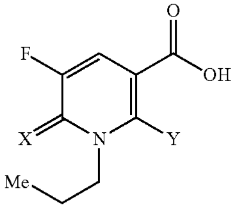
I-31
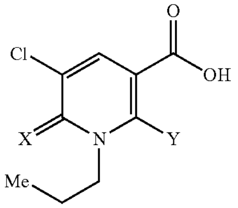
I-32
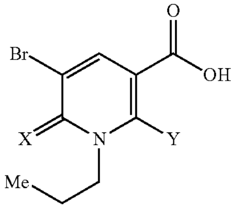
I-33
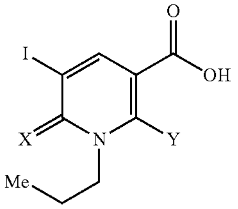
I-34
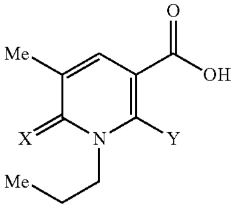
I-35
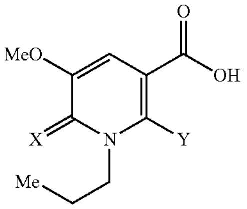
I-36
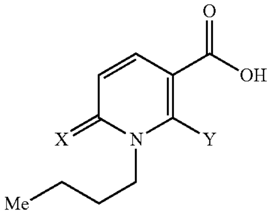

TABLE 4-continued
I-37
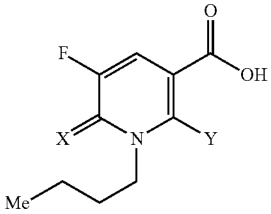
I-38
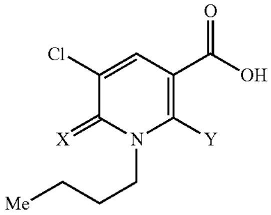
I-39
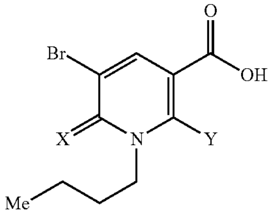
I-40
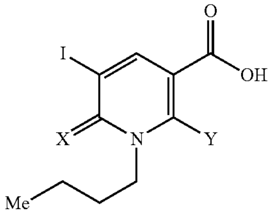
I-41
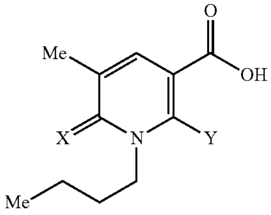
I-42
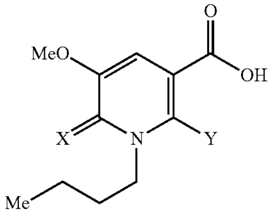
I-43
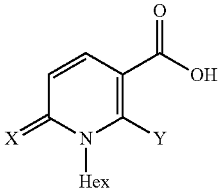
I-44
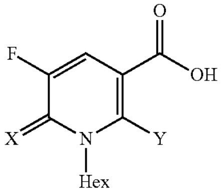
TABLE 4-continued
I-45
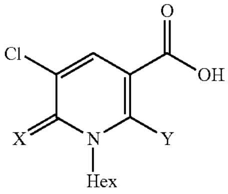
I-46
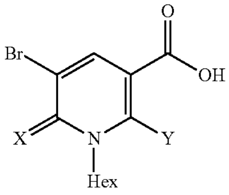
I-47
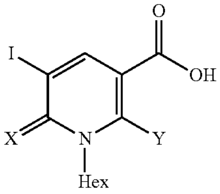
I-48
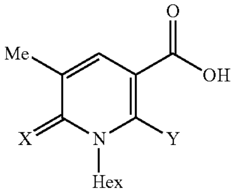
I-49
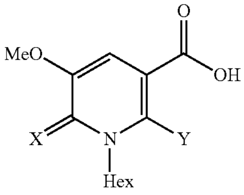
I-50
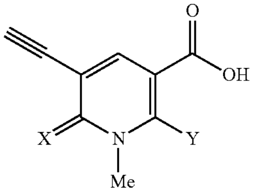
I-51
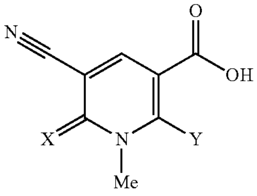
I-52
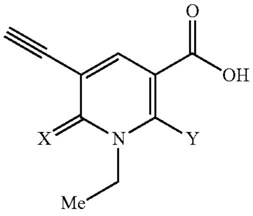

TABLE 4-continued

I-53

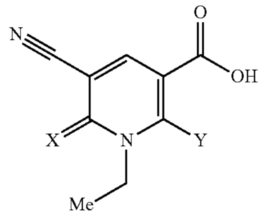

I-54

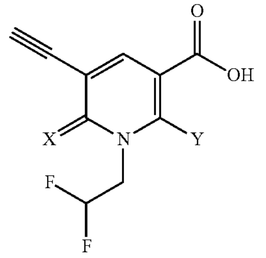

I-55

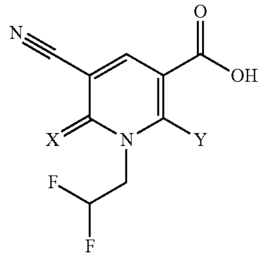

I-56

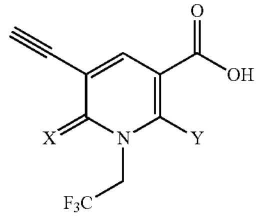

I-57

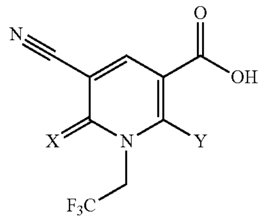

I-58

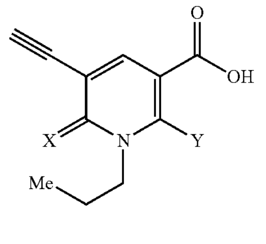

I-59

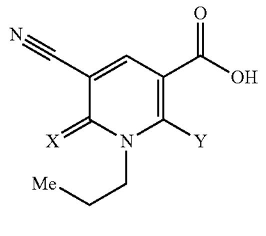

TABLE 4-continued

I-60

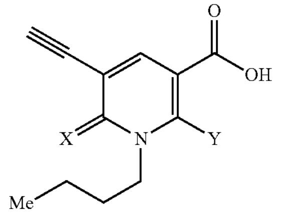

Various reaction conditions for Crutius rearrangement have been known, and appropriate conditions may be set so that the compound represented by Formula (I) of the present invention are obtained. Hereinbelow described in Production Method O is an example in which tertiary butanol is used.

[Production Method O]

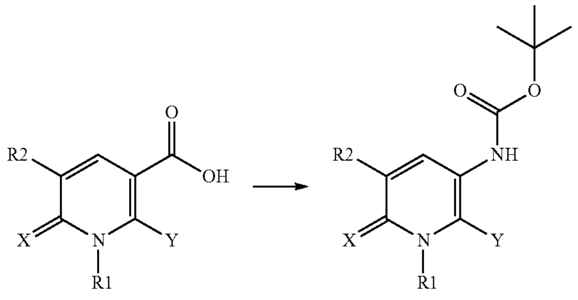

(2) (1b)

wherein R1, R2, X and Y are the same as defined above.

Production Method O is a method for obtaining a compound represented by Formula (1b) among the compound represented by Formula (1), which comprises reacting a compound represented by Formula (2) with an azide compound in the presence of tertiary butanol.

Examples of the azide compound used in this reaction include diphenylphosphoryl azide and the like.

The amount of the azide compound used in this reaction is not particularly limited as long as the amount is 1 equivalent or more relative to the compound represented by Formula (2) and the intended reaction proceeds. The amount is usually 1 equivalent or more and 10 equivalents or less.

The amount of tertiary butanol used in this reaction is not particularly limited as long as the amount is 1 equivalent or more relative to the compound represented by Formula (2) and the intended reaction proceeds. It is also possible to use tertiary butanol itself as a solvent.

Examples of the solvent used in this reaction include alcohol solvents, such as tertiary butanol; ether solvents, such as diisopropyl ether, methyl-t-butyl ether, dimethoxyethane, tetrahydrofuran and dioxane; benzene-based solvents, such as toluene, xylene, benzene, chlorobenzene and dichlorobenzene; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (2).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane and chloroform; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1b), may be dehydrated with a drying agent, such as sodium sulfate and magnesium sulfate, but this is not essential.

With respect to the reaction mixture obtained above, which contains the compound represented by Formula (1b), the solvent may be evaporated under reduced pressure as long as the compound is not decomposed.

The reaction mixture obtained after the evaporation of the solvent, which contains the compound represented by Formula (1b), may be purified by washing, reprecipitation, recrystallization, column chromatography and the like using an appropriate solvent. The purification method may be appropriately selected depending on the desired purity.

[Production Method P]

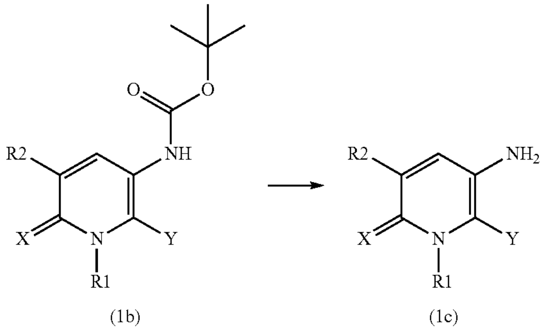

wherein R1, R2, X and Y are the same as defined above.

Production Method P is a method for obtaining a compound represented by Formula (1c) among the compound represented by Formula (1), which comprises reacting a compound represented by Formula (1b) with an acid.

Examples of the acid used in this reaction include inorganic acids, such as hydrochloric acid and hydrobromic acid; and organic acids, such as methanesulfonic acid, p-toluenesulfonic acid and trifluoroacetic acid. The acid is not particularly limited as long as the intended reaction proceeds.

The amount of the acid used in this reaction is not particularly limited as long as the amount is a catalytic amount or more relative to the compound represented by Formula (1b) and the intended reaction proceeds. The amount is usually 1 equivalent or more, and it is also possible to use the acid as a solvent.

The solvent used in this reaction is not particularly limited as long as the intended reaction proceeds, and examples of the solvent include acid solvents, such as hydrochloric acid and trifluoroacetic acid; ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1b).

The temperature for carrying out this reaction is not particularly limited as long as the intended reaction proceeds, and is usually −20° C. or higher and 180° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1c), may be dehydrated with a drying agent, such as sodium sulfate and magnesium sulfate, but this is not essential.

With respect to the reaction mixture obtained above, which contains the compound represented by Formula (1c), the solvent may be evaporated under reduced pressure as long as the compound is not decomposed.

The reaction mixture obtained after the evaporation of the solvent, which contains the compound represented by Formula (1c), may be purified by washing, reprecipitation, recrystallization, column chromatography and the like using an appropriate solvent. The purification method may be appropriately selected depending on the desired purity.

[Production Method Q]

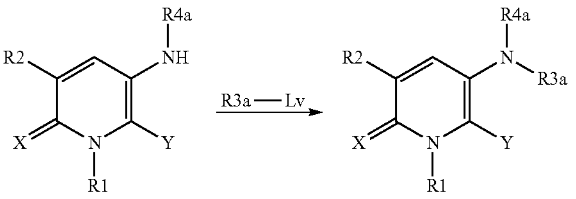

(1d)

(1e)

wherein R3a represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), a C1-C6 haloalkyl group having a phenyl group optionally substituted with 0 to 5 substituent D (with the proviso that when there are two or more substituents D, they are independent to each other), an Rc-L- (wherein Rc and L are the same as defined above) or an ReC(═O)— (wherein Re is the same as defined above), R4a represents a hydrogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other), a C1-C6 haloalkyl group having a phenyl group optionally substituted with 0 to 5 substituent D (with the proviso that when there are two or more substituents D, they are independent to each other), an Rc-L- (wherein Rc and L are the same as defined above) or an ReC(═O)— (wherein Re is the same as defined above), and R1, R2, Lv, X and Y are the same as defined above.

Production Method Q is a method for obtaining a compound represented by Formula (1e) among the compound represented by Formula (1), which comprises reacting a compound represented by Formula (1d) with R3a-Lv in a solvent in the presence of a base.

The R3a-Lv used in this reaction is commercially available or can be produced by a conventionally known method.

The amount of the R3a-Lv used in this reaction is not particularly limited as long as the amount is 1 equivalent or more relative to the compound represented by Formula (1d) and the intended reaction proceeds. The amount is usually 1 equivalent or more and 50 equivalents or less.

Examples of the base used in this reaction include inorganic bases, such as sodium carbonate, potassium carbonate, cesium carbonate and sodium hydride; and organic bases, such as triethylamine, tributylamine, diisopropylethylamine, pyridine, 4-dimethylaminopyridine, collidine and lutidine. The base is not particularly limited as long as the intended reaction proceeds.

The amount of the base used in this reaction is not particularly limited as long as the amount is 1 equivalent or more relative to the compound represented by Formula (1d) and the intended reaction proceeds. The amount is usually 1 equivalent or more and 50 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1d).

The temperature for carrying out this reaction is not particularly limited as long as the intended reaction proceeds, and is usually −20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1e), may be dehydrated with a drying agent, such as sodium sulfate and magnesium sulfate, but this is not essential.

With respect to the reaction mixture obtained above, which contains the compound represented by Formula (1e), the solvent may be evaporated under reduced pressure as long as the compound is not decomposed.

The reaction mixture obtained after the evaporation of the solvent, which contains the compound represented by Formula (1e), may be purified by washing, reprecipitation, recrystallization, column chromatography and the like using an appropriate solvent. The purification method may be appropriately selected depending on the desired purity.

[Production Method R]

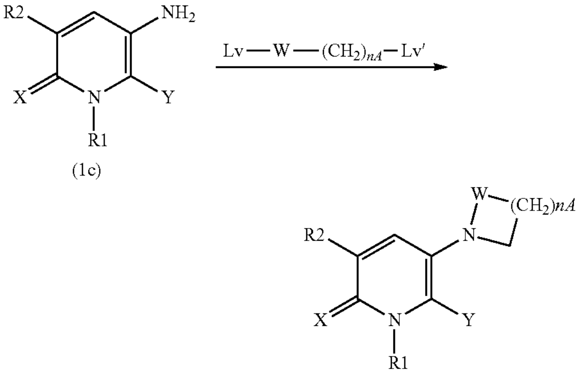

(1c)

(1f)

wherein Lv and Lv' are independent to each other and each represents a leaving group, such as a methanesulfonyl group, a trifluoromethanesulfonyl group, a p-toluenesulfonyl group and a halogen atom, W represents —CH2- or —C(=O)—, nA represents an integer of 0 to 5, and R1, R2, X and Y are the same as defined above.

Production Method R is a method for obtaining a compound represented by Formula (1f) among the compound represented by Formula (1), which comprises reacting a compound represented by Formula (1c) with Lv-W—(CH2)nA-Lv' in a solvent in the presence of a base.

The Lv-W—(CH2)nA-Lv' used in this reaction is commercially available or can be produced by a conventionally known method.

The amount of the Lv-W—(CH2)nA-Lv' used in this reaction is not particularly limited as long as the amount is 1 equivalent or more relative to the compound represented by Formula (1c) and the intended reaction proceeds. The amount is usually 1 equivalent or more and 5 equivalents or less.

Examples of the base used in this reaction include inorganic bases, such as sodium carbonate, potassium carbonate, cesium carbonate and sodium hydride; and organic bases, such as triethylamine, tributylamine, diisopropylethylamine, pyridine, 4-dimethylaminopyridine, collidine and lutidine. The base is not particularly limited as long as the intended reaction proceeds.

The amount of the base used in this reaction is not particularly limited as long as the amount is 2 equivalents or more relative to the compound represented by Formula (1c) and the intended reaction proceeds. The amount is usually 2 equivalent or more and 50 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1c).

The temperature for carrying out this reaction is not particularly limited as long as the intended reaction proceeds, and is usually −20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (if), may be dehydrated with a drying agent, such as sodium sulfate and magnesium sulfate, but this is not essential.

With respect to the reaction mixture obtained above, which contains the compound represented by Formula (if), the solvent may be evaporated under reduced pressure as long as the compound is not decomposed.

The reaction mixture obtained after the evaporation of the solvent, which contains the compound represented by Formula (if), may be purified by washing, reprecipitation, recrystallization, column chromatography and the like using an appropriate solvent. The purification method may be appropriately selected depending on the desired purity.

[Production Method S]

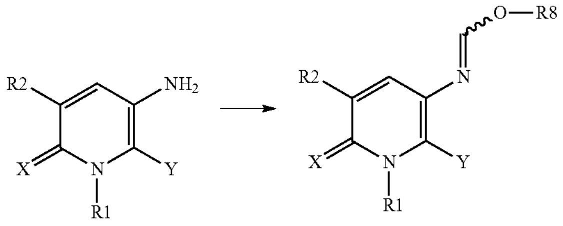

(1c) (1g)

wherein R8 represents a C1-C6 alkyl group, and R1, R2, X and Y are the same as defined above.

Production Method S is a method for obtaining a compound represented by Formula (1g) among the compound represented by Formula (1), which comprises reacting a compound represented by Formula (1c) with an orthoformate in the presence of an acid.

The wavy line in the compound represented by Formula (1g) represents a moiety which may be in the E-configuration or Z-configuration. The ratio of these configurations is not particularly limited, and this compound may be present as a single isomer with one of these configurations or a mixture of isomers of any ratio.

Examples of the orthoformate used in this reaction include trimethyl orthoformate, triethyl orthoformate, tripropyl orthoformate and triisopropyl orthoformate, and they are commercially available or can be produced by a conventionally known method.

The amount of the orthoformate used in this reaction is not particularly limited as long as the amount is 1 equivalent or more relative to the compound represented by Formula (1c) and the intended reaction proceeds. The orthoformate can be used as a solvent.

Examples of the acid used in this reaction include inorganic acids, such as hydrochloric acid, hydrobromic acid and phosphoric acid; and organic acids, such as acetic acid, methanesulfonic acid, p-toluenesulfonic acid and trifluoroacetic acid. The acid is not particularly limited as long as the intended reaction proceeds.

The amount of the acid used in this reaction is not particularly limited as long as the intended reaction proceeds and may be a catalytic amount. The amount is usually 0.01 equivalent or more and 10 equivalents or less relative to the compound of the Formula (1c).

The solvent used in this reaction is not particularly limited as long as the intended reaction proceeds, and examples of the solvent include orthoformates represented by $HC(OR8)_3$ (R8 is the same as defined above); ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound of the Formula (1c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1g), may be dehydrated with a drying agent, such as sodium sulfate and magnesium sulfate, but this is not essential.

With respect to the reaction mixture obtained above, which contains the compound represented by Formula (1g), the solvent may be evaporated under reduced pressure as long as the compound is not decomposed.

The reaction mixture obtained after the evaporation of the solvent, which contains the compound represented by Formula (1g), may be purified by washing, reprecipitation, recrystallization, column chromatography and the like using an appropriate solvent. The purification method may be appropriately selected depending on the desired purity.

[Production Method T]

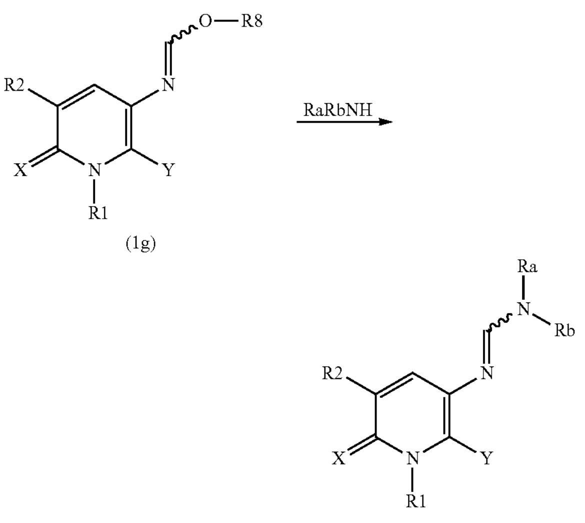

(1g)

(1h)

wherein R1, R2, Ra, Rb, X and Y are the same as defined above.

Production Method T is a method for obtaining a compound represented by Formula (1h) among the compounds represented by Formula (1), which comprises reacting a compound represented by Formula (1g) with RaRbNH.

The RaRbNH used in this reaction is commercially available or can be produced by a conventionally known method.

The amount of the RaRbNH used in this reaction is not particularly limited as long as the amount is 1 equivalent or more relative to the compound represented by Formula (1g) and the intended reaction proceeds. The amount is usually 1 equivalent or more and 100 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichloro-benzene; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride, and sulfur based solvents, such as dimethylsulfoxide and sulfolane; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1g).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1h), may be dehydrated with a drying agent, such as sodium sulfate and magnesium sulfate, but this is not essential.

With respect to the reaction mixture obtained above, which contains the compound represented by Formula (1h), the solvent may be evaporated under reduced pressure as long as the compound is not decomposed.

The reaction mixture obtained after the evaporation of the solvent, which contains the compound represented by Formula (1h), may be purified by washing, reprecipitation, recrystallization, column chromatography and the like using an appropriate solvent. The purification method may be appropriately selected depending on the desired purity.

[Production Method U]

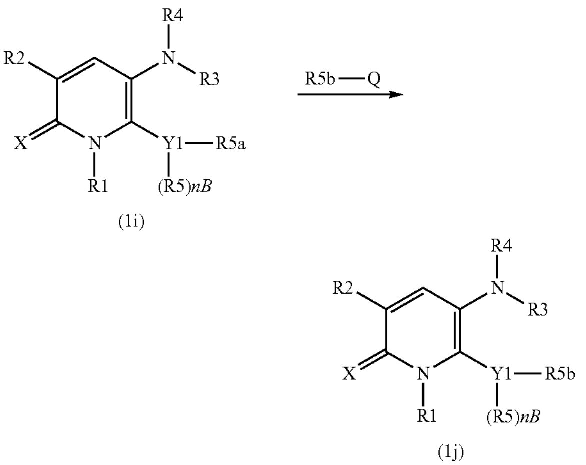

(1i)

(1j)

wherein R5a represents a halogen atom, R5b represents a C1-C6 alkoxy group optionally substituted with substituent G, a C1-C6 haloalkoxy group, a C3-C8 cycloalkoxy group optionally substituted with substituent G, a C2-C6 alkenyloxy group optionally substituted with substituent G, a C2-C6 haloalkenyloxy group, a C3-C6 alkynyloxy group optionally substituted with substituent G or a C3-C6 haloalkynyloxy group, Y1 represents a phenyl group having R5a which is optionally nB substituted with R5 or a pyridyl group having R5a which is optionally nB substituted with R5, when Y1 is a phenyl group, nB represents an integer of 0 to 4 (with the proviso that when there are two or more R5, they are independent to each other) and when Y1 is a pyridyl group, nB represents an integer of 0 to 3 (with the proviso that when there are two or more R5, they are independent to each other), and R1, R2, R3, R4, Q and X are the same as defined above.

Production Method U is a method for obtaining a compound represented by Formula (1j) wherein R5b represents a C1-C6 alkoxy group optionally substituted with substituent G, a C1-C6 haloalkoxy group, a C3-C8 cycloalkoxy group optionally substituted with substituent G, a C2-C6 alkenyloxy group optionally substituted with substituent G, a C2-C6 haloalkenyloxy group, a C3-C6 alkynyloxy group optionally substituted with substituent G or a C3-C6 haloalkynyloxy group, Y1 represents a phenyl group having R5a which is optionally nB substituted with R5 or a pyridyl group having R5a which is optionally nB substituted with R5, when Y1 is a phenyl group, nB represents an integer of 0 to 4 (with the proviso that when there are two or more R5, they are independent to each other), and when Y1 is a pyridyl group, nB represents an integer of 0 to 3 (with the proviso that when there are two or more R5, they are independent to each other) among the compounds represented by Formula (1), which comprises reacting a compound represented by Formula (1i) with R5b-Q in a solvent.

The R5b-Q used in this reaction is commercially available or can be produced by a conventionally known method. Preferable Q is a hydrogen atom or alkali metals such as sodium and potassium.

The amount of the R5b-Q used in this reaction is not particularly limited as long as the amount is 1 equivalent or more relative to the compound represented by Formula (1i) and the intended reaction proceeds. The amount is usually 1 equivalent or more and 30 equivalents or less. When Q represents a hydrogen atom, this compound can be used as a solvent.

The base used in this reaction is preferably an inorganic base, such as sodium carbonate, potassium carbonate, cesium carbonate and sodium hydride. When Q is an alkali metal, use of the base is not essential.

The amount of the base used in this reaction is not particularly limited as long as the amount is 1 equivalent or more relative to the compound represented by Formula (1i) and the intended reaction proceeds. The amount is usually 1 equivalent or more and 30 equivalents or less.

The solvent used in this reaction is not particularly limited as long as the intended reaction proceeds, and examples of the solvent include alcohol solvents represented by R5b-H; ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1i).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1j), may be dehydrated with a drying agent, such as sodium sulfate and magnesium sulfate, but this is not essential.

With respect to the reaction mixture obtained above, which contains the compound represented by Formula (1j), the solvent may be evaporated under reduced pressure as long as the compound is not decomposed.

The reaction mixture obtained after the evaporation of the solvent, which contains the compound represented by Formula (1j), may be purified by washing, reprecipitation, recrystallization, column chromatography and the like using an appropriate solvent. The purification method may be appropriately selected depending on the desired purity.

[Production Method V]

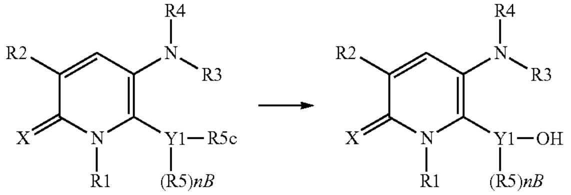

(1k) (1l)

wherein R5c represents a C1-C6 alkoxy group, and R1, R2, R3, R4, R5, nB, X and Y1 are the same as defined above.

Production Method V is a method for obtaining a compound represented by Formula (1l) having a hydroxyl group among the compound represented by Formula (1), which comprises reacting a compound represented by Formula (1k) with an acid.

Examples of the acid used in this reaction include halogenated boron compounds, such as boron trichloride and boron tribromide, and the like.

The amount of the acid used in this reaction is not particularly limited as long as the amount is 1 equivalent or more relative to the compound represented by Formula (1k) and the intended reaction proceeds. The amount is usually 1 equivalent or more and 10 equivalents or less.

The solvent used in this reaction is not particularly limited as long as the intended reaction proceeds, and examples of the solvent include benzene-based solvents, such as benzene, toluene, xylene, mesitylene, chlorobenzene and dichlorobenzene; nitrile-based solvent such as acetonitrile; halogen-based solvents, such as dichloromethane, dichloroethane, chloroform and carbon tetrachloride; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1k).

The temperature for carrying out this reaction is not particularly limited as long as the intended reaction proceeds, and is usually −80° C. or higher and 100° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1l), may be dehydrated with a drying agent, such as sodium sulfate and magnesium sulfate, but this is not essential.

With respect to the reaction mixture obtained above, which contains the compound represented by Formula (1l), the solvent may be evaporated under reduced pressure as long as the compound is not decomposed.

The reaction mixture obtained after the evaporation of the solvent, which contains the compound represented by Formula (1l), may be purified by washing, reprecipitation, recrystallization, column chromatography and the like using an appropriate solvent. The purification method may be appropriately selected depending on the desired purity.

[Production Method W]

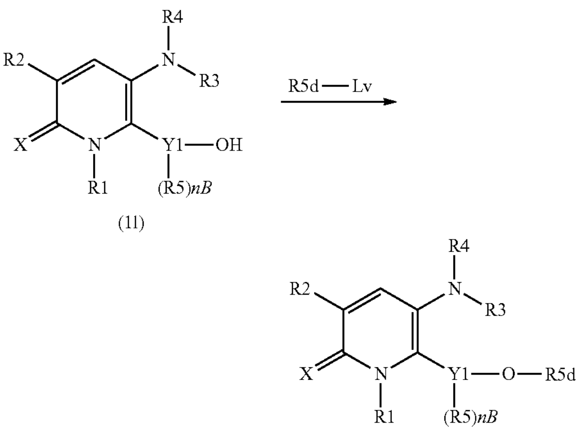

(1l)

(1m)

wherein R5d represents a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G, a C2-C6 haloalkenyl group, a C3-C6 alkynyl group optionally substituted with substituent G, a C3-C6 haloalkynyl group or an RdC(═O)— (wherein Rd is the same as defined above), and R1, R2, R3, R4, R5, nB, Lv, X and Y1 are the same as defined above.

Production Method W is a method for obtaining a compound represented by Formula (1m) wherein R5d is a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G, a C2-C6 haloalkenyl group, a C2-C6 alkynyl group optionally substituted with substituent G, a C3-C6 haloalkynyl group or an RdC(═O)— (wherein Rd is the same as defined above) among the compounds represented by Formula (1), which comprises reacting a compound represented by Formula (1l) with R5d-Lv in a solvent in the presence of a base.

The R5d-Lv used in this reaction is commercially available or can be produced by a conventionally known method.

The amount of the R5d-Lv used in this reaction is not particularly limited as long as the amount is 1 equivalent or more relative to the compound represented by Formula (1l) and the intended reaction proceeds. The amount is usually 1 equivalent or more and 10 equivalents or less.

Examples of the base used in this reaction include inorganic bases, such as sodium carbonate, potassium carbonate, cesium carbonate and sodium hydride; and organic bases, such as triethylamine, tributylamine, diisopropylethylamine, pyridine, 4-dimethylaminopyridine, collidine and lutidine. The base is not particularly limited as long as the intended reaction proceeds.

The amount of the base used in this reaction is not particularly limited as long as the amount is 1 equivalent or more relative to the compound represented by Formula (1l) and the intended reaction proceeds. The amount is usually 1 equivalent or more and 10 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1l).

The temperature for carrying out this reaction is not particularly limited as long as the intended reaction proceeds, and is usually −20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1m), may be dehydrated with a drying agent, such as sodium sulfate and magnesium sulfate, but this is not essential.

With respect to the reaction mixture obtained above, which contains the compound represented by Formula (1m), the solvent may be evaporated under reduced pressure as long as the compound is not decomposed.

The reaction mixture obtained after the evaporation of the solvent, which contains the compound represented by Formula (1m), may be purified by washing, reprecipitation, recrystallization, column chromatography and the like using an appropriate solvent. The purification method may be appropriately selected depending on the desired purity.

[Production Method X]

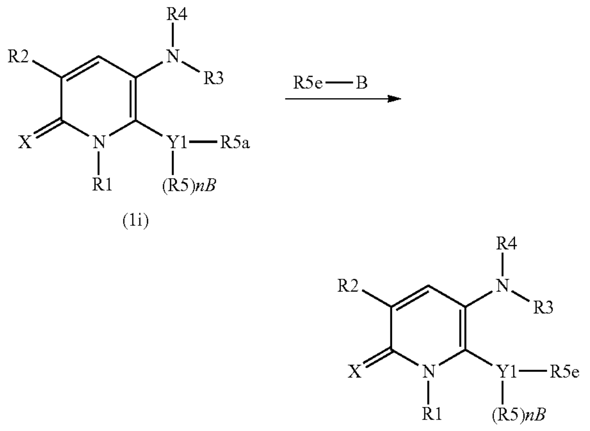

(1i)

(1n)

wherein R5e represents a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G or a C2-C6 haloalkenyl group, R5e-B represents an organic boronic acid derivative, and R1, R2, R3, R4, R5, R5a, nB, X and Y1 are the same as defined above.

Production Method X is a method for obtaining a compound represented by Formula (1n) wherein R5e is a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G or a C2-C6 haloalkenyl group among the compound represented by Formula (1), which comprises obtaining it by Suzuki-Miyaura coupling in which a compound represented by Formula (1i) is reacted with an organic boronic acid (R5e-B) in the presence of a transition metal and a base.

In Formula (1n), preferable R5a is a chlorine atom, a bromine atom or an iodine atom.

The R5e-B used in this reaction represents an organic boronic acid derivative, such as an organic boronic acid and an organic boronic acid ester, and this compound is commercially available or can be produced by a conventionally known method.

Production Method X can be carried out in substantially the same manner as in Production Method J, except that a compound represented by Formula (1i) and R5e-B are used in place of the compound represented by Formula (7b) and R2d-B in Production Method J, respectively.

[Production Method Y]

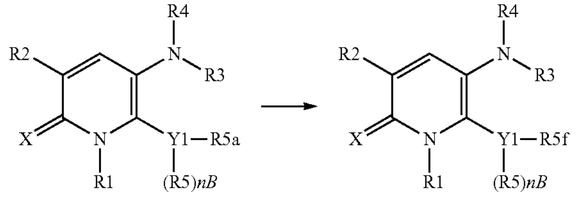

(1i) (1o)

wherein R5f represents a C2-C6 alkynyl group optionally substituted with substituent G or a C2-C6 haloalkynyl group, and R1, R2, R3, R4, R5, R5a, nB, X and Y1 are the same as defined above.

Production Method Y is a method for obtaining a compound represented by Formula (1o) wherein R5f is a C2-C6 alkynyl group optionally substituted with substituent G or a C2-C6 haloalkynyl group among the compound represented by Formula (1), which comprises obtaining it by Sonogashira coupling in which a compound represented by Formula (1i) is reacted with a terminal-alkyne compound in the presence of a transition metal and a base.

In Formula (1i), preferable R5a is a chlorine atom, a bromine atom or an iodine atom.

The terminal-alkyne compound used in this reaction is commercially available or can be produced by a conventionally known method. As the terminal-alkyne compound, trimethylsilylacetylene may also be used.

Production Method Y can be carried out in substantially the same manner as in Production Method K, except that a compound represented by Formula (1i) is used in place of the compound represented by Formula (7b) in Production Method K.

[Production Method Z]

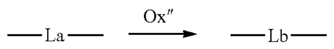

(La) (Lb)

wherein La represents S, Lb represents SO or $SO_2$, and Ox" represents an oxidizing agent.

Production Method Z is a method for obtaining a compound represented by Formula (Lb) among the compounds represented by Formula (1) wherein each Lb contained in R1, R2, R3, R4 and R5 is SO or $SO_2$, which comprises reacting a compound represented by Formula (La) among the compounds represented by Formula (1) wherein each La contained in R1, R2, R3, R4 and R5 is S with an oxidizing agent (Ox") in a solvent.

Examples of the oxidizing agent used in this reaction include peroxides, such as hydrogen peroxide solution and meta-chloroperoxybenzoic acid. It is also possible to add a transition metal, such as sodium tungstate.

The amount of the oxidizing agent used in this reaction is usually 1.0 equivalent or more and 1.2 equivalents or less relative to the compound represented by Formula (La) when SO is produced, and usually 2 equivalents or more and 10 equivalents or less when $SO_2$ is produced. When a transition metal is added, the amount is usually 0.001 equivalent or more and 1 equivalent or less.

The solvent used in this reaction is not particularly limited as long as the intended reaction proceeds, and examples of the solvent include water solvent; acidic solvents, such as acetic acid; benzene-based solvents, such as benzene, toluene, xylene, mesitylene, chlorobenzene and dichlorobenzene; nitrile-based solvent such as acetonitrile; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (La).

The temperature for carrying out this reaction is not particularly limited as long as the intended reaction proceeds, and is usually −10° C. or higher and 120° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (Lb), may be dehydrated with a drying agent, such as sodium sulfate and magnesium sulfate, but this is not essential.

With respect to the reaction mixture obtained above, which contains the compound represented by Formula (Lb), the solvent may be evaporated under reduced pressure as long as the compound is not decomposed.

The reaction mixture obtained after the evaporation of the solvent, which contains the compound represented by Formula (Lb), may be purified by washing, reprecipitation, recrystallization, column chromatography and the like using an appropriate solvent. The purification method may be appropriately selected depending on the desired purity.

[Production Method AA]

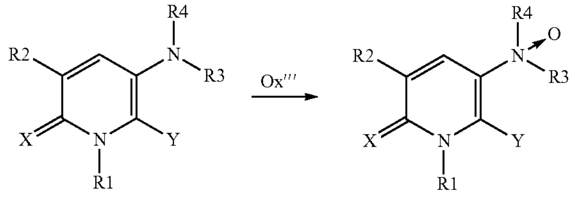

(1) (1a)

wherein Ox'" represents an oxidizing agent, and R1, R2, R3, R4, X and Y are the same as defined above.

Production Method AA is a method for obtaining a compound represented by Formula (1a) among the compound represented by Formula (1) which is in an N— oxide form, which comprises reacting a compound represented by Formula (1) with an oxidizing agent (Ox'") in a solvent.

Examples of the oxidizing agent used in this reaction include peroxides, such as hydrogen peroxide solution and meta-chloroperoxybenzoic acid. It is also possible to add a transition metal, such as sodium tungstate.

The amount of the oxidizing agent used in this reaction is not particularly limited as long as the amount is 1 equivalent or more relative to the compound represented by Formula (1) and the intended reaction proceeds. The amount is usually 1 equivalent or more and 10 equivalents or less.

The solvent used in this reaction is not particularly limited as long as the intended reaction proceeds, and examples of the solvent include water solvent; acidic solvents, such as acetic acid; benzene-based solvents, such as benzene, toluene, xylene, mesitylene, chlorobenzene and dichlorobenzene; nitrile-based solvent such as acetonitrile; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1).

The temperature for carrying out this reaction is not particularly limited as long as the intended reaction proceeds, and is usually −10° C. or higher and 120° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1a), may be dehydrated with a drying agent, such as sodium sulfate and magnesium sulfate, but this is not essential.

With respect to the reaction mixture obtained above, which contains the compound represented by Formula (1a), the solvent may be evaporated under reduced pressure as long as the compound is not decomposed.

The reaction mixture obtained after the evaporation of the solvent, which contains the compound represented by Formula (1a), may be purified by washing, reprecipitation, recrystallization, column chromatography and the like using an appropriate solvent. The purification method may be appropriately selected depending on the desired purity.

Various reaction conditions for reductive amination have been known, and appropriate conditions may be set so that the compound represented by Formula (1) of the present invention are obtained. Hereinbelow described in Production Method AB is an example in which sodium triacetoxyborohydride is used.

[Production Method AB]

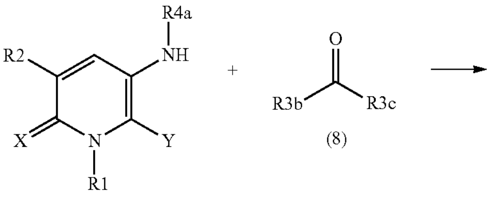

(1d)

(8)

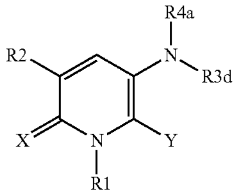

(1p)

wherein R3b and R3c are independent to each other and each represent a hydrogen atom, a C1-C5 alkyl group optionally substituted with substituent C, a C1-C5 haloalkyl group, a C3-C8 cycloalkyl group optionally substituted with substituent C, a C2-C5 alkenyl group optionally substituted with substituent C, a C2-C5 haloalkenyl group, a C2-C5 alkynyl group optionally substituted with substituent C, a C2-C5 haloalkynyl group, a phenyl group optionally substituted with 0 to 5 substituent D (with the proviso that when there are two or more substituents D, they are independent to each other), a C1-C5 alkyl group having a phenyl group optionally substituted with 0 to 5 substituent D (with the proviso that when there are two or more substituents D, they are independent to each other) or a C1-C5 haloalkyl group having a phenyl group optionally substituted with 0 to 5 substituent D (with the proviso that when there are two or more substituents D, they are independent to each other), or R3b and R3c in combination with the carbon atom to which they are bonded represent a C3-C8 cycloalkyl group optionally substituted with substituent C, R3d represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a phenyl group optionally substituted with 0 to 5 substituent D (with the proviso that when there are two or more substituents D, they are independent to each other), a C1-C6 alkyl group having a phenyl group optionally substituted with 0 to 5 substituent D (with the proviso that when there are two or more substituents D, they are independent to each other) or a C1-C6 haloalkyl group having a phenyl group optionally substituted with 0 to 5 substituent D (with the proviso that when there are two or more substituents D, they are independent to each other), and R1, R2, R4a, X and Y are the same as defined above.

Production Method AB is a method for obtaining a compound represented by Formula (1p) among the compound represented by Formula (1), which comprises reacting a compound represented by Formula (1d) with a compound represented by Formula (8) in a solvent in the presence of sodium triacetoxyborohydride.

The compound represented by Formula (8) used in this reaction is commercially available or can be produced by a conventionally known method.

The amount of the compound represented by Formula (8) used in this reaction relative to the compound represented by Formula (1d) is not particularly limited as long as the intended reaction proceeds, and is usually 1 equivalent or more and 30 equivalents or less.

The amount of sodium triacetoxyborohydride used in this reaction is not particularly limited as long as the amount is 1 equivalent or more relative to the compound represented by Formula (1d) and the intended reaction proceeds. The amount is usually 1 equivalent or more and 30 equivalents or less.

In order to smoothly proceed with this reaction, it is possible to add acetic acid. The amount of acetic acid to be added is not particularly limited as long as the intended reaction proceeds. The amount is usually 1 equivalent or more and 10 equivalents or less.

The solvent used in this reaction is not particularly limited as long as the intended reaction proceeds, and examples of the solvent include water solvent; ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; halogen-based solvents, such as dichloromethane, dichloroethane, chloroform and carbon tetrachloride; nitrile-based solvent such as acetonitrile; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1d).

The temperature for carrying out this reaction is not particularly limited as long as the intended reaction proceeds, and is usually −20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1p), may be dehydrated with a drying agent, such as sodium sulfate and magnesium sulfate, but this is not essential.

With respect to the reaction mixture obtained above, which contains the compound represented by Formula (1p), the solvent may be evaporated under reduced pressure as long as the compound is not decomposed.

The reaction mixture obtained after the evaporation of the solvent, which contains the compound represented by Formula (1p), may be purified by washing, reprecipitation, recrystallization, column chromatography and the like using an appropriate solvent. The purification method may be appropriately selected depending on the desired purity.

[Production Method AC]

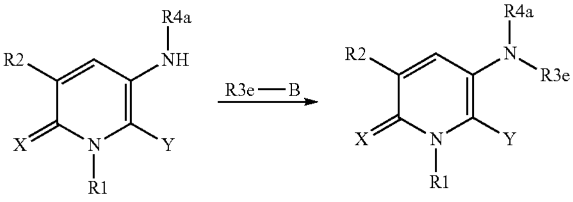

(1d) (1q)

wherein R3e represents a phenyl group optionally substituted with 0 to 5 substituent D (with the proviso that when there are two or more substituents D, they are independent to each other), R3e-B represents an organic boronic acid derivative, and R1, R2, R4a, X and Y are the same as defined above.

Production Method AC is a method for obtaining a compound represented by Formula (1q) wherein R3e is a phenyl group optionally substituted with 0 to 5 substituent D (with the proviso that when there are two or more substituents D, they are independent to each other), which comprises subjecting a compound represented by Formula (1d) and an organic boronic acid derivative represented by R3e-B (wherein R3e are the same as defined above) to Chan-Lam-Evans coupling reaction in a solvent, in the presence of a copper reagent and a base, in air or under oxygen atmosphere.

The organic boronic acid derivative R3e-B used in this reaction is commercially available or can be produced by a conventionally known method.

The amount of the organic boronic acid derivative R3e-B used in this reaction is not particularly limited as long as the amount is 1 equivalent or more relative to the compound represented by Formula (1d) and the intended reaction proceeds. The amount is usually 1 equivalent or more and 30 equivalents or less.

Examples of the copper reagent used in this reaction include copper(II) acetate monohydrate, copper(II) acetylacetonate and the like, preferably copper(II) acetate monohydrate.

The amount of the copper reagent used in this reaction is not particularly limited as long as the amount is 1 equivalent or more relative to the compound represented by Formula (1d) and the intended reaction proceeds. The amount is usually 1 equivalent or more and 10 equivalents or less.

Examples of the base used in this reaction include triethylamine, tributylamine, diisopropylethylamine, pyridine, dimethylaminopyridine and the like, preferably triethylamine or pyridine.

The amount of the base used in this reaction is not particularly limited as long as the amount is 1 equivalent or more relative to the compound represented by Formula (1d) and the intended reaction proceeds. The amount is usually 1 equivalent or more and 10 equivalents or less.

The solvent used in this reaction is not particularly limited as long as the intended reaction proceeds, and examples of the solvent include alcohol solvents, such as methanol, ethanol and isopropanol; ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 1 time by weight or more and 200 times by weight or less relative to the compound represented by Formula (1d).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkali aqueous solution having dissolved therein potassium hydroxide, sodium hydroxide, sodium carbonate, potassium carbonate, sodium hydrogen carbonate, potassium hydrogen carbonate, ammonia or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1q), may be dehydrated with a drying agent, such as sodium sulfate and magnesium sulfate, but this is not essential.

With respect to the reaction mixture obtained above, which contains the compound represented by Formula (1q), the solvent may be evaporated under reduced pressure as long as the compound is not decomposed.

The reaction mixture obtained after the evaporation of the solvent, which contains the compound represented by Formula (1q), may be purified by washing, reprecipitation, recrystallization, column chromatography and the like using an appropriate solvent. The purification method may be appropriately selected depending on the desired purity.

[Production Method AD]

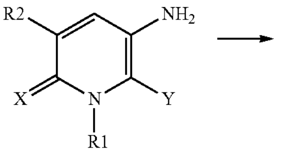

(1c)

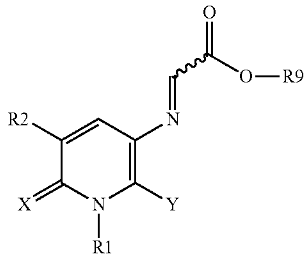

(1r)

wherein R9 represents a C1-C6 alkyl group optionally substituted with substituent B, a C1-C6 haloalkyl group or a C3-C8 cycloalkyl group, and R1, R2, X and Y are the same as defined above.

Production Method AD is a method for obtaining a compound represented by Formula (1r) among the compounds represented by Formula (1), which comprises reacting a compound represented by Formula (1c) with a glyoxylic acid ester in a solvent.

The wavy line in the compound represented by Formula (1r) represents a moiety which may be in the E-configuration or Z-configuration. The ratio of these configurations is not particularly limited, and this compound may be present as a single isomer with one of these configurations or a mixture of isomers of any ratio.

Examples of the glyoxylic acid ester used in this reaction include methyl glyoxlate, ethyl glyoxlate, isopropyl glyoxlate, butyl glyoxlate and the like, and this compound is commercially available or can be produced by a conventionally known method.

The amount of the glyoxylic acid ester used in this reaction is not particularly limited as long as the amount is 1 equivalent or more relative to the compound represented by Formula (1c) and the intended reaction proceeds. This compound can be used as a solvent.

The solvent used in this reaction is not particularly limited as long as the intended reaction proceeds, and examples of the solvent include the glyoxylic acid ester represented by OHC—C(=O)O—R9 (R9 is the same as defined above); ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile-based solvent such as acetonitrile; amide-based solvents, such as N-methylpyrrolidone, N,N-dimethylformamide and N,N-dimethylacetamide; urea-based solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone-based solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds. The amount is usually 3 times by weight or more and 200 times by weight or less relative to the compound represented by Formula (1c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as benzene-based solvents, such as toluene, xylene, benzene, chlorobenzene and dichlorobenzene; ester solvents, such as ethyl acetate, isopropyl acetate and butyl acetate; ether solvents, such as diethyl ether, diisopropyl ether and methyl-t-butyl ether; halogen-based solvents, such as dichloromethane, dichloroethane, chloroform and carbon tetrachloride; hydrocarbon solvents, such as hexane, heptane, cyclohexane and methylcyclohexane; and the like. In addition, these solvents may be used individually or in combination in any ratio. The number of times of the liquid separating operation is not particularly limited, and the operation can be carried out depending on the desired purity and yield.

The reaction mixture obtained above, which contains the compound represented by Formula (1r), may be dehydrated with a drying agent, such as sodium sulfate and magnesium sulfate, but this is not essential.

With respect to the reaction mixture obtained above, which contains the compound represented by Formula (1r), the solvent may be evaporated under reduced pressure as long as the compound is not decomposed.

The reaction mixture obtained after the evaporation of the solvent, which contains the compound represented by Formula (1r), may be purified by washing, reprecipitation, recrystallization, column chromatography and the like using an appropriate solvent. The purification method may be appropriately selected depending on the desired purity.

The compound represented by Formula (1) can be produced by arbitrarily combining Production Method A to Production Method AD shown above. Alternatively, the compound represented by Formula (1) can be also produced by arbitrarily combining a conventionally known method with Production Method A to Production Method AD.

The compound of the present invention represented by Formula (1) can control pests harmful to plants, and thus can be used as a pesticide. Specific examples of such a pesticide include fungicides, insecticides, herbicides, plant growth regulators and the like. A fungicide is preferred.

The compound of the present invention can be used as an agricultural and horticultural fungicide in farms, paddy fields, tea gardens, orchards, meadows, grasses, forests, gardens, roadside trees, etc. for plant disease control.

A plant disease referred to in the present invention means that a systemic, abnormal pathological symptom, such as wilting, damping-off, yellowing, dwarfism and spindly growth, or a partial pathological symptom, such as spotting, leaf blight, mosaic pattern, leaf rolling, die back, root rot, club root and knotting, is induced in a plant including crops, flowering plants, flowering trees, and shrubs and trees. That is, this term means that a plant becomes ill. Examples of major pathogens that cause plant diseases include fungi, bacteria, spiroplasmas, phytoplasmas, viruses, viroids, parasitic higher plants, nematodes and the like. The compound of the present invention is effective against fungi, but the effectiveness may not be limited to that against fungi.

Major diseases caused by fungi are fungal diseases. Examples of fungi (pathogens) that cause fungal diseases include *Plasmodiophora, Oomycetes, Zygomycetes, Ascomycetes, Basidiomycetes* and *Deuteromycetes*, etc. Examples of *Plasmodiophora* include club root fungus, potato powdery scab fungus and beet necrotic yellow vein virus; examples of *Oomycetes* include blight fungus, downy mildew fungus, *Pythium* species fungus and *Aphanomyces* species fungus; examples of *Zygomycetes* include *Rhizopus* species fungus; examples of Ascomycetes include peach leaf curl fungus, corn brown spot fungus, rice blast fungus, powdery mildew fungus, anthracnose fungus, fusarium head blight fungus, bakanae disease fungus and sclerotial disease fungus; examples of *Basidiomycetes* include rust disease fungus, smut fungus, violet root rot fungus, blister blight fungus and rice sheath blight fungus; and examples of *Deuteromycetes* include gray mold fungus, *Alternaria* species fungus, *Fusarium* species fungus, *Penicillium* species fungus, *Rhizoctonia* species fungus and southern blight fungus.

The compound of the present invention is effective against various plant diseases. With respect to the names of diseases and their pathogens, specific examples are given bellow.

Rice: blast (*Magnaporthe grisea*), sheath blight (*Thanatephorus cucumeris*), brown sclerotial disease (*Ceratobasidium setariae*), brown small sclerotial disease (*Waitea circinata*), brown sheath blight (*Thanatephorus cucumeris*), globular sclerotial disease (*Sclerotium hydrophilum*), red sclerotial disease (*Wairea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling blight (*Pythium* spp., *Fusarium* spp., *Trichoderma* spp., *Rhizopus* spp., *Rhizoctonia solani, Mucor* sp., *Phoma* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seedling blight (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat and barley: powdery mildew (*Blumeria graminis* f.sp. *hordei*; f.sp. *tritici*), rust (*Puccinia striiformis, Puccinia graminis, Puccinia recondita, Puccinia hordei*), barley stripe (*Pyrenophora graminea*), net blotch (*Pyrenophora teres*), *Fusarium* head blight (*Gibberella zeae, Fusarium culmorum, Fusarium avenaceum, Monographella nivalis*), *Typhula* snow blight (*Typhula incarnata, Typhula ishikariensis, Monographella nivalis*), loose smut (*Ustilago nuda*), stinking smut (*Tilletia caries, Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), seedling blight (*Gaeumannomyces graminis*), anthracnose (*Colletotrichum graminicola*), ergot (*Claviceps purpurea*), leaf spot (*Cochliobolus sativus*), bacterial black node (*Pseudomonas syringae* pv. *syringae*);

corn: ear rot (*Gibberella zeae*, etc.), damping-off (*Fusarium avenaceum, Penicillium* spp., *Pythium* spp., *Rhizoctonia* spp.), rust (*Puccinia sorghi*), brown spot (*Cochliobolus heterostrophus*), smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*);

grapes: downy mildew (*Plasmopara viticola*), rust (*Physopella ampelopsidis*), powdery mildew (*Uncinula necator*), scab (*Elsinoe ampelina*), ripe rot (*Glomerella cingulata, Colletotrichum acutatum*), black rot (*Guignardia bidwellii*), *Phomopsis* leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*); apples: powdery mildew (*Podosphaera leucotricha*), black spot disease (*Venturia inaequalis*), *Alternaria* leaf spot (*Alternaria mali*), rust (*Gymnosporangium yamadae*), blossom blight (*Monilinia mali*), apple canker (*Valsa ceratosperma*), ring spot (*Botryosphaeria berengeriana*), anthracnose (*Colletotrichum acutatum, Glomerella cingulata*), fly speck (*Zygophiala jamaicensis*), sooty spot (*Gloeodes pomigena*), fruit spot (*Mycosphaerella pomi*), violet root rot (*Helicobasidium mompa*), white root rot (*Rosellinia necatrix*), canker (*Phomopsis mali, Diaporthe tanakae*), apple blotch (*Diplocarpon mali*), apples: fire blight (*Erwinia amylovora*), crown gall (*Agrobacterium tumefaciens*), hairy root disease (*Agrobacterium rhizogenes*);

Japanese pears: black spot (*Alternaria kikuchiana*), pear scab (*Venturia nashicola*), rust (*Gymnosporangium asiaticum*), ring spot (*Botryosphaeria berengeriana* f.sp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudomonas syringae* pv. *syringae*); European pears: blight (*Phytophthora cactorum, Phytophthora syringae*), bacterial shoot blight (*Erwinia* sp.); peaches: black spot (*Cladosporium carpophilum*), *Phomopsis* rot (*Phomopsis* sp.), blight (*Phytophthora* sp.), anthracnose (*Colletotrichum gloeosporioides*), leaf curl (*Taphrina deformans*), bacterial shot hole (*Xanthomonas campestris* pv. *pruni*), crown gall (*Agrobacterium tumefaciens*); cherries: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis (*Pseudomonas syringae* pv. *syringae*); persimmons: anthracnose (*Glomerella cingulata*), leaf spot (*Cercospora kaki; Mycosphaerella nawae*), powdery mildew (*Phyllactinia kakikora*), crown gall (*Agrobacterium tumefaciens*); citrus fruits: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xanthomonas campestris* pv. *citri*), bacterial brown spot (*Pseudomonas syringae* pv. *syringae*), greening disease (*Liberibactor asiaticus*), crown gall (*Agrobacterium tumefaciens*);

tomatoes, cucumbers, beans, strawberries, potatoes, cabbage, eggplants, lettuce and the like: gray mold (*Botrytis cinerea*); tomatoes, cucumbers, beans, strawberries, potatoes, rapeseed, cabbage, eggplants, lettuce and the like: sclerotial disease (*Sclerotinia sclerotiorum*); various vegetables such as tomatoes, cucumbers, beans, Japanese radishes, watermelons, eggplants, rapeseed, green peppers, spinach, beets and the like: seedling damping-off (*Rhizoctonia* spp., *Pythium* spp., *Fusarium* spp., *Phythophthora* spp., *Sclerotinia sclerotiorum*, etc.); solanaceous plants: bacterial wilt (*Ralstonia solanacearum*); melons: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium oxysporum*), late blight (*Phytophthora parasitica, Phytophthora melonis, Phytophthora nicotianae, Phytophthora drechsleri, Phytophthora capsici*, etc.), bacterial brown spot (*Xanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus);

tomatoes: ring spot (*Alternaria solani*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporioides*), canker (*Clavibacter michiganensis*), pith necrosis (*Pseudomonas corrugata*), bacterial black spot (*Pseudomonas viridiflava*), soft rot (*Erwinia carotovora* subsp. *carotovora*), bacterial leaf gall (*Crynebacterium* sp.), yellowing wilt (*Phytoplasma asteris*), yellow dwarf (Tobacco leaf curl subgroup III geminivirus); eggplants: powdery mildew (*Sphaerotheca fuliginea*, etc.), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Erwinia chrysanthemi*), soft rot (*Erwinia carotovora* subsp. *carotovora*), bacterial spot (*Pseudomonas* sp.); rapeseed: black spot (*Alternaria brassicae*), black rot (*Xanthomonas campestris* pv. *campestris*), bacterial black spot (*Pseudomonas syringae* pv. *maculicola*), soft rot (*Erwinia carotovora*); cruciferous vegetables: black spot (*Alternaria brassicae*, etc.), white spot (*Cercosporella brassicae*), black leg (*Phoma lingam*), club root (*Plasmodiophora brassicae*), downy mildew (*Peronospora parasitica*), black rot (*Xanthomonas campestris* pv. *campestris*), bacterial black spot (*Pseudomonas syringae* pv. *maculicola*), soft rot (*Erwinia carotovora* subsp. *carotovora*);

cabbage: club foot (*Thanatephorus cucumeris*), yellowing wilt (*Fusarium oxysporum*), *alternaria* sooty spot (*Alternaria brassisicola*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe* glycines), black spot (*Diaporthe phaseolorum*), *Rhizoctonia* root rot (*Rhizoctonia solani*), stem rot (*Phytophthora sojae*), downy mildew (*Peronospora manshurica*), rust (*Phakopsora pachyrhizi*), anthracnose (*Colletotrichum truncatum*, etc.), leaf scald (*Xanthomonas campestris* pv. glycines), bacterial spot (*Pseudomonas syringae* pv. *glycinea*); green beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xanthomonas campestris* pv. *phaseoli*);

peanuts: leaf spot (*Mycosphaerella berkeleyi*), brown spot (*Mycosphaerella arachidis*), bacterial wilt (*Ralstonia solanacearum*); garden peas: powdery mildew (*Erysiphe pisi*), downy mildew (*Peronospora pisi*), bacterial stem blight (*Pseudomonas syringae* pv. *pisi*), bacterial stem rot (*Xanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*);

carrots: leaf blight (*Alternaria dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae*, etc.), anthracnose (*Glomerella cingulata*, etc.), fruit rot (*Pythium ultimum*), bacterial wilt (*Ralstonia solanacearum*), angular leaf spot (*Xanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), bacterial wilt (*Ralstonia solanacearum*), tobacco mosaic virus (Tobacco mosaic virus);

coffee: rust (*Hemileia vastatrix*); banana: black sigatoka (*Mycosphaerella fijiensis*), panama disease (*Fusarium oxysporum* f.sp *cubense*); cotton: damping-off (*Fusarium oxysporum*), frosty mildew (*Ramularia areola*); sunflowers: sclerotial disease (*Sclerotinia sclerotiorum*), angular leaf spot (*Xanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa*, etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), *chrysanthemum virescence* (*Phytoplasma aurantifolia*); grasses: brown patch disease (*Rhizoctonia solani*), dollar spot disease (*Sclerotinia homoeocarpa*), *curvularia* leaf blight (*Curvularia* sp.), rust (*Puccinia zoysiae*), *helminthosporium* leaf blight (*Cochliobolus* sp.), scald (*Rhynchosporium secalis*), *Zoysia* decline (*Gaeumannomyces graminis*), anthracnose (*Colletotrichum* sp.), *typhula* brown snow blight (*Typhula incarnata*), *typhula* black snow blight (*Typhula ishikariensis*), *Sclerotinia* (*Myriosclerotinia borealis*), fairy ring disease (*Marasmius oreades*, etc.), *Pythium* blight (*Pythium aphanidermatum*, etc.), blast (*Pyricularia grisea*) and the like.

The compound of the present invention may be used with the present compound alone, but preferably can be mixed with a solid carrier, liquid carrier, gas carrier, surfactant, adhesive agent, dispersant, stabilizer, or the like and used as a composition, such as a powder, a water-dispersible powder, water-dispersible granules, a water-soluble powder, water-soluble granules, granules, an emulsion, a liquid, a microemulsion, an aqueous suspension preparation, an aqueous emulsion preparation or a suspoemulsion preparation. The form of the composition is not limited to the above-mentioned ones as long as the effects are exhibited.

Specific examples of formulations, which are not limitative, are given below.

Preparation Example 1: Flowable

The compound of the present invention (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 part by mass), xanthan gum (0.2 part by mass) and ion exchanged water (78.7 parts by mass) are mixed to thereby obtain a slurry. The resultant slurry is wet-milled with Dyno-Mill KDL using glass beads having a diameter of 1.0 mm to thereby obtain a flowable.

Preparation Example 2: Emulsion

The compound of the present invention (5 parts by mass) is dissolved in a mixed solution of xylene (40 parts by mass) and cyclohexane (35 parts by mass). Tween 20 (20 parts by mass) is added to and mixed with the resultant solution to thereby obtain an emulsion.

Preparation Example 3: Water-Dispersible Powder

The compound of the present invention (10 parts by mass), white carbon (10 parts by mass), polyvinyl alcohol (2 parts by mass), dioctylsulfosuccinic acid sodium salt (0.5 part by mass), alkylbenzene sulfonic acid sodium salt (5 parts by mass), calcined diatomaceous earth (10 parts by mass) and kaolinite clay (62.5 parts by mass) are mixed thoroughly, and the resultant mixture is pulverized by an air mill to thereby obtain a water-dispersible powder.

Hereinbelow, explanation is made with respect to application of the composition of the present invention (an agricultural and horticultural pest control agent, an agricultural and horticultural fungicide).

As an example of a method for applying the composition comprising the compound of the present invention, there can be mentioned a method comprising bringing the composition into contact with a plant body or seeds, or a method comprising preparing cultivation soil containing the composition and bringing the cultivation soil into contact with the roots or underground stem of a plant. Specific examples of such method include a treatment of spraying the composition onto the stem and leaves of a plant individual, an injection treatment, a treatment of seedling nursery boxes, a cell tray treatment, a treatment of spraying the composition to plant seeds, a treatment of coating plant seeds with the composition, a treatment of immersing plant seeds into the composition, a treatment of dressing plant seeds with the composition, a treatment of spraying the composition onto the surface of soil, soil mixing after the treatment of spraying the composition onto the surface of the soil, a treatment of injecting the composition into soil, soil mixing after the treatment of injecting the composition into soil, a treatment of irrigating the composition into soil, soil mixing after the treatment of irrigating the composition into soil, and the like. The composition exhibits adequate effects when applied by any method usually used by a person skilled in the art.

The term "plant" referred to in the present invention means a creature which thrives by photosynthesis without moving. Specific examples of the plants include rice, wheat, barley, corn, coffee, bananas, grapes, apples, Japanese pears, peaches, cherries, persimmons, citrus fruits, soybeans, green beans, cotton, strawberries, potatoes, cabbage, lettuce, tomatoes, cucumbers, eggplants, watermelons, beets, spinach, poded peas, squash, sugar cane, tobacco, green peppers, sweet potatoes, taro potatoes, konjak, cotton, sunflowers, roses, tulips, chrysanthemums, turf grasses and the like, and F1 hybrids thereof and the like. Also included are gene recombinant crops created by artificially manipulating gene or the like, which does not occur in nature and, as examples, there can be mentioned agricultural and horticultural crops including soybeans, corn, cotton and the like to which resistance to herbicides had been imparted; rice, tobacco and the like acclimated to cold climates; corn, cotton and the like to which an ability to produce insecticidal substances had been imparted; and the like. Further, there can also be mentioned trees, such as pines, ash trees, ginkgos, maples, oaks, poplars and zelkova. The term "plant body" referred to in the present invention collectively means all the parts constituting an individual of the above-mentioned plant, and examples of such parts include stems, leaves, roots, seeds, flowers, fruits and the like.

The term "seed" referred to in the present invention means a matter which stores nutrients for germination of young plant and is used for agricultural breeding. Specific examples of seeds include seeds of corn, soybeans, cotton, rice, beets, wheat, barley, sunflowers, tomato, cucumbers, eggplants, spinach, poded peas, squash, sugar cane, tobacco, green peppers, rape and the like and F1 hybrids thereof and the like; seed potatoes of taro potatoes, potatoes, sweet potatoes, konjak and the like; bulbs of edible lilies, tulips and the like; seed bulbs of scallions and the like; and seeds, tubers and the like of gene recombinant crops.

The amount and concentration for the application of the composition comprising the compound of the present invention may vary depending on the target crop, target disease, degree of occurrence of the disease, dosage form of the compound, application method, various environmental conditions and the like and, in the case of spraying or irrigating, 0.1 to 10,000 g per hectare as the amount of the active ingredient is suitable, and 10 to 1,000 g per hectare is preferred. The amount used for the seed treatment is 0.0001 to 1,000 g, preferably 0.001 to 100 g, per 1 kg of seeds as an amount of effective ingredient. When the composition comprising the compound of the present invention is used for a treatment of spraying the composition onto the stem and leaves of a plant individual, a treatment of spraying the composition onto the surface of soil, a treatment of injecting the composition into soil or a treatment of irrigating the composition into soil, the treatment may be carried out after the composition is diluted with a suitable carrier to a suitable concentration. When the composition comprising the compound of the present invention is brought into contact with the plant seeds, the plant seeds may be subjected to immersion, dressing, spraying or coating treatment after the composition is diluted to a suitable concentration. The amount of the composition used for the immersion, dressing, spraying or coating treatment as the amount of the effective ingredient is usually approximately 0.05 to 50%, preferably 0.1 to 30%, relative to the dry weight of the plant seeds. However, the amount may be appropriately set depending on the form of the composition or the kind of the plant seeds to be treated and is not limited to these ranges.

If necessary, the compound of the present invention can be used in the form of a mixture with another agricultural chemical, such as pesticides including fungicides, insecticides (including acaricides and nematicides), herbicides, microbial inoculants and plant growth regulators; disease control agents comprising nucleic acids as an active ingredient (WO 2014/062775); soil improvers; fertilizing substances and the like. As examples of methods in which the compound of the present invention is used in the form of a mixture with another agricultural chemical, there can be mentioned: a method in which the compound of the present invention formulated into one preparation together with another agricultural chemical is used; a method in which both of them each separately formulated into one preparation are mixed prior to use and used as the resultant mixture; a method in which both of them each separately formulated into one preparation are simultaneously but separately used; and a method in which both of them are each separately formulated into one preparation and, after one of these preparations is used, the rest of these preparations is used.

Specific examples of components (including the salts, isomers and N-oxides thereof) contained in the fungicide which can be used in the form of a mixture with the compound of the present invention are indicated as Group b given below. However, the known fungicides are not limited to these examples.

Group b:

b-1: Phenylamide-Based Fungicides

As phenylamide-based fungicides, there can be mentioned [b-1.1] benalaxyl, [b-1.2] benalaxyl-M or kiralaxyl, [b-1.3] furalaxyl, [b-1.4] metalaxyl, [b-1.5] metalaxyl-M or mefenoxam, [b-1.6] oxadixyl, [b-1.7] ofurace, and the like.

b-2: Karyokinesis and Cell Division Inhibitors

As karyokinesis and cell division inhibitors, there can be mentioned [b-2.1] benomyl, [b-2.2] carbendazim, [b-2.3]

fuberidazole, [b-2.4] thiabendazole, [b-2.5] thiophanate, [b-2.6] thiophanate-methyl, [b-2.7] diethofencarb, [b-2.8] zoxamide, [b-2.9] ethaboxam, [b-2.10] pencycuron, [b-2.11] fluopicolide, [b-2.12] phenamacril, and the like.

b-3: Succinate Dehydrogenase Inhibitors (SDHI Agent)

As succinate dehydrogenase inhibitors (SDHI agent), there can be mentioned [b-3.1] benodanil, [b-3.2] benzovindiflupyr, [b-3.3] bixafen, [b-3.4] boscalid, [b-3.5] carboxin, [b-3.6] fenfuram, [b-3.7] fluopyram, [b-3.8] flutolanil, [b-3.9] fluxapyroxad, [b-3.10] furametpyr, [b-3.11] isofetamid, [b-3.12] isopyrazam, [b-3.13] mepronil, [b-3.14] oxycarboxin, [b-3.15] penthiopyrad, [b-3.16] penflufen, [b-3.17] pydiflumetofen, [b-3.18] sedaxane, [b-3.19] thifluzamide, [b-3.20] pyraziflumid, and the like.

b-4: Quinone Outside Inhibitors (QoI Agent)

As quinone outside inhibitors (QoI agent), there can be mentioned [b-4.1] azoxystrobin, [b-4.2] coumoxystrobin, [b-4.3] dimoxystrobin, [b-4.4] enoxastrobin, [b-4.5] famoxadone, [b-4.6] fenamidone, [b-4.7] fenaminstrobin, [b-4.8] flufenoxystrobin, [b-4.9] fluoxastrobin, [b-4.10] kresoxim-methyl, [b-4.11] mandestrobin, [b-4.12] metominostrobin, [b-4.13] orysastrobin, [b-4.14] picoxystrobin, [b-4.15] pyraclostrobin, [b-4.16] pyrametostrobin, [b-4.17] pyraoxystrobin, [b-4.18] pyribencarb, [b-4.19] triclopyricarb, [b-4.20] trifloxystrobin, and the like.

b-5: Quinone Inside Inhibitors (QiI Agent)

As quinone inside inhibitors (QiI agent), there can be mentioned [b-5.1] cyazofamid, [b-5.2] amisulbrom, and the like.

b-6: Oxidative Phosphorylation Decoupling Inhibitors

As oxidative phosphorylation decoupling inhibitors, there can be mentioned [b-6.1] binapacryl, [b-6.2] meptyldinocap, [b-6.3] dinocap, [b-6.4] fluazinam, and the like.

b-7: Quinone Outside Stigmaterin Binding Subsite Inhibitors (QoSI Agent)

As quinone outside stigmaterin binding subsite inhibitors (QoSI agent), there can be mentioned [b-7.1] ametoctradin, and the like.

b-8: Amino Acid Biosynthesis Inhibitors

As amino acid biosynthesis inhibitors, there can be mentioned [b-8.1] cyprodinil, [b-8.2] mepanipyrim, [b-8.3] pyrimethanil, and the like.

b-9: Protein Biosynthesis Inhibitors

As protein biosynthesis inhibitors, there can be mentioned [b-9.1] streptomycin, [b-9.2] blasticidin-S, [b-9.3] kasugamycin, [b-9.4] oxytetracycline, and the like.

b-10: Signal Transduction Inhibitors

As signal transduction inhibitors, there can be mentioned [b-10.1] fenpiclonil, [b-10.2] fludioxonil, [b-10.3] quinoxyfen, [b-10.4] proquinazid, [b-10.5] chlozolinate, [b-10.6] dimethachlone, [b-10.7] iprodione, [b-10.8] procymidone, [b-10.9] vinclozolin, and the like.

b-11: Lipid and Cell Membrane Biosynthesis Inhibitors

As lipid and cell membrane biosynthesis inhibitors, there can be mentioned [b-11.1] edifenphos, [b-11.2] iprobenfos, [b-11.3] pyrazophos, [b-11.4] isoprothiolane, [b-11.5] biphenyl, [b-11.6] chloroneb, [b-11.7] dicloran, [b-11.8] quintozene, [b-11.9] tecnazene, [b-11.10] tolclofos-methyl, [b-11.11] etridiazole (echlomezol or etridiazole), [b-11.12] iodocarb, [b-11.13] propamocarb, [b-11.14] prothiocarb, and the like.

b-12: Demethylation Inhibitors (DMI Agent)

As demethylation inhibitors (DMI agent), there can be mentioned [b-12.1] azaconazole, [b-12.2] bitertanol, [b-12.3] bromuconazole, [b-12.4] cyproconazole, [b-12.5] difenoconazole, [b-12.6] diniconazole, [b-12.7] diniconazole-M, [b-12.8] epoxiconazole, [b-12.9] etaconazole, [b-12.10] fenarimol, [b-12.11] fenbuconazole, [b-12.12] fluquinconazole, [b-12.13] quinconazole, [b-12.14] flusilazole, [b-12.15] flutriafol, [b-12.16] hexaconazole, [b-12.17] imazalil, [b-12.18] imibenconazole, [b-12.19] ipconazole, [b-12.20] metconazole, [b-12.21] myclobutanil, [b-12.22] nuarimol, [b-12.23] oxpoconazole, [b-12.24] oxpoconazole fumarate, [b-12.25] pefurazoate, [b-12.26] penconazole, [b-12.27] prochloraz, [b-12.28] propiconazole, [b-12.29] prothioconazole, [b-12.30] pyrifenox, [b-12.31] pyrisoxazole, [b-12.32] simeconazole, [b-12.33] tebuconazole, [b-12.34] tetraconazole, [b-12.35] triadimefon, [b-12.36] triadimenol, [b-12.37] triflumizole, [b-12.38] triforine, [b-12.39] triticonazole, [b-12.40] mefentrifluconazole, [b-12.41] ipfentrifluconazole, and the like.

b-13: Amine-Based Fungicides

As amine-based fungicides, there can be mentioned [b-13.1] aldimorph, [b-13.2] dodemorph, [b-13.3] fenpropimorph, [b-13.4] tridemorph, [b-13.5] fenpropidin, [b-13.6] piperalin, [b-13.7] spiroxamine, and the like.

b-14: 3-Ketoreductase Inhibitors in C4-Position Demethylation of Sterol Biosynthesis As 3-ketoreductase inhibitors in C4-position demethylation of sterol biosynthesis, there can be mentioned [b-14.1] fenhexamid, [b-14.2] fenpyrazamine, and the like.

b-15: Squalene Epoxidase Inhibitors of Sterol Biosynthesis

As squalene epoxidase inhibitors of sterol biosynthesis, there can be mentioned [b-15.1] pyributicarb, [b-15.2] naftifine, [b-15.3] terbinafine, and the like.

b-16: Cell Wall Biosynthesis Inhibitors

As cell wall biosynthesis inhibitors, there can be mentioned [b-16.1] polyoxins, [b-16.2] dimethomorph, [b-16.3] flumorph, [b-16.4] pyrimorph, [b-16.5] benthiavalicarb, [b-16.6] benthivalicarb-isopropyl, [b-16.7] iprovalicarb, [b-16.8] mandipropamid, [b-17.9] valifenalate, and the like.

b-17: Melanine Biosynthesis Inhibitors

As melanine biosynthesis inhibitors, there can be mentioned [b-17.1] phthalide or fthalide, [b-17.2] pyroquilone, [b-17.3] tricyclazole, [b-17.4] carpropamid, [b-17.5] diclocymet, [b-17.6] fenoxanil, [b-17.7] tolprocarb, and the like.

b-18: Host Plant Resistance Inducers

As host plant resistance inducers, there can be mentioned [b-18.1] acibenzolar-S-methyl, [b-18.2] probenazole, [b-18.3] tiadinil, [b-18.4] isotianil, [b-18.5] laminarin, and the like.

b-19: Dithiocarbamate-Based Fungicides

As dithiocarbamate-based fungicides, there can be mentioned [b-19.1] mancozeb or manzeb, [b-19.2] maneb, [b-19.3] metiram, [b-19.4] propineb, [b-19.5] thiram, [b-19.6] zineb, [b-19.7] ziram, [b-19.8] ferbam, and the like.

b-20: Phthalimide-Based Fungicides

As phthalimide-based fungicides, there can be mentioned [b-20.1] captan, [b-20.2] captafol, [b-20.3] folpet, [b-20.4] fluorofolpet, and the like.

b-21: Guanidine-Based Fungicides

As guanidine-based fungicides, there can be mentioned [b-21.1] guazatine, [b-21.2] iminoctadine, [b-21.3] iminoctadine albesilate, [b-21.4] iminoctadine triacetate, and the like.

b-22: Multi-Site Contact Activity Type Fungicides

As multi-site contact activity type fungicides, there can be mentioned [b-22.1] basic copper chloride (copper oxychloride), [b-22.2] copper(II) hydroxide, [b-22.3] basic copper sulfate (copper hydroxide sulfate), [b-22.4] organocopper compound, [b-22.5] dodecylbenzenesulphonic acid bisethylenediamine copper[II] complex salt (DBEDC), [b-22.6] sulfur (sulphur), [b-22.7] fluoroimide, [b-22.8] chlorothalonil, [b-22.9] dichlofluanid, [b-22.10] tolylfluanid,

[b-22.11] anilazine, [b-22.12] dithianon, [b-22.13] chinomethionat or quinomethionate, [b-22.14] extract from the cotyledons of lupine plantlets (BLAD), and the like.

b-23: Other Fungicides

As the other fungicides, there can be mentioned [b-23.1] dichlobentiazox, [b-23.2] fenpicoxamid, [b-23.3] dipymetitrone, [b-23.4] bupirimate, [b-23.5] dimethirimol, [b-23.6] ethirimol, [b-23.7] triphenyl tin acetate (fentin acetate), [b-23.8] triphenyltin chloride (fentin chloride), [b-23.9] triphenyltin hydroxide (fentin hydroxide), [b-23.10] oxolinic acid, [b-23.11] hymexazol, [b-23.12] octhilinone, [b-23.13] fosetyl, [b-23.14] phosphorous acid, [b-23.15] sodium phosphite, [b-23.16] ammonium phosphite, [b-23.17] potassium phosphite, [b-23.18] tecloftalam, [b-23.19] triazoxide, [b-23.20] flusulfamide, [b-23.21] diclomezine, [b-23.22] silthiofam, [b-23.23] diflumetorim, [b-23.24] methasulfocarb, [b-23.25] cyflufenamid, [b-23.26] metrafenone, [b-23.27] pyriofenone, [b-23.28] dodine, [b-23.29] flutianil, [b-23.30] ferimzone, [b-23.31] oxathiapiprolin, [b-23.32] tebufloquin, [b-23.33] picarbutrazox, [b-23.34] validamycins, [b-23.35] cymoxanil, [b-23.36] quinofumelin,

[b-23.37] the compound represented by Formula (s1)

(s1)

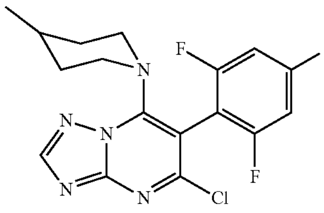

(see WO 98/046607),

[b-23.38] the compound represented by Formula (s2)

(s2)

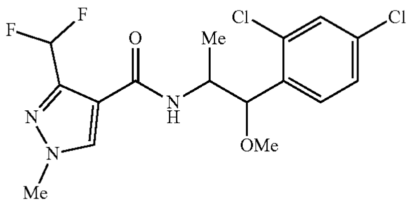

(see WO 08/148570),

[b-23.39] the compound represented by Formula (s3)

(s3)

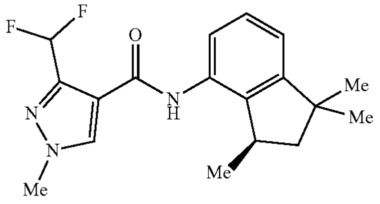

(see WO 92/012970),

[b-23.40] the compound represented by Formula (s4)

(s4)

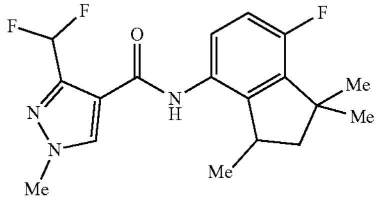

(see WO 12/084812),

[b-23.41] the compound represented by Formula (s5) (gougerotin)

(s5)

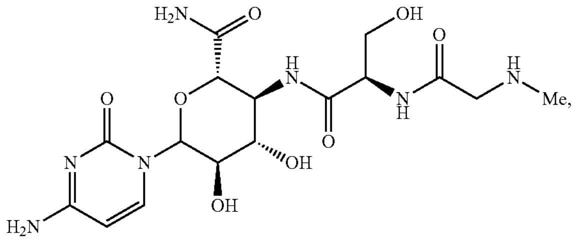

[b-23.42] the compound represented by Formula (s6) (ningnanmycin)

(s6)

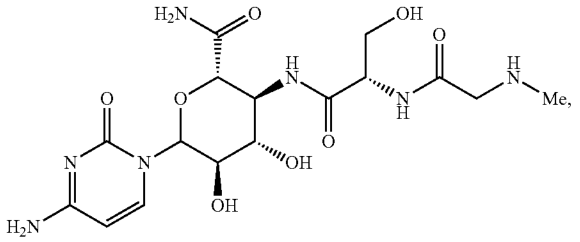

[b-23.43] the compound represented by Formula (s7)

(s7)

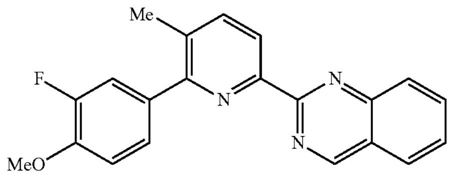

(see WO 10/136475),

[b-23.44] the compound represented by Formula (s8)

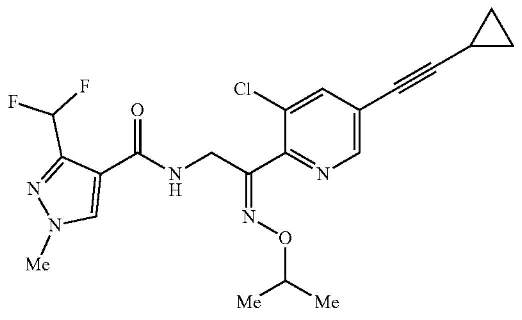
(s8)

(see WO 14/010737),

[b-23.45] the compound represented by Formula (s9)

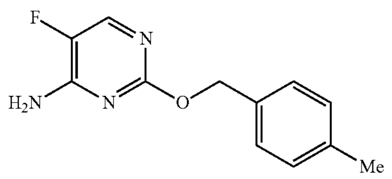
(s9)

(see WO 11/085084),

[b-23.46] the compound represented by Formula (s10)

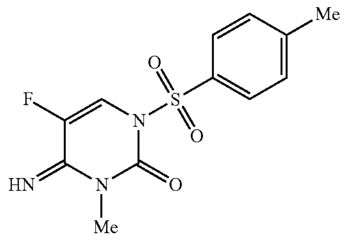
(s10)

(see WO 11/137002),

[b-23.47] the compound represented by Formula (s11)

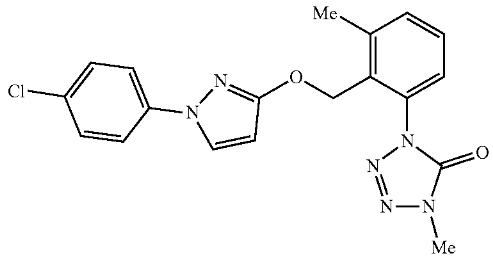
(s11)

(see WO 13/162072),

[b-23.48] the compound represented by Formula (s12)

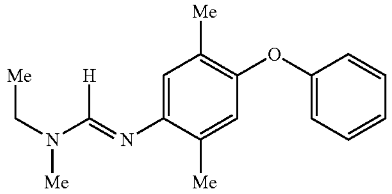
(s12)

(see WO 08/110313),

[b-23.49] the compound represented by Formula (s13)

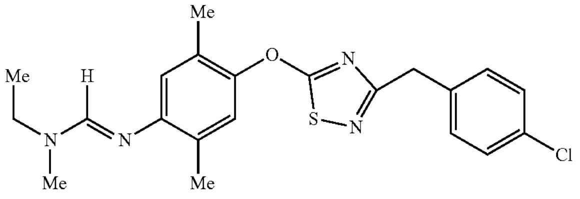
(s13)

(see WO 09/156098),

[b-23.50] the compound represented by Formula (s14)

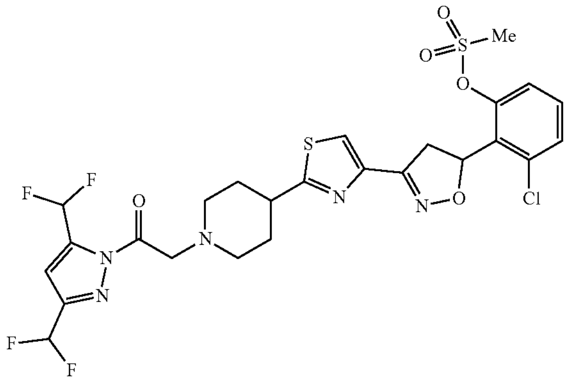
(s14)

(see WO 12/025557),

[b-23.51] the compound represented by Formula (s15)

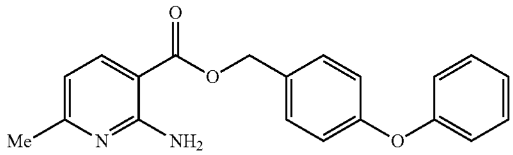
(s15)

(see WO 14/006945),

[b-23.52] the compound represented by Formula (s16)

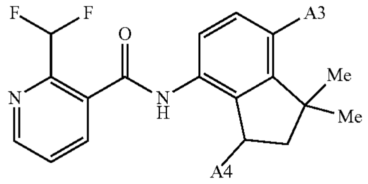

(s16)

[wherein A3 represents a hydrogen atom, a halogen atom, a C1-C6 alkyl group, a C1-C6 haloalkyl group or a cyano group, and A4 represents a hydrogen atom, a C1-C6 alkyl group, a C1-C6 haloalkyl group or a C3-C8 cycloalkyl group] (see WO 14/095675),

[b-23.53] the compound represented by Formula (s17)

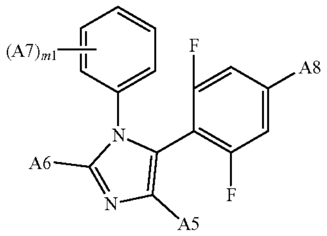

(s17)

[wherein m1 represents an integer of 0 to 3, A5 and A6 are independent to each other and each represent a halogen atom or a C1-C6 alkyl group, A7 and A8 are independent to each other and each represent a halogen atom or a C1-C6 alkoxy group and, when m1 is 2 or more, each of the 2 or more A7's independently represents a substituent which may be the same as or different] (see WO 09/137538 and WO 09/137651),

[b-23.54] the compound represented by Formula (s18)

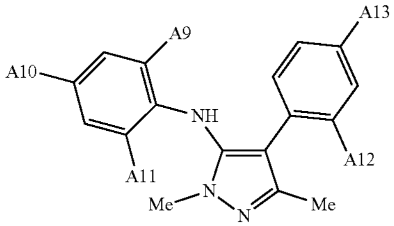

(s18)

[wherein A9 and A10 are independent to each other, and each represents a hydrogen atom or halogen atom, A11 represents a halogen atom, A12 represents a halogen atom or a C1-C6 alkyl group, and A13 represents a halogen atom, a cyano group, a C1-C6 alkyl group or a C1-C6 alkoxy group] (see WO 12/031061),

[b-23.55] the compound represented by Formula (s19)

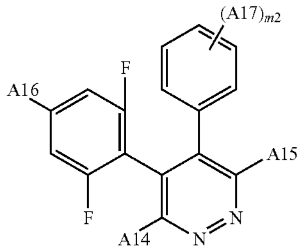

(s19)

[wherein m2 represents an integer of 0 to 6, A14 and A15 are independent to each other, and each represent a halogen atom, a cyano group or C1-C6 alkyl group, A16 represents a hydrogen atom, a halogen atom or a C1-C6 alkoxy group, A17 represents a halogen atom or a C1-C6 alkoxy group, and when m2 is 2 or more, the 2 or more A17's each independently represent a substituent which may be the same or different] (see WO 05/121104),

[b-23.56] the compound represented by Formula (s20)

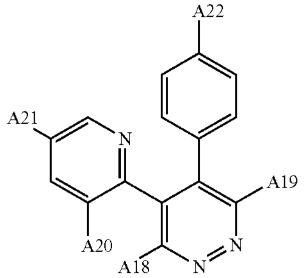

(s20)

[wherein A18 and A19 are independent to each other, and each represents a halogen atom, a cyano group or a C1-C6 alkyl group, and A20, A21 and A22 are independent to each other and each represent a hydrogen atom, a halogen atom or a C1-C6 alkoxy group] (see WO 07/066601),

[b-23.57] the compound represented by Formula (s21)

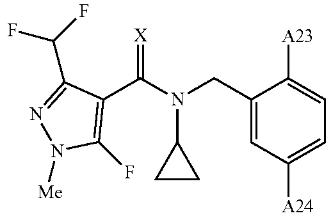

(s21)

[wherein A23 and A24 are independent to each other, and each represent a hydrogen atom, a halogen atom, a C1-C6 alkyl group or a C3-C8 cycloalkyl group, and X represents an oxygen atom or a sulfur atom] (see WO 07/087906, WO 09/016220 and WO 10/130767),

[b-23.58] the compound represented by Formula (s22)

(s22)

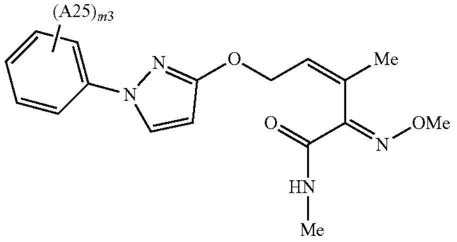

[wherein m3 represents an integer of 0 to 5, A25 represents a halogen atom, a C1-C6 alkyl group, a C1-C6 haloalkyl group, a C1-C6 alkoxy group, a C1-C6 haloalkoxy group or a C3-C8 cycloalkyl group and, when m3 is 2 or more, each of the 2 or more A25's independently represents a substituent which may be the same or different] (see WO 13/092224),

[b-23.59] the compound represented by Formula (s23)

(s23)

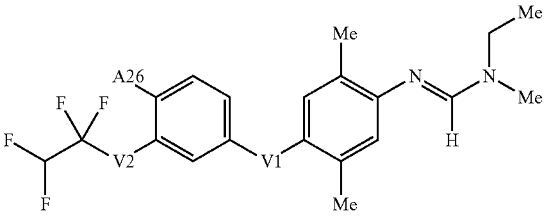

[wherein A26 represents a hydrogen atom or a halogen atom, and V1 and V2 are independent to each other and each represent an oxygen atom or a sulfur atom] (see WO 12/025450),

[b-23.60] the compound represented by Formula (s24) or Formula (s25)

(s24)

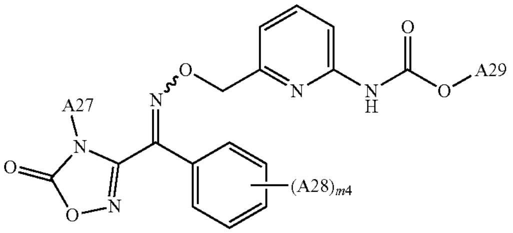

(s25)

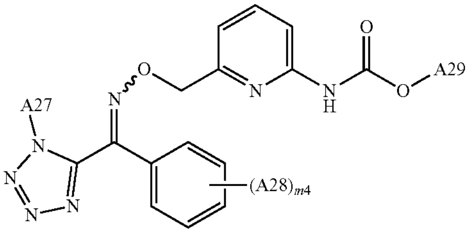

[wherein m4 represents an integer of 0 to 5, A27 represents a C1-C6 alkyl group, A28 represents a halogen atom, a cyano group, a C1-C6 alkyl group or a C1-C6 haloalkyl group, when m4 is 2 or more, each of the 2 or more A28's independently represents a substituent which may be the same or different, and A29 represents a C1-C6 alkyl group, a C2-C6 alkenyl group or a C3-C6 alkynyl group] (see WO 13/037717),

[b-23.61] the compound represented by Formula (s26) or Formula (s27)

(s26)

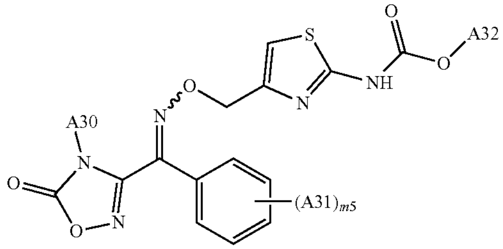

(s27)

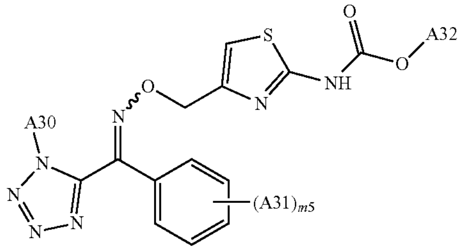

[wherein m5 represents an integer of 0 to 5, A30 represents a C1-C6 alkyl group, A31 represents a halogen atom, a cyano group, a C1-C6 alkyl group or a C1-C6 haloalkyl group, when m5 is 2 or more, each of the 2 or more A31's independently represents a substituent which may be the same or different, and A32 represents a C1-C6 alkyl group, a C2-C6 alkenyl group or a C3-C6 alkynyl group] (see WO 13/037717),

[b-23.62] the compound represented by Formula (s28)

(s28)

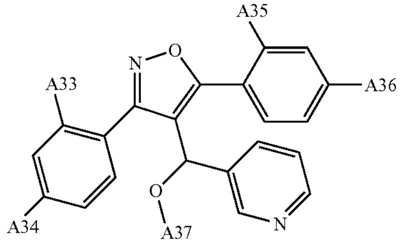

[wherein A33, A34, A35 and A36 are independent to each other and each represent a hydrogen atom or a halogen atom, and A37 represents a hydrogen atom, acetyl group or a benzoyl group] (see WO 06/031631 and WO 10/069882),

[b-23.63] the compound represented by Formula (s29)

(s29)

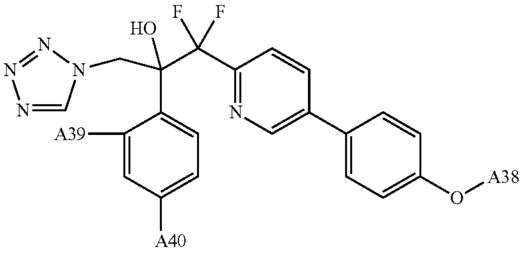

[wherein A38 represents a C1-C6 alkyl group or a C1-C6 haloalkyl group, and A39 and A40 are independent to each other and each represent a hydrogen atom or a halogen atom] (see WO 14/043376),

[b-23.64] the compound represented by Formula (s30)

(s30)

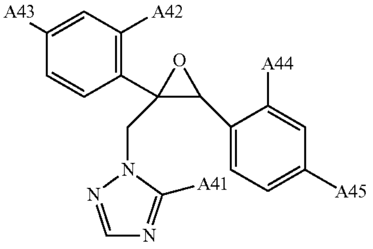

[wherein A41 represents a hydrogen atom, a sulfhydryl group (—SH), a thiocyanate group (—SCN) or a C1-C6 alkylthio group, and A42, A43, A44 and A45 are independent to each other and each represent a hydrogen atom or a halogen atom] (see WO 09/077443),

[b-23.65] the compound represented by Formula (s31) or Formula (s32)

(s31)

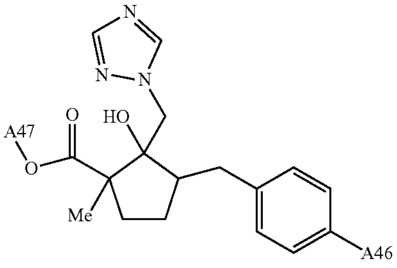

(s32)

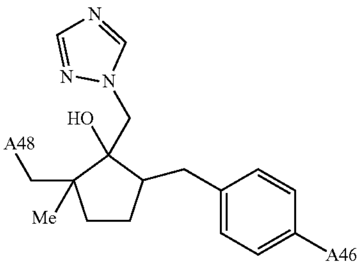

[wherein A46 represents a hydrogen atom or halogen atom, and A47 represents a C1-C6 alkyl group, and A48 represents a halogen atom] (see WO 11/070771),

[b-23.66] the compound represented by Formula (s33)

(s33)

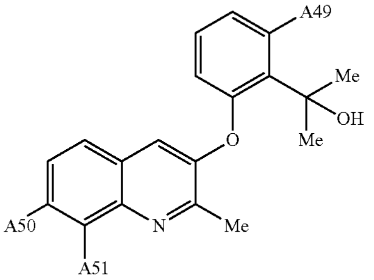

[wherein A49, A50 and A51 are independent to each other and each represent a hydrogen atom or a halogen atom] (see WO 11/081174), and the like.

Specific examples of components (including the salts, isomers and N-oxides thereof) contained in the insecticide which can be used in the form of a mixture with the compound of the present invention are indicated as Group c given below. However, the known insecticides are not limited to these examples.

Group c:

c-1: Carbamate-Based Acetylcholine Esterase (AChE) Inhibitors

As carbamate-based acetylcholine esterase (AChE) inhibitors, there can be mentioned [c-1.1] phosphocarb, [c-1.2] alanycarb, [c-1.3] butocarboxim, [c-1.4] butoxycarboxim, [c-1.5] thiodicarb, [c-1.6] thiofanox, [c-1.7] aldicarb, [c-1.8] bendiocarb, [c-1.9] benfuracarb, [c-1.10] carbaryl, [c-1.11] carbofuran, [c-1.12] carbosulfan, [c-1.13] ethiofencarb, [c-1.14] fenobucarb, [c-1.15] formetanate, [c-1.16] furathiocarb, [c-1.17] isoprocarb, [c-1.18] methiocarb, [c-1.19] methomyl, [c-1.20] oxamyl, [c-1.21] pirimicarb, [c-1.22] propoxur, [c-1.23] trimethacarb, [c-1.24] XMC (3,5-xylyl methylcarbamate), [c-1.25] allyxycarb, [c-1.26] aldoxycarb, [c-1.27] bufencarb, [c-1.28] butacarb, [c-1.29] carbanolate, [c-1.30] metolcarb, [c-1.31] xylylcarb, [c-1.32] fenothiocarb, [c-1.33] xylylcarb, [c-1.34] bendiocarb, and the like.

c-2: Organic Phosphorus-Based Acetylcholine Esterase (AChE) Inhibitors

As organic phosphorus-based acetylcholine esterase (AChE) inhibitors, there can be mentioned [c-2.1] acephate, [c-2.2] azamethiphos, [c-2.3] azinphos-methyl, [c-2.4] azinphos-ethyl, [c-2.5] ethephon, [c-2.6] cadusafos, [c-2.7] chlorethoxyfos, [c-2.8] chlorfenvinphos, [c-2.9] chlormephos, [c-2.10] chlorpyrifos, [c-2.11] chlorpyrifos-methyl, [c-2.12] coumaphos, [c-2.13] cyanophos, [c-2.14] demeton-S-methyl, [c-2.15] diazinon, [c-2.16] dichlofenthion, [c-2.17] dichlorvos, [c-2.18] dicrotophos, [c-2.19] dimethoate, [c-2.20] dimethylvinphos, [c-2.21] disulfoton, [c-2.22] O-ethyl O-4-nitrophenyl phenylphosphonothioate, [c-2.23] ethion, [c-2.24] ethoprophos, [c-2.25] famphur, [c-2.26] fenamiphos, [c-2.27] fenitrothion, [c-2.28] fenthion, [c-2.29] fosthiazate, [c-2.30] heptenophos, [c-2.31] isofenphos-methyl, [c-2.32] Isocarbophos, [c-2.33] isoxathion, [c-2.34] malathion, [c-2.35] mecarbam, [c-2.36] methamidophos, [c-2.37] methidathion, [c-2.38] mevinphos, [c-2.39] monocrotophos, [c-2.40] naled, [c-2.41] omethoate, [c-2.42] oxydemeton-methyl, [c-2.43] parathions, [c-2.44] parathion-methyl, [c-2.45] phenthoate, [c-2.46] phorate, [c-2.47] phosalone, [c-2.48] phosmet, [c-2.49] phosphamidon, [c-2.50] phoxim, [c-2.51] pirimiphos-methyl, [c-2.52] profenofos, [c-2.53] propetamphos, [c-2.54] prothiofos, [c-2.55] pyraclofos, [c-2.56] pyridaphenthion, [c-2.57] quinalphos, [c-2.58] sulfotep, [c-2.59] tebupirimfos, [c-2.60] temephos, [c-2.61] terbufos, [c-2.62] thiometon, [c-2.63] triazophos, [c-2.64] trichlorfon, [c-2.65] vamidothion, [c-2.66] chlorothion, [c-2.67] bromfenvinfos, [c-2.68] bromophos, [c-2.69] bromophos-ethyl, [c-2.70] butathiofos, [c-2.71] carbophenothion, [c-2.72] chlorphoxim, [c-2.73] sulprofos, [c-2.74] diamidafos, [c-2.75] tetrachlorvinphos, [c-2.76] propaphos, [c-2.77] mesulfenfos, [c-2.78] dioxabenzofos, [c-2.79] etrimfos, [c-2.80] oxydeprofos, [c-2.81] formothion, [c-2.82] fensulfothion, [c-2.83] isazofos, [c-2.84] imicyafos, [c-2.85] isamidofos, [c-2.86] thionazin, [c-2.87] fosthietan, and the like.

c-3: GABAergic Chlorine Ion Channel Blockers

As GABAergic chlorine ion channel blockers, there can be mentioned [c-3.1] chlordane, [c-3.2] endosulfan, [c-3.3] lindane, [c-3.4] dienochlor, [c-3.5] ethiprole, [c-3.6] fipronil, [c-3.7] acetoprole, and the like.

c-4: Sodium Channel Modulators

As sodium channel modulators, there can be mentioned [c-4.1] acrinathrin, [c-4.2] allethrin [(1R)-isomer], [c-4.3] bifenthrin, [c-4.4] bioallethrin, [c-4.5] bioallethrin S-cyclopentenyl isomer, [c-4.6] bioresmethrin, [c-4.7] cycloprothrin, [c-4.8] cyfluthrin, [c-4.9] beta-cyfluthrin, [c-4.10] cyhalothrin, [c-4.11] gamma-cyhalothrin, [c-4.12] lambda-cyhalothrin, [c-4.13] cypermethrin, [c-4.14] alpha-cypermethrin, [c-4.15] beta-cypermethrin, [c-4.16] theta-cypermethrin, [c-4.17] zeta-cypermethrin, [c-4.18] cyphenothrin [(1R)-trans-isomer], [c-4.19] deltamethrin, [c-4.20] empenthrin [(EZ)-(1R)-isomer], [c-4.21] esfenvalerate, [c-4.22] ethofenprox, [c-4.23] fenpropathrin, [c-4.24] fenvalerate, [c-4.25] flucythrinate, [c-4.26] flumethrin, [c-4.27] tau-fluvalinate, [c-4.28] halfenprox, [c-4.29] imiprothrin, [c-4.30] methothrin, [c-4.31] metofluthrin, [c-4.32] epsilon-metofluthrin, [c-4.33] momfluorothrin, [c-4.34] epsilon-momfluorothrin, [c-4.35] permethrin, [c-4.36] phenothrin [(1R)-trans-isomer], [c-4.37] prallethrin, [c-4.38] resmethrin, [c-4.39] kadethrin, [c-4.40] silafluofen, [c-4.41] tefluthrin, [c-4.42] tetramethrin, [c-4.43] tetramethrin [(1R)-isomer], [c-4.44] tralomethrin, [c-4.45] transfluthrin, [c-4.46] ZXI8901 (3-(4-bromophenoxy)phenyl]-cyanomethyl 4-(difluoromethoxy)-α-(1-methylethyl)benzeneacetate), [c-4.47] biopermethrin, [c-4.48] furamethrin, [c-4.49] profluthrin, [c-4.50] flubrocythrinate, [c-4.51] dimefluthrin, [c-4.52] DDT (dichloro-diphenyl-trichloroethane), [c-4.53] methoxychlor, [c-4.54] phenothrin, [c-4.55] fluvalinate, and the like.

c-5: Nicotinic Acetylcholine Receptor (nAChR) Competitive Modulators

As nicotinic acetylcholine receptor (nAChR) competitive modulators, there can be mentioned [c-5.1] acetamiprid, [c-5.2] clothianidin, [c-5.3] dinotefuran, [c-5.4] imidacloprid, [c-5.5] nitenpyram, [c-5.6] thiacloprid, [c-5.7] thiamethoxam, [c-5.8] nicotine, [c-5.9] nicotine sulfate, [c-5.10] sulfoxaflor, [c-5.11] flupyradifurone, [c-5.12] triflumezopyrim, and the like.

c-6: Nicotinic Acetylcholine Receptor (nAChR) Allosteric Modulators

As nicotinic acetylcholine receptor (nAChR) allosteric modulators, there can be mentioned [c-6.1] spinosad, [c-6.2] spinetoram, and the like.

c-7: Glutamate-Gated Chloride Ion Channel (GluCl) Allosteric Modulators

As glutamate-gated chloride ion channel (GluCl) allosteric modulators, there can be mentioned [c-7.1] abamectin, [c-7.2] emamectin benzoate, [c-7.3] lepimectin, [c-7.4] milbemectin, and the like.

c-8: Juvenile Hormone Analogues

As juvenile hormone analogues, there can be mentioned [c-8.1] hydroprene, [c-8.2] kinoprene, [c-8.3] methoprene, [c-8.4] fenoxycarb, [c-8.5] pyriproxyfen, and the like.

c-9: Nonspecific (Multisite) Inhibitors

As nonspecific (multisite) inhibitors, there can be mentioned [c-9.1] methyl bromide, [c-9.2] chloropicrin, [c-9.3] cryolite, [c-9.4] sulfuryl fluoride, [c-9.5] borax, [c-9.6] boric acid, [c-9.7] disodium octaborate, [c-9.8] sodium metaborate, [c-9.9] tartar emetic, [c-9.10] dazomet, [c-9.11] metam, [c-9.12] carbam sodium salt (methamsodium), and the like.

c-10: Chordotonal Organ TRPV Channel Modulators

Chordotonal organ TRPV channel modulators, there can be mentioned [c-10.1] pymetrozine, [c-10.2] pyrifluquinazon, and the like.

c-11: Acari Growth Inhibitors

As acari growth inhibitors, there can be mentioned [c-11.1] clofentezine, [c-11.2] diflovidazin, [c-11.3] hexythiazox, [c-11.4] etoxazole, and the like.

c-12: Mitochondrial ATP Synthase Inhibitors

As mitochondrial ATP synthase inhibitors, there can be mentioned [c-12.1] diafenthiuron, [c-12.2] azocyclotin, [c-12.3] cyhexatin, [c-12.4] fenbutatin oxide, [c-12.5] propargite, [c-12.6] tetradifon, and the like.

c-13: Uncouplers of Oxidative Phosphorylation Via Disruption of Proton Gradient

As uncouplers of oxidative phosphorylation via disruption of proton gradient, there can be mentioned [c-13.1] chlorfenapyl, [c-13.2] DNOC (dinitro-ortho-cresol), [c-13.3] binapacryl, [c-13.4] sulfluramid, and the like.

c-14: Nicotinic Acetylcholine Receptor (nAChR) Channel Blockers

As nicotinic acetylcholine receptor (nAChR) channel blockers, there can be mentioned [c-14.1] bensultap, [c-14.2] cartap hydrochloride, [c-14.3] thiocyclam, [c-14.4] monosultap, and the like.

c-15: Chitin Biosynthesis Inhibitors Type 0

As chitin biosynthesis inhibitors type 0, there can be mentioned [c-15.1] bistrifluron, [c-15.2] chlorfluazuron, [c-15.3] diflubenzuron, [c-15.4] flucycloxuron, [c-15.5] flufenoxuron, [c-15.6] hexaflumuron, [c-15.7] lufenuron, [c-15.8] novaluron, [c-15.9] noviflumuron, [c-15.10] teflubenzuron, [c-15.11] triflumuron, and the like.

c-16: Chitin Biosynthesis Inhibitor Type 1

As chitin biosynthesis inhibitor type 1, there can be mentioned [c-16.1] buprofezin, and the like.

c-17: Diptera Insect Molting Inhibitors

As diptera insect molting inhibitors, there can be mentioned [c-17.1] cyromazine, and the like.

c-18: Molting Hormone (Ecdysone) Receptor Agonists

As molting hormone (ecdysone) receptor agonists, there can be mentioned [c-18.1] chromafenozide, [c-18.2] halofenozide, [c-18.3] methoxyfenozide, [c-18.4] tebufenozide, and the like.

c-19: Octopamine Receptor Agonists

As octopamine receptor agonists, there can be mentioned [c-19.1] amitraz, and the like.

c-20: Mitochondrial Electron Transport System Complex III Inhibitors

As mitochondrial electron transport system complex III inhibitors, there can be mentioned [c-20.1] hydramethylnon, [c-20.2] acequinocyl, [c-20.3] fluacrypyrim, [c-20.4] bifenazate, and the like.

c-21: Mitochondrial Electron Transport System Complex I Inhibitors (METI)

As mitochondrial electron transport system complex I inhibitors (METI), there can be mentioned [c-21.1] fenazaquin, [c-21.2] fenpyroximate, [c-21.3] pyridaben, [c-21.4] pylimidifen, [c-21.5] tebufenpyrad, [c-21.6] tolfenpyrad, [c-21.7] rotenone, and the like.

c-22: Voltage-Gated Sodium Channel Blockers

As voltage-gated sodium channel blockers, there can be mentioned [c-22.1] indoxacarb, [c-22.2] metaflumizone, and the like.

c-23: Acetyl CoA Carboxylase Inhibitors

As acetyl CoA carboxylase inhibitors, there can be mentioned [c-23.1] spirodiclofen, [c-23.2] spiromesifen, [c-23.3] spirotetramat, and the like.

c-24: Mitochondrial Electron Transport System Complex IV Inhibitors

As mitochondrial electron transport system complex IV inhibitors, there can be mentioned [c-24.1] aluminum phosphide, [c-24.2] calcium phosphide, [c-24.3] hydrogen phosphide (phosphine), [c-24.4] zinc phosphide, [c-24.5] calcium cyanide, [c-24.6] sodium cyanide, [c-24.7] potassium cyanide, and the like.

c-25: Mitochondrial Electron Transport System Complex II Inhibitors

As mitochondrial electron transport system complex II inhibitors, there can be mentioned [c-25.1] cyenopyrafen, [c-25.2] cyflumetofen, [c-25.3] pyflubumide, and the like.

c-26: Ryanodine Receptor Modulators

As ryanodine receptor modulators, there can be mentioned [c-26.1] chlorantraniliprole, [c-26.2] cyantraniliprole, [c-26.3] flubendiamide, and the like.

c-27: Target Site-Unspecified Chordotonal Organ Modulators

As target site-unspecified chordotonal organ modulators, there can be mentioned [c-27.1] flonicamid, and the like.

c-28: Other Insecticides

As the other insecticides, there can be mentioned [c-28.1] azadirachtin, [c-28.2] benzoximate, [c-28.3] phenisobromolate, [c-28.4] chinomethionat, [c-28.5] dicofol, [c-28.6] pyridalyl, [c-28.7] bromopropylate, [c-28.8] triazamate, [c-28.9] dicyclanil, [c-28.10] dinobuton, [c-28.11] dinocap, [c-28.12] hydrogen cyanide, [c-28.13] methyl iodide, [c-28.14] karanjin, [c-28.15] mercury chloride, [c-28.16] methyl isothiocyanate, [c-28.17] pentachlorophenol, [c-28.18] phosphine, [c-28.19] piperonyl butoxide, [c-28.20] polynactin complex (polynactins), [c-28.21] sabadilla), [c-28.22] sulcofuron salt (sulcofuron-sodium), [c-28.23] tribufos, [c-28.24] aldrin, [c-28.25] amidithion, [c-28.26] amidothioate, [c-28.27] aminocarb, [c-28.28] amiton, [c-28.29] aramite, [c-28.30] athidathion, [c-28.31] azothoate, [c-28.32] barium polysulphide, [c-28.33] benclothiaz, [c-28.34] 5-(1,3-benzodioxol-5-yl)-3-hexylcyclohexa-2-enone, [c-28.35] 1,1-bis(4-chlorophenyl)-2-ethoxyethanol, [c-28.36] butonate, [c-28.37] butopyronoxyl, [c-28.38] 2-(2-butoxyethoxy)ethyl thiocyanate, [c-28.39] camphechlor, [c-28.40] chlorbenside, [c-28.41] chlordecone, [c-28.42] chlordimeform, [c-28.43] chlorfenethol, [c-28.44] chlorfenson, [c-28.45] fluazuron, [c-28.46] metaldehyde, [c-28.47] bialaphos, [c-28.48] levamisol hydrochloride (levamisol), [c-28.49] amidoflumet, [c-28.50] pyrafluprole, [c-28.51] pyriprole, [c-28.52] tralopyril, [c-28.53] flupyrazofos, [c-28.54] diofenolan, [c-28.55] chlorobenzilate, [c-28.56] flufenzine, [c-28.57] benzomate, [c-28.58] flufenerim, [c-28.59] albendazole, [c-28.60] oxibendazole, [c-28.61] fenbendazole, [c-28.62] metam-sodium, [c-28.63] 1,3-dichloropropene, [c-28.64] flometoquin, [c-28.65] cyclaniliprole, [c-28.66] tetraniliprole, [c-28.67] broflanilide, [c-28.68] dicloromezotiaz, [c-28.69] ethylene dibromide, [c-28.70] acrylonitrile, [c-28.71] bis(2-chloroethyl)ether, [c-28.72] 1-bromo-2-chloroethane, [c-28.73] 3-bromo-1-chloroprop-1-ene, [c-28.74] bromocyclen, [c-28.75] carbon disulfide, [c-28.76] carbon tetrachloride (tetrachloromethane), [c-28.77] nemadectin, [c-28.78] cymiazole, [c-28.79] calcium polysulfide, [c-28.80] cytokinin, [c-28.81] 2-(octylthio)ethanol, [c-28.82] potassium oleate, [c-28.83] sodium oleate, [c-28.84] machine oil, [c-28.85] tar oil, [c-28.86] anabasine, [c-28.87] morantel tartrate, [c-28.88] pyrethrum, [c-28.89] rape seed oil, [c-28.90] soybean lecithin, [c-28.91] starch, [c-28.92] hydroxypropyl starch, [c-28.93] fatty acid glyceride (decanoyloctanoylglycerol), [c-28.94] propylene glycol mono fatty acid ester (propylene glycol fatty acid ester), [c-28.95] diatomaceous earth (diatomite), [c-28.96] afoxolaner, [c-28.97] fluazaindolizine, [c-28.98] afidopyropen, [c-28.99] cyhalodiamide, [c-28.100] tioxazafen, [c-28.101] fluhexafon, [c-28.102] fluralaner, [c-28.103] fluxametamide, [c-28.104] tetrachlorantraniliprole, [c-28.105] sarolaner, [c-28.106] lotilaner, [c-28.107] cycloxaprid, [c-28.108] fluensulfone, [c-28.109] TPIC (tripropyl isocyanurate), [c-28.110] D-D (1,3-Dichloropropene), [c-28.111] peroxocarbonate, [c-28.112] MB-599 (verbutin), [c-28.113] bis(2,3,3,3-tetrachloro-propyl)ether, [c-28.114] DCIP (bis(2-chloro-1-methylethyl)ether), [c-28.115] ENT-8184 (N-(2-Ethylhexyl)bicyclo[2.2.1] hept-5-ene-2,3-dicarboximide), [c-28.116] Bayer 22408 (O,O-diethyl O-naphthalimido phosphorothioate), [c-28.117] Bayer 32394 (tris(1-dodecyl-3-methyl-2-phenylbenzimidazolium)hexacyanoferrate),

[c-28.118] the compound represented by Formula (s34)

(s34)

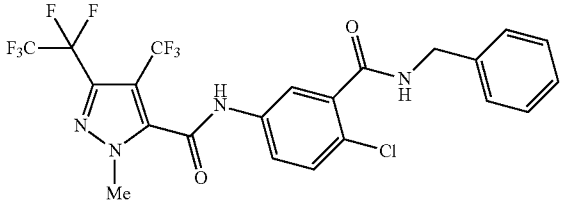

(see WO 10/051926),

[c-28.119] the compound represented by Formula (s35)

(s35)

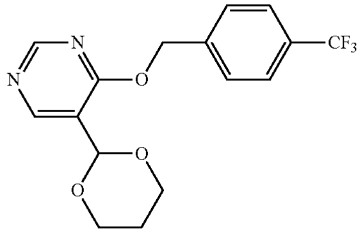

(see WO 13/115391), (s36)

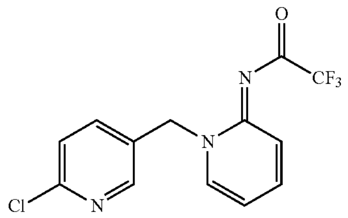

(see WO 12/029672),

[c-28.121] the compound represented by Formula (s37)

(s37)

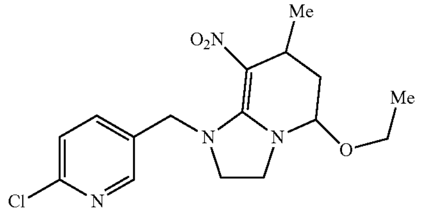

(see WO 06/056108),

[c-28.122] the compound represented by Formula (s38)

(s38)

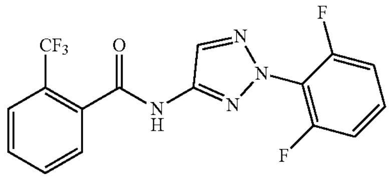

(see WO 14/053450 and WO 15/144683),

[c-28.123] the compound represented by Formula (s39)

(s39)

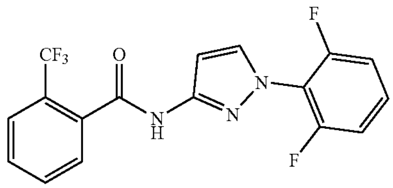

(see WO 14/053450 and WO 15/144683),

[c-28.124] the compound represented by Formula (s40)

(s40)

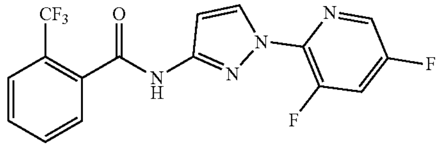

(see WO 14/053450 and WO 15/144683),

[c-28.125] the compound represented by Formula (s41)

(s41)

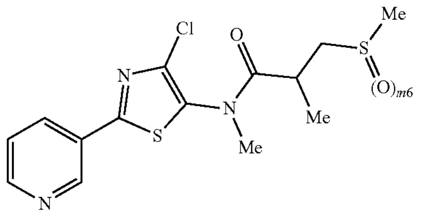

[wherein m6 represents an integer of 0 to 2] (see WO 10/129497),

[c-28.126] the compound represented by Formula (s42)

(s42)

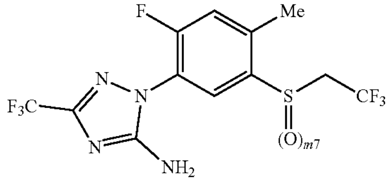

[wherein m7 represents an integer of 0 to 2] (see WO 11/152320),

[c-28.127] the compound represented by Formula (s43)

(s43)

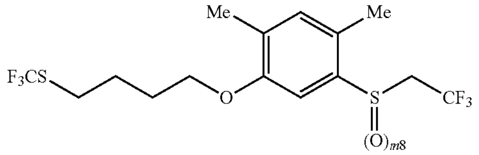

[wherein m8 represents an integer of 0 to 2] (see JP 2015-160813A),

[c-28.128] the compound represented by Formula (s44)

(s44)

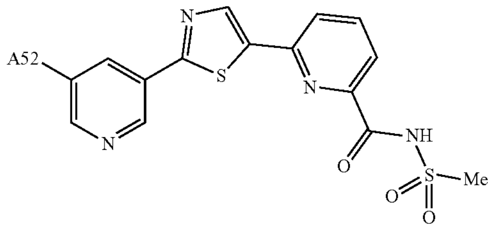

[wherein A52 represents a hydrogen atom or a fluorine atom] (see WO 11/134964 and WO 14/005982),

[c-28.129] the compound represented by Formula (s45)

(s45)

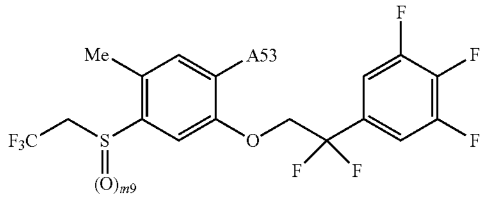

[wherein m9 represents an integer of 0 to 2, and A53 represents a fluorine atom or a chlorine atom] (see WO 15/025826),

[c-28.130] the compound represented by Formula (s46)

(s46)

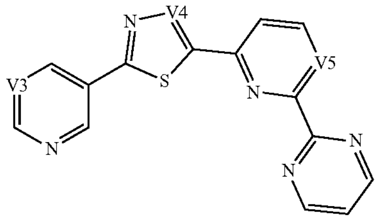

[wherein V3 represents a nitrogen atom, a carbon atom or C—F, V4 and V5 are independent to each other, and each represent a nitrogen atom or a carbon atom] (see WO 11/134964 and WO 14/005982),

[c-28.131] the compound represented by Formula (s47)

(s47)

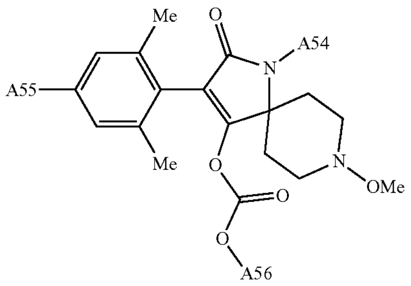

[wherein A54 represents a hydrogen atom, a methyl group, a methoxy group or an ethoxy group, A55 represents a chlorine atom or a methyl group, and A56 represents a methyl group or an ethyl group] (see WO 09/049851),

[c-28.132] the compound represented by Formula (s48)

(s48)

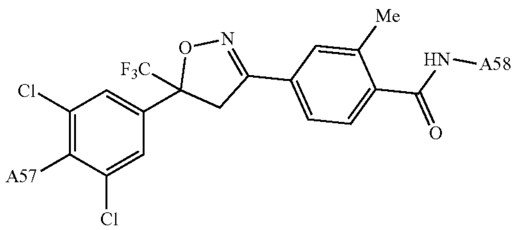

[wherein A57 represents a hydrogen atom, a fluorine atom or a chlorine atom, and A58 represents one partial structure selected from the group consisting of

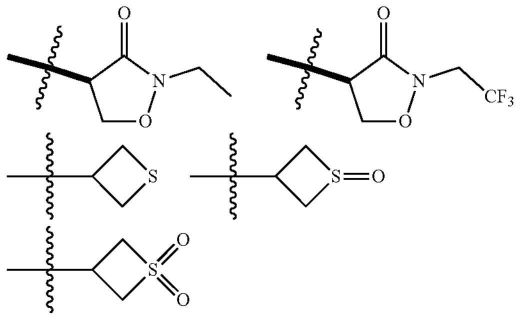

(see WO 11/067272),

[c-28.133] the compound represented by Formula (s49)

(s49)

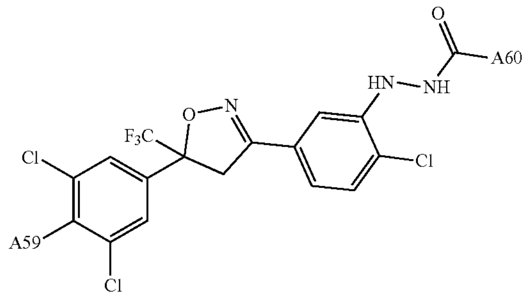

[wherein A59 represents a hydrogen atom, a fluorine atom or a chlorine atom, and A60 represents a partial structure selected from the group consisting of

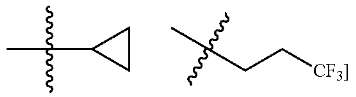

(see WO 10/090344),

[c-28.134] the compound represented by Formula (s50)

(s50)

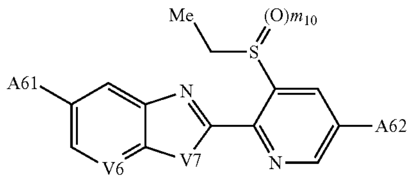

[wherein m10 represents an integer of 0 to 2, A61 represents a trifluoromethyl group, a trifluoromethylthio group, a trifluoromethylsulfinyl group or a trifluoromethylsulfonyl group, A62 represents a hydrogen atom or a trifluoromethyl group, V6 represents a nitrogen atom or a carbon atom, and V7 represents an oxygen atom or an N-methyl group] (see WO 14/104407),

[c-28.135] the compound represented by Formula (s51)

(s51)

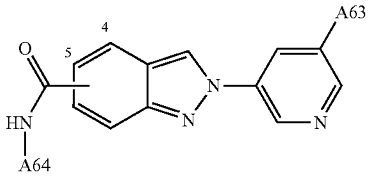

[wherein A63 represents a hydrogen atom or a fluorine atom, the amide group is bonded to the 4-position or the 5-position, and A64 represents a partial structure selected from the group consisting of

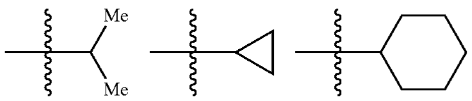

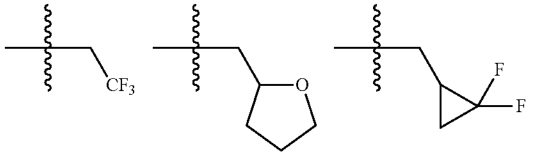

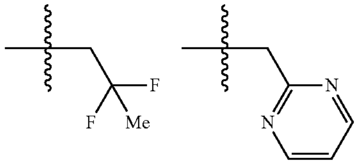

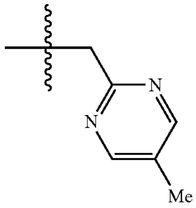

]

(see WO 15/038503, WO 16/144351 and WO 16/144678), [c-28.136] the compound represented by Formula (s52)

(s52)

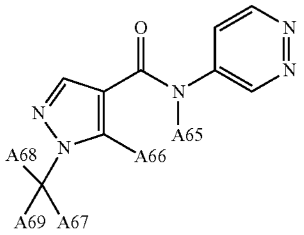

[wherein A65 represents a hydrogen atom, a C1-C6 alkyl group or a C1-C6 haloalkyl group, A66 represents a hydrogen atom, a halogen atom or a C1-C6 alkyl group, A67 and A68 are independent to each other and each represent a hydrogen atom, a C1-C6 alkyl group optionally substituted with a cyano group, an alkyl group optionally substituted with a methoxy group, an alkyl group optionally substituted with an ethoxy group or a C3-C8 cycloalkyl group, and A69 represents a hydrogen atom, a cyano group, a C1-C6 haloalkyl group optionally substituted with a cyano group, a C1-C6 alkyl group or a C3-C8 cycloalkyl group] (see WO 12/143317 and WO 16/016369),

[c-28.137] the compound represented by Formula (s53) or Formula (s54)

(s53)

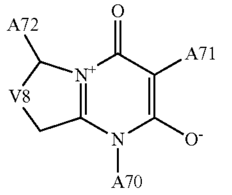

(s54)

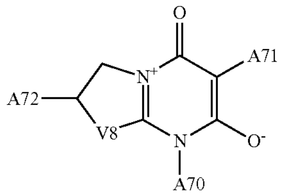

[wherein A70 represents a methyl group, an ethyl group, an isopropyl group, a 2,2,2-trifluoroethyl group or a phenyl group, A71 represents a partial structure selected from the group consisting of

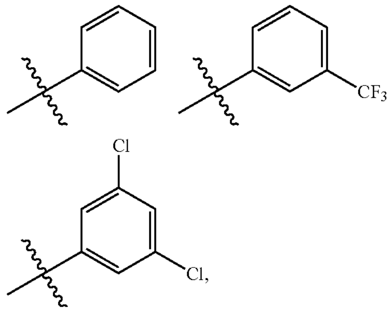

A72 represents a partial structure selected from the group consisting of

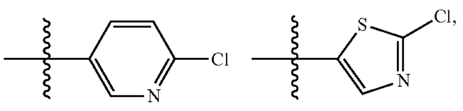 [SMILES: *c1ccc(Cl)nc1 ; *c1cnc(Cl)s1]

and V8 represents an oxygen atom, a sulfur atom, $—CH_2$- or $—CH_2CH_2$-] (see WO 14/167084 and WO 16/055431),

[c-28.138] the compound represented by Formula (s55)

(s55)

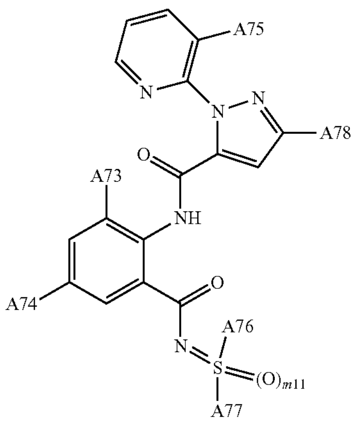

[wherein m11 represents an integer of 0 to 1, A73 represents a chlorine atom, a bromine atom, a methyl group or a trifluoromethyl group, A74 represents a hydrogen atom, a chlorine atom, a bromine atom, a cyano group or a trifluoromethyl group, A75 represents a hydrogen atom, a chlorine atom or a bromine atom, A76 and A77 are independent to each other and each represent a C1-C6 alkyl group or a C3-C8 cycloalkyl group, and A78 represents a chlorine atom, a bromine atom, a cyano group, a nitro group, a difluoromethyl group or a trifluoromethyl group] (see WO 13/024009),

[c-28.139] the compound represented by Formula (s56)

(s56)

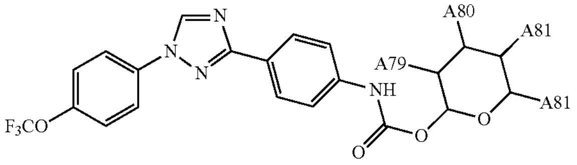

[wherein A79, A80, A81 and A82 are independent to each other and each represent a hydrogen atom, a halogen atom, a C1-C6 alkyl group, a C1-C6 haloalkyl group, a C1-C6 alkoxy group or a C3-C8 cycloalkoxy group] (see WO 12/027521),

[c-28.140] the compound represented by Formula (s57)

(s57)

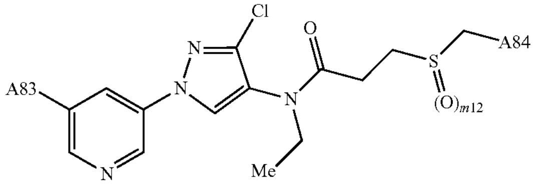

[wherein m12 represents an integer of 0 to 2, A83 represents a hydrogen atom or a fluorine atom, and A84 represents a partial structure selected from the group consisting of

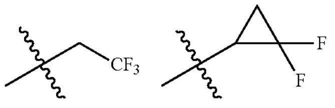 [SMILES: *CC(F)(F)F ; *C1CC1(F)F]

(see WO 13/162715),

[c-28.141] acynonapyr,

[c-28.142] the compound represented by Formula (s59)

(s59)

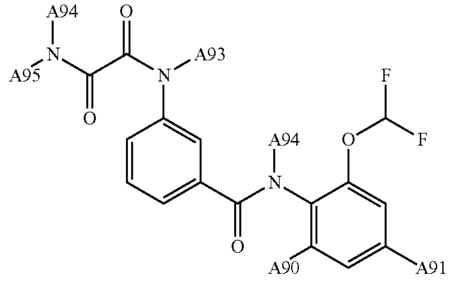

[wherein A90 represents a halogen atom, a C1-C6 alkyl group or a C1-C6 haloalkyl group, A91 represents a C1-C6 haloalkyl group, A92 and A93 are independent to each other and each represent a hydrogen atom, a C1-C6 alkyl group, an acetyl group, a propiniyl group, a methanesulfonylethyl group, a methoxycarbonyl group or an ethoxycarbonyl group, and A94 and A95 are independent to each other and each represent a hydrogen atom, a C1-C6 alkyl group or a C1-C6 haloalkyl group] (see WO 12/164698), and the like.

The ratio of mixing of the compound of the present invention with a pest control agent is not particularly limited, as long as the effects are effected. The weight ratio of the pest control agent relative to the compound of the present invention is usually 0.001 to 1,000, preferably 0.01 to 100.

EXAMPLES

Hereinbelow, the present invention will be described in more detail with reference to the following Examples, but not limited to these Examples.

Synthetic Example 1

Synthesis of 5-chloro-2-(2,6-difluorophenyl)-1-ethyl-6-oxo-1,6-dihydro-pyridine-3-carboxylic acid

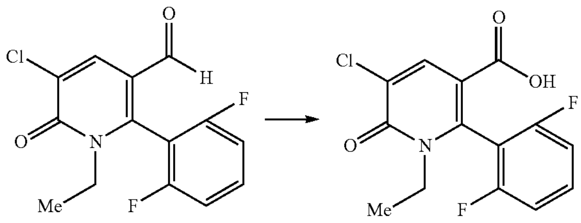 [SMILES: CCn1c(-c2c(F)cccc2F)c(C=O)cc(Cl)c1=O ; CCn1c(-c2c(F)cccc2F)c(C(=O)O)cc(Cl)c1=O]

To a mixed solution in 6.75 ml of water, 20.25 ml of THF and 20.25 ml of tertiary butanol containing 1.5 g of 5-chloro-2-(2,6-difluorophenyl)-1-ethyl-6-oxo-1,6-dihydropyridine-3-carboaldehyde, 2.36 ml of 2-methyl-2-butene and 786 mg of sodium dihydrogen phosphate dehydrate, 1.71 g of sodium chlorite (80% by weight) was added, and the resultant mixture was stirred at room temperature for 2.5 hours. Water and ethyl acetate were added to the reaction mixture and layers were separated. Then, the obtained organic layer was successively washed with an aqueous sodium thiosulfate solution and a saturated saline solution, and dried over sodium sulfate. The solvent was evaporated under reduced pressure, and the obtained solid was washed with isopropyl ether. The title compound was obtained as 1.42 g of a white solid.

$^1$H-NMR ($CDCl_3$) δ: 8.21 (1H, s), 7.54-7.50 (1H, m), 7.05-7.04 (2H, m), 3.93 (2H, q, J=7.2 Hz), 1.16 (3H, t, J=7.2 Hz).

Synthetic Example 2

Synthesis of tert-butyl (5-chloro-2-(2,6-difluorophenyl)-1-ethyl-6-oxo-1,6-dihydropyridin-3-yl)carbamate (Compound No.: 1)

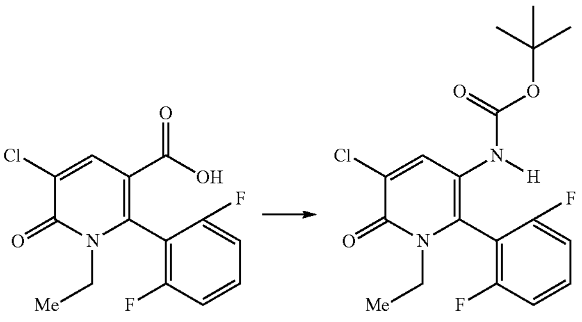 [SMILES: CCn1c(-c2c(F)cccc2F)c(C(=O)O)cc(Cl)c1=O ; CCn1c(-c2c(F)cccc2F)c(NC(=O)OC(C)(C)C)cc(Cl)c1=O]

To 20 ml of tertiary butanol containing 1.42 g of 5-chloro-2-(2,6-difluoro-phenyl)-1-ethyl-6-oxo-1,6-dihydropyridine-3-carboxylic acid were added 2.93 ml of diphenylphosphoryl azide and 1.89 ml of triethylamine, and the resultant mixture was stirred at room temperature for one hour and further at 80° C. for 2 hours. After cooling to room temperature, water and ethyl acetate were added to the reaction mixture and the layers were separated. The obtained organic layer was washed with a saturated saline solution, and dried over sodium sulfate. The solvent was evaporated under reduced pressure, and the obtained solid was washed with a mixed solvent of ethyl acetate and isopropyl ether. The title compound was obtained as 1.09 g of a white solid.

Synthetic Example 3

Synthesis of 5-amino-3-chloro-6-(2,6-difluorophenyl)-1-ethylpyridin-2(1H)-one (Compound No.: 59)

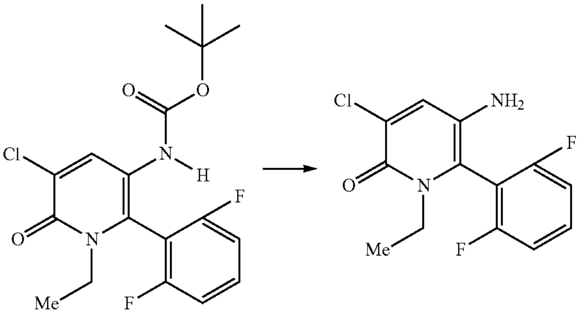 [SMILES: CCn1c(-c2c(F)cccc2F)c(NC(=O)OC(C)(C)C)cc(Cl)c1=O ; CCn1c(-c2c(F)cccc2F)c(N)cc(Cl)c1=O]

4.5 ml of a dichloromethane solution containing 0.58 g of tert-butyl (5-chloro-2-(2,6-difluorophenyl)-1-ethyl-6-oxo-1,6-dihydropyridin-3-yl)carbamate and 1.5 ml of trifluoroacetic acid was stirred at room temperature for one hour. The reaction mixture was added to a mixed solution comprising a saturated aqueous solution of sodium hydrogen carbonate and ethyl acetate, potassium carbonate was added until foaming was ceased, and then the layers were separated. The obtained organic layer was washed with a saturated saline solution, and dried over sodium sulfate. The solvent was evaporated under reduced pressure, and the obtained residue was purified by silica gel column chromatography. The title compound was obtained as 0.38 g of a yellow solid.

Synthetic Example 4

Synthesis of tert-butyl (5-chloro-2-(2,6-difluorophenyl)-1-ethyl-6-oxo-1,6-dihydropyridin-3-yl)(methyl) carbamate (Compound No.: 2)

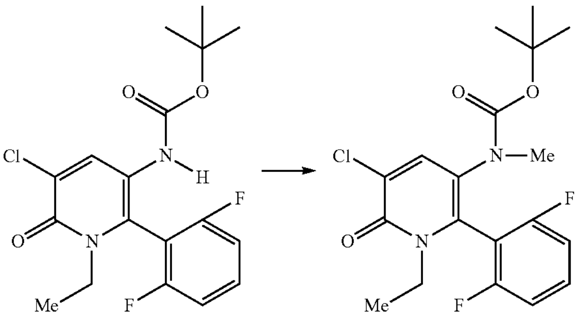 [SMILES: CCn1c(-c2c(F)cccc2F)c(NC(=O)OC(C)(C)C)cc(Cl)c1=O ; CCn1c(-c2c(F)cccc2F)c(N(C)C(=O)OC(C)(C)C)cc(Cl)c1=O]

4 ml of a DMF solution containing 200 mg of tert-butyl (5-chloro-2-(2,6-difluorophenyl)-1-ethyl-6-oxo-1,6-dihydropyridin-3-yl)carbamate, 508 mg of cesium carbonate and 97 μl of methyl iodide was stirred at room temperature for 3 hours. Water and ethyl acetate were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 202 mg of a white amorphous.

Synthetic Example 5

Synthesis of 3-chloro-6-(2,6-difluorophenyl)-1-ethyl-5-(methylamino)-pyridin-2(1H)-one (Compound No.: 3)

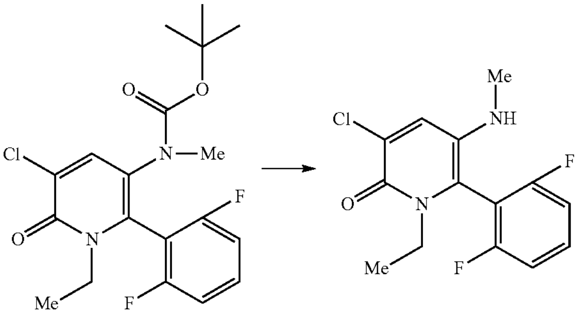 [SMILES: CCn1c(-c2c(F)cccc2F)c(N(C)C(=O)OC(C)(C)C)cc(Cl)c1=O ; CCn1c(-c2c(F)cccc2F)c(NC)cc(Cl)c1=O]

3 ml of a dichloromethane solution containing 200 mg of tert-butyl (5-chloro-2-(2,6-difluorophenyl)-1-ethyl-6-oxo-1,6-dihydropyridin-3-yl)(methyl)-carbamate and 0.5 ml of trifluoroacetic acid was stirred at room temperature overnight. The reaction mixture was added to a mixed solution comprising an aqueous saturated solution of sodium hydrogen carbonate and ethyl acetate, and the layers were separated. The obtained organic layer was washed with a saturated saline solution, and dried over sodium sulfate. The solvent was evaporated under reduced pressure, and the title compound was obtained as 139 mg of a yellow solid.

Synthetic Example 6

Synthesis of 3-chloro-6-(2,6-difluorophenyl)-5-(dimethylamino)-1-ethyl-pyridin-2(1H)-one (Compound No.: 4)

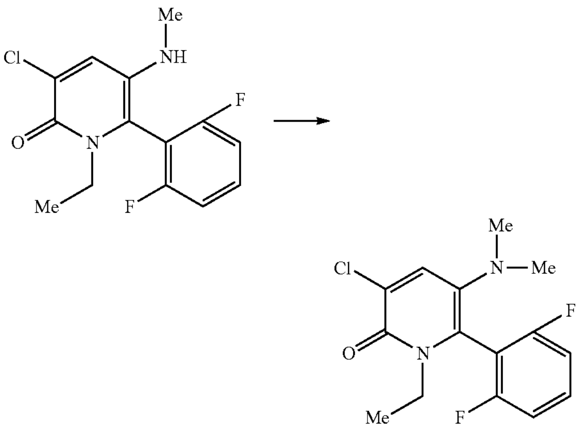

2 ml of a dichloroethane solution containing 30 mg of 3-chloro-6-(2,6-difluorophenyl)-1-ethyl-5-(methylamino)pyridin-2(1H)-one, 74 μl of aqueous formaldehyde solution (37% by weight), 80 mg of sodium triacetoxyborohydride (80% by weight) and 6 μl of acetic acid was stirred at room temperature overnight. An aqueous saturated solution of sodium hydrogen carbonate and ethyl acetate were added to the reaction mixture, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 21 mg of a white solid.

Synthetic Example 7

Synthesis of 3-chloro-6-(2,6-difluorophenyl)-1-ethyl-5-(ethyl(methyl)-amino)pyridin-2(1H)-one (Compound No.: 5)

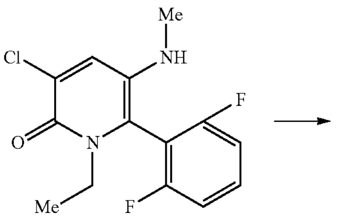

-continued

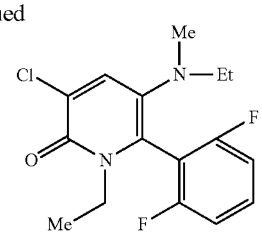

2 ml of a DMF solution containing 55 mg of 3-chloro-6-(2,6-difluorophenyl)-1-ethyl-5-(methylamino)pyridin-2(1H)-one, 600 mg of cesium carbonate and 147 μl of ethyl iodide was stirred at 70° C. for 4 hours, and further at 90° C. for 8 hours. After cooling to room temperature, ethyl acetate and water were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 44 mg of a pale yellow solid.

Synthetic Example 8

Synthesis of methyl N-(5-chloro-2-(2,6-difluorophenyl)-1-ethyl-6-oxo-1,6-dihydropyridin-3-yl)formimidate

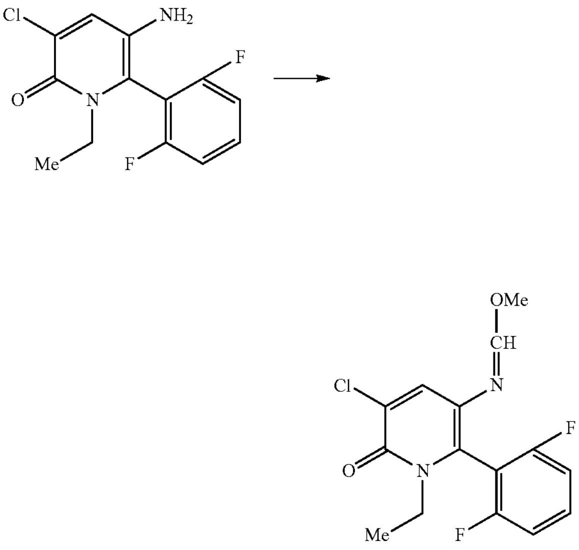

3 ml of trimethyl orthoformate containing 100 mg of 5-amino-3-chloro-6-(2,6-difluorophenyl)-1-ethylpyridin-2(1H)-one and 7 mg of p-toluenesulfonic acid monohydrate was stirred for one hour under reflux. After cooling to room temperature, the solvent was evaporated under reduced pressure. The obtained residue was purified by silica gel column chromatography. The title compound was obtained as 106 mg of a pale pink solid.

$^1$H-NMR ($CDCl_3$) δ: 7.70 (1H, s), 7.47-7.45 (1H, m), 7.47 (1H, s), 7.02 (2H, dd, J=8.4, 7.2 Hz), 3.95 (2H, q, J=7.2 Hz), 3.46 (3H, d, J=0.5 Hz), 1.15 (3H, t, J=7.2 Hz).

Synthetic Example 9

Synthesis of 3-chloro-6-(2,6-difluorophenyl)-1-ethyl-5-((pyrrolidin-1-yl-methylene)amino)pyridin-2(1H)-one (Compound No.: 8)

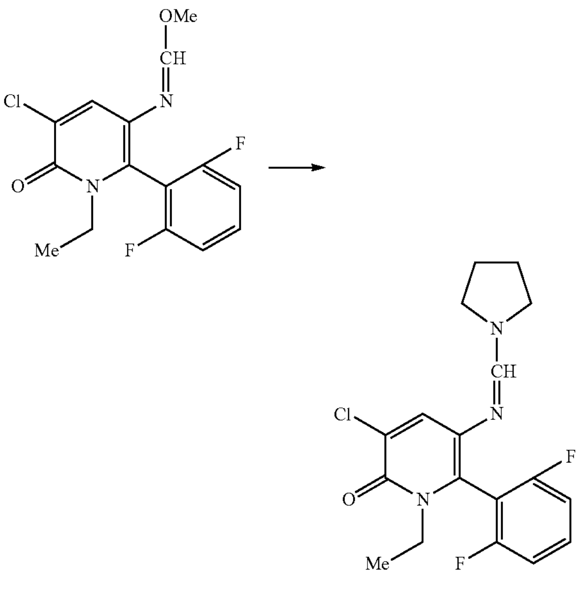

3 ml of a dioxane solution containing 40 mg of methyl N-(5-chloro-2-(2,6-difluorophenyl)-1-ethyl-6-oxo-1,6-dihydropyridin-3-yl)formimidate and 200 μl of pyrrolidine was stirred at 80° C. for 15 hours. After cooling to room temperature, the solvent was evaporated under reduced pressure. The obtained residue was purified by silica gel column chromatography. The title compound was obtained as 43 mg of a yellow solid.

Synthetic Example 10

Synthesis of 5-chloro-1-ethyl-2-(4-fluorophenyl)-6-oxo-1,6-dihydro-pyridine-3-carboxylic acid

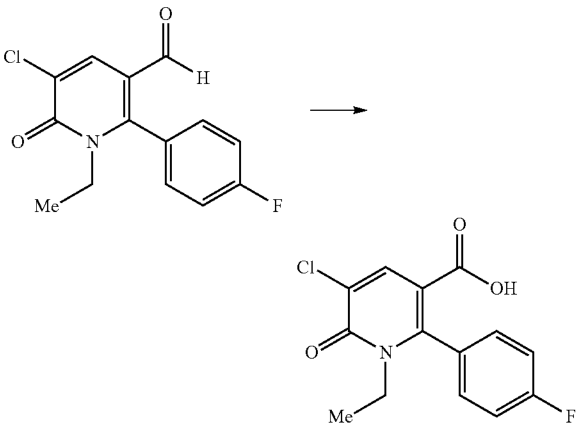

To a mixed solution in 7.5 ml of water, 22.5 ml of THF and 22.5 ml of tertiary butanol containing 1.5 g of 5-chloro-1-ethyl-2-(4-fluorophenyl)-6-oxo-1,6-dihydropyridine-3-carboaldehyde, 2.43 ml of 2-methyl-2-butene and 795 mg of sodium dihydrogen phosphate dehydrate, 1.72 g of sodium chlorite (80% by weight) was added, and the mixture was stirred at room temperature for 3 hours. Water and ethyl acetate were added to the reaction mixture, the layers were separated. The obtained organic layer was successively washed with an aqueous sodium thiosulfate solution and a saturated saline solution, and dried over sodium sulfate. The solvent was evaporated under reduced pressure, and the obtained solid was washed with isopropyl ether. The title compound was obtained as 1.00 g of a yellow solid.

$^1$H-NMR ($CDCl_3$) δ: 8.17 (1H, s), 7.25-7.17 (4H, m), 3.86 (2H, q, J=7.1 Hz), 1.13 (3H, t, J=7.1 Hz).

Synthetic Example 11 tert-Butyl (5-chloro-1-ethyl-2-(4-fluorophenyl)-6-oxo-1,6-dihydropyridin-3-yl)carbamate (Compound No.: 14)

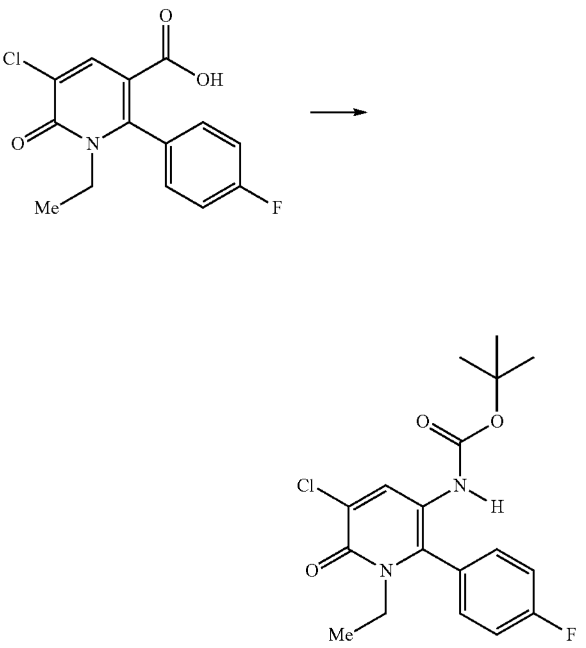

To 20 ml of tertiary butanol containing 1.64 g of 5-chloro-1-ethyl-2-(4-fluorophenyl)-6-oxo-1,6-dihydropyridine-3-carboxylic acid were added 1.82 g of diphenylphosphoryl azide and 0.92 ml of triethylamine, and the resultant mixture was stirred at room temperature for one hour and further at 80° C. for 2 hours. After cooling to room temperature, water and ethyl acetate were added to the reaction mixture and the layers were separated. The obtained organic layer was washed with a saturated saline solution, and dried over sodium sulfate. The solvent was evaporated under reduced pressure, and the obtained residue was purified by silica gel column chromatography. The title compound was obtained as 0.63 g of a pale yellow solid.

Synthetic Example 12

Synthesis of tert-butyl (5-chloro-1-ethyl-2-(4-fluorophenyl)-6-oxo-1,6-dihydropyridin-3-yl)(ethyl) carbamate (Compound No.: 17)

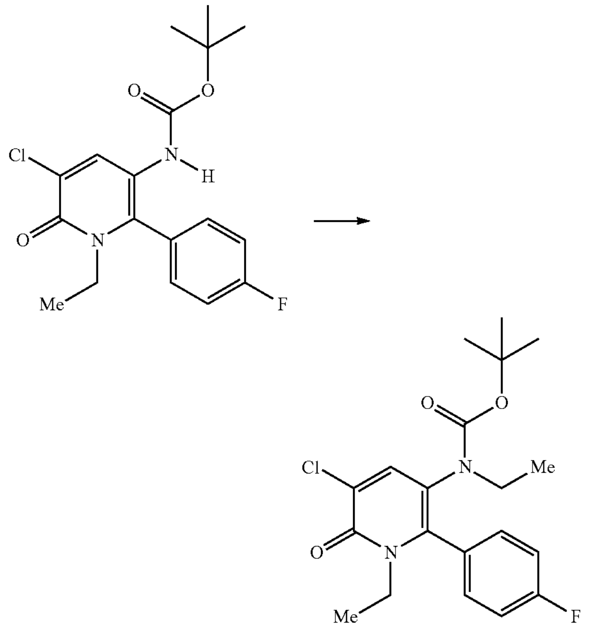

2 ml of a DMF solution containing 200 mg of tert-butyl (5-chloro-1-ethyl-2-(4-fluorophenyl)-6-oxo-1,6-dihydropyridin-3-yl)carbamate, 534 mg of cesium carbonate and 112 μl of ethyl iodide was stirred at 55° C. for 1.5 hours. After cooling to room temperature, water and ethyl acetate were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 190 mg of a white solid.

Synthetic Example 13

Synthesis of 3-chloro-1-ethyl-5-(ethylamino)-6-(4-fluorophenyl)pyridin-2(1H)-one (Compound No.: 20)

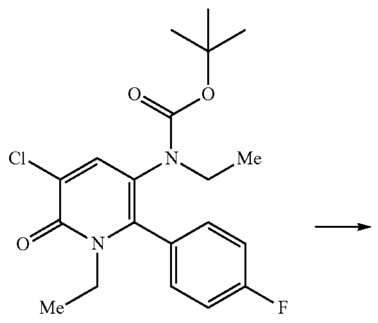

-continued

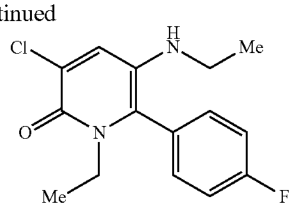

1.6 ml of a dichloromethane solution containing 159 mg of tert-butyl (5-chloro-1-ethyl-2-(4-fluorophenyl)-6-oxo-1,6-dihydropyridin-3-yl)(ethyl)carbamate and 0.4 ml of trifluoroacetic acid was stirred at room temperature overnight. The reaction mixture was added to a mixed solution comprising an aqueous saturated solution of sodium hydrogen carbonate and ethyl acetate, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 113 mg of a green solid.

Synthetic Example 14

Synthesis of 5-chloro-2-(2-chloro-4-fluorophenyl)-1-ethyl-6-oxo-1,6-dihydropyridine-3-carboxylic acid

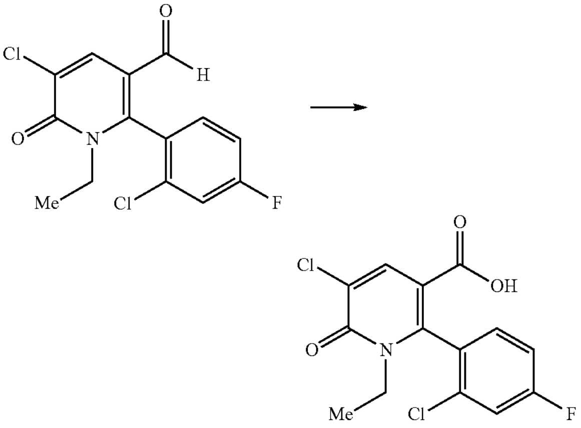

To a mixed solution in 7 ml of water, 21 ml of THF and 21 ml of tertiary butanol containing 1.4 g of 5-chloro-2-(2-chloro-4-fluorophenyl)-1-ethyl-6-oxo-1,6-dihydropyridine-3-carboaldehyde prepared in accordance with Reference Examples 1 to 6, 2.13 ml of 2-methyl-2-butene and 695 mg of sodium dihydrogen phosphate dihydrate was added 1.51 g of sodium chlorite (80% by weight), and the resultant mixture was stirred at room temperature for 2 hours. Water and ethyl acetate were added to the reaction mixture, and the layers were separated. The obtained organic layer was successively washed with an aqueous sodium thiosulfate solution and a saturated saline solution, and dried over sodium sulfate. The solvent was evaporated under reduced pressure, and the obtained solid was washed with isopropyl ether. The title compound was obtained as 1.31 g of a white solid.

$^1$H-NMR ($CDCl_3$) δ: 8.20 (1H, s), 7.28-7.27 (1H, m), 7.21 (1H, dd, J=8.6, 5.8 Hz), 7.14-7.12 (1H, m), 4.14-4.11 (1H, m), 3.58 (1H, td, J=13.6, 6.8 Hz), 1.14 (3H, t, J=7.2 Hz).

Synthetic Example 15

Synthesis of tert-butyl (5-chloro-2-(2-chloro-4-fluorophenyl)-1-ethyl-6-oxo-1,6-dihydropyridin-3-yl) carbamate (Compound No.: 27)

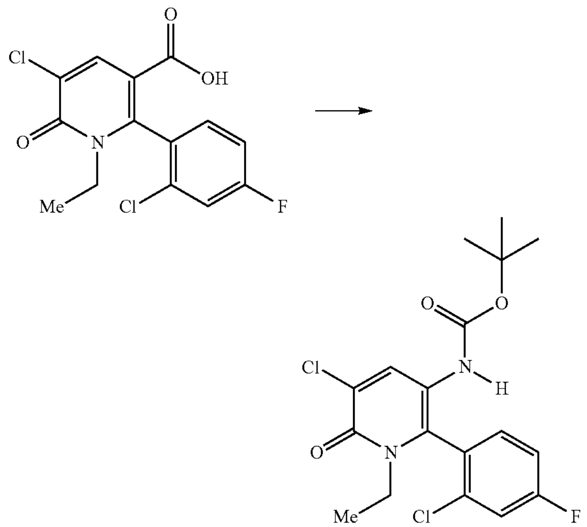

To 25 ml of tertiary butanol containing 1.31 g of 5-chloro-2-(2-chloro-4-fluorophenyl)-1-ethyl-6-oxo-1,6-dihydropyridine-3-carboxylic acid were added 1.11 ml of diphenylphosphoryl azide and 717 ml of triethylamine, and resultant the mixture was stirred at room temperature for 2 hours, and further at 80° C. for 2 hours. After cooling to room temperature, water and ethyl acetate were added to the reaction mixture and the layers were separated. The obtained organic layer was washed with a saturated saline solution, and dried over sodium sulfate. The solvent was evaporated under reduced pressure, and the obtained was purified by silica gel column chromatography. The title compound was obtained as 0.87 g of a white solid.

Synthetic Example 16

Synthesis of 5-amino-3-chloro-6-(2-chloro-4-fluorophenyl)-1-ethylpyridin-2(1H)-one (Compound No.: 32)

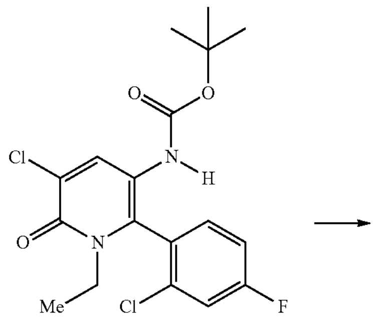

-continued

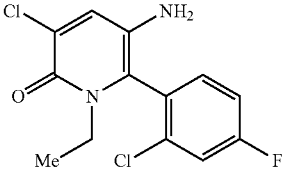

4 ml of a dichloromethane solution containing 0.40 g of tert-butyl (5-chloro-2-(2-chloro-4-fluorophenyl)-1-ethyl-6-oxo-1,6-dihydropyridin-3-yl)carbamate and 1 ml of trifluoroacetic acid was stirred at room temperature for 4 hours. The reaction mixture was added to a mixed solution comprising an aqueous saturated solution of sodium hydrogen carbonate and ethyl acetate, and the layers were separated. The obtained organic layer was washed with a saturated saline solution, and dried over sodium sulfate. The solvent was evaporated under reduced pressure, and the title compound was obtained as 0.30 g of a yellow solid.

Synthetic Example 17

Synthesis of 3-chloro-6-(2-chloro-4-fluorophenyl)-1-ethyl-5-(piperidin-1-yl)pyridin-2(1H)-one (Compound No.: 44)

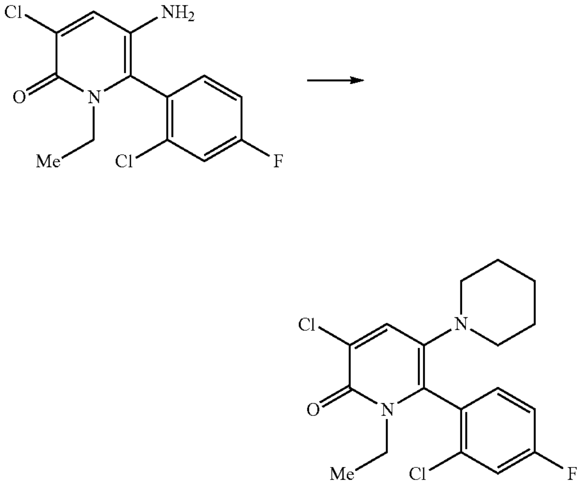

0.5 ml of DMF containing 50 mg of 5-amino-3-chloro-6-(2-chloro-4-fluorophenyl)-1-ethylpyridin-2(1H)-one, 57 mg of 1,5-dibromopentane and 162 mg of cesium carbonate was reacted at 70° C. for 10 hours. After cooling to room temperature, water and ethyl acetate were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 17 mg of a red solid.

Synthetic Example 18

Synthesis of 3-chloro-6-(2-chloro-4-fluorophenyl)-1-ethyl-5-(4-methyl-piperidin-1-yl)pyridin-2(1H)-one (Compound No.: 365)

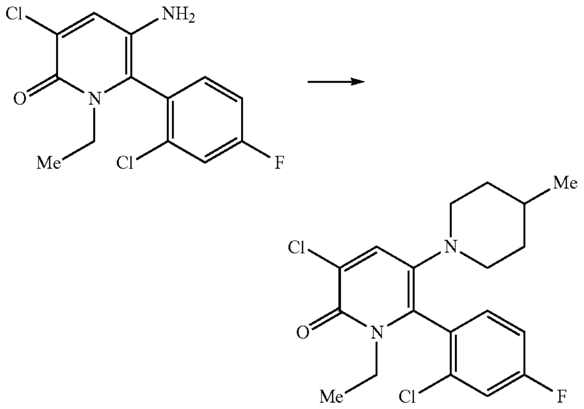

1.5 ml of DMF containing 150 mg of 5-amino-3-chloro-6-(2-chloro-4-fluorophenyl)-1-ethylpyridin-2(1H)-one, 608 mg of 1,5-dibromo-3-methylpentane and 487 mg of cesium carbonate was reacted at 70° C. for 10 hours. After cooling to room temperature, water and ethyl acetate were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 61 mg of a pale yellow solid.

Synthetic Example 19

Synthesis of 3-chloro-6-(2,6-difluorophenyl)-1-ethyl-5-morpholinopyridin-2(1H)-one (Compound No.: 426)

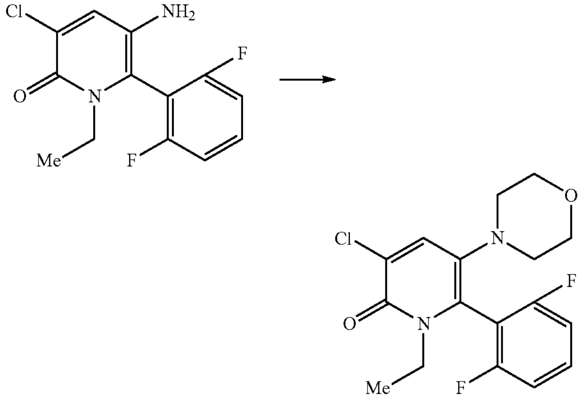

2 ml of DMF containing 180 mg of 5-amino-3-chloro-6-(2,6-difluoro-phenyl)-1-ethylpyridin-2(1H)-one, 176 mg of bis(2-bromoethyl)ether and 616 mg of cesium carbonate was reacted at 50° C. for 2 hours. Then, 1.03 g of cesium carbonate was added, and the resultant mixture was reacted at 100° C. for 8 hours. After cooling to room temperature, an aqueous saturated ammonium chloride solution and ethyl acetate were added to the reaction mixture, and the layers were separated. The obtained organic layer was washed with a saturated saline solution, and dried over sodium sulfate. The solvent was evaporated under reduced pressure, and the obtained residue was purified by silica gel column chromatography. The obtained solid was washed with hexane to thereby obtain the title compound as 87 mg of a pale yellow solid.

Synthetic Example 20

Synthesis of 3-chloro-6-(2,6-difluorophenyl)-1-ethyl-5-(phenylamino)pyridin-2(1H)-one (Compound No.: 317)

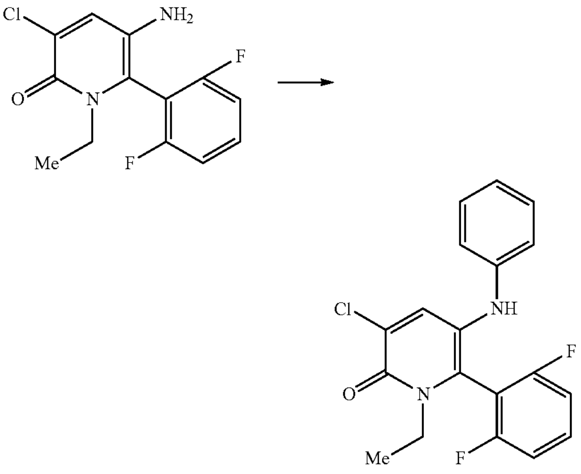

To 3 ml of acetonitrile solution containing 150 mg of 5-amino-3-chloro-6-(2,6-difluorophenyl)-1-ethylpyridin-2(1H)-one were added 193 mg of phenylboronic acid, 0.22 ml of triethylamine and 144 mg of copper(II) acetate, and the resultant mixture was stirred at 60° C. for 2 hours in the presence of air. After cooling to room temperature, an aqueous saturated ammonium chloride solution and ethyl acetate were added to the reaction mixture, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 113 mg of a yellow solid.

Reference Example 1

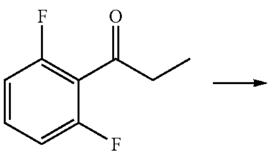

-continued

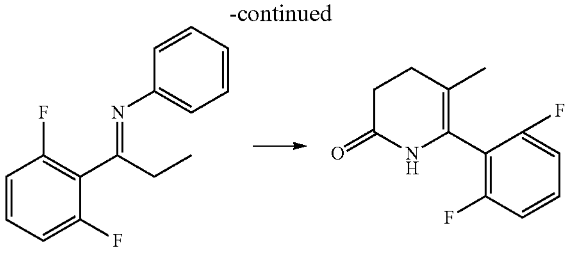

Step 1: Synthesis of 1-(2,6-difluorophenyl)-N-phenylpropane-1-imine

To 100 ml of a dichloromethane solution containing 11.74 g of aniline and 17.01 g of trimethylamine was added dropwise 50 ml of a dichloromethane solution containing 23.91 g of titanium tetrachloride under ice-cooling. To the reaction liquid was added dropwise 30 ml of a dichloromethane solution containing 14.30 g of 1-(2,6-difluorophenyl) propan-1-one, the temperature of the liquid was raised from ice-cooling to room temperature, and the liquid was stirred overnight. To the obtained reaction mixture was added 1N hydrochloric acid and the layers were separated, and drying over sodium sulfate was carried out. The solvent was evaporated under reduced pressure to obtain 21.10 g of a dark green oily substance containing the title compound, which substance was used in the next reaction without further purification.

Step 2: Synthesis of 6-(2,6-difluorophenyl)-5-methyl-3,4-dihydropyridin-2(1H)-one To 200 ml of a dioxane solution containing 21.10 g of 1-(2,6-difluorophenyl)-N-phenylpropane-1-imine obtained in Step 1 and 12.33 g of aluminum chloride was added 6.57 g of acrylamide monomer, and the resultant mixture was stirred at 90° C. for 3 hours. The solvent of the reaction mixture was evaporated under reduced pressure until the amount of the reaction mixture was approximately reduced to half, 1N hydrochloric acid and ethyl acetate were added and the layers were separated. The obtained organic layer was washed with a saturated saline solution, and dried over sodium sulfate. The solvent was evaporated under reduced pressure, and the obtained residue was purified by silica gel column chromatography. The obtained solid was washed with isopropyl ether, and the title compound was obtained as 11.65 g of a white solid.

$^{1}$H-NMR ($CDCl_3$) δ: 7.36-7.34 (1H, m), 6.97-6.94 (2H, m), 6.52 (1H, br s), 2.61-2.59 (2H, m), 2.48-2.47 (2H, m), 1.63 (3H, s).

Reference Example 2

Synthesis of 6-(2,6-difluorophenyl)-1-ethyl-5-methyl-3,4-dihydropyridin-2(1H)-one

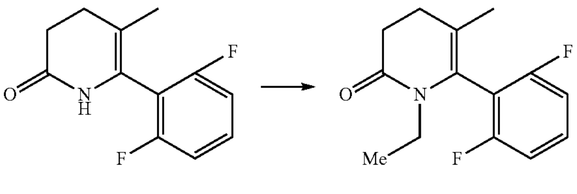 [SMILES: CC1=C(c2c(F)cccc2F)NC(=O)CC1 ; CCN1C(=O)CCC(C)=C1c1c(F)cccc1F]

120 ml of a DMF solution containing 12.40 g of 6-(2,6-difluorophenyl)-5-methyl-3,4-dihydropyridin-2(1H)-one, 54.30 g of cesium carbonate and 25.99 g of ethyl iodide was stirred at 50° C. for 3.5 hours. Then, 27.15 g of cesium carbonate and 13.01 g of ethyl iodide were additionally added, and the resultant mixture was stirred at 50° C. for 2 hours, and further at 60° C. for 1.5 hours. After cooling to room temperature, the reaction mixture was filtered to remove insoluble materials. The solvent of the filtrate was evaporated under reduced pressure, ethyl acetate and water were added and the layers were separated. The obtained organic layer was successively washed with an aqueous sodium thiosulfate solution and a saturated saline solution, and dried over sodium sulfate. The solvent was evaporated under reduced pressure, and the obtained solid was washed with isopropyl ether. The title compound was obtained as 11.98 g of a white solid.

$^{1}$H-NMR ($CDCl_3$) δ: 7.38-7.35 (1H, m), 6.97-6.96 (2H, m), 3.33 (2H, q, J=7.1 Hz), 2.60-2.58 (2H, m), 2.38-2.36 (2H, m), 1.59 (3H, s), 0.91 (3H, t, J=7.1 Hz).

Reference Example 3

Synthesis of 6-(2,6-difluorophenyl)-1-ethyl-5-methylpyridin-2(1H)-one

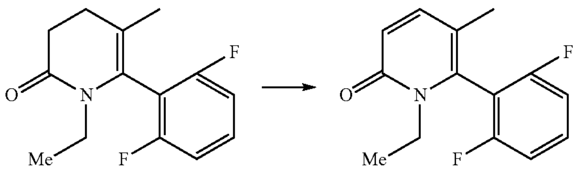 [SMILES: CCN1C(=O)CCC(C)=C1c1c(F)cccc1F ; CCn1c(-c2c(F)cccc2F)c(C)ccc1=O]

170 ml of a toluene solution containing 11.98 g of 6-(2,6-difluorophenyl)-1-ethyl-5-methyl-3,4-dihydropyridin-2(1H)-one and 21.65 g of 2,3-dichloro-5,6-dicyano-p-benzoquinone was stirred at 120° C. for 1.5 hours. After cooling to room temperature, the reaction mixture was filtered to remove insoluble materials. The solvent of the filtrate was evaporated under reduced pressure, and the obtained residue was purified by silica gel column chromatography. The obtained solid was washed with isopropyl ether, and the title compound was obtained as 9.34 g of a pale yellow solid.

$^{1}$H-NMR ($CDCl_3$) δ: 7.50-7.49 (1H, m), 7.27 (2H, d, J=9.5 Hz), 7.09-7.06 (2H, m), 6.63 (1H, d, J=9.5 Hz), 3.83 (2H, q, J=7.1 Hz), 1.80 (3H, s), 1.10 (3H, t, J=7.1 Hz).

Reference Example 4

Synthesis of 3-chloro-6-(2,6-difluorophenyl)-1-ethyl-5-methylpyridin-2(1H)-one

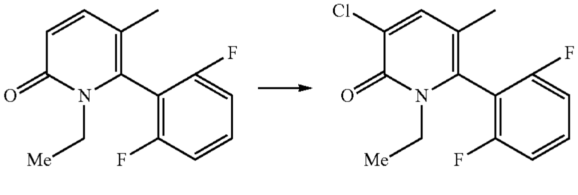 [SMILES: CCn1c(-c2c(F)cccc2F)c(C)ccc1=O ; CCn1c(-c2c(F)cccc2F)c(C)cc(Cl)c1=O]

110 ml of a DMF solution containing 11.36 g of 6-(2,6-difluorophenyl)-1-ethyl-5-methylpyridin-2(1H)-one and 6.69 g of N-chlorosuccinimide was stirred at 70° C. for 50 minutes. After cooling to room temperature, the solvent of the reaction mixture was evaporated under reduced pressure. Ethyl acetate and water were added to the resultant residue, and the layers were separated. The obtained organic layer was successively washed with an aqueous sodium thiosulfate solution and a saturated saline solution, and dried over sodium sulfate. The solvent was evaporated under reduced pressure, and the obtained solid was washed with isopropyl ether. The title compound was obtained as 11.41 g of a white solid.

$^1$H-NMR ($CDCl_3$) δ: 7.53-7.49 (1H, m), 7.50 (1H, s), 7.09-7.07 (2H, m), 3.88 (2H, q, J=7.1 Hz), 1.81 (3H, s), 1.12 (3H, t, J=7.1 Hz).

Reference Example 5

Synthesis of 3-chloro-5-(dibromomethyl)-6-(2,6-difluorophenyl)-1-ethyl-pyridin-2(1H)-one

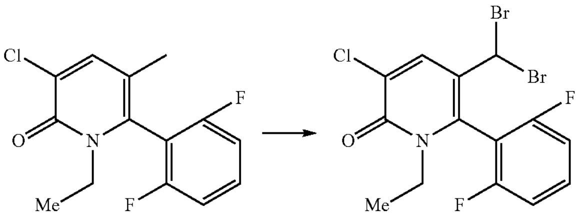 [SMILES: CCn1c(-c2c(F)cccc2F)c(C)cc(Cl)c1=O ; CCn1c(-c2c(F)cccc2F)c(C(Br)Br)cc(Cl)c1=O]

To 230 ml of chlorobenzene solution containing 12.65 g of 3-chloro-6-(2,6-difluorophenyl)-1-ethyl-5-methylpyridin-2(1H)-one were added 16.67 g of N-bromosuccinimide and 366 mg of azobisisobutyronitrile, and the resultant mixture was stirred at 110° C. for 50 minutes. After cooling to room temperature, water and dichloromethane were added to the reaction mixture and the layers were separated. The obtained organic layer was washed with an aqueous sodium thiosulfate solution, and dried over sodium sulfate. The solvent was evaporated under reduced pressure, and the obtained solid was washed with isopropyl ether. The title compound was obtained as 16.88 g of a pale brown solid.

$^1$H-NMR ($CDCl_3$) δ: 8.13 (1H, s), 7.65-7.63 (1H, m), 7.18 (2H, dd, J=8.5, 6.8 Hz), 5.96 (1H, s), 3.82 (2H, q, J=7.1 Hz), 1.13 (3H, t, J=7.1 Hz).

Reference Example 6

Synthesis of 5-chloro-2-(2,6-difluorophenyl)-1-ethyl-6-oxo-1,6-dihydro-pyridine-3-carboaldehyde

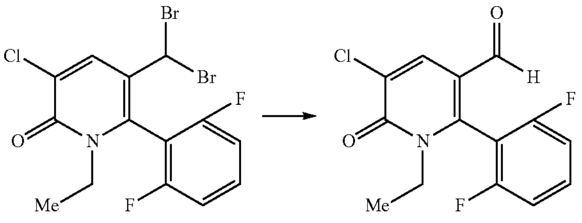 [SMILES: CCn1c(-c2c(F)cccc2F)c(C(Br)Br)cc(Cl)c1=O ; CCn1c(-c2c(F)cccc2F)c(C=O)cc(Cl)c1=O]

To 380 ml of acetonitrile containing 18.95 g of 3-chloro-5-(dibromomethyl)-6-(2,6-difluorophenyl)-1-ethylpyridin-2(1H)-one was added 190 ml of an aqueous solution containing 21.87 g of silver nitrate, and the resultant mixture was stirred at room temperature for 15 minutes. The obtained reaction mixture was filtered to remove insoluble materials. The solvent of the filtrate was evaporated under reduced pressure, water and ethyl acetate were added and the layers were separated. The obtained organic layer was washed with 1N hydrochloric acid and a saturated saline solution, and dried over sodium sulfate. The solvent was evaporated under reduced pressure, and the obtained solid was washed with isopropyl ether. The title compound was obtained as 11.37 g of a pale yellow solid.

$^1$H-NMR ($CDCl_3$) δ: 9.19 (1H, t, J=1.0 Hz), 8.13 (1H, s), 7.67-7.63 (1H, m), 7.18-7.16 (2H, m), 3.94 (2H, q, J=7.1 Hz), 1.19 (3H, t, J=7.1 Hz).

Reference Example 7

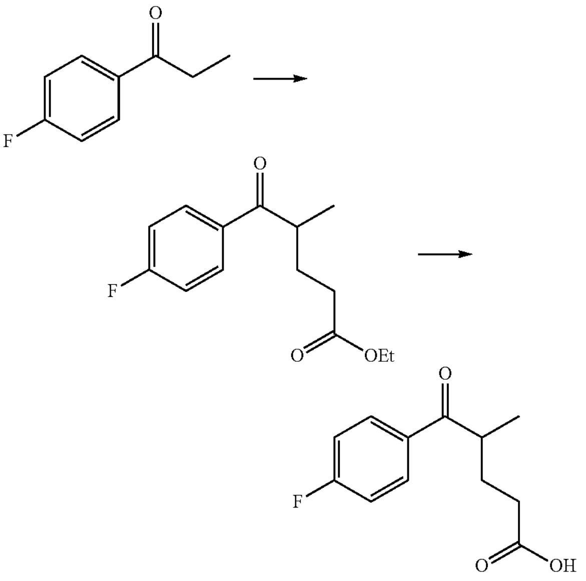

Step 1: Synthesis of ethyl 5-(4-fluorophenyl)-4-methyl-5-oxopentanoate

To 250 ml of a THF solution containing 25.0 g of 4-fluoropropiophenone were added 3.69 g of potassium t-butoxide and 17.27 g of ethyl acrylate, and the resultant mixture was stirred under ice-cooling for 3 hours. An aqueous saturated ammonium chloride solution and ethyl acetate were added to the resultant mixture, and the layers were separated. The obtained organic layer was washed with a saturated saline solution, and dried over sodium sulfate. The solvent was evaporated under reduced pressure, and the title compound was obtained as 41.5 g of a yellow oily substance. This substance was used in the next reaction without further purification.

$^1$H-NMR ($CDCl_3$) δ: 8.01-8.00 (2H, m), 7.17-7.11 (2H, m), 4.11 (2H, q, J=7.2 Hz), 3.55-3.53 (1H, m), 2.42-2.27 (1H, m), 2.19-2.12 (1H, m), 1.78-1.74 (1H, m), 1.23 (3H, t, J=7.2 Hz), 1.21 (3H, d, J=7.0 Hz).

Step 2: Synthesis of 5-(4-fluorophenyl)-4-methyl-5-oxopentanoic acid 200 ml of THF and 100 ml of water were added to 41.5 g of ethyl 5-(4-fluorophenyl)-4-methyl-5-oxopentanoate obtained in Step 1, 20.71 g of lithium hydroxide monohydrate was added and the resultant mixture was stirred at 60° C. for 3 hours. After cooling to room temperature, THF in the reaction mixture was evaporated under reduced pressure. Water and diethyl ether were added and the layers were separated. 12N hydrochloric acid and ethyl acetate were added to the obtained aqueous layer and the layers were separated. The obtained organic layer was washed with a saturated saline solution, and dried over sodium sulfate. The solvent was evaporated under reduced pressure, and the title compound was obtained as 34.0 g of a brown oily substance.

$^1$H-NMR ($CDCl_3$) δ: 8.02-7.98 (2H, m), 7.16-7.13 (2H, m), 3.56-3.53 (1H, m), 2.49-2.33 (2H, m), 2.18-2.15 (1H, m), 1.79-1.77 (1H, m), 1.22 (3H, d, J=7.0 Hz).

Reference Example 8

Synthesis of 6-(4-fluorophenyl)-5-methyl-3,4-dihydropyridin-2(1H)-one

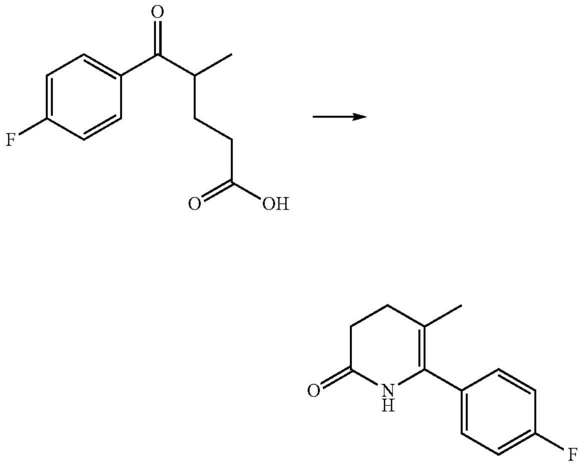

340 ml of an acetic acid solution containing 34.0 g of 5-(4-fluorophenyl)-4-methyl-5-oxopentanoic acid and 233.7 g of ammonium acetate was stirred at 90° C. for 3 hours, and then further stirred at 120° C. for 5 hours. After cooling to room temperature, ethyl acetate and water were added to the reaction mixture and the layers were separated. The obtained organic layer was washed with a saturated saline solution, and dried over sodium sulfate. Evaporation of the solvent was carried out under reduced pressure, and the precipitates were washed with diisopropyl ether. The obtained brown solid (17.8 g) was the title compound.

$^1$H-NMR ($CDCl_3$) δ: 7.29-7.25 (2H, m), 7.11-7.06 (2H, m), 6.77 (1H, s), 2.58-2.55 (2H, m), 2.43-2.41 (2H, m), 1.73 (3H, t, J=0.9 Hz).

Reference Example 9

Synthesis of 1-ethyl-6-(4-fluorophenyl)-5-methyl-3,4-dihydropyridin-2(1H)-one

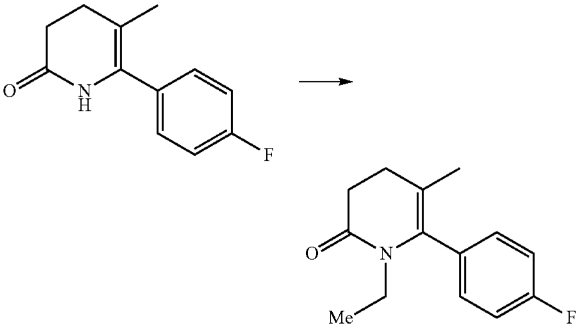

To 173 ml of a DMF solution containing 17.3 g of 6-(4-fluorophenyl)-5-methyl-3,4-dihydropyridin-2(1H)-one were added 20.17 ml of ethyl iodide and 82.16 g of cesium carbonate, and the resultant mixture was stirred at 70° C. for 3 hours, and then further stirred at 90° C. for 8 hours. After cooling to room temperature, water and ethyl acetate were added to the reaction mixture and the layers were separated. The obtained organic layer was successively washed with water and a saturated saline solution, and dried over magnesium sulfate. The solvent was evaporated under reduced pressure, and the obtained residue was purified by silica gel column chromatography. The title compound was obtained as 8.11 g of a pale yellow oily substance.

$^1$H-NMR ($CDCl_3$) δ: 7.19-7.16 (2H, m), 7.12-7.07 (2H, m), 3.33 (2H, q, J=7.0 Hz), 2.59-2.54 (2H, m), 2.33-2.30 (2H, m), 1.60 (3H, s), 0.89 (3H, t, J=7.0 Hz).

Reference Example 10

Synthesis of 1-ethyl-6-(4-fluorophenyl)-5-methylpyridin-2(1H)-one

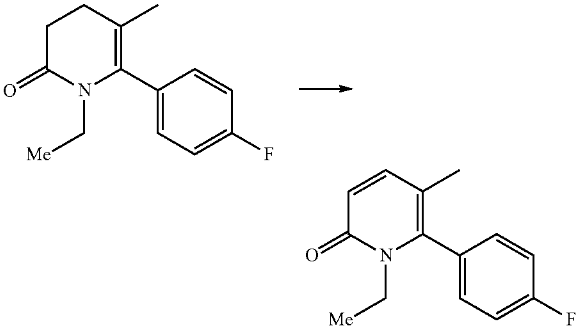

130 ml of a toluene solution containing 8.11 g of 1-ethyl-6-(4-fluorophenyl)-5-methyl-3,4-dihydropyridin-2(1H)-one and 15.79 g of 2,3-dichloro-5,6-dicyano-p-benzoquinone was stirred at 90° C. for 4 hours. After cooling to room temperature, the reaction mixture was filtered to remove insoluble materials. The solvent of the filtrate was evaporated under reduced pressure, and the obtained residue was purified by silica gel column chromatography. The title compound was obtained as 6.30 g of a yellow solid substance.

$^1$H-NMR ($CDCl_3$) δ: 7.25-7.18 (5H, m), 6.58 (1H, d, J=9.3 Hz), 3.79 (2H, q, J=7.1 Hz), 1.73 (3H, s), 1.09 (3H, t, J=7.1 Hz).

Reference Example 11

Synthesis of 3-chloro-1-ethyl-6-(4-fluorophenyl)-5-methylpyridin-2(1H)-one

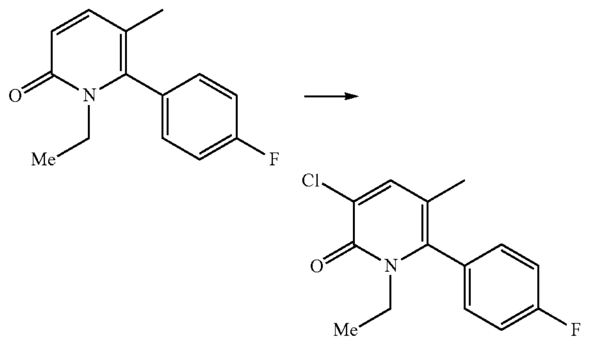

63 ml of a DMF solution containing 6.30 g of 1-ethyl-6-(4-fluorophenyl)-5-methylpyridin-2(1H)-one and 4.00 g of N-chlorosuccinimide was stirred at 70° C. for 3 hours. After cooling to room temperature, ethyl acetate and water were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 6.25 g of a brown solid.

$^1$H-NMR ($CDCl_3$) δ: 7.47 (1H, s), 7.23-7.21 (4H, m), 3.84 (2H, q, J=7.1 Hz), 1.75 (3H, s), 1.11 (3H, t, J=7.1 Hz).

Reference Example 12

Synthesis of 3-chloro-5-(dibromomethyl)-1-ethyl-6-(4-fluorophenyl)pyridin-2(1H)-one

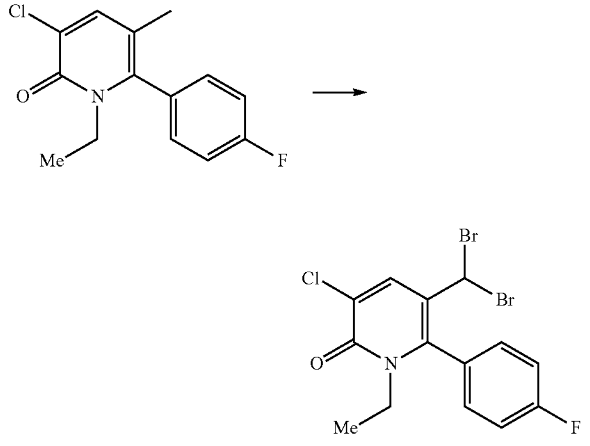

To 100 ml of a chlorobenzene solution containing 5.17 g of 3-chloro-1-ethyl-6-(4-fluorophenyl)-5-methylpyridin-2(1H)-one were added 7.25 g of N— bromosuccinimide and 318 mg of azobisisobutyronitrile, and the resultant mixture was stirred at 90° C. for 4 hours. After cooling to room temperature, water and dichloromethane were added to the reaction mixture and the layers were separated. The obtained organic layer was washed with an aqueous sodium thiosulfate solution, and dried over sodium sulfate. The solvent was evaporated under reduced pressure, and the obtained solid was washed with isopropyl ether. The title compound was obtained as 7.37 g of a brown solid.

$^1$H-NMR ($CDCl_3$) δ: 8.09 (1H, s), 7.35-7.29 (4H, m), 5.86 (1H, s), 3.78 (2H, q, J=7.0 Hz), 1.11 (3H, t, J=7.0 Hz).

Reference Example 13

Synthesis of 5-chloro-1-ethyl-2-(4-fluorophenyl)-6-oxo-1,6-dihydro-pyridine-3-carboaldehyde

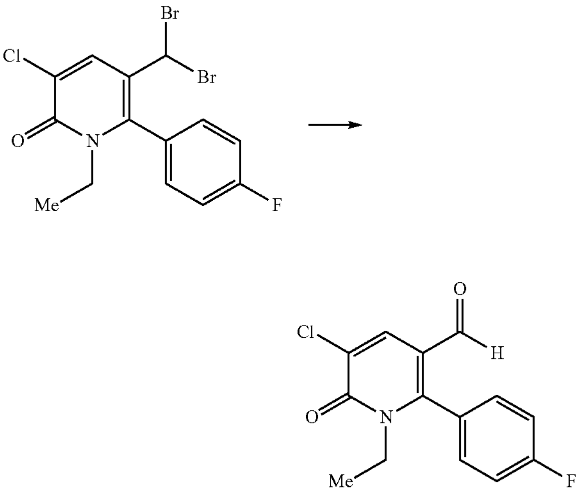

To 130 ml of an acetonitrile containing 8.67 g of 3-chloro-5-(dibromomethyl)-1-ethyl-6-(4-fluorophenyl)pyridin-2(1H)-one was added 65 ml of an aqueous solution containing 10.41 g of silver nitrate and the resultant mixture was stirred at room temperature for 3 hours. The obtained reaction mixture was filtered to remove insoluble materials. The solvent of the filtrate was evaporated under reduced pressure, water and ethyl acetate were added and the layers were separated. The obtained organic layer was washed with 1N hydrochloric acid and a saturated saline solution, and dried over sodium sulfate. The solvent was evaporated under reduced pressure, and the obtained solid was washed with isopropyl ether. The title compound was obtained as 5.01 g of a yellow solid.

$^1$H-NMR ($CDCl_3$) δ: 9.09 (1H, s), 8.11 (1H, s), 7.40-7.39 (2H, m), 7.31-7.29 (2H, m), 3.90 (2H, q, J=7.1 Hz), 1.18 (3H, t, J=7.1 Hz).

The compounds synthesized in accordance with the above-mentioned examples are illustrated in Table 5, but the present invention is not limited to these compounds.

TABLE 5

| Compound | R1 | R2 | R3 | R4 | X | Y |
|---|---|---|---|---|---|---|
| 1 | Et | Cl | H | t-BuOC(═O)— | O | 2,6-di-F—Ph |
| 2 | Et | Cl | Me | t-BuOC(═O)— | O | 2,6-di-F—Ph |
| 3 | Et | Cl | H | Me | O | 2,6-di-F—Ph |
| 4 | Et | Cl | Me | Me | O | 2,6-di-F—Ph |
| 5 | Et | Cl | Me | Et | O | 2,6-di-F—Ph |
| 6 | Et | Cl | Me2N—CH═ | | O | 2,6-di-F—Ph |
| 7 | Et | Cl | Me(Et)N—CH═ | | O | 2,6-di-F—Ph |
| 8 | Et | Cl | (pyrrolidin-1-yl)—CH= | | O | 2,6-di-F—Ph |
| 9 | Et | Cl | Et | t-BuOC(=O)— | O | 2,6-di-F—Ph |
| 10 | Et | Cl | Et | Et | O | 2,6-di-F—Ph |
| 11 | Et | Cl | Et | Pr | O | 2,6-di-F—Ph |
| 12 | Et | N≡C— | —(CH2)5— | | O | 4-F—Ph |
| 13 | Et | Cl | Me | Et | O | 2,4,6-tri-F—Ph |
| 14 | Et | Cl | H | t-BuOC(═O)— | O | 4-F—Ph |
| 15 | Et | Cl | Me | t-BuOC(═O)— | O | 4-F—Ph |
| 16 | Et | Cl | H | Me | O | 4-F—Ph |
| 17 | Et | Cl | Et | t-BuOC(—O)— | O | 4-F—Ph |
| 18 | Et | Cl | Me | Me | O | 4-F—Ph |
| 19 | Et | Cl | Me | Et | O | 4-F—Ph |
| 20 | Et | Cl | H | Et | O | 4-F—Ph |
| 21 | Et | Cl | H | H | O | 4-F—Ph |
| 22 | Et | Cl | Et | Et | O | 4-F—Ph |
| 23 | Et | Cl | Me | Et | O | 2,6-di-F-4-MeO—Ph |
| 24 | Et | Cl | Me | Ac | O | 4-F—Ph |
| 25 | Et | Cl | Et | Ac | O | 4-F—Ph |
| 26 | Et | Cl | H | Ac | O | 2,6-di-F—Ph |
| 27 | Et | Cl | H | t-BuOC(═O)— | O | 2-Cl-4-F—Ph |
| 28 | Et | Cl | Me | Ac | O | 2,6-di-F—Ph |
| 29 | Et | Cl | Et | Ac | O | 2,6-di-F—Ph |
| 30 | Et | Cl | Me | t-BuOC(═O)— | O | 2-Cl-4-F—Ph |
| 31 | Et | Cl | Et | t-BuOC(═O)— | O | 2-Cl-4-F—Ph |
| 32 | Et | Cl | H | H | O | 2-Cl-4-F—Ph |
| 33 | Et | Cl | H | Me | O | 2-Cl-4-F—Ph |
| 34 | Et | Cl | H | Et | O | 2-Cl-4-F—Ph |
| 35 | Et | Cl | Me | Me | O | 2-Cl-4-F—Ph |
| 36 | Et | Cl | Me | Et | O | 2-Cl-4-F—Ph |
| 37 | Et | Cl | Et | Et | O | 2-Cl-4-F—Ph |
| 38 | Et | Cl | Me | Ac | O | 2-Cl-4-F—Ph |
| 39 | Et | Cl | Et | Ac | O | 2-Cl-4-F—Ph |
| 40 | Et | Cl | —(CH2)3—C(—O)— | | O | 2-Cl-4-F—Ph |
| 41 | Et | Cl | —(CH2)4—C(═O)— | | O | 2-Cl-4-F—Ph |
| 42 | Et | Cl | H | MeOC(=O)— | O | 2-Cl-4-F—Ph |
| 43 | Et | Cl | —(CH2)4— | | O | 2-Cl-4-F—Ph |
| 44 | Et | Cl | —(CH2)5— | | O | 2-Cl-4-F—Ph |
| 45 | Et | Cl | H | Pr | O | 4-F—Ph |
| 46 | Et | Cl | H | Bu | O | 4-F—Ph |
| 47 | Et | Cl | H | H | O | 2-Cl-4-MeO—Ph |
| 48 | Et | Cl | H | Me | O | 2-Cl-4-MeO—Ph |
| 49 | Et | Cl | H | Et | O | 2-Cl-4-MeO—Ph |
| 50 | Et | Cl | H | Pr | O | 2-Cl-4-MeO—Ph |
| 51 | Et | Cl | H | Bu | O | 2-Cl-4-MeO—Ph |
| 52 | Et | Cl | Me | Me | O | 2-Cl-4-MeO—Ph |
| 53 | Et | Cl | Me | Et | O | 2-Cl-4-MeO—Ph |
| 54 | Et | Cl | H | Ac | O | 2-Cl-4-MeO—Ph |
| 55 | Et | Cl | H | Ac | O | 2-Cl-4-F—Ph |
| 56 | Et | Cl | Et | Et | O | 2-Cl-4-MeO—Ph |
| 57 | Et | Cl | H | PhCH2— | O | 2-Cl-4-MeO—Ph |
| 58 | Et | Cl | H | PhCH2— | O | 2-Cl-4-F—Ph |
| 59 | Et | Cl | H | H | O | 2,6-di-F—Ph |
| 60 | Et | Cl | H | Et | O | 2,6-di-F—Ph |
| 61 | Et | Br | H | Me | O | 2,4,6-tri-F—Ph |
| 62 | Et | Br | H | Et | O | 2,4,6-tri-F—Ph |
| 63 | Et | Br | H | H | O | 2,4,6-tri-F—Ph |
| 64 | Et | Br | Me | Me | O | 2,4,6-tri-F—Ph |
| 65 | Et | Br | Me | Et | O | 2,4,6-tri-F—Ph |
| 66 | Et | Cl | H | Me | O | 4-N≡C—Ph |
| 67 | Et | Cl | H | Et | O | 4-N≡C—Ph |
| 68 | Et | Cl | H | H | O | 4-N≡C—Ph |
| 69 | Et | Br | Et | Et | O | 2,4,6-tri-F—Ph |
| 70 | Et | Br | H | H | O | 2,6-di-F-4-MeO—Ph |
| 71 | Et | Br | H | Me | O | 2,6-di-F-4-MeO—Ph |
| 72 | Et | Br | H | Et | O | 2,6-di-F-4-MeO—Ph |
| 73 | Et | Br | H | Me | O | 2,4-di-F-6-MeO—Ph |
| 74 | Et | Br | H | Et | O | 2,4-di-F-6-MeO—Ph |
| 75 | Et | Br | Me | Me | O | 2,6-di-F-4-MeO—Ph |
| 76 | Et | Br | Me | Et | O | 2,6-di-F-4-MeO—Ph |
| 77 | Et | Br | Et | Et | O | 2,6-di-F-4-MeO—Ph |
| 78 | F2CHCH2— | Cl | H | H | O | 4-F—Ph |

TABLE 5-continued

| Compound | R1 | R2 | R3 | R4 | X | Y |
|---|---|---|---|---|---|---|
| 79 | F2CHCH2— | Cl | H | Me | O | 4-F—Ph |
| 80 | F2CHCH2— | Cl | H | Et | O | 4-F—Ph |
| 81 | Me | Cl | Me | Et | O | 2,4,6-tri-F—Ph |
| 82 | Me | Cl | Et | Et | O | 2,4,6-tri-F—Ph |
| 83 | Et | Cl | H | F2CHCH2— | O | 4-F—Ph |
| 84 | Et | Cl | H | HC≡CCH2— | O | 4-F—Ph |
| 85 | Me | Br | Me | Et | O | 2,4,6-tri-F—Ph |
| 86 | Me | Br | Et | Et | O | 2,4,6-tri-F—Ph |
| 87 | Me | Br | Me | Et | O | 2,6-di-F-4-MeO—Ph |
| 88 | Me | Br | Et | Et | O | 2,6-di-F-4-MeO—Ph |
| 89 | Et | Cl | H | H | O | 4-Br—Ph |
| 90 | Et | Cl | H | Me | O | 4-Br—Ph |
| 91 | Et | Cl | H | Et | O | 4-Br—Ph |
| 92 | Et | Cl | H | H | O | 4-MeO—Ph |
| 93 | Et | Cl | H | Me | O | 4-MeO—Ph |
| 94 | Et | Cl | H | Et | O | 4-MeO—Ph |
| 95 | Et | Br | H | H | O | 4-F—Ph |
| 96 | Et | HC≡C— | H | t-BuOC(═O)— | O | 4-F—Ph |
| 97 | Et | HC≡C— | H | H | O | 4-F—Ph |
| 98 | Et | Cl | Et | Et | O | 2,4,6-tri-F—Ph |
| 99 | Et | Cl | Et | Et | O | 2,6-di-F-4-MeO—Ph |
| 100 | Et | Br | Me | Ph | O | 2,4,6-tri-F—Ph |
| 101 | Et | Br | Me | H2C—CHCH2— | O | 2,4,6-tri-F—Ph |
| 102 | Et | Br | Me | HC≡CCH2— | O | 2,4,6-tri-F—Ph |
| 103 | Et | Cl | H | Ph | O | 4-F—Ph |
| 104 | Et | Br | | —(CH2)5— | O | 2,4,6-tri-F—Ph |
| 105 | Et | Br | H | i-Pr | O | 2,4,6-tri-F—Ph |
| 106 | Et | Br | Me | N≡CCH2— | O | 2,4,6-tri-F—Ph |
| 107 | Et | Br | Me | i-Pr | O | 2,4,6-tri-F—Ph |
| 108 | Et | Br | H | Pr | O | 2,4,6-tri-F—Ph |
| 109 | Bu | Cl | H | H | O | 4-F—Ph |
| 110 | Hex | Cl | H | H | O | 4-F—Ph |
| 111 | Et | Br | H | Ph | O | 2,4,6-tri-F—Ph |
| 112 | Et | Br | Me | Pr | O | 2,4,6-tri-F—Ph |
| 113 | Et | Br | Et | Pr | O | 2,4,6-tri-F—Ph |
| 114 | Et | Cl | H | Ph | O | 2,4,6-tri-F—Ph |
| 115 | Et | Cl | | EtOC(═O)—CH═ | O | 2,4,6-tri-F—Ph |
| 116 | Et | Br | | —(CH2)4— | O | 2,4,6-tri-F—Ph |
| 117 | Et | Br | H | c-Hex | O | 2,4,6-tri-F—Ph |
| 118 | Et | Br | Me | c-Hex | O | 2,4,6-tri-F—Ph |
| 119 | Et | Br | H | 2-Me—Ph | O | 2,4,6-tri-F—Ph |
| 120 | Et | Br | H | c-Pent | O | 2,4,6-tri-F—Ph |
| 121 | Et | Br | Me | c-Pent | O | 2,4,6-tri-F—Ph |
| 122 | Et | Br | H | 4-Cl—Ph | O | 2,4,6-tri-F—Ph |
| 123 | Et | Br | H | 4-MeO—Ph | O | 2,4,6-tri-F—Ph |
| 124 | Et | Cl | Me | i-Pr | O | 2,4,6-tri-F—Ph |
| 125 | Et | Cl | Me | i-Pr | O | 2,6-di-F-4-MeO—Ph |
| 126 | Et | Br | Me | i-Pr | O | 2,6-di-F-4-MeO—Ph |
| 127 | Et | Br | Me | 4-Cl—Ph | O | 2,4,6-tri-F—Ph |
| 128 | Et | Br | Me | 4-MeO—Ph | O | 2,4,6-tri-F—Ph |
| 129 | Et | Br | Et | H2C═CHCH2— | O | 2,4,6-tri-F—Ph |
| 130 | Et | Br | Et | HC≡CCH2— | O | 2,4,6-tri-F—Ph |
| 131 | Et | Br | Et | i-Pr | O | 2,4,6-tri-F—Ph |
| 132 | Et | Br | Et | i-Pr | O | 2,6-di-F-4-MeO—Ph |
| 133 | Et | Cl | Et | i-Pr | O | 2,4,6-tri-F—Ph |
| 134 | Et | Cl | Et | i-Pr | O | 2,6-di-F-4-MeO—Ph |
| 135 | Et | Br | H | sec-Bu | O | 2,4,6-tri-F—Ph |
| 136 | Et | Br | Me | sec-Bu | O | 2,4,6-tri-F—Ph |
| 137 | Et | Br | Et | sec-Bu | O | 2,4,6-tri-F—Ph |
| 138 | Et | Br | Me | i-Bu | O | 2,4,6-tri-F—Ph |
| 139 | Et | Br | Me | sec-Bu | O | 2,6-di-F-4-MeO—Ph |
| 140 | Et | Br | Et | sec-Bu | O | 2,6-di-F-4-MeO—Ph |
| 141 | Et | Cl | Me | H2C═CHCH2— | O | 2,4,6-tri-F—Ph |
| 142 | Et | Cl | Me | HC≡CC2— | O | 2,4,6-tri-F—Ph |
| 143 | Et | Cl | Et | H2C═CHCH2— | O | 2,4,6-tri-F—Ph |
| 144 | Et | Cl | Et | HC≡CCH2— | O | 2,4,6-tri-F—Ph |
| 145 | Et | Br | H | 4-Me—Ph | O | 2,4,6-tri-F—Ph |
| 146 | Et | Br | Me | 4-Me—Ph | O | 2,4,6-tri-F—Ph |
| 147 | Et | Br | Me | H3CC≡CCH2— | O | 2,4,6-tri-F—Ph |
| 148 | Et | Br | Et | H3CC≡CCH2— | O | 2,4,6-tri-F—Ph |
| 149 | Et | Cl | Me | H3CC≡CCH2— | O | 2,4,6-tri-F—Ph |
| 150 | Et | Cl | Et | H3CC≡CCH2— | O | 2,4,6-tri-F—Ph |
| 151 | Et | Cl | H | H | O | 3,4-di-F—Ph |
| 152 | F2CHCH2— | Cl | Et | Et | O | 2,4,6-tri-F—Ph |
| 153 | F2CHCH2— | Cl | Me | i-Pr | O | 2,4,6-tri-F—Ph |
| 154 | F2CHCH2— | Cl | Et | i-Pr | O | 2,4,6-tri-F—Ph |
| 155 | F2CHCH2— | Cl | Et | Et | O | 2,6-di-F-4-MeO—Ph |
| 156 | F2CHCH2— | Br | Me | i-Pr | O | 2,4,6-tri-F—Ph |

TABLE 5-continued

| Compound | R1 | R2 | R3 | R4 | X | Y |
|---|---|---|---|---|---|---|
| 157 | F2CHCH2— | Br | Et | i-Pr | O | 2,4,6-tri-F—Ph |
| 158 | F2CHCH2— | Cl | Me | HC≡CCH2— | O | 2,4,6-tri-F—Ph |
| 159 | F2CHCH2— | Cl | Et | HC≡CCH2— | O | 2,4,6-tri-F—Ph |
| 160 | F2CHCH2— | Br | Me | HC≡CCH2— | O | 2,4,6-tri-F—Ph |
| 161 | F2CHCH2— | Br | Et | HC≡CCH2— | O | 2,4,6-tri-F—Ph |
| 162 | Et | Cl | Me | i-Pr | O | 2-Cl-4-F—Ph |
| 163 | Et | Cl | H | i-Pr | O | 2,6-di-F—Ph |
| 164 | Et | Cl | HC≡CCH2— | i-Pr | O | 2,4,6-tri-F—Ph |
| 165 | Et | Cl | Me | i-Pr | O | 4-F—Ph |
| 166 | Et | Br | Me | i-Pr | O | 4-F—Ph |
| 167 | Et | Cl | Et | i-Pr | O | 4-F—Ph |
| 168 | Et | Br | Et | i-Pr | O | 4-F—Ph |
| 169 | Et | Cl | Me | i-Pr | O | 2,6-di-F—Ph |
| 170 | Et | Cl | Et | i-Pr | O | 2,6-di-F—Ph |
| 171 | Et | Cl | H | H | O | 3,5-di-F—Ph |
| 172 | Et | Cl | H | H | O | Ph |
| 173 | Et | Br | H | H | O | Ph |
| 174 | Et | Cl | H | i-Pr | O | Ph |
| 175 | Et | Br | H | i-Pr | O | Ph |
| 176 | Et | Br | H | 3-Cl—Ph | O | 2,4,6-tri-F—Ph |
| 177 | Et | Br | Me | 3-Cl—Ph | O | 2,4,6-tri-F—Ph |
| 178 | Et | Br | H | 3-MeO—Ph | O | 2,4,6-tri-F—Ph |
| 179 | Et | Br | Me | 3-MeO—Ph | O | 2,4,6-tri-F—Ph |
| 180 | Et | Br | H | H | O | 2,6-di-F—Ph |
| 181 | Et | Cl | HC≡CCH2- | HC≡CCH2— | O | 2,6-di-F—Ph |
| 182 | Et | Cl | H | (CH3)2CH(CH3)CH— | O | 2,6-di-F—Ph |
| 183 | Et | Cl | Me | HC≡CCH2— | O | 2,6-di-F—Ph |
| 184 | Et | Cl | H | HC≡CCH2— | O | 2,6-di-F—Ph |
| 185 | Et | Cl | Me | i-Pr | O | Ph |
| 186 | Et | Br | Me | i-Pr | O | Ph |
| 187 | Et | Cl | Et | i-Pr | O | Ph |
| 188 | Et | Br | Et | i-Pr | O | Ph |
| 189 | Et | Cl | Et | HC≡CCH2— | O | Ph |
| 190 | Et | Br | Et | HC≡CCH2— | O | Ph |
| 191 | Et | Cl | Et | Et | O | Ph |
| 192 | Et | Br | Et | Et | O | Ph |
| 193 | Et | Cl | Me | PhCH2— | O | 2,4,6-tri-F—Ph |
| 194 | Et | Br | Me | PhCH2— | O | 2,4,6-tri-F—Ph |
| 195 | Et | Cl | Et | PhCH2— | O | 2,4,6-tri-F—Ph |
| 196 | Et | Br | Et | PhCH2— | O | 2,4,6-tri-F—Ph |
| 197 | Et | Cl | Me | (CH3)2CH(CH3)CH— | O | 2,6-di-F—Ph |
| 198 | Et | Br | Me | HC≡CCH2— | O | 2,6-di-F—Ph |
| 199 | Et | Br | H | i-Pr | O | 2,6-di-F—Ph |
| 200 | Et | Br | Me | F3CCH2— | O | 2,6-di-F—Ph |
| 201 | Et | Cl | Me | i-Pr | O | 2-Cl—Ph |
| 202 | Et | Br | Me | i-Pr | O | 2-Cl—Ph |
| 203 | Et | Cl | Et | i-Pr | O | 2-Cl—Ph |
| 204 | Et | Br | Et | i-Pr | O | 2-Cl—Ph |
| 205 | Et | Cl | Et | HC≡CCH2— | O | 2-Cl—Ph |
| 206 | Et | Br | Et | HC≡CCH2— | O | 2-Cl—Ph |
| 207 | Et | Br | Me | Et | O | 2,6-di-F—Ph |
| 208 | Et | Br | Me | i-Pr | O | 2,6-di-F—Ph |
| 209 | Et | Cl | F3CCH2— | F3CCH2— | O | 2,6-di-F—Ph |
| 210 | Me | Cl | H | H | O | 4-F—Ph |
| 211 | Pr | Cl | H | H | O | 4-F—Ph |
| 212 | Et | Cl | H | i-Pr | O | 2-Cl-4-F—Ph |
| 213 | Et | Br | H | i-Pr | O | 2-Cl-4-F—Ph |
| 214 | Et | Br | Me | i-Pr | O | 2-Cl-4-F—Ph |
| 215 | Et | Cl | Et | i-Pr | O | 2-Cl-4-F—Ph |
| 216 | Et | Br | Et | i-Pr | O | 2-Cl-4-F—Ph |
| 217 | Et | Cl | Me | HC≡CCH2— | O | 2-Cl-4-F—Ph |
| 218 | Et | Br | Me | HC≡CCH2— | O | 2-Cl-4-F—Ph |
| 219 | Et | Cl | Et | HC≡CCH2— | O | 2-Cl-4-F—Ph |
| 220 | Et | Br | Et | HC≡CCH2— | O | 2-Cl-4-F—Ph |
| 221 | Et | Cl | H | i-Pr | O | 2-Cl-4-MeO—Ph |
| 222 | Et | Br | H | i-Pr | O | 2-Cl-4-MeO—Ph |
| 223 | Et | Cl | Me | i-Pr | O | 2-Cl-4-MeO—Ph |
| 224 | Et | Br | Me | i-Pr | O | 2-Cl-4-MeO—Ph |
| 225 | Et | Cl | Me | HC≡CCH2— | O | 2-Cl-4-MeO—Ph |
| 226 | Et | Br | Me | HC≡CCH2— | O | 2-Cl-4-MeO—Ph |
| 227 | Et | Cl | Et | HC≡CCH2— | O | 2-Cl-4-MeO—Ph |
| 228 | Et | Br | Et | HC≡CCH2— | O | 2-Cl-4-MeO—Ph |
| 229 | F2CHCH2— | Br | Et | Et | O | 2,4,6-tri-F—Ph |
| 230 | F2CHCH2— | Br | Et | Et | O | 2,6-di-F-4-MeO—Ph |
| 231 | Et | Cl | Me | F2CHCH2— | O | 2-Cl-4-F—Ph |
| 232 | Et | Br | Me | F2CHCH2— | O | 2-Cl-4-F—Ph |
| 233 | Et | Cl | Et | F2CHCH2— | O | 2-Cl-4-F—Ph |
| 234 | Et | Br | Et | F2CHCH2— | O | 2-Cl-4-F—Ph |

TABLE 5-continued

| Compound | R1 | R2 | R3 | R4 | X | Y |
|---|---|---|---|---|---|---|
| 235 | Et | Cl | Me | Ac | O | 2,4,6-tri-F—Ph |
| 236 | Et | Cl | Et | Ac | O | 2,4,6-tri-F—Ph |
| 237 | Et | Cl | H | i-Pr | O | 2,4,6-tri-F—Ph |
| 238 | Et | Cl | H | MeOC(═O)— | O | 2,4,6-tri-F—Ph |
| 239 | Et | Br | H | i-Pr | O | 4-F—Ph |
| 240 | Et | Cl | Me | MeOC(═O)— | O | 2,4,6-tri-F—Ph |
| 241 | Et | Cl | Et | MeOC(—O)— | O | 2,4,6-tri-F—Ph |
| 242 | Et | Cl | Me | i-Pr | O | 2,6-di-F-4-HC≡CCH2O-Ph |
| 243 | Et | Br | Me | i-Pr | O | 2,6-di-F-4-HC═CCH2O—Ph |
| 244 | Et | Cl | Me | i-Pr | O | 2,6-di-F-4-MeOCH2CH2O—Ph |
| 245 | Et | Br | Me | i-Pr | O | 2,6-di-F-4-MeOCH2CH2O—Ph |
| 246 | Et | Cl | H | Me | O | Ph |
| 247 | Et | Br | H | Me | O | Ph |
| 248 | Et | Cl | H | Et | O | Ph |
| 249 | Et | Br | H | Et | O | Ph |
| 250 | Et | Cl | H | i-Pr | O | 4-F—Ph |
| 251 | Et | Cl | Me | HC≡CCH2— | O | 2,6-di-F-4-HC≡CCH2O—Ph |
| 252 | Et | Br | Me | HC≡CCH2— | O | 2,6-di-F-4-HC≡CCH2O—Ph |
| 253 | Et | Cl | Me | HC≡CCH2— | O | 2,6-di-F-4-MeOCH2CH2O—Ph |
| 254 | Et | Br | Me | HC≡CCH2— | O | 2,6-di-F-4-MeOCH2CH2O—Ph |
| 255 | Et | Cl | H | H | O | 2,4-di-F—Ph |
| 256 | Et | Br | H | H | O | 2,4-di-F—Ph |
| 257 | Et | Br | H | F2CHCH2— | O | 2,6-di-F—Ph |
| 258 | Et | Br | Me | F2CHCH2— | O | 2,6-di-F—Ph |
| 259 | Et | Br | Et | F2CHCH2— | O | 2,6-di-F—Ph |
| 260 | Et | Cl | Me | HC≡CCH2— | O | 2,6-di-F-4-MeO—Ph |
| 261 | Et | Br | Me | HC≡CCH2— | O | 2,6-di-F-4-MeO—Ph |
| 262 | Et | Cl | H | i-Pr | O | 2,4-di-F—Ph |
| 263 | Et | Br | H | i-Pr | O | 2,4-di-F—Ph |
| 264 | Et | Cl | Me | i-Pr | O | 2,4-di-F—Ph |
| 265 | Et | Br | Me | i-Pr | O | 2,4-di-F—Ph |
| 266 | Et | Cl | Et | Et | O | 2,4-di-F—Ph |
| 267 | Et | Br | Et | Et | O | 2,4-di-F—Ph |
| 268 | Et | Cl | H | Me | O | 2,4-di-F—Ph |
| 269 | Et | Br | H | Me | O | 2,4-di-F—Ph |
| 270 | Et | Cl | Me | HC≡CCH2— | O | 2,4-di-F—Ph |
| 271 | Et | Br | Me | HC≡CCH2— | O | 2,4-di-F—Ph |
| 272 | Et | Br | | —(CH2)4— | O | 2-Cl-4-F—Ph |
| 273 | Et | Br | | —(CH2)5— | O | 2-Cl-4-F—Ph |
| 274 | Et | Cl | H | Et | O | 2,4-di-F—Ph |
| 275 | Et | Br | H | Et | O | 2,4-di-F—Ph |
| 276 | Et | Cl | Et | HC≡CCH2— | O | 2,4-di-F—Ph |
| 277 | Et | Br | Et | HC═CCH2— | O | 2,4-di-F—Ph |
| 278 | Et | Cl | H | H | O | 2-Br-4-F—Ph |
| 279 | Et | Br | H | H | O | 2-Br-4-F—Ph |
| 280 | Et | Cl | Et | Et | O | 2-Br-4-F—Ph |
| 281 | Et | Br | Et | Et | O | 2-Br-4-F—Ph |
| 282 | Et | Cl | H | i-Pr | O | 2-Br-4-F—Ph |
| 283 | Et | Br | H | i-Pr | O | 2-Br-4-F—Ph |
| 284 | Et | Cl | Me | i-Pr | O | 2-Br-4-F—Ph |
| 285 | Et | Br | Me | i-Pr | O | 2-Br-4-F—Ph |
| 286 | Et | Cl | H | Ph | O | 2-Cl-4-F—PH |
| 287 | Et | Br | H | Ph | O | 2-Cl-4-F—Ph |
| 288 | Et | Cl | Me | Ph | O | 2-Cl-4-F—Ph |
| 289 | Et | Br | Me | Ph | O | 2-Cl-4-F—Ph |
| 290 | Et | Cl | H | Me | O | 2-Br-4-F—Ph |
| 291 | Et | Br | H | Me | O | 2-Br-4-F—Ph |
| 292 | Et | Cl | Me | HC═CCH2— | O | 2-Br-4-F—Ph |
| 293 | Et | Br | Me | HC≡CCH2— | O | 2-Br-4-F—Ph |
| 294 | Et | Cl | H | Ph | O | 2,4-di-F—Ph |
| 295 | Et | Br | H | Ph | O | 2,4-di-F—Ph |
| 296 | Et | Cl | Me | Ph | O | 2,4-di-F—Ph |
| 297 | Et | Br | Me | Ph | O | 2,4-di-F—Ph |
| 298 | Et | Cl | H | Et | O | 2-Br-4-F—Ph |
| 299 | Et | Br | H | Et | O | 2-Br-4-F—Ph |
| 300 | Et | Cl | Et | HC≡CCH2— | O | 2-Br-4-F—Ph |
| 301 | Et | Br | Et | HC═CCH2— | O | 2-Br-4-F—Ph |
| 302 | Et | Cl | H | F2CHCH2— | O | 2,6-di-F—Ph |
| 303 | Et | Cl | Me | F2CHCH2— | O | 2,6-di-F—Ph |
| 304 | Et | Cl | Et | F2CHCH2— | O | 2,6-di-F—Ph |
| 305 | Et | Cl | H | Ph | O | 2-Br-4-F—Ph |
| 306 | Et | Br | H | Ph | O | 2-Br-4-F—Ph |
| 307 | Et | Cl | Me | Ph | O | 2-Br-4-F—Ph |
| 308 | Et | Br | Me | Ph | O | 2-Br-4-F—Ph |
| 309 | Et | Cl | H | F2CHCH2— | O | 2-Cl-4-F—Ph |
| 310 | Et | Br | H | F2CHCH2— | O | 2-Cl-4-F—Ph |
| 311 | Et | Cl | Et | Ph | O | 2-Br-4-F—Ph |
| 312 | Et | Br | Et | Ph | O | 2-Br-4-F—Ph |

TABLE 5-continued

| Compound | R1 | R2 | R3 | R4 | X | Y |
|---|---|---|---|---|---|---|
| 313 | Et | Cl | | —(CH2)4— | O | 2-Br-4-F—Ph |
| 314 | Et | Br | | —(CH2)4— | O | 2-Br-4-F—Ph |
| 315 | Et | Cl | | —(CH2)5— | O | 2-Br-4-F—Ph |
| 316 | Et | Br | | —(CH2)5— | O | 2-Br-4-F—Ph |
| 317 | Et | Cl | H | Ph | O | 2,6-di-F—Ph |
| 318 | Et | Cl | H | 4-F—Ph | O | 2,6-di-F—Ph |
| 319 | Et | Cl | H | 2-Cl-4-F—Ph | O | 2,6-di-F—Ph |
| 320 | Et | Cl | Et | HC≡CCH2— | O | 2,6-di-F—Ph |
| 321 | Et | Br | H | Et | O | 2,6-di-F—Ph |
| 322 | Et | Br | Et | Et | O | 2,6-di-F—Ph |
| 323 | Et | Br | Et | HC≡CCH2— | O | 2,6-di-F—Ph |
| 324 | Et | Cl | Me | F2CHCH2— | O | 2-Br-4-F—Ph |
| 325 | Et | Br | Me | F2CHCH2— | O | 2-Br-4-F—Ph |
| 326 | Et | Cl | Et | F2CHCH2— | O | 2-Br-4-F—Ph |
| 327 | Et | Br | Et | F2CHCH2— | O | 2-Br-4-F—Ph |
| 328 | Et | Br | Me | HC≡CCH2— | O | 2-Cl-6-F—Ph |
| 329 | Et | Br | Et | HC≡CCH2— | O | 2-Cl-6-F—Ph |
| 330 | Et | Br | Me | Et | O | 2-Cl-6-F—Ph |
| 331 | Et | Br | Et | Et | O | 2-Cl-6-F—Ph |
| 332 | Et | Br | H | i-Pr | O | 2-Cl-6-F—Ph |
| 333 | Et | Br | Me | i-Pr | O | 2-Cl-6-F—Ph |
| 334 | Et | Br | H | H | O | 2-Cl-6-F—Ph |
| 335 | Et | Cl | | —(CH2)4— | O | 2,4-di-F—Ph |
| 336 | Et | Br | | —(CH2)4— | O | 2,4-di-F—Ph |
| 337 | Et | Cl | | —(CH2)5— | O | 2,4-di-F—Ph |
| 338 | Et | Br | | —(CH2)5— | O | 2,4-di-F—Ph |
| 339 | Et | Br | Me | Et | O | 2-Cl-4-F—Ph |
| 340 | Et | Br | Et | Et | O | 2-Cl-4-F—Ph |
| 341 | Et | Cl | Me | Et | O | 2-Cl—Ph |
| 342 | Et | Br | Me | Et | O | 2-Cl—Ph |
| 343 | Et | Cl | Me | HC≡CCH2— | O | 2-Cl—Ph |
| 344 | Et | Cl | Me | F2CHCH2— | O | 2-Cl—Ph |
| 345 | Et | Cl | Me | F2CHCH2— | O | 2-F—Ph |
| 346 | Et | Cl | Et | F2CHCH2— | O | 2-F—Ph |
| 347 | Et | Cl | Et | F2CHCH2— | O | 4-F-2-Me—Ph |
| 348 | Et | Cl | H | H | O | 4-F-2-Me—Ph |
| 349 | Et | Br | Me | Et | O | 2-Cl-4-MeO—Ph |
| 350 | Et | Br | Et | Et | O | 2-Cl-4-MeO—Ph |
| 351 | Et | Cl | H | N≡CCH2— | O | 2-Cl-4-F—Ph |
| 352 | Et | Cl | Me | N≡CCH2— | O | 2-Cl-4-F—Ph |
| 353 | Et | Br | Me | N≡CCH2— | O | 2-Cl-4-F—Ph |
| 354 | Et | Br | Me | F2CHCH2— | O | 2-Cl-6-F—Ph |
| 355 | Et | Br | H | H | O | 4-F-2-Me—Ph |
| 356 | Et | Br | H | F2CHCH2— | O | 4-F-2-Me—Ph |
| 357 | Et | Br | H | i-Pr | O | 4-F-2-Me—Ph |
| 358 | Et | Br | Et | Et | O | 4-F-2-Me—Ph |
| 359 | Et | Br | Me | i-Pr | O | 4-F-2-Me—Ph |
| 360 | Et | Br | Me | HC≡CCH2— | O | 2-Cl—Ph |
| 361 | Et | Cl | Me | F2CHCH2— | O | 2,4-di-F—Ph |
| 362 | Et | Br | Me | F2CHCH2— | O | 2,4-di-F—Ph |
| 363 | Et | Cl | H | EtS(═O)2— | O | 2-Cl-4-F—Ph |
| 364 | Et | Cl | Me | EtS(═O)2— | O | 2-Cl-4-F—Ph |
| 365 | Et | Cl | | —CH2CH2CH(CH3)CH2CH2— | O | 2-Cl-4-F—Ph |
| 366 | Et | Cl | Et | Et | O | 2-Cl—Ph |
| 367 | Et | Br | Et | Et | O | 2-Cl—Ph |
| 368 | Et | Cl | Me | Et | O | 2-Br—Ph |
| 369 | Et | Cl | Me | i-Pr | O | 2-Br—Ph |
| 370 | Et | Cl | Me | HC≡CCH2— | O | 2-Br—Ph |
| 371 | Et | Cl | Me | F2CHCH2— | O | 2-Br—Ph |
| 372 | Et | Cl | Et | Et | O | 2-Br—Ph |
| 373 | Et | Cl | Et | HC≡CCH2— | O | 2-Br—Ph |
| 374 | Et | Br | Me | F2CHCH2— | O | 4-F-2-Me—Ph |
| 375 | Et | Br | Et | F2CHCH2— | O | 4-F-2-Me—Ph |
| 376 | Et | Br | H | Me | O | 4-F-2-Me—Ph |
| 377 | Et | Br | H | Et | O | 4-F-2-Me—Ph |
| 378 | Et | Br | Me | HC≡CCH2— | O | 4-F-2-Me—Ph |
| 379 | Et | Br | Et | HC≡CCH2— | O | 4-F-2-Me—Ph |
| 380 | Et | Br | Me | Et | O | 4-F-2-Me—Ph |
| 381 | Et | Cl | Me | HC≡CCH2— | O | 2-F—Ph |
| 382 | Et | Cl | Et | HC≡CCH2— | O | 2-F—Ph |
| 383 | Et | Cl | Et | Et | O | 2-F—Ph |
| 384 | Et | Cl | H | i-Pr | O | 2-F—Ph |
| 385 | Et | Cl | Me | i-Pr | O | 2-F—Ph |
| 386 | Et | Cl | Me | F2CHCH2— | O | 4-F-2-Me—Ph |
| 387 | Et | Cl | H | i-Pr | O | 4-F-2-Me—Ph |
| 388 | Et | Cl | Et | Et | O | 4-F-2-Me—Ph |
| 389 | Et | Cl | H | Me | O | 4-F-2-Me—Ph |
| 390 | Et | Cl | H | Et | O | 4-F-2-Me—Ph |

TABLE 5-continued

| Compound | R1 | R2 | R3 | R4 | X | Y |
|---|---|---|---|---|---|---|
| 391 | Et | Cl | Me | i-Pr | O | 4-F-2-Me—Ph |
| 392 | Et | Cl | Me | HC≡CCH2— | O | 4-F-2-Me—Ph |
| 393 | Et | Cl | Et | HC≡CCH2— | O | 4-F-2-Me—Ph |
| 394 | Et | Cl | Me | Et | O | 4-F-2-Me—Ph |
| 395 | Et | Cl | H | F2CHCH2— | O | 4-F-2-Me—Ph |
| 396 | Et | Br | Et | Et | O | 2-Br—Ph |
| 397 | Et | Br | H | Me | O | 2-Br—Ph |
| 398 | Et | Br | Me | Et | O | 2-Br—Ph |
| 399 | Et | Br | Me | i-Pr | O | 2-Br—Ph |
| 400 | Et | Br | Me | HC≡CCH2— | O | 2-Br—Ph |
| 401 | Et | Br | Et | F2CHCH2— | O | 2-Br—Ph |
| 402 | Et | Br | Me | F2CHCH2— | O | 2-Br—Ph |
| 403 | Et | Br | Et | HC≡CCH2— | O | 2-Br—Ph |
| 404 | Et | Br | Me | F2CHCH2— | O | 2-Cl—Ph |
| 405 | Et | Br | Et | F2CHCH2— | O | 2-Cl—Ph |
| 406 | Et | Cl | Et | F2CHCH2— | O | 2-Cl—Ph |
| 407 | Et | Cl | Et | F2CHCH2— | O | 2-Br—Ph |
| 408 | Et | Cl | MeO(C═O)— | F3CCH2— | O | 2-Cl-4-F—Ph |
| 409 | Et | Br | MeO(C═O)— | F3CCH2— | O | 2-Cl-4-F—Ph |
| 410 | Et | Cl | H | c-Pr—CH2— | O | 2-Cl-4-F—Ph |
| 411 | Et | Cl | Me | c-Pr—CH2— | O | 2-Cl-4-F—Ph |
| 412 | Et | Br | Me | HC≡CCH2— | O | 2-F—Ph |
| 413 | Et | Cl | Me | Pr | O | 2-Cl-4-F—Ph |
| 414 | Et | Cl | Me | Bu | O | 2-Cl-4-F—Ph |
| 415 | Et | Br | Me | Pr | O | 2-Cl-4-F—Ph |
| 416 | Et | Br | Me | Bu | O | 2-Cl-4-F—Ph |
| 417 | Et | Cl | Pr | Pr | O | 2-Cl-4-F—Ph |
| 418 | Et | Cl | Bu | Bu | O | 2-Cl-4-F—Ph |
| 419 | Et | Cl | Me | Et | O | 2-F—Ph |
| 420 | Et | Br | Et | HC≡CCH2— | O | 2-F—Ph |
| 421 | Et | Br | Me | Et | O | 2-F—Ph |
| 422 | Et | Br | Me | F2CHCH2— | O | 2-F—Ph |
| 423 | Et | Br | Et | F2CHCH2— | O | 2-F—Ph |
| 424 | Et | Br | Et | Et | O | 2-F—Ph |
| 425 | Et | Br | Me | i-Pr | O | 2-F—Ph |
| 426 | Et | Cl | —(CH2)2—O—(CH2)2— | | O | 2,6-di-F—Ph |
| 427 | Et | Cl | H | Me | O | 2-Cl—Ph |
| 428 | Et | Cl | H | H | O | 2-Cl—Ph |
| 429 | Et | Br | H | H | O | 2-Cl—Ph |
| 430 | Et | Cl | H | H | O | 2-Br—Ph |
| 431 | Et | Br | H | H | O | 2-Br—Ph |
| 432 | Et | Cl | H | Me | O | 2-Br—Ph |
| 433 | Et | Br | H | Me | O | 2-Cl—Ph |
| 434 | Et | Cl | H | H | O | 2-F—Ph |
| 435 | Et | Br | H | H | O | 2-F—Ph |
| 436 | Et | Cl | H | Me | O | 2-F—Ph |
| 437 | Et | Br | H | Me | O | 2-F—Ph |

Next, with regard to the compounds shown in Table 5, $^{1}$H-NMR data thereof are shown in Table 6.

TABLE 6

| Compound | $^{1}$H-NMR |
|---|---|
| 1 | $^{1}$H-NMR ($CDCl_3$) δ: 7.86 (1H, br s), 7.56-7.54 (1H, m), 7.11-7.09 (2H, m), 5.59 (1H, br s), 3.90 (2H, q, J = 7.1 Hz), 1.35 (9H, s), 1.12 (3H, t, J = 7.1 Hz). |
| 2 | $^{1}$H-NMR ($CDCl_3$) δ: 7.51-7.47 (2H, m), 7.07-7.04 (2H, m), 4.03-3.99 (1H, br m), 3.79-3.75 (1H, br m), 2.85 (3H, s), 1.32 (9H, s), 1.15 (3H, t, J = 7.0 Hz). |
| 3 | $^{1}$H-NMR ($CDCl_3$) δ: 7.56-7.53 (1H, m), 7.50 (1H, s), 7.12 (2H, dd, J = 8.4, 7.0 Hz), 3.85 (2H, q, J = 7.1 Hz), 2.71 (3H, s), 1.11 (3H, t, J = 7.1 Hz). |
| 4 | $^{1}$H-NMR ($CDCl_3$) δ: 7.71 (1H, s), 7.48-7.44 (1H, m), 7.04 (2H, dd, J = 8.4, 7.2 Hz), 3.88 (2H, q, J = 7.0 Hz), 2.39 (6H, s), 1.12 (3H, t, J = 7.0 Hz). |
| 5 | $^{1}$H-NMR ($CDCl_3$) δ: 7.65 (1H, s), 7.47-7.44 (1H, m), 7.04-7.00 (2H, m), 3.89 (2H, q, J = 7.2 Hz), 2.60 (2H, q, J = 7.2 Hz), 2.40 (3H, s), 1.13 (3H, t, J = 7.2 Hz), 0.77 (3H, t, J = 7.2 Hz). |
| 6 | $^{1}$H-NMR ($CDCl_3$) δ: 7.49 (1H, s), 7.44-7.41 (1H, m), 7.38 (1H, s), 6.99 (2H, dd, J = 8.4, 7.2 Hz), 3.95 (2H, q, J = 7.1 Hz), 2.89 (3H, s), 2.60 (2H, s), 1.14 (3H, t, J = 7.1 Hz). |
| 7 | $^{1}$H-NMR ($CDCl_3$) δ: 7.49 (1H, br s), 7.41-7.33 (2H, m), 6.99 (2H, dd, J = 8.3, 7.0 Hz), 3.95 (2H, q, J = 7.1 Hz), 3.15 (2H, br s), 2.86 (3H, br s, minor), 2.60 (3H, br s, major), 1.14 (3H, t, J = 7.1 Hz), 1.09 (3H, br s, major), 0.76 (3H, br s, minor). |
| 8 | $^{1}$H-NMR ($CDCl_3$) δ: 7.61 (1H, s), 7.50 (1H, s), 7.42-7.41 (1H, m), 7.00-6.97 (2H, m), 3.95 (2H, q, J = 7.1 Hz), 3.36 (2H, br s), 3.02 (2H, br s), 1.81-1.79 (4H, br m), 1.14 (3H, t, J = 7.1 Hz). |
| 9 | $^{1}$H-NMR ($CDCl_3$) δ: 7.53-7.47 (1H, m), 7.44 (1H, br s), 7.06-7.03 (2H, m), 3.88 (2H, q, J = 7.0 Hz), 3.58 (1H, br s), 2.74 (1H, br s), 1.34 (9H, s), 1.15 (3H, t, J = 7.0 Hz), 1.06 (3H, t, J = 7.0 Hz). |

TABLE 6-continued

| Compound | $^1$H-NMR |
|---|---|
| 10 | $^1$H-NMR ($CDCl_3$) δ: 7.61 (1H, s), 7.46-7.45 (1H, m), 7.02 (2H, dd, J = 8.3, 7.3 Hz), 3.90 (2H, q, J = 7.1 Hz), 2.65 (4H, q, J = 7.1 Hz), 1.13 (3H, t, J = 7.1 Hz), 0.80 (6H, t, J = 7.1 Hz). |
| 11 | $^1$H-NMR ($CDCl_3$) δ: 7.63 (1H, s), 7.46-7.44 (1H, m), 7.01 (2H, dd, J = 8.6, 7.3 Hz), 3.89 (2H, q, J = 7.2 Hz), 2.64 (2H, q, J = 7.2 Hz), 2.56-2.54 (2H, m), 1.22-1.19 (2H, m), 1.13 (3H, t, J = 7.2 Hz), 0.81 (3H, t, J = 7.2 Hz), 0.64 (3H, t, J = 7.2 Hz). |
| 12 | $^1$H-NMR ($CDCl_3$) δ: 7.85 (1H, s), 7.25-7.18 (4H, m), 3.89 (2H, q, J = 7.1 Hz). 2.54-2.52 (4H, m), 1.35-1.22 (6H, m), 1.14 (3H, t, J = 7.1 Hz). |
| 13 | $^1$H-NMR ($CDCl_3$) δ: 7.64 (1H, s), 6.82-6.80 (2H, m), 3.89 (2H, q, J = 7.1 Hz), 2.60 (2H, q, J = 7.2 Hz), 2.40 (3H, s), 1.13 (3H, t, J = 7.1 Hz), 0.78 (3H, t, J = 7.2 Hz). |
| 14 | $^1$H-NMR ($CDCl_3$) δ: 7.91 (1H, br s), 7.35-7.21 (4H, m), 5.37 (1H, br s), 3.83 (2H, q, J = 7.0 Hz), 1.38 (9H, s), 1.11 (3H, t, J = 7.0 Hz). |
| 15 | $^1$H-NMR ($CDCl_3$) δ: 7.49-7.42 (1H, br m), 7.25-7.14 (4H, br m), 3.89-3.81 (2H, br m), 2.73 (3H, d, J = 11.3 Hz), 1.36 (9H, d, J = 19.9 Hz), 1.14 (3H, q, J = 7.0 Hz). |
| 16 | $^1$H-NMR ($CDCl_3$) δ: 7.46 (1H, s), 7.31-7.24 (4H, m), 3.82 (2H, q, J = 7.0 Hz), 2.66 (3H, s), 1.11 (3H, t, J = 7.0 Hz). |
| 17 | $^1$H-NMR ($CDCl_3$) δ: 7.45-7.37 (1H, br m), 7.23-7.13 (4H, br m), 3.87-3.84 (2H, br m), 3.49-3.27 (1H, br m), 2.74-2.61 (1H, br m), 1.38 (9H, d, J = 6.6 Hz), 1.13 (3H, br s), 0.99 (3H, t, J = 7.2 Hz). |
| 18 | $^1$H-NMR ($CDCl_3$) δ: 7.67 (1H, s), 7.25-7.15 (4H, m), 3.84 (2H, q, J = 7.1 Hz), 2.35 (6H, s), 1.11 (3H, t, J = 7.1 Hz). |
| 19 | $^1$H-NMR ($CDCl_3$) δ: 7.62 (1H, s), 7.22-7.14 (4H, m), 3.85 (2H, q, J = 7.0 Hz), 2.60 (2H, q, J = 7.1 Hz), 2.35 (3H, s), 1.11 (3H, t, J = 7.0 Hz), 0.77 (3H, t, J = 7.1 Hz). |
| 20 | $^1$H-NMR ($CDCl_3$) δ: 7.46 (1H, s), 7.31-7.24 (4H, m), 3.81 (2H, q, J = 7.1 Hz), 2.96 (2H, q, J = 7.1 Hz), 1.11 (3H, t, J = 7.1 Hz), 1.01 (3H, t, J = 7.1 Hz). |
| 21 | $^1$H-NMR ($CDCl_3$) δ: 7.33-7.31 (3H, m), 7.29-7.25 (2H, m), 3.82 (2H, q, J = 7.0 Hz), 1.11 (3H, t, J = 7.0 Hz). |
| 22 | $^1$H-NMR ($CDCl_3$) δ: 7.58 (1H, s), 7.21-7.13 (4H, m), 3.85 (2H, q, J = 7.1 Hz), 2.64 (4H, q, J = 7.2 Hz), 1.12 (3H, t, J = 7.1 Hz), 0.80 (6H, t, J = 7.2 Hz). |
| 23 | $^1$H-NMR ($CDCl_3$) δ: 7.63 (1H, s), 6.56 (2H, d, J = 9.2 Hz), 3.91 (2H, q, J = 7.1 Hz), 3.86 (3H, s), 2.61 (2H, q, J = 7.1 Hz), 2.41 (3H, s), 1.13 (3H, t, J = 7.1 Hz), 0.79 (3H, t, J = 7.1 Hz). |
| 24 | $^1$H-NMR ($CDCl_3$) δ: 7.47 (1H, s, major), 7.29-7.14 (4H, m, major), 3.92-3.78 (2H, m, major), 2.83 (3H, s, major), 1.92 (3H, s, major), 1.18-1.12 (3H, m, major). $^1$H-NMR ($CDCl_3$) δ: 7.42 (1H, s, minor), 7.40-7.38 (1H, m, minor), 7.29-7.14 (3H, m, minor), 3.92-3.78 (2H, m, minor), 2.87 (3H, s, minor), 1.91 (3H, s, minor), 1.18-1.12 (3H, m, minor). |
| 25 | $^1$H-NMR ($CDCl_3$) δ: 7.42 (1H, s, major), 7.28-7.12 (4H, m, major), 3.92-3.80 (3H, m, major), 2.52-2.49 (1H, m, major), 1.94 (3H, s. major), 1.16 (3H, t, J = 7.0 Hz, major), 1.04 (3H, t, J = 7.2 Hz, major). $^1$H-NMR ($CDCl_3$) δ: 7.40-7.36 (2H, m, minor), 7.28-7.12 (3H, m, minor), 3.92-3.80 (2H, m, minor), 3.33-3.30 (1H, m, minor), 2.88-2.85 (1H, m, minor), 1.95 (3H, s, minor), 1.14 (3H, t, J = 7.1 Hz, minor), 1.10 (3H, t, J = 7.2 Hz, minor). |
| 26 | $^1$H-NMR ($CDCl_3$) δ: 7.84 (1H, s), 7.57-7.55 (1H, m), 7.14-7.09 (2H, m), 6.42 (1H, s), 3.94-3.89 (2H, m), 1.90 (3H, d, J = 3.9 Hz), 1.16-1.10 (3H, m). |
| 27 | $^1$H-NMR ($CDCl_3$) δ: 7.85 (1H, br s), 7.36-7.33 (2H, m), 7.17 (1H, ddd, J = 8.5, 7.8, 2.7 Hz), 5.37 (1H, br s), 4.08-4.03 (1H, m), 3.56-3.53 (1H, m), 1.37 (9H, s), 1.12 (3H, t, J = 7.1 Hz). |
| 28 | $^1$H-NMR ($CDCl_3$) δ: 7.56-7.51 (2H, m), 7.13-7.07 (2H, m), 3.94-3.84 (2H, m), 2.86 (3H, d, J = 0.7 Hz), 1.94-1.93 (3H, m), 1.17 (3H, t, J = 7.1 Hz). |
| 29 | $^1$H-NMR ($CDCl_3$) δ: 7.54 (1H, tt, J = 8.4, 3.5 Hz), 7.45 (1H, s), 7.09 (2H, tdt, J = 8.6, 3.7, 1.0 Hz), 3.99-3.86 (2H, m), 3.85-3.78 (1H, m), 2.61-2.57 (1H, m), 1.95 (3H, d, J = 1.5 Hz), 1.17 (3H, t, J = 7.1 Hz), 1.04 (3H, t, J = 7.2 Hz). |
| 30 | $^1$H-NMR ($CDCl_3$) δ: 7.49-7.46 (1H, br m), 7.30-7.28 (2H, br m), 7.10-7.06 (1H, br m), 4.26-4.25 (1H, br m), 3.38 (1H, br s), 2.78 (3H, s), 1.40-1.36 (9H, m), 1.12-1.10 (3H, m). |
| 31 | $^1$H-NMR ($CDCl_3$) δ: 7.49-7.32 (3H, br m), 7.15-7.05 (1H, br m), 4.36-4.33 (1H, br m), 3.50-3.33 (2H, br m), 2.86-2.71 (1H, br m), 1.39-1.37 (9H, br m), 1.15-1.05 (3H, br m), 1.03-1.01 (3H, br m). |
| 32 | $^1$H-NMR ($CDCl_3$) δ: 7.37-7.35 (3H, m), 7.20 (1H, ddd, J = 8.6, 7.5, 2.4 Hz), 4.07-4.04 (1H, m), 3.52-3.49 (1H, m), 1.11 (3H, t, J = 7.0 Hz). |
| 33 | $^1$H-NMR ($CDCl_3$) δ: 7.48 (1H, s), 7.36 (1H, dd, J = 8.3, 2.7 Hz), 7.33 (1H, dd, J = 8.5, 5.9 Hz), 7.20 (1H, ddd, J = 8.5, 7.8, 2.7 Hz), 4.10-4,03 (1H, m), 3.53-3.47 (1H, m), 2.69 (3H, s), 1.11 (3H, t, J = 7.1 Hz). |
| 34 | $^1$H-NMR ($CDCl_3$) δ: 7.47 (1H, s), 7.37 (1H, dd, J = 8.3, 2.5 Hz), 7.32 (1H, dd, J = 8.5, 5.9 Hz), 7.20 (1H, ddd, J = 8.5, 7.8, 2.5 Hz), 4.10-4.03 (1H, m), 3.51-3.46 (1H, m), 3.07-2.94 (2H, m), 1.11 (3H, t, J = 7.1 Hz), 1.03 (3H, t, J = 7.1 Hz). |
| 35 | $^1$H-NMR ($CDCl_3$) δ: 7.70 (1H, s), 7.29-7.28 (1H, m), 7.23 (1H, dd, J = 8.5, 5.9 Hz), 7.12 (1H, ddd, J = 8.5, 8.1, 2.4 Hz), 4.13-4.08 (1H, m), 3.54-3.49 (1H, m), 2.38 (6H, s), 1.11 (3H, t, J = 7.0 Hz). |
| 36 | $^1$H-NMR ($CDCl_3$) δ: 7.64 (1H, s), 7.27-7.26 (1H, m), 7.21 (1H, dd, J = 8.5, 5.9 Hz), 7.11 (1H, ddd, J = 8.5, 7.8, 2.4 Hz), 4.17-4.12 (1H, m), 3.52-3.48 (1H, m), 2.67-2.54 (2H, m), 2.38 (3H, s), 1.11 (3H, t, J = 7.0 Hz), 0.80 (3H, t, J = 7.2 Hz). |
| 37 | $^1$H-NMR ($CDCl_3$) δ: 7.60 (1H, s), 7.27-7.25 (1H, m), 7.22 (1H, dd, J = 8.7, 6.0 Hz), 7.10 (1H, ddd, J = 8.7, 7.8, 2.4 Hz), 4.23-4.19 (1H, m), 3.49-3.44 (1H, m), 2.67-2.65 (4H, m), 1.10 (3H, t, J = 7.1 Hz), 0.82 (6H, t, J = 7.2 Hz). |
| 38 | $^1$H-NMR (DMSO-D6, 80 C. deg.) δ: 7.98 (1H, br s), 7.77 (1H, br s), 7.63 (1H, br s), 7.41 (1H, br s), 4.00 (1H, br s), 3.40 (1H, br s), 2.75-2.69 (3H, br m), 1.88-1.87 (3H, br m), 1.04 (3H, br s). |
| 39 | $^1$H-NMR (DMSO-D6, 80 C. deg.) δ: 7.86-7.78 (1H, br m), 7.66-7.63 (2H, br m), 7.40 (1H, t, J = 7.3 Hz), 3.96-3.94 (1H, br m), 3.61 (1H, br s), 3,44-3.38 (1H, br m), 2.70-2.59 (1H, br m), 1.90-1.89 (3H, br m), 1.05-1.04 (3H, br m), 0.93-0.92 (3H, br m). |
| 40 | $^1$H-NMR ($CDCl_3$) δ: 7.50-7.47 (2H, m), 7.29 (1H, dd, J = 8.2, 2.6 Hz), 7.12 (1H, ddd, J = 8.5, 7.8, 2.4 Hz), 4.28-4.24 (1H, m), 3.48-3.37 (2H, m), 3.18 (1H, ddd, J = 9.5, 8.3, 5.4 Hz), 2.36-2.28 (1H, m), 2.12-2.06 (1H, m), 2.01-1.98 (1H,m), 1.77-1.70 (1H, m), 1.11 (3H, t, J = 7.1 Hz). |
| 41 | $^1$H-NMR ($CDCl_3$) δ: 7.50-7.45 (2H, m), 7.29 (1H, dd, J = 8.2, 2.6 Hz), 7.10 (1H, ddd, J = 8.5, 7.8, 2.4 Hz), 4.34-4.29 (1H, m), 3.40-3.36 (2H, m), 3.16-3.10 (1H, m), 2.37 (1H, td, J = 12.1, 5.5 Hz), 2.10-2.02 (1H, m), 1.71-1.69 (2H, m), 1.50-1.49 (1H, m), 1.37-1.34 (1H, m), 1.11 (3H, t, J = 7.1 Hz). |

TABLE 6-continued

| Compound | $^1$H-NMR |
|---|---|
| 42 | $^1$H-NMR ($CDCl_3$) δ: 7.90 (1H, br s), 7.34 (2H, dd, J = 8.1, 2.7 Hz), 7.18 (1H, ddd, J = 8.5, 7.8, 2.4 Hz), 5.53 (1H, br s), 4.07-4.03 (1H, m), 3.65 (3H, s), 3.55 (1H, q, J = 7.0 Hz), 1.12 (3H, t, J = 7.0 Hz). |
| 43 | $^1$H-NMR ($CDCl_3$) δ: 7.65 (1H, s), 7.28-7.25 (2H, m), 7.10 (1H, ddd, J = 8.5, 7.8, 2.4 Hz), 4.19-4.14 (1H, m), 3.53-3.48 (1H, m), 2.72 (4H, t, J = 6.5 Hz), 1.73-1.63 (4H, m), 1.09 (3H, t, J = 7.1 Hz). |
| 44 | $^1$H-NMR ($CDCl_3$) δ: 7.64 (1H, s), 7.28-7.27 (1H, m), 7.20 (1H, dd, J = 8.5, 5.9 Hz), 7.11 (1H, ddd, J = 8.5, 7.8, 2.4 Hz), 4.12-4.09 (1H, m), 3.64-3.59 (1H, m), 2.62-2.50 (4H, m), 1.34-1.24 (6H, m), 1.12 (3H, t, J = 7.1 Hz). |
| 45 | $^1$H-NMR ($CDCl_3$) δ: 7.45 (1H, s), 7.31-7.23 (4H, m), 3.81 (2H, q, J = 7.1 Hz), 2.87 (2H, t, J = 7.1 Hz), 2.47 (1H, br s), 1.40-1.36 (2H, m), 1.11 (3H, t, J = 7.l Hz), 0.79 (3H, t, J = 7.1 Hz). |
| 46 | $^1$H-NMR ($CDCl_3$) δ: 7.45 (1H, s), 731-7.24 (4H, m), 3.81 (2H, q, J = 7.0 Hz), 2.90 (2H, t, J = 7.1 Hz), 1.37-1.30 (2H, m), 1.26-1.15 (2H, m), 1.11 (3H, t, J = 7.0 Hz), 0.85 (3H, t, J = 7.1 Hz). |
| 47 | $^1$H-NMR ($CDCl_3$) δ: 7.36 (1 H, s), 7.26 (1H, d, J = 8.6 Hz), 7.13 (1H, d, J = 2.6 Hz), 6.99 (1H, dd, J = 8.6, 2.6 Hz), 4.08-4.05 (1H, m), 3.89 (3H, s), 3.58-3.54 (1H, m), 1.12 (3H, t, J = 7.0 Hz). |
| 48 | $^1$H-NMR ($CDCl_3$) δ: 7.49 (1H, s), 7.22 (1H, d, J = 8.6 Hz), 7.12 (1H, d, J = 2.4 Hz), 6.98 (1H, dd, J = 8.6, 2.4 Hz), 4.10-4.05 (1H, m), 3.89 (3H, s), 3.56-3.53 (1H, m), 2.69 (3H, s), 1.11 (3H, t, J = 7.0 Hz). |
| 49 | $^1$H-NMR ($CDCl_3$) δ: 7.49 (1H, br s), 7.22 (1H, d, J = 8.6 Hz), 7.12 (1H, d, J = 2.4 Hz), 6.98 (1H, dd, J = 8.6, 2.4 Hz), 4.10-4.05 (1H, m), 3.89 (3H, s), 3.54-3.51 (1H, m), 3.05-2.94 (2H. m), 1.11 (3H, t, J = 7.2 Hz), 1.04 (3H, t, J = 7.0 Hz). |
| 50 | $^1$H-NMR ($CDCl_3$) δ: 7.46 (1H, s), 7.21 (1H, d, J = 8.6 Hz), 7.12 (1H, d, J = 2.4 Hz), 6.98 (1H, dd, J = 8.6, 2.8 Hz), 4.09-4.05 (1H, m), 3.89 (3H, s), 3.54-3.51 (1H, m), 2.95-2.86 (2H, m), 1.42-1.39 (2H, m), 1.11 (3H, t, J = 7.0 Hz), 0.81 (3H, t, J = 7.3 Hz). |
| 51 | $^1$H-NMR ($CDCl_3$) δ: 7.48 (1H, s), 7.21 (1H, d, J = 8.4 Hz), 7.12 (1H, d, J = 2.6 Hz), 6.98 (1H, dd, J = 8.4, 2.6 Hz), 4.10-4.07 (1H, m), 3.89 (3H, s), 3.53-3.51 (1H, m), 2.98-2.89 (2H, m), 1.40-1.34 (2H, m), 1.23-1.20 (2H, m), 1.11 (3H, t, J = 7.0 Hz), 0.86 (3H, t, J = 7.3 Hz). |
| 52 | $^1$H-NMR ($CDCl_3$) δ: 7.69 (1H, s), 7.13 (1H, d, J = 8.4 Hz), 7.05 (1H, d, J = 2.6 Hz), 6.91 (1H, dd, J = 8.4, 2.6 Hz), 4.12-4.10 (1H, m), 3.87 (3H, s), 3.56-3.53 (1H, m), 2.40 (6H, s), 1.10 (3H, t, J = 7.0 Hz). |
| 53 | $^1$H-NMR ($CDCl_3$) δ: 7.63 (1H, s), 7.12 (1H, d, J = 8.5 Hz), 7.03 (1H, d, J = 2.5 Hz), 6.90 (1H, dd, J = 8.5, 2.5 Hz), 4.16-4.13 (1H, m), 3.87 (3H, s), 3.56-3.52 (1H, m), 2.66-2.58 (2H, m), 2.40 (3H, s), 1.10 (3H, t, J = 7.0 Hz), 0.81 (3H, t, J = 7.0 Hz). |
| 54 | $^1$H-NMR ($CDCl_3$) δ: 7.90 (1H, s), 7.24 (1H, d, J = 8.6 Hz), 7.09 (1H, d, J = 2.5 Hz), 6.96 (1H, dd, J = 8.6, 2.5 Hz), 6.20 (1H, br s), 4.10-4.03 (1H, m), 3.89 (3H. s), 3.60-3.55 (1H, m), 1.89 (3H, s). 1.11 (3H, t, J = 7.1 Hz). |
| 55 | $^1$H-NMR ($CDCl_3$) δ: 7.78 (1H, s), 7.37-7.34 (2H, m), 7.20-7.15 (1H, m), 6.22 (1H, br s), 4.10-4.05 (1H, m), 3.55-3.52 (1H, m), 1.88 (3H, s), 1.12 (3H, t, J = 7.1 Hz). |
| 56 | $^1$H-NMR ($CDCl_3$) δ: 7.59 (1H, s), 7.12 (1H, d, J = 8.6 Hz), 7.02 (1H, d, J = 2.8 Hz), 6.90 (1H, dd, J = 8.6, 2.8 Hz), 4.23-4.19 (1H, m), 3.87 (3H, s), 3.52-3.49 (1H, m), 2.68-2.66 (4H, m), 1.10 (3H, t, J = 7.0 Hz), 0.83 (6H, t, J = 7.2 Hz). |
| 57 | $^1$H-NMR ($CDCl_3$) δ: 7.47 (1H, s), 7.33-7.28 (3H, m), 7.17 (2H, dd, J = 7.7, 1.6 Hz), 7.09 (1H, d, J = 2.6 Hz), 7.00 (1H, d, J = 8.5 Hz), 6.90 (1H, dd, J = 8.5, 2.6 Hz), 4.14-4.13 (2H, m), 4.08-4.03 (1H, m), 3.87 (3H, s), 3.54-3.49 (1H, m), 1.09 (3H, t, J = 7.1 Hz). |
| 58 | $^1$H-NMR ($CDCl_3$) δ: 7.48 (1H, s), 7.33-7.30 (5H, m), 7.14-7.09 (3H, m), 4.12 (2H, s), 4.04 (1H, dd, J = 13.3, 7.0 Hz), 3.47 (1H, dd, J = 13.3, 7.0 Hz), 1.09 (3H, t, J = 7.0 Hz). |
| 59 | $^1$H-NMR ($CDCl_3$) δ: 7.55-7.54 (1H, m), 7.36 (1H, s), 7.12 (2H, t, J = 7.6 Hz), 3.86 (2H, t, J = 7.1 Hz), 1.11 (3H, t, J = 7.1 Hz). |
| 60 | $^1$H-NMR ($CDCl_3$) δ: 7.59-7.53 (1H, m), 7.50 (1H, br s), 7.12 (2H, dd, J = 8.4, 6.9 Hz), 3.84 (2H, q, J = 7.1 Hz), 3.02 (2H, q, J = 7.2 Hz), 1.11 (3H, t, J = 7.1 Hz), 1.04 (3H, t, J = 6.8 Hz). |
| 61 | $^1$H-NMR ($CDCl_3$) δ: 7.70 (1H, s), 6.92-6.87 (2H, m), 3.84 (2H, q, J = 7.1 Hz), 2.71 (3H, s), 2.47 (1H, br s), 1.12 (3H, t, J = 7.1 Hz). |
| 62 | $^1$H-NMR ($CDCl_3$) δ: 7.69 (1H, s), 6.91-6.89 (2H, m), 3.83 (2H, q, J = 7.1 Hz), 3.01 (2H, q, J = 7.0 Hz), 2.29 (1H, br s), 1.11 (3H, t, J = 7.1 Hz), 1.04 (3H, t, J = 7.0 Hz). |
| 63 | $^1$H-NMR ($CDCl_3$) δ: 7.56 (1H, s), 6.93-6.87 (2H, m), 3.84 (2H, q, J = 7.1 Hz), 2.84 (2H, s), 1.11 (3H, t, J = 7.1 Hz). |
| 64 | $^1$H-NMR ($CDCl_3$) δ: 7.90 (1H, s), 6.81 (2H, dd, J = 8.5, 7.1 Hz), 3.87 (2H, q, J = 7.1 Hz), 2.39 (6H, s), 1.13 (3H, t, J = 7.1 Hz). |
| 65 | $^1$H-NMR ($CDCl_3$) δ: 7.84 (1H, s), 6.80 (2H, dd, J = 8.5, 7.1 Hz), 3.88 (2H, q, J = 7.1 Hz), 2.60 (2H, q, J = 7.2 Hz), 2.40 (3H, s), 1.13 (3H, t, J = 7.1 Hz), 0.78 (3H, t, J = 7.2 Hz). |
| 66 | $^1$H-NMR ($CDCl_3$) δ: 7.88-7.87 (2H, m), 7.48-7.46 (3H, m), 3.79 (2H, q, J = 7.0 Hz), 2.66 (3H, s), 2.38 (1H, br s), 1.11 (3H, t, J = 7.0 Hz). |
| 67 | $^1$H-NMR ($CDCl_3$) δ: 7.88-7.87 (2H, m), 7.47-7.46 (3H, m), 3.77 (2H, q, J = 7.0 Hz), 2.96 (2H, q, J = 7.1 Hz), 2.23 (1H, s), 1.11 (3H, t, J = 7.0 Hz), 1.01 (3H, t, J = 7.1 Hz). |
| 68 | $^1$H-NMR ($CDCl_3$) δ: 7.88 (2H, dq, J = 8.1, 1.1 Hz), 7.50 (2H, dq, J = 8.1, 1.1 Hz), 7.33 (1H, s), 3.79 (2H, q, J = 7.0 Hz), 2.75 (2H, s), 1.11 (3H, t, J = 7.0 Hz). |
| 69 | $^1$H-NMR ($CDCl_3$) δ: 7.80 (1H, s), 6.80 (2H, dd, J = 8.5, 7.1 Hz), 3.89 (2H, q, J = 7.1 Hz), 2.65 (4H, q, J = 7.2 Hz), 1.13 (3H, t, J = 7.1 Hz), 0.81 (6H, t, J = 7.2 Hz). |
| 70 | $^1$H-NMR ($CDCl_3$) δ: 7.55 (1H, s), 6.67-6.61 (2H, m), 3.89-3.81 (5H, m), 2.84 (2H, br s), 1.11 (3H, t, J = 7.1 Hz). |
| 71 | $^1$H-NMR ($CDCl_3$) δ: 7.68 (1H, s), 6.64 (2H, dd, J = 13.9, 5.4 Hz), 3.88-3.85 (5H, m), 2.71 (3H, s), 2.54 (1H, br s), 1.12 (3H, t, J = 7.0 Hz). |
| 72 | $^1$H-NMR ($CDCl_3$) δ: 7.67 (1H, s), 6.66-6.61 (2H, m), 3.87-3.84 (5H, m), 3.01 (2H, q, J = 7.1 Hz), 2.38 (1H, s), 1.11 (3H, t, J = 7.1 Hz), 1.04 (3H, t, J = 7.1 Hz). |
| 73 | $^1$H-NMR ($CDCl_3$) δ: 7.67 (1H, s), 6.66-6.59 (2H, m), 3.99-3.92 (1H, m), 3.80 (3H, s), 3.66-3.61 (1H, m), 2.69 (3H, s), 2.47 (1H, s), 1.08 (3H, t, J = 7.1 Hz). |
| 74 | $^1$H-NMR ($CDCl_3$) δ: 7.66 (1H, s), 6.64-6.61 (2H, m), 3.97-3.94 (1H, m), 3.80 (3H, s), 3.66-3.61 (1H, m), 2.99 (2H, q, J = 7.1 Hz), 2.30 (1H, s), 1.08 (3H, t, J = 7.1 Hz), 1.01 (3H, t, J = 7.1 Hz). |

TABLE 6-continued

| Compound | $^1$H-NMR |
| --- | --- |
| 75 | $^1$H-NMR ($CDCl_3$) δ: 7.88 (1H, s), 6.57 (2H, d, J = 8.9 Hz), 3.89 (2H, q, J = 7.1 Hz), 3.86 (3H, s), 2.40 (6H, s), 1.12 (3H, t, J = 7.1 Hz). |
| 76 | $^1$H-NMR ($CDCl_3$) δ: 7.82 (1H, s), 6.56 (2H, dd, J = 14.4, 5.4 Hz), 3.91 (2H, q, J = 7.1 Hz), 3.86 (3H, s), 2.61 (2H, q, J = 7.2 Hz), 2.41 (3H, s), 1.13 (3H, t, J = 7.1 Hz), 0.79 (3H, t, J = 7.2 Hz). |
| 77 | $^1$H-NMR ($CDCl_3$) δ: 7.78 (1H, s), 6.55 (2H, dd, J = 14.4, 5.4 Hz), 3.91 (2H, q, J = 7.2 Hz), 3.86 (3H, s), 2.66 (4H, q, J = 7.1 Hz), 1.13 (3H, t, J = 7.2 Hz), 0.82 (6H, t, J = 7.1 Hz). |
| 78 | $^1$H-NMR ($CDCl_3$) δ: 7.40 (1H, s), 7.32-7.26 (4H, m), 6.25 (1H, tt, J = 57.2, 4.7 Hz), 4.04 (2H, td, J = 12.5, 4.7 Hz), 2.83 (2H, br s). |
| 79 | $^1$H-NMR ($CDCl_3$) δ: 7.55 (1H, s), 7.28 (4H, d, J = 7.0 Hz), 6.27 (1H, tt, J = 57.0, 4.6 Hz), 4.04 (2H, td, J = 12.5, 4.6 Hz), 2.68 (3H, s). |
| 80 | $^1$H-NMR ($CDCl_3$) δ: 7.54 (1H, s), 7.27 (4H, d, J = 7.0 Hz), 6.26 (1H, tt, J = 57.2, 4.7 Hz), 4.03 (2H, td, J = 12.5, 4.8 Hz), 2.98 (2H, q, J = 7.1 Hz), 1.02 (3H, t, J = 7.1 Hz). |
| 81 | $^1$H-NMR ($CDCl_3$) δ: 7.65 (1H, s), 6.84-6.77 (2H, m), 3.39 (3H, s), 2.61 (2H, q, J = 7.2 Hz), 2.42 (3H, s), 0.77 (3H, t, J = 7.2 Hz). |
| 82 | $^1$H-NMR ($CDCl_3$) δ: 7.61 (1H, s), 6.83-6.77 (2H, m), 3.39 (3H, s), 2.66 (4H, q, J = 7.2 Hz), 0.82 (6H, t, J = 7.2 Hz). |
| 83 | $^1$H-NMR ($CDCl_3$) δ: 7.45 (1H, s), 7.32-7.25 (4H, m), 5.71 (1H, tt, J = 55.7, 3.8 Hz), 3.81 (2H, q, J = 7.1 Hz), 3.30-3.20 (2H, m), 2.71 (1H, s), 1.11 (3H, t, J = 7.1 Hz). |
| 84 | $^1$H-NMR ($CDCl_3$) δ: 7.50 (1H, s), 7.33-7.31 (2H, m), 7.29-7.24 (2H, m), 3.82 (2H, q, J = 7.1 Hz), 3.68 (2H, d, J = 2.4 Hz), 2.22 (1H, t, J = 2.4 Hz), 1.12 (3H, t, J = 7.1 Hz). |
| 85 | $^1$H-NMR ($CDCl_3$) δ: 7.85 (1H, s), 6.82-6.79 (2H, m), 3.39 (3H, s), 2.61 (2H, q, J = 7.2 Hz), 2.42 (3H, s), 0.77 (3H, t, J = 7.2 Hz). |
| 86 | $^1$H-NMR ($CDCl_3$) δ: 7.80 (1H, s), 6.81-6.79 (2H, m), 3.39 (3H, s), 2.66 (4H, q, J = 7.2 Hz), 0.82 (6H, t, J = 7.2 Hz). |
| 87 | $^1$H-NMR ($CDCl_3$) δ: 7.83 (1H, s), 6.58-6.54 (2H, m), 3.86 (3H, s), 3.39 (3H, s), 2.61 (2H, q, J = 7.2 Hz), 2.43 (3H, s), 0.78 (3H, t. J = 7.2 Hz). |
| 88 | $^1$H-NMR ($CDCl_3$) δ: 7.79 (1H, s), 6.57-6.53 (2H, m), 3.86 (3H, s), 3.40 (3H, s), 2.66 (4H, q, J = 7.2 Hz), 0.82 (6H, t, J = 7.2 Hz). |
| 89 | $^1$H-NMR ($CDCl_3$) δ: 7.71 (2H, dt, J = 8.8, 2.1 Hz), 7.31 (1H, s), 7.21 (2H, dt, J = 8.8, 2.1 Hz), 3.82 (2H, q, J = 7.1 Hz), 2.75 (2H, br s), 1.11 (3H, t, J = 7.1 Hz). |
| 90 | $^1$H-NMR ($CDCl_3$) δ: 7.70 (2H, dt, J = 8.8, 2.1 Hz), 7.45 (1H, s), 7.18 (2H, dt, J = 8.8, 2.1 Hz), 3.82 (2H, q, J = 7.1 Hz), 2.65 (3H, s), 2.51 (1H, br s), 1.11 (3H, t, J = 7.1 Hz). |
| 91 | $^1$H-NMR ($CDCl_3$) δ: 7.70 (2H, dt, J = 8.8, 2.2 Hz), 7.45 (1H, s), 7.18 (2H, dt, J = 8.8, 2.2 Hz), 3.81 (2H, q, J = 7.1 Hz), 2.96 (2H, q, J = 7.1 Hz), 2.36 (1H, br s), 1.11 (3H, t, J = 7.1 Hz), 1.01 (3H, t, J = 7.1 Hz). |
| 92 | $^1$H-NMR ($CDCl_3$) δ: 7.32 (1H, s), 7.23 (2H, dt, J = 9.3, 2.6 Hz), 7.06 (2H, dt, J = 9.3, 2.6 Hz), 3.88 (3H, s), 3.85 (2H, q, J = 7.1 Hz), 2.78 (2H, br s), 1.11 (3H, t, J = 7.1 Hz). |
| 93 | $^1$H-NMR ($CDCl_3$) δ: 7.44 (1H, s), 7.20 (2H, dt, J = 9.3, 2.4 Hz), 7.05 (2H, dt, J = 9.3, 2.4 Hz), 3.88 (3H, s), 3.85 (2H, q, J = 7.1 Hz), 2.64 (3H, s), 1.11 (3H, t, J = 7.1 Hz). |
| 94 | $^1$H-NMR ($CDCl_3$) δ: 7.44 (1H, s), 7.20 (2H, dt, J = 9.3, 2.4 Hz), 7.05 (2H, dt, J = 9.3, 2.4 Hz), 3.89 (3H, s), 3.84 (2H, q, J = 7.0 Hz), 2.95 (2H, q, J = 7.1 Hz), 2.47 (1H, br s), 1.11 (3H, t, J = 7.0 Hz), 1.00 (3H, t, J = 7.1 Hz). |
| 95 | $^1$H-NMR ($CDCl_3$) δ: 7.53 (1H, s), 7.35-7.30 (2H, m), 7.28-7.24 (2H, m), 3.82 (2H, q, J = 7.1 Hz), 2.74 (2H, br s), 1.11 (3H, t, J = 7.1 Hz). |
| 96 | $^1$H-NMR ($CDCl_3$) δ: 7.89 (1H, s), 7.31-7.21 (4H, m), 5.33 (1H, br s), 3.80 (2H, q, J = 7.0 Hz), 3.35 (1H, s), 1.37 (9H, s), 1.11 (3H, t, J = 7.0 Hz). |
| 97 | $^1$H-NMR ($CDCl_3$) δ: 7.33-7.32 (3H, m), 7.29-7.23 (2H, m), 3.79 (2H, q, J = 7.1 Hz), 3.35 (1H, s), 2.76 (2H, br s), 1.10 (3H, t, J = 7.1 Hz). |
| 98 | $^1$H-NMR ($CDCl_3$) δ: 7.60 (1H, s), 6.81-6.79 (2H, m), 3.89 (2H, q, J = 7.2 Hz), 2.65 (4H, q, J = 7.2 Hz), 1.14 (3H, t, J = 7.2 Hz), 0.81 (6H, t, J = 7.2 Hz). |
| 99 | $^1$H-NMR ($CDCl_3$) δ: 7.59 (1H, s), 6.57-6.53 (2H, m), 3.91 (2H, q, J = 7.2 Hz), 3.86 (3H, s), 2.66 (4H, q, J = 7.2 Hz), 1.13 (3H, t, J = 7.2 Hz), 0.82 (6H, t, J = 7.2 Hz). |
| 100 | $^1$H-NMR ($CDCl_3$) δ: 7.68 (1H, s), 7.19-7.14 (2H, m), 6.78 (1H, t, J = 7.4 Hz), 6.73 (2H, dd, J = 8.3, 7.4 Hz), 6.58 (2H, d, J = 8.3 Hz), 3.92 (2H, q, J = 7.1 Hz), 2.92 (3H, s), 1.19 (3H, t, J = 7.1 Hz). |
| 101 | $^1$H-NMR ($CDCl_3$) δ: 7.84 (1H, s), 6.84-6.78 (2H, m). 5.46-5.37 (1H, m), 5.01-4.99 (1H, m), 4.97 (1H, dq, J = 10.3, 1.4 Hz), 3.88 (2H, q, J = 7.1 Hz), 3.17 (2H, d, J = 6.3 Hz), 2.39 (3H, s), 1.13 (3H, t, J = 7.1 Hz). |
| 102 | $^1$H-NMR ($CDCl_3$) δ: 8.12 (1H, s), 6.83-6.81 (2H, m), 3.88 (2H, q, J = 7.0 Hz), 3.34 (2H, d, J = 2.4 Hz), 2.54 (3H, s), 2.29 (1H, t, J = 2.4 Hz), 1.13 (3H, t, J = 7.1 Hz). |
| 103 | $^1$H-NMR ($CDCl_3$) δ: 7.65 (1H. s), 7.25-7.20 (2H, m), 7.19-7.13 (4H, m), 6.83 (1H, tt, J = 7.3, 1.0 Hz), 6.58-6.56 (2H, m), 4.53 (1H, s), 3.88 (2H, q, J = 7.1 Hz), 1.16 (3H, t, J = 7.1 Hz). |
| 104 | $^1$H-NMR ($CDCl_3$) δ: 7.85 (1H, s). 6.82-6.80 (2H, m), 3.91 (2H, q, J = 7.0 Hz), 2.57 (4H, t, J = 5.0 Hz), 1.34-1.25 (6H, m), 1.14 (3H, t, J = 7.2 Hz). |
| 105 | $^1$H-NMR ($CDCl_3$) δ: 7.69 (1H, s), 6.91-6.87 (2H, m), 3.82 (2H, q, J = 7.1 Hz), 3.36-3.31 (1H, m), 1.11 (3H, t, J = 7.1 Hz), 1.00 (6H, d, J = 6.1 Hz). |
| 106 | $^1$H-NMR ($CDCl_3$) δ: 8.07 (1H, s), 6.86-6.84 (2H, m), 3.87 (2H, q, J = 7.1 Hz), 3.49 (2H, s), 2.63 (3H, s), 1.13 (3H, t, J = 7.1 Hz). |
| 107 | $^1$H-NMR ($CDCl_3$) δ: 7.83 (1H, s), 6.81-6.79 (2H, m), 3.90 (2H, q, J = 7.0 Hz). 2.75-2.70 (1H, m), 2.41 (3H, s), 1.12 (3H, t, J = 7.0 Hz), 0.81 (6H, d, J = 6.4 Hz). |
| 108 | $^1$H-NMR ($CDCl_3$) δ: 7.69 (1H, s), 6.90-6.89 (2H, m), 3.83 (2H, q, J = 7.0 Hz), 2.92 (2H, t, J = 7.2 Hz), 1.42-1.41 (2H, m), 1.11 (3H, t, J = 7.0 Hz), 0.82 (3H, t. J = 7.2 Hz). |
| 109 | $^1$H-NMR ($CDCl_3$) δ: 7.35-7.30 (2H. m), 7.28-7.24 (3H, m), 3.74-3.72 (2H, m), 1.53-1.47 (2H, m), 1.14-1.11 (2H, m), 0.74 (3H, t, J = 7.4 Hz). |
| 110 | $^1$H-NMR ($CDCl_3$) δ: 7.34-7.30 (2H, m), 7.27-7.24 (3H, m), 3.73-3.71 (2H, m), 1.53-1.47 (2H, m), 1.18-1.16 (2H, m), 1.10-1.06 (4H, m), 0.80 (3H, t, J = 7.2 Hz). |
| 111 | $^1$H-NMR ($CDCl_3$) δ: 7.83 (1H, s), 7.18-7.15 (2H, m), 6.84-6.76 (3H, m), 6.59-6.57 (2H, m), 4.65 (1H, s), 3.92 (2H, q, J = 7.1 Hz), 1.16 (3H, t, J = 7.1 Hz). |

TABLE 6-continued

| Compound | $^1$H-NMR |
|---|---|
| 112 | $^1$H-NMR ($CDCl_3$) δ: 7.85 (1H, s), 6.81-6.79 (2H, m), 3.88 (2H, q, J = 7.1 Hz), 2.51 (2H, t, J = 7.3 Hz), 2.38 (3H, s), 1.22-1.19 (2H, m), 1,13 (3H, t, J = 7.1 Hz), 0.63 (3H, t, J = 7.3 Hz). |
| 113 | $^1$H-NMR ($CDCl_3$) δ: 7.81 (1H, s), 6.81-6.79 (2H, m), 3.88 (2H, q, J = 7.1 Hz), 2.64 (2H, q, J = 7.2 Hz), 2.56-2.54 (2H, m), 1.24-1.20 (3H, m), 1.13 (3H, t, J = 7.1 Hz), 0 82 (3H, t, J = 7.2 Hz), 0.67 (3H, t, J = 7.3 Hz). |
| 114 | $^1$H-NMR ($CDCl_3$) δ: 7.63 (1H, s), 7.17-7.15 (2H, m), 6.85-6.77 (3H, m), 6.60-6.56 (2H, m), 4.64 (1H, br s), 3.92 (2H, q, J = 7.1 Hz), 1.16 (3H, t, J = 7.1 Hz). |
| 115 | $^1$H-NMR ($CDCl_3$) δ: 7.79 (1H, s), 7.77 (1H, s), 6.83-6.81 (2H, m), 4.24 (2H, q, J = 7.2 Hz), 4.01 (2H, q, J = 7.2 Hz), 1.27 (3H, t, J = 7.2 Hz), 1.19 (3H, t, J = 7.2 Hz). |
| 116 | $^1$H-NMR ($CDCl_3$) δ: 7.86 (1H, s), 6.81-6.78 (2H, m), 3.88 (2H, q, J = 7.1 Hz), 2.75-2.73 (4H, m), 1.73-1.68 (4H, m), 1.12 (3H, t, J = 7.1 Hz). |
| 117 | $^1$H-NMR ($CDCl_3$) δ: 7.68 (1H, s), 6.90-6.88 (2H, m), 3.81 (2H, q, J = 7.1 Hz), 2.95-2.92 (1H, m), 1.87-1.83 (2H, m), 1.65-1.60 (3H, m), 1.28-1.23 (2H, m), 1.11 (3H, t, J = 7.1 Hz), 1.08-1.07 (1H, m), 0.87-0.80 (2H, m). |
| 118 | $^1$H-NMR ($CDCl_3$) δ: 7.83 (1H, s), 6.80-6.79 (2H, m), 3.89 (2H, q, J = 6.9 Hz), 2.43 (3H, s), 2.28 (1H, s), 1.67-1.64 (2H, m), 1.54-1.51 (1H, m), 1.48-1.46 (2H, m), 1.14-1.05 (5H, m), 0.95-0.89 (3H, m). |
| 119 | $^1$H-NMR ($CDCl_3$) δ: 7.78 (1H, s), 7.06-7.02 (2H, m), 6.78-6.76 (3H, m), 6.56 (1H, d, J = 8.0 Hz), 4.49 (1H, s), 3.93 (2H, q, J = 7.0 Hz), 2.03 (3H, s), 1.16 (3H, t, J = 7.0 Hz). |
| 120 | $^1$H-NMR ($CDCl_3$) δ: 7.72 (1H, s), 6.90-6.87 (2H, m), 3.82 (2H, q, J = 7.1 Hz), 3.63-3.58 (1H, m), 1.86-1.82 (2H, m), 1.52-1.48 (4H, m), 1.22-1.20 (2H, m), 1.11 (3H, t, J = 7.1 Hz). |
| 121 | $^1$H-NMR ($CDCl_3$) δ: 7.84 (1H, s), 6.81-6.79 (2H, m), 3.88 (2H, q, J = 7.1 Hz), 3.04-2.96 (1H, m), 2.36 (3H, s), 1.57-1.53 (2H, m), 1.49-1.44 (4H, m), 1.14-1.12 (5H, m). |
| 122 | $^1$H-NMR ($CDCl_3$) δ: 7.78 (1H, s), 7.11 (2H, dt, J = 9.4, 2.7 Hz), 6.80-6.78 (2H, m), 6.49 (2H, dt, J = 9.4, 2.7 Hz), 4.65 (1H, s), 3.92 (2H, q, J = 7.1 Hz), 1.16 (3H, t, J = 7.1 Hz). |
| 123 | $^1$H-NMR ($CDCl_3$) δ: 7.77 (1H, s), 6.82-6.80 (2H, m), 6.76 (2H, dt, J = 9.5, 3.0 Hz), 6.60 (2H, dt, J = 9.5, 3.0 Hz), 4.41 (1H, s), 3.91 (2H, q, J = 7.1 Hz), 3.75 (3H, s), 1.16 (3H, t, J = 7.1 Hz). |
| 124 | $^1$H-NMR ($CDCl_3$) δ: 7.63 (1H, s), 6.83-6.78 (2H, m), 3.90 (2H, q, J = 7.1 Hz), 2.76-2.70 (1H, m), 2.40 (3H, s), 1.13 (3H, t, J = 7.1 Hz), 0.81 (6H, d, J = 6.3 Hz). |
| 125 | $^1$H-NMR ($CDCl_3$) δ: 7.62 (1H, s), 6.55 (2H, d, J = 9.2 Hz), 3.92 (2H, q, J = 7.0 Hz), 3.86 (3H, s), 2.77-2.72 (1H, m), 2.41 (3H, s), 1.12 (3H, t, J = 7.0 Hz), 0.81 (6H, d, J = 6.4 Hz). |
| 126 | $^1$H-NMR ($CDCl_3$) δ: 7.82 (1H, s), 6.55 (2H, d, J = 9.2 Hz), 3.92 (2H, q, J = 7.0 Hz), 3.86 (3H, s), 2.77-2.72 (1H, m), 2.41 (3H, s), 1.12 (3H, 1, J = 7.0 Hz), 0.81 (6H, d, J = 6.4 Hz). |
| 127 | $^1$H-NMR ($CDCl_3$) δ: 7.66 (1H, s), 7.11 (2H, dt, J = 9.8, 2.8 Hz), 6.77-6.73 (2H, m), 6.49 (2H, dt, J = 9.8, 2.8 Hz), 3.91 (2H, q, J = 7.1 Hz), 2.90 (3H, s), 1.18 (3H, t, J = 7.1 Hz). |
| 128 | $^1$H-NMR ($CDCl_3$) δ: 7.66 (1H, s), 6.77-6.73 (4H, m), 6.55 (2H, dt, J = 9.2, 2.9 Hz), 3.93-3.88 (2H, m), 3.74 (3H, s), 2.87 (3H, s), 1.18 (3H, t, J = 7.2 Hz). |
| 129 | $^1$H-NMR ($CDCl_3$) δ: 7.80 (1H, s), 6.82-6.78 (2H, m), 5.52-5.42 (1H, m), 5.01-4.95 (2H. m), 3.89 (2H, q, J = 7.1 Hz), 3.22 (2H, dt, J = 6.1, 1.3 Hz), 2.67 (2H, q, J = 7.2 Hz), 1.13 (3H, t, J = 7.1 Hz), 0.80 (3H, t, J = 7.2 Hz). |
| 130 | $^1$H-NMR ($CDCl_3$) δ: 8.10 (1H, s), 6.82-6.80 (2H, m), 3.88 (2H, q, J = 7.0 Hz), 3.40 (2H, d, J = 2.4 Hz), 2.85 (2H, q, J = 7.1 Hz), 2.29 (1H, t, J = 2.4 Hz), 1.13 (3H, t, J = 7.0 Hz), 0.84 (3H, t, J = 7.1 Hz). |
| 131 | $^1$H-NMR ($CDCl_3$) δ: 7.82 (1H, s), 6.83-6.78 (2H, m), 3.88 (2H, q, J = 7.0 Hz), 2.87-2.81 (1H, m), 2.73 (2H, q, J = 7.1 Hz), 1.13 (3H, t, J = 7.0 Hz), 0.85-0.82 (9H, m). |
| 132 | $^1$H-NMR ($CDCl_3$) δ: 7.81 (1H, s), 6.56 (2H, dd, J = 11.9, 2.8 Hz), 3.91 (2H, q, J = 7.0 Hz), 3.86 (3H, s), 2.89-2.84 (1H, m), 2.74 (2H, q, J = 7.1 Hz), 1.13 (3H, t, J = 7.0 Hz), 0.85 (3H, t, J = 7.1 Hz), 0.82 (6H, d, J = 6.7 Hz). |
| 133 | $^1$H-NMR ($CDCl_3$) δ: 7.62 (1H, s), 6.83-6.79 (2H, m), 3.88 (2H, q, J = 7.0 Hz), 2.87-2.81 (1H, m), 2.73 (2H, q, J = 7.2 Hz), 1.14 (3H, t, J = 7.0 Hz), 0.84-0.83 (9H, m). |
| 134 | $^1$H-NMR ($CDCl_3$) δ: 7.61 (1H, s), 6.56 (2H, dd, J = 12.2, 2.9 Hz), 3.91 (2H. q, J = 7.1 Hz), 3.86 (3H, s), 2.90-2.83 (1H, m), 2.74 (2H, q, J = 7.2 Hz), 1.13 (3H, t, J = 7.1 Hz), 0.85-0.83 (9H, m). |
| 135 | $^1$H-NMR ($CDCl_3$) δ: 7.66 (1H, s), 6.90-6.87 (2H, m), 3.86-3.77 (2H, m), 3.10-3.07 (1H, m), 2.11 (1H, br s), 1.40-1.37 (1H, m), 1.30-1.19 (1H, m), 1.11 (3H, t, J = 7.1 Hz), 0.97 (3H, d, J = 6.3 Hz), 0.81 (3H, t, J = 7.4 Hz). |
| 136 | $^1$H-NMR ($CDCl_3$) δ: 7.84 (1H, s), 6.82-6.78 (2H, m), 3.98-3.95 (1H, m), 3.83-3.79 (1H, m), 2.48-2.42 (1H, m), 2.39 (3H, s), 1.21-1.16 (2H, m), 1.12 (3H, t, J = 7.1 Hz), 0.81 (3H, d, J = 6.3 Hz), 0.47 (3H, t, J = 7.2 Hz). |
| 137 | $^1$H-NMR ($CDCl_3$) δ: 7.84 (1H, s), 6.82-6.80 (2H, m), 3.96-3.92 (1H, m), 3.80-3.76 (1H, m), 2.78-2.75 (1H, m), 2.72-2.65 (1H, m), 2.53-2.46 (1H, m), 1.24-1.18 (2H, m), 1.13 (3H, t, J = 7.2 Hz), 0.86-0.83 (6H, m), 0.49 (3H, t, J = 7.4 Hz). |
| 138 | $^1$H-NMR ($CDCl_3$) δ: 7.86 (1H, s), 6.81-6.79 (2H, m), 3.88 (2H, q, J = 7.1 Hz). 2.35 (3H, s), 2.31 (2H, d, J = 7.3 Hz), 1.59-1.52 (1H, m), 1.13 (3H, t, J = 7.1 Hz), 0.59 (6H, d, J = 6.6 Hz). |
| 139 | $^1$H-NMR ($CDCl_3$) δ: 7.82 (1H, s), 6.56-6.54 (2H, m), 4.00-3.97 (1H, m), 3.86-3.82 (4H, m), 2.49-2.46 (1H, m), 2.39 (3H, s), 1.26-1.23 (1H, m), 1.19-1.17 (1H, m), 1.11 (3H, t, J = 7.2 Hz), 0.81 (3H, d, J = 6.4 Hz), 0.48 (3H, t, J = 7.5 Hz). |
| 140 | $^1$H-NMR ($CDCl_3$) δ: 7.83 (1H, s), 6.57-6.55 (2H, m), 3.98-3.94 (1H, m), 3.84-3.80 (4H, m), 2.78-2.75 (1H, m), 2.71-2.66 (1H, m), 2.55-2.49 (1H, m), 1.26-1.15 (2H, m), 1.12 (3H, t, J = 7.2 Hz), 0.86 (3H, t, J = 7.0 Hz), 0.82 (3H, d, J = 6.4 Hz), 0.50 (3H, t, J = 7.3 Hz). |
| 141 | $^1$H-NMR ($CDCl_3$) δ: 7.64 (1H, s), 6.82-6.80 (2H, m), 5.46-5.38 (1H, m), 5.01-4.96 (2H, m), 3.89 (2H, q, J = 7.1 Hz), 3.17 (2H, d, J = 6.4 Hz), 2.39 (3H, s), 1.13 (3H, t, J = 7.1 Hz). |
| 142 | $^1$H-NMR ($CDCl_3$) δ: 7.92 (1H, s), 6.83-6.81 (2H, m), 3.88 (2H, q, J = 7.1 Hz), 3.34 (2H, d, J = 2.3 Hz), 2.54 (3H, s), 2.29 (1H, t, J = 2.3 Hz), 1.13 (3H, t, J = 7.1 Hz). |
| 143 | $^1$H-NMR ($CDCl_3$) δ: 7.60 (1H, s), 6.81-6.80 (2H, m), 5.51-5.43 (1H, m), 5.01-4.96 (2H, m), 3.89 (2H, q, J = 7.1 Hz), 3.21 (2H, dt, J = 6.1, 1.4 Hz), 2.67 (2H, q, J = 7.1 Hz), 1.14 (3H, t, J = 7.1 Hz), 0.80 (3H, t, J = 7.1 Hz). |

TABLE 6-continued

| Compound | $^1$H-NMR |
|---|---|
| 144 | $^1$H-NMR ($CDCl_3$) δ: 7.90 (1H, s), 6.82-6.80 (2H, m), 3.88 (2H, q, J = 7.1 Hz), 3.40 (2H, d, J = 2.4 Hz), 2.85 (2H, q, J = 7.1 Hz), 2.28 (1H, t, J = 2.4 Hz), 1.13 (3H, t, J = 7.1 Hz), 0.84 (3H, t, J = 7.1 Hz). |
| 145 | $^1$H-NMR ($CDCl_3$) δ: 7.81 (1H, s), 6.98 (2H, dt, J = 9.0,2.0 Hz), 6.80-6.78 (2H, m), 6.52 (2H, dt, J = 9.0, 2.0 Hz), 4.53 (1H, s), 3.91 (2H, q, J = 7.1 Hz), 2.24 (3H, s), 1.16 (3H, t, J = 7.1 Hz). |
| 146 | $^1$H-NMR ($CDCl_3$) δ: 7.66 ( 1H, s), 6.98 (2H, d, J = 8.1 Hz), 6.74-6.72 (2H, m), 6.51-6.49 (2H, m), 3.92 (2H, q, J = 7.1 Hz), 2.88 (3H, s), 2.24 (3H, s), 1.18 (3H, t, J = 7.1 Hz). |
| 147 | $^1$H-NMR ($CDCl_3$) δ: 8.10 (1H, s), 6.82-6.79 (2H, m), 3.88 (2H, q, J = 7.1 Hz), 3.27 (2H, q, J = 2.4 Hz), 2.50 (3H, s). 1.83 (3H, t, J = 2.4 Hz), 1.12 (3H, t, J = 7.1 Hz). |
| 148 | $^1$H-NMR ($CDCl_3$) δ: 8.09 (1H, s), 6.81-6.79 (2H, m), 3.87 (2H, q, J = 7.1 Hz), 3.32 (2H, q, J = 2.3 Hz), 2.81 (2H, q, J = 7.2 Hz), 1.84 (3H, t, J = 2.3 Hz), 1.13 (3H, t, J = 7.1 Hz), 0.82 (3H, t, J = 7.2 Hz). |
| 149 | $^1$H-NMR ($CDCl_3$) δ: 7.89 (1H, s). 6.82-6.80 (2H, m), 3.88 (2H, q, J = 7.1 Hz), 3.27 (2H, q, J = 2.3 Hz), 2.50 (3H, s), 1.82 (3H, t, J = 2.3 Hz), 1.12 (3H, t, J = 7.1 Hz). |
| 150 | $^1$H-NMR ($CDCl_3$) δ: 7.88 (1H, s), 6.81-6.79 (2H, m), 3.88 (2H, q, J = 7.0 Hz), 3.33 (2H, q, J = 2.3 Hz), 2.81 (2H, q, J = 7.1 Hz), 1.83 (3H, t, J = 2.3 Hz), 1.13 (3H, t, J = 7.0 Hz), 0.82 (3H, t, J = 7.1 Hz). |
| 151 | $^1$H-NMR ($CDCl_3$) δ: 7.38 (1H, dt, J = 10.1, 8.5 Hz), 7.21-7.17 (1H, m), 7.11-7.09 (1H, m), 3.85-3.80 (2H, m), 1.13 (3H, t, J = 7.0 Hz). |
| 152 | $^1$H-NMR ($CDCl_3$) δ: 7.67 (1H, s), 6.82-6.80 (2H, m), 6.14 (1H, tt, J = 56.6, 4.5 Hz), 4.14 (2H, td, J = 12.7, 4.5 Hz), 2.66 (4H, q, J = 7.1 Hz), 0.82 (6H, t, J = 7.1 Hz). |
| 153 | $^1$H-NMR ($CDCl_3$) δ: 7.70 (1H, s), 6.82-6.79 (2H, m), 6.13 (1H, tt, J = 56.6, 4.5 Hz), 4.15 (2H, td, J = 12.8, 4.5 Hz), 2.74-2.69 (1H, m), 2.43 (3H, s), 0.81 (6H, d, J = 6.7 Hz). |
| 154 | $^1$H-NMR ($CDCl_3$) δ: 7.70 (1H, s), 6.84-6.79 (2H, m), 6.15 (1H, tt, J = 56.4, 4.4 Hz), 4.13 (2H, td, J = 12.8, 4.4 Hz), 2.86-2.81 (1H, m), 2.75 (2H, q, J = 7.1 Hz), 0.87 (3H, t, J = 7.1 Hz), 0.82 (6H, d, J = 6.7 Hz). |
| 155 | $^1$H-NMR ($CDCl_3$) δ: 7.66 (1H, s), 6.56 (2H, d, J = 9.5 Hz), 6.14 (1H, tt, J = 56.7, 4.5 Hz), 4.18 (2H, td, J = 12.8, 4.5 Hz), 3.87 (3H, s), 2.67 (4H, q, J = 7.2 Hz), 0.82 (6H, t, J = 7.2 Hz). |
| 156 | $^1$H-NMR ($CDCl_3$) δ: 7.90 (1H, s), 6.82-6.79 (2H, m), 6.12 (1H, tt, J = 56.6, 4.5 Hz), 4.15 (2H, td, J = 12.8, 4.5 Hz), 2.75-2.69 (1H, m), 2.43 (3H, s), 0.81 (6H, d, J = 6.3 Hz). |
| 157 | $^1$H-NMR ($CDCl_3$) δ: 7.89 (1H, s), 6.84-6.79 (2H, m), 6.15 (1H, tt, J = 56.6, 4.5 Hz), 4.13 (2H, td, J = 12.8, 4.5 Hz), 2.87-2.81 (1H, m), 2.76 (2H, q, J = 7.2 Hz), 0.86 (3H, t, J = 7.2 Hz), 0.82 (6H, d, J = 6.6 Hz). |
| 158 | $^1$H-NMR ($CDCl_3$) δ: 8.00 (1H, s), 6.83-6.82 (2H, m), 6.12 (1H, tt, J = 56.4, 4.5 Hz), 4.13 (2H, td, J = 12.7, 4.5 Hz), 3.34 (2H, d, J = 2.3 Hz), 2.56 (3H, s), 2.30 (1H, t, J = 2.3 Hz). |
| 159 | $^1$H-NMR ($CDCl_3$) δ: 7.99 (1H, s), 6.83-6.81 (2H, m), 6.13 (1H, tt, J = 56.4, 4.5 Hz), 4.13 (2H, td, J = 12.8, 4.5 Hz), 3.41 (2H, d, J = 2.4 Hz), 2.86 (2H, q, J = 7.2 Hz), 2.30 (1H, t, J = 2.4 Hz), 0.84 (3H, t, J = 7.2 Hz). |
| 160 | $^1$H-NMR ($CDCl_3$) δ: 8.19 (1H, d, J = 0.5 Hz), 6.83-6.81 (2H, m), 6.12 (1H, tt, J = 56.4, 4.5 Hz), 4.13 (2H, td, J = 12.8, 4.5 Hz), 3.34 (2H, d, J = 2.4 Hz), 2.56 (3H, s), 2.30-2.30 (1H, m). |
| 161 | $^1$H-NMR ($CDCl_3$) δ: 8.18 (1H, s), 6.83-6.80 (2H, m), 6.13 (1H, tt, J = 56.6, 4.5 Hz), 4.13 (2H, td, J = 12.8, 4.5 Hz), 3.41 (2H, d, J = 2.4 Hz), 2.86 (2H, q, J = 7.1 Hz), 2.30 (1H, t, J = 2.4 Hz), 0.84 (3H, t, J = 7.1 Hz). |
| 162 | $^1$H-NMR ($CDCl_3$) δ: 7.63 (1H, s), 7.27-7.25 (1H, m), 7.23 (1H, dd, J = 8.7, 6.0 Hz), 7.12-7.09 (1H, m), 4.16 (1H, dq, J = 13.6, 7.2 Hz), 3.54 (1H, dq, J = 13.6, 7.2 Hz), 2.75 (1H, dq, J = 6.4, 6.4 Hz), 2.38 (3H, s), 1.10 (3H, t, J = 7.2 Hz), 0.82 (3H, d, J = 6.4 Hz), 0.77 (3H, d, J = 6.4 Hz). |
| 163 | $^1$H-NMR ($CDCl_3$) δ: 7.55 (1H, tt, J = 8.4, 6.4 Hz), 7.48 (1H, s), 7.13-7.10 (2H, m), 3.83 (2H, q, J = 7.1 Hz), 3.34 (1H, dq, J = 6.3, 6.3 Hz), 2.09 (1H, br s), 1.11 (3H, t, J = 7.1 Hz), 0.99 (6H, d, J = 6.3 Hz). |
| 164 | $^1$H-NMR ($CDCl_3$) δ: 7.95 (1H, s), 6.83-6.78 (2H, m), 3.87 (2H, q, J = 7.1 Hz), 3.49 (2H, d, J = 2.3 Hz), 3.30-3.24 (1H, m), 2.29 (1H, t, J = 2.3 Hz), 1.13 (3H, t, J = 7.1 Hz), 0.89 (6H, d, J = 6.3 Hz). |
| 165 | $^1$H-NMR ($CDCl_3$) δ: 7.61 (1H, s), 7.21-7.14 (4H, m), 3.87 (2H, q, J = 7.0 Hz), 2.78-2.73 (1H, m), 2.35 (3H, s), 1.12 (3H, t, J = 7.0 Hz), 0.78 (6H, d, J = 6.4 Hz). |
| 166 | $^1$H-NMR ($CDCl_3$) δ: 7.81 (1H, s), 7.22-7.13 (4H, m), 3.87 (2H, q, J = 7.0 Hz), 2.78-2.73 (1H, m), 2.35 (3H, s), 1.11 (3H, t, J = 7.0 Hz), 0.78 (6H, d, J = 6.4 Hz). |
| 167 | $^1$H-NMR ($CDCl_3$) δ: 7.60 (1H, s), 7.22-7.12 (4H, m), 3.86 (2H, q, J = 7.0 Hz), 2.83-2.76 (1H, m), 2.71 (2H, q, J = 7.2 Hz), 1.12 (3H, t, J = 7.0 Hz), 0.85 (3H, t, J = 7.2 Hz), 0.77 (6H, d, J = 6.6 Hz). |
| 168 | $^1$H-NMR ($CDCl_3$) δ: 7.80 (1H, s), 7.22-7.13 (4H, m), 3.86 (2H, q, J = 7.0 Hz), 2.82-2.76 (1H, m), 2.71 (2H, q, J = 7.2 Hz), 1.12 (3H, t, J = 7.0 Hz), 0.85 (3H, t, J = 7.2 Hz), 0.77 (6H, d, J = 6.6 Hz). |
| 169 | $^1$H-NMR ($CDCl_3$) δ: 7.64 (1H, s), 7.45 (1H, tt, J = 8.4, 6.4 Hz), 7.03-7.01 (2H, m), 3.91 (2H, q, J = 7.1 Hz), 2.74 (1H, dq, J = 6.4, 6.4 Hz), 2.41 (3H, s), 1.12 (3H, t, J = 7.1 Hz). 0.79 (6H, d, J = 6.4 Hz). |
| 170 | $^1$H-NMR ($CDCl_3$) δ: 7.63 (1H, s), 7.45 (1H, tt, J = 8.4, 6.4 Hz), 7.03-7.01 (2H, m), 3.89 (2H, q, J = 7.1 Hz), 2.88-2.83 (1H, m), 2.73 (2H, q, J = 7.1 Hz), 1.14 (3H, t, J = 7.1 Hz), 0.85 (3H, t, J = 7.1 Hz), 0.79 (6H, d, J = 6.7 Hz). |
| 171 | $^1$H-NMR ($CDCl_3$) δ: 7.32 (1H, s), 7.00 (1H, tt, J = 8.7, 2.3 Hz), 6.91-6.89 (2H, m), 3.83 (2H, q, J = 7.0 Hz), 1.15 (3H, t, J = 7.0 Hz). |
| 172 | $^1$H-NMR ($CDCl_3$) δ: 7.58-7.51 (3H, m), 7.35 (1H, s), 7.32-7.31 (2H, m), 3.84 (2H, q, J = 7.0 Hz), 1.11 (3H, t, J = 7.0 Hz). |
| 173 | $^1$H-NMR ($CDCl_3$) δ: 7.58-7.50 (4H, m), 7.32-7.32 (2H, m), 3.84 (2H, q, J = 7.0 Hz), 2.74 (2H, br s), 1.11 (3H, t, J = 7.0 Hz). |
| 174 | $^1$H-NMR ($CDCl_3$) δ: 7.58-7.51 (3H, m), 7.49 (1H, s), 7.29-7.27 (2H, m), 3.81 (2H, q, J = 7.1 Hz), 3.32-3.26 (1H, m), 1.11 (3H, t, J = 7.1 Hz), 0.98 (6H, d, J = 6.3 Hz). |
| 175 | $^1$H-NMR ($CDCl_3$) δ; 7.66 (1H, s), 7.58-7.51 (3H, m), 7.28-7.25 (2H, m), 3.81 (2H, q, J = 7.1 Hz), 3.32-3.26 (1H, m), 2.23 (1H, br s), 1.11 (3H, t, J = 7.1 Hz), 0.96 (6H, d, J = 6.1 Hz). |
| 176 | $^1$H-NMR ($CDCl_3$) δ: 7.80 (1H, s), 7.06 (1H, t, J = 8.0 Hz), 6.81-6.76 (3H, m), 6.54 (1H, t, J = 2.0 Hz), 6.43-6.41 (1H, m), 4.72 (1H, s), 3.93 (2H, q, J = 7.0 Hz), 1.16 (3H, t, J = 7.0 Hz). |

TABLE 6-continued

| Compound | $^1$H-NMR |
|---|---|
| 177 | $^1$H-NMR ($CDCl_3$) δ: 7.67 (1H, s), 7.06 (1H, t, J = 8.1 Hz), 6.76-6.73 (3H, m). 6.53 (1H, t, J = 2.1 Hz), 6.43-6.41 (1H, m), 3.92 (2H, q, J = 7.1 Hz), 2.92 (3H, s), 1.19 (3H, t, J = 7.1 Hz). |
| 178 | $^1$H-NMR ($CDCl_3$) δ: 7.84 (1H, s), 7.06 (1H, t, J = 8.1 Hz), 6.80-6.78 (2H, m), 6.37 (1H, ddd, J = 8.1, 2.2, 0.9 Hz), 6.17 (1H, ddd, J = 7.8, 2.2, 0.9 Hz), 6.10 (1H, t, J = 2.2 Hz), 4.66 (1H, s), 3.92 (2H, q, J = 7.1 Hz), 3.73 (3H, s), 1.16 (3H, t, J = 7.1 Hz). |
| 179 | $^1$H-NMR ($CDCl_3$) δ: 7.68 (1H, s), 7.07 (1H, t, J = 8.2 Hz), 6.76-6.73 (2H, m), 6.35 (1H, dd, J = 8.2, 2.3 Hz), 6.18 (1H, dd, J = 8.2, 2.3 Hz), 6.11 (1H, t, J = 2.3 Hz), 3.91 (2H, q, J = 7.1 Hz), 3.73 (3H, s), 2.91 (3H,s), 1.18 (3H, t, J = 7.1 Hz). |
| 180 | $^1$H-NMR ($CDCl_3$) δ: 7.58-7.51 (2H, m), 7.15-7.09 (2H, m), 3.85 (2H, q, J = 7.1 Hz), 2.84 (2H, br s), 1.11 (3H, t, J = 7.1 Hz). |
| 181 | $^1$H-NMR ($CDCl_3$) δ: 7.97 (1H, s), 7.51-7.45 (1H, m), 7.06-7.03 (2H, m), 3.89 (2H, q, J = 7.0 Hz), 3.57 (4H, d, J = 2.4 Hz), 2.24 (2H, t, J = 2.4 Hz), 1.13 (3H, t, J = 7.0 Hz). |
| 182 | $^1$H-NMR ($CDCl_3$) δ: 7.55 (1H, tt, J = 8.6, 6.4 Hz), 7.45 (1H, s), 7.12-7.11 (2H, m), 3.86-3.81 (2H, m), 3.02-3.00 (1H, m), 1.59-1.57 (2H, m), 1.11 (3H, t, J = 7.0 Hz), 0.88 (3H, d, J = 6.7 Hz), 0.80 (3H, d, J = 7.0 Hz), 0.68 (3H, d, J = 6.7 Hz). |
| 183 | $^1$H-NMR ($CDCl_3$) δ: 7.94 (1H, s), 7.47 (1H, tt, J = 8.6, 6.4 Hz), 7.05-7.03 (2H, m), 3.88 (2H, q, J = 7.1 Hz), 3.34 (2H, d, J = 2.4 Hz), 2.54 (3H, s), 2.28 (1H, t, J = 2.4 Hz), 1.12 (3H, t, J = 7.1 Hz). |
| 184 | $^1$H-NMR ($CDCl_3$) δ: 7.57-7.55 (2H, m), 7.15-7.09 (2H, m), 3.85 (2H, q, J = 7.1 Hz), 3.70 (2H, d, J = 2.3 Hz), 2.70 (1H, br s), 2.22 (1H, t, J = 2.3 Hz), 1.12 (3H, t, J = 7.1 Hz). |
| 185 | $^1$H-NMR ($CDCl_3$) δ: 7.62 (1H, s), 7.47-7.41 (3H, m), 7.22-7.21 (2H, m), 3.87 (2H, q, J = 7.0 Hz), 2.81-2.74 (1H, m), 2.35 (3H, s), 1.12 (3H, t, J = 7.0 Hz), 0.76 (6H, d, J = 6.3 Hz). |
| 186 | $^1$H-NMR ($CDCl_3$) δ: 7.81 (1H, s), 7.47-7.41 (3H, m), 7.22-7.20 (2H, m), 3.87 (2H, q, J = 7.0 Hz), 2.81-2.74 (1H, m), 2.35 (3H, s), 1.12 (3H, t, J = 7.0 Hz), 0.76 (6H, d, J = 6.3 Hz). |
| 187 | $^1$H-NMR ($CDCl_3$) δ: 7.61 (1H s), 7.47-7.40 (3H, m), 7.22-7.20 (2H, m), 3.86 (2H, q, J = 7.0 Hz), 2.84-2.79 (1H, m), 2.71 (2H, q, J = 7.1 Hz), 1.13 (3H, t, J = 7.0 Hz), 0.86 (3H, t, J = 7.1 Hz), 0.75 (6H, d, J = 6.4 Hz). |
| 188 | $^1$H-NMR ($CDCl_3$) δ: 7.80 (1H, s), 7.47-7.40 (3H, m), 7.22-7.21 (2H, m), 3.86 (2H, q, J = 7.0 Hz), 2.84-2.78 (1H, m), 2.71 (2H, q, J = 7.0 Hz), 1.12 (3H, t, J = 7.0 Hz), 0.86 (3H, t, J = 7.0 Hz), 0.75 (6H, d, J = 6.7 Hz). |
| 189 | $^1$H-NMR ($CDCl_3$) δ: 7.83 (1H, s), 7.48-7.43 (3H, m), 7.24-7.20 (2H, m), 3.84 (2H, q, J = 7.0 Hz), 3.31 (2H, d, J = 2.4 Hz), 2.82 (2H, q, J = 7.1 Hz), 2.27 (1H, t, J = 2.4 Hz), 1.12 (3H, t, J = 7.0 Hz), 0.85 (3H, t, J = 7.1 Hz). |
| 190 | $^1$H-NMR ($CDCl_3$) δ: 8.03 (1H, s), 7.48-7.43 (3H, m), 7.24-7.20 (2H, m), 3.84 (2H, q, J = 7.0 Hz), 3.31 (2H, d, J = 2.4 Hz), 2.82 (2H, q, J = 7.1 Hz), 2.27 (1H, t, J = 2.4 Hz), 1.12 (3H, t, J = 7.0 Hz), 0.84 (3H, t, J = 7.1 Hz). |
| 191 | $^1$H-NMR ($CDCl_3$) δ: 7.59 (1H, s), 7.47-7.41 (3H, m), 7.22-7.18 (2H, m), 3.85 (2H, q, J = 7.1 Hz), 2.64 (4H, q, J = 7.2 Hz), 1.12 (3H, t, J = 7.1 Hz), 0.80 (6H, t, J = 7.2 Hz). |
| 192 | $^1$H-NMR ($CDCl_3$) δ: 7.78 (1H, s), 7.45-7.43 (3H, m), 7.20-7.19 (2H, m), 3.85 (2H, q, J = 7.0 Hz), 2.64 (4H, q, J = 7.1 Hz), 1.12 (3H, t, J = 7.0 Hz), 0.80 (6H, t, J = 7.1 Hz). |
| 193 | $^1$H-NMR ($CDCl_3$) δ: 7.72 (1H, s), 7.21-7.20 (3H, m), 6.84-6.83 (4H, m), 3.90 (2H, q, J = 7.0 Hz), 3.70 (2H, s), 2.33 (3H, s), 1.15 (3H, t, J = 7.0 Hz). |
| 194 | $^1$H-NMR ($CDCl_3$) δ: 7.92 (1H, s), 7.21-7.20 (3H, m), 6.84-6.83 (4H, m), 3.90 (2H, q, J = 7.0 Hz), 3.70 (2H, s), 2.33 (3H, s), 1.15 (3H, t, J = 7.0 Hz). |
| 195 | $^1$H-NMR ($CDCl_3$) δ: 7.63 (1H, s), 7.21-7.20 (3H, m), 6.86-6.85 (2H, m), 6.82-6.80 (2H, m), 3.90 (2H, q, J = 7.1 Hz), 3.76 (2H, s), 2.62 (2H, q, J = 7.1 Hz), 1.15 (3H, t, J = 7.1 Hz), 0.82 (3H, t, J = 7.1 Hz). |
| 196 | $^1$H-NMR ($CDCl_3$) δ: 7.83 (1H, s), 7.21-7.20 (3H, m), 6.85-6.80 (4H, m), 3.90 (2H, q, J = 7.2 Hz), 3.76 (2H, s), 2.62 (2H, q, J = 7.2 Hz), 1.15 (3H, t, J = 7.2 Hz), 0.81 (3H, t, J = 7.2 Hz). |
| 197 | $^1$H-NMR ($CDCl_3$) δ: 7.65 (1H, s), 7.43 (1H, tt, J = 8.4, 6.4 Hz), 7.02-7.01 (2H, m), 3.98-3.93 (1H, m), 3.85-3.79 (1H, m), 2.39 (3H, s), 2.31-2.26 (1H, m), 1.63-1.60 (1H, m), 1.11 (3H, t, J = 7.0 Hz), 0.76 (3H, d, J = 6.4 Hz), 0.48 (3H, d, J = 6.7 Hz), 0.43 (3H, d, J = 6.7 Hz). |
| 198 | $^1$H-NMR ($CDCl_3$) δ: 8.13 (1H, s), 7.47 (1H, tt, J = 8.4, 6.4 Hz), 7.06-7.02 (2H, m), 3.88 (2H, q, J = 7.1 Hz), 3.34 (2H, d, J = 2.4 Hz), 2.54 (3H, s), 2.29 (1H, t, J = 2,4 Hz), 1.12 (3H, t, J = 7.1 Hz). |
| 199 | $^1$H-NMR ($CDCl_3$) δ: 7.69 (1H, s), 7.55 (1H, tt, J = 8.5, 6.4 Hz), 7.14-7.09 (2H, m), 3.83 (2H, q, J = 7.1 Hz), 3.36-3.30 (1H, m), 2.07-2.05 (1H, m), 1.11 (3H, t, J = 7.1 Hz), 0.99 (6H, d, J = 6.3 Hz). |
| 200 | $^1$H-NMR ($CDCl_3$) δ: 7.75-7.69 (1H, m), 7.57-7.49 (1H, m), 7.10-7.05 (2H, m), 4.48 (1H, dq, J = 12.7, 8.5 Hz), 4.29 (1H, dq, J = 12.7, 8.5 Hz), 3.92-3.85 (2H, m), 2.97-2.93 (3H, m), 1.15 (3H, t, J = 7.1 Hz). |
| 201 | $^1$H-NMR ($CDCl_3$) δ: 7.64 (1H, s), 7.51-7.49 (1H, m), 7.43-7.34 (2H, m), 7.25-7.23 (1H, m), 4.17-4.14 (1H, m), 3.58-3.52 (1H, m), 2.81-2.74 (1H, m), 2.39 (3H, s), 1.10 (3H, t, J = 7.1 Hz), 0.81 (3H, d, J = 6.3 Hz), 0.75 (3H, d, J = 6.6 Hz). |
| 202 | $^1$H-NMR ($CDCl_3$) δ: 7.83 (1H, s), 7.51-7.48 (1H, m), 7.42-7.34 (2H, m), 7.25-7.22 (1H, m), 4.18-4.13 (1H, m), 3.58-3.53 (1H, m), 2.80-2.73 (1H, m), 2.39 (3H, s), 1.10 (3H, t, J = 7.1 Hz), 0.80 (3H, d, J = 6.3 Hz), 0.74 (3H, d, J = 6.6 Hz). |
| 203 | $^1$H-NMR ($CDCl_3$) δ: 7.63 (1H, s), 7.49 (1H, dd, J = 7.9, 1.3 Hz), 7.43-7.34 (2H, m), 7.28-7.25 (1H, m), 4.32-4.26 (1H, m), 3.46-3.41 (1H, m), 2.95-2.88 (1H, m), 2.77-2.68 (2H, m), 1.10 (3H, t, J = 7.1 Hz), 0.88 (3H, t, J = 7.2 Hz), 0.81 (3H, d, J = 6.6 Hz), 0.71 (3H, d, J = 6.6 Hz). |
| 204 | $^1$H-NMR ($CDCl_3$) δ: 7.82 (1H, s), 7.50-7.48 (1H, m), 7.41 (1H, td, J = 7.6,1.6 Hz), 7.36 (1H, td, J = 7.6, 1.6 Hz), 7.27-7.25 (1H, m), 4.30-4.27 (1H, m), 3.45-3.42 (1H, m), 2.94-2.88 (1H, m), 2.77-2.67 (2H, m), 1.10 (3H, t, J = 7.0 Hz), 0.88 (3H, t, J = 7.0 Hz), 0.81 (3H, d, J = 6.7 Hz), 0.71 (3H, d, J = 6.7 Hz). |
| 205 | $^1$H-NMR ($CDCl_3$) δ: 7.89 (1H, s), 7.52-7.50 (1H, m), 7.42 (1H, td, J = 7.6, 1.7 Hz), 7.37 (1H, td, J = 7.6, 1.7 Hz), 7.25-7.23 (1H, m), 4.16-4.11 (1H, m), 3.52-3.49 (1H, m), 3.38 (2H, ddd, J = 37.8, 17.6, 2.3 Hz), 2.89-2.80 (2H, m), 2.27 (1H, t, J = 2.3 Hz), 1.11 (3H, t, J = 7.1 Hz), 0.85 (3H, t, J = 7.2 Hz). |
| 206 | $^1$H-NMR ($CDCl_3$) δ: 8.08 (1H, s), 7.52-7.49 (1H, m), 7.42 (1H, td, J = 7.5, 1.6 Hz), 7.37 (1H, td, J = 7.5, 1.6 Hz), 7.24 (1H, dd, J = 7.5,1.6 Hz), 4.16-4.11 (1H, m), 3.53-3.48 (1H, m), 3.38 (2H, ddd, J = 38.1, 17.6, 2.3 Hz), 2.89-2.80 (2H, m), 2.28 (1H, t, J = 2.3 Hz), 1.11 (3H, t, J = 7.1 Hz), 0.85 (3H, t, J = 7.1 Hz). |

TABLE 6-continued

| Compound | $^1$H-NMR |
|---|---|
| 207 | $^1$H-NMR ($CDCl_3$) δ: 7.84 (1H, s), 7.45 (1H, tt, J = 8.4, 6.4 Hz), 7.04-7.01 (2H, m), 3.89 (2H, q, J = 7.1 Hz), 2.60 (2H, q, J = 7.1 Hz), 2.40 (3H, s), 1.13 (3H, t, J = 7.1 Hz), 0.76 (3H, t, J = 7.1 Hz). |
| 208 | $^1$H-NMR ($CDCl_3$) δ: 7.84 (1H, s), 7.44 (1H, tt, J = 8.4, 6.4 Hz), 7.03-6.99 (2H, m), 3.91 (2H, q, J = 7.1 Hz), 2.77-2.70 (1H, m), 2.41 (3H, s), 1.12 (3H, t, J = 7.1 Hz), 0.79 (6H, d, J = 6.7 Hz). |
| 209 | $^1$H-NMR ($CDCl_3$) δ: 7.62-7.52 (2H, m), 7.14-7.11 (2H, m), 4.58-4.53 (1H, m), 4.37-4.33 (2H, m), 3.93-3.86 (2H, m), 3.20-3.18 (1H, m), 1.16 (3H, t, J = 7.1 Hz). |
| 210 | $^1$H-NMR ($CDCl_3$) δ: 7.35 (1H, s), 7.32-7.23 (4H, m), 3.27 (3H, s). |
| 211 | $^1$H-NMR ($CDCl_3$) δ: 7.33-7.23 (5H, m), 3.71-3.67 (2H, m), 1.56-1.53 (2H, m), 0.71 (3H, t, J = 7.4 Hz). |
| 212 | $^1$H-NMR ($CDCl_3$) δ: 7.47 (1H, s), 7.36 (1H, dd, J = 8.0, 2.7 Hz), 7.31 (1H, dd, J = 8.6, 6.1 Hz), 7.20 (1H, ddd, J = 8.6, 8.0, 2.7 Hz), 4.12-4.07 (1H, m), 3.45-3.42 (1H, m), 3.37-3.32 (1H, m), 1.10 (3H, t, J = 7.0 Hz), 1.02 (3H, d, J = 6.1 Hz), 1.00 (3H, d, J = 6.4 Hz). |
| 213 | $^1$H-NMR ($CDCl_3$) δ: 7.67 (1H, s), 7.36 (1H, dd, J = 8.0, 2.6 Hz), 7.31 (1H, dd, J = 8.6, 5.8 Hz), 7.20 (1H, ddd, J = 8.6, 8.0, 2.6 Hz), 4.10-4.08 (1H, m), 3.45-3.43 (1H, m), 3.37-3.32 (1H, m), 1.10 (3H, t, J = 7.0 Hz), 1.01 (3H, d, J = 6.1 Hz), 0.99 (3H, d, J = 6.1 Hz). |
| 214 | $^1$H-NMR ($CDCl_3$) δ: 7.83 (1H, s), 7.26 (1H, dd, J = 8.3, 2.5 Hz), 7.22 (1H, dd, J = 8.7, 5.8 Hz), 7.10 (1H, ddd, J = 8.7, 8.3, 2.5 Hz), 4.16-4.14 (1H, m), 3.55-3.52 (1H, m), 2.77-2.72 (1H, m), 2.39 (3H, s), 1.10 (3H, t, J = 7.0 Hz), 0.82 (3H, d, J = 6.4 Hz), 0.77 (3H, d, J = 6.4 Hz). |
| 215 | $^1$H-NMR ($CDCl_3$) δ: 7.62 (1H, s), 7.27-7.23 (2H, m), 7.11 (1H, ddd, J = 8.8, 8.2, 2.4 Hz), 4.31-4.28 (1H, m), 3.45-3.38 (1H, m), 2.92-2.85 (1H, m), 2.73 (2H, dq, J = 2.0, 7.1 Hz), 1.10 (3H, t, J = 7.1 Hz), 0.87 (3H, t, J = 7.1 Hz), 0.83 (3H, d, J = 6.6 Hz), 0.75 (3H, d, J = 6.6 Hz). |
| 216 | $^1$H-NMR ($CDCl_3$) δ: 7.82 (1H, s), 7.27-7.23 (2H, m), 7.11 (1H, ddd, J = 8.8, 8.3, 2.4 Hz), 4.31-4.26 (1H, m), 3.43-3.39 (1H, m), 2.92-2.85 (1H, m), 2.73 (2H, dq, J = 2.0, 7.1 Hz), 1.09 (3H, t, J = 7.1 Hz), 0.87 (3H, t, J = 7.1 Hz), 0.83 (3H, d, J = 6.6 Hz), 0.75 (3H, d, J = 6.8 Hz). |
| 217 | $^1$H-NMR ($CDCl_3$) δ: 7.90 (1H, s), 7.28-7.25 (2H, m), 7.12 (1H, ddd, J = 8.6, 7.8, 2.4 Hz), 4.11-4.06 (1H, m), 3.56-3.51 (1H, m), 3.31 (2H, dq, J = 2.4, 16.0 Hz), 2.53 (3H, s), 2.28 (1H, t, J = 2.4 Hz), 1.11 (3H, t, J = 7.1 Hz). |
| 218 | $^1$H-NMR ($CDCl_3$) δ: 8.09 (1H, s), 7.29-7.23 (2H, m), 7.12 (1H, ddd, J = 8.3, 7.8, 2.4 Hz), 4.11-4.06 (1H, m), 3.56-3.51 (1H, m), 3.31 (2H, dq, J = 2.4, 15.9 Hz), 2.53 (3H, s), 2.29 (1H, t, J = 2.4 Hz), 1.11 (3H, t, J = 7.1 Hz). |
| 219 | $^1$H-NMR ($CDCl_3$) δ: 7.87 (1H, s), 7.27-7.23 (2H, m), 7.11 (1H, ddd, J = 8.5, 7.8, 2.5 Hz), 4.16-4.11 (1H, m), 3.52-3.47 (1H, m), 3.37 (2H, dq, J = 2.4, 17.8 Hz), 2.88-2.80 (2H, m), 2.28 (1H, t, J = 2.4 Hz), 1.11 (3H, t, J = 7.1 Hz), 0.86 (3H, t, J = 7.2 Hz). |
| 220 | $^1$H-NMR ($CDCl_3$) δ: 8.07 (1H, s), 7.27-723 (2H, m), 7.11 (1H, ddd, J = 8.5, 7.8, 2.4 Hz), 4.16-4.11 (1H, m), 3.52-3.47 (1H, m), 3.37 (2H, dq, J = 2.4, 17.7 Hz), 2.88-2.80 (2H, m), 2.28 (1H, t, J = 2.4 Hz), 1.11 (3H, t, J = 7.1 Hz), 0.86 (3H, t, J = 7.2 Hz). |
| 221 | $^1$H-NMR ($CDCl_3$) δ: 7.46 (1H, s), 7.19 (1H, d, J = 8.6 Hz), 7.11 (1H, d, J = 2.4 Hz), 6.97 (1H, dd, J = 8.6, 2.4 Hz), 4.13-4.04 (1H, m), 3.90 (3H, s), 3.50-3.47 (1H, m), 3.37-3.32 (1H, m), 2.18 (1H, s), 1.10 (3H, t, J = 7.0 Hz), 1.01 (3H, d, J = 6.1 Hz), 0.99 (3H, d, J = 6.4 Hz). |
| 222 | $^1$H-NMR ($CDCl_3$) δ: 7.66 (1H, s), 7.19 (1H, d, J = 8.6 Hz), 7.11 (1H, d, J = 2.4 Hz), 6.97 (1H, dd, J = 8.6, 2.8 Hz), 4.11-4.07 (1H, m), 3.90 (3H, s), 3.51-3.47 (1H, m), 3.37-3.32 (1H, m), 2.17 (1H, s), 1.10 (3H, t, J = 7.0 Hz), 1.01 (3H, d, J = 6.4 Hz). 0.99 (3H, d, J = 6.1 Hz). |
| 223 | $^1$H-NMR ($CDCl_3$) δ: 7.62 (1H, s), 7.12 (1H, d, J = 8.5 Hz), 7.02 (1H, d, J = 2.6 Hz), 6.90 (1H, dd, J = 8.5, 2.6 Hz), 4.18-4.14 (1H, m), 3.87 (3H, s), 3.60-3.55 (1H, m), 2.81-2.74 (1H, m), 2.39 (3H, s), 1.10 (3H, t, J = 7.1 Hz), 0.82 (3H, d, J = 6.3 Hz), 0.78 (3H, d, J = 6.3 Hz). |
| 224 | $^1$H-NMR ($CDCl_3$) δ: 7.81 (1H, s), 7.12 (1H, d, J = 8.5 Hz), 7.02 (1H, d, J = 2.4 Hz), 6.89 (1H, dd, J = 8.5, 2.4 Hz), 4.18-4.13 (1H, m), 3.87 (3H, s), 3.60-3.55 (1H, m), 2.81-2.74 (1H, m), 2.39 (3H, s), 1.10 (3H, t, J = 7.0 Hz), 0.82 (3H, d, J = 6.3 Hz), 0.77 (3H, d, J = 6.6 Hz). |
| 225 | $^1$H-NMR ($CDCl_3$) δ: 7.88 (1H, s), 7.14 (1H, d, J = 8.5 Hz), 7.04 (1H, d, J = 2.5 Hz), 6.91 (1H, dd, J = 8.5, 2.5 Hz), 4.12-4.07 (1H, m), 3.87 (3H, s), 3.59-3.54 (1H, m), 3.32 (2H, dq, J = 2.4, 15.8 Hz), 2.54 (3H, s), 2.28 (1H, t, J = 2.4 Hz), 1.10 (3H, t, J = 7.1 Hz). |
| 226 | $^1$H-NMR ($CDCl_3$) δ: 8.08 (1H, s), 7.14 (1H, d, J = 8.6 Hz), 7.04 (1H, d, J = 2.4 Hz), 6.91 (1H, dd, J = 8.6, 2.4 Hz), 4.11-4.07 (1H, m), 3.87 (3H, s), 3.59-3.55 (1H, m), 3.32 (2H, dq, J = 2.3, 17.8 Hz), 2.54 (3H, s), 2.28 (1H, t, J = 2.3 Hz), 1.10 (3H, t, J = 7.0 Hz). |
| 227 | $^1$H-NMR ($CDCl_3$) δ: 7.86 (1H, s), 7.12 (1H, d, J = 8.5 Hz), 7.03 (1H, d, J = 2.5 Hz), 6.90 (1H, dd, J = 8.5, 2.5 Hz), 4.16-4.12 (1H, m), 3.87 (3H, s), 3.56-3.51 (1H, m), 3.38 (2H, dq, J = 2.4, 17.7 Hz), 2.86-2.84 (2H, m), 2.27 (1H, t, J = 2.4 Hz), 1.11 (3H, t, J = 7.1 Hz), 0.87 (3H, t, J = 7.1 Hz). |
| 228 | $^1$H-NMR ($CDCl_3$) δ: 8.05 (1H, s), 7.12 (1H, d, J = 8.5 Hz), 7.03 (1H, d, J = 2.5 Hz), 6.90 (1H, dd, J = 8.5, 2.5 Hz), 4.15-4.12 (1H, m), 3.87 (3H, s), 3.56-3.51 (1H, m), 3.38 (2H, dq, J = 2.4, 17.8 Hz), 2.91-2.79 (2H, m), 2.27 (1H, t, J = 2.4 Hz), 1.10 (3H, t, J = 7.1 Hz), 0.87 (3H, t, J = 7.2 Hz). |
| 229 | $^1$H-NMR ($CDCl_3$) δ: 7.87 (1H, s), 6.82-6.79 (2H, m), 6.13 (1H, tt, J = 56.5,4.5 Hz), 4.14 (2H, td, J = 12.8, 4.5 Hz), 2.66 (4H, q, J = 7.1 Hz), 0.82 (6H, t, J = 71 Hz). |
| 230 | $^1$H-NMR ($CDCl_3$) δ: 7.85 (1H, s), 6.56 (2H, d, J = 9.5 Hz), 6.14 (1H, tt, J = 56.7, 4.5 Hz), 4.18 (2H, td, J = 12.8, 4.5 Hz), 3.87 (3H, s), 2.67 (4H, q, J = 7.1 Hz), 0.82 (6H, t, J = 7.1 Hz). |
| 231 | $^1$H-NMR ($CDCl_3$) δ: 7.63 (1H, s), 7.30 (1H, dd, J = 8.2, 2.5 Hz), 7.26-7.23 (1H, m), 7.15 (1H, ddd, J = 8.6, 7.8, 2.5 Hz), 5.36 (1H, tt, J = 55.9, 4.3 Hz), 4.13 (1H, dt, J = 20.3, 7.1 Hz), 3.50 (1H, dt, J = 20.3, 7.1 Hz), 2.98-2.93 (2H, m), 2.53 (3H, s), 1.11 (3H, t, J = 7.1 Hz). |
| 232 | $^1$H-NMR ($CDCl_3$) δ: 7.83 (1H, s), 7.30 (1H, dd, J = 8.3, 2.4 Hz), 7.24-7.23 (1H, m), 7.15 (1H, ddd, J = 8.6, 7.8, 2.4 Hz), 5.36 (1H, tt, J = 55.9, 4.3 Hz), 4.15-4.10 (1H, m), 3.52-3.47 (1H, m), 2.98-2.93 (2H, m), 2.53 (3H, s), 1.11 (3H, t, J = 7.1 Hz). |
| 233 | $^1$H-NMR ($CDCl_3$) δ: 7.60 (1H, s), 7.28-7.26 (2H, m), 7.15 (1H, ddd, J = 8.5, 7.8, 2.4 Hz), 5.42 (1H, tdd, J = 55.9, 4.9, 3.7 Hz), 4.22-4.18 (1H, m), 3.45-3.42 (1H, m), 3.11-2.91 (2H, m), 2.86-2.76 (2H, m), 1.11 (3H, t, J = 7.0 Hz), 0.87 (3H, t, J = 7.1 Hz). |
| 234 | $^1$H-NMR ($CDCl_3$) δ: 7.80 (1H, s), 7.28-726 (2H, m), 7.14 (1H, ddd, J = 8.5, 7.8, 2.4 Hz), 5.42 (1H, tdd, J = 55.9, 4.8, 3.7 Hz), 4.21-4.18 (1H, m), 3.46-3.41 (1H, m), 3.11-2.92 (2H, m), 2.83-2.78 (2H, m), 1.11 (3H, t, J = 7.1 Hz), 0.87 (3H, t, J = 7.1 Hz). |

TABLE 6-continued

| Compound | $^1$H-NMR |
|---|---|
| 235 | $^1$H-NMR ($CDCl_3$) δ: 7.50 (1H, s, minor), 7.48 (1H, s, major), 6.92-6.84 (2H, m, major, minor), 3.94-3.83 (2H, m, major, minor), 3.06 (3H, s, minor), 2.88 (3H, d, J = 0.7 Hz, major), 1.97 (3H, s, minor), 1.93 (3H, d, J = 1.0 Hz, major), 1.18 (3H, t, J = 7.1 Hz, major, minor). |
| 236 | $^1$H-NMR ($CDCl_3$) δ: 7.45 (1H, s), 6.89-6.86 (2H, m), 4.00-3.92 (2H, m), 3.84-3.78 (1H, m), 2.58-2.55 (1H, m), 1.93 (3H, d, J = 1.5 Hz), 1.18 (3H, t, J = 7.2 Hz), 1.06 (3H, t, J = 7.0 Hz). |
| 237 | $^1$H-NMR ($CDCl_3$) δ: 7.48 (1H, s), 6.92-6.87 (2H, m), 3.82 (2H, q, J = 7.1 Hz), 3.38-3.31 (1H, m), 2.09 (1H, s), 1.11 (3H, t, J = 7.2 Hz), 1.01 (6H, d, J = 6.4 Hz). |
| 238 | $^1$H-NMR ($CDCl_3$) δ: 7.89 (1H, s), 6.89-6.87 (2H, m), 5.63 (1H, s), 3.89 (2H, q, J = 7.1 Hz), 3.66 (3H, s), 1.13 (3H, t, J = 7.1 Hz). |
| 239 | $^1$H-NMR ($CDCl_3$) δ: 7.65 (1H, s), 7.26-7.24 (4H, m), 3.80 (2H, q, J = 7.1 Hz), 3.33-3.27 (1H, m), 2.14 (1H, s), 1.10 (3H, t, J = 7.1 Hz), 0.98 (6H, d, J = 6.1 Hz). |
| 240 | $^1$H-NMR ($CDCl_3$) δ: 7.50 (1H, s), 6.86-6.82 (2H, m), 4.03-3.98 (1H, m), 3.78-3.75 (1H, m), 3.57 (3H, s), 2.94 (3H, s), 1.16 (3H, t, J = 7.0 Hz). |
| 241 | $^1$H-NMR ($CDCl_3$) δ: 7.46 (1H, s), 6.85-6.83 (2H, m), 3.88-3.86 (2H, m), 3.64-3.60 (4H, br m), 2.83-2.81 (1H, m), 1.16 (3H, t, J = 7.2 Hz), 1.11 (3H, t, J = 7.0 Hz). |
| 242 | $^1$H-NMR ($CDCl_3$) δ: 7.62 (1H, s), 6.65 (2H, d, J = 8.9 Hz), 4.74 (2H, d, J = 2.4 Hz), 3.92 (2H, q, J = 7.1 Hz), 2.76-2.71 (1H, m), 2.62 (1H, t, J = 2.4 Hz), 2.41 (3H, s), 1.13 (3H. t, J = 7.0 Hz), 0.81 (6H, d, J = 6.4 Hz). |
| 243 | $^1$H-NMR ($CDCl_3$) δ: 7.82 (1H, s), 6.65 (2H, d, J = 8.6 Hz), 4.74 (2H, d, J = 2.4 Hz), 3.92 (2H, q, J = 7.1 Hz), 2.76-2.71 (1H, m), 2.62 (1H, t, J = 2.4 Hz), 2.41 (3H, s), 1.13 (3H, t, J = 7.1 Hz), 0.81 (6H, d, J = 6.4 Hz). |
| 244 | $^1$H-NMR ($CDCl_3$) δ: 7.62 (1H, s), 6.59 (2H, d, J = 9.0 Hz), 4.15-4.14 (2H, m), 3.91 (2H, q, J = 7.1 Hz), 3.79-3.77 (2H, m), 3.47 (3H, s), 2.77-2.71 (1H, m), 2.40 (3H, s), 1.11 (3H, t, J = 7.1 Hz), 0.81 (6H, d, J = 6.6 Hz). |
| 245 | $^1$H-NMR ($CDCl_3$) δ: 7.81 (1H, s), 6.58 (2H, d. J = 9.0 Hz), 4.16-4.13 (2H, m), 3.91 (2H, q, J = 7.1 Hz), 3.79-3.77 (2H, m), 3.47 (3H, s), 2.77-2.71 (1H, m), 2.40 (3H, s), 1.11 (3H, t, J = 7.1 Hz), 0.81 (6H, d, J = 6.3 Hz). |
| 246 | $^1$H-NMR ($CDCl_3$) δ: 7.56-7.53 (3H, m), 7.47 (1H, s), 7.30-7.28 (2H, m), 3.83 (2H, q, J = 7.0 Hz), 2.65 (3H, s). 1.12 (3H, t, J = 7.0 Hz). |
| 247 | $^1$H-NMR ($CDCl_3$) δ: 7.66 (1H, s), 7.58-7.51 (3H, m), 7.30-7.28 (2H, m), 3.83 (2H, q, J = 7.0 Hz), 2.64 (3H, s), 2.53 (1H, s), 1.11 (3H, t, J = 7.0 Hz). |
| 248 | $^1$H-NMR ($CDCl_3$) δ: 7.59-7.51 (4H, m), 7.32-7.29 (2H, m), 3.82 (2H, q, J = 7.1 Hz), 2.95 (2H, q, J = 7.1 Hz), 1.11 (3H, t, J = 7.1 Hz), 1.01 (3H, t, J = 7.1 Hz). |
| 249 | $^1$H-NMR ($CDCl_3$) δ: 7.66 (1H, s), 7.55-7.53 (3H, m), 7.29-7.28 (2H, m), 3.82 (2H, q, J = 7.0 Hz), 2.95 (2H, q, J = 7.1 Hz), 2.37 (1H, br s), 1.11 (3H, t, J = 7.0 Hz), 0.99 (3H, t, J = 7.1 Hz). |
| 250 | $^1$H-NMR ($CDCl_3$) δ: 7.45 (1H, s), 7.27-7.24 (4H, m), 3.80 (2H, q, J = 7.0 Hz), 3.33-3.28 (1H, m), 1.10 (3H, t, J = 7.0 Hz), 0.98 (6H, d, J = 6.4 Hz). |
| 251 | $^1$H-NMR ($CDCl_3$) δ: 7.92 (1H, s), 6.67 (2H, d, J = 8.9 Hz), 4.74 (2H, d, J = 2.4 Hz), 3.90 (2H, q, J = 7.1 Hz), 3.34 (2H, d, J = 2.4 Hz), 2.64 (1H, t, J = 2.4 Hz), 2.54 (3H, s), 2.28 (1H, t, J = 2.4 Hz), 1.13 (3H, t, J = 7.1 Hz). |
| 252 | $^1$H-NMR ($CDCl_3$) δ: 8.11 (1H, s), 6.69-6.65 (2H, m), 4.74 (2H, d, J = 2.4 Hz), 3.89 (2H, q, J = 7.1 Hz), 3.34 (2H, d, J = 2.4 Hz), 2.63 (1H, t, J = 2.4 Hz), 2.55 (3H, s), 2.29 (1H, t, J = 2.4 Hz), 1.12 (3H, t, J = 7.1 Hz). |
| 253 | $^1$H-NMR ($CDCl_3$) δ: 7.91 (1H, s), 6.60 (2H, d, J = 8.9 Hz), 4.16-4.14 (2H, m), 3.89 (2H, q, J = 7.1 Hz), 3.79-3.77 (2H, m), 3.47 (3H, s), 3.34 (2H, d, J = 2.4 Hz), 2.54 (3H. s), 2.28 (1H, t, J = 2.4 Hz), 1.11 (3H, t, J = 7.1 Hz). |
| 254 | $^1$H-NMR ($CDCl_3$) δ: 8.10 (1H, s), 6.60 (2H, d, J = 8.9 Hz), 4.16-4.14 (2H, m), 3.89 (2H, q, J = 7.0 Hz), 3.79-3.77 (2H, m), 3.47 (3H, s), 3.34 (2H, d, J = 2.4 Hz), 2.54 (3H, s), 2.28 (1H, t, J = 2.4 Hz), 1.11 (3H, t, J = 7.0 Hz). |
| 255 | $^1$H-NMR ($CDCl_3$) δ: 7.34-7.31 (2H, m), 7.13-7.08 (1H, m), 7.05 (1H, td, J = 9.0, 2.7 Hz), 3.97-3.92 (1H, m), 3.76-3.69 (1H, m), 2.79 (2H, br s), 1.10 (3H, t, J = 7.1 Hz). |
| 256 | $^1$H-NMR ($CDCl_3$) δ: 7.55 (1H, s), 7.32 (1H, td, J = 8.2, 6.2 Hz), 7.12-7.07 (1H, m), 7.05 (1H, td, J = 8.9, 2.5 Hz), 3.97-3.92 (1H, m), 3.73-3.69 (1H, m), 2.78 (2H, s), 1.10 (3H, t, J = 7.1 Hz). |
| 257 | $^1$H-NMR ($CDCl_3$) δ: 7.71 (1H, s), 7.57 (1H, tt, J = 8.4, 6.4 Hz), 7.15-7.11 (2H, m), 5.69 (1H, tt, J = 55.8, 4.4 Hz), 3.85 (2H, q, J = 7.2 Hz), 3.29-3.25 (2H, m), 2.64-2.63 (1H, m), 1.11 (3H, t, J = 7.2 Hz). |
| 258 | $^1$H-NMR ($CDCl_3$) δ: 7.85 (1H, s), 7.50 (1H, tt, J = 8.4, 6.4 Hz), 7.07-7.05 (2H, m), 5.34 (1H, tt, J = 55.9, 4.4 Hz), 3.88 (2H, q, J = 7.1 Hz), 2.96 (2H, td, J = 14.2, 4.4 Hz), 2.54 (3H, s), 1.13 (3H, t, J = 7.1 Hz). |
| 259 | $^1$H-NMR ($CDCl_3$) δ: 7.82 (1H, s), 7.50 (1H, tt, J = 8.4,6.4 Hz), 7.08-7.04 (2H, m), 5.42 (1H, tt, J = 55.6, 4.9 Hz). 3.88 (2H, q, J = 7.1 Hz), 3.02 (2H, td, J = 14.6, 4.9 Hz), 2.80 (2H, q, J = 7.2 Hz), 1.13 (3H, t, J = 7.1 Hz), 0.84 (3H, t, J = 7.2 Hz). |
| 260 | $^1$H-NMR ($CDCl_3$) δ: 7.91 (1H, s), 6.59-6.55 (2H, m), 3.90 (2H, q, J = 7.1 Hz), 3.86 (3H, s), 3.35 (2H, d, J = 2.4 Hz), 2.54 (3H, s), 2.28 (1H, t, J = 2.4 Hz), 1.12 (3H, t, J = 7.1 Hz). |
| 261 | $^1$H-NMR ($CDCl_3$) δ: 8.10 (1H, s), 6.59-6.55 (2H, m), 3.90 (2H, q, J = 7.1 Hz), 3.86 (3H, s), 3.35 (2H, d, J = 2.4 Hz), 2.55 (3H, s), 2.29 (1H, t, J = 2.4 Hz), 1.12 (3H, t, J = 7.1 Hz). |
| 262 | $^1$H-NMR ($CDCl_3$) δ: 7.46 (1H, s), 7.29-7.24 (1H, m), 7.12-7.02 (2H, m), 3.93-3.90 (1H, m), 3.71-3.67 (1H, m), 3.36-3.29 (1H, m), 2.12 (1H, s), 1.10 (3H, t, J = 7.1 Hz), 1.00 (3H, d, J = 6.3 Hz), 0.98 (3H, d, J = 6.1 Hz). |
| 263 | $^1$H-NMR ($CDCl_3$) δ: 7.67 (1H, s), 7.29-7.23 (1H, m), 7.12-7.02 (2H, m), 3.94-3.89 (1H, m), 3.71-3.67 (1H, m), 3.35-3.29 (1H, m), 2.09 (1H, s), 1.10 (3H, t, J = 7.1 Hz), 1.00 (3H, d, J = 6.3 Hz), 0.98 (3H, d, J = 6.3 Hz). |
| 264 | $^1$H-NMR ($CDCl_3$) δ: 7.62 (1H, s), 7.17 (1H, td, J = 8.2, 6.3 Hz), 7.02-6.92 (2H, m), 4.00-3.95 (1H, m), 3.84-3.77 (1H, m), 2.77-2.71 (1H, m), 2.37 (3H, s), 1.11 (3H, t, J = 7.1 Hz), 0.79 (6H, t, J = 6.7 Hz). |
| 265 | $^1$H-NMR ($CDCl_3$) δ: 7.82 (1H, s), 7.17 (1H, td, J = 8.2, 6.3 Hz), 7.02-6.92 (2H, m), 3.99-3.95 (1H, m), 3.81-3.78 (1H, m), 2.77-2.71 (1H, m), 2.38 (3H, s), 1.11 (3H, t, J = 7.1 Hz), 0.79 (6H, t, J = 7.0 Hz). |

TABLE 6-continued

| Compound | $^1$H-NMR |
|---|---|
| 266 | $^1$H-NMR ($CDCl_3$) δ: 7.59 (1H, s), 7.16 (1H, td, J = 8.2, 6.3 Hz), 7.02-6.97 (1H, m), 6.94 (1H, td, J = 9.0, 2.4 Hz), 4.00-3.95 (1H, m), 3.78-3.75 (1H, m), 2.70-2.60 (4H, m), 1.12 (3H, t, J = 7.1 Hz), 0.80 (6H, t, J = 7.1 Hz). |
| 267 | $^1$H-NMR ($CDCl_3$) δ: 7.79 (1H, s), 7.16 (1H, td, J = 8.2, 6.3 Hz), 7.02-6.97 (1H, m), 6.94 (1H, td, J = 9.0, 2.4 Hz), 4.00-3.95 (1H, m), 3.78-3.75 (1H, m), 2.69-2.60 (4H, m), 1.12 (3H, t, J = 7.1 Hz), 0.80 (6H, t, J = 7.1 Hz). |
| 268 | $^1$H-NMR ($CDCl_3$) δ: 7.47 (1H, s), 7.31-7.28 (1H, m), 7.12-7.08 (1H, m), 7.05 (1H, td, J = 8.9, 2.4 Hz), 3.96-3.93 (1H, m), 3.73-3.71 (1H, m), 2.69 (3H, s), 1.11 (3H, t, J = 7.0 Hz). |
| 269 | $^1$H-NMR ($CDCl_3$) δ: 7.68 (1H, s), 7.31-7.27 (1H, m), 7.10-7.09 (1H, m), 7.04 (1H, td, J = 8.8, 2.7 Hz), 3.95-3.93 (1H, m), 3.73-3.71 (1H, m), 2.68 (3H, s), 2.45 (1H, s), 1.10 (3H, t, J = 7.0 Hz). |
| 270 | $^1$H-NMR ($CDCl_3$) δ: 7.88 (1H, s), 7.21 (1H, td, J = 8.3, 6.1 Hz), 7.04-6.94 (2H, m), 3.94-3.90 (1H, m), 3.84-3.78 (1H, m), 3.30 (2H, ddd, J = 21.8, 17.3, 2.4 Hz), 2.51 (3H, s), 2.27 (1H, t, J = 2.4 Hz), 1.11 (3H, t, J = 7.1 Hz). |
| 271 | $^1$H-NMR ($CDCl_3$) δ: 8.07 (1H, s), 7.21 (1H, td, J = 8.3, 6.1 Hz), 7.04-6.94 (2H, m), 3.94-3.89 (1H, m), 3.84-3.77 (1H, m), 3.30 (2H, ddd, J = 22.0, 17.2, 2.4 Hz), 2.51 (3H, s), 2.28 (1H, t, J = 2.4 Hz), 1.11 (3H, t, J = 7.1 Hz). |
| 272 | $^1$H-NMR ($CDCl_3$) δ: 7.85 (1H, s), 7.26-7.24 (2H, m), 7.10 (1H, td, J = 8.3, 2.5 Hz), 4.18-4.15 (1H, m), 3.52-3.49 (1H, m), 2.72-2.69 (4H, m), 1.70-1.64 (4H, m), 1.09 (3H, t, J = 7.0 Hz). |
| 273 | $^1$H-NMR ($CDCl_3$) δ: 7.84 (1H, s), 7.28-7.27 (1H, m), 7.20 (1H, dd, J = 8.4, 6.0 Hz), 7.10 (1H, td, J = 8.4, 2.4 Hz), 4.12-4.06 (1H, m), 3.62-3.60 (1H, m), 2.61-2.59 (2H, m), 2.54-2.52 (2H, m), 1.31-1.26 (6H, m), 1.12 (3H, t, J = 7.0 Hz). |
| 274 | $^1$H-NMR ($CDCl_3$) δ: 7.53 (1H, s), 7.31 (1H, q, J = 7.2 Hz), 7.11 (1H, td, J = 8.0, 2.4 Hz), 7.05 (1H, td, J = 8.9, 2.4 Hz), 3.94-3.92 (1H, m), 3.71-3.69 (1H, m), 3.03-2.96 (2H, m), 1.10 (3H, t, J = 7.2 Hz), 1.05 (3H, t, J = 7.0 Hz). |
| 275 | $^1$H-NMR ($CDCl_3$) δ: 7.67 (1H, s), 7.30-7.27 (1H, m), 7.10 (1H, td, J = 8.2, 2.4 Hz), 7.05 (1H, td, J = 8.9, 2.4 Hz), 3.95-3.89 (1H, m), 3.75-3.67 (1H, m), 3.02-2.95 (2H, m), 1.10 (3H, t, J = 7.0 Hz). 1.02 (3H, t, J = 7.0 Hz). |
| 276 | $^1$H-NMR ($CDCl_3$) δ: 7.86 (1H, s), 7.19 (1H, td, J = 8.2, 6.2 Hz), 7.03-6.93 (2H, m), 3.96-3.89 (1H, m), 3.84-3.77 (1H, m), 3.35 (2H, ddd, J = 21.7, 17.6, 2.4 Hz), 2.82 (2H, q, J = 7.1 Hz), 2.27 (1H, t, J = 2.4 Hz), 1.12 (3H, t, J = 7.1 Hz), 0.83 (3H, t, J = 7.1 Hz). |
| 277 | $^1$H-NMR ($CDCl_3$) δ: 8.05 (1H, s), 7.19 (1H, td, J = 8.2, 6.2 Hz), 7.01-6.95 (2H, m), 3.95-3.89 (1H, m), 3.83-3.76 (1H, m), 3.35 (2H, ddd, J = 22.0, 17.6, 2.4 Hz), 2.82 (2H, q, J = 7.2 Hz), 2.28 (1H, t, J = 2.4 Hz), 2.17 (0H, s), 1.12 (3H, t, J = 7.1 Hz), 0.83 (3H, t, J = 7.2 Hz). |
| 278 | $^1$H-NMR ($CDCl_3$) δ: 7.54 (1H, dd, J = 7.9, 2.6 Hz), 7.37-7.35 (2H, m), 7.26-7.24 (1H, m), 4.12-4.07 (1H, m), 3.49-3.44 (1H, m), 2.74 (2H, s), 1.12 (3H, t, J = 7.0 Hz). |
| 279 | $^1$H-NMR ($CDCl_3$) δ: 7.55-7.52 (2H, m), 7.36 (1H, dd, J = 8.5, 5.9 Hz), 7.26-7.23 (1H, m), 4.11-4.07 (1H, m), 3.48-3.45 (1H, m), 2.72 (2H, s), 1.12 (3H, t, J = 7.1 Hz). |
| 280 | $^1$H-NMR ($CDCl_3$) δ: 7.60 (1H, s), 7.44 (1H, dd, J = 8.0, 2.6 Hz), 7.23 (1H, dd, J = 8.6, 5.8 Hz), 7.15 (1H, ddd, J = 8.6, 8.0, 2.6 Hz), 4.28-4.26 (1H, m), 3.43-3.39 (1H, m), 2.71-2.64 (4H, m), 1.11 (3H, t, J = 7.2 Hz), 0.83 (6H, t, J = 7.2 Hz). |
| 281 | $^1$H-NMR ($CDCl_3$) δ: 7.79 (1H, s), 7.44 (1H, dd, J = 8.1, 2.6 Hz), 7.22 (1H, dd, J = 8.6, 5.8 Hz), 7.15 (1H, ddd, J = 8.6, 8.1, 2.6 Hz), 4.28-4.25 (1H, m), 3.43-3.40 (1H, m), 2.71-2.64 (4H. m), 1.10 (3H, t, J = 7.0 Hz). 0.83 (6H, t. J = 7.0 Hz). |
| 282 | $^1$H-NMR ($CDCl_3$) δ: 7.54 (1H, dd, J = 8.0, 2.6 Hz), 7.47 (1H, s), 7.31 (1H, dd, J = 8.5, 5.9 Hz), 7.25-7.23 (1H, m), 4.16-4.11 (1H, m), 3.40-3.34 (2H, m), 2.03 (1H, s), 1.11 (3H, t, J = 7.1 Hz), 1.04 (3H, d, J = 6.3 Hz), 1.00 (3H, d, J = 6.3 Hz). |
| 283 | $^1$H-NMR ($CDCl_3$) δ: 7.67 (1H, s), 7.55-7.52 (1H, m), 7.31 (1H, dd, J = 8.5, 5.9 Hz), 7.26-7.22 (1H, m), 4.15-4.12 (1H, m), 3.43-3.33 (2H, m), 2.02 (1H, s), 1.11 (3H, t, J = 7.1 Hz), 1.03 (3H, d, J = 6.3 Hz), 0.99 (3H, d, J = 6.3 Hz). |
| 284 | $^1$H-NMR ($CDCl_3$) δ: 7.63 (1H, s), 7.44 (1H, dd, J = 7.9, 2.5 Hz), 7.23 (1H, dd, J = 8.5, 5.9 Hz), 7.15 (1H, ddd, J = 8.5, 7.9, 2.5 Hz), 4.22-4.17 (1H, m), 3.52-3.47 (1H, m), 2.80-2.73 (1H, m), 1.11 (3H, t, J = 7.1 Hz), 0.83 (3H, d, J = 6.3 Hz), 0.76 (3H, d, J = 6.6 Hz). |
| 285 | $^1$H-NMR ($CDCl_3$) δ: 7.83 (1H, s), 7.44 (1H, dd, J = 8.0, 2.4 Hz), 7.23 (1H, dd, J = 8.4, 5.7 Hz), 7.15 (1H, ddd, J = 8.4, 8.0, 2.4 Hz), 4.21-4.16 (1H, m), 3.52-3.47 (1H, m), 2.81-2.71 (1H, m), 2.40 (3H, s), 1.11 (3H, t, J = 7.0 Hz), 0.83 (3H, d, J = 6.6 Hz), 0.76 (3H, d, J = 6.6 Hz). |
| 286 | $^1$H-NMR ($CDCl_3$) δ: 7.66 (1H, s), 7.29 (1H, dd, J = 8.2,2.6 Hz), 7.23 (1H, dd, J = 8.6, 5.8 Hz), 7.16 (2H, t, J = 8.0 Hz), 7.07 (1H, ddd, J = 8.6, 8.2, 2.6 Hz), 6.82 (1H, t, J = 7.5 Hz), 6.60-6.57 (2H, m), 4.55 (1H, s), 4.11-4.08 (1H, m), 3.60-3.58 (1H, m), 1.15 (3H, t, J = 7.0 Hz). |
| 287 | $^1$H-NMR ($CDCl_3$) δ: 7.86 (1H, s), 7.28 (1H, dd, J = 8.3, 2.4 Hz), 7.23 (1H, dd, J = 8.6, 5.8 Hz), 7.16 (2H, t, J = 7.8 Hz), 7.08-7.04 (1H, m), 6.82 (1H, td, J = 7.3, 0.9 Hz), 6.58 (2H, dd, J = 7.6, 0.9 Hz), 4.55 (1H, s), 4.11-4.07 (1H, m), 3.61-3.58 (1H, m), 1.15 (3H, t, J = 7.2 Hz). |
| 288 | $^1$H-NMR ($CDCl_3$) δ: 7.50 (1H, s), 7.23 (1H, dd, J = 8.2, 2.6 Hz), 7.19-7.17 (2H, m), 7.14 (1H, dd, J = 8.6, 5.8 Hz), 6.93 (1H, ddd, J = 8.6, 8.2, 2.6 Hz), 6.77-6.76 (1H, m), 6.53-6.50 (2H, m), 4.33-4.29 (1H, m), 3.46-3.43 (1H, m), 2.86 (3H, s), 1.15 (3H, t, J = 7.0 Hz). |
| 289 | $^1$H-NMR ($CDCl_3$) δ: 7.70 (1H, s), 7.23 (1H, dd, J = 8.3, 2.4 Hz), 7.20-7.16 (2H, m), 7.14 (1H, dd, J = 8.9, 5.8 Hz), 6.93 (1H, ddd, J = 8.9, 8.3, 2.4 Hz), 6.77 (1H, tt, J = 7.3, 0.9 Hz), 6.52-6.51 (2H, m), 4.31-4.29 (1H, m), 3.47-3.44 (1H, m), 2.86 (3H, s), 1.14 (3H, t, J = 7.0 Hz). |
| 290 | $^1$H-NMR ($CDCl_3$) δ: 7.54 (1H, dd, J = 7.9, 2.6 Hz), 7.48 (1H, s), 7.33 (1H, dd, J = 8.5, 5.6 Hz), 7.24-7.22 (1H, m), 4.13-4.08 (1H, m), 3.48-3.43 (1H, m), 2.70 (3H, s), 2.37 (1H, s), 1.12 (3H, t, J = 7.1 Hz). |
| 291 | $^1$H-NMR ($CDCl_3$) δ: 7.69 (1H, s), 7.54 (1H, dd, J = 8.1, 2.4 Hz), 7.32 (1H, dd, J = 8.5, 5.9 Hz), 7.24-7.22 (1H, m), 4.13-4.08 (1H, m), 3.48-3.43 (1H, m), 2.70 (3H, s), 2.36 (1H, s), 1.12 (3H, t, J = 7.1 Hz). |
| 292 | $^1$H-NMR ($CDCl_3$) δ: 7.90 (1H, s), 7.46 (1H, dd, J = 8.1, 2.5 Hz), 7.26-7.25 (1H, m), 7.17 (1H, ddd, J = 8.6, 8.1, 2.5 Hz), 4.16-4.11 (1H, m), 3.49-3.46 (1H, m), 3.32 (2H, dq, J = 2.4, 17.7 Hz), 2.54 (3H, s), 2.29 (1H, t, J = 2.4 Hz), 1.12 (3H, t, J = 7.0 Hz). |

TABLE 6-continued

| Compound | $^1$H-NMR |
|---|---|
| 293 | $^1$H-NMR ($CDCl_3$) δ: 8.09 (1H, s), 7.45 (1H, dd, J = 8.1, 2.4 Hz), 7.25 (1H, dd, J = 8.5, 5.6 Hz), 7.17 (1H, ddd, J = 8.5, 8.1, 2.4 Hz), 4.16-4.11 (1H, m), 3.50-3.45 (1H, m), 3.32 (2H, dq, J = 2.4, 17.4 Hz), 2.55 (3H, s), 2.29 (1H, t, J = 2.4 Hz), 1.11 (3H, t, J = 7.1 Hz). |
| 294 | $^1$H-NMR ($CDCl_3$) δ: 7.64 (1H, s), 7.23-7.14 (3H, m), 7.00-6.93 (2H, m), 6.82 (1H, tt, J = 7.4, 1.1 Hz), 6.59-6.55 (2H, m), 4.60 (1H, s), 4.01-3.97 (1H, m), 3.82-3.79 (1H, m), 1.15 (3H, t, J = 7.1 Hz). |
| 295 | $^1$H-NMR ($CDCl_3$) δ: 7.84 (1H, s), 7.23-7.14 (3H, m), 7.00-6.93 (2H, m), 6.82 (1H, tt, J = 7.4, 1.0 Hz), 6.58-6.55 (2H, m), 4.60 (1H, s), 4.01-3.97 (1H, m), 3.82-3.79 (1H, m), 1.15 (3H, t, J = 7.1 Hz). |
| 296 | $^1$H-NMR ($CDCl_3$) δ: 7.48 (1H, s), 7.20-7.09 (3H, m), 6.93-6.82 (2H, m), 6.76 (1H, tt, J = 7.4, 1.1 Hz), 6.52-6.48 (2H, m), 4.08-3.99 (1H, m), 3.81-3.72 (1H, m), 2.85 (3H, s), 1.16 (3H, t, J = 7.1 Hz). |
| 297 | $^1$H-NMR ($CDCl_3$) δ: 7.69 (1H, s), 7.20-7.09 (3H,m), 6.92-6.83 (2H, m), 6.76 (1H, tt, J = 7.3, 1.0 Hz), 6.52-6.49 (2H, m), 4.08-3.99 (1H, m), 3.81-3.72 (1H, m), 2.85 (3H, s), 1.16 (3H, t, J = 7.0 Hz). |
| 298 | $^1$H-NMR ($CDCl_3$) δ: 7.54 (1H, dd, J = 8.1, 2.4 Hz), 7.47 (1H, s), 7.32 (1H, dd, J = 8.5, 5.9 Hz), 7.27-7.22 (1H, m), 4.15-4.06 (1H, m), 3.48-3.39 (1H, m), 3.06-2.96 (2H, m), 2.23 (1H, s), 1.12 (3H, t, J = 7.1 Hz), 1.04 (3H, t, J = 7.1 Hz). |
| 299 | $^1$H-NMR ($CDCl_3$) δ: 7.68 (1H, s), 7.54 (1H, dd, J = 8.1, 2.4 Hz), 7.32 (1H, dd, J = 8.4, 5.7 Hz), 7.26-7.22 (1H, m), 4.15-4.06 (2H, m), 3.49-3.39 (1H, m), 3.05-2.96 (2H, m), 2.21 (1H, s), 1.12 (3H, t, J = 7.1 Hz), 1.04 (3H, t, J = 7.2 Hz). |
| 300 | $^1$H-NMR ($CDCl_3$) δ: 7.88 (1H, s), 7.45 (1H, dd, J = 8.1, 2.4 Hz), 7.24 (1H, dd, J = 8.5, 5.9 Hz), 7.16 (1H, ddd, J = 8.5, 8.1, 2.4 Hz), 4.23-4.16 (1H, m), 3.38 (2H, ddd, J = 47.6, 17.7, 2.3 Hz), 2.91-2.79 (2H, m), 2.28 (1H, t, J = 2.3 Hz). 1.11 (3H, t, J = 7.1 Hz), 0.87 (3H, t, J = 7.2 Hz). |
| 301 | $^1$H-NMR ($CDCl_3$) δ: 8.07 (1H, s), 7.44 (1H, dd, J = 8.1, 2.4 Hz), 7.24 (1H, dd, J = 8.5, 5.9 Hz), 7.16 (1H, ddd, J = 8.5, 8.1, 2.4 Hz), 4.23-4.14 (1H, m), 3.38 (3H, ddd, J = 48.0, 17.8, 2.3 Hz), 2.91-2.79 (2H, m), 2.28 (1H, t, J = 2.3 Hz), 1.11 (3H, t, J = 7.0 Hz), 0.87 (3H, t, J = 7.1 Hz). |
| 302 | $^1$H-NMR ($CDCl_3$) δ: 7.57 (1H, tt, J = 8.5, 6.4 Hz), 7.51 (1H, s), 7.26 (1H, br s), 7.15-7.12 (2H, m), 5.70 (1H, tt, J = 55.9, 4.1 Hz), 3.85 (2H, q, J = 7.1 Hz), 3.27 (2H, td, J = 14.5, 4.1 Hz), 1.12 (3H, t, J = 7.1 Hz). |
| 303 | $^1$H-NMR ($CDCl_3$) δ: 7.65 (1H, s), 7.50 (1H, tt, J = 8.4, 6.4 Hz), 7.10-7.04 (2H, m), 5.35 (1H, tt, J = 55.8, 4.4 Hz), 3.88 (2H, q, J = 7.1 Hz), 2.96 (2H, td, J = 14.2, 4.4 Hz), 2.54 (3H, s), 1.13 (3H, t, J = 7.1 Hz). |
| 304 | $^1$H-NMR ($CDCl_3$) δ: 7.62 (1H, s), 7.50 (1H, tt, J = 8.4, 6.4 Hz), 7.07-7.05 (2H, m). 5.42 (1H, tt, J = 55.4, 4.5 Hz), 3.88 (2H, q, J = 7.1 Hz), 3.01 (2H, td, J = 14.2, 4.5 Hz), 2.80 (2H, q, J = 7.1 Hz), 1.13 (3H, t, J = 7.1 Hz), 0.84 (3H, t, J = 7.1 Hz). |
| 305 | $^1$H-NMR ($CDCl_3$) δ: 7.66 (1H, s), 7.47 (1H, dd, J = 8.1, 2.4 Hz), 7.23 (1H, dd, J = 8.5, 5.9 Hz), 7.19-7.14 (2H, m), 7.11 (1H, ddd, J = 8.5, 8.1, 2.4 Hz), 6.82 (1H, tt, J = 7.3, 1.2 Hz), 6.61-6.58 (2H, m), 4.55 (1H, s), 4.15-4.12 (1H, m), 3.56-3.51 (1H, m), 1.17 (3H, t, J = 7.1 Hz). |
| 306 | $^1$H-NMR ($CDCl_3$) δ: 7.87 (1H, s), 7.46 (1H, dd, J = 8.0, 2.4 Hz), 7.23 (1H, dd, J = 8.5, 5.9 Hz), 7.18-7.14 (2H, m), 7.11 (1H, ddd, J = 8.5, 8.0, 2.4 Hz), 6.82 (1H, tt, J = 7.3, 1.0 Hz), 6.61-6.57 (2H, m), 4.55 (1H, s), 4.15-4.11 (1H, m), 3.56-3.51 (1H, m), 1.16 (3H, t, J = 7.0 Hz). |
| 307 | $^1$H-NMR ($CDCl_3$) δ: 7.50 (1H, s), 7.41 (1H, dd, J = 8.1, 2.5 Hz), 7.20-7.17 (2H, m), 7.13 (1H, dd, J = 8.6, 5.5 Hz), 6.96 (1H, ddd, J = 8.6, 8.1, 2.5 Hz), 6.77 (1H, t, J = 7.3 Hz), 6.52 (2H, d, J = 8.0 Hz), 4.40-4.34 (1H, m), 3.43-3.36 (1H, m), 2.87 (3H, s), 1.14 (3H, t, J = 7.0 Hz). |
| 308 | $^1$H-NMR ($CDCl_3$) δ: 7.70 (1H, t, J = 3.5 Hz), 7.41 (1H, dd, J = 8.0, 2.4 Hz), 7.21-7.16 (2H, m), 7.13 (1H, dd, J = 8.6, 5.8 Hz), 6.96 (1H, ddd, J = 8.6, 8.0, 2.4 Hz), 6.77 (1H, tt, J = 7.3, 1.0 Hz), 6.53-6.50 (2H, m), 4.38-4.35 (1H, m), 3.42-3.39 (1H, m), 2.87 (3H, s), 1.14 (3H, t, J = 7.0 Hz). |
| 309 | $^1$H-NMR ($CDCl_3$) δ: 7.48 (1H, s), 7.38 (1H, dd, J = 8.1, 2.4 Hz), 7.33 (1H, dd, J = 8.5, 5.9 Hz), 7.21 (1H, ddd, J = 8.5, 8.1, 2.4 Hz), 5.72 (1H, tt, J = 55.7, 3.9 Hz), 4.12-4.03 (1H, m), 3.50-3.46 (1H, m), 3.29 (2H, td, J = 14.7, 3.9 Hz), 2.60 (1H, s), 1.11 (3H, t, J = 7.1 Hz). |
| 310 | $^1$H-NMR ($CDCl_3$) δ: 7.69 (1H, s), 7.37 (1H, dd, J = 8.0, 2.6 Hz), 7.33 (1H, dd, J = 8.5, 5.9 Hz), 7.21 (1H, ddd, J = 8.5, 8.0, 2.6 Hz), 5.72 (1H, tt, J = 55.7, 3.8 Hz), 4.12-4.03 (1H, m), 3.51-3.45 (1H, m), 3.28 (2H, td, J = 14.6, 3.8 Hz), 2.58 (1H, s), 1.11 (3H, t, J =7.1 Hz). |
| 311 | $^1$H-NMR ($CDCl_3$) δ: 7.47 (1H, s), 7.41 (1H, dd, J = 8.0, 2.5 Hz), 7.21-7.16 (2H, m), 7.14 (1H, dd, J = 8.7, 5.7 Hz), 6.97 (1H, ddd, J = 8.7, 8.0, 2.5 Hz), 6.76 (1H, t, J = 7.2 Hz), 6.53 (2H, d, J = 8.1 Hz), 4.46-4.38 (1H, m), 3.42-3.33 (1H, m), 3.32-3.19 (2H, m), 1.13 (3H, t, J = 7.0 Hz), 0.98 (3H, t, J = 7.1 Hz). |
| 312 | $^1$H-NMR ($CDCl_3$) δ: 7.67 (1H, s), 7.41 (1H, dd, J = 8.1, 2.4 Hz), 7.20-7.12 (3H, m), 6.97 (1H, ddd, J = 8.6, 8.1, 2.4 Hz), 6.76 (1H, tt, J = 7.3, 1.0 Hz), 6.53 (2H, dd, J = 8.8, 1.0 Hz), 4.46-4.36 (1H, m), 3.43-3.34 (1H, m), 3.33-3.20 (2H, m), 1.13 (3H, t, J = 7.1 Hz), 0.98 (3H, t, J = 7.1 Hz). |
| 313 | $^1$H-NMR ($CDCl_3$) δ: 7.64 (1H, s), 7.44 (1H, dd, J = 8.1, 2.4 Hz), 7.27 (1H, dd, J = 8.6, 5.7 Hz), 7.15 (1H, ddd, J = 8.6, 8.1, 2.4 Hz), 4.26-4.15 (1H, m), 3.52-3.42 (1H, m), 2.73 (4H, s), 1.73-1.64 (4H, m), 1.10 (3H, t, J = 7.1 Hz). |
| 314 | $^1$H-NMR ($CDCl_3$) δ: 7.84 (1H, s), 7.44 (1H, dd, J = 8.2, 2.5 Hz), 7.27-7.25 (1H, m), 7.14 (1H, ddd, J = 8.6, 8.2, 2.5 Hz), 4.24-4.15 (1H, m), 3.53-3.42 (1H, m), 2.74-2.69 (4H, m), 1.70-1.63 (4H, m), 1.10 (3H, t, J = 7.1 Hz). |
| 315 | $^1$H-NMR ($CDCl_3$) δ: 7.64 (1H, s), 7.45 (1H, dd, J = 8.1, 2.5 Hz), 7.20 (1H, dd, J = 8.6, 5.8 Hz), 7.15 (1H, ddd, J = 8.6, 8.1, 2.5 Hz), 4.17-4.09 (1H, m), 3.61-3.53 (1H, m), 2.64-2.61 (2H, m), 2.56-2.51 (2H, m), 1.34-1.20 (6H, m), 1.13 (3H, t, J = 7.0 Hz). |
| 316 | $^1$H-NMR ($CDCl_3$) δ: 7.84 (1H, s), 7.45 (1H, dd, J = 8.0, 2.4 Hz), 7.20 (1H, dd, J = 8.6, 5.8 Hz), 7.15 (1H, ddd, J = 8.0, 8.6, 2.4 Hz), 4.16-4.09 (1H, m), 3.61-3.54 (1H, m), 2.64-2.61 (2H, m), 2.55-2.52 (2H, m), 1.34-1.23 (6H, m), 1.13 (3H, t, J = 7.0 Hz). |
| 317 | $^1$H-NMR ($CDCl_3$) δ: 7.65 (1H, s), 7.44 (1H, tt, J = 8.4, 6.4 Hz), 7.16-7.15 (2H, m), 7.03-7.00 (2H, m), 6.82-6.80 (1H, m), 6.60-6.59 (2H, m), 4.66 (1H, s), 3.93 (2H, q, J = 7.1 Hz), 1.16 (3H, t, J = 7.1 Hz). |
| 318 | $^1$H-NMR ($CDCl_3$) δ: 7.58 (1H, s), 7.46 (1H, tt, J = 8.4, 6.4 Hz), 7.04-7.01 (2H, m), 6.89-6.84 (2H, m), 6.56-6.53 (2H, m), 4.55 (1H, s), 3.92 (2H, q, J = 7.0 Hz), 1.15 (3H, t, J = 7.0 Hz). |
| 319 | $^1$H-NMR ($CDCl_3$) δ: 7.58 (1H, s), 7.45 (1H, tt, J = 8.4, 6.4 Hz). 7.02-6.99 (2H, m), 6.95 (1H, dd, J = 8.1, 3.1 Hz), 6.82 (1H, ddd, J = 9.2, 8.1, 3.1 Hz), 6.55 (1H, dd, J = 9.2, 5.2 Hz), 5.11 (1H, s), 3.94 (2H, q, J = 7.1 Hz), 1.16 (3H, t, J = 7.1 Hz). |

TABLE 6-continued

| Compound | $^1$H-NMR |
|---|---|
| 320 | $^1$H-NMR ($CDCl_3$) δ: 7.92 (1H, s), 7.49-7.43 (1H, m), 7.03 (2H, t, J = 8.0 Hz), 3.88 (2H, q, J = 7.1 Hz), 3.40 (2H, d, J = 2.2 Hz), 2.85 (2H, q, J = 7.1 Hz), 2.28 (1H, t, J = 2.2 Hz), 1.13 (3H, t, J = 7.2 Hz), 0.82 (3H, t, J = 7.2 Hz). |
| 321 | $^1$H-NMR ($CDCl_3$) δ: 7.69 (1H, s), 7.58-7.52 (1H, m), 7.14-7.10 (2H, m), 3.84 (2H, q, J = 7.1 Hz), 3.01 (2H, q, J = 7.1 Hz), 1.72 (1H, br s), 1.11 (3H, t, J = 7.1 Hz), 1.03 (3H, t, J = 7.1 Hz). |
| 322 | $^1$H-NMR ($CDCl_3$) δ: 7.80 (1H, s), 7.49-7.42 (1H, m), 7.04-7.00 (2H, m), 3.89 (2H, q, J = 7.1 Hz), 2.65 (4H, q, J = 7.1 Hz), 1.13 (3H, t, J = 7.1 Hz), 0.80 (6H, t, J = 7.1 Hz). |
| 323 | $^1$H-NMR ($CDCl_3$) δ: 8.11 (1H, s), 7.49-7.43 (1H, m), 7.05-7.01 (2H, m), 3.88 (2H, q, J = 7.1 Hz), 3.40 (2H, d, J = 2.4 Hz), 2.85 (2H, q, J = 7.1 Hz), 2.28 (1H, t, J = 2.4 Hz), 1,13 (3H, t, J = 7.1 Hz), 0.82 (3H, t, J = 7.1 Hz). |
| 324 | $^1$H-NMR ($CDCl_3$) δ: 7.63 (1H, s), 7.48 (1H, dd, J = 8.1, 2.4 Hz), 7.27-7.17 (2H, m), 5.36 (1H, tt, J = 55.9, 4.4 Hz), 4.24-4.14 (1H, m), 3.49-3.40 (1H, m), 2.96 (2H, td, J = 14.3, 4.4 Hz), 2.54 (3H, s), 1.12 (3H, t, J = 7.1 Hz). |
| 325 | $^1$H-NMR ($CDCl_3$) δ: 7.83 (1H, s), 7.48 (1H, dd, J = 8.1, 2.4 Hz), 7.25-7.17 (2H, m), 5.36 (1H, tt, J = 55.8, 4.4 Hz), 4.23-4.14 (1H, m). 3.49-3.40 (1H, m), 2.97 (2H, td, J = 14.3, 4.4 Hz), 2.55 (3H, s), 1.11 (3H, t, J = 7.0 Hz). |
| 326 | $^1$H-NMR ($CDCl_3$) δ: 7.60 (1H, s), 7.47 (1H, dd, J = 8.0, 2.8 Hz), 7.27-7.25 (1H, m), 7.19 (1H, ddd, J = 8.6, 8.0, 2.8 Hz), 5.43 (1H, tdd, J = 56.0, 4.9, 3.7 Hz), 4.31-4.23 (1H, m), 3.42-3.33 (1H, m), 3.10-2.94 (2H, m), 2.88-2.76 (2H, m), 1.11 (3H, t, J = 7.0 Hz), 0.88 (3H, t, J = 7.2 Hz). |
| 327 | $^1$H-NMR ($CDCl_3$) δ: 7.80 (1H, s), 7.47 (1H, dd, J = 7.9, 2.6 Hz), 7.28-7.24 (1H, m), 7.19 (1H, ddd, J = 8.6, 7.9, 2.6 Hz), 5.42 (1H, tdd, J = 55.9, 4.8, 3.9 Hz), 4.26 (1H, td, J = 13.6, 6.8 Hz), 3.38 (1H, td, J = 13.7, 6.7 Hz), 3.11-2.95 (2H, m), 2.88-2.76 (2H, m), 1.11 (3H, t, J = 7.0 Hz), 0.88 (3H, t, J = 7.0 Hz). |
| 328 | $^1$H-NMR ($CDCl_3$) δ: 8.16 (1H, s), 7.43 (1H, td, J = 8.4, 5.8 Hz), 7.34 (1H, dt, J = 8.4, 1.0 Hz), 7.15 (1H, td, J = 8.4, 1.0 Hz), 4.10-4.03 (1H, m), 3.64-3.56 (1H, m), 3.35 (2H, ddd, J = 23.2, 17.4, 2.4 Hz), 2.56 (3H, s), 2.30 (1H, t, J = 2.4 Hz), 1.12 (3H, t, J = 7.0 Hz). |
| 329 | $^1$H-NMR ($CDCl_3$) δ: 8.13 (1H, s), 7.42 (1H, td, J = 8.3, 5.9 Hz), 7.33 (1H, dt, J = 8.3, 1.0 Hz), 7.14 (1H, td, J = 8.3, 1.1 Hz), 4.12-4.10 (1H, m), 3.58-3.56 (1H, m), 3.42 (2H, ddd, J = 29.0, 17.7, 2.4 Hz), 2.90-2.81 (2H, m), 2.29 (1H, t, J = 2.4 Hz), 1.13 (3H, t, J = 7.2 Hz), 0.84 (3H, t, J = 7.2 Hz). |
| 330 | $^1$H-NMR ($CDCl_3$) δ: 7.85 (1H, s), 7.42 (1H, td, J = 8.3, 5.8 Hz), 7.33 (1H, dt, J = 8.3, 1.0 Hz), 7.13 (1H, td, J = 8.3, 1.1 Hz), 4.12-4.05 (1H, m), 3,65-3.57 (1H, m), 2.61 (2H, q, J = 7.2 Hz), 2.41 (3H, s), 1.13 (3H, t, J = 7.2 Hz), 0.79 (3H, t, J = 7.0 Hz). |
| 331 | $^1$H-NMR ($CDCl_3$) δ: 7.81 (1H, s), 7.42 (1H, td, J = 8.3, 5.9 Hz), 7.32 (1H, dt, J = 8.3, 1.0 Hz), 7.13 (1H, td, J = 8.3, 1.0 Hz), 4.18-4.10 (1H, m), 3.63-3.53 (1H, m), 2.67 (4H, q, J = 7.1 Hz), 1.13 (3H, t, J = 7.1 Hz), 0.81 (6H, t, J = 7.1 Hz). |
| 332 | $^1$H-NMR ($CDCl_3$) δ: 7.70 (1H, s), 7.51 (1H, td, J = 8.2, 5.8 Hz), 7.42 (1H, d, J = 8.2 Hz), 7.21 (1H, td, J = 8.2, 1.1 Hz), 4.02-3.93 (1H, m), 3.64-3.56 (1H, m), 3.39-3.33 (1H, m), 2.04 (1H, s), 1.12 (3H, t, J = 7.1 Hz), 1.02 (3H, d, J = 6.3 Hz), 0.98 (3H, d, J = 6.1 Hz). |
| 333 | $^1$H-NMR ($CDCl_3$) δ: 7.85 (1H, s), 7.41 (1H, td, J = 8.3, 5.9 Hz), 7.32 (1H, dt, J = 8.3, 1.0 Hz), 7.12 (1H, td, J = 8.3, 1.0 Hz), 4.11-4.05 (1H, m), 3.70-3.63 (1H, m), 2.78-2.72 (1H, m), 2.41 (3H, s), 1.12 (3H, t, J = 7.0 Hz), 0.80 (3H, d, J = 6.4 Hz), 0.77 (3H, d, J = 6.7 Hz). |
| 334 | $^1$H-NMR ($CDCl_3$) δ: 7.58 (1H, s), 7.50 (1H, td, J = 8.3, 5.8 Hz), 7.42 (1H, dt, J = 8.3, 1.0 Hz), 7.22 (1H, td, J = 8.3, 1.0 Hz), 3.99-3.90 (1H, m), 3.71-3.63 (1H, m), 2.78 (2H, s), 1.13 (3H, t, J = 7.0 Hz). |
| 335 | $^1$H-NMR ($CDCl_3$) δ: 7.64 (1H, s), 7.22 (1H, td, J = 7.6, 6.8 Hz), 7.01-6.92 (2H, m), 4.04-3.95 (1H, m), 3.80-3.70 (1H, m), 2.73-2.67 (4H, m), 1.73-1.63 (4H, m), 1.10 (3H, t, J = 7.1 Hz). |
| 336 | $^1$H-NMR ($CDCl_3$) δ: 7 84 (1H, s), 7.21 (1H, td, J = 8.2, 6.3 Hz), 7.01-6.92 (2H, m), 4.03-3.94 (1H, m), 3.80-3.71 (1H, m), 2.72-2.67 (4H, m), 1.72-1.62 (4H, m), 1.10 (3H, t, J = 7.0 Hz). |
| 337 | $^1$H-NMR ($CDCl_3$) δ: 7.65 (1H, s), 7.17 (1H, td, J = 8.3, 6.1 Hz), 7.02-6.99 (1H, m), 6.96 (1H, td, J = 9.0, 2.4 Hz), 4.00-3.93 (1H, m), 3.87-3.80 (1H, m), 2.60-2.50 (4H, m), 1.34-1.25 (6H, m), 1.12 (3H, t, J = 7.2 Hz). |
| 338 | $^1$H-NMR ($CDCl_3$) δ: 7.82 (1H, s), 7.16 (1H, td, J = 8.2, 6.3 Hz), 7.01-6.92 (2H, m), 4.00-3.91 (1H, m), 3.87-3.78 (1H, m), 2.59-2.50 (4H, m), 1.35-1.24 (6H, m), 1.11 (3H, t, J = 7.1 Hz). |
| 339 | $^1$H-NMR ($CDCl_3$) δ: 7.83 (1H, s), 7.28-7.25 (1H, m), 7.21 (1H, dd, J = 8.5, 5.9 Hz), 7.11 (1H, ddd, J = 8.5, 7.8, 2.4 Hz), 4.18-4.09 (1H, m), 3.55-3.46 (1H, m), 2.66-2.55 (2H, m), 2.38 (3H, s), 1.10 (3H, t, J = 7.1 Hz), 0.80 (3H, t, J = 7.1 Hz). |
| 340 | $^1$H-NMR ($CDCl_3$) δ: 7.79 (1H, s), 7.27-7.24 (1H, m), 7.22 (1H, dd, J = 8.5, 5.9 Hz), 7.10 (1H, ddd, J = 8.5, 7.8, 2.4 Hz), 4.25-4.16 (1H, m), 3.51-3.42 (1H, m), 2.71-2.61 (4H, m), 1.10 (3H, t, J = 7.1 Hz), 0.82 (6H, t, J = 7.1 Hz). |
| 341 | $^1$H-NMR ($CDCl_3$) δ: 7.65 (1H, s), 7.51 (1H, dd, J = 7.9, 1.3 Hz), 7.45-7.35 (2H, m), 7.23 (1H, dd, J = 7.2, 2.1 Hz), 4.14 (1H, dt. J = 20.3, 7.1 Hz), 3.51 (1H, dt, J = 20.3, 7.1 Hz), 2.65-2.54 (2H, m), 2.39 (3H, s), 1.11 (3H, t, J = 7.1 Hz), 0.79 (3H, t, J = 7.2 Hz). |
| 342 | $^1$H-NMR ($CDCl_3$) δ: 7.84 (1H, s), 7.50 (1H, dd, J = 7.8, 1.5 Hz), 7.44-7.39 (1H, m), 7.39-7.34 (1H, m), 7.23 (1H, dd, J = 7.4, 1.8 Hz), 4.14 (1H, dq, J = 13.4, 7.1 Hz), 3.52 (1H, dq, J = 13.4, 7.1 Hz), 2.65-2.56 (2H, m), 2.39 (3H, s), 1.10 (3H, t, J = 7.1 Hz), 0.78 (3H, t, J = 7.2 Hz). |
| 343 | $^1$H-NMR ($CDCl_3$) δ: 7.91 (1H, s), 7.52 (1H, dd, J = 7.9,1.3 Hz), 7.45-7.37 (2H, m), 7.26 (1H, dd, J = 7.3, 2.0 Hz), 4.09 (1H, dq, J = 13.3, 7.1 Hz), 3.54 (1H, dq, J = 13.3, 7.1 Hz), 3.35 (1H, dd, J = 17.5, 2.3 Hz), 3.28 (1H, dd, J = 17.5, 2.3 Hz), 2.54 (3H, s), 2.28 (1H, t, J = 2.3 Hz), 1.11 (3H, t, J = 7.1 Hz). |
| 344 | $^1$H-NMR ($CDCl_3$) δ: 7.64 (1H, s), 7.55-7.53 (1H, m), 7.49-7.39 (2H, m), 7.27-7.24 (1H, m), 5.23 (1H, tt, J = 56.0, 4.4 Hz), 4.13 (1H, dq, J = 13.2, 7.1 Hz), 3.52 (1H, dq, J = 13.2, 7.1 Hz), 2.94 (2H, td, J = 14.2, 4.4 Hz), 2.54 (3H, s), 1.11 (3H, t, J = 7.1 Hz). |
| 345 | $^1$H-NMR ($CDCl_3$) δ: 7.64 (1H, s), 7.53-7.47 (1H, m), 7.32-7.28 (1H, m), 7.25-7.19 (2H, m), 5.25 (1H, tt, J = 56.0, 4.3 Hz), 3.97-3.90 (1H, m), 3.84-3.76 (1H, m), 2.97-2.91 (2H, m), 2.53 (3H, s), 1.12 (3H, t, J = 7.0 Hz). |
| 346 | $^1$H-NMR ($CDCl_3$) δ: 7.60 (1H, s), 7.53-7.47 (1H, m), 7.30-7.27 (1H, m), 7.24-7.18 (2H, m), 5.34 (1H, tt, J = 56.0, 4.3 Hz), 3.96-3.91 (1H, m), 3.82-3.77 (1H, m), 3.03-2.95 (2H, m), 2.79 (2H, q, J = 7.1 Hz), 1.12 (3H, t, J = 7.1 Hz), 0.84 (3H, t, J = 7.1 Hz). |

TABLE 6-continued

| Compound | $^1$H-NMR |
| --- | --- |
| 347 | $^1$H-NMR ($CDCl_3$) δ: 7.60 (1H, s), 7.13 (1H, dd, J = 8.4, 5.7 Hz), 7.07-7.00 (2H, m), 5.28 (1H, tt, J = 56.0, 4.3 Hz), 4.25-4.16 (1H, m), 3.41-3.33 (1H, m), 3.05-2.74 (4H, m), 2.10 (3H, s), 1.07 (3H, t, J = 7.0 Hz), 0.89 (3H, t, J = 7.2 Hz). |
| 348 | $^1$H-NMR ($CDCl_3$) δ: 7.34 (1H, s), 7.22 (1H, dd, J = 8.4, 5.7 Hz), 7.12-7.05 (2H, m), 4.14-4.07 (1H, m), 3.45-3.38 (1H, m), 2.73 (2H, br s), 2.15 (3H, s), 1.09 (3H, t, J = 7.0 Hz). |
| 349 | $^1$H-NMR ($CDCl_3$) δ: 7.82 (1H, s), 7.11 (1H, d, J = 8.5 Hz), 7.03 (1H, d, J = 2.4 Hz), 6.90 (1H, dd, J = 8.5, 2.4 Hz), 4.19-4.10 (1H, m), 3.87 (3H, s), 3.58-3.50 (1H, m), 2.68-2.55 (2H, m), 2.40 (3H, s), 1.10 (3H, t, J = 7.1 Hz), 0.81 (3H, t, J = 7.2 Hz). |
| 350 | $^1$H-NMR ($CDCl_3$) δ: 7.78 (1H, s), 7.12 (1H, d, J = 8.5 Hz), 7.02 (1H, d, J = 2.4 Hz), 6.89 (1H, dd, J = 8.5, 2.4 Hz), 4.25-4.16 (1H, m), 3.87 (3H, s), 3.55-3.46 (1H, m), 2.73-2.61 (4H, m), 1.10 (3H, t, J = 7.1 Hz), 0.83 (6H, t, J = 7.1 Hz). |
| 351 | $^1$H-NMR ($CDCl_3$) δ: 7.49 (1H, s), 7.44 (1H, dd, J = 8.6, 5.8 Hz), 7.37 (1H, dd, J = 8.1, 2.6 Hz), 7.25-7.22 (1H, m), 4.12-4.04 (1H, m), 3.86-3.83 (2H, m), 3.53-3.46 (1H, m), 2.75-2.72 (1H, m), 1.13 (3H, t, J = 7.2 Hz). |
| 352 | $^1$H-NMR ($CDCl_3$) δ: 7.85 (1H, s), 7.31 (1H, dd, J = 8.3, 2.4 Hz), 7.25 (1H, dd, J = 8.8, 5.8 Hz), 7.16 (1H, ddd, J = 8.8, 8.3, 2.4 Hz), 4.12-4.04 (1H, m), 3.57-3.40 (3H, m), 2.62 (3H, s), 1.12 (3H, t, J = 7.0 Hz). |
| 353 | $^1$H-NMR ($CDCl_3$) δ: 8.04 (1H, s), 7.31 (1H, dd, J = 8.3, 2.6 Hz), 7.25 (4H, dd, J = 8.8, 5.8 Hz), 7.16 (1H, ddd, J = 8.8, 8.8, 2.6 Hz), 4.11-4.04 (1H, m), 3.57-3.40 (3H, m), 2.62 (3H, s), 1.12 (3H, t, J = 7.0 Hz). |
| 354 | $^1$H-NMR ($CDCl_3$) δ: 7.85 (1H, s), 7.46 (1H, td, J = 8.4, 6.1 Hz), 7.36 (1H, dt, J = 8.4, 1.0 Hz), 7.17 (1H, td, J = 8.4, 1.0 Hz), 5.32 (1H, tt, J = 56.0, 4.4 Hz), 4.13-4.06 (1H, m), 3.62-3.55 (1H, m), 2.96 (2H, td, J = 14.2, 4.4 Hz), 2.56 (3H, s), 1.13 (3H, t, J = 7.0 Hz). |
| 355 | $^1$H-NMR ($CDCl_3$) δ: 7.56 (1H, s), 7.22 (1H, dd, J = 8.3, 5.9 Hz), 7.13-7.04 (2H, m), 4.10 (1H, dq, J = 14.0, 7.0 Hz), 3.42 (1H, dq, J = 14.0, 7.0 Hz), 2.74 (2H, br s), 2.15 (3H, s), 1.08 (3H, t, J = 7.1 Hz). |
| 356 | $^1$H-NMR ($CDCl_3$) δ: 7.67 (1H, s), 7.19 (1H, dd, J = 8.3,5.6 Hz), 7.14-7.06 (2H, m), 5.71 (1H, tt, J = 55.7, 3.7 Hz), 4.13 (1H, dq, J = 14.0, 7.0 Hz), 3.37 (1H, dq, J = 14.0, 7.0 Hz), 3.33-3.23 (2H, m), 2.69-2.59 (1H, m), 2.12 (3H, s), 1.09 (3H, t, J = 7.0 Hz). |
| 357 | $^1$H-NMR ($CDCl_3$) δ: 7.66 (1H, s), 7.17 (1H, dd, J = 8.3, 5.8 Hz), 7.12-7.05 (2H, m), 4.18-4.11 (1H, m), 3.38-3.31 (2H, m), 2.11 (3H, s), 1.08 (3H, t, J = 7.0 Hz), 0.98 (6H, t, J = 6.6 Hz). |
| 358 | $^1$H-NMR ($CDCl_3$) δ: 7.78 (1H, s), 7.10 (1H, dd, J = 8.3, 5.9 Hz), 7.03-6.96 (2H, m), 4.17 (1H, dq, J = 14.0, 7.0 Hz), 3.43 (1H, dq, J = 14.0, 7.0 Hz), 2.71-2.58 (4H, m), 2.10 (3H, s), 1.07 (3H, t, J = 7.0 Hz), 0.81 (6H, t, J = 7.0 Hz). |
| 359 | $^1$H-NMR ($CDCl_3$) δ: 7.81 (1H, s), 7.11 (1H, dd, J = 8.4, 5.7 Hz), 7.03-6.96 (2H,m), 4.09 (1H, dq, J = 14.0, 7.0 Hz), 3.55 (1H, dq, J = 14.0, 7.0 Hz), 2.74-2.69 (1H, m), 2.38 (3H, s), 2.10 (3H, s), 1.07 (3H, t, J = 7.0 Hz), 0.83 (3H, d, J = 6.4 Hz), 0.68 (3H, d, J = 6.4 Hz). |
| 360 | $^1$H-NMR ($CDCl_3$) δ: 8.11 (1H, s), 7.52 (1H, dd, J = 7.9, 1.3 Hz), 7.45-7.36 (2H, m), 7.26 (1H, dd, J = 7.7, 2.0 Hz), 4.08 (1H, dq, J = 13.4, 7.1 Hz), 3.54 (1H, dq, J = 13.4, 7.1 Hz), 3.35 (1H, dd, J = 17.6, 2.3 Hz), 3.28 (1H, dd, J = 17.6, 2.3 Hz), 2.54 (3H, s), 2.29 (1H, t, J = 2.3 Hz), 1.10 (3H, t, J = 7.1 Hz). |
| 361 | $^1$H-NMR ($CDCl_3$) δ: 7.63 (1H, s), 7.20 (1H, td, J = 8.2, 6.2 Hz), 7.07-6.97 (2H, m), 5.36 (1H, tt, J = 55.8, 4.3 Hz), 3.97-3.88 (1H, m), 3.84-3.76 (1H, m), 3.00-2.91 (2H, m), 2.52 (3H, s). 1.12 (3H, t, J = 7.1 Hz). |
| 362 | $^1$H-NMR ($CDCl_3$) δ: 7.83 (1H, s), 7.20 (1H, td, J = 8.2, 6.2 Hz), 7.07-6.96 (2H, m), 5.36 (1H, tt, J = 55.9, 4.3 Hz), 3.97-3.88 (1H, m), 3.84-3.75 (1H, m), 3.00-2.91 (2H, m), 2.52 (3H, s), 1.12 (3H, t, J = 7.1 Hz). |
| 363 | $^1$H-NMR ($CDCl_3$) δ: 7.78 (1H, s), 7.41 (1H, dd, J = 8.7, 5.7 Hz), 7.37 (1H, dd, J = 8.1, 2.4 Hz), 7.25-7.21 (1H, m), 5.33 (1H, s), 4.11-4.02 (1H, m), 3.61-3.52 (1H, m), 2.99-2.83 (2H, m), 1.18 (3H, t, J = 7.3 Hz), 1.12 (3H, t, J = 7.1 Hz). |
| 364 | $^1$H-NMR ($CDCl_3$) δ: 7.60 (1H, s), 7.55 (1H, s), 7.29 (1H, dd J = 8.3, 2.4 Hz), 7.18 (1H, ddd, J = 8.8, 8.3, 2.6 Hz), 4.12 (1H, s), 3.48-3.45 (1H, br m), 2.97 (3H, s), 2.93-2.80 (2H, br m), 1.23 (3H, d, J = 24.5 Hz), 1.13 (3H, t, J = 7.2 Hz). |
| 365 | $^1$H-NMR ($CDCl_3$) δ: 7.66 (1H, s), 7.28-7.26 (1H, m), 7.20 (1H, dd, J = 8.4, 6.0 Hz), 7.11 (1H, ddd, J = 8.8, 8.4, 2.4 Hz), 4.13-4.06 (1H, m), 3.64-3.56 (1H, m), 2.76-2.73 (1H, m), 2.58-2.51 (2H, m), 2.47 (1H, td, J = 11.6, 2.5 Hz), 1.51-1.46 (1H, m), 1.45-1.40 (1H, m), 1.30-1.24 (1H, m), 1.12 (3H, t, J = 7.0 Hz), 0.87-0.80 (4H, m), 0.68 (1H, ddd, J = 23.2, 11.6, 4.2 Hz). |
| 366 | $^1$H-NMR ($CDCl_3$) δ: 7.61 (1H, s), 7.50 (1H, dd, J = 8.0, 1.2 Hz), 7.41 (1H, ddd, J = 8.0, 7.4, 1.8 Hz), 7.37 (1H, ddd, J = 7.6, 7.4, 1.2 Hz), 7.24 (1H, dd, J = 7.6, 1.8 Hz), 4.21 (1H, dq, J = 13.6, 7.2 Hz), 3.48 (1H, dq, J = 13.6, 7.2 Hz), 2.72-2.61 (4H, m), 1.11 (3H, t, J = 7.2 Hz), 0.81 (6H, 1, J = 7.0 Hz). |
| 367 | $^1$H-NMR ($CDCl_3$) δ: 7.80 (1H, s), 7.49 (1H, dd, J = 7.9, 1.3 Hz), 7.44-7.34 (2H, m), 7.23 (1H, dd, J = 7.4, 1.8 Hz), 4.20 (1H, dq, J = 13.4, 7.1 Hz), 3.48 (1H, dq, J = 13.4, 7.1 Hz), 2.71-2.62 (4H, m), 1.10 (3H, t, J = 7.1 Hz), 0.81 (6H, t, J = 7.1 Hz). |
| 368 | $^1$H-NMR ($CDCl_3$) δ: 7.69 (1H, dd, J = 7.7, 1.2 Hz), 7.65 (1H, s), 7.43 (1H, td, J = 7.7, 1.2 Hz), 7.33 (1H, td, J = 7.7, 1.7 Hz), 7.24 (1H, dd, J = 7.7, 1.7 Hz), 4.19 (1H, dq, J = 13.5, 7.0 Hz), 3.47 (1H, dq, J = 13.5, 7.0 Hz), 2.68-2.54 (2H, m), 2.40 (3H, s), 1.11 (3H, t, J = 7.0 Hz), 0.79 (3H, t, J = 7.2 Hz). |
| 369 | $^1$H-NMR ($CDCl_3$) δ: 7.68 (1H, dd, J = 7.6, 1.2 Hz), 7.64 (1H, s), 7.42 (1H, td, J = 7.6, 1.2 Hz), 7.32 (1H, td, J = 7.6, 1.8 Hz), 7.25 (1H, dd, J = 7.6, 1.8 Hz), 4.20 (1H, dq, J = 13.1, 7.2 Hz), 3.52 (1H, dq, J = 13.1, 7.2 Hz), 2.79 (1H, sept, J = 6.4 Hz), 2.40 (3H, s), 1.11 (3H, t, J = 7.2 Hz), 0.81 (3H, d, J = 6.4 Hz), 0.74 (3H, d, J = 6.4 Hz). |
| 370 | $^1$H-NMR ($CDCl_3$) δ: 7.92 (1H, s), 7.70 (1H, dd, J = 8.1, 1.2 Hz), 7.44 (1H, ddd, J = 7.6. 7.4, 1.2 Hz), 7.35 (1H, ddd, J = 8.1, 7.6, 1.8 Hz), 7.26 (1H, dd, J = 7.4, 1.8 Hz), 4.13 (1H, dq, J = 13.4, 7.1 Hz), 3.37 (1H, dd, J = 17.5, 2.3 Hz), 3.29 (1H, dd, J = 17.5, 2.3 Hz), 2.55 (3H, s), 2.29 (1H, t, J = 2.3 Hz), 1.11 (3H, t, J = 7.1 Hz). |
| 371 | $^1$H-NMR ($CDCl_3$) δ: 7.72 (1H, dd, J = 8.1, 1.1 Hz), 7.64 (1H, s), 7.47 (1H, ddd, J = 7.8, 7.5, 1.1 Hz), 7.37 (1H, ddd, J = 8.1, 7.8, 1.7 Hz), 7.26 (1H, dd, J = 7.5, 1.7 Hz), 5.23 (1H, tt, J = 56.1, 4.4 Hz), 4.18 (1H, dq, J = 13.4, 7.0 Hz), 3.47 (1H, dq, J = 13.4, 7.0 Hz), 2.99-2.92 (2H, m), 2.55 (3H, s), 1.11 (3H, t, J = 7.0 Hz). |

TABLE 6-continued

| Compound | $^1$H-NMR |
|---|---|
| 372 | $^1$H-NMR ($CDCl_3$) δ: 7.68 (1H, dd, J = 7.7, 1.1 Hz), 7.61 (1H, s), 7.42 (1H, td, J = 7.7, 1.1 Hz), 7.33 (1H, td, J = 1.7 Hz), 7.25 (1H, dd, J = 7.7, 1.7 Hz), 4.27 (1H, dq, J = 13.8, 7.1 Hz), 3.43 (1H, dq, J = 13.8, 7.1 Hz), 2.72-2.64 (4H, m), 1.11 (3H, t, J = 7.1 Hz), 0.82 (6H, t, J = 7.1 Hz). |
| 373 | $^1$H-NMR ($CDCl_3$) δ: 7.90 (1H, s), 7.69 (1H, dd, J = 8.1, 1.1 Hz), 7.46-7.40 (1H, m), 7.36-7.32 (1H, m), 7.25 (1H, dd, J = 7.5, 1.7 Hz), 4.19 (1H, dq, J = 13.7, 7.0 Hz), 3.458 (1H, dd, J = 17.7, 2.4 Hz), 3.456 (1H, dq, J = 13.7, 7.0 Hz), 3.34 (1H, dd, J = 17.7, 2.4 Hz), 2.91-2.80 (2H, m), 2.28 (1H, t, J = 2.3 Hz), 1.11 (3H, t, J = 7.0 Hz), 0.86 (3H, t, J = 7.2 Hz). |
| 374 | $^1$H-NMR ($CDCl_3$) δ: 7.83 (1H, s), 7.13-7.00 (3H, m), 5.13 (1H, tt, J = 56.0, 4.4 Hz), 4.11 (1H, dq, J = 14.2, 7.1 Hz), 3.48 (1H, dq, J = 14.2, 7.1 Hz), 2.93-2.84 (2H, m), 2.56 (3H, s), 2.11 (3H, s), 1.08 (3H, t, J = 7.1 Hz). |
| 375 | $^1$H-NMR ($CDCl_3$) δ: 7.79 (1H, s), 7.13 (1H, dd, J = 8.4, 5.7 Hz), 7.06-7.00 (2H, m), 5.27 (1H, tt, J = 55.9, 4.3 Hz), 4.20 (1H, dq, J = 14.2, 7.1 Hz), 3.38 (1H, dq, J = 14.2, 7.1 Hz), 3.05-2.75 (4H, m), 2.10 (3H, s), 1.07 (3H, t, J = 7.1 Hz), 0.89 (3H, t, J = 7.1 Hz). |
| 376 | $^1$H-NMR ($CDCl_3$) δ: 7.67 (1H, s), 7.18 (1H, dd, J = 8.4, 5.7 Hz), 7.12-7.04 (2H, m), 4.13 (1H, dq, J = 14.0, 7.0 Hz), 3.41 (1H, dq, J = 14.0, 7.0 Hz), 2.67 (3H, s), 2.11 (3H, s), 1.09 (3H, t, J = 7.0 Hz). |
| 377 | $^1$H-NMR ($CDCl_3$) δ: 7.66 (1H, s), 7.18 (1H, dd, J = 8.4, 5.7 Hz), 7.12-7.05 (2H, m), 4.13 (1H, dq, J = 14.0, 7.0 Hz), 3.38 (1H, dq, J = 14.0, 7.0 Hz), 2.98 (2H, ddd, J = 14.0, 7.0, 1.0 Hz). 2.12 (3H, s), 1.08 (3H, t, J = 7.0 Hz), 1.01 (3H, t, J = 7.0 Hz). |
| 378 | $^1$H-NMR ($CDCl_3$) δ: 8.03 (1H, s), 7.13 (1H, dd, J = 8.3, 5.8 Hz), 7.05-6.98 (2H, m), 4.07 (1H, dq, J = 14.0, 7.0 Hz), 3.50 (1H, dq, J = 14.0, 7.0 Hz), 3.25 (2H, dd, J = 7.5, 2.3 Hz), 2.54 (3H, s), 2.27 (1H, t, J = 2.3 Hz), 2.12 (3H, s), 1.07 (3H, t, J = 7.0 Hz). |
| 379 | $^1$H-NMR ($CDCl_3$) δ: 8.01 (1H, s), 7.11 (1H, dd, J = 8.4, 5.7 Hz), 7.04-6.97 (2H, m), 4.12 (1H, dq, J = 14.0, 7.0 Hz), 3.46 (1H, dq, J = 14.0,7.0 Hz), 3.30 (2H, d, J = 2.2 Hz), 2.90-2.77 (2H, m), 2.27 (1H, t, J = 2.2 Hz), 2.11 (3H, s), 1.07 (3H, t, J = 7.0 Hz), 0.86 (3H, t, J = 7.0 Hz). |
| 380 | $^1$H-NMR ($CDCl_3$) δ: 7.82 (1H, s), 7.10 (1H, dd, J = 8.3, 5.9 Hz), 7.04-6.96 (2H, m), 4.10 (1H, dq, J = 14.0, 7.0 Hz), 3.48 (1H, dq, J = 14.0, 7.0 Hz), 2.58 (2H, q, J = 7.0 Hz), 2.37 (3H, s), 2.10 (3H, s), 1.07 (3H, t, J = 7.0 Hz), 0.77 (3H, t, J = 7.0 Hz). |
| 381 | $^1$H-NMR ($CDCl_3$) δ: 7.89 (1H, s), 7.51-7.44 (1H, m), 7.29-7.17 (3H, m), 3.97-3.88 (1H, m), 3.85-3.76 (1H, m), 3.31 (2H, dd, J = 4.2, 2.4 Hz), 2.52 (3H, s), 2.27 (1H, t, J = 2.4 Hz), 1.11 (3H, t, J = 7.0 Hz). |
| 382 | $^1$H-NMR ($CDCl_3$) δ: 7.87 (1H, s), 7.50-7.44 (1H, m), 7.28-7.24 (2H, m), 7.22-7.16 (2H, m), 3.96-3.89 (1H, m), 3.84-3.75 (1H, m), 3.43-3.30 (2H, m), 2.83 (2H, q, J = 7.1 Hz), 2.27 (1H, t, J = 2.3 Hz), 1.12 (3H, t, J = 7.1 Hz), 0.83 (3H, t, J = 7.1 Hz). |
| 383 | $^1$H-NMR ($CDCl_3$) δ: 7.60 (1H, s), 7.49-7.43 (1H, m), 7.26-7.22 (1H, m), 7.20-7.15 (2H, m), 4.04-3.92 (1H, m), 3.83-3.72 (1H, m), 2.72-2.57 (4H, m), 1.12 (3H, t, J = 7.1 Hz), 0.80 (6H, t, J = 7.1 Hz). |
| 384 | $^1$H-NMR ($CDCl_3$) δ: 7.59-7.52 (1H, m), 7.47 (1H, s), 7.36-7.32 (1H, m), 7.30-7.25 (2H, m), 3.99-3.88 (1H, m), 3.76-3.66 (1H, m), 3.35-3.28 (1H, m), 1.10 (3H, t, J = 7.0 Hz), 0.98 (6H, dd, J = 9.2, 6.2 Hz). |
| 385 | $^1$H-NMR ($CDCl_3$) δ: 7.63 (1H, s), 7.48-7.42 (1H, m), 7.26-7.22 (1H, m), 7.21-7.15 (2H, m), 4.03-3.93 (1H, m), 3.84-3.77 (1H, m), 2.80-2.70 (1H, m), 2.38 (3H, s), 1.11 (3H, t, J = 7.1 Hz), 0.79-0.75 (6H, m). |
| 386 | $^1$H-NMR ($CDCl_3$) δ: 7.63 (1H, s), 7.13-7.00 (3H, m), 5.13 (1H, tt, J = 56.0, 4.4 Hz), 4.16-4.07 (1H, m), 3.52-3.43 (1H, m), 2.93-2.84 (2H, m), 2.55 (3H, s), 2.11 (3H, s), 1.08 (3H, t, J = 7.0 Hz). |
| 387 | $^1$H-NMR ($CDCl_3$) δ: 7.46 ( 1H, s), 7.17 (1H, dd, J = 8.3, 5.9 Hz), 7.12-7.04 (2H, m), 4.19-4.10 (1H, m), 3.39-3.30 (2H, m), 2.11 (3H, s), 2.08 (1H, br s), 1.08 (3H, t, J = 7.1 Hz), 0.99 (6H, dd, J = 6.3, 5.1 Hz). |
| 388 | $^1$H-NMR ($CDCl_3$) δ: 7.59 (1H, s), 7.10 (1H, dd, J = 8.4, 5.7 Hz), 7.03-6.96 (2H, m), 4.21-4.13 (1H, m), 3.47-3.38 (1H, m), 2.71-2.58 (4H, m), 2.10 (3H, s), 1.07 (3H, t, J = 7.0 Hz), 0.81 (6H, t, J = 7.1 Hz). |
| 389 | $^1$H-NMR ($CDCl_3$) δ: 7.50 (1H, s), 7.19 (1H, dd, J = 8.4, 5.7 Hz), 7.12-7.05 (2H, m), 4.17-4.10 (1H, m), 3.43-3.36 (1H, m), 2.67 (3H, s), 2.12 (3H, s), 1.59 (1H, br s), 1.09 (3H, t, J = 7.0 Hz). |
| 390 | $^1$H-NMR ($CDCl_3$) δ: 7.46 (1H, s), 7.18 (1H, dd, J = 5.8, 8.3 Hz), 7.12-7.06 (2H, m), 4.17-4.10 (1H, m), 3.42-3.35 (1H, m), 2.98 (2H, q, J = 7.0 Hz), 2.28 (1H, br s), 2.12 (3H, s), 1.09 (3H, t, J = 7.0 Hz), 1.01 (3H, t, J = 7.0 Hz). |
| 391 | $^1$H-NMR ($CDCl_3$) δ: 7.62 (1H, s), 7.11 (1H, dd, J = 8.3, 5.6 Hz), 7.03-6.96 (2H, m), 4.14-4.05 (1H, m), 3.59-3.51 (1H, m), 2.77-2.67 (1H, m), 2.38 (3H, s), 2.09 (3H, s), 1.08 (3H, t, J = 7.1 Hz), 0.83 (3H, d, J = 6.6 Hz), 0.68 (3H, d, J = 6.6 Hz). |
| 392 | $^1$H-NMR ($CDCl_3$) δ: 7.84 (1H, s), 7.13 (1H, dd, J = 8.3, 5.9 Hz), 7.05-6.98 (2H, m), 4.11-4.02 (1H, m), 3.55-3.46 (1H, m), 3.25 (2H, ddd, J = 23.0, 17.5, 2.4 Hz), 2.53 (3H, s), 2.27 (1H, t, J = 2.4 Hz), 2.12 (3H, s), 1.07 (3H, t, J = 7.0 Hz). |
| 393 | $^1$H-NMR ($CDCl_3$) δ: 7.82 (1H, s), 7.12 (1H, dd, J = 8.3, 5.9 Hz), 7.04-6.97 (2H, m), 4.16-4.08 (1H, m), 3.50-3.41 (1H, m), 3.32 (1H, dd, J = 17.8, 2.3 Hz), 3.28 (1H, dd, J = 17.8, 2.3 Hz), 2.92-2.75 (2H, m), 2.26 (1H, t, J = 2.3 Hz), 2.11 (3H, s), 1.08 (3H, t, J = 7.1 Hz), 0.86 (3H, t, J = 7,1 Hz). |
| 394 | $^1$H-NMR ($CDCl_3$) δ: 7.63 (1H, s), 7.10 (1H, dd, J = 8.3, 5.9 Hz), 7.04-6.96 (2H, m), 4.15-4.06 (1H, m), 3.52-3.43 (1H, m), 2.58 (2H, q, J = 7.2 Hz), 2.37 (3H, s), 2.10 (3H, s), 1.07 (3H, t, J = 7.2 Hz), 0.78 (3H, t, J =7.2 Hz). |
| 395 | $^1$H-NMR ($CDCl_3$) δ: 7.47 (1H, s), 7.20 (1H, dd, J = 8.3, 5.9 Hz), 7.14-7.06 (2H, m), 5.71 (1H, tt, J = 55.7, 3.7 Hz), 4.18-4.10 (1H, m), 3.41-3.33 (1H, m), 3.28 (2H, td, J = 14.9, 3.7 Hz), 2.66 (1H, br s), 2.12 (3H, s), 1.09 (3H, t, J = 7.1 Hz). |
| 396 | $^1$H-NMR ($CDCl_3$) δ: 7.80 (1H, s), 7.68-7.66 (1H, m), 7.42-7.40 (1H, m), 7.33-7.31 (1H, m), 7.25-7.23 (1H, m), 4.29-4.23 (1H, m), 3.45-3.42 (1H, m), 2.72-2.64 (4H, m), 1.10 (3H, t, J = 7.1 Hz), 0.82 (6H, t, J = 7.2 Hz). |
| 397 | $^1$H-NMR ($CDCl_3$) δ: 7.79-7.78 (1H, m), 7.69 (1H, s), 7.52-7.50 (1H, m), 7.43-7.39 (1H, m), 7.33-7.31 (1H, m), 4.13-4.10 (1H, m), 3.49-3.46 (1H, m), 2.70 (3H, s), 2.36 (1H, br s), 1.12 (6H, t, J = 7.0 Hz). |
| 398 | $^1$H-NMR ($CDCl_3$) δ: 7.84 (1H, s), 7.69-7.67 (1H, m), 7.43-7.41 (1H, m), 7.34-7.32 (1H, m), 7.24-7.22 (1H, m), 4.20-4.17 (1H, m), 3.50-3.45 (1H, m), 2.63-2.59 (2H, m), 2.40 (3H, s), 1.11 (3H, t, J = 7.1 Hz), 0.79 (3H, t, J = 7.1 Hz). |

TABLE 6-continued

| Compound | $^1$H-NMR |
|---|---|
| 399 | $^1$H-NMR ($CDCl_3$) δ: 7.83 (1H, s), 7.69-7.67 (1H, m), 7.42-7.40 (1H, m), 7.32-7.31 (1H, m), 7.25-7.23 (1H, m), 4.21-4.16 (1H, m), 3.55-3.50 (1H, m), 2.81-2.76 (1H, m), 2.40 (3H, s), 1.11 (3H, t, J = 7.0 Hz), 0.81 (3H, d, J = 6.4 Hz), 0.73 (3H, d, J = 6.4 Hz). |
| 400 | $^1$H-NMR ($CDCl_3$) δ: 8.11 (1H, s), 7.71-7.69 (1H, m), 7.44-7.43 (1H, m), 7.35-7.33 (1H, m), 7.27-7.25 (1H, m), 4.14-4.11 (1H, m), 3.51-3.47 (1H, m), 3.37 (1H, dd, J = 17.4, 2.4 Hz), 3.29 (1H, dd, J = 17.4, 2.4 Hz), 2.55 (3H, s), 2.30-2.29 (1H, m), 1.11 (3H, t, J = 7.2 Hz). |
| 401 | $^1$H-NMR ($CDCl_3$) δ: 7.80 (1H, s), 7.72-7.70 (1H, m), 7.47-7.45 (1H, m), 7.39-7.36 (1H, m), 7.28-7.26 (1H, m), 5.33 (1H, tt, J = 56.0, 4.3 Hz), 4.28-4.24 (1H, m), 3.42-3.39 (1H, m), 3.04-2.97 (2H, m), 2.91-2.77 (2H, m), 1.11 (3H, t, J = 7.2 Hz), 0.88 (3H, t, J = 7.2 Hz). |
| 402 | $^1$H-NMR ($CDCl_3$) δ: 7.84 (1H, s), 7.73-7.71 (1H, m), 7.47-7.46 (1H, m), 7.39-7.37 (1H, m), 7.26-7.25 (1H, m), 5.23 (1H, tt, J = 55.9, 4.4 Hz), 4.20-4.14 (1H, m), 3.50-3.45 (1H, m), 2.98-2.94 (2H, m), 2.56 (3H, s), 1.12 (3H, t, J = 7.1 Hz). |
| 403 | $^1$H-NMR ($CDCl_3$) δ: 8.09 (1H, s), 7.70-7.68 (1H, m), 7.43-7.42 (1H, m), 7.35-7.33 (1H, m), 7.25-7.23 (1H, m), 4.20-4.17 (1H, m), 3.48-3.44 (2H, m), 3.33 (1H, dd, J = 17.6, 2.4 Hz), 2.88-2.83 (2H, m), 2.29-2.28 (1H, m), 1.11 (3H, t, J = 7.1 Hz), 0.86 (3H, t, J = 7.1 Hz). |
| 404 | $^1$H-NMR ($CDCl_3$) δ: 7.84 (1H, s), 7.54 (1H, dd, J = 7.9, 1.3 Hz), 7.49-7.39 (2H, m), 7.26 (1H, dd, J = 7.7, 2.3 Hz), 5.23 (1H, tt, J = 56.0, 4.4 Hz), 4.13 (1H, dq, J = 13.6, 7.1 Hz), 3.52 (1H, dq, J = 13.6, 7.1 Hz), 2.95 (2H, td, J = 14.2, 4.4 Hz), 2.54 (3H, s), 1.11 (3H, t, J = 7.1 Hz). |
| 405 | $^1$H-NMR ($CDCl_3$) δ: 7.81 (1H, s), 7.53 (1H, dd, J = 8.1, 1.5 Hz), 7.48-7.43 (1H, m), 7.43-7.39 (1H, m), 7.26 (1H, dd, J = 7.4, 1.8 Hz), 5.47-5.17 (1H, m), 4.23-4.13 (1H, m), 3.51-3.42 (1H, m), 3.10-2.91 (2H, m), 2.88-2.76 (2H, m), 1.11 (3H, t, J = 7.1 Hz), 0.87 (3H, t, J = 7.0 Hz). |
| 406 | $^1$H-NMR ($CDCl_3$) δ: 7.61 (1H, s), 7.53 (1H, dd, J = 7.9, 1.3 Hz), 7.49-7.43 (1H, m), 7.43-7.39 (1H, m), 7.26 (1H, dd, J = 7.3, 2.0 Hz), 5.32 (1H, tdd, J = 56.1, 4.9, 3.9 Hz), 4.20 (1H, dq, J = 13.6, 7.1 Hz), 3.46 (1H, dq, J = 13.6, 7.1 Hz), 3.10-2.90 (2H, m), 2.89-2.75 (2H, m), 1.11 (3H, t, J = 7.1 Hz), 0.87 (3H, t, J = 7.2 Hz). |
| 407 | $^1$H-NMR ($CDCl_3$) δ: 7.71 (1H, dd, J = 8.1, 1.1 Hz), 7.61 (1H, s), 7.49-7.45 (1H, m), 7.39-7.36 (1H, m), 7.27 (1H, dd, J = 7.6, 1.8 Hz), 5.33 (1H, tdd, J = 56.1, 4.9, 3.7 Hz), 4.27 (1H, dq, J = 13.6, 7.0 Hz), 3.40 (1H, dq, J = 13.6, 7.0 Hz), 3.11-2.94 (2H, m), 2,90-2.77 (2H, m), 1.11 (3H, t, J = 7.0 Hz), 0.88 (3H, t, J =7.2 Hz). |
| 408 | $^1$H-NMR ($CDCl_3$) δ: 7.56-7.50 (1H, br m), 7.42-7.20 (2H, br m), 7.17-7.16 (1H, br m), 4.31-3.91 (2H, br m), 3.76-3.68 (3H, br m), 3.58-3.10 (2H, br m), 1.17-1.10 (3H, br m). |
| 409 | $^1$H-NMR ($CDCl_3$) δ: 7.73-7.72 (1H, br m), 7.40-7.19 (2H, br m), 7.17-7.14 (1H, br m), 4.31-4.05 (2H, br m), 3.76-3.68 (3H, m), 3.56-3.05 (2H, m), 1.16-1.10 (3H, m). |
| 410 | $^1$H-NMR ($CDCl_3$) δ: 7.51 (1H, s), 7.38 (1H, dd, J = 8.1, 2.4 Hz), 7.35 (1H, dd, J = 8.6, 5.8 Hz), 7.21 (1H, ddd, J = 8.6, 8.1, 2.4 Hz), 4.12-4.05 (1H, m), 3.52-3.44 (1H, m), 2.82 (1H, dd, J = 12.7, 7.1 Hz), 2.76 (1H, dd, J = 12.7, 7.1 Hz), 1.11 (3H, t, J = 7.0 Hz), 0.89-0.84 (1H, m), 0.46-0.39 (2H, m), 0.03 (2H, d, J = 5.2 Hz). |
| 411 | $^1$H-NMR ($CDCl_3$) δ: 7.66 (1H, s), 7.28-7.26 (1H, m), 7.24 (1H, dd, J = 8.6, 5.8 Hz), 7.11 (1H, ddd, J = 8.6, 8.1, 2.4 Hz), 4.17-4.11 (1H, m), 3.54-3.48 (1H, m), 2.46 (3H, s), 2.40 (2H, dd, J = 6.7, 1.5 Hz), 1.11 (3H, t, J = 7.0 Hz), 0.61-0.53 (1H, m), 0.38-0.35 (2H, m), −0.08-−0.11 (2H, m). |
| 412 | $^1$H-NMR ($CDCl_3$) δ: 8.09 (1H, s), 7.52-7.44 (1H, m), 7.29-7.16 (3H, m), 3.95-3.88 (1H, m), 3.84-3.77 (1H, m), 3.32-3.29 (2H, m), 2.52 (3H, s), 2.27 (1H, t, J = 2.4 Hz), 1.11 (3H, t, J = 7.1 Hz). |
| 413 | $^1$H-NMR ($CDCl_3$) δ: 7.65 (1H, s), 7.28-7.25 (1H, m), 7.22 (1H, dd, J = 8.7, 6.0 Hz), 7.11 (1H, ddd, J = 8.7, 8.1, 2.4 Hz), 4.19-4.11 (1H, m), 3.54-3.45 (1H, m), 2.56-2.44 (2H, m), 2.36 (3H, s), 1.27-1.17 (2H, m), 1.11 (3H, t, J = 7.0 Hz), 0.60 (3H, t, J = 7.4 Hz). |
| 414 | $^1$H-NMR ($CDCl_3$) δ: 7.65 (1H, s), 7.28-7.26 (1H, m), 7.22 (1H, dd, J = 8.5, 6.0 Hz), 7.11 (1H, ddd, J = 8.5, 8.1, 2.4 Hz), 4.19-4.12 (1H, m), 3.53-3.45 (1H, m), 2.60-2.50 (2H, m), 2.38 (3H, s), 1.21-1.15 (2H, m), 1.11 (3H, t, J = 7.1 Hz), 1.08-0.99 (2H, m), 0.79 (3H, t, J = 7.1 Hz). |
| 415 | $^1$H-NMR ($CDCl_3$) δ: 7.84 (1H, s), 7.27-7.25 (1H, m), 7.22 (1H, dd, J = 8.5, 5.9 Hz), 7.11 (1H, ddd, J = 8.5, 8.1, 2.4 Hz), 4.18-4.11 (1H, m), 3.53-3.46 (1H, m), 2.55-2.45 (2H, m), 2.36 (3H, s), 1.26-1.17 (2H, m), 1.10 (3H, t, J = 7.1 Hz), 0.60 (3H, t, J = 7.3 Hz). |
| 416 | $^1$H-NMR ($CDCl_3$) δ: 7.84 (1H, s), 7.28-7.25 (1H, m), 7.21 (1H, dd, J = 8.5, 6.0 Hz), 7.11 (1H, ddd, J = 8.5, 8.1, 2.4 Hz), 4.17-4.12 (1H, m), 3.52-3.46 (1H, m), 2.56-2.50 (2H, m), 2.36 (3H, s), 1.19-1.13 (2H, m), 1.10 (3H, t, J = 7.0 Hz), 1.06-0.97 (2H, m), 0.79 (3H, t, J = 7.3 Hz). |
| 417 | $^1$H-NMR ($CDCl_3$) δ: 7.63 (1H, s), 7.24-7.21 (2H, m), 7.10 (1H, ddd, J = 8.5, 8.1, 2.4 Hz), 4.28-4.19 (1H, m), 3.45-3.38 (1H, m), 2.58-2.49 (4H, m), 1.30-1.16 (4H, m), 1.09 (3H, t, J = 7.1 Hz), 0.68 (6H, t, J = 7.3 Hz). |
| 418 | $^1$H-NMR ($CDCl_3$) δ: 7.62 (1H, s), 7.27-7.24 (1H, m), 7.21 (1H, dd, J = 8.5, 5.9 Hz), 7.11 (1H, ddd, J = 8.5, 8.1, 2.4 Hz), 4.27-4.20 (1H, m), 3.46-3.38 (1H, m), 2.57 (4H, t, J = 7.4 Hz), 1.23-1.04 (11H, m), 0.82 (6H, t, J = 7.2 Hz). |
| 419 | $^1$H-NMR ($CDCl_3$) δ: 7.64 (1H, s), 7.49-7.44 (1H, m), 7.27-7.23 (1H, m), 7.21-7.16 (2H, m), 4.00-3.90 (1H, m), 3.83-3.74 (1H, m), 2.65-2.56 (2H, m), 2.38 (3H, s), 1.11 (3H, t, J = 7.0 Hz), 0.76 (3H, t, J = 7.1 Hz). |
| 420 | $^1$H-NMR ($CDCl_3$) δ: 8.07 (1H, s), 7.52-7.44 (1H, m), 7.27-7.23 (1H, m), 7.22-7.17 (2H, m), 3.95-3.89 (1H, m), 3.84-3.77 (1H, m), 3.37-3.35 (2H, m), 2.83 (2H, q, J = 7.1 Hz), 2.28 (1H, t, J = 2.3 Hz), 1.12 (3H, t, J = 7.1 Hz), 0.83 (3H, t, J = 7.1 Hz). |
| 421 | $^1$H-NMR ($CDCl_3$) δ: 7.83 (1H, s), 7.49-7.44 (1H, m), 7.27-7.23 (1H, m), 7.21-7.15 (2H, m), 3.99-3.90 (1H, m), 3.83-3.76 (1H, m), 2.64-2.57 (2H, m), 2.38 (3H, s), 1.11 (3H, t, J = 7.1 Hz), 0.76 (3H, t, J = 7.1 Hz). |
| 422 | $^1$H-NMR ($CDCl_3$) δ: 7.84 (1H, s), 7.55-7.47 (1H, m), 7.33-7.27 (1H, m), 7.25-7.18 (2H, m), 5.25 (1H, tt, J = 55.9, 4.4 Hz), 3.98-3.89 (1H, m), 3.85-3.76 (1H, m), 2.99-2.90 (2H, m), 2.53 (3H, s), 1.12 (3H, t, J = 7.1 Hz). |
| 423 | $^1$H-NMR ($CDCl_3$) δ: 7.80 (1H, s), 7.53-7.47 (1H, m), 7.30-7.27 (1H, m), 7.24-7.18 (2H, m), 5.34 (1H, tt, J = 56.1, 4.4 Hz), 3.99-3.90 (1H, m), 3.82-3.76 (1H, m), 3.03-2.96 (2H, m), 2.79 (2H, q, J = 7.0 Hz). 1.12 (3H, t, J = 7.0 Hz), 0.84 (3H, t, J = 7.0 Hz). |
| 424 | $^1$H-NMR ($CDCl_3$) δ: 7.80 (1H, s), 7.49-7.43 (1H, m), 7.26-7.22 (1H, m), 7.19-7.16 (2H, m), 4.01-3.94 (1H, m), 3.81-3.74 (1H, m), 2.68-2.61 (4H, m), 1.12 (3H, t, J = 7.0 Hz), 0.80 (6H, t, J = 7.0 Hz). |

TABLE 6-continued

| Compound | $^1$H-NMR |
|---|---|
| 425 | $^1$H-NMR ($CDCl_3$) δ: 7.83 (1H, s), 7.48-7.42 (1H, m), 7.26-7.22 (1H, m), 7.21-7.15 (2H, m), 4.01-3.94 (1H, m), 3.84-3.78 (1H, m), 2.78-2.72 (1H, m), 2.38 (3H, s), 1.11 (3H, t, J = 7.1 Hz), 0.79-0.74 (6H, m). |
| 426 | $^1$H-NMR ($CDCl_3$) δ: 7.67 (1H, s), 7.53-7.45 (1H, m), 7.09-7.01 (2H, m), 3.92 (2H, q, J = 7.2 Hz), 3.44-3.38 (4H, m), 2.68-2.61 (4H, m), 1.14 (3H, t, J = 7.1 Hz). |
| 427 | $^1$H-NMR ($CDCl_3$) δ: 7.60 (1H, dd, J = 7.8, 1.4 Hz), 7.52-7.44 (2H, m), 7.49 (1H, s), 7.33 (1H, dd, J = 7.3, 2.1 Hz), 4.08 (1H, dq, J = 13.6, 7.2 Hz), 3.52 (1H, dq, J = 13.6, 7.2 Hz), 2.69 (3H, s), 1.59 (1H, br s), 1.11 (3H, t, J = 7.2 Hz). |
| 428 | $^1$H-NMR ($CDCl_3$) δ: 7.62-7.59 (1H, m), 7.52-7.44 (2H, m), 7.37-7.35 (2H, m), 4.09-4.04 (1H, m), 3.55-3.51 (1H, m), 1.11 (3H, t, J = 7.1 Hz). |
| 429 | $^1$H-NMR ($CDCl_3$) δ: 7.61-7.59 (1H, m), 7.56 (1H, s), 7.51-7.45 (2H, m), 7.37-7.35 (1H, m), 4.08-4.05 (1H, m), 3.56-3.51 (1H, m), 2.74 (1H, s), 1.11 (3H, t, J = 7.2 Hz). |
| 430 | $^1$H-NMR ($CDCl_3$) δ: 7.79 (1H, dd, J = 7.6, 1.2 Hz), 7.52 (1H, td, J = 7.6, 1.2 Hz), 7.41 (1H, ddd, J = 8.1, 7.6,1.2 Hz), 7.37-7.35 (2H, m), 4.15-4.06 (1H, m), 3.53-3.44 (1H, m), 2.72 (2H, s), 1.13 (3H, t, J = 7.1 Hz). |
| 431 | $^1$H-NMR ($CDCl_3$) δ: 7.78 (1H, dd, J = 8.0, 1.2 Hz), 7.56 (1H, s), 7.52 (1H, td, J = 7.6, 1.2 Hz), 7.41 (1H, ddd, J = 8.0, 7.6, 1.2 Hz), 7.35 (1H, dd, J = 7.6, 1.2 Hz), 4.09-4.07 (1H, m), 3.53-3.45 (1H, m), 2.73 (2H, s), 1.12 (3H, t, J = 7.0 Hz). |
| 432 | $^1$H-NMR ($CDCl_3$) δ: 7.79 (1H, dd, J = 8.0, 1.2 Hz), 7.51 (1H, td, J = 7.5, 1.2 Hz), 7.49 (1H, s), 7.41 (1H, ddd, J = 8.0, 7.5, 1.2 Hz), 7.33 (1H, dd, J = 7.5, 1.2 Hz), 4.15-4.08 (1H, m), 3.51-3.44 (1H, m), 2.70 (3H, s), 1.13 (3H, t, J = 7.2 Hz). |
| 433 | $^1$H-NMR ($CDCl_3$) δ: 7.69 (1H, s), 7.60 (1H, dd, J = 7.8, 1.5 Hz), 7.50 (1H, td, J = 7.8,1.5 Hz), 7.46 (1H, td, J = 7.8, 1.5 Hz), 7.32 (1H, dd, J = 7.8, 1.5 Hz), 4.12-4.04 (1H, m), 3.56-3.49 (1H, m), 2.69 (3H, s), 1.11 (3H, t, J = 7.0 Hz). |
| 434 | $^1$H-NMR ($CDCl_3$) δ: 7.58-7.52 (1H, m), 7.37-7.32 (3H, m), 7.29 (1H, d, J = 8.8 Hz), 3.99-3.92 (1H, m), 3.77-3.69 (1H, m), 2.77 (2H, br s), 1.11 (3H, t, J = 7.1 Hz). |
| 435 | $^1$H-NMR ($CDCl_3$) δ: 7.58-7.52 (2H, m), 7.37-7.28 (3H, m), 4.00-3.91 (1H, m), 3.77-3.70 (1H, m), 2.78 (2H, s), 1.10 (3H, t, J = 7.1 Hz). |
| 436 | $^1$H-NMR ($CDCl_3$) δ: 7.58-7.52 (1H, m), 7.48 (1H, s), 7.35 (1H, td, J = 7.5, 1.1 Hz), 7.31-7.26 (2H, m), 3.99-3.92 (1H, m), 3.78-3.70 (1H, m), 2.68 (3H, s), 2.51 (1H, s), 1.11 (3H, t, J = 7.1 Hz). |
| 437 | $^1$H-NMR ($CDCl_3$) δ: 7.68 (1H, s), 7.57-7.53 (1H, m), 7.34 (1H, td, J = 7.6, 1.0 Hz), 7.30-7.27 (2H, m), 3,99-3.92 (1H, m), 3.77-3.71 (1H, m), 2.68 (3H, s), 2.48 (1H, s), 1.11 (3H, t, J = 7,0 Hz). |

Next, it is specifically shown that the compounds of the present invention are effective against plant diseases, but the compounds are not limited to these examples.

With respect to each Test Example given below, the degree of disease development was evaluated as a value with increments of 0.05, regarding the degree of disease development for plants with no onset of disease as 0 and that for plants of untreated group as 3. Further, from the degrees of disease development, a control value was calculated according to the calculation formula below.

<Control value>

$$\text{Control value}=100\{1-(n/3)\}$$

n=Degree of disease development of each chemical treated group

[Test Example A] Rice Blast

Test plants (rice variety: Sachikaze) were cultivated until the second leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with rice blast fungi (*Magnaporthe grisea*) by spraying a conidial suspension of 1 to $2\times10^5$ conidia/ml. After the inoculation, the plants were allowed to stand, for about 24 hours, in a moist chamber with the room temperature of 20 to 23° C. to promote the onset of disease. The degree of disease development after 6 to 10 days from the inoculation was investigated to evaluate the effect of the chemical solution.

As a result, the compounds shown below showed the control value greater than 50%.

Compound No.: 4, 5, 8, 9, 10, 13, 14, 23, 24, 36, 53, 56, 57, 64, 65, 69, 70, 73, 74, 75, 76, 77, 82, 85, 86, 88, 95, 98, 99, 100, 101, 102, 104, 106, 107, 111, 112, 113, 114, 118, 121, 122, 124, 125, 126, 127, 129, 130, 131, 132, 133, 134, 136, 137, 138, 139, 140, 141, 142, 143, 144, 145, 146, 147, 148, 149, 150, 152, 153, 155, 156, 157, 158, 159, 160, 161, 164, 169, 170, 176, 177, 179, 181, 183, 198, 200, 201, 202, 205, 207, 208, 217, 218, 219, 220, 223, 226, 229, 230, 231, 232, 233, 234, 238, 240, 241, 242, 251, 252, 253, 254, 258, 259, 260, 264, 265, 266, 269, 270, 271, 286, 287, 288, 289, 292, 293, 294, 296, 297, 300, 301, 303, 304, 306, 307, 308, 316, 317, 318, 319, 320, 322, 323, 324, 325, 326, 327, 328, 330, 331, 333, 338, 339, 342, 343, 344, 345, 346, 347, 349, 350, 352, 353, 354, 361, 362, 364, 365, 371, 385, 396, 402, 403, 404, 405, 408, 412, 420, 422, 423, 424, 425, 426, 430, 433, 434, 435 and 436

[Test Example B] Tomato Gray Mold

Test plants (tomato variety: Oogata Fukuju) were cultivated until three to five first leaves (true leaves) appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with gray mold fungi (*Botrytis cinerea*) by spraying a conidial suspension of 4 to $8\times10^5$ conidia/ml. After the inoculation, the plants were allowed to stand, for about 48 hours, in a moist chamber with the room temperature of 20 to 23° C. to promote the onset of disease. The degree of disease development after 2 to 3 days from the inoculation was investigated to evaluate the effect of the chemical solution.

As a result, the compounds shown below showed the control value greater than 50%.

Compound No.: 4, 5, 8, 10, 11, 12, 13, 18, 19, 22, 23, 25, 27, 28, 29, 35, 36, 37, 44, 47, 48, 49, 50, 51, 52, 53, 54, 56, 57, 58, 60, 64, 65, 69, 70, 71, 72, 75, 76, 77, 81, 82, 84, 85, 86, 87, 88, 96, 98, 99, 100, 101, 102, 104, 105, 106, 107, 108, 111, 112, 113, 114, 116, 117, 118, 119, 120, 121, 122, 123, 124, 125, 126, 129, 130, 131, 132, 133, 134, 135, 136, 137, 138, 139, 140, 141, 142, 143, 144, 145, 147, 148, 149, 150, 152, 153, 154, 155, 156, 157, 158, 159, 160, 161, 162, 163, 164, 165, 166, 167, 168, 169, 170, 176, 177, 181, 183, 184, 185, 186, 189, 190, 192, 197, 198, 199, 200, 201, 202, 204, 205, 206, 207, 208, 209, 212, 213, 214, 215, 216, 217, 218, 219, 220, 221, 222, 223, 224, 225, 226, 227, 228, 229, 230, 231, 232, 233, 234, 235, 236, 237, 240, 241, 242, 243, 244, 245, 251, 252, 253, 254, 257, 258, 259, 260, 261, 264, 265, 266, 267, 270, 271, 272, 273, 276, 277, 280, 281, 282, 283, 284, 285, 286, 287, 289, 292, 293, 294, 295, 296, 297, 300, 301, 302, 303, 304, 305, 306, 307, 308, 310, 311, 314, 315, 316, 317, 318, 319, 320, 321, 322, 323, 324, 325, 326, 327, 328, 329, 330, 331, 332, 333, 335, 336, 337, 338, 339, 340, 341, 342, 343, 344, 345, 346, 347, 349, 350, 353, 354, 358, 359, 360, 361, 362, 365, 366, 367, 368, 369, 370, 371, 372, 373, 374, 375, 378, 379, 380, 381, 382, 383, 385, 386, 388, 391, 392, 393, 394, 396, 398, 399, 400, 401, 402, 404, 405, 407, 408, 409, 411, 412, 413, 414, 415, 416, 417, 419, 420, 421, 423, 424, 425, 426 and 431

[Test Example C] Cabbage Alternaria Sooty Spot

Test plants (cabbage variety: Shikidori) were cultivated until the cotyledons extended after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with cabbage alternaria sooty spot fungi (*Alternaia brassicicola*) by spraying a conidial suspension of 4 to $8\times10^5$ conidia/ml. After the inoculation, the plants were allowed to stand, for about 48 hours, in a moist chamber with the room temperature of 20 to 23° C. to promote the onset of disease. The degree of disease development after 2 to 3 days from the inoculation was investigated to evaluate the effect of the chemical solution.

As a result, the compounds shown below showed the control value greater than 50%.

Compound No.: 1, 2, 3, 4, 5, 6, 7, 8, 9, 10, 13, 19, 22, 23, 26, 29, 30, 31, 33, 34, 35, 36, 37, 40, 41, 42, 43, 44, 49, 50, 51, 52, 53, 54, 56, 57, 58, 60, 62, 64, 65, 69, 70, 71, 72, 73, 74, 75, 76, 77, 81, 82, 84, 85, 86, 87, 88, 89, 90, 91, 93, 94, 95, 97, 98, 99, 100, 101, 102, 104, 105, 106, 107, 108, 111, 112, 113, 114, 116, 117, 118, 119, 120, 121, 122, 123, 124, 125, 126, 128, 129, 130, 131, 132, 133, 134, 135, 136, 137, 138, 139, 140, 141, 142, 143, 144, 145, 147, 148, 149, 150, 152, 153, 154, 155, 156, 157, 158, 159, 160, 161, 162, 163, 165, 166, 169, 170, 176, 177, 179, 181, 182, 183, 184, 185, 186, 193, 194, 197, 198, 199, 200, 201, 202, 203, 205, 206, 207, 208, 209, 211, 212, 213, 214, 215, 216, 217, 218, 219, 220, 221, 222, 223, 224, 225, 226, 227, 228, 229, 230, 231, 232, 233, 234, 235, 236, 237, 238, 240, 241, 242, 243, 244, 245, 251, 252, 253, 254, 257, 258, 259, 260, 261, 262, 263, 264, 265, 266, 267, 270, 271, 272, 273, 274, 275, 276, 277, 280, 281, 284, 285, 286, 287, 288, 289, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 349, 350, 352, 353, 354, 355, 358, 359, 360, 361, 362, 364, 365, 366, 367, 368, 370, 371, 372, 373, 374, 375, 376, 378, 379, 380, 381, 382, 383, 384, 385, 386, 388, 391, 392, 393, 394, 396, 398, 399, 400, 401, 402, 403, 404, 405, 406, 407, 408, 409, 410, 411, 412, 413, 414, 415, 416, 417, 418, 419, 420, 421, 422, 423, 424, 425 and 426

[Test Example D] Barley Powdery Mildew

Test plants (barley variety: Akashinriki) were cultivated until the first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with barley powdery mildew fungi (*Blumeria graminis* f.sp. *hordei*) by sprinkling flicked conidiospores. The degree of disease development after 6 to 10 days from the inoculation was investigated to evaluate the effect of the chemical solution.

As a result, the compounds shown below showed the control value greater than 50%.

Compound No.: 2, 4, 5, 9, 10, 11, 23, 29, 30, 36, 37, 62, 63, 64, 65, 69, 72, 74, 76, 77, 82, 86, 87, 88, 98, 99, 100, 101, 102, 104, 105, 107, 111, 112, 113, 114, 115, 116, 117, 118, 119, 121, 124, 125, 126, 129, 130, 131, 132, 133, 134, 136, 137, 138, 139, 140, 141, 142, 143, 144, 146, 147, 148, 149, 150, 152, 153, 154, 155, 156, 157, 158, 159, 160, 161, 163, 169, 170, 183, 185, 197, 198, 199, 200, 205, 207, 208, 209, 214, 215, 217, 218, 223, 224, 229, 230, 231, 232, 233, 234, 235, 236, 237, 240, 241, 242, 243, 244, 245, 251, 252, 254, 258, 259, 261, 264, 265, 266, 267, 271, 303, 304, 317, 318, 319, 320, 322, 323, 324, 325, 326, 327, 330, 331, 333, 344, 345, 354, 361, 362, 374, 381, 382, 383, 385, 388, 392, 394, 402, 404, 405, 407, 408, 409, 413, 414, 415, 416, 419, 420 and 421

[Test Example E] Wheat Brown Rust

Test plants (wheat variety: Norin 61) were cultivated until the first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with wheat brown rust fungi (*Puccinia recondita*) by spraying a uredospore suspension of 1 to $2\times10^5$ spores/ml. After the inoculation, the plants were allowed to stand, for about 24 hours, in a moist chamber with the room temperature of 20 to 23° C. to promote the onset of disease. The degree of disease development after 7 to 10 days from the inoculation was investigated to evaluate the effect of the chemical solution.

As a result, the compounds shown below showed the control value greater than 50%.

Compound No.: 4, 5, 6, 8, 9, 10, 11, 13, 20, 23, 34, 35, 36, 37, 52, 53, 56, 60, 64, 65, 69, 70, 72, 75, 76, 77, 81, 82, 85, 86, 87, 88, 92, 98, 99, 100, 101, 102, 104, 105, 106, 107, 108, 111, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 146, 147, 148, 149, 150, 152, 153, 154, 155, 156, 157, 158, 159, 160, 161, 162, 164, 165, 169, 170, 176, 177, 179, 180, 181, 182, 183, 185, 191, 192, 197, 198, 199, 200, 201, 202, 205, 206, 207, 208, 209, 210, 211, 212, 213, 214, 215, 217, 218, 219, 220, 221, 222, 223, 224, 225, 226, 227, 228, 229, 230, 231, 232, 233, 234, 235, 236, 237, 238, 240, 241, 242, 243, 244, 245, 246, 247, 248, 249, 250, 251, 252, 253, 254, 255, 256, 257, 258, 259, 260, 261, 262, 263, 264, 265, 266, 267, 270, 271, 273, 274, 276, 277, 281, 282, 283, 286, 287, 289, 291, 292, 293, 294, 295, 296, 297, 298, 299, 300, 301, 302, 303, 304, 305, 306, 307, 308, 309, 310, 311, 315, 316, 317, 318, 319, 320, 321, 322, 323, 324, 325, 326, 327, 328, 329, 330, 331, 332, 333, 334, 337, 338, 339, 340, 341, 342, 343, 344, 345, 346, 347, 348, 349, 350, 354, 355, 358, 359, 360, 361, 362, 364, 365, 366, 368, 370, 371, 373, 374, 376, 377, 379, 381, 382, 383, 384, 385, 388, 391, 392, 393, 394, 401, 402, 404, 405, 407, 408, 409, 410, 412, 413, 414, 415, 416, 417, 419, 420, 421, 423 and 426

[Test Example F] Tomato Late Blight

Test plants (tomato variety: Oogata Fukuju) were cultivated until three to five first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with tomato late blight fungi (*Phytophthora infestans*) by spraying a zoosporangial suspension of $8\times10^3$ zoosporangia/ml. After the inoculation, the plants were allowed to stand, for about 24 hours, in a moist chamber with the room temperature of 20° C. to promote the onset of disease. The degree of disease development after 5 to 10 days from the inoculation was investigated to evaluate the effect of the chemical solution.

As a result, the compounds shown below showed the control value greater than 50%.

Compound No.: 20, 21, 33, 47, 48, 51, 66, 67, 68, 70, 92, 95, 111, 114, 125, 138, 141, 144, 145, 148, 158, 159, 171, 172, 173, 174, 175, 210, 211, 246, 247, 255, 256, 268, 269, 272, 275, 278, 279, 287, 288, 290, 291, 321, 348, 376, 387, 389, 390, 395, 397, 430, 431, 434, 435, 436 and 437

[Test Example G] Grape Downy Mildew

Test plants (grape variety: Neomuscat) were cultivated until three to four first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with grape downy mildew fungus (*Plasmopara viticola*) by spraying a zoosporangial suspension of 1 to $2\times10^4$ zoosporangia/ml. After the inoculation, the plants were allowed to stand, for about 24 hours, in a moist chamber with the room temperature of 20° C. to promote the onset of disease. The degree of disease development after 7 to 10 days from the inoculation was investigated to evaluate the effect of the chemical solution.

As a result, the compounds shown below showed the control value greater than 50%.

Compound No.: 4, 9, 15, 16, 18, 19, 20, 21, 23, 32, 33, 34, 45, 46, 47, 48, 49, 50, 51, 52, 53, 55, 56, 57, 58, 59, 60, 61, 62, 63, 66, 67, 68, 70, 71, 72, 73, 74, 76, 77, 78, 79, 80, 82, 83, 84, 86, 88, 89, 90, 91, 92, 93, 94, 95, 97, 98, 99, 100, 101, 105, 107, 108, 109, 110, 111, 112, 113, 114, 115, 116, 117, 118, 119, 120, 122, 123, 125, 126, 129, 130, 132, 134, 135, 136, 137, 138, 139, 141, 142, 143, 144, 145, 147, 148, 149, 150, 151, 155, 158, 159, 163, 166, 169, 170, 171, 172, 173, 174, 175, 178, 179, 180, 181, 182, 183, 184, 185, 186, 188, 189, 190, 197, 198, 199, 200, 207, 208, 209, 210, 211, 212, 213, 217, 218, 220, 221, 222, 223, 230, 237, 238, 239, 241, 244, 245, 246, 247, 248, 249, 250, 251, 252, 253, 254, 255, 256, 257, 258, 259, 262, 263, 264, 265, 266, 268, 269, 274, 275, 276, 278, 279, 282, 283, 286, 287, 288, 289, 290, 291, 293, 294, 295, 297, 298, 299, 301, 302, 303, 304, 306, 307, 308, 309, 310, 313, 317, 318, 319, 320, 321, 322, 323, 325, 326, 327, 331, 348, 351, 357, 376, 387, 389, 390, 395, 397, 422, 424, 425, 426, 427, 428, 429, 430, 431, 432, 433, 434, 435, 436 and 437

[Test Example H] Cucumber Anthracnose

Test plants (cucumber variety: Sagami Hanjiro) were cultivated until one first leaf appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with cucumber anthracnose fungi (*Colletotrichum orbiculare*) by spraying a conidial suspension of 2 to $4\times10^5$ conidia/ml. After the inoculation, the plants were allowed to stand, for about 24 hours, in a moist chamber with the room temperature of 20 to 23° C. to promote the onset of disease. The degree of disease development after 6 to 10 days from the inoculation was investigated to evaluate the effect of the chemical solution.

As a result, the compounds shown below showed the control value greater than 50%.

Compound No.: 3, 4, 5, 6, 8, 9, 10, 13, 16, 17, 18, 19, 20, 21, 22, 23, 32, 33, 34, 35, 36, 37, 38, 39, 42, 43, 44, 45, 46, 47, 48, 49, 50, 51, 52, 53, 56, 57, 58, 59, 60, 62, 64, 65, 69, 70, 71, 72, 73, 74, 75, 76, 77, 82, 84, 85, 86, 87, 88, 89, 90, 91, 92, 93, 94, 95, 97, 98, 99, 100, 101, 102, 103, 104, 105, 106, 107, 108, 109, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 163, 165, 166, 169, 170, 171, 172, 173, 174, 175, 176, 177, 181, 183, 184, 185, 186, 187, 188, 191, 192, 193, 195, 196, 197, 198, 199, 200, 201, 202, 205, 206, 207, 208, 210, 212, 213, 214, 217, 218, 219, 220, 221, 223, 224, 225, 226, 227, 229, 230, 231, 232, 233, 234, 235, 237, 238, 240, 241, 242, 243, 244, 245, 246, 247, 248, 249, 250, 251, 252, 253, 254, 255, 257, 258, 259, 260, 261, 262, 264, 265, 266, 267, 268, 269, 270, 271, 272, 273, 276, 277, 278, 279, 280, 281, 282, 283, 284, 285, 286, 287, 288, 289, 290, 291, 292, 293, 294, 296, 297, 298, 299, 300, 301, 302, 303, 304, 305, 306, 307, 310, 313, 314, 315, 316, 317, 318, 319, 320, 321, 322, 323, 324, 325, 326, 328, 330, 331, 332, 333, 334, 335, 337, 338, 339, 340, 341, 342, 343, 344, 345, 346, 347, 348, 349, 350, 354, 355, 356, 358, 361, 362, 363, 365, 366, 371, 376, 377, 378, 380, 383, 384, 385, 386, 387, 388, 389, 390, 391, 392, 394, 395, 396, 397, 398, 399, 401, 402, 404, 405, 406, 407, 408, 410, 411, 412, 413, 414, 415, 416, 417, 419, 420, 421, 422, 423, 424, 425, 426, 427, 428, 429, 430, 431, 432, 433, 434, 435, 436 and 437

INDUSTRIAL APPLICABILITY

The pyridone compound of the present invention is a novel compound and can control plant diseases. Therefore, the compound is valuable as a pesticide, for example, an agricultural and horticultural pest control agent, in particular an agricultural and horticultural fungicide.

The disclosure in Japanese Patent Application No. 2017-113810 (filing date: Jun. 8, 2017) is entirely incorporated herein by reference.

All publications, patent applications and technical standards mentioned in the present specification are herein incorporated by reference to the same extent as if each individual publication, patent application or technical standard was specifically and individually indicated to be incorporated by reference.

The invention claimed is:

1. A compound represented by Formula (1)

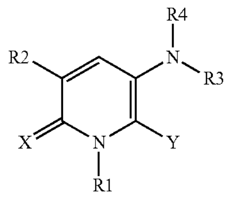

(1)

wherein R1 represents
- a hydroxyl group,
- a cyano group,
- a C1-C6 alkyl group optionally substituted with substituent A,
- a C1-C6 haloalkyl group,
- a C3-C8 cycloalkyl group optionally substituted with substituent A,
- a C2-C6 alkenyl group optionally substituted with substituent A,
- a C2-C6 haloalkenyl group,
- a C2-C6 alkynyl group optionally substituted with substituent A,
- a C2-C6 haloalkynyl group,
- a C1-C6 alkoxy group optionally substituted with substituent A,
- a C1-C6 haloalkoxy group,
- a C3-C8 cycloalkoxy group optionally substituted with substituent A,
- a C2-C6 alkenyloxy group optionally substituted with substituent A,
- a C2-C6 haloalkenyloxy group,
- a C3-C6 alkynyloxy group optionally substituted with substituent A,
- a C3-C6 haloalkynyloxy group, or
- an RaRbN— wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group;

R2 represents
- a hydrogen atom,
- a cyano group,
- a nitro group,
- a halogen atom,
- a C1-C6 alkyl group optionally substituted with substituent A,
- a C1-C6 haloalkyl group,
- a C3-C8 cycloalkyl group optionally substituted with substituent A,
- a C2-C6 alkenyl group optionally substituted with substituent A,
- a C2-C6 haloalkenyl group,
- a C2-C6 alkynyl group optionally substituted with substituent A,
- a C2-C6 haloalkynyl group,
- a C1-C6 alkoxy group optionally substituted with substituent A,
- a C1-C6 haloalkoxy group,
- a C3-C8 cycloalkoxy group optionally substituted with substituent A,
- a C2-C6 alkenyloxy group optionally substituted with substituent A,
- a C2-C6 haloalkenyloxy group,
- a C3-C6 alkynyloxy group optionally substituted with substituent A,
- a C3-C6 haloalkynyloxy group,
- an Rc-L- wherein Rc represents a C1-C6 alkyl group or a C1-C6 haloalkyl group, and L represents S, SO or $SO_2$,
- an RaRbN— wherein Ra and Rb are the same as defined above, or
- an RdC(═O)— wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— wherein Ra and Rb are the same as defined above;

R3 and R4 are independent to each other, and each represents
- a hydrogen atom,
- a C1-C6 alkyl group optionally substituted with substituent C,
- a C1-C6 haloalkyl group,
- a C3-C8 cycloalkyl group optionally substituted with substituent C,
- a C2-C6 alkenyl group optionally substituted with substituent C,
- a C2-C6 haloalkenyl group,
- a C2-C6 alkynyl group optionally substituted with substituent C,
- a C2-C6 haloalkynyl group,
- a C1-C6 alkoxy group optionally substituted with substituent C,
- a C1-C6 haloalkoxy group,
- a C3-C8 cycloalkoxy group optionally substituted with substituent C,
- a C2-C6 alkenyloxy group optionally substituted with substituent C,
- a C2-C6 haloalkenyloxy group, a C3-C6 alkynyloxy group optionally substituted with substituent C, a C3-C6 haloalkynyloxy group, a phenyl group optionally substituted with 0 to 5 substituent D with the proviso that when there are two or more substituents D, they are independent to each other, a C1-C6 alkyl group having a phenyl group optionally substituted with 0 to 5 substituent D with the proviso that when there are two or more substituents D, they are independent to each other, a C1-C6 haloalkyl group having a phenyl group optionally substituted with 0 to 5 substituent D with the proviso that when there are two or more substituents D, they are independent to each other, an Rc-L- wherein Rc and L are the same as defined above, or an ReC(=O)— wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— wherein Ra and Rb are the same as defined above, or R3 and R4 in combination with the nitrogen atom to which they are bonded form an aziridinyl group optionally substituted with substituent E, an azetidinyl group optionally substituted with substituent E, a pyrrolidinyl group optionally substituted with substituent E, a piperidinyl group optionally substituted with substituent E, a homopiperidinyl group optionally substituted with substituent E, an azocanyl group optionally substituted with substituent E, a morpholinyl group optionally substituted with substituent E or a C1-C6 alkylidene group optionally substituted with substituent F;

X represents an oxygen atom or a sulfur atom;

Y represents a phenyl group optionally substituted with 0 to 5 R5 with the proviso that when there are two or more R5, they are independent to each other, a pyridyl group optionally substituted with 0 to 4 R5 with the proviso that when there are two or more R5, they are independent to each other, a pyridazinyl group optionally substituted with 0 to 3 R5 with the proviso that when there are two or more R5, they are independent to each other, a pyrimidinyl group optionally substituted with 0 to 3 R5 with the proviso that when there are two or more R5, they are independent to each other, a pyradinyl group optionally substituted with 0 to 3 R5 with the proviso that when there are two or more R5, they are independent to each other, a triazinyl group optionally substituted with 0 to 2 R5 with the proviso that when there are two R5, they are independent to each other, a tetrazinyl group optionally substituted with R5, a thienyl group optionally substituted with 0 to 3 R5 with the proviso that when there are two or more R5, they are independent to each other, a thiazolyl group optionally substituted with 0 to 2 R5 with the proviso that when there are two R5, they are independent to each other, an isothiazolyl group optionally substituted with 0 to 2 R5 with the proviso that when there are two R5, they are independent to each other, or a thiadiazolyl group optionally substituted with R5, R5 represents a hydroxyl group, a cyano group, a nitro group, a halogen atom, a C1-C6 alkyl group optionally substituted with substituent G, a C1-C6 haloalkyl group, a C3-C8 cycloalkyl group optionally substituted with substituent G, a C2-C6 alkenyl group optionally substituted with substituent G, a C2-C6 haloalkenyl group, a C2-C6 alkynyl group optionally substituted with substituent G, a C2-C6 haloalkynyl group, a C1-C6 alkoxy group optionally substituted with substituent G, a C1-C6 haloalkoxy group, a C3-C8 cycloalkoxy group optionally substituted with substituent G, a C2-C6 alkenyloxy group optionally substituted with substituent G, a C2-C6 haloalkenyloxy group, a C3-C6 alkynyloxy group optionally substituted with substituent G, a C3-C6 haloalkynyloxy group, an RdC(=O)— wherein Rd is the same as defined above, an RdC(=O)O— wherein Rd is the same as defined above, an Rc-L- wherein Rc and L are the same as defined above, or an RaRbN— wherein Ra and Rb are the same as defined above; and the substituent A is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— wherein Ra and Rb are the same as defined above, and an Rc-L- wherein Rc and L are the same as defined above;

the substituent B is at least one member selected from the group consisting of a cyano group, a C1-C6 alkoxy group, a C1-C6 haloalkoxy group and a C3-C8 cycloalkoxy group;

the substituent C is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group and an Rc-L- wherein Rc and L are the same as defined above;

the substituent D is at least one member selected from the group consisting of a hydroxyl group, a cyano group, a nitro group, a halogen atom, a C1-C6 alkyl group optionally substituted with substituent B, a C1-C6 haloalkyl group, a C3-C8 cycloalkyl group, a C1-C6 alkoxy group, a C1-C6 haloalkoxy group and a C3-C8 cycloalkoxy group;

the substituent E is at least one member selected from the group consisting of an oxo group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group;

the substituent F is at least one member selected from the group consisting of, a C1-C6 alkoxy group, an RaRbN— wherein Ra and Rb are the same as defined above and RdC(═O)— wherein Rd is the same as defined above;

the substituent G is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an RaRbN— wherein Ra and Rb are the same as defined above, an Rc-L- wherein Rc and L are the same as defined above, an RdC(═O)— wherein Rd is the same as defined above, an RdC(═O)O— wherein Rd is the same as defined above, and a group of a 3-6 membered ring containing 1-2 oxygen atoms, or a salt thereof.

2. The compound according to claim 1, wherein

R1 represents
- a C1-C6 alkyl group optionally substituted with substituent A,
- a C1-C6 haloalkyl group,
- a C2-C6 alkenyl group optionally substituted with substituent A,
- a C2-C6 haloalkenyl group,
- a C2-C6 alkynyl group optionally substituted with substituent A, or
- a C2-C6 haloalkynyl group;

R2 represents
- a hydrogen atom,
- a cyano group,
- a halogen atom,
- a C1-C6 alkyl group optionally substituted with substituent A,
- a C1-C6 haloalkyl group,
- a C2-C6 alkynyl group optionally substituted with substituent A,
- a C2-C6 haloalkynyl group,
- a C1-C6 alkoxy group optionally substituted with substituent A,
- a C1-C6 haloalkoxy group,
- an Rc-L- wherein Rc represents a C1-C6 alkyl group or a C1-C6 haloalkyl group, and L represents S, SO or $SO_2$, or
- an RdC(═O)— wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group;

R3 and R4 are independent to each other, and each represents
- a hydrogen atom,
- a C1-C6 alkyl group optionally substituted with substituent C,
- a C1-C6 haloalkyl group,
- a C3-C8 cycloalkyl group optionally substituted with substituent C,
- a C2-C6 alkenyl group optionally substituted with substituent C,
- a C2-C6 haloalkenyl group,
- a C2-C6 alkynyl group optionally substituted with substituent C,
- a C2-C6 haloalkynyl group,
- a phenyl group optionally substituted with 0 to 5 substituent D with the proviso that when there are two or more substituents D, they are independent to each other,
- a C1-C6 alkyl group having a phenyl group optionally substituted with 0 to 5 substituent D with the proviso that when there are two or more substituents D, they are independent to each other,
- an Rc-L- wherein Rc and L are the same as defined above, or
- an ReC(═O)— wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— wherein Ra and Rb are the same as defined above, or R3 and R4 in combination with the nitrogen atom to which they are bonded form
- a pyrrolidinyl group optionally substituted with substituent E,
- a piperidinyl group optionally substituted with substituent E,
- a morpholinyl group optionally substituted with substituent E, or
- a C1-C6 alkylidene group optionally substituted with substituent F;

Y represents
- a phenyl group optionally substituted with 0 to 5 R5 with the proviso that when there are two or more R5, they are independent to each other, or
- a pyridyl group optionally substituted with 0 to 4 R5 with the proviso that when there are two or more R5, they are independent to each other, R5 represents
- a hydroxyl group,
- a cyano group,
- a halogen atom,
- a C1-C6 alkyl group optionally substituted with substituent G,
- a C1-C6 alkoxy group optionally substituted with substituent G,
- a C1-C6 haloalkoxy group,
- a C2-C6 alkenyloxy group optionally substituted with substituent G, a C2-C6 haloalkenyloxy group,
a C3-C6 alkynyloxy group optionally substituted with substituent G,
a C3-C6 haloalkynyloxy group, or
an RdC(=O)O— wherein Rd is the same as defined above, or a salt thereof.

3. The compound according to claim 2, wherein

R1 represents
a C1-C6 alkyl group optionally substituted with substituent A, or
a C1-C6 haloalkyl group;

R2 represents
a hydrogen atom,
a cyano group,
a halogen atom,
a C1-C6 alkyl group optionally substituted with substituent A,
a C2-C6 alkynyl group optionally substituted with substituent A, or
a C1-C6 alkoxy group optionally substituted with substituent A;

R3 and R4 are independent to each other, and each represents
a hydrogen atom,
a C1-C6 alkyl group optionally substituted with substituent C,
a C1-C6 haloalkyl group,
a C3-C8 cycloalkyl group optionally substituted with substituent C,
a C2-C6 alkenyl group optionally substituted with substituent C,
a C2-C6 alkynyl group optionally substituted with substituent C,
a phenyl group optionally substituted with 0 to 5 substituent D with the proviso that when there are two or more substituents D, they are independent to each other,
a C1-C6 alkyl group having a phenyl group optionally substituted with 0 to 5 substituent D with the proviso that when there are two or more substituents D, they are independent to each other,
an Rc-L- wherein Rc represents a C1-C6 alkyl group or a C1-C6 haloalkyl group, and L represents S, SO or $SO_2$, or
an ReC(=O)— wherein Re represents a hydrogen atom, a C1-C6 alkyl group optionally substituted with substituent B, a C1-C6 haloalkyl group, a C3-C8 cycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C8 cycloalkoxy group, a C2-C6 alkenyloxy group, a C2-C6 haloalkenyloxy group, a C3-C6 alkynyloxy group, a C3-C6 haloalkynyloxy group or an RaRbN— wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group, or R3 and R4 in combination with the nitrogen atom to which they are bonded form
a pyrrolidinyl group optionally substituted with substituent E,
a piperidinyl group optionally substituted with substituent E,
a morpholinyl group optionally substituted with substituent E, or
a C1-C6 alkylidene group optionally substituted with substituent F;

Y represents
a phenyl group optionally substituted with 0 to 5 R5 with the proviso that when there are two or more R5, they are independent to each other, R5 represents
a hydroxyl group,
a cyano group,
a halogen atom,
a C1-C6 alkyl group optionally substituted with substituent G,
a C1-C6 alkoxy group optionally substituted with substituent G,
a C2-C6 alkenyloxy group optionally substituted with substituent G, or
a C3-C6 alkynyloxy group optionally substituted with substituent G, or a salt thereof.

4. An agricultural and horticultural pest control agent comprising the compound of claim 1 or a salt thereof as an active ingredient.

5. An agricultural and horticultural fungicide comprising the compound of claim 1 or a salt thereof as an active ingredient.

6. A method for controlling plants diseases, which comprises applying the agricultural and horticultural pest control agent of claim 4 to a plant, a plant seed or a soil for growing a plant.

7. A method for controlling plants diseases, which comprises applying the agricultural and horticultural fungicides of claim 5 to a plant, a seed of a plant or a soil for growing a plant.

8. A compound represented by Formula (2)

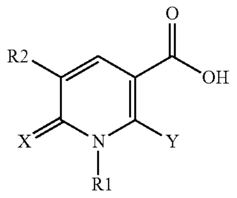

(2)

wherein

R1 represents
a hydroxyl group,
a cyano group,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
a C1-C6 alkoxy group optionally substituted with substituent A, a C1-C6 haloalkoxy group,
a C3-C8 cycloalkoxy group optionally substituted with substituent A,
a C2-C6 alkenyloxy group optionally substituted with substituent A,
a C2-C6 haloalkenyloxy group,
a C3-C6 alkynyloxy group optionally substituted with substituent A,
a C3-C6 haloalkynyloxy group, or
an RaRbN— wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group;

R2 represents
a hydrogen atom,
a cyano group,
a nitro group,
a halogen atom,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
a C1-C6 alkoxy group optionally substituted with substituent A,
a C1-C6 haloalkoxy group,
a C3-C8 cycloalkoxy group optionally substituted with substituent A,
a C2-C6 alkenyloxy group optionally substituted with substituent A,
a C2-C6 haloalkenyloxy group,
a C3-C6 alkynyloxy group optionally substituted with substituent A,
a C3-C6 haloalkynyloxy group,
an Rc-L- wherein Rc represents a C1-C6 alkyl group or a C1-C6 haloalkyl group, and L represents S, SO or $SO_2$,
an RaRbN— wherein Ra and Rb are the same as defined above, or
an RdC(=O)— wherein Rd represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— wherein Ra and Rb are the same as defined above;

X represents an oxygen atom or a sulfur atom;

Y represents
a phenyl group optionally substituted with 0 to 5 R5 with the proviso that when there are two or more R5, they are independent to each other,
a pyridyl group optionally substituted with 0 to 4 R5 with the proviso that when there are two or more R5, they are independent to each other,
a pyridazinyl group optionally substituted with 0 to 3 R5 with the proviso that when there are two or more R5, they are independent to each other,
a pyrimidinyl group optionally substituted with 0 to 3 R5 with the proviso that when there are two or more R5, they are independent to each other,
a pyradinyl group optionally substituted with 0 to 3 R5 with the proviso that when there are two or more R5, they are independent to each other,
a triazinyl group optionally substituted with 0 to 2 R5 with the proviso that when there are two R5, they are independent to each other,
a tetrazinyl group optionally substituted with R5,
a thienyl group optionally substituted with 0 to 3 R5 with the proviso that when there are two or more R5, they are independent to each other,
a thiazolyl group optionally substituted with 0 to 2 R5 with the proviso that when there are two R5, they are independent to each other,
an isothiazolyl group optionally substituted with 0 to 2 R5 with the proviso that when there are two R5, they are independent to each other, or
a thiadiazolyl group optionally substituted with R5, R5 represents
a hydroxyl group,
a cyano group,
a nitro group,
a halogen atom,
a C1-C6 alkyl group optionally substituted with substituent G,
a C1-C6 haloalkyl group,
a C3-C8 cycloalkyl group optionally substituted with substituent G,
a C2-C6 alkenyl group optionally substituted with substituent G,
a C2-C6 haloalkenyl group,
a C2-C6 alkynyl group optionally substituted with substituent G,
a C2-C6 haloalkynyl group,
a C1-C6 alkoxy group optionally substituted with substituent G,
a C1-C6 haloalkoxy group,
a C3-C8 cycloalkoxy group optionally substituted with substituent G,
a C2-C6 alkenyloxy group optionally substituted with substituent G,
a C2-C6 haloalkenyloxy group,
a C3-C6 alkynyloxy group optionally substituted with substituent G,
a C3-C6 haloalkynyloxy group,
an RdC(=O)— wherein Rd is the same as defined above,
an RdC(=O)O— wherein Rd is the same as defined above,
an Rc-L- wherein Rc and L are the same as defined above, or
an RaRbN— wherein Ra and Rb are the same as defined above, the substituent A is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— wherein Ra and Rb are the same as defined above, and an Rc-L- wherein Rc and L are the same as defined above;

the substituent B is at least one member selected from the group consisting of a cyano group, a C1-C6 alkoxy group, a C1-C6 haloalkoxy group and a C3-C8 cycloalkoxy group; and the substituent G is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an RaRbN— wherein Ra and Rb are the same as defined above, an Rc-L- wherein Rc and L are the same as defined above, an RdC(═O)— wherein Rd is the same as defined above, an RdC(═O)O— wherein Rd is the same as defined above, and a group of a 3-6 membered ring containing 1-2 oxygen atoms, or a salt thereof.

* * * * *